US012606543B2

(12) United States Patent
Slassi

(10) Patent No.: US 12,606,543 B2
(45) Date of Patent: Apr. 21, 2026

(54) INDOLE DERIVATIVES AS SEROTONERGIC AGENTS USEFUL FOR THE TREATMENT OF DISORDERS RELATED THERETO

(71) Applicant: MINDSET PHARMA INC., Quebec (CA)

(72) Inventor: Abdelmalik Slassi, Ontario (CA)

(73) Assignee: MINDSET PHARMA INC., St-Laurent (CA)

( * ) Notice: Subject to any disclaimer, the term of this patent is extended or adjusted under 35 U.S.C. 154(b) by 0 days.

(21) Appl. No.: 19/189,862

(22) Filed: Apr. 25, 2025

(65) Prior Publication Data

US 2025/0250256 A1 Aug. 7, 2025

Related U.S. Application Data

(63) Continuation of application No. PCT/IB2024/000644, filed on Nov. 12, 2024.

(60) Provisional application No. 63/598,683, filed on Nov. 14, 2023, provisional application No. 63/598,703, filed on Nov. 14, 2023.

(51) Int. Cl.

| | |
|---|---|
| *C07D 403/06* | (2006.01) |
| *A61K 31/404* | (2006.01) |
| *A61K 31/4439* | (2006.01) |
| *A61K 31/506* | (2006.01) |
| *C07D 405/14* | (2006.01) |
| *C07D 409/14* | (2006.01) |

(52) U.S. Cl.

CPC .......... *C07D 403/06* (2013.01); *A61K 31/404* (2013.01); *A61K 31/4439* (2013.01); *A61K 31/506* (2013.01); *C07D 405/14* (2013.01); *C07D 409/14* (2013.01)

(58) Field of Classification Search

CPC .. C07D 403/06; C07D 405/14; C07D 409/14; A61K 31/404; A61K 31/4439

See application file for complete search history.

(56) References Cited

U.S. PATENT DOCUMENTS

| | | | |
|---|---|---|---|
| 5,545,644 | A | 8/1996 | Macor et al. |
| 5,559,129 | A | 9/1996 | Macor et al. |
| 5,559,246 | A | 9/1996 | Macor |
| 5,578,612 | A | 11/1996 | Macor et al. |
| 5,607,951 | A | 3/1997 | Macor et al. |
| 5,618,834 | A | 4/1997 | Butler |
| 5,654,431 | A | 8/1997 | Meng et al. |
| 5,852,049 | A | 12/1998 | Perez et al. |
| 2003/0212070 | A1 | 11/2003 | Schwink et al. |
| 2004/0132714 | A1 | 7/2004 | Zhou et al. |
| 2009/0062367 | A1 | 3/2009 | Czarnik |
| 2019/0276440 | A1 | 9/2019 | Zhao et al. |
| 2024/0166630 | A1 | 5/2024 | Slassi et al. |

FOREIGN PATENT DOCUMENTS

| | | | | |
|---|---|---|---|---|
| CN | 102936240 | A | 2/2013 | |
| EP | 0714659 | A2 | 6/1996 | |
| FR | 2814166 | A1 | 3/2002 | |
| WO | 92/06973 | A1 | 4/1992 | |
| WO | 93/11106 | A1 | 6/1993 | |
| WO | 93/20073 | A1 | 10/1993 | |
| WO | 93/21177 | A1 | 10/1993 | |
| WO | WO-9321178 | A1 * | 10/1993 | ........... C07D 405/14 |
| WO | 94/10171 | A1 | 5/1994 | |
| WO | 94/24127 | A1 | 10/1994 | |
| WO | 95/21166 | A1 | 8/1995 | |
| WO | 95/21167 | A1 | 8/1995 | |
| WO | 96/09288 | A1 | 3/1996 | |
| WO | 96/11195 | A1 | 4/1996 | |
| WO | 96/26936 | A1 | 9/1996 | |
| WO | 98/27089 | A1 | 6/1998 | |
| WO | 00/04019 | A1 | 1/2000 | |

(Continued)

OTHER PUBLICATIONS

International Search Report and Written Opinion of PCT International Application No. PCT/CA2022/050296, dated May 18, 2022, whole document.

Database Registry [Online]—Chemical Abstracts Service, STN International May 10, 2016, Aurora Fine Chemicals Catalogue, 2-Methoxy-1-[2-[(5-methoxy-2-methyl-1H-indol-3-yl)methyl]-1-pyrrolidinyl]ethanone—Registry No. 1907596-90-0.

Database Registry [Online]—Chemical Abstracts Service, STN International Mar. 20, 2013, [(2R)-1-Methyl-2-pyrrolidinyl][5-[(trifluoromethyl)sulfonyl]-1H-indol-3-yl]methanone—Registry No. 1425840-20-5.

(Continued)

*Primary Examiner* — James H Alstrum-Acevedo
*Assistant Examiner* — Manahil Mirghani Ali Abdalhameed
(74) *Attorney, Agent, or Firm* — RAPHAEL BELLUM PLLC

(57) ABSTRACT

The present disclosure relates to indole derivatives of general Formula (I), to processes for their preparation, to compositions including indole derivatives of general Formula (I), and to their use in activation of a serotonin receptors in a cell, as well as to treating diseases, disorders, or conditions by activation of a serotonin receptors in a cell. The diseases, disorders, or conditions include, for example, psychosis, mental illnesses and CNS disorders.

Formula (I)

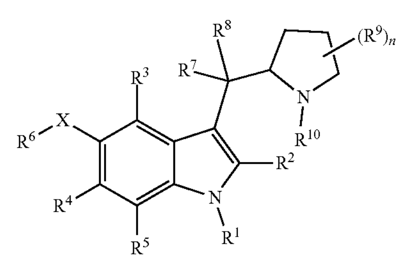

26 Claims, 5 Drawing Sheets

(56) References Cited

FOREIGN PATENT DOCUMENTS

| | | | |
|---|---|---|---|
| WO | 00/005229 | A1 | 2/2000 |
| WO | 2004/024730 | A1 | 3/2004 |
| WO | 2004/106298 | A1 | 12/2004 |
| WO | 2004/106346 | A1 | 12/2004 |
| WO | 2005/097261 | A1 | 10/2005 |
| WO | 2006/020930 | A2 | 2/2006 |
| WO | 2008/100448 | A2 | 8/2008 |
| WO | 2010/149761 | A1 | 12/2010 |
| WO | 2018/064465 | A1 | 4/2018 |
| WO | 2018/094106 | A2 | 5/2018 |
| WO | 2020/181194 | A1 | 9/2020 |
| WO | 2021/155467 | A1 | 8/2021 |
| WO | 2021/155468 | A1 | 8/2021 |
| WO | 2022/183288 | A1 | 3/2022 |
| WO | 2023/019366 | A1 | 8/2022 |
| WO | 2022183287 | A1 | 9/2022 |
| WO | 2022/246554 | A1 | 12/2022 |
| WO | 2022/256554 | A1 | 12/2022 |
| WO | 2023/201423 | A1 | 10/2023 |
| WO | 2024/168098 | A2 | 8/2024 |

OTHER PUBLICATIONS

Database Registry [Online]—Chemical Abstracts Service, STN International Mar. 20, 2013, Phenylmethyl (2R)-2-[[5-[(trifluoromethyl)sulfonyl]-1H-indol-3-yl]carbonyl]-1-pyrrolidinecarboxylate—Registry No. 1425840-01-2.

International Search Report and Written Opinion of PCT International Application No. PCT/IB2024/000644 dated Mar. 11, 2025 (pending processing).

Nirogi et al., "Synthesis and Structure Activity Relationship of Rigidized Indolyl Pyrrolidine Derivatives as 5-HT6 Receptor Ligands," Asian Journal of Chemistry 2013, 25(16), 9293-9298.

Dukat et al., "Binding of Serotonin and N1-Benzenesulfonyltryptamine-Related Analogs at Human 5-HT6 Serotonin Receptors: Receptor Modeling Studies," J. Med. Chem. 2008, 51, 603-611.

U.S. Appl. No. 63/444,171, filed Feb. 8, 2023.

U.S. Appl. No. 63/613,234, filed Dec. 21, 2023.

Database Registry [Online]—Chemical Abstracts Service, STN International Aug. 2, 2017, Aurora Fine Chemicals Catalogue, 4-chloro-5-methyl-3-(2-pyrrolidinylmethyl)-1H-indole—Registry No. 2107058-48-8.

Database Registry [Online]—Chemical Abstracts Service, STN International Aug. 1, 2017, Aurora Fine Chemicals Catalogue, 7-chloro-5-methyl-3-(2-pyrrolidinylmethyl)-1H-indole—Registry No. 2106485-68-9.

Database Registry [Online]—Chemical Abstracts Service, STN International Jun. 18, 2016, Aurora Fine Chemicals Catalogue, 5-(1-methylethyl)-3-(2-pyrrolidinylmethyl)-1H-indole—Registry No. 1783394-66-0.

Database Registry [Online]—Chemical Abstracts Service, STN International Aug. 18, 2017, Aurora Fine Chemicals Catalogue, 5-(1,1-dimethylethyl)-1-methyl-3-(2-pyrrolidinylmethyl)-1H-indole—Registry No. 2116083-14-6.

Database Registry [Online]—Chemical Abstracts Service, STN International Dec. 7, 2011, Database: GVK Bio, (5S)-5-[[3-[[(2R)-1-(1-methoxyethyl)-2-pyrrolidinyl]methyl]-1H-indol-5-yl]methyl]-2-oxazolidinone—Registry No. 1350000-36-0.

PubChem-SID-132577726, Modify Date: May 31, 2019.

PubChem-SID-368573951, Modify Date: May 25, 2018.

PubChem-SID-472924996, Modify Date: Dec. 2, 2022.

Mohammad-Zadeh et al., "Serotonin: a review," J. Vet. Pharmacol. Therap. 2008, 31, pp. 187-199.

* cited by examiner

INDOLE DERIVATIVES AS SEROTONERGIC AGENTS USEFUL FOR THE TREATMENT OF DISORDERS RELATED THERETO

CROSS-REFERENCE TO RELATED APPLICATIONS AND CLAIMS OF PRIORITY

This application is a continuation application of International Application No. PCT/IB2024/000644 filed on Nov. 12, 2024, which claims the benefit of priority of U.S. Provisional Application No. 63/598,683 filed on Nov. 14, 2023, and U.S. Provisional Application No. 63/598,703 filed on Nov. 14, 2023, the complete disclosures of all of which are incorporated herein by reference and priority of each being claimed.

FIELD

The disclosure relates to indole derivatives of general Formula (I) for the treatment of different conditions that are treated by activation of serotonin receptors, for example, mental illnesses and neurological disease, in the fields of psychiatry, neurobiology, and pharmacotherapy. The present disclosure further comprises methods for making the compounds of Formula (I) and corresponding intermediates.

BACKGROUND

Mental health disorders, or mental illness, refer to a wide range of disorders that include, but are not limited to, depressive disorders, anxiety and panic disorders, schizophrenia, eating disorders, substance misuse disorders, post-traumatic stress disorder, attention deficit/hyperactivity disorder and obsessive-compulsive disorder. Many mental health disorders, as well as neurological disorders, are impacted by alterations, dysfunction, degeneration, and/or damage to the brain's serotonergic system, which may explain, in part, common endophenotypes and comorbidities among neuropsychiatric and neurological diseases.

The field of psychedelic neuroscience has witnessed a recent renaissance following a decade of restricted research due to the evolving legal status of psychedelics. Psychedelics (serotonergic hallucinogens) are powerful psychoactive substances that alter perception and mood and affect numerous cognitive processes. Today there is a consensus that psychedelics are agonists or partial agonists at serotonin 5-hydroxytryptamine 2A (5-$HT_{2A}$) receptors.

Psychedelics have both rapid onset and persisting effects long after their acute effects, which includes changes in mood and brain function. Long lasting effects may result from their unique receptor affinities, which affect neurotransmission via neuromodulatory systems that serve to modulate brain activity, i.e., neuroplasticity, and promote cell survival, are neuroprotective, and modulate brain neuroimmune systems. The mechanisms which lead to these long-term neuromodulatory changes may be linked to epigenetic modifications, gene expression changes and modulation of pre- and post-synaptic receptor densities. These, previously under-researched, psychedelic drugs may potentially provide the next generation of neurotherapeutics, where treatment resistant psychiatric and neurological diseases, e.g., depression, post-traumatic stress disorder, dementia, and addiction, may become treatable with attenuated pharmacological risk profiles.

Although there is a general perception that psychedelic drugs are dangerous, from a physiologic safety standpoint, they are one of the safest known classes of central nervous system (CNS) drugs. Preliminary data show that psychedelic administration in humans results in a unique profile of effects and potential adverse reactions that need to be appropriately addressed to maximize safety. The primary safety concerns are largely psychologic, rather than physiologic, in nature. Somatic effects vary but are relatively insignificant, even at doses that elicit powerful psychologic effects. Psilocybin, when administered in a controlled setting, has frequently been reported to cause transient, delayed headache, with incidence, duration, and severity increased in a dose-related manner [Johnson et al., Drug Alcohol Depend (2012) 123(1-3):132-140]. It has been found that repeated administration of psychedelics leads to a very rapid development of tolerance known as tachyphylaxis, a phenomenon believed to be mediated, in part, by 5-$HT_{2A}$ receptors. In fact, several studies have shown that rapid tolerance to psychedelics correlates with downregulation of 5-$HT_{2A}$ receptors. For example, daily LSD administration selectively decreased 5-$HT_2$ receptor density in the rat brain [Buckholtz et al., Eur. J. Pharmacol. 1990, 109:421-425. 1985; Buckholtz et al., Life Sci. 1985, 42:2439-2445].

Classic psychedelics and dissociative psychedelics are known to have rapid onset antidepressant and anti-addictive effects, unlike any currently available treatment. Randomized clinical control studies have confirmed antidepressant and anxiolytic effects of classic psychedelics in humans.

Psilocybin (4-phosphoryloxy-N,N-dimethyltryptamine) has the chemical formula $C_{12}H_{17}N_2O_4P$. It is a tryptamine-based prodrug and is one of the major psychoactive constituents in mushrooms of the psilocybe species. It was first isolated from psilocybe mushrooms by Hofmann in 1957, later synthesized by him in 1958 [Passie et al., Addict Biol., 2002, 7(4):357-364], and was used in psychiatric, psychological research and in psychotherapy during the early to mid-1960s up until its controlled drug scheduling in 1970 in the United States, and up until the 1980s in Germany [Passie 2005; Passie et al., Addict Biol., 2002, 7(4):357-364]. Research into the effects of psilocybin resumed in the mid-1990s, and it is currently the preferred compound for use in studies of the effects of serotonergic hallucinogens [Carter et al., J. Cogn. Neurosci., 2005 17(10):1497-1508; Gouzoulis-Mayfrank et al., Neuropsychopharmacology 1999, 20(6):565-581; Hasler et al, Psychopharmacology (Berl) 2004, 172(2):145-156], likely because it has a shorter duration of action and suffers from less notoriety than LSD. Like other members of this class, psilocybin induces sometimes profound changes in perception, cognition, and emotion, including emotional lability.

In humans as well as other mammals, psilocybin is transformed into the active metabolite psilocin, or the 4-hydroxy-N,N-dimethyltryptamine parent compound. It is likely that psilocin partially or wholly produces most of the subjective and physiological effects of psilocybin in humans and non-human animals. Recently, human psilocybin research confirmed the 5-$HT_{2A}$ activity of psilocybin via the parent psilocin, and provides some support for indirect effects on dopamine through 5-$HT_{2A}$ activity and possible activity at other serotonin receptors. In fact, the most consistent finding for involvement of other receptors in the actions of psychedelics is the 5-$HT_{1A}$ receptor. That is particularly true for tryptamines and LSD, which generally have significant affinity and functional potency at this receptor. It is known that 5-$HT_{1A}$ receptors are colocalized with 5-$HT_{2A}$ receptors on cortical pyramidal cells [Martín-Ruiz et al., J Neurosci. 2001, 21(24):9856-986], where the two receptor types have opposing functional effects [Araneda et al., Neuroscience 1991, 40(2):399-412].

Although the exact role of the 5-$HT_{2A}$ receptor, and other 5-$HT_2$ receptor family members, is not well understood with respect to the amygdala, it is evident that the 5-$HT_{2A}$ receptor plays an important role in emotional responses and is an important target to be considered in the actions of 5-$HT_{2A}$ agonist psychedelics. In fact, a majority of known 5-$HT_{2A}$ agonists produce hallucinogenic effects in humans, and rodents generalize from one 5-$HT_{2A}$ agonist to others, as between psilocybin and LSD [Aghajanian et al., Eur J Pharmacol., 1999, 367(2-3):197-206; Nichols at al., J Neurochem., 2004, 90(3):576-584]. Psilocybin has a stronger affinity for the human 5-$HT_{2A}$ receptor than for the rat receptor and it has a lower K(i) for both 5-$HT_{2A}$ and 5-$HT_{2C}$ receptors than LSD. Moreover, results from a series of drug-discrimination studies in rats found that 5-$HT_{2A}$ antagonists, but not 5-$HT_{1A}$ antagonists, prevented rats from recognizing psilocybin [Winter et al., Pharmacol Biochem Behav., 2007, 87(4):472-480]. Daily doses of LSD and psilocybin reduce 5-$HT_2$ receptor density in rat brain.

Today, psilocybin is one of the most widely used psychedelics in human studies due to its relative safety, moderately long active duration, and good absorption in subjects. There remains strong research and therapeutic potential for psilocybin as recent studies have shown varying degrees of success in neurotic disorders, alcoholism, depression associated with major depressive disorder, treatment resistant depression and in terminally ill cancer patients, obsessive compulsive disorder, addiction, anxiety, post-traumatic stress disorder, and even cluster headaches.

Recent developments include several double-blind placebo-controlled phase 2 studies of psilocybin-assisted psychotherapy in patients with treatment resistant depression, major depressive disorder, and cancer-related psychosocial distress that demonstrate unprecedented positive relief of anxiety and depression. Two recent small pilot studies of psilocybin-assisted psychotherapy also have shown positive benefit in treating both alcohol and nicotine addiction. Recently, blood oxygen level-dependent functional magnetic resonance imaging (fMRI) and magnetoencephalography (MEG) have been employed for in vivo brain imaging in humans after administration of a psychedelic, and results indicate that intravenously administered psilocybin and LSD produce decreases in oscillatory power in areas of the brain's default mode network [Nichols D E. Pharmacol Rev., 2016, 68(2):264-355].

Preliminary studies using positron emission tomography (PET) showed that psilocybin ingestion (15 or 20 mg orally) increased absolute metabolic rate of glucose in frontal, and to a lesser extent in other, cortical regions as well as in striatal and limbic subcortical structures in healthy participants, suggesting that some of the key behavioral effects of psilocybin involve the frontal cortex [Gouzoulis-Mayfrank et al., Neuropsychopharmacology, 1999, 20(6):565-581; Vollenweider et al., Brain Res. Bull. 2001, 56(5):495-507]. Although 5-$HT_{2A}$ agonism is widely recognized as the primary action of classic psychedelic agents, psilocybin has less affinity for a wide range of other pre- and post-synaptic serotonin and dopamine receptors, as well as the serotonin reuptake transporter [Tyls et al., Eur. Neuropsychopharmacol., 2014, 24(3):342-356]. Psilocybin activates 5-$HT_{1A}$ receptors, which may contribute to antidepressant/anti-anxiety effects.

Depression and anxiety are two of the most common psychiatric disorders worldwide. Depression is a multifaceted condition characterized by episodes of mood disturbances alongside other symptoms such as anhedonia, psychomotor complaints, feelings of guilt, attentional deficits, and suicidal tendencies, all of which can range in severity. Similarly, anxiety disorders are a collective of etiologically complex disorders characterized by intense psychosocial distress and other symptoms depending on the subtype. Anxiety associated with life-threatening disease is the only anxiety subtype that has been studied in terms of psychedelic-assisted therapy. Pharmacological and psychosocial interventions are commonly used to manage this type of anxiety, but their efficacy is mixed and limited such that they often fail to provide satisfactory emotional relief. Recent interest into the use of psychedelic-assisted therapy may represent a promising alternative for patients with depression and anxiety that are ineffectively managed by conventional methods.

Generally, the psychedelic treatment model consists of administering the orally-active drug to induce a mystical experience lasting approximately 4-9 h depending on the psychedelic [Halberstadt, Behav Brain Res., 2015, 277:99-120; Nichols, Pharmacol. Rev., 2016, 68(2): 264-355]. This enables participants to work through and integrate difficult feelings and situations, leading to enduring anti-depressant and anxiolytic effects. Classical psychedelics like psilocybin and LSD are being studied as potential candidates. In one study with classical psychedelics for the treatment of depression and anxiety associated with life-threatening disease, it was found that, in a supportive setting, psilocybin and LSD consistently produced significant and sustained anti-depressant and anxiolytic effects.

Psychedelic treatment is generally well-tolerated with few if any persisting adverse effects. Regarding the mechanisms of action of psychedelics, they mediate their main therapeutic effects biochemically via serotonin receptor agonism, and psychologically by generating meaningful psycho-spiritual experiences that contribute to mental flexibility. Given the limited success rates of current treatments for anxiety and mood disorders, and considering the high morbidity associated with these conditions, there is potential for psychedelics to provide symptom relief in patients inadequately managed by conventional methods.

Further emerging clinical research and evidence suggest psychedelic-assisted therapy also shows potential as an alternative treatment for refractory substance use disorders and mental health conditions, and thus may be an important tool in a crisis where existing approaches have yielded limited success [dos Santos et al., Ther Adv Psychopharmacol., 2016, 6(3):193-213]. Similarly encouraging are findings from a recent pilot study of psilocybin-assisted therapy for tobacco use disorder, demonstrating abstinence rates of 80% at six months follow-up and 67% at 12 months follow-up [Johnson et al., https://www.ncbi.nlm.nih.gov/pubmed/27441452, J Drug Alcohol Abuse, 2017, 43(1):55-60; Johnson et al., Psychopharmacol. 2014, 28(11):983-992]; such rates are considerably higher than any documented in the tobacco cessation literature. Notably, mystical-type experiences generated from the psilocybin sessions were significantly correlated with positive treatment outcomes. These results coincide with bourgeoning evidence from recent clinical trials lending support to the effectiveness of psilocybin-assisted therapy for treatment-resistant depression and end-of-life anxiety [Carhart-Harris et al., Neuropsychopharmacology, 2017, 42(11):2105-2113]. Research on the potential benefits of psychedelic-assisted therapy for opioid use disorder (OUD) is beginning to emerge, and accumulating evidence supports a need to advance this line of investigation. Available evidence from earlier randomized clinical trials suggests a promising role for treating OUD: higher rates of abstinence were observed among participants receiving high dose LSD and ketamine-assisted therapies for heroin addiction compared to controls at long-term follow-up. Recently, a large United States population study among 44,000 individuals found that psychedelic use was associated with 40% reduced risk of opioid abuse and 27% reduced risk of opioid dependence in the following year, as defined by DSM-IV criteria [Pisano et al., J Psychopharmacol., 2017, 31(5):606-613]. Similarly, a protective moderating effect of psychedelic use was found on the relationship between prescription opioid use and suicide risk among marginalized women [Argento et al., J Psychopharmacol., 2018, 32(12):1385-1391]. Despite the promise of these preliminary findings with classical psychedelic agents, further research is warranted to determine how psychedelics may ameliorate the opioid crisis response. Meanwhile, growing evidence on the safety and efficacy of psilocybin for the treatment of mental and substance use disorders should help to motivate further clinical investigation into its use as a novel intervention for OUD.

Regular doses of psychedelics also ameliorate sleep disturbances, which are highly prevalent in depressed patients with more than 80% of depressed patients having complaints of poor sleep quality. The sleep symptoms are often unresolved by first-line treatment and are associated with a greater risk of relapse and recurrence. Interestingly, sleep problems often appear before other depression symptoms, and subjective sleep quality worsens before the onset of an episode in recurrent depression. Two other studies assessing electroencephalographic (EEG) brain activity during sleep showed that psychedelics, such as LSD, positively affect sleep patterns. It further was suggested that a single dose of a psychedelic causes a reset of the biological clock underlying sleep/wake cycles and thereby enhances cognitive-emotional processes in depressed people but also improves feelings of well-being and enhances mood in healthy individuals [Kuypers, Medical Hypotheses, 2019, 125:21-24].

In a systematic meta-analysis of clinical trials from 1960-2018 researching the therapeutic use of psychedelic treatment in patients with serious or terminal illnesses and related psychiatric illness, it was found that psychedelic therapy (mostly with LSD) may improve cancer-related depression, anxiety, and fear of death. Four randomized controlled clinical trials were published between 2011 and 2016, mostly with psilocybin treatment, that demonstrated psychedelic-assisted treatment can produce rapid, robust, and sustained improvements in cancer-related psychological and existential distress. [Ross S, Int Rev Psychiatry, 2018, 30(4):317-330]. Many patients facing cancer or other life-threatening illnesses experience significant existential distress related to loss of meaning or purpose in life, which can be associated with hopelessness, demoralization, powerlessness, perceived burdensomeness, and a desire for hastened death. Those features are also often at the core of clinically significant anxiety and depression, and they can substantially diminish quality of life in this patient population. The alleviation of these core features of existential distress should be among the central aims of palliative care. Accordingly, several manualized psychotherapies for cancer-related existential distress have been developed in recent years, with an emphasis on dignity and meaning-making. However, there are currently no pharmacologic interventions for existential distress per se, and available pharmacologic treatments for depressive symptoms in patients with cancer have not demonstrated superiority over placebo. There remains a need for additional effective treatments for those conditions [Rosenbaum et al., Curr. Oncol., 2019, 26(4): 225-226].

Recently, there has been growing interest in a new dosing paradigm for psychedelics, such as psilocybin and LSD, referred to colloquially as microdosing. Under this paradigm, sub-perceptive doses of the serotonergic hallucinogens, approximately 10% or less of the full dose, are taken on a more consistent basis of once each day, every other day, or every three days, or a permutation of the same. Not only is this dosing paradigm more consistent with current standards in pharmacological care, but it may be particularly beneficial for certain conditions, such as Alzheimer's disease, other neurodegenerative diseases, attention deficit disorder, attention deficit hyperactivity disorder, and for certain patient populations such as elderly, juvenile, and patients that are fearful of or opposed to psychedelic assisted therapy. Moreover, this approach may be particularly well suited for managing cognitive deficits and preventing neurodegeneration. For example, subpopulations of low attentive and low motivated rats demonstrate improved performance on the 5-choice serial reaction time and progressive ratio tasks, respectively, following doses of psilocybin below the threshold for eliciting the classical wet dog shake behavioral response associated with hallucinogenic doses (Blumstock et al., WO 2020/157569 A1). Similarly, treatment of patients with hallucinogenic doses of 5-$HT_{2A}$ agonists is associated with increased BDNF and activation of the mTOR pathway, which are thought to promote neuroplasticity and are hypothesized to serve as molecular targets for the treatment of dementias and other neurodegenerative disorders (Ly et al., Cell Rep., 2018, 23(11):3170-3182). Additionally, several groups have demonstrated that low, non-hallucinogenic and non-psychomimetic, doses of 5-$HT_{2A}$ agonists also show similar neuroprotective and increased neuroplasticity effects (neuroplastogens) and reduced neuroinflammation, which could be beneficial in treatment of both neurodegenerative and neurodevelopmental diseases and chronic disorders (Manfredi et al., WO 2020/181194, Flanagan et al., Int. Rev. Psychiatry, 2018, 13:1-13; Nichols et al., 2016, Psychedelics as medicines; an emerging new paradigm). This repeated, lower dose paradigm may extend the utility of these compounds to additional indications and may prove useful for wellness applications.

Psychosis is often referred to as an abnormal state of mind that is characterized by hallucinatory experiences, delusional thinking, and disordered thoughts. Moreover, this state is accompanied by impairments in social cognition, inappropriate emotional expressions, and bizarre behavior. Most often, psychosis develops as part of a psychiatric disorder, of which it represents an integral part of schizophrenia. It corresponds to the most florid phase of the illness. The very first manifestation of psychosis in a patient (i.e., in vivo) is referred to as first-episode psychosis. It reflects a critical transitional stage toward the chronic establishment of the disease, that is presumably mediated by progressive structural and functional abnormalities seen in diagnosed patients. [ACS Chem. Neurosci., 2018, 9, 2241-2251]. Anecdotal evidence suggests that low, non-hallucinogenic doses (microdosing) of psychedelics that are administered regularly can reduce symptoms of schizophrenia and psychosis.

SUMMARY

This Summary is provided to introduce a selection of representative concepts in a simplified form, which representative concepts are further described below in the Detailed Description. This Summary is not intended to identify key features or essential features of the claimed subject matter, nor is it intended to be used to limit the scope of the claimed subject matter.

The present disclosure includes a compound of Formula (I):

Formula (I)

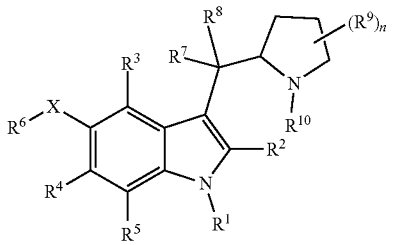

or a pharmaceutically acceptable salt, solvate, and/or prodrug thereof, wherein

X is absent or selected from O, S, S(O), and $SO_2$;

$R^1$ is selected from H, $C_1$-$C_6$alkyl, $C_1$-$C_6$alkyleneP(O)$(OR^{11})_2$, $C_1$-$C_6$alkyleneOP(O)$(OR^{11})_2$, C(O)$R^{11}$, $CO_2R^{11}$, C(O)N$(R^{11})_2$, S(O)$R^{11}$, and $SO_2R^{11}$;

$R^2$ is selected from H, halo, and $C_1$-$C_6$alkyl;

$R^3$, $R^4$, and $R^5$ are independently selected from H, CN, halo, $C_1$-$C_6$alkyl, $C_2$-$C_6$alkenyl, and $C_2$-$C_6$alkynyl;

$R^6$ is selected from H, $C_1$-$C_{10}$alkyl, $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_7$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{13}$, and C(O)$R^{13}$;

$R^7$ and $R^8$ are independently selected from H, halo, and $C_1$-$C_6$alkyl;

each $R^9$ is independently selected from halo, $C_1$-$C_6$alkyl, OH, O$C_1$-$C_6$alkyl, $C_1$-$C_6$alkyleneOH, and $C_1$-$C_6$alkyleneO$C_1$-$C_6$alkyl;

$R^{10}$ is selected from H, $C_1$-$C_6$alkyl, $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{15}$, and C(O)$R^{15}$;

Z is selected from O, C(O), $NR^{16}$C(O), $NR^{16}$C(O)O, C(O)$NR^{16}$, OC(O)$NR^{16}$, and $NR^{16}$;

Z' is selected from O, C(O), $NR^{17}$C(O), $NR^{17}$C(O)O, C(O)$NR^{17}$, OC(O)$NR^{17}$, and $NR^{17}$;

n is an integer selected from 0, 1, 2, 3, and 4;

$R^{11}$, $R^{13}$, $R^{15}$, $R^{16}$, and $R^{17}$ are independently selected from H and $C_1$-$C_6$alkyl;

$R^{12}$ and $R^{14}$ are independently selected from H, $C_1$-$C_6$alkyl, $C_3$-$C_7$cycloalkyl, $C_3$-$C_{10}$heterocycloalkyl, $C_6$-$C_{10}$aryl, and $C_5$-$C_{10}$heteroaryl, the latter four groups being optionally substituted with one to four substituents independently selected from halo, $C_1$-$C_4$alkyl, O$C_1$-$C_4$alkyl, and C(O)$C_1$-$C_4$alkyl, and available hydrogen atoms are optionally replaced with a halogen atom and/or available atoms are optionally replaced with an alternate isotope thereof, provided when X is O, $R^1$, $R^2$, $R^3$, $R^4$, $R^5$, $R^7$, and $R^8$ are H or D, n is 0, and $R^6$ is H, $CH_3$, or $CD_3$, then $R^{10}$ is not H, $CH_3$, or $CD_3$, provided when X is O, $R^1$, $R^2$, $R^3$, $R^4$, $R^5$, $R^7$, and $R^8$ are H or D and n is 0, and $R^6$ is $CH_3$ or $CHF_2$, then $R^{10}$ is not H, $CH_3$, or $CD_3$, and provided when X is absent and $R^6$ is H, then either n is not 0 or $R^{10}$ is not H or $C_1$-$C_6$alkyl.

In some embodiments, provided (1) when X is absent, then $R^6$ is not H, D, or halogen, and (2) when X is O, S, S(O), or $SO_2$, then each $R^9$ is not independently selected from H, D, halogen, $C_1$-$C_6$alkyl, $C_1$-$C_6$deuteroalkyl, $C_1$-$C_6$haloalkyl, and $C_1$-$C_6$deuterohaloalkyl and/or $R_{10}$ is not selected from H, D, halogen, $C_1$-$C_6$alkyl, $C_1$-$C_6$deuteroalkyl, $C_1$-$C_6$haloalkyl, and $C_1$-$C_6$deuterohaloalkyl.

In some embodiments, provided when X is absent, then $R^6$ is not H, D, or halogen.

In some embodiments, including when X is O, S, S(O), or $SO_2$, each $R^9$ is not independently selected from H, D, halogen, $C_1$-$C_6$alkyl, $C_1$-$C_6$deuteroalkyl, $C_1$-$C_6$haloalkyl, and $C_1$-$C_6$deuterohaloalkyl.

In some embodiments, including when X is O, S, S(O), or $SO_2$, $R_{10}$ is not selected from H, D, halogen, $C_1$-$C_6$alkyl, $C_1$-$C_6$deuteroalkyl, $C_1$-$C_6$haloalkyl, and $C_1$-$C_6$deuterohaloalkyl.

In some embodiments, provided (1) when X is absent, then $R^6$ is not H, D, or halogen, and (2) when X is O, S, S(O), or $SO_2$, then each $R^9$ is not independently selected from H, D, halogen, $C_1$-$C_6$alkyl, $C_1$-$C_6$deuteroalkyl, $C_1$-$C_6$haloalkyl, and $C_1$-$C_6$deuterohaloalkyl.

In some embodiments, provided (1) when X is absent, then $R^6$ is not H, D, or halogen, and (2) when X is O, S, S(O), or $SO_2$, then $R_{10}$ is not selected from H, D, halogen, $C_1$-$C_6$alkyl, $C_1$-$C_6$deuteroalkyl, $C_1$-$C_6$haloalkyl, and $C_1$-$C_6$deuterohaloalkyl.

In a further embodiment, the compounds of the disclosure are used as medicaments. Accordingly, the disclosure also includes a compound of the disclosure for use as a medicament.

The present disclosure includes a method for activating a serotonin receptor in a cell, either in a biological sample or in a patient, comprising administering an effective amount of one or more compounds of the disclosure to the cell.

The present disclosure also includes a method of treating psychosis or psychotic symptoms comprising administering a therapeutically effective amount of one or more compounds of the disclosure to a subject in need thereof.

The present disclosure also includes a method of treating a mental illness comprising administering a therapeutically effective amount of one or more compounds of the disclosure to a subject in need thereof.

The disclosure additionally provides a process for the preparation of compounds of the disclosure. General and specific processes are discussed in more detail below and set forth in the examples below.

This disclosure further provides intermediates for the compounds disclosed herein, methods of making the intermediates, and methods for making the compounds from the intermediates.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments but should be given the broadest interpretation consistent with the description as a whole.

BRIEF DESCRIPTION OF THE DRAWINGS

The embodiments of the disclosure will be described in greater detail with reference to the attached drawings, which are incorporated herein by reference and in which.

DETAILED DESCRIPTION OF EXEMPLARY EMBODIMENTS

I. Definitions

Figure 1:
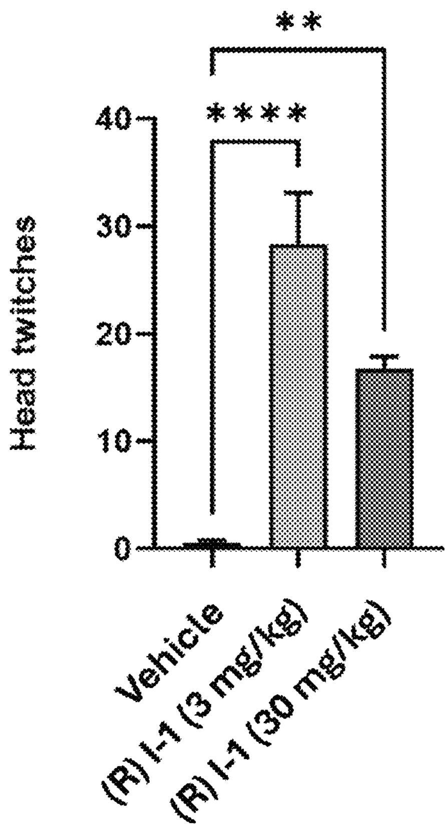
FIG. 1 is a bar graph showing the effect of various doses of exemplary compound of Formula I-1, (R) I-1, on head-twitch response (HTR) in male C57BL6 mice. The mice were treated with exemplary compound (R) I-1 (3 mg/kg, 30 mg/kg, SC) by SC route, and the total number of head twitches were recorded over a 20 min period. Induction of head twitches elicited by 5-$HT_{2A}$ receptor agonists is believed to represent a behavioural proxy of their psychedelic effects. Data presented as mean±S.E.M. Analysed using one-way ANOVA with Fishers post-hoc LSD. *p<0.05, **p<0.01, *p<0.0001, #Acute effects of test compounds (20-minute post SC. dosing)
Figure 2:
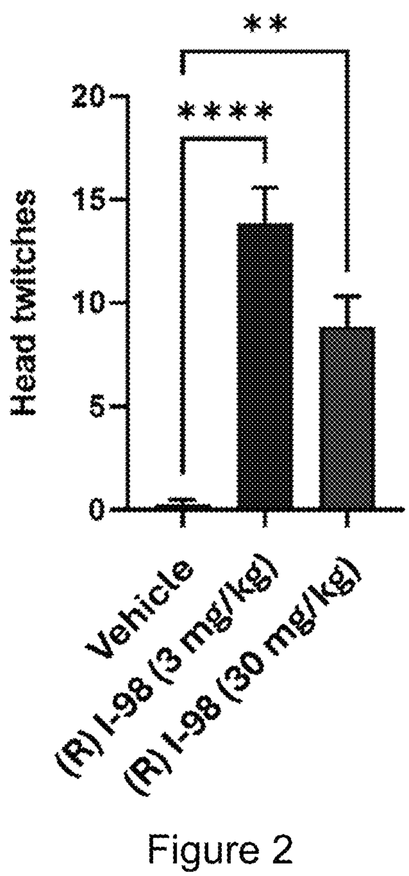
FIGS. 2 to 5 are bar graphs showing the effect of various doses of exemplary compounds of Formula (I), specifically (R) I-98, (R) I-244, (R) I-245, and cis (R) I-248, respectively, on head-twitch response (HTR) in male C57BL6 mice. The mice were treated with exemplary compound (R) I-98, (R) I-244, (R) I-245, or cis (R) I-248 (3 mg/kg, 30 mg/kg, SC) by SC route (N=6 mice/dose), and the total number of head twitches were recorded over a 1 h period. Induction of head twitches elicited by 5-$HT_{2A}$ receptor agonists is believed to represent a behavioral proxy of their psychedelic effects. Data presented as mean±S.E.M. Analysed using one-way ANOVA with Fishers post-hoc LSD. *p<0.05, **p<0.01, *p<0.0001. #Acute effects of test compounds (20-minute post SC. dosing).
Figure 3:
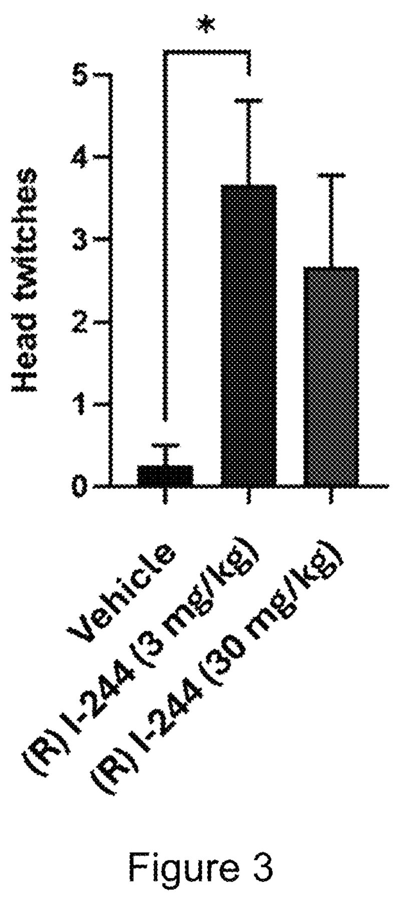
Figure 4:
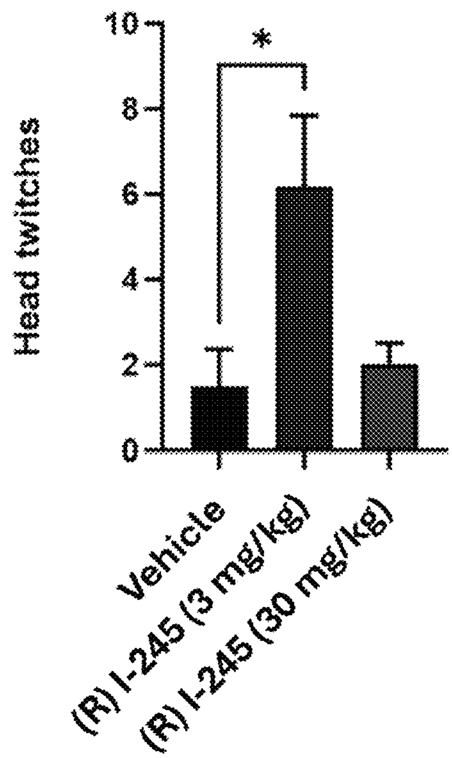
Figure 5:
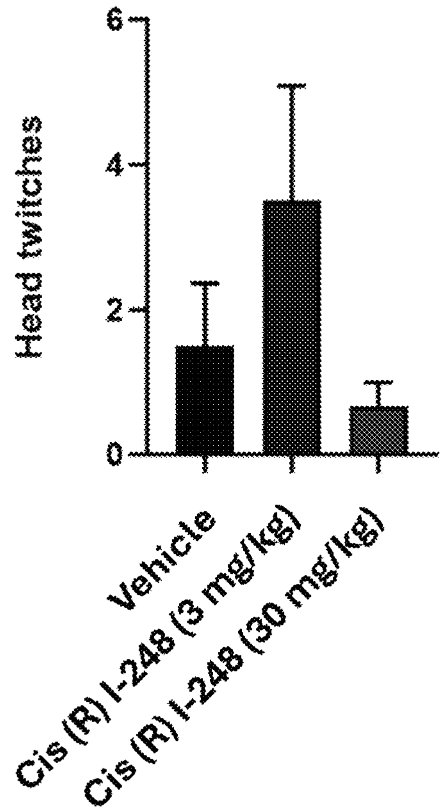

Unless otherwise indicated, the definitions and embodiments described in this and other sections are intended to be applicable to all embodiments and aspects of the present disclosure herein described for which they are suitable as would be understood by a person skilled in the art.

The term "compound(s) of the disclosure" or "compound (s) of the present disclosure" and the like, as used herein, refers to a compound Formula (I) (including Formula (I-A), (I-B), (I-C), (I-D), (I-E), (I-F), (I-G), (I-H), (I-I), (I-J), (I-K), (I-L), and (I-M) that fall within the scope of Formula (I)) and includes pharmaceutically acceptable salts, solvates, and/or prodrugs thereof.

The term "composition(s) of the disclosure" or "composition(s) of the present disclosure" and the like, as used herein, refers to a composition, such a pharmaceutical composition, comprising one or more compounds of the disclosure.

The term "and/or," as used herein, means that the listed items are present, or used, individually or in combination. In effect, this term means that "at least one of" or "one or more" of the listed items is used or present. The term "and/or" with respect to pharmaceutically acceptable salts and/or solvates thereof means that the compounds of the disclosure exist as individual salts and solvates, as well as a combination of, for example, a salt of a solvate of a compound of the disclosure. As used herein, the term "and/or" means either or both (or any combination or all of the terms or expressed referred to), e.g., "A, B, and/or C" encompasses A alone, B alone, C alone, A and B, A and C, B and C, and A, B, and C.

As used in the present disclosure, the singular forms "a," "an," and "the" include plural references unless the content clearly dictates otherwise. For example, an embodiment including "a compound" should be understood to present certain aspects with one compound, or two or more additional compounds. It will be understood by those with skill in the art that if a specific number of an introduced claim element is intended, such intent will be explicitly recited in the claim, and in the absence of such recitation no such limitation is present. For a non-limiting example, as an aid to understanding, the appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to embodiments containing only one such element, even when the same claim includes the introductory phrase "one or more" or "at least one" and indefinite articles such as "a" or "an"; the same holds true for the use in the claims of definite articles.

As used in this disclosure and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives, as used herein, are intended to be closed terms that specify the presence of the stated features, elements, components, groups, integers and/or steps and also exclude the presence of other unstated features, elements, components, groups, integers, and/or steps.

The term "consisting essentially of," as used herein, is intended to specify the presence of the stated features, elements, components, groups, integers and/or steps as well as those that do not materially affect the basic and novel characteristic(s) of these features, elements, components, groups, integers and/or steps.

In embodiments comprising an "additional" or "second" component, such as an additional or second compound, the second component, as used herein, is chemically different from the other components or first component. A "third" component is different from the other, first and second components and further enumerated or "additional" components are similarly different. "First," "second," "third," etc. in this context is not meant to imply an order or sequence, other than the order in which the terms appear in the claims, unless the claims clearly indicate otherwise.

The term "suitable," as used herein, means that the selection of the particular compound or conditions would depend on the specific synthetic manipulation to be performed, the identity of the molecule(s) to be transformed and/or the specific use for the compound, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The terms “about,” “substantially,” and “approximately,” as used herein, mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The present description refers to a number of chemical terms and abbreviations used by those skilled in the art. Nevertheless, definitions of selected terms are provided for clarity and consistency.

The term “alkyl,” as used herein, whether it is used alone or as part of another group, means straight or branched chain, saturated alkyl groups. The number of carbon atoms that are possible in the referenced alkyl group are indicated by the prefix “$C_{n1}$-$C_{n2}$.” Thus, for example, the term “$C_1$-$C_6$alkyl” (or “$C_{1-6}$alkyl”) means an alkyl group having 1, 2, 3, 4, 5, or 6 carbon atoms and includes, for example, any of the hexyl alkyl and pentyl alkyl isomers as well as n-, iso-, sec- and tert-butyl, n- and iso-propyl, ethyl, and methyl. As another example, “$C_1$-$C_4$alkyl” refers to n-, iso-, sec- and tert-butyl, n- and isopropyl, ethyl, and methyl.

The term “alkenyl,” as used herein, whether it is used alone or as part of another group, means straight or branched chain, unsaturated alkyl groups containing at least one double bond. The number of carbon atoms that are possible in the referenced alkenyl group are indicated by the prefix “$C_{n1}$-$C_{n2}$.” For example, the term $C_2$-$C_6$alkenyl (or $C_{2-6}$alkenyl) means an alkenyl group having 2, 3, 4, 5, or 6 carbon atoms.

The term “alkynyl,” as used herein, whether it is used alone or as part of another group, means straight or branched chain, unsaturated alkyl groups containing at least one triple bond. The number of carbon atoms that are possible in the referenced alkynyl group are indicated by the prefix “$C_{n1}$-$C_{n2}$.” For example, the term $C_2$-$C_6$alkynyl (or $C_{2-6}$alkynyl) means an alkynyl group having 2, 3, 4, 5, or 6 carbon atoms.

The term “cycloalkyl,” as used herein, whether it is used alone or as part of another group, means a saturated carbocyclic group containing one or more rings. The number of carbon atoms that are possible in the referenced cycloalkyl group are indicated by the numerical prefix “$C_{n1}$-$C_{n2}$.” For example, the term $C_{3-7}$cycloalkyl (or $C_{3-7}$cycloalkyl) means a cycloalkyl group having 3, 4, 5, 6, or 7 carbon atoms.

The term “heterocycloalkyl,” as used herein, whether it is used alone or as part of another group, refers to cyclic groups containing at least one non-aromatic ring in which one or more of the atoms are a heteromoiety selected from O, S, and N, including oxidized or substituted versions thereof (e.g., S(O) and $SO_2$), and the remaining atoms are C. Heterocycloalkyl groups are either saturated or unsaturated (i.e., contain one or more double bonds) and/or optionally comprise one or more C═O groups (i.e., one or more carbon atoms in the ring is oxidized to C═O). When a heterocycloalkyl group contains the prefix $C_{n1}$-$C_{n2}$ this prefix indicates the number of carbon atoms in the corresponding carbocyclic group, in which one or more, suitably 1 to 5, of the ring atoms is replaced with a heteromoiety as selected from O, S, and N including oxidized or substituted versions thereof, and the remaining atoms are C. Heterocycloalkyl groups may also be preceded by “n1- to n2-membered” which refers to the total number of atoms in the group. Heterocycloalkyl groups are optionally benzofused.

The term “aryl,” as used herein, whether it is used alone or as part of another group, refers to carbocyclic groups containing at least one aromatic ring.

The term “heteroaryl,” as used herein, whether it is used alone or as part of another group, refers to cyclic groups containing at least one heteroaromatic ring in which one or more of the atoms are a heteromoiety selected from O, S, and N, including oxidized or substituted versions thereof (e.g., S(O) and $SO_2$), and the remaining atoms are C. When a heteroaryl group contains the prefix $C_{n1-n2}$ this prefix indicates the number of carbon atoms in the corresponding carbocyclic group, in which one or more, suitably 1 to 5, of the ring atoms is replaced with a heteroatom as defined above. Heteroaryl groups may also be preceded by “n1- to n2-membered” which refers to the total number of atoms in the group. Heteroaryl groups are optionally benzofused.

All cyclic groups, including aryl, heteroaryl, heterocycloalkyl, and cycloalkyl groups, contain one or more than one ring (i.e., are polycyclic). When a cyclic group contains more than one ring, the rings may be fused, bridged, spirofused, or linked by a bond.

The term “benzofused,” as used herein, refers to a polycyclic group in which a benzene ring is fused with another ring.

A first ring being “fused” with a second ring means the first ring and the second ring share two adjacent atoms there between.

A first ring being “bridged” with a second ring means the first ring and the second ring share two non-adjacent atoms there between.

A first ring being “spirofused” with a second ring means the first ring and the second ring share one atom there between.

The term “halogen” (or “halo”) whether it is used alone or as part of another group, refers to a halogen atom and includes fluoro, chloro, bromo, and iodo.

The term “haloalkyl,” as used herein, refers to an alkyl group as defined above in which one or more of the available hydrogen atoms have been independently replaced with a halogen. Thus, for example, “$C_{1-6}$haloalkyl” (or “$C_1$-$C_6$haloalkyl”) refers to a $C_1$ to $C_6$ linear or branched alkyl group as defined above with one or more halogen substituents.

As used herein, the term “haloalkenyl” refers to an alkenyl group as defined above in which one or more of the available hydrogen atoms have been independently replaced with a halogen. Thus, for example, “$C_{2-6}$haloalkenyl” (or “$C_2$-$C_6$haloalkenyl”) refers to a $C_2$ to $C_6$ linear or branched alkenyl group as defined above with one or more halogen substituents.

As used herein, the term “haloalkynyl” refers to an alkynyl group as defined above in which one or more of the available hydrogen atoms have been independently replaced with a halogen. Thus, for example, “$C_{2-6}$haloalkynyl” (or “$C_2$-$C_6$haloalkynyl”) refers to a $C_2$ to $C_6$ linear or branched alkynyl group as defined above with one or more halogen substituents.

The term “deuteroalkyl,” as used herein, refers to an alkyl group as defined above in which one or more of the available hydrogen atoms have been independently replaced with a deuterium. Thus, for example, “$C_{1-6}$deuteroalkyl” (or “$C_1$-$C_6$deuteroalkyl”) refers to a $C_1$ to $C_6$ linear or branched alkyl group as defined above with one or more deuterium substituents.

The term “deuteroalkenyl,” as used herein, refers to an alkenyl group as defined above in which one or more of the available hydrogen atoms have been independently replaced with a deuterium. Thus, for example, "$C_{2-6}$deuteroalkenyl" (or "$C_2$-$C_6$deuteroalkenyl") refers to a $C_2$ to $C_6$ linear or branched alkenyl group as defined above with one or more deuterium substituents.

The term "deuteroalkynyl," as used herein, refers to an alkynyl group as defined above in which one or more of the available hydrogen atoms have been independently replaced with a deuterium. Thus, for example, "$C_{2-6}$deuteroalkynyl" (or "$C_2$-$C_6$deuteroalkynyl") refers to a $C_2$ to $C_6$ linear or branched alkynyl group as defined above with one or more deuterium substituents.

The term "fluoroalkyl," as used herein, refers to an alkyl group as defined above in which one or more of the available hydrogen atoms have been independently replaced with a fluorine. Thus, for example, "$C_{1-6}$fluoroalkyl" (or "$C_1$-$C_6$fluoroalkyl") refers to a $C_1$ to $C_6$ linear or branched alkyl group as defined above with one or more fluorine substituents.

The term "fluoroalkenyl," as used herein, refers to an alkenyl group as defined above in which one or more of the available hydrogen atoms have been independently replaced with a fluorine. Thus, for example, "$C_{2-6}$fluoroalkenyl" (or "$C_2$-$C_6$fluoroalkenyl") refers to a $C_2$ to $C_6$ linear or branched alkenyl group as defined above with one or more fluorine substituents.

The term "fluoroalkynyl," as used herein, refers to an alkynyl group as defined above in which one or more of the available hydrogen atoms have been independently replaced with a fluorine. Thus, for example, "$C_{2-6}$fluoroalkynyl" (or "$C_2$-$C_6$fluoroalkynyl") refers to a $C_2$ to $C_6$ linear or branched alkynyl group as defined above with one or more fluorine substituents.

The term "deuterohaloalkyl," as used herein, refers to an alkyl group as defined above in which one or more of the available hydrogen atoms have been independently replaced with a deuterium and one or more of the available hydrogen atoms have been independently replaced with a halogen. Thus, for example, "$C_{1-6}$deuterohaloalkyl" (or "$C_1$-$C_6$deuterohaloalkyl") refers to a $C_1$ to $C_6$ linear or branched alkyl group as defined above with one or more deuterium substituents and one or more halogen substituents.

The term "deuterohaloalkenyl," as used herein, refers to an alkenyl group as defined above in which one or more of the available hydrogen atoms have been independently replaced with a deuterium and one or more of the available hydrogen atoms have been independently replaced with a halogen. Thus, for example, "$C_{2-6}$deuterohaloalkenyl" (or "$C_2$-$C_6$deuterohaloalkenyl") refers to a $C_2$ to $C_6$ linear or branched alkenyl group as defined above with one or more deuterium substituents and one or more halogen substituents.

The term "deuterohaloalkynyl," as used herein, refers to an alkynyl group as defined above in which one or more of the available hydrogen atoms have been independently replaced with a deuterium and one or more of the available hydrogen atoms have been independently replaced with a halogen. Thus, for example, "$C_{2-6}$deuterohaloalkynyl" (or "$C_2$-$C_6$deuterohaloalkynyl") refers to a $C_2$ to $C_6$ linear or branched alkynyl group as defined above with one or more deuterium substituents and one or more halogen substituents.

The term "deuterofluoroalkyl," as used herein, refers to an alkyl group as defined above in which one or more of the available hydrogen atoms have been independently replaced with a deuterium and one or more of the available hydrogen atoms have been independently replaced with a fluorine. Thus, for example, "$C_{1-6}$deuterofluoroalkyl" (or "$C_1$-$C_6$deuterofluoroalkyl") refers to a $C_1$ to $C_6$ linear or branched alkyl group as defined above with one or more deuterium substituents and one or more fluorine substituents.

The term "deuterofluoroalkenyl," as used herein, refers to an alkenyl group as defined above in which one or more of the available hydrogen atoms have been independently replaced with a deuterium and one or more of the available hydrogen atoms have been independently replaced with a fluorine. Thus, for example, "$C_{2-6}$deuterofluoroalkenyl" (or "$C_2$-$C_6$deuterofluoroalkenyl") refers to a $C_2$ to $C_6$ linear or branched alkenyl group as defined above with one or more deuterium substituents and one or more fluorine substituents.

The term "deuterofluoroalkynyl," as used herein, refers to an alkynyl group as defined above in which one or more of the available hydrogen atoms have been independently replaced with a deuterium and one or more of the available hydrogen atoms have been independently replaced with a fluorine. Thus, for example, "$C_{2-6}$deuterofluoroalkynyl" (or "$C_2$-$C_6$deuterofluoroalkynyl") refers to a $C_2$ to $C_6$ linear or branched alkynyl group as defined above with one or more deuterium substituents and one or more fluorine substituents.

The suffix "ene" at the end of a group (for example "alkylene" or "alkenylene") means that the group is bivalent, that is that it is bonded to two variables each on a different end of or location on the group.

The term "optionally substituted," as used herein, means that the subject group is unsubstituted or substituted and the terms "optionally substituted" and "unsubstituted or substituted" are used interchangeably herein. As used herein, when referring to more than one item or "each" item, "optionally substituted" and "unsubstituted or substituted" means that the items are independently unsubstituted or substituted with respect to one another, e.g., for item A and item B, both may be substituted, both may be unsubstituted, or one may be substituted and the other unsubstituted. Additionally, as used herein, the term "optionally substituted" when referring to more than one item means that if more than one of the items is substituted, the substitutions may be independent from one another, e.g., for item A and item B that are both substituted, item A may have a first substitution and item B may have a second substitution that is the same or different from the first substitution of item A.

As used herein, the term "one or more" item includes a single item selected from the list as well as two or more items (e.g., mixtures) selected from the list.

The term "substituted," as used herein, means, unless otherwise indicated, that the referenced group is substituted with one or more substituents independently selected from halo, $C_1$-$C_4$alkyl, $OC_1$-$C_4$alkyl, $C_1$-$C_4$haloalkyl, $OC_1$-$C_4$haloalkyl, CN, OH, $NH_2$, $NH(C_1$-$C_4$alkyl), $N(C_1$-$C_4$alkyl)($C_1$-$C_4$alkyl), $SC_1$-$C_4$alkyl, $S(O)C_1$-$C_4$alkyl, $SO_2C_1$-$C_4$alkyl, $CO_2H$, $CO_2C_1$-$C_4$alkyl, $C(O)NH_2$, $C(O)NHC_1$-$C_4$alkyl, $C(O)N(C_1$-$C_4$alkyl)($C_1$-$C_4$alkyl), $C_3$-$C_6$cycloalkyl, and a 3- to 6-membered heterocyclic ring including 1 to 2 ring heteromoieties selected from O, S, S(O), $SO_2$, N, NH, and $NC_1$-$C_4$alkyl.

When a group is substituted with more than one substituent selected from a list of substituents, each of the substituents is independently selected from the listed group of substituents.

The term "available," as in "available hydrogen atoms" or "available atoms" refers to atoms that would be known to a person skilled in the art to be capable of replacement by a substituent.

The term "alternate isotope thereof," as used herein, refers to an isotope of an element that is other than the isotope that is most abundant in nature.

The term "all available atoms are optionally replaced with alternate isotope thereof" or "available atoms are optionally replaced with alternative isotope thereof," as used herein, means that available atoms, optionally each and every available atom, are optionally and independently replaced with an isotope of that atom having the same atomic number, but an atomic mass or mass number different from the atomic mass or mass number predominantly found in nature. When a compound comprises an atom that has been replaced with an alternate isotope thereof, the compound comprises that alternate isotope in greater amounts than would otherwise be present in the compound if said replacement had not taken place.

The term "all available hydrogen atoms are optionally replaced with a halogen atom" or "available hydrogen atoms are optionally replaced with a halogen atom," as used herein, means that available hydrogen atoms, optionally each and every available hydrogen atom, are optionally and independently replaced with a halogen atom.

The term "all available hydrogen atoms are optionally replaced with a fluorine atom and/or a chlorine atom" or "available hydrogen atoms are optionally replaced with a fluorine atoms and/or a chlorine atom," as used herein, means that available hydrogen atoms, optionally each and every available hydrogen atom, are optionally and independently replaced with a fluorine atom or a chlorine atom.

The term "pharmaceutically acceptable" means compatible with the treatment of subjects.

The term "pharmaceutically acceptable carrier" means a non-toxic solvent, dispersant, excipient, adjuvant, or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with, the treatment of subjects.

An acid addition salt suitable for, or compatible with, the treatment of subjects is any non-toxic organic or inorganic acid addition salt of any basic compound.

A base addition salt suitable for, or compatible with, the treatment of subjects is any non-toxic organic or inorganic base addition salt of any acidic compound.

The term "solvate," as used herein, means a compound, or a salt or prodrug of a compound, wherein molecules of a suitable solvent are incorporated in the crystal lattice. A suitable solvent is physiologically tolerable at the dosage administered.

The term "prodrug," as used herein, means a compound, or salt of a compound, that, after administration, is converted into an active drug.

The term "protecting group" or "PG" and the like, as used herein, refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry," McOmie, J. F. W. Ed., Plenum Press, 1973, in Greene, T. W. and Wuts, P. G. M., "Protective Groups in Organic Synthesis," John Wiley & Sons, 3$^{rd}$ Edition, 1999 and in Kocienski, P. Protecting Groups, 3rd Edition, 2003, Georg Thieme Verlag (The Americas).

The term "subject," as used herein, includes all members of the animal kingdom including mammals, and suitably refers to humans. Thus, the methods of the present disclosure are applicable to both human therapy and veterinary applications.

The term "treating" or "treatment," as used herein, and as is well understood in the art, means an approach for obtaining beneficial or desired results, including clinical results. Beneficial or desired clinical results include, but are not limited to, alleviation or amelioration of one or more symptoms or conditions, diminishment of extent of disease, stabilized (i.e., not worsening) state of disease, preventing spread of disease, delay, or slowing of disease progression, amelioration or palliation of the disease state, diminishment of the reoccurrence of disease and remission (whether partial or total), whether detectable or undetectable. "Treating" and "treatment" can also mean prolonging survival as compared to expected survival if not receiving treatment. "Treating" and "treatment," as used herein, also include prophylactic treatment. Treatment methods comprise administering to a subject a therapeutically effective amount of one or more of the compounds of the disclosure and optionally consist of a single administration, or alternatively comprise a series of administrations.

As used herein, the term "effective amount" or "therapeutically effective amount" means an amount of one or more compounds of the disclosure that is effective, at dosages and for periods of time necessary to achieve the desired result. For example, in the context of treating a disease, disorder, or condition mediated or treated by agonism or activation of serotonergic receptors and downstream second messengers, an effective amount is an amount that, for example, increases said activation compared to the activation without administration of the one or more compounds.

"Palliating" a disease, disorder, or condition means that the extent and/or undesirable clinical manifestations of a disease, disorder, or condition are lessened and/or time course of the progression is slowed or lengthened, as compared to not treating the disorder.

The term "administered," as used herein, means administration of a therapeutically effective amount of one or more compounds or compositions of the disclosure to a cell, tissue, organ, or subject.

The term "prevention" or "prophylaxis," or synonym thereto, as used herein, refers to a reduction in the risk or probability of a patient becoming afflicted with a disease, disorder, or condition or manifesting a symptom associated with a disease, disorder, or condition.

The term "disease, disorder, or condition," as used herein, refers to a disease, disorder, or condition treated or treatable by activation and/or binding of any serotonin receptor ($5HT_1$ to $5HT_7$) and their sub-receptors and subtypes (e.g., 5-$HT_{1A}$, 5-$HT_{2A}$, 5-$HT_{2B}$, 5-$HT_{2C}$) and particularly using one or more compounds of the disclosure herein described.

The term "treating a disease, disorder, or condition by activation of a serotonin receptor," as used herein, means that the disease, disorder, or condition to be treated is affected by, modulated by and/or has some biological basis, either direct or indirect, that includes serotonergic activity, in particular increases in serotonergic activity. These diseases respond favorably when serotonergic activity associated with the disease, disorder, or condition is agonized by one or more of the compounds or compositions of the disclosure.

The term "activation," as used herein, includes agonism, partial agonist, and positive allosteric modulation of a serotonin receptor.

The term "5-$HT_{2A}$," as used herein, means the 5-$HT_{2A}$ receptor subtype of the 5-HT2 serotonin receptor.

The terms "5-$HT_{1A}$," as used herein, means the 5-$HT_{1A}$ receptor subtypes of the 5-HT1 serotonin receptor.

The term "5-$HT_{2B}$," as used herein, means the 5-$HT_{2B}$ receptor subtype of the 5-HT2 serotonin receptor.

The term "5-$HT_{2C}$," as used herein, means the 5-$HT_{2C}$ receptor subtype of the 5-HT2 serotonin receptor.

The term "therapeutic agent," as used herein, refers to any drug or active agent that has a pharmacological effect when administered to a subject.

II. Compounds

The present disclosure includes a compound of Formula (I):

Formula (I)

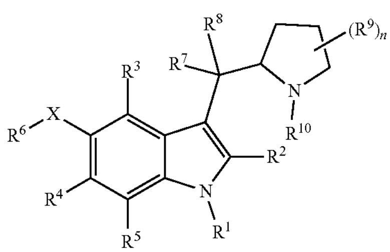

or a pharmaceutically acceptable salt, solvate, and/or prodrug thereof, wherein:

X is absent or selected from O, S, S(O), and $SO_2$;

$R^1$ is selected from H, $C_1$-$C_6$alkyl, $C_1$-$C_6$alkyleneP(O)$(OR^{11})_2$, $C_1$-$C_6$alkyleneOP(O)$(OR^{11})_2$, C(O)$R^{11}$, $CO_2R^{11}$, C(O)N$(R^{11})_2$, S(O)$R^{11}$, and $SO_2R^{11}$;

$R^2$ is selected from H, halo, and $C_1$-$C_6$alkyl;

$R^3$, $R^4$, and $R^5$ are independently selected from H, CN, halo, $C_1$-$C_6$alkyl, $C_2$-$C_6$alkenyl, and $C_2$-$C_6$alkynyl;

$R^6$ is selected from H, $C_1$-$C_{10}$alkyl, $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_7$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{13}$, and C(O)$R^{13}$;

$R^7$ and $R^8$ are independently selected from H, halo, and $C_1$-$C_6$alkyl;

each $R^9$ is independently selected from halo, $C_1$-$C_6$alkyl, OH, O$C_1$-$C_6$alkyl, $C_1$-$C_6$alkyleneOH, and $C_1$-$C_6$alkyleneO$C_1$-$C_6$alkyl;

$R^{10}$ is selected from H, $C_1$-$C_6$alkyl, $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{15}$, and C(O)$R^{15}$;

Z is selected from O, C(O), $NR^{16}$C(O), $NR^{16}$C(O)O, C(O)$NR^{16}$, OC(O)$NR^{16}$, and $NR^{16}$;

Z' is selected from O, C(O), $NR^{17}$C(O), $NR^{17}$C(O)O, C(O)$NR^{17}$, OC(O)$NR^{17}$, and $NR^{17}$;

n is an integer selected from 0, 1, 2, 3, and 4;

$R^{11}$, $R^{13}$, $R^{15}$, $R^{16}$, and $R^{17}$ are independently selected from H and $C_1$-$C_6$alkyl;

$R^{12}$ and $R^{14}$ are independently selected from H, $C_1$-$C_6$alkyl, $C_3$-$C_7$cycloalkyl, $C_3$-$C_{10}$heterocycloalkyl, $C_6$-$C_{10}$aryl, and $C_5$-$C_{10}$heteroaryl, the latter four groups being optionally substituted with one to four substituents independently selected from halo, $C_1$-$C_4$alkyl, O$C_1$-$C_4$alkyl, and C(O)$C_1$-$C_4$alkyl, and available hydrogen atoms are optionally replaced with a halogen atom and/or available atoms are optionally replaced with an alternate isotope thereof, provided when X is O, $R^1$, $R^2$, $R^3$, $R^4$, $R^5$, $R^7$, and $R^8$ are H or D, n is 0, and $R^6$ is H, $CH_3$, or $CD_3$, then $R^{10}$ is not H, $CH_3$, or $CD_3$;

provided when X is O, $R^1$, $R^2$, $R^3$, $R^4$, $R^5$, $R^7$, and $R^8$ are H or D and n is 0, and $R^6$ is $CH_3$ or $CHF_2$, then $R^{10}$ is not H, $CH_3$, or $CD_3$; and provided when X is absent and $R^6$ is H, then either n is not 0 or $R^{10}$ is not H or $C_1$-$C_6$alkyl.

According to one or more embodiments, the present disclosure includes a compound of Formula (I) as defined above or a pharmaceutically acceptable salt, solvate, and/or prodrug thereof, wherein:

X is selected from S, S(O), and $SO_2$;

$R^1$ is selected from H, $C_1$-$C_6$alkyl, $C_1$-$C_6$alkyleneP(O)$(OR^{11})_2$, $C_1$-$C_6$alkyleneOP(O)$(OR^{11})_2$, C(O)$R^{11}$, $CO_2R^{11}$, C(O)N$(R^{11})_2$, S(O)$R^{11}$, and $SO_2R^{11}$;

$R^2$ is selected from H, halo, and $C_1$-$C_6$alkyl;

$R^3$, $R^4$, and $R^5$ are independently selected from H, CN, halo, $C_1$-$C_6$alkyl, $C_2$-$C_6$alkenyl, and $C_2$-$C_6$alkynyl;

$R^6$ is selected from H, $C_1$-$C_{10}$alkyl, $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_7$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{13}$, and C(O)$R^{13}$;

$R^7$ and $R^8$ are independently selected from H, halo, and $C_1$-$C_6$alkyl;

each $R^9$ is independently selected from halo, $C_1$-$C_6$alkyl, OH, O$C_1$-$C_6$alkyl, $C_1$-$C_6$alkyleneOH, and $C_1$-$C_6$alkyleneO$C_1$-$C_6$alkyl;

$R^{10}$ is selected from H, $C_1$-$C_6$alkyl, $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{15}$, and C(O)$R^{15}$;

Z is selected from O, C(O), $NR^{16}$C(O), $NR^{16}$C(O)O, C(O)$NR^{16}$, OC(O)$NR^{16}$, and $NR^{16}$;

Z' is selected from O, C(O), $NR^{17}$C(O), $NR^{17}$C(O)O, C(O)$NR^{17}$, OC(O)$NR^{17}$, and $NR^{17}$;

n is an integer selected from 0, 1, 2, 3, and 4;

$R^{11}$, $R^{13}$, $R^{15}$, $R^{16}$, and $R^{17}$ are independently selected from H and $C_1$-$C_6$alkyl;

$R^{12}$ and $R^{14}$ are independently selected from H, $C_1$-$C_6$alkyl, $C_3$-$C_7$cycloalkyl, $C_3$-$C_{10}$heterocycloalkyl, $C_6$-$C_{10}$aryl, and $C_5$-$C_{10}$heteroaryl, the latter four groups being optionally substituted with one to four substituents independently selected from halo, $C_1$-$C_4$alkyl, $OC_1$-$C_4$alkyl, and $C(O)C_1$-$C_4$alkyl, and available hydrogen atoms are optionally replaced with a halogen atom and/or available atoms are optionally replaced with an alternate isotope thereof.

According to one or more embodiments, the present disclosure includes a compound of Formula (I) as defined above or a pharmaceutically acceptable salt, solvate, and/or prodrug thereof, wherein:

X is absent or O;

$R^1$ is selected from H, $C_1$-$C_6$alkyl, $C_1$-$C_6$alkyleneP(O)$(OR^{11})_2$, $C_1$-$C_6$alkyleneOP(O)$(OR^{11})_2$, $C(O)R^{11}$, $CO_2R^{11}$, $C(O)N(R^{11})_2$, $S(O)R^{11}$, and $SO_2R^{11}$;

$R^2$ is selected from H, halo, and $C_1$-$C_6$alkyl;

$R^3$, $R^4$, and $R^5$ are independently selected from H, CN, halo, $C_1$-$C_6$alkyl, $C_2$-$C_6$alkenyl, and $C_2$-$C_6$alkynyl;

$R^6$ is selected from H, $C_1$-$C_{10}$alkyl, $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_7$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{13}$, and $C(O)R^{13}$;

$R^7$ and $R^8$ are independently selected from H, halo, and $C_1$-$C_6$alkyl;

each $R^9$ is independently selected from halo, $C_1$-$C_6$alkyl, OH, $OC_1$-$C_6$alkyl, $C_1$-$C_6$alkyleneOH, and $C_1$-$C_6$alkyleneO$C_1$-$C_6$alkyl;

$R^{10}$ is selected from H, $C_1$-$C_6$alkyl, $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{15}$, and $C(O)R^{15}$;

Z is selected from O, C(O), $NR^{16}C(O)$, $NR^{16}C(O)O$, $C(O)NR^{16}$, $OC(O)NR^{16}$, and $NR^{16}$;

Z' is selected from O, C(O), $NR^{17}C(O)$, $NR^{17}C(O)O$, $C(O)NR^{17}$, $OC(O)NR^{17}$, and $NR^{17}$;

n is an integer selected from 0, 1, 2, 3, and 4;

$R^{11}$, $R^{13}$, $R^{15}$, $R^{16}$, and $R^{17}$ are independently selected from H and $C_1$-$C_6$alkyl;

$R^{12}$ and $R^{14}$ are independently selected from H, $C_1$-$C_6$alkyl, $C_3$-$C_7$cycloalkyl, $C_3$-$C_{10}$heterocycloalkyl, $C_6$-$C_{10}$aryl, and $C_5$-$C_{10}$heteroaryl, the latter four groups being optionally substituted with one to four substituents independently selected from halo, $C_1$-$C_4$alkyl, $OC_1$-$C_4$alkyl, and $C(O)C_1$-$C_4$alkyl, and available hydrogen atoms are optionally replaced with a halogen atom and/or available atoms are optionally replaced with an alternate isotope thereof, provided when X is O, $R^1$, $R^2$, $R^3$, $R^4$, $R^5$, $R^7$, and $R^8$ are H or D, n is 0, and $R^6$ is H, $CH_3$, or $CD_3$, then $R^{10}$ is not H, $CH_3$, or $CD_3$;

provided when X is O, $R^1$, $R^2$, $R^3$, $R^4$, $R^5$, $R^7$, and $R^8$ are H or D and n is 0, and $R^6$ is $CH_3$ or $CHF_2$, then $R^{10}$ is not H, $CH_3$, or $CD_3$; and provided when X is absent and $R^6$ is H, then either n is not 0 or $R^{10}$ is not H or $C_1$-$C_6$alkyl.

In some embodiments, especially but not necessarily when X is O, n is 0, 1, 2, 3, or 4, $R^9$ is selected from halo or $C_1$-$C_6$alkyl, $R^{10}$ is H or $C_1$-$C_6$alkyl, and $R^6$ is H, or substituted or unsubstituted $C_1$-$C_6$alkyl, $C_2$-$C_6$alkenyl, $C_2$-$C_6$alkynyl, $C_3$-$C_7$-cycloalkyl, $C_3$-$C_7$heterocycloalkyl, $C_6$-$C_{10}$aryl or $C_5$-$C_{10}$heteroaryl, available hydrogen atoms are optionally replaced with a halogen atom (i.e., all available hydrogen atoms in H, $C_1$-$C_6$alkyl, $C_2$-$C_6$alkenyl, $C_2$-$C_6$alkynyl, $C_3$-$C_7$cycloalkyl, $C_3$-$C_7$heterocycloalkyl, $C_6$-$C_{10}$aryl and $C_5$-$C_{10}$heteroaryl are not optionally replaced with deuterium). In some embodiments, when X is 0, n is 0, 1, 2, 3, or 4, $R^9$ is halo or $C_1$-$C_6$alkyl, $R^{10}$ is H or $C_1$-$C_6$alkyl, and $R^6$ is H or substituted or unsubstituted $C_1$-$C_6$alkyl, $C_2$-$C_6$alkenyl, $C_2$-$C_6$alkynyl, $C_3$-$C_7$cycloalkyl, $C_3$-$C_7$heterocycloalkyl, $C_6$-$C_{10}$aryl, or $C_5$-$C_{10}$heteroaryl, the compound of Formula (I) does not comprise deuterium.

In some embodiments, when available hydrogen atoms in a group are optionally replaced with a halogen atom, the halogen atom is selected from F, Cl, and Br. In some embodiments, when available hydrogen atoms in a group are optionally replaced with a halogen atom, the halogen atom is selected from F and Br. In some embodiments, when available hydrogen atoms are replaced with a halogen atom, the halogen atom is selected from F and Cl. In some embodiments, when available hydrogen atoms in a group are optionally replaced with a halogen atom, the halogen atom is F.

In some embodiments, available hydrogen atoms are optionally independently replaced with an alternate isotope thereof. In some embodiments, the alternate isotope of hydrogen is deuterium.

Therefore, in some embodiments, available hydrogen atoms are optionally replaced with a halogen atom and/or available hydrogen atoms are optionally replaced with deuterium. In some embodiments, especially when X is S, S(O), or $SO_2$, and for other embodiments in which X is O or absent, when available hydrogen atoms in a group are optionally replaced with a halogen atom, the halogen atom is selected from F, Cl, and I. In some embodiments, especially when X is S, S(O), or $SO_2$, and for other embodiments of X as well, when available hydrogen atoms in a group are optionally replaced with a halogen atom, the halogen atom is selected from F and I. In some embodiments, available hydrogen atoms are optionally replaced with a fluorine atom and/or a chlorine atom and/or available hydrogen atoms are optionally replaced with deuterium. In some embodiments, available hydrogen atoms are optionally replaced with a fluorine atom and/or available hydrogen atoms are replaced with deuterium. In some embodiments, available hydrogen atoms are optionally replaced with a fluorine atom and/or a chlorine atom.

In some embodiments, the compounds of the disclosure are isotopically enriched with deuterium. In some embodiments, one or more of $R^1$, $R^2$, $R^3$, $R^4$, $R^5$, $R^6$, $R^7$ $R^8$, $R^9$, $R^{10}$, $R^{11}$, $R^{12}$, $R^{13}$, $R^{14}$, $R^{15}$, $R^{16}$, and $R^{17}$ independently comprises one or more deuterium or one or more of $R^1$, $R^2$, $R^3$, $R^4$, $R^5$, $R^6$, $R^7$ $R^8$, $R^9$, $R^{10}$, $R^{11}$, $R^{12}$, $R^{13}$ $R^{14}$, $R^{15}$, $R^{16}$, and $R^{17}$ independently is deuterium.

In some embodiments, particularly when X is selected from S, S(O), and $SO_2$, but also when X is O or absent, when $R^9$ is halo or $C_1$-$C_6$alkyl, $R^{10}$ is H or $C_1$-$C_6$alkyl, n is 0, 1, 2, 3, or 4 and $R^6$ is H, or substituted or unsubstituted $C_1$-$C_6$alkyl, $C_2$-$C_6$alkenyl, $C_2$-$C_6$alkynyl, $C_3$-$C_7$cycloalkyl, $C_3$-$C_7$heterocycloalkyl, $C_6$-$C_{10}$aryl, or $C_5$-$C_{10}$heteroaryl, available hydrogen atoms are optionally replaced with a halogen atom (e.g., available hydrogen atoms in H, $C_1$-$C_6$alkyl, $C_2$-$C_6$alkenyl, $C_2$-$C_6$alkynyl, $C_3$-$C_7$cycloalkyl, $C_3$-$C_7$heterocycloalkyl, $C_6$-$C_{10}$aryl, and $C_5$-$C_{10}$heteroaryl are not optionally replaced with deuterium). In some embodiments, when $R^9$ is halo or $C_1$-$C_6$alkyl, $R^{10}$ is H or $C_1$-$C_6$alkyl, n is 0, 1, 2, 3, or 4 and $R^6$ is H or substituted or unsubstituted $C_1$-$C_6$alkyl, $C_2$-$C_6$alkenyl, $C_2$-$C_6$alkynyl, $C_3$-$C_7$cycloalkyl, $C_3$-$C_7$heterocycloalkyl, $C_6$-$C_{10}$aryl, or $C_5$-$C_{10}$heteroaryl, the compound of Formula (I) does not comprise deuterium.

In some embodiments, particularly when X is absent or O, as well as when X is S, S(O), or $SO_2$, when $R^{10}$ is selected from H and $C_1$-$C_6$alkyl, available hydrogen atoms in H and $C_1$-$C_6$alkyl of $R^{10}$ are optionally replaced with a halogen atom (e.g., available hydrogen atoms in H and $C_1$-$C_6$alkyl of $R^{10}$ are not optionally replaced with deuterium). In some embodiments, when $R_{10}$ is selected from H and $C_1$-$C_6$alkyl, the compound of Formula (I) does not comprise deuterium.

In some embodiments, X is S(O), as shown in the structure below:

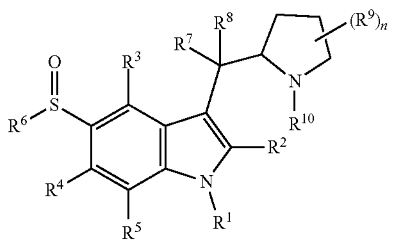

In some embodiments, X is $SO_2$, as shown in the structure below:

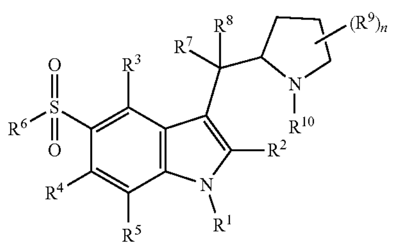

In some embodiments, X is S, as shown in the structure below:

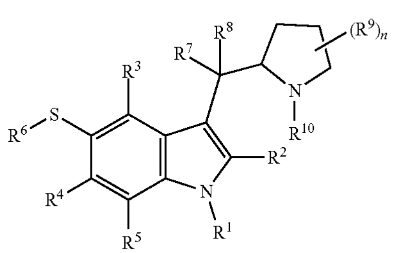

In some embodiments, X is absent (e.g., a direct bond), as shown in the structure below.

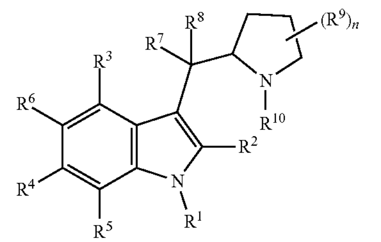

In some embodiments, X is O, as shown in the structure below.

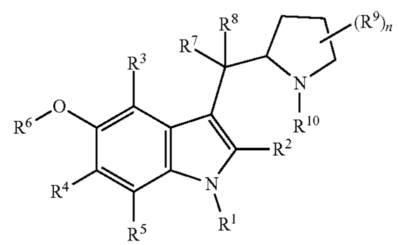

In some embodiments, $R^1$ is selected from $S(O)R^{11}$ and $SO_2R^{11}$.

In some embodiments, $R^1$ is selected from H, $C_1$-$C_4$alkyl, $C_1$-$C_3$alkyleneP(O)$(OR^{11})_2$, $C_1$-$C_4$alkyleneOP(O)$(OR^{11})_2$, $C(O)R^{11}$, $CO_2R^{11}$, and $C(O)N(R^{11})_2$, wherein available hydrogen atoms are optionally replaced with an iodine atom, a fluorine atom, and/or a chlorine atom and/or available hydrogen atoms are optionally replaced with deuterium. In some embodiments, $R^1$ is selected from H, $C_1$-$C_4$alkyl, $C_1$-$C_4$alkyleneP(O)$(OR^{11})_2$, $C_1$-$C_4$alkyleneOP(O)$(OR^{11})_2$, $C(O)R^{11}$, $CO_2R^{11}$, and $C(O)N(R^{11})_2$, wherein available hydrogen atoms are optionally replaced with a fluorine atom and/or a chlorine atom and/or available hydrogen atoms are optionally replaced with deuterium. In some embodiments, $R^1$ is selected from H, $C_1$-$C_3$alkyl, $CH_2P(O)(OR^{11})_2$, $CH_2CH_2P(O)(OR^{11})_2$, $CH_2CH(CH_3)P(O)(OR^{11})_2$, $CH(CH_3)CH_2P(O)(OR^{11})_2$, $CH(CH_3)P(O)(OR^{11})_2$, $CH(CH_2CH_3)P(O)(OR^{11})_2$, $(CH_2)OP(O)(OR^{11})_2$, $C(O)R^{11}$, and $CO_2R^{11}$, wherein available hydrogen atoms are optionally replaced with a fluorine atom and/or a chlorine atom and/or available hydrogen atoms are optionally replaced with deuterium. In some embodiments, $R^1$ is selected from H, $CH_3$, $CH_2CH_3$, $CH_2P(O)(OR^{11})_2$, $CH(CH_3)P(O)(OR^{11})_2$, and $(CH_2)OP(O)(OR^{11})_2$, wherein available hydrogen atoms are optionally replaced with a fluorine atom and/or a chlorine atom and/or available hydrogen atoms are optionally replaced with deuterium. In some embodiments, $R^1$ is selected from H, $CH_3$, $CH_2CH_3$, $CH_2P(O)(OR^{11})_2$, $CH(CH_3)P(O)(OR^{11})_2$, and $(CH_2)OP(O)(OR^{11})_2$, wherein available hydrogen atoms are optionally replaced with a fluorine atom and/or a chlorine atom and/or available hydrogen atoms are optionally replaced with deuterium. In some embodiments, $R^1$ is selected from H, $CH_3$, $CH_2CH_3$, $CH_2P(O)(OR^{11})_2$, and $(CH_2)OP(O)(OR^{11})_2$, wherein available hydrogen atoms are optionally replaced with a fluorine atom and/or a chlorine atom and/or available hydrogen atoms are optionally replaced with deuterium. In some embodiments, $R^1$ is selected from H, $CH_3$, $CH_2CH_3$, $CH_2P(O)(OR^{11})_2$, $(CH_2)OP(O)(OR^{11})_2$, $C(O)R^{11}$, and $CO_2R^{11}$, wherein available hydrogen atoms are optionally replaced with a fluorine atom and/or a chlorine atom and/or available hydrogen atoms are optionally replaced with deuterium. In some embodiments, $R^1$ is selected from H, $CH_3$, and $CH_2CH_3$, wherein available hydrogen atoms are optionally replaced with a fluorine atom and/or a chlorine atom and/or available hydrogen atoms are optionally replaced with deuterium. In some embodiments, $R^1$ is selected from H and D. In some embodiments, $R^1$ is H. In some embodiments, $R^1$ is D. In some embodiments, $R^1$ is $CD_3$. In some embodiments, $R^1$ is $CH_3$.

In some embodiments, $R^2$ is selected from H, halo, and $C_1$-$C_4$alkyl wherein available hydrogen atoms are optionally replaced with a halogen atom and/or available atoms are optionally replaced with an alternate isotope thereof. In some embodiments, $R^2$ is selected from H, halo, and $C_1$-$C_4$alkyl wherein available hydrogen atoms are optionally replaced with an iodine atom, a fluorine atom, and/or a chlorine atom and/or available hydrogen atoms are optionally replaced with deuterium. In some embodiments, $R^2$ is selected from H, halo, and $C_1$-$C_4$alkyl wherein available hydrogen atoms are optionally replaced with a fluorine atom and/or a chlorine atom and/or available hydrogen atoms are optionally replaced with deuterium. In some embodiments, $R^2$ is selected from H, D, F, Cl, Br, $C_1$-$C_4$alkyl, $C_1$-$C_4$fluoroalkyl, $C_1$-$C_4$deuteroalkyl, and $C_1$-$C_4$deuterofluoroalkyl. In some embodiments, $R^2$ is selected from H, D, F, Br, Cl, $CH_3$, $CD_2H$, $CDH_2$, $CD_3$, $CF_3$, $CHF_2$, $CH_2F$, $CH_2CH_3$, $CH_2CH_2F$, $CF_2CF_3$, $CH_2CH_2D$, $CH_2CD_2H$, and $CD_2CD_3$. In some embodiments, $R^2$ is selected from H, D, F, $CH_3$, $CD_2H$, $CDH_2$, $CD_3$, $CF_3$, $CHF_2$, $CH_2F$, $CH_2CH_3$, $CH_2CH_2F$, $CH_2CF_2H$, $CH_2CF_3$, $CF_2CF_3$, $CH_2CH_2D$, $CH_2CD_2H$, and $CD_2CD_3$. In some embodiments, $R^2$ is selected from H, D, $CH_3$, $CF_3$, $CHF_2$, $CH_2F$, $CD_2H$, $CDH_2$, and $CD_3$. In some embodiments, $R^2$ is selected from H, D, $CH_3$, $CF_3$, and $CD_3$. In some embodiments, $R^2$ is H. In some embodiments, $R^2$ is D. In some embodiments, $R^2$ is $CD_3$. In some embodiments, $R^2$ is $CH_3$.

In some embodiments, $R^3$ is selected from H, halo, CN, $C_1$-$C_4$alkyl, $C_2$-$C_4$alkenyl, and $C_2$-$C_4$alkynyl, wherein available hydrogen atoms are optionally replaced with a halogen atom and/or available atoms are optionally replaced with an alternate isotope thereof. In some embodiments, $R^3$ is selected from H, halo, CN, $C_1$-$C_4$alkyl, $C_2$-$C_4$alkenyl, and $C_2$-$C_4$alkynyl, wherein available hydrogen atoms are optionally replaced with an iodine atom, a fluorine atom, and/or a chlorine atom and/or available hydrogen atoms are optionally replaced with deuterium. In some embodiments, $R^3$ is selected from H, halo, CN, $C_1$-$C_4$alkyl, $C_2$-$C_4$alkenyl, and $C_2$-$C_4$alkynyl, wherein available hydrogen atoms are optionally replaced with a fluorine atom and/or a chlorine atom and/or available hydrogen atoms are optionally replaced with deuterium. In some embodiments, $R^3$ is selected from H, D, CN, halo, $C_1$-$C_4$alkyl, $C_1$-$C_4$fluoroalkyl, $C_1$-$C_4$deuteroalkyl, $C_1$-$C_4$deuterofluoroalkyl, $C_2$-$C_4$alkenyl, $C_2$-$C_4$fluoroalkenyl, $C_2$-$C_4$deuteroalkenyl, $C_2$-$C_4$deuterofluoroalkenyl, $C_2$-$C_4$alkynyl, $C_2$-$C_4$deuteroalkynyl, $C_2$-$C_4$fluoroalkynyl, and $C_2$-$C_4$deuterofluoroalkynyl. In some embodiments, $R^3$ is selected from H, D, CN, halo, $C_1$-$C_4$alkyl, $C_1$-$C_4$fluoroalkyl, $C_1$-$C_4$deuteroalkyl, $C_1$-$C_4$deuterofluoroalkyl, $C_2$-$C_4$alkenyl, and $C_2$-$C_4$fluoroalkenyl. In some embodiments, $R^3$ is selected from H, D, CN, F, Cl, Br, $C_1$-$C_4$alkyl, $C_1$-$C_4$fluoroalkyl, $C_1$-$C_4$deuteroalkyl, and $C_1$-$C_4$deuterofluoroalkyl. In some embodiments, $R^3$ is selected from H, D, CN, F, Br, Cl, $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3$, $CF_2CF_3$, $CH_2CH_2D$, $CH_2CD_2H$, $CH_2CD_3$, and $CD_2CD_3$. In some embodiments, $R^3$ is selected from H, D, CN, F, Cl, $CH_3$, $CD_2H$, $CDH_2$, $CD_3$, $CF_2H$, $CFH_2$, and $CF_3$. In some embodiments, $R^3$ is selected from H, F, and D. In some embodiments, $R^3$ is selected from H, F, and Cl. In some embodiments, $R^3$ is selected from H and D. In some embodiments, $R^3$ is H.

In some embodiments, $R^3$ is selected from H, CN, $C_1$-$C_4$alkyl, $C_1$-$C_4$haloalkyl, $C_2$-$C_4$alkenyl, $C_2$-$C_4$haloalkenyl, $C_2$-$C_4$alkynyl, and $C_2$-$C_4$haloalkynyl, wherein available atoms are optionally replaced with an alternate isotope thereof. In some embodiments, $R^3$ is selected from H, CN, $C_1$-$C_4$alkyl, $C_1$-$C_4$fluoroalkyl, $C_2$-$C_4$alkenyl, $C_2$-$C_4$fluoroalkenyl, $C_2$-$C_4$alkynyl, and $C_2$-$C_4$fluoroalkynyl, wherein available hydrogen atoms are optionally replaced with deuterium. In some embodiments, $R^3$ is selected from H, D, $C_1$-$C_4$alkyl, $C_1$-$C_4$fluoroalkyl, $C_1$-$C_4$deuteroalkyl, $C_1$-$C_4$deuterofluoroalkyl, $C_2$-$C_4$alkenyl, $C_2$-$C_4$fluoroalkenyl, $C_2$-$C_4$deuteroalkenyl, $C_2$-$C_4$deuterofluoroalkenyl, $C_2$-$C_4$alkynyl, $C_2$-$C_4$deuteroalkynyl, $C_2$-$C_4$fluoroalkynyl, and $C_2$-$C_4$deuterofluoroalkynyl. In some embodiments, $R^3$ is selected from H, D, CN, $C_1$-$C_4$alkyl, $C_1$-$C_4$fluoroalkyl, $C_1$-$C_4$deuteroalkyl, $C_1$-$C_4$deuterofluoroalkyl, $C_2$-$C_4$alkenyl, $C_2$-$C_4$fluoroalkenyl, $C_2$-$C_4$deuteroalkenyl, and $C_2$-$C_4$deuterofluoroalkenyl. In some embodiments, $R^3$ is selected from H, D, CN, $C_1$-$C_4$alkyl, $C_1$-$C_4$fluoroalkyl, $C_1$-$C_4$deuteroalkyl, and $C_1$-$C_4$deuterofluoroalkyl. In some embodiments, $R^3$ is selected from H, D, CN, $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3$, $CF_2CF_3$, $CH_2CH_2D$, $CH_2CD_2H$, $CH_2CD_3$, and $CD_2CD_3$. In some embodiments, $R^3$ is H.

In some embodiments, $R^4$ and $R^5$ are independently selected from H, halo, CN, $C_1$-$C_4$alkyl, $C_2$-$C_4$alkenyl, and $C_2$-$C_4$alkynyl, wherein available hydrogen atoms are optionally replaced with a halogen atom and/or available atoms are optionally replaced with an alternate isotope thereof. In some embodiments, $R^4$ and $R^5$ are independently selected from H, halo, CN, $C_1$-$C_4$alkyl, $C_2$-$C_4$alkenyl, and $C_2$-$C_4$alkynyl, wherein available hydrogen atoms are optionally replaced with an iodine atom, a fluorine atom, and/or a chlorine atom and/or available hydrogen atoms are optionally replaced with deuterium. In some embodiments, $R^4$ and $R^5$ are independently selected from H, halo, CN, $C_1$-$C_4$alkyl, $C_2$-$C_4$alkenyl, and $C_2$-$C_4$alkynyl, wherein available hydrogen atoms are optionally replaced with a fluorine atom and/or a chlorine atom and/or available hydrogen atoms are optionally replaced with deuterium. In some embodiments, $R^4$ and $R^5$ are independently selected from H, D, CN, halo, $C_1$-$C_4$alkyl, $C_1$-$C_4$fluoroalkyl, $C_1$-$C_4$deuteroalkyl, $C_1$-$C_4$deuterofluoroalkyl, $C_2$-$C_4$alkenyl, $C_2$-$C_4$fluoroalkenyl, $C_2$-$C_4$deuteroalkenyl, $C_2$-$C_4$deuterofluoroalkenyl, $C_2$-$C_4$alkynyl, $C_2$-$C_4$deuteroalkynyl, $C_2$-$C_4$fluoroalkynyl, and $C_2$-$C_4$deuterofluoroalkynyl. In some embodiments, $R^4$ and $R^5$ are independently selected from H, D, CN, halo, $C_1$-$C_4$alkyl, $C_1$-$C_4$fluoroalkyl, $C_1$-$C_4$deuteroalkyl, $C_1$-$C_4$deuterofluoroalkyl, $C_2$-$C_4$alkenyl, $C_2$-$C_4$fluoroalkenyl, $C_2$-$C_4$alkynyl, and $C_2$-$C_4$fluoroalkynyl. In some embodiments, $R^4$ and $R^5$ are independently selected from H, D, CN, F, Cl, Br, $C_1$-$C_4$alkyl, $C_1$-$C_4$fluoroalkyl, $C_1$-$C_4$deuteroalkyl, and $C_1$-$C_4$deuterofluoroalkyl. In some embodiments, $R^4$ and $R^5$ are independently selected from H, D, CN, F, Cl, Br, $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3$, $CF_2CF_3$, $CH_2CH_2D$, $CH_2CD_2H$, $CH_2CD_3$, and $CD_2CD_3$. In some embodiments, $R^4$ and $R^5$ are independently selected from H, D, CN, F, Cl, Br, $CH_3$, $CD_2H$, $CDH_2$, $CD_3$, $CF_2H$, $CFH_2$, and $CF_3$. In some embodiments, $R^4$ and $R^5$ are independently selected from H, F, and D. In some embodiments, $R^4$ and $R^5$ are independently selected from H and D. In some embodiments, $R^4$ and $R^5$ are both H.

In some embodiments, each of $R^3$, $R^4$, and $R^5$ is H. In some embodiments, each of $R^2$, $R^3$, $R^4$, and $R^5$ is H. In some embodiments, at least one of $R^3$, $R^4$, and $R^5$ is D. In some embodiments, each of $R^2$, $R^3$, $R^4$, and $R^5$ is D.

In some embodiments, $R^6$ is selected from H, $C_1$-$C_6$alkyl, $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted with one to four substituents independently selected from halo, $C_1$-$C_6$alkyl, $OR^{13}$, and $C(O)R^{13}$, and wherein available hydrogen atoms are optionally replaced with a halogen atom and/or available atoms are optionally replaced with an alternate isotope thereof. In some embodiments, $R^6$ is selected from $C_1$-$C_6$alkyl, $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted with one to four substituents independently selected from halo, $C_1$-$C_6$alkyl, $OR^{13}$, and $C(O)R^{13}$, and wherein available hydrogen atoms are optionally replaced with an iodine atom, a fluorine atom, and/or a chlorine atom and/or available hydrogen atoms are optionally replaced with deuterium. In some embodiments, $R^6$ is selected from $C_1$-$C_6$alkyl, $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted with one to four substituents independently selected from halo, $C_1$-$C_6$alkyl, $OR^{13}$, and $C(O)R^{13}$, and wherein available hydrogen atoms are optionally replaced with a fluorine atom and/or a chlorine atom and/or available hydrogen atoms are optionally replaced with deuterium.

In some embodiments, $R^6$ is $C_1$-$C_6$alkyl, wherein available hydrogen atoms are optionally replaced with a fluorine atom and/or a chlorine atom and/or available hydrogen atoms are optionally replaced with deuterium. In some embodiments, particularly when X is S, S(O), or $SO_2$, as well as when X is O or absent, $R^6$ is selected from $C_1$-$C_6$alkyl, $C_1$-$C_6$fluoroalkyl, $C_1$-$C_6$deuteroalkyl, and $C_1$-$C_6$deuterofluoroalkyl. In some embodiments, $R^6$ is selected from $C_1$-$C_6$alkyl, $C_1$-$C_6$fluoroalkyl, $C_1$-$C_6$deuteroalkyl, and $C_1$-$C_6$deuterofluoroalkyl. In some embodiments, $R^6$ is selected from $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3$, $CF_2CF_3$, $CH_2CH_2D$, $CH_2CD_2H$, $CH_2CD_3$, $CD_2CD_3$, $CH_2CH_2CH_3$, $CH_2CH_2CHF_2$, $CH_2CH_2CFH_2$, $CH_2CH_2CF_3$, $CH_2CH_2CHD_2$, $CH_2CH_2CDH_2$, $CH_2CH_2CD_3CH(CH_3)_2$, $CH(CF_3)_2$, $CH(CHF_2)_2$, $CH(CFH_2)_2$, $CH(CD_3)_2$, $CH(CHD_2)_2$, $CH(CDH_2)_2$, $C(CH_3)_3$, $C(CF_3)_3$, $C(CHF_2)_3$, $C(CFH_2)_3$, $C(CD_3)_3$, $C(CHD_2)_3$, $C(CDH_2)_3$, $CH_2CH_2CH_2CH_3$, $CH_2CH_2CH_2CF_3$, $CH_2CH_2CH_2CD_3$, $CH_2CH(CH_3)_2$, $CH_2CH(CD_3)_2$, $CH_2CH(CF_3)_2$, $CH(CH_3)CH_2CH_3$, $CH(CH_3)CH_2CF_3$, $CH(CH_3)CH_2CD_3$, $CH_2CH(CH_3)CH_3$, $CH_2CH(CH_3)$ $CF_3$, $CH_2CH(CH_3)$ $CD_3$, $CH_2C(CH_3)_3$, $CH_2C(CF_3)_3$, $CH_2C(CD_3)_3$, $CH_2CH_2C(CH_3)_3$, $CH_2CH_2C(CF_3)_3$, and $CH_2CH_2C(CD_3)_3$. In some embodiments, $R^6$ is selected from $CH_3$, $CF_2H$, $CFH_2$, $CF_3$, $CH_2CH_3$, $CH_2CH_2F$, $CH_2CF_2H$, $CH_2CF_3$, $CH_2CH_2CH_3$, $CH_2CH_2CHF_2$, $CH_2CH_2CFH_2$, $CH_2CH_2CF_3$, $CH(CH_3)_2$, $CH(CF_3)_2$, $C(CH_3)_3$, $C(CF_3)_3$, $CH_2CH_2CH_2CH_3$, $CH_2CH_2CH_2CF_3$, $CH_2CH_2CH_2CHF_2$, $CH_2CH(CH_3)_2$, $CH_2CH(CF_3)_2$, $CH(CH_3)CH_2CH_3$, $CH(CH_3)CH_2CF_3$, $CH_2C(CH_3)_3$, $CH_2C(CF_3)_3$, $CH_2CH_2C(CH_3)_3$, and $CH_2CH_2C(CF_3)_3$. In some embodiments $R^6$ is selected from $CH_3$, $CH_2CH_3$, $CH_2CF_3$, $CH_2CH_2CH_3$, $CH(CH_3)_2$, $CH_2C(CH_3)_3$, $CH_2CH_2C(CH_3)_3$, $CD_3$, $CF_3$, $CHF_2$, CHEF, $CH_2CF_2H$, $CH_2CH_2F$, $CH_2CH_2CHF_2$, $CH_2CH_2CF_3$, and $CH_2CH_2CH_2CF_3$. In some embodiments, especially for when X is S, S(O), or $SO_2$, and for other embodiments in which X is O or absent, $R^6$ is selected from $CH_3$, $CD_2H$, $CDH_2$, $CD_3$, $CF_2H$, $CFH_2$, $CF_3$, $CH_2CF_2H$, $CH_2CH_2CF_3$, $CH_2CH_2CH_2CF_3$, $CH_2CH_3$, $CH_2CH_2CH_3$, $CH(CH_3)_2$, $C(CH_3)_3$, $CH_2CH(CH_3)_2$, $CH(CH_3)CH_2CH_3$, and $CH_2C(CH_3)_3$. In some embodiments, especially for when X is absent or oxygen, and for other embodiments of X, $R^6$ is selected from H, D, $CH_3$, $CD_2H$, $CDH_2$, $CD_3$, $CF_2H$, $CFH_2$, $CF_3$, $CH_2CF_2H$, $CH_2CH_3$, $CH_2CH_2CH_3$, $CH_2CH_2CF_3$, $CH_2CH_2CH_2CF_3$, $CH(CH_3)_2$, $C(CH_3)_3$, $CH_2CH(CH_3)_2$, $CH(CH_3)CH_2CH_3$, and $CH_2C(CH_3)_3$. In some embodiments, $R^6$ is selected from $CH_3$, $CD_3$, $CD_2H$, $CDH_2$, $CF_2H$, $CH_2CF_2H$, $CFH_2$, and $CF_3$. In some embodiments, $R^6$ is selected from $CH_3$ and $CD_3$. In some embodiments, $R^6$ is $CH_3$.

In some embodiments, $R^6$ is selected from $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted with one to four substituents independently selected from halo, $C_1$-$C_6$alkyl, $OR^{13}$, and $C(O)R^{13}$, and wherein available hydrogen atoms are optionally replaced with a fluorine atom and/or a chlorine atom and/or available hydrogen atoms are optionally replaced with deuterium.

In some embodiments, $R^6$ is selected from $C_4$-$C_6$alkenyl and $C_2$-$C_6$alkynyl wherein available hydrogen atoms are optionally replaced with a fluorine atom and/or a chlorine atom and/or available hydrogen atoms are optionally replaced with deuterium. In some embodiments, $R^6$ is selected from $C_2$-$C_6$alkenyl, $C_2$-$C_6$fluoroalkenyl, $C_2$-$C_6$deuteroalkenyl, $C_2$-$C_6$deuterofluoroalkenyl, $C_2$-$C_6$alkynyl, $C_2$-$C_6$fluoroalkynyl, $C_2$-$C_6$deuteroalkynyl, and $C_2$-$C_6$deuterofluoroalkynyl. In some embodiments, $R^6$ is selected from $C_2$-$C_4$alkenyl, $C_2$-$C_4$fluoroalkenyl, $C_2$-$C_6$deuteroalkenyl, $C_2$-$C_6$deuterofluoroalkenyl, $C_2$-$C_4$alkynyl, $C_2$-$C_4$fluoroalkynyl, $C_2$-$C_4$deuteroalkynyl, and $C_2$-$C_4$deuterofluoroalkynyl. In some embodiments, $R^6$ is selected from $CH{=}CH_2$, $CH_2CH{=}CH_2$, $CF_2CH{=}CH_2$, $CD_2CH{=}CH_2$, $CH{=}CH_2CH_3$, $CH{=}CH_2CF_3$, $CH{=}CH_2CHF_2$, $CH{=}CH_2CH_2F$, $CH{=}CH_2CD_3$, $CH{=}CH_2CHD_2$, $CH{=}CH_2CH_2D$, $C{\equiv}CH$, $C{\equiv}CCH_3$, $C{\equiv}CCF_3$, $C{\equiv}CCHF_2$, $C{\equiv}CCFH_2$, $C{\equiv}CCD_3$, $C{\equiv}CCHD_2$, $C{\equiv}CCDH_2$, $CH_2C{\equiv}CH$, $CF_2C{\equiv}CH$, $CD_2C{\equiv}CH$, $CH_2C{\equiv}CCH_3$, $CF_2C{\equiv}CCH_3$, $CD_2C{\equiv}CCH_3$, $CH_2C{\equiv}CCD_3$, $CF_2C{\equiv}CCD_3$, $CD_2C{\equiv}CCD_3$, $CH_2C{\equiv}CCF_3$, $CF_2C{\equiv}CCF_3$, $CD_2C{\equiv}CCF_3$, $CH_2C{\equiv}CCHD_2$, $CF_2C{\equiv}CHD_2$, $CD_2C{\equiv}CHD_2$, $CH_2C{\equiv}CHF_2$, $CF_2C{\equiv}CHF_2$, and $CD_2C{\equiv}CHF_2$. In some embodiments, $R^6$ is selected from CH═$CH_2$, $CH_2CH$═$CH_2$, C≡CH C≡$CCH_3$, $CH_2C$≡CH, and $CH_2C$≡$CCH_3$.

In some from $C_1$-$C_6$alkyleneZ$R^{12}$, $C_2$-$C_6$alkenyleneZ$R^{12}$, and $C_2$-$C_6$alkynyleneZ$R^{12}$, wherein available hydrogen atoms are optionally replaced with a fluorine atom and/or a chlorine atom and/or available hydrogen atoms are optionally replaced with deuterium.

In some embodiments, $R^6$ is selected d from $C_1$-$C_6$alkyleneZ$R^{12}$, $C_1$-$C_6$fluoroalkyleneZ$R^{12}$, $C_1$-$C_6$deuteroalkyleneZ$R^{12}$, $C_1$-$C_6$deuterofluoroalkyleneZ$R^{12}$, $C_2$-$C_6$alkenyleneZ$R^{12}$, $C_2$-$C_6$fluoroalkenyleneZ$R^{12}$, $C_2$-$C_6$deuteroalkenyleneZ$R^{12}$, $C_2$-$C_6$deuterofluoroalkenyleneZ$R^{12}$, $C_6$alkynyleneZ$R^{12}$, $C_2$-$C_6$fluoroalkynyleneZ$R^{12}$, $C_2$-$C_6$deuteroalkynyleneZ$R^{12}$, and $C_2$-$C_6$deuterofluoroalkynyleneZ$R^{12}$. In some embodiments, $R^6$ is selected from $C_1$-$C_6$alkyleneZ$R^{12}$, $C_1$-$C_6$fluoroalkyleneZ$R^{12}$, $C_1$-$C_6$deuteroalkyleneZ$R^{12}$, $C_1$-$C_6$deuterofluoroalkyleneZ$R^{12}$, $C_2$-$C_6$alkenyleneZ$R^{12}$, and $C_2$-$C_6$alkynyleneZ$R^{12}$. In some embodiments, $R^6$ is selected from $C_1$-$C_4$alkyleneZ$R^{12}$, $C_1$-$C_4$fluoroalkyleneZ$R^{12}$, $C_1$-$C_4$deuteroalkyleneZ$R^{12}$, $C_1$-$C_4$deuterofluoroalkyleneZ$R^{12}$, $C_2$-$C_4$alkenyleneZ$R^{12}$, $C_2$-$C_4$fluoroalkenyleneZ$R^{12}$, $C_2$-$C_4$deuteroalkenyleneZ$R^{12}$, $C_2$-$C_4$deuterofluoroalkenyleneZ$R^{12}$, $C_2$-$C_4$alkynyleneZ$R^{12}$, $C_2$-$C_4$fluoroalkynyleneZ$R^{12}$, $C_2$-$C_4$deuteroalkynyleneZ$R^{12}$, and $C_2$-$C_4$deuterofluoroalkynyleneZ$R^{12}$. In some embodiments, $R^6$ is selected from $C_1$-$C_4$alkyleneZ$R^{12}$, $C_1$-$C_4$fluoroalkyleneZ$R^{12}$, $C_1$-$C_4$deuteroalkyleneZ$R^{12}$, $C_1$-$C_4$deuterofluoroalkyleneZ$R^{12}$, $C_2$-$C_4$alkenyleneZ$R^{12}$, and $C_2$-$C_4$alkynyleneZ$R^{12}$.

In some embodiments, $R^6$ is selected from $CH_2ZR^{12}$. $CH_2CH_2ZR^{12}$, $CH_2CH_2CH_2ZR^{12}$, $CH_2CH_2CH_2CH_2ZR^{12}$, $CH(CH_3)CH_2ZR^{12}$, $CH(CH_3)CH_2CH_2ZR^{12}$, $CH_2CH(CH_3)ZR^{12}$, $CF_2ZR^{12}$, $CFHZR^{12}$, $CH_2CHFZR^{12}$, $CH_2CF_2ZR^{12}$, $CF_2CF_2ZR^{12}$, $CH_2CH_2CF_2ZR^{12}$, $CH_2CH_2CFHZR^{12}$, $CH_2CH_2CF_2ZR^{12}$, $CH(CH_3)CF_2ZR^{12}$, $CH(CH_3)CHFZR^{12}$, $CH_2CH_2CH_2CF_2ZR^{12}$, $CH_2CH_2CH_2CHFZR^{12}$, $CH(CH_3)CH_2CF_2ZR^{12}$, $CH(CH_3)CH_2CHFZR^{12}$, $CD_2ZR^{12}$, $CDHZR^{12}$, $CH_2CHDZR^{12}$, $CH_2CD_2ZR^{12}$, $CD_2CD_2ZR^{12}$, $CH_2CH_2CD_2ZR^{12}$, $CH_2CH_2CDHZR^{12}$, $CH_2CH_2CD_2ZR^{12}$, $CH(CH_3)$ $CD_2ZR^{12}$, $CH(CH_3)CHDZR^{12}$, $CH_2CH_2CH_2CD_2ZR^{12}$, $CH_2CH_2CH_2CHDZR^{12}$, $CH(CH_3)CH_2CD_2ZR^{12}$, $CH(CH_3)CH_2CHDZR^{12}$, CH═CHZ$R^{12}$, $CH_2CH$═CHZ$R^{12}$, C≡CZ$R^{12}$, C≡$CCH_2ZR^{12}$, $CH_2C$≡CZ$R^{12}$, and $CH_2C$≡$CH_2ZR^{12}$. In some embodiments, $R^6$ is selected from $CH_2ZR^{12}$, $CH_2CH_2ZR^{12}$, $CH_2CH_2CH_2ZR^{12}$, $CH_2CH_2CH_2CH_2ZR^{12}$, $CH(CH_3)CH_2ZR^{12}$, $CH(CH_3)CH_2CH_2ZR^{12}$, $CH_2CH(CH_3)$ $ZR^{12}$, CH═CHZ$R^{12}$, $CH_2CH$═CHZ$R^{12}$, CH═$CH_2CHZR^{12}$, C≡$CCH_2ZR^{12}$, $CH_2C$≡CZ$R^{12}$, and $CH_2C$≡$CH_2ZR^{12}$.

In some embodiments, $R^6$ is selected from $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, each of which is optionally substituted with one to four substituents independently selected from halo, $C_1$-$C_6$alkyl, $OR^{13}$, and C(O)$R^{13}$, and wherein available hydrogen atoms are optionally replaced with a fluorine atom and/or a chlorine atom and/or available hydrogen atoms are optionally replaced with deuterium. In some embodiments, $R^6$ is selected from $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, $C_1$-$C_4$alkylene$C_5$-$C_{10}$heteroaryl, $C_1$-$C_4$fluoroalkylene$C_3$-$C_7$cycloalkyl, $C_1$-$C_4$fluoroalkylene$C_3$-$C_{10}$heterocycloalkyl, $C_1$-$C_4$fluoroalkylene$C_6$-$C_{10}$aryl, $C_1$-$C_4$fluoroalkylene$C_5$-$C_{10}$heteroaryl, $C_1$-$C_4$deuteroalkylene$C_3$-$C_7$cycloalkyl, $C_1$-$C_4$deuteroalkylene$C_3$-$C_{10}$heterocycloalkyl, $C_1$-$C_4$deuteroalkylene$C_6$-$C_{10}$aryl, $C_1$-$C_4$deuteroalkylene$C_5$-$C_{10}$heteroaryl, $C_1$-$C_4$deuterofluoroalkylene$C_3$-$C_7$cycloalkyl, $C_1$-$C_4$deuterofluoroalkylene$C_3$-$C_{10}$heterocycloalkyl, $C_1$-$C_4$deuterofluoroalkylene$C_6$-$C_{10}$aryl, and $C_1$-$C_4$deuterofluoroalkylene$C_5$-$C_{10}$heteroaryl, in which each of the cyclic groups is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and C(O)$R^{13}$, and wherein available hydrogen atoms are optionally replaced with a fluorine atom and/or a chlorine atom and/or available hydrogen atoms are optionally replaced with deuterium. In some embodiments, $R^6$ is selected from $C_3$-$C_7$cycloalkyl, $C_3$-$C_{10}$heterocycloalkyl, $C_6$-$C_{10}$aryl, $C_5$-$C_{10}$heteroaryl, $C_1$-$C_2$alkylene$C_3$-$C_7$cycloalkyl, $C_1$-$C_2$alkylene$C_3$-$C_{10}$heterocycloalkyl, $C_1$-$C_2$alkylene$C_6$-$C_{10}$aryl, $C_1$-$C_2$alkylene$C_5$-$C_{10}$heteroaryl, $C_1$-$C_2$fluoroalkylene$C_3$-$C_7$cycloalkyl, $C_1$-$C_2$fluoroalkylene$C_3$-$C_{10}$heterocycloalkyl, $C_1$-$C_2$fluoroalkylene$C_6$-$C_{10}$aryl, $C_1$-$C_2$fluoroalkylene$C_5$-$C_{10}$heteroaryl, $C_1$-$C_2$deuteroalkylene$C_3$-$C_7$cycloalkyl, $C_1$-$C_2$deuteroalkylene$C_3$-$C_{10}$heterocycloalkyl, $C_1$-$C_2$deuteroalkylene$C_6$-$C_{10}$aryl, $C_1$-$C_2$deuteroalkylene$C_5$-$C_{10}$heteroaryl, $C_1$-$C_2$deuterofluoroalkylene$C_3$-$C_7$cycloalkyl, $C_1$-$C_2$deuterofluoroalkylene$C_3$-$C_{10}$heterocycloalkyl, $C_1$-$C_2$deuterofluoroalkylene$C_6$-$C_{10}$aryl, and $C_1$-$C_2$deuterofluoroalkylene$C_5$-$C_{10}$heteroaryl, in which each of the cyclic groups is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and C(O)$R^{13}$, and wherein available hydrogen atoms are atoms are optionally replaced with deuterium.

In some embodiments, the $C_3$-$C_7$cycloalkyl in $R^6$ is selected from cyclopropyl, cyclobutyl, cyclopentyl, cyclohexyl, and cycloheptyl, each of which is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and C(O)$R^{13}$, and wherein available hydrogen atoms are optionally replaced with a fluorine atom and/or a chlorine atom and/or available hydrogen atoms are optionally replaced with deuterium. In some embodiments, the $C_3$-$C_7$cycloalkyl in $R^6$ is selected from cyclopropyl, cyclobutyl, cyclopentyl, and cyclohexyl, each of which is optionally substituted with one to three substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and C(O)$R^{13}$ and wherein available hydrogen atoms are optionally replaced with a fluorine atom and/or a chlorine atom and/or available hydrogen atoms are optionally replaced with deuterium. In some embodiments, the $C_3$-$C_7$cycloalkyl in $R^6$ is selected from cyclopropyl, cyclobutyl, cyclopentyl, and cyclohexyl, each of which is optionally substituted with one or two substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and C(O)$R^{13}$, and wherein available hydrogen atoms are optionally replaced with a fluorine atom and/or a chlorine atom and/or available hydrogen atoms are optionally replaced with deuterium.

In some embodiments, the $C_3$-$C_{10}$heterocycloalkyl in $R^6$ is a monocyclic $C_3$-$C_7$heterocycloalkyl or a bicyclic $C_7$-$C_{10}$heterocycloalkyl, each of which is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and $C(O)R^{13}$.

In some embodiments, the monocyclic $C_3$-$C_7$heterocycloalkyl in $R^6$ is selected from aziridinyl, oxiranyl, thiiranyl, oxaxiridinyl, dioxiranyl, 1,3-dioxolanyl, azetidinyl, oxetanyl, theitanyl, diazetidinyl, dioxetanyl, dithietanyl, tetrahydrofuranyl, tetrahydrothiophenyl, 2H-1λ3-thiophenyl, pyrrolidinyl, imidazolidinyl, pyrazolidinyl, isoxothiolidinyl, thiazolidinyl, isothiazolidinyl, imidazolidinyl, imidazolinyl, dioxolanyl, dithiolanyl, triazolyl, dioxazolyl, dithiazolyl, tetrazolyl, oxatetrazolyl, tetrahydropyranyl, dihydropyranyl, isothiazolidinyl, morpholinyl, 2-oxopiperazinyl, 2-oxopiperidinyl, 2-oxopyrrolidinyl, piperidinyl, piperazinyl, tetrahydropyridinyl, thiomorpholinyl, thiomorpholinyl sulfoxide, thiomorpholinyl dioxide, dioxanyl, thiazolinyl, thianyl, thianyl oxide, thianyl dioxide, dithianyl, azepanyl, pyrazolidinyl, oxepanyl, thiepanyl, diazepanyl, and 2,5-pyrrolidinedionyl (e.g., succinimidyl), each of which is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and $C(O)R^{13}$, and wherein available hydrogen atoms are optionally replaced with a fluorine atom and/or a chlorine atom and/or available hydrogen atoms are optionally replaced with deuterium. In some embodiments, the monocyclic $C_3$-$C_7$heterocycloalkyl in $R^6$ is selected from oxetanyl, tetrahydrofuranyl, tetrahydrothiophenyl, 2H-1λ3-thiophenyl, pyrrolidinyl, imidazolidinyl, tetrahydropyranyl, dihydropyranyl, 2-oxopiperazinyl, 2-oxopiperidinyl, 2-oxopyrrolidinyl, piperidinyl, piperazinyl, thianyl, thianyl oxide, thianyl dioxide, dithianyl, and 2,5-pyrrolidinedionyl, each of which is optionally substituted with one to three, or one or two, substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and $C(O)R^{13}$, and wherein available hydrogen atoms are optionally replaced with a fluorine atom and/or a chlorine atom and/or available hydrogen atoms are optionally replaced with deuterium.

In some embodiments, the bicyclic $C_7$-$C_{10}$heterocycloalkyl in $R^6$ is selected from benzoisoxazolyl, dihydrobenzofuranyl, dihydrobenzothienyl, benzopyranyl, benzothiopyranyl, chromanyl, isochromanyl, dihydroindenyl, isoindolinyl, 1-oxoisoindolinyl, 3-oxoisoindolinyl, 1,3-dioxoisoindolinyl (e.g., phthalimido), octahydroisoindolinyl, octahydro-isoindolin-1-onyl (e.g., tetrahydroisoquinoline), and hexahydroisoindoline-1,3-dionyl (e.g., cis-hexahydrophthalimidyl), each of which is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and $C(O)R^{13}$, and wherein available hydrogen atoms are optionally replaced with a fluorine atom and/or a chlorine atom and/or available hydrogen atoms are optionally replaced with deuterium. In some embodiments, the bicyclic $C_7$-$C_{10}$heterocycloalkyl in $R^6$ is selected from isoindolinyl, 1-oxoisoindolinyl, 3-oxoisoindolinyl, 1,3-dioxoisoindolinyl, octahydro-1H-isoindolinyl, octahydro-1H-isoindolin-1-onyl, and hexahydro-1H-isoindoline-1,3-dionyl, each of which is optionally substituted with one to three, or one or two, substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and $C(O)R^{13}$, and wherein available hydrogen atoms are optionally replaced with a fluorine atom and/or a chlorine atom and/or available hydrogen atoms are optionally replaced with deuterium.

In some embodiments, the $C_6$-$C_{10}$aryl in $R^6$ is phenyl, optionally substituted with one to four, one to three, or one or two, substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and $C(O)R^{13}$, and wherein available hydrogen atoms are optionally replaced with a fluorine atom and/or a chlorine atom and/or available hydrogen atoms are optionally replaced with deuterium.

In some embodiments, the $C_5$-$C_{10}$heteroaryl in $R^6$ is selected from azepinyl, benzofuranyl, benzofurazanyl, benzothiazolyl, benzothienyl, benzoxazolyl, cinnolinyl, furanyl, imidazolyl, indolinyl, indolyl, isoquinolinyl, isothiazolyl, naphthyridinyl, oxadiazolyl, 2-oxoazepinyl, oxazolyl, oxadiazolyl, thiadiazolyl, pyridyl, pyrazinyl, pyrazolyl, pyridazinyl, pyrimidinyl, pyrrolidinyl, pyrrolyl, quinazolinyl, quinolinyl, quinoxalinyl, thiazolyl, thienofuranyl, triazolyl, and thienyl (e.g., thiophenyl), each of which is optionally substituted with one to four, one to three, or one or two, substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and $C(O)R^{13}$, and wherein available hydrogen atoms are optionally replaced with a fluorine atom and/or a chlorine atom and/or available hydrogen atoms are optionally replaced with deuterium.

In some embodiments, the substituents on $R^6$ are independently selected from one to four of F, Cl, Br, $CH_3$, $CH_2CH_3$, $CH_2CH_2CH_3$, $CH(CH_3)_2$, $C(CH_3)_3$, $CD_2H$, $CDH_2$, $CD_3$, $CF_3$, $CHF_2$, $CH_2F$, $CH_2CH_2F$, $CF_2CF_3$, $CH_2CH_2D$, $CH_2CD_2H$, $CD_2CD_3$, $OR^{14}$, and $C(O)R^{14}$. In some embodiments, the substituents on $R^6$ are independently selected from one to three of F, Cl, $CH_3$, $CH_2CH_3$, $CH_2CH_2CH_3$, $CH(CH_3)_2$, $CH(CH_3)_2$, $CD_2H$, $CDH_2$, $CD_3$, $CF_3$, $CHF_2$, $CH_2F$, $OR^{14}$, and $C(O)R^{14}$. In some embodiments one, more, or all the substituents on $R^6$ are independently selected from one or two of F, Cl, $CH_3$, $CH(CH_3)_2$, $CH(CH_3)_2$, $CF_3$, $CHF_2$, $CH_2F$, $OR^{14}$, and $C(O)R^{14}$.

In some embodiments, Z is selected from $NR^{16}C(O)$, $NR^{16}C(O)O$, $C(O)NR^{16}$, $OC(O)NR^{16}$, and $NR^{16}$. In some embodiments, Z is selected from O, C(O), $NR^{16}C(O)$, and $NR^{16}C(O)O$. In some embodiments, Z is O. In some embodiments, Z is C(O). In some embodiments, Z is $NR^{16}C(O)$. In some embodiments, Z is $NR^{16}C(O)O$.

In some embodiments, $R^7$ and $R^8$ are independently selected from H, halo, and $C_1$-$C_4$alkyl, wherein available hydrogen atoms are optionally replaced with a halogen atom and/or available atoms are optionally replaced with an alternate isotope thereof. In some embodiments, $R^7$ and $R^8$ are independently selected from H, halo, and $C_1$-$C_4$alkyl, wherein available hydrogen atoms are optionally replaced with an iodine atom, a fluorine atom, and/or a chlorine atom and/or available hydrogen atoms are optionally replaced with deuterium. In embodiments for when X is S, S(O), or $SO_2$, as well as embodiments in which X is O or absent, $R^7$ and $R^8$ are independently selected from H, D, F, Cl, Br, $C_1$-$C_4$alkyl, $C_1$-$C_4$fluoroalkyl, $C_1$-$C_4$deuteroalkyl, and $C_1$-$C_4$deuterofluoroalkyl. In some embodiments, $R^7$ and $R^8$ are independently selected from H, halo and $C_1$-$C_4$alkyl, wherein available hydrogen atoms are optionally replaced with a fluorine atom and/or a chlorine atom and/or available hydrogen atoms are optionally replaced with deuterium. In some embodiments, $R^7$ and $R^8$ are independently selected from H, D, F, Cl, Br, $C_1$-$C_4$alkyl, $C_1$-$C_4$fluoroalkyl, $C_1$-$C_4$deuteroalkyl, and $C_1$-$C_4$deuterofluoroalkyl.

In some embodiments, $R^7$ and $R^8$ are independently selected from H, F, Br, Cl, $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3CF_2CF_3$, $CH_2CH_2D$, $CH_2CD_2H$, and $CD_2CD_3$. In some embodiments, $R^7$ and $R^8$ are independently selected from H, D, F, Br, Cl, $CH_3$, $CD_2H$, $CDH_2$, $CD_3$, $CF_2H$, $CFH_2$, $CF_3$, $CH_2CH_3$, $CH_2CH_2D$, $CH_2CD_2H$, and $CD_2CD_3$. In some embodiments, $R^7$ and $R^8$ are independently selected from H, D, F, Br, $CH_3$, $CF_2H$, $CFH_2$, $CF_3$, $CD_2H$, $CDH_2$, and $CD_3$. In some embodiments $R^7$ and $R^8$ are independently selected from H, D, F, $CH_3$, $CF_3$, and $CD_3$. In some embodiments, $R^7$ and $R^8$ are independently selected from H, D, $CH_3$, and $CD_3$. In some embodiments, $R^7$ and $R^8$ are independently selected from H, F, and D. In some embodiments, $R^7$ and $R^8$ are independently selected from H and D. In some embodiments, $R^7$ and $R^8$ are both H. In some embodiments, $R^7$ and $R^8$ are both D. In some embodiments, $R^7$ is H. In some embodiments, $R^7$ is D. In some embodiments, $R^8$ is H. In some embodiments, $R^8$ is D.

In some embodiments, each $R^9$ is independently selected from D, halo, $C_1$-$C_4$alkyl, OH, $OC_1$-$C_4$alkyl, $C_1$-$C_4$alkyleneOH, and $C_1$-$C_4$alkyleneO$C_1$-$C_6$alkyl, wherein available hydrogen atoms are optionally replaced with a halogen atom and/or available atoms are optionally replaced with an alternate isotope thereof. In some embodiments, each $R^9$ is independently selected from D, halo, $C_1$-$C_4$alkyl, OH, $OC_1$-$C_4$alkyl, $C_1$-$C_4$alkyleneOH, and $C_1$-$C_4$alkyleneO$C_1$-$C_6$alkyl, wherein available hydrogen atoms are optionally replaced with an iodine atom, a fluorine atom, and/or a chlorine atom and/or available hydrogen atoms are optionally replaced with deuterium. In some embodiments, each $R^9$ is independently selected from D, halo, $C_1$-$C_4$alkyl, OH, $OC_1$-$C_4$alkyl, $C_1$-$C_4$alkyleneOH, and $C_1$-$C_4$alkyleneO$C_1$-$C_6$alkyl, wherein available hydrogen atoms are optionally replaced with a fluorine atom and/or a chlorine atom and/or available hydrogen atoms are optionally replaced with deuterium.

In some embodiments, at least one $R^9$ is selected from halo and $C_1$-$C_4$alkyl, wherein available hydrogen atoms are optionally replaced with a fluorine atom and/or a chlorine atom and/or available hydrogen atoms are optionally replaced with deuterium. In some embodiments, at least one $R^9$ is selected from F, Cl, Br, $C_1$-$C_4$alkyl, $C_1$-$C_4$fluoroalkyl, $C_1$-$C_4$deuteroalkyl, and $C_1$-$C_4$deuterofluoroalkyl. In some embodiments, at least one $R^9$ is selected from F, Cl, Br, OH, $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3$, $CF_2CF_3$, $CH_2CH_2D$, $CH_2CD_2H$, $CH_2CD_3CD_2CD_3$, $CH_2CH_2CH_3$, $CH_2CH_2CHF_2$, $CH_2CH_2CFH_2$, $CH_2CH_2CF_3$, $CH_2CH_2CHD_2$, $CH_2CH_2CDH_2$, $CH_2CH_2CD_3CH(CH_3)_2$, $CH(CF_3)_2$, $CH(CHF_2)_2$, $CH(CFH_2)_2$, $CH(CD_3)_2$, $CH(CHD_2)_2$, $CH(CDH_2)_2$, $C(CH_3)_3$, $C(CF_3)_3$, $C(CHF_2)_3$, $C(CFH_2)_3$, $C(CD_3)_3$, $C(CHD_2)_3$, $C(CDH_2)_3$, $CH_2CH_2CH_2CH_3$, $CH_2CH_2CH_2CF_3$, $CH_2CH_2CH_2CD_3$, $CH_2CH(CH_3)_2$, $CH_2CH(CD_3)_2$, $CH_2CH(CF_3)_2$, $CH(CH_3)CH_2CH_3$, $CH(CH_3)CH_2CF_3$, $CH(CH_3)CH_2CD_3$, $CH_2C(CH_3)_3$, $CH_2C(CF_3)_3$, $CH_2C(CD_3)_3$, $CH_2CH_2C(CH_3)_3$, $CH_2CH_2C(CF_3)_3$, and $CH_2CH_2C(CD_3)_3$. In some embodiments, at least one $R^9$ is selected from F, Cl, $CH_3$, $CF_2H$, $CFH_2$, $CF_3$, and $CD_3$.

In some embodiments, at least one $R^9$ is selected from OH, $OC_1$-$C_4$alkyl, $C_1$-$C_4$alkyleneOH, and $C_1$-$C_4$alkyleneO$C_1$-$C_6$alkyl, wherein available hydrogen atoms are optionally replaced with a fluorine atom and/or a chlorine atom and/or available hydrogen atoms are optionally replaced with deuterium. In some embodiments, at least one $R^9$ is selected from OH, $OC_1$-$C_4$alkyl, $OC_1$-$C_4$deuteroalkyl, $OC_1$-$C_4$fluoroalkyl, $OC_1$-$C_4$deuterofluoroalkyl, $C_1$-$C_4$alkyleneOH, $C_1$-$C_4$fluoroalkyleneOH, $C_1$-$C_4$deuteroalkyleneOH, $C_1$-$C_4$deuterofluoroalkyleneOH, $C_1$-$C_4$alkyleneO$C_1$-$C_4$alkyl, $C_1$-$C_4$alkyleneO$C_1$-$C_4$fluoroalkyl, $C_1$-$C_4$alkyleneO$C_1$-$C_4$deuteroalkyl, $C_1$-$C_4$alkyleneO$C_1$-$C_4$deuterofluoroalkyl, $C_1$-$C_4$fluoroalkyleneO$C_1$-$C_4$alkyl, $C_1$-$C_4$deuteroalkyleneO$C_1$-$C_4$alkyl, $C_1$-$C_4$deuterofluoroalkyleneO$C_1$-$C_4$alkyl, $C_1$-$C_4$fluoroalkyleneO$C_1$-$C_4$fluoroalkyl, $C_1$-$C_4$fluoroalkyleneO$C_1$-$C_4$deuteroalkyl, $C_1$-$C_4$deuteroalkyleneO$C_1$-$C_4$fluoroalkyl, $C_1$-$C_4$deuteroalkyleneO$C_1$-$C_4$deuteroalkyl, $C_1$-$C_4$deuterofluoroalkyleneO$C_1$-$C_4$fluoroalkyl, $C_1$-$C_4$fluoroalkyleneO$C_1$-$C_4$deuterofluoroalkyl, and $C_1$-$C_4$deuterofluoroalkyleneO$C_1$-$C_4$deuterofluoroalkyl. In some embodiments, at least one $R^9$ is selected from OH, $OC_1$-$C_4$alkyl, $OC_1$-$C_4$deuteroalkyl, $OC_1$-$C_4$fluoroalkyl, $OC_1$-$C_4$deuterofluoroalkyl, $C_1$-$C_4$alkyleneOH, $C_1$-$C_4$fluoroalkyleneOH, $C_1$-$C_4$alkyleneO$C_1$-$C_4$alkyl, $C_1$-$C_4$alkyleneO$C_1$-$C_4$fluoroalkyl, $C_1$-$C_4$alkyleneO$C_1$-$C_4$deuteroalkyl, and $C_1$-$C_4$alkyleneO$C_1$-$C_4$deuterofluoroalkyl. In some embodiments, at least one $R^9$ is selected from OH, $OC_1$-$C_4$alkyl, $OC_1$-$C_4$deuteroalkyl, $OC_1$-$C_4$fluoroalkyl, $OC_1$-$C_4$deuterofluoroalkyl, $C_1$-$C_4$alkyleneOH, $C_1$-$C_4$fluoroalkyleneOH, $C_1$-$C_4$deuteroalkyleneOH, $C_1$-$C_4$deuterofluoroalkyleneOH, $C_1$-$C_4$alkyleneO$C_1$-$C_3$alkyl, and $C_1$-$C_4$alkyleneO$C_1$-$C_3$fluoroalkyl.

In some embodiments, at least one $R^9$ is selected from OH, $OCH_3$, $OCD_2H$, $OCDH_2$, $OCD_3$, $OCF_2H$, $OCFH_2$, $OCF_3$, $OCH_2CH_3$, $OCH_2CH_2F$, $OCH_2CF_2H$, $OCH_2CF_3$, $OCF_2CF_3$, $OCH_2CH_2D$, $OCH_2CD_2H$, $OCH_2CD_3OCD_2CD_3$, $OCH_2CH_2CH_3$, $OCH_2CH_2CHF_2$, $OCH_2CH_2CFH_2$, $OCH_2CH_2CF_3$, $OCH_2CH_2CHD_2$, $OCH_2CH_2CDH_2$, $OCH_2CH_2CD_3$, $OCH(CH_3)_2$, $OCH(CF_3)_2$, $OCH(CHF_2)_2$, $OCH(CFH_2)$, $OCH(CD_3)_2$, $OCH(CHD_2)_2$, $OCH(CDH_2)_2$, $OC(CH_3)_3$, $OC(CF_3)_3$, $OC(CHF_2)_3$, $OC(CFH_2)_3$, $OC(CD_3)_3$, $OC(CHD_2)_3$, $OC(CDH_2)_3$, $OCH_2CH_2CH_2CH_3$, $OCH_2CH_2CH_2CF_3$, $OCH_2CH_2CH_2CD_3$, $OCH_2CH(CH_3)_2$, $OCH_2CH(CD_3)_2$, $OCH_2CH(CF_3)_2$, $OCH(CH_3)CH_2CH_3$, $OCH(CH_3)CH_2CF_3$, $OCH(CH_3)CH_2CD_3$, $OCH_2C(CH_3)_3$, $OCH_2C(CF_3)_3$, $OCH_2C(CD_3)_3$, $OCH_2CH_2C(CH_3)_3$, $OCH_2CH_2C(CF_3)_3$, $OCH_2CH_2C(CD_3)_3$, $CH_2OH$, $CF_2OH$, $CD_2OH$, $CH_2CH_2OH$, $CF_2CF_2OH$, $CH_2CF_2OH$, $CH_2CD_2OH$, $CD_2CD_2OH$, $CH_2OCH_3$, $CH_2OCD_2H$, $CH_2OCDH_2$, $CH_2OCD_3$, $CH_2OCF_3$, $CH_2OCHF_2$, $CH_2OCH_2F$, $CH_2CH_2OCH_3$, $CH_2CH_2OCD_2H$, $CH_2CH_2OCDH_2$, $CH_2CH_2OCD_3$, $CH_2CH_2OCF_3$, $CH_2CH_2OCHF_2$, and $CH_2CH_2OCH_2F$. In some embodiments, at least one $R^9$ is selected from OH, $OCH_3$, $OCF_2H$, $OCFH_2$, $OCF_3$, and $OCD_3$.

In some embodiments, n is an integer selected from 0, 1, and 2. In some embodiments, n is 2. In some embodiments, n is an integer selected from 0 and 1. In some embodiments, n is 1. In some embodiments, n is 0.

In some embodiments, $R^{10}$ is selected from H, $C_1$-$C_6$alkyl, $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted with one to four substituents independently selected from halo, $C_1$-$C_6$alkyl, $OR^{15}$, and $C(O)R^{15}$, and wherein available hydrogen atoms are optionally replaced with a halogen atom and/or available atoms are optionally replaced with an alternate isotope thereof. In some embodiments, $R^{10}$ is selected from H, $C_1$-$C_6$alkyl, $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted with one to four substituents independently selected from halo, $C_1$-$C_6$alkyl, $OR^{15}$, and $C(O)R^{15}$, and wherein available hydrogen atoms are optionally replaced with an iodine atom, a fluorine atom, and/or a chlorine atom and/or available hydrogen atoms are optionally replaced with deuterium. In some embodiments, $R^{10}$ is selected from H, $C_1$-$C_6$alkyl, $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted with one to four substituents independently selected from halo, $C_1$-$C_6$alkyl, $OR^{15}$, and $C(O)R^{15}$, and wherein available hydrogen atoms are optionally replaced with a fluorine atom and/or a chlorine atom and/or available hydrogen atoms are optionally replaced with deuterium.

In some embodiments, one of $R^6$ and $R^{10}$ is not H, $C_1$-$C_6$alkyl, $C_1$-$C_6$fluoroalkyl, $C_1$-$C_6$deuteroalkyl, or $C_1$-$C_6$deuterofluoroalkyl. In some embodiments, one of $R^6$ and $R^{10}$ is not H, $C_1$-$C_6$fluoroalkyl, $C_1$-$C_6$deuteroalkyl, or $C_1$-$C_6$deuterofluoroalkyl. In some embodiments, $R^6$ is selected from $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted with one to four substituents independently selected from halo, $C_1$-$C_6$alkyl, $OR^{13}$, and $C(O)R^{13}$, and $R^{10}$ is selected from H and $C_1$-$C_6$alkyl, wherein available hydrogen atoms are optionally replaced with a halogen atom and/or available atoms are optionally replaced with an alternate isotope thereof.

In some embodiments, $R^6$ is selected from H and $C_1$-$C_6$alkyl, and $R^{10}$ is selected from $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted one to four substituents independently selected from halo, $C_1$-$C_6$alkyl, $OR^{15}$, and $C(O)R^{15}$, wherein available hydrogen atoms are optionally replaced with a halogen atom and/or available atoms are optionally replaced with an alternate isotope thereof.

In some embodiments, $R^{10}$ is selected from H and $C_1$-$C_6$alkyl, wherein available hydrogen atoms are optionally replaced with a fluorine atom and/or a chlorine atom and/or available hydrogen atoms are optionally replaced with deuterium. In some embodiments, $R^{10}$ is selected from H, D, $C_1$-$C_6$alkyl, $C_1$-$C_6$deuteroalkyl, $C_1$-$C_6$fluoroalkyl, and $C_1$-$C_6$deuteroalkyl. In some embodiments, $R^{10}$ is selected from H, D, $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3$, $CF_2CF_3$, $CH_2CH_2D$, $CH_2CD_2H$, $CH_2CD_3CD_2CD_3$, $CH_2CH_2CH_3$, $CH_2CH_2CHF_2$, $CH_2CH_2CFH_2$, $CH_2CH_2CF_3$, $CH_2CH_2CHD_2$, $CH_2CH_2CDH_2$, $CH_2CH_2CD_3CH(CH_3)_2$, $CH(CF_3)_2$, $CH(CHF_2)_2$, $CH(CFH_2)_2$, $CH(CD_3)_2$, $CH(CHD_2)_2$, $CH(CDH_2)_2$, $C(CH_3)_3$, $C(CF_3)_3$, $C(CHF_2)_3$, $C(CFH_2)_3$, $C(CD_3)_3$, $C(CHD_2)_3$, $C(CDH_2)_3$, $CH_2CH_2CH_2CH_3$, $CH_2CH_2CH_2CF_3$, $CH_2CH_2CH_2CD_3$, $CH_2CH(CH_3)_2$, $CH_2CH(CD_3)_2$, $CH_2CH(CF_3)_2$, $CH(CH_3)CH_2CH_3$, $CH(CH_3)CH_2CF_3$, $CH(CH_3)CH_2CD_3$, $CH_2CH(CH_3)CH_3$, $CH_2CH(CH_3)$ $CF_3$, $CH_2CH(CH_3)$ $CD_3$, $CH_2C(CH_3)_3$, $CH_2C(CF_3)_3$, $CH_2C(CD_3)_3$, $CH_2CH_2C(CH_3)_3$, $CH_2CH_2C(CF_3)_3$, and $CH_2CH_2C(CD_3)_3$. In some embodiments, $R^{10}$ is selected from H, $CH_3$, $CF_2H$, $CFH_2$, $CF_3$, $CH_2CH_3$, $CH_2CH_2F$, $CH_2CF_2H$, $CH_2CF_3$, $CH_2CH_2CH_3$, $CH_2CH_2CHF_2$, $CH_2CH_2CFH_2$, $CH_2CH_2CF_3$, $CH(CH_3)_2$, $CH(CF_3)_2$, $C(CH_3)_3$, $C(CF_3)_3$, $CH_2CH_2CH_2CH_3$, $CH_2CH_2CH_2CF_3$, $CH_2CH_2CH_2CHF_2$, $CH_2CH(CH_3)_2$, $CH_2CH(CF_3)_2$, $CH(CH_3)CH_2CH_3$, $CH(CH_3)CH_2CF_3$, $CH_2C(CH_3)_3$, $CH_2C(CF_3)_3$, $CH_2CH_2C(CH_3)_3$, and $CH_2CH_2C(CF_3)_3$. In some embodiments $R^{10}$ is selected from H, $CH_3$, $CH_2CH_3$, $CH_2CF_3$, $CH_2CH_2CH_3$, $CH(CH_3)_2$, $CH_2C(CH_3)_3$, $CH_2CH_2C(CH_3)_3$, $CD_3$, $CF_3$, $CHF_2$, $CH_2F$, $CH_2CF_2H$, $CH_2CH_2F$, $CH_2CH_2CHF_2$, and $CH_2CH_2CF_3$.

In some embodiments, $R^{10}$ is selected from $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted one to four substituents independently selected from halo, $C_1$-$C_6$alkyl, $OR^{15}$, and $C(O)R^{15}$, and wherein available hydrogen atoms are optionally replaced with a fluorine atom and/or a chlorine atom and/or available hydrogen atoms are optionally replaced with deuterium.

In some embodiments, $R^{10}$ is selected from $C_4$-$C_6$alkenyl and $C_2$-$C_6$alkynyl wherein available hydrogen atoms are optionally replaced with a fluorine atom and/or a chlorine atom and/or available hydrogen atoms are optionally replaced with deuterium. In some embodiments, $R^{10}$ is selected from $C_2$-$C_6$alkenyl, $C_2$-$C_6$fluoroalkenyl, $C_2$-$C_6$deuteroalkenyl, $C_2$-$C_6$deuterofluoroalkenyl, $C_2$-$C_6$alkynyl, $C_2$-$C_6$fluoroalkynyl, $C_2$-$C_6$deuteroalkynyl, and $C_2$-$C_6$deuterofluoroalkynyl. In some embodiments, $R^{10}$ is selected from $C_2$-$C_4$alkenyl, $C_2$-$C_4$fluoroalkenyl, $C_2$-$C_6$deuteroalkenyl, $C_2$-$C_6$deuterofluoroalkenyl, $C_2$-$C_4$alkynyl, $C_2$-$C_4$fluoroalkynyl, $C_2$-$C_4$deuteroalkynyl, and $C_2$-$C_4$deuterofluoroalkynyl. In some embodiments, $R^{10}$ is selected from $CH{=}CH_2$, $CH_2CH{=}CH_2$, $CF_2CH{=}CH_2$, $CD_2CH{=}CH_2$, $CH{=}CH_2CH_3$, $CH{=}CH_2CF_3$, $CH{=}CH_2CHF_2$, $CH{=}CH_2CH_2F$, $CH{=}CH_2CD_3$, $CH{=}CH_2CHD_2$, $CH{=}CH_2CH_2D$, $C{\equiv}CH$, $C{\equiv}CCH_3$, $C{\equiv}CCF_3$, $C{\equiv}CCHF_2$, $C{\equiv}CCFH_2$, $C{\equiv}CCD_3$, $C{\equiv}CCHD_2$, $C{\equiv}CCDH_2$, $CH_2C{\equiv}CH$, $CF_2C{\equiv}CH$, $CD_2C{\equiv}CH$, $CH_2C{\equiv}CCH_3$, $CF_2C{\equiv}CCH_3$, $CD_2C{\equiv}CCH_3$, $CH_2C{\equiv}CCD_3$, $CF_2C{\equiv}CCD_3$, $CD_2C{\equiv}CCD_3$, $CH_2C{\equiv}CCF_3$, $CF_2C{\equiv}CCF_3$, $CD_2C{\equiv}CCF_3$, $CH_2C{\equiv}CCHD_2$, $CF_2C{\equiv}CHD_2$, $CD_2C{\equiv}CHD_2$, $CH_2C{\equiv}CHF_2$, $CF_2C{\equiv}CHF_2$, and $CD_2C{\equiv}CHF_2$. In some embodiments, $R^{10}$ is selected from $CH{=}CH_2$, $CH_2CH{=}CH_2$, $C{\equiv}CH$ $C{\equiv}CCH_3$, $CH_2C{\equiv}CH$, and $CH_2C{\equiv}CCH_3$.

In some embodiments, $R^{10}$ is selected from $C_1$-$C_6$alkyleneZ'$R^{14}$, $C_2$-$C_6$alkenyleneZ'$R^{14}$, and $C_2$-$C_6$alkynyleneZ'$R^{14}$, wherein available hydrogen atoms are optionally replaced with a fluorine atom and/or a chlorine atom and/or available hydrogen atoms are optionally replaced with deuterium. In some embodiments, $R^{10}$ is selected from $C_1$-$C_6$alkyleneZ'$R^{14}$, $C_2$-$C_6$alkenyleneZ'$R^{14}$, and $C_2$-$C_6$alkynyleneZ'$R^{14}$, wherein available hydrogen atoms are optionally replaced with a fluorine atom and/or a chlorine atom and/or available hydrogen atoms are optionally replaced with deuterium.

In some embodiments, $R^{10}$ is selected from $C_1$-$C_6$alkyleneZ'$R^{14}$, $C_1$-$C_6$fluoroalkyleneZ'$R^{14}$, $C_1$-$C_6$deuteroalkyleneZ'$R^{14}$, $C_1$-$C_6$deuterofluoroalkyleneZ'$R^{14}$, $C_2$-$C_6$alkenyleneZ'$R^{14}$, $C_2$-$C_6$fluoroalkenyleneZ'$R^{14}$, $C_2$-$C_6$deuteroalkenyleneZ'$R^{14}$, $C_2$-$C_6$deuterofluoroalkenyleneZ'$R^{14}$, $C_2$-$C_6$alkynyleneZ'$R^{14}$, $C_2$-$C_6$fluoroalkynyleneZ'$R^{14}$, $C_2$-$C_6$deuteroalkynyleneZ'$R^{14}$, and $C_2$-$C_6$deuterofluoroalkynyleneZ'$R^{14}$. In some embodiments, $R^{10}$ is selected from $C_1$-$C_6$alkyleneZ'$R^{14}$, $C_1$-$C_6$fluoroalkyleneZ'$R^{14}$, $C_1$-$C_6$deuteroalkyleneZ'$R^{14}$, $C_1$-$C_6$deuterofluoroalkyleneZ'$R^{14}$, $C_2$-$C_6$alkenyleneZ'$R^{14}$, and $C_2$-$C_6$alkynyleneZ'$R^{14}$. In some embodiments, $R^{10}$ is selected from $C_1$-$C_4$alkyleneZ'$R^{14}$, $C_1$-$C_4$fluoroalkyleneZ$R^{14}$, $C_1$-$C_4$deuteroalkyleneZ'$R^{14}$, $C_1$-$C_4$deuterofluoroalkyleneZ'$R^{14}$, $C_2$-$C_4$alkenyleneZ'$R^{14}$, $C_2$-$C_4$fluoroalkenyleneZ'$R^{14}$, $C_2$-$C_4$deuteroalkenyleneZ'$R^{14}$, $C_2$-$C_4$deuterofluoroalkenyleneZ'$R^{14}$, $C_2$-$C_4$alkynyleneZ'$R^{14}$, $C_2$-$C_4$fluoroalkynyleneZ'$R^{14}$, $C_2$-$C_4$deuteroalkynyleneZ'$R^{14}$, and $C_2$-$C_4$deuterofluoroalkynyleneZ'$R^{14}$. In some embodiments, $R^{10}$ is selected from $C_1$-$C_4$alkyleneZ'$R^{14}$, $C_1$-$C_4$fluoroalkyleneZ'$R^{14}$, $C_1$-$C_4$deuteroalkyleneZ'$R^{14}$, $C_1$-$C_4$deuterofluoroalkyleneZ'$R^{14}$, $C_2$-$C_4$alkenyleneZ'$R^{14}$, and $C_2$-$C_4$alkynyleneZ'$R^{14}$.

In some embodiments, $R^{10}$ is selected from $CH_2Z'R^{14}$, $CH_2CH_2Z'R^{14}$, $CH_2CH_2CH_2Z'R^{14}$, $CH_2CH_2CH_2CH_2Z'R^{14}$, $CH(CH_3)CH_2Z'R^{14}$, $CH(CH_3)CH_2CH_2Z'R^{14}$, $CH_2CH(CH_3)Z'R^{14}$. $CF_2Z'R^{14}$, $CFHZ'R^{14}$, $CH_2CHFZ'R^{14}$, $CH_2CF_2Z'R^{14}$, $CF_2CF_2Z'R^{14}$, $CH_2CH_2CF_2Z'R^{14}$, $CH_2CH_2CFHZ'R^{14}$, $CH_2CH_2CF_2Z'R^{14}$, $CH(CH_3)CF_2Z'R^{14}$, $CH(CH_3)CHFZ'R^{14}$, $CH_2CH_2CH_2CF_2Z'R^{14}$, $CH_2CH_2CH_2CHFZ'R^{14}$, $CH(CH_3)CH_2CF_2Z'R^{14}$, $CH(CH_3)CH_2CHFZ'R^{14}$, $CD_2Z'R^{14}$, $CDHZ'R^{14}$, $CH_2CHDZ'R^{14}$, $CH_2CD_2Z'R^{14}$, $CD_2CD_2Z'R^{14}$, $CH_2CH_2CD_2Z'R^{14}$, $CH_2CH_2CDHZ'R^{14}$, $CH_2CH_2CD_2Z'R^{14}$, $CH(CH_3)CD_2Z'R^{14}$, $CH(CH_3)CHDZ'R^{14}$, $CH_2CH_2CH_2CD_2Z'R^{14}$, $CH_2CH_2CH_2CHDZ'R^{14}$, $CH(CH_3)CH_2CD_2Z'R^{14}$, $CH(CH_3)CH_2CHDZ'R^{14}$, $CH{=}CHZ'R^{14}$, $CH_2CH{=}CHZ'R^{14}$, $C{\equiv}CZ'R^{14}$, $C{\equiv}CCH_2Z'R^{14}$, $CH_2C{\equiv}CZ'R^{14}$, and $CH_2C{\equiv}CH_2Z'R^{14}$. In some embodiments, $R^{10}$ is selected from $CH_2Z'R^{14}$, $CH_2CH_2Z'R^{14}$, $CH_2CH_2CH_2Z'R^{14}$, $CH_2CH_2CH_2CH_2Z'R^{14}$, $CH(CH_3)CH_2Z'R^{14}$, $CH(CH_3)CH_2CH_2Z'R^{14}$, $CH_2CH(CH_3)Z'R^{14}$, $CH{=}CHZ'R^{14}$, $CH_2CH{=}CHZ'R^{14}$, $CH{=}CH_2CHZ'R^{14}$, $C{\equiv}CCH_2Z'R^{14}$, $CH_2C{\equiv}CZ'R^{14}$, and $CH_2C{\equiv}CH_2Z'R^{14}$.

In some embodiments, $R^{10}$ is selected from $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, each of which is optionally substituted with one to four substituents independently selected from halo, $C_1$-$C_6$alkyl, $OR^{15}$, and $C(O)R^{15}$, and wherein available hydrogen atoms are optionally replaced with a fluorine atom and/or a chlorine atom and/or available hydrogen atoms are optionally replaced with deuterium. In some embodiments, $R^{10}$ is selected from $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, $C_1$-$C_4$alkylene$C_5$-$C_{10}$heteroaryl, $C_1$-$C_4$fluoroalkylene$C_3$-$C_7$cycloalkyl, $C_1$-$C_4$fluoroalkylene$C_3$-$C_{10}$heterocycloalkyl, $C_1$-$C_4$fluoroalkylene$C_6$-$C_{10}$aryl, $C_1$-$C_4$fluoroalkylene$C_5$-$C_{10}$heteroaryl, $C_1$-$C_4$deuteroalkylene$C_3$-$C_7$cycloalkyl, $C_1$-$C_4$deuteroalkylene$C_3$-$C_{10}$heterocycloalkyl, $C_1$-$C_4$deuteroalkylene$C_6$-$C_{10}$aryl, $C_1$-$C_4$deuteroalkylene$C_5$-$C_{10}$heteroaryl, and $C_1$-$C_4$deuterofluoroalkylene$C_3$-$C_7$cycloalkyl, $C_1$-$C_4$deuterofluoroalkylene$C_3$-$C_{10}$heterocycloalkyl, $C_1$-$C_4$deuterofluoroalkylene$C_6$-$C_{10}$aryl, and $C_1$-$C_4$deuterofluoroalkylene$C_5$-$C_{10}$heteroaryl, in which each of the cyclic groups is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally replaced with a fluorine atom and/or a chlorine atom and/or available hydrogen atoms are optionally replaced with deuterium. In some embodiments, $R^{10}$ is selected from $C_3$-$C_7$cycloalkyl, $C_3$-$C_{10}$heterocycloalkyl, $C_6$-$C_{10}$aryl, $C_5$-$C_{10}$heteroaryl, $C_1$-$C_2$alkylene$C_3$-$C_7$cycloalkyl, $C_1$-$C_2$alkylene$C_3$-$C_{10}$heterocycloalkyl, $C_1$-$C_2$alkylene$C_6$-$C_{10}$aryl, $C_1$-$C_2$alkylene$C_5$-$C_{10}$heteroaryl, $C_1$-$C_2$fluoroalkylene$C_3$-$C_7$cycloalkyl, $C_1$-$C_2$fluoroalkylene$C_3$-$C_{10}$heterocycloalkyl, $C_1$-$C_2$fluoroalkylene$C_6$-$C_{10}$aryl, $C_1$-$C_2$fluoroalkylene$C_5$-$C_{10}$heteroaryl, $C_1$-$C_2$deuteroalkylene$C_3$-$C_7$cycloalkyl, $C_1$-$C_2$deuteroalkylene$C_3$-$C_{10}$heterocycloalkyl, $C_1$-$C_2$deuteroalkylene$C_6$-$C_{10}$aryl, $C_1$-$C_2$deuteroalkylene$C_5$-$C_{10}$heteroaryl, $C_1$-$C_2$deuterofluoroalkylene$C_3$-$C_7$cycloalkyl, $C_1$-$C_2$deuterofluoroalkylene$C_3$-$C_{10}$heterocycloalkyl, $C_1$-$C_2$deuterofluoroalkylene$C_6$-$C_{10}$aryl, and $C_1$-$C_2$deuterofluoroalkylene$C_5$-$C_{10}$heteroaryl, in which each of the cyclic groups is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally replaced with a fluorine atom and/or a chlorine atom and/or available hydrogen atoms are optionally replaced with deuterium.

In some embodiments, the $C_3$-$C_7$cycloalkyl in $R^{10}$ is selected from cyclopropyl, cyclobutyl, cyclopentyl, cyclohexyl, and cycloheptyl, each or which is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally replaced with a fluorine atom and/or a chlorine atom and/or available hydrogen atoms are optionally replaced with deuterium. In some embodiments, the $C_3$-$C_7$cycloalkyl in $R^{10}$ is selected from cyclopropyl, cyclobutyl, cyclopentyl, and cyclohexyl, each of which is optionally substituted with one to three substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally replaced with a fluorine atom and/or a chlorine atom and/or available hydrogen atoms are optionally replaced with deuterium. In some embodiments, the $C_3$-$C_7$cycloalkyl in $R^{10}$ is selected from cyclopropyl, cyclobutyl, cyclopentyl, and cyclohexyl, each of which is optionally substituted with one or two substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally replaced with a fluorine atom and/or a chlorine atom and/or available hydrogen atoms are optionally replaced with deuterium.

In some embodiments, the $C_3$-$C_{10}$heterocycloalkyl in $R^{10}$ is a monocyclic $C_3$-$C_7$heterocycloalkyl or a bicyclic $C_7$-$C_{10}$heterocycloalkyl, each of which is optionally substituted with one to four, one to three, or one or two, substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally replaced with a fluorine atom and/or a chlorine atom and/or available hydrogen atoms are optionally replaced with deuterium.

In some embodiments, the monocyclic $C_3$-$C_7$heterocycloalkyl in $R^{10}$ is selected from aziridinyl, oxiranyl, thiiranyl, oxaxiridinyl, dioxiranyl, 1,3-dioxolanyl, azetidinyl, oxetanyl, theitanyl, diazetidinyl, dioxetanyl, dithietanyl, tetrahydrofuranyl, tetrahydrothiophenyl, 2H-1λ3-thiophenyl, pyrrolidinyl, imidazolidinyl, pyrazolidinyl, isoxothiolidinyl, thiazolidinyl, isothiazolidinyl, imidazolidinyl, imidazolinyl, dioxolanyl, dithiolanyl, triazolyl, dioxazolyl, dithiazolyl, tetrazolyl, oxatetrazolyl, tetrahydropyranyl, dihydropyranyl, isothiazolidinyl, morpholinyl, 2-oxopiperazinyl, 2-oxopiperidinyl, 2-oxopyrrolidinyl, piperidinyl, piperazinyl, tetrahydropyridinyl, thiomorpholinyl, thiomorpholinyl sulfoxide, thiomorpholinyl dioxide, dioxanyl, thiazolinyl, thianyl, thianyl oxide, thianyl dioxide, dithianyl, azepanyl, pyrazolidinedionyl, oxepanyl, thiepanyl, diazepanyl, and 2,5-pyrrolidinedionyl (e.g., succinimidyl), each of which is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally replaced with a fluorine atom and/or a chlorine atom and/or available hydrogen atoms are optionally replaced with deuterium. In some embodiments, the monocyclic $C_3$-$C_7$heterocycloalkyl in $R^{10}$ is selected from oxetanyl, tetrahydrofuranyl, tetrahydrothiophenyl, 2H-1λ3-thiophenyl, pyrrolidinyl, imidazolidinyl, tetrahydropyranyl, dihydropyranyl, 2-oxopiperazinyl, 2-oxopiperidinyl, 2-oxopyrrolidinyl, piperidinyl, piperazinyl, thianyl, thianyl oxide, thianyl dioxide, dithianyl, and 2,5-pyrrolidinedionyl, each of which is optionally substituted with one to three, or one or two, substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally replaced with a fluorine atom and/or a chlorine atom and/or available hydrogen atoms are optionally replaced with deuterium.

In some embodiments, the bicyclic $C_7$-$C_{10}$heterocycloalkyl in $R^{10}$ is selected from benzoisoxazolyl, dihydrobenzofuranyl, dihydrobenzothienyl, benzopyranyl, benzothiopyranyl, chromanyl, isochromanyl, dihydroindenyl, isoindolinyl, 1-oxoisoindolinyl, 3-oxoisoindolinyl, 1,3-dioxoisoindolinyl (e.g., phthalimido), octahydroisoindolinyl, octahydro-isoindolin-1-onyl (e.g., tetrahydroisoquinoline), and hexahydroisoindoline-1,3-dionyl (e.g., cis-hexahydrophthalimidyl), each of which is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally replaced with a fluorine atom and/or a chlorine atom and/or available hydrogen atoms are optionally replaced with deuterium. In some embodiments, the bicyclic $C_7$-$C_{10}$heterocycloalkyl in $R^{10}$ is selected from isoindolinyl, 1-oxoisoindolinyl, 3-oxoisoindolinyl, 1,3-dioxoisoindolinyl, octahydro-1H-isoindolinyl, octahydro-1H-isoindolin-1-onyl, and hexahydro-1H-isoindoline-1,3-dionyl, each of which is optionally substituted with one to three, or one or two, substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally replaced with a fluorine atom and/or a chlorine atom and/or available hydrogen atoms are optionally replaced with deuterium.

In some embodiments, the $C_6$-$C_{10}$aryl in $R^{10}$ is phenyl, optionally substituted with one to four, one to three, or one or two, substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally replaced with a fluorine atom and/or a chlorine atom and/or available hydrogen atoms are optionally replaced with deuterium.

In some embodiments, the $C_5$-$C_{10}$heteroaryl in $R^{10}$ is selected from azepinyl, benzofuranyl, benzofurazanyl, benzothiazolyl, benzothienyl, benzoxazolyl, cinnolinyl, furanyl, imidazolyl, indolinyl, indolyl, isoquinolinyl, isothiazolyl, naphthyridinyl, oxadiazolyl, 2-oxoazepinyl, oxazolyl, oxadiazolyl, thiadiazolyl, pyridyl, pyrazinyl, pyrazolyl, pyridazinyl, pyrimidinyl, pyrrolidinyl, pyrrolyl, quinazolinyl, quinolinyl, quinoxalinyl, thiazolyl, thienofuranyl, triazolyl, and thienyl (e.g., thiophenyl), each of which is optionally substituted with one to four, one to three, or one or two, substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally replaced with a fluorine atom and/or a chlorine atom and/or available hydrogen atoms are optionally replaced with deuterium.

In some embodiments, the substituents on $R^{10}$ are independently selected from one to four of F, Cl, Br, $CH_3$, $CH_2CH_3$, $CH_2CH_2CH_3$, $CH(CH_3)_2$, $C(CH_3)_3$, $CD_2H$, $CDH_2$, $CD_3$, $CF_3$, $CHF_2$, $CH_2F$, $CH_2CH_2F$, $CF_2CF_3$, $CH_2CH_2D$, $CH_2CD_2H$, $CD_2CD_3$, $OR^{15}$, and $C(O)R^{15}$. In some embodiments, the substituents on $R^{10}$ are independently selected from one to three of F, Cl, $CH_3$, $CH_2CH_3$, $CH_2CH_2CH_3$, $CH(CH_3)_2$, $CH(CH_3)_2$, $CD_2H$, $CDH_2$, $CD_3$, $CF_3$, $CHF_2$, $CH_2F$, $OR^{15}$, and $C(O)R^{15}$. In some embodiments, the substituents on $R^{10}$ are independently selected from one or two of F, Cl, $CH_3$, $CH(CH_3)_2$, $CH(CH_3)_2$, $CF_3$, $CHF_2$, $CH_2F$, $OR^{15}$, and $C(O)R^{15}$.

In some embodiments, particularly when X is absent or O, as well as for X is S, S(O), or $SO_2$, $R^6$ is selected from $C_1$-$C_4$fluoroalkyl, $C_1$-$C_4$alkyleneZ$R^{12}$, and $C_1$-$C_4$fluoroalkyleneZ$R^{12}$ or $R^{10}$ is selected from $C_1$-$C_4$fluoroalkyl, $C_1$-$C_4$alkyleneZ'$R^{14}$, and $C_1$-$C_4$fluoroalkyleneZ'$R^{14}$. In some embodiments, particularly when X is absent or O, as well as other embodiments, $R^6$ is selected from $C_1$-$C_4$alkyleneZ$R^{12}$ and $C_1$-$C_4$fluoroalkyleneZ$R^{12}$ or $R^{10}$ is selected from $C_1$-$C_4$alkyleneZ'$R^{14}$ and $C_1$-$C_4$fluoroalkyleneZ'$R^{14}$.

In some embodiments, particularly when X is absent or O, or when X is S, S(O), or $SO_2$, Z' is selected from $NR^{17}C(O)$, $NR^{17}C(O)O$, $C(O)NR^{17}$, $OC(O)NR^{17}$, and $NR^{17}$. In some embodiments, Z is selected from O, C(O), $NR^{17}C(O)$, and $NR^{17}C(O)O$. In some embodiments, Z' is O. In some embodiments, Z' is C(O). In some embodiments, Z' is $NR^{17}C(O)$. In some embodiments, Z' is $NR^{17}C(O)O$.

In some embodiments, $R^{12}$ and $R^{14}$ are independently selected from H, $C_1$-$C_4$alkyl, $C_3$-$C_7$cycloalkyl, $C_3$-$C_7$heterocycloalkyl, $C_6$-$C_{10}$aryl, and $C_5$-$C_{10}$heteroaryl, the latter four groups being optionally substituted with one to four substituents independently selected from F, Cl, Br, $C_1$-$C_4$alkyl, $OC_1$-$C_4$alkyl, and $C(O)C_1$-$C_4$alkyl, and wherein available hydrogen atoms are optionally replaced with a halogen atom and/or available atoms are optionally replaced with an alternate isotope thereof. In some embodiments, $R^{12}$ and $R^{14}$ are independently selected from H, $C_1$-$C_4$alkyl, $C_3$-$C_7$cycloalkyl, $C_3$-$C_7$heterocycloalkyl, $C_6$-$C_{10}$aryl, and $C_5$-$C_{10}$heteroaryl, the latter four groups being optionally substituted with one to three substituents independently selected from F, Cl, $C_1$-$C_4$alkyl, and $OC_1$-$C_4$alkyl, and wherein available hydrogen atoms are optionally replaced with an iodine atom, a fluorine atom, and/or a chlorine atom and/or available hydrogen atoms are optionally replaced with deuterium. In some embodiments, $R^{12}$ and $R^{14}$ are independently selected from H, $C_1$-$C_4$alkyl, $C_3$-$C_7$-cycloalkyl, $C_3$-$C_7$heterocycloalkyl, $C_6$-$C_{10}$aryl, and $C_5$-$C_{10}$heteroaryl, the latter four groups being optionally substituted with one to three substituents independently selected from F, Cl, $C_1$-$C_4$alkyl, and $OC_1$-$C_4$alkyl, and wherein available hydrogen atoms are optionally replaced with a fluorine atom and/or a chlorine atom and/or available hydrogen atoms are optionally replaced with deuterium.

In some embodiments, $R^{12}$ and $R^{14}$ are independently selected from H and $C_1$-$C_6$alkyl, wherein available hydrogen atoms are optionally replaced with a fluorine atom and/or a chlorine atom and/or available hydrogen atoms are optionally replaced with deuterium. In some embodiments, $R^{12}$ and $R^{14}$ are independently selected from H, D, $C_1$-$C_6$alkyl, $C_1$-$C_6$fluoroalkyl, $C_1$-$C_6$deuteroalkyl, and $C_1$-$C_6$deuterofluoroalkyl.

In some embodiments, $R^{12}$ and $R^{14}$ are independently selected from H, D, $CH_3$, $CH_2CH_3$, $CH_2CH_2CH_3$, $CH(CH_3)_2$, $C(CH_3)_3$, $CH_2CH_2CH_2CH_3$, $CH_2CH(CH_3)_2$, $CH(CH_3)CH_2CH_3$, $CF_2H$, $CFH_2$, $CF_3$, $CH_2CH_2F$, $CH_2CF_2H$, $CH_2CF_3$, $CF_2CF_3$, $CH_2CH_2CHF_2$, $CH_2CH_2CFH_2$, $CH_2CH_2CF_3$, $CH(CF_3)_2$, $CH(CHF_2)_2$, $CH(CFH_2)_2$, $C(CF_3)_3$, $C(CHF_2)_3$, $C(CFH_2)_3$, $CH_2CH_2CH_2CF_3$, $CH_2CH(CF_3)_2$, $CH(CH_3)CH_2CF_3$, $CD_2H$, $CDH_2$, $CD_3$, $CH_2CH_2D$, $CH_2CD_2H$, $CH_2CD_3$, $CD_2CD_3$, $CH_2CH_2CHD_2$, $CH_2CH_2CDH_2$, $CH_2CH_2CD_3$, $CH(CD_3)_2$, $CH(CHD_2)_2$, $CH(CDH_2)_2$, $C(CD_3)_3$, $C(CHD_2)_3$, $C(CDH_2)_3$, $CH_2CH_2CH_2CD_3$, $CH_2CH(CD_3)_2$, and $CH(CH_3)CH_2CD_3$. In some embodiments, $R^{12}$ and $R^{14}$ are independently selected from H, D, $CH_3$, $CH_2CH_3$, $CH(CH_3)_2$, $C(CH_3)_3$, $CF_2H$, $CFH_2$, $CF_3$, $CH_2CH_2F$, $CH_2CF_2H$, $CH_2CF_3$, $CH(CF_3)_2$, $CH(CHF_2)_2$, $CH(CFH_2)_2$, $C(CF_3)_3$, $C(CHF_2)_3$, $C(CFH_2)_3$, $CD_2H$, $CDH_2$, $CD_3$, $CH_2CH_2D$, $CH_2CD_2H$, $CH_2CD_3$, $CH(CD_3)_2$, $CH(CHD_2)_2$, $CH(CDH_2)_2$, $C(CD_3)_3$, $C(CHD_2)_3$, and $C(CDH_2)_3$. In some embodiments, $R^{12}$ and $R^{14}$ are independently selected from H, D, $CH_3$, $CH(CH_3)_2$, $C(CH_3)_3$, $CF_2H$, $CDF_2$, $CF_3$, $CD_2H$, $CDH_2$, and $CD_3$.

In some embodiments, $R^{12}$ and $R^{14}$ are independently selected from $C_3$-$C_7$cycloalkyl, $C_3$-$C_{10}$heterocycloalkyl, $C_6$-$C_{10}$aryl, and $C_5$-$C_{10}$heteroaryl, each of which is optionally substituted with one to four substituents independently selected from halo, $C_1$-$C_4$alkyl, $OC_1$-$C_4$alkyl, and $C(O)C_1$-$C_4$alkyl, and wherein available hydrogen atoms are optionally replaced with a fluorine atom and/or a chlorine atom and/or available hydrogen atoms are optionally replaced with deuterium.

In some embodiments, the $C_3$-$C_7$cycloalkyl in $R^{12}$ and/or $R^{14}$ is independently selected from cyclopropyl, cyclobutyl, cyclopentyl, cyclohexyl, and cycloheptyl, each of which is optionally substituted with one to four substituents independently selected from halo, $C_1$-$C_4$alkyl, $OC_1$-$C_4$alkyl, and $C(O)C_1$-$C_4$alkyl, and wherein available hydrogen atoms are optionally replaced with a fluorine atom and/or a chlorine atom and/or available hydrogen atoms are optionally replaced with deuterium.

In some embodiments, the $C_3$-$C_{10}$heterocycloalkyl in $R^{12}$ and/or $R^{14}$ is independently a monocyclic $C_3$-$C_7$heterocycloalkyl or a bicyclic $C_7$-$C_{10}$heterocycloalkyl, each of which is optionally substituted with one to four substituents independently selected from halo, $C_1$-$C_4$alkyl, $OC_1$-$C_4$alkyl, and $C(O)C_1$-$C_4$alkyl, and wherein available hydrogen atoms are optionally replaced with a fluorine atom and/or a chlorine atom and/or available hydrogen atoms are optionally replaced with deuterium.

In some embodiments, the monocyclic $C_3$-$C_7$heterocycloalkyl in $R^{12}$ and/or $R^{14}$ is independently selected from aziridinyl, oxiranyl, thiiranyl, oxaxiridinyl, dioxiranyl, 1,3-dioxolanyl, azetidinyl, oxetanyl, theitanyl, diazetidinyl, dioxetanyl, dithietanyl, tetrahydrofuranyl, tetrahydrothiophenyl, 2H-1λ3-thiophenyl, pyrrolidinyl, imidazolidinyl, pyrazolidinyl, isoxothiolidinyl, thiazolidinyl, isothiazolidinyl, imidazolidinyl, imidazolinyl, dioxolanyl, dithiolanyl, triazolyl, dioxazolyl, dithiazolyl, tetrazolyl, oxatetrazolyl, tetrahydropyranyl, dihydropyranyl, isothiazolidinyl, morpholinyl, 2-oxopiperazinyl, 2-oxopiperidinyl, 2-oxopyrrolidinyl, piperidinyl, piperazinyl, tetrahydropyridinyl, thiomorpholinyl, thiomorpholinyl sulfoxide, thiomorpholinyl dioxide, dioxanyl, thiazolinyl, thianyl, thianyl oxide, thianyl dioxide, dithianyl, azepanyl, pyrazolidinyl, oxepanyl, thiepanyl, diazepanyl, and 2,5-pyrrolidinedionyl (e.g., succinimidyl), each of which is optionally substituted with one to four substituents independently selected from halo, $C_1$-$C_4$alkyl, $OC_1$-$C_4$alkyl, and $C(O)C_1$-$C_4$alkyl, and wherein available hydrogen atoms are optionally replaced with a fluorine atom and/or a chlorine atom and/or available hydrogen atoms are optionally replaced with deuterium. In some embodiments, the monocyclic $C_3$-$C_7$heterocycloalkyl in $R^{12}$ and/or $R^{14}$ is independently selected from oxetanyl, tetrahydrofuranyl, tetrahydrothiophenyl, 2H-1λ3-thiophenyl, pyrrolidinyl, imidazolidinyl, tetrahydropyranyl, dihydropyranyl, 2-oxopiperazinyl, 2-oxopiperidinyl, 2-oxopyrrolidinyl, piperidinyl, piperazinyl, thianyl, thianyl oxide, thianyl dioxide, dithianyl, and 2,5-pyrrolidinedionyl, each of which is optionally substituted with one to four substituents independently selected from halo, $C_1$-$C_4$alkyl, $OC_1$-$C_4$alkyl, and $C(O)C_1$-$C_4$alkyl, and wherein available hydrogen atoms are optionally replaced with a fluorine atom and/or a chlorine atom and/or available hydrogen atoms are optionally replaced with deuterium.

In some embodiments, the bicyclic $C_7$-$C_{10}$heterocycloalkyl in $R^{12}$ and/or $R^{14}$ is independently selected from benzoisoxazolyl, dihydrobenzofuranyl, dihydrobenzothienyl, benzopyranyl, benzothiopyranyl, chromanyl, isochromanyl, dihydroindenyl, isoindolinyl, 1-oxoisoindolinyl, 3-oxoisoindolinyl, 1,3-dioxoisoindolinyl (e.g., phthalimido), octahydroisoindolinyl, octahydro-isoindolin-1-onyl (e.g., tetrahydroisoquinoline), and hexahydroisoindoline-1,3-dionyl (e.g., cis-hexahydrophthalimidyl), each of which is optionally substituted with one to four substituents independently selected from halo, $C_1$-$C_4$alkyl, $OC_1$-$C_4$alkyl, and $C(O)C_1$-$C_4$alkyl, and wherein available hydrogen atoms are optionally replaced with a fluorine atom and/or a chlorine atom and/or available hydrogen atoms are optionally replaced with deuterium. In some embodiments, the bicyclic $C_7$-$C_{10}$heterocycloalkyl in $R^{12}$ and/or $R^{14}$ is independently selected from isoindolinyl, 1-oxoisoindolinyl, 3-oxoisoindolinyl, 1,3-dioxoisoindolinyl, octahydro-1H-isoindolinyl, octahydro-1H-isoindolin-1-onyl, and hexahydro-1H-isoindoline-1,3-dionyl, each of which is optionally substituted with one to four substituents independently selected from halo, $C_1$-$C_4$alkyl, $OC_1$-$C_4$alkyl, and $C(O)C_1$-$C_4$alkyl, and wherein available hydrogen atoms are optionally replaced with a fluorine atom and/or a chlorine atom and/or available hydrogen atoms are optionally replaced with deuterium.

In some embodiments, the $C_6$-$C_{10}$aryl in $R^{12}$ and/or $R^{14}$ is independently phenyl, which is optionally substituted with one to four substituents independently selected from halo, $C_1$-$C_4$alkyl, $OC_1$-$C_4$alkyl, and $C(O)C_1$-$C_4$alkyl, and wherein available hydrogen atoms are optionally replaced with a fluorine atom and/or a chlorine atom and/or available hydrogen atoms are optionally replaced with deuterium.

In some embodiments, the $C_5$-$C_{10}$heteroaryl in $R^{12}$ and/or $R^{14}$ is independently selected from azepinyl, benzofuranyl, benzofurazanyl, benzothiazolyl, benzothienyl, benzoxazolyl, cinnolinyl, furanyl, imidazolyl, indolinyl, indolyl, isoquinolinyl, isothiazolyl, naphthyridinyl, oxadiazolyl, 2-oxoazepinyl, oxazolyl, oxadiazolyl, thiadiazolyl, pyridyl, pyrazinyl, pyrazolyl, pyridazinyl, pyrimidinyl, pyrrolidinyl, pyrrolyl, quinazolinyl, quinolinyl, quinoxalinyl, thiazolyl, thienofuranyl, triazolyl, and thienyl (e.g., thiophenyl), each of which is optionally substituted with one to four substituents independently selected from halo, $C_1$-$C_4$alkyl, $OC_1$-$C_4$alkyl, and $C(O)C_1$-$C_4$alkyl, and wherein available hydrogen atoms are atoms are optionally replaced with deuterium.

In some embodiments, the substituents on $R^{12}$ and/or $R^{14}$ are independently selected from one to four, one to three, or one or two, of F, Cl, Br, $CH_3$, $CH_2CH_3$, $CH_2CH_2CH_3$, $CH(CH_3)_2$, $C(CH_3)_3$, $CD_2H$, $CDH_2$, $CD_3$, $CF_3$, $CHF_2$, $CH_2F$, $CH_2CH_2F$, $CF_2CF_3$, $CH_2CH_2D$, $CH_2CD_2H$, $CD_2CD_3$, $OCH_3$, $OCH_2CH_3$, $OCH_2CH_2CH_3$, $OCH(CH_3)_2$, $OC(CH_3)_3$, $OCD_2H$, $OCDH_2$, $OCD_3$, $OCF_3$, $OCHF_2$, $OCH_2F$, $OCH_2CH_2F$, $OCF_2CF_3$, $OCH_2CH_2D$, $OCH_2CD_2H$, $OCD_2CD_3$, $C(O)CH_3$, $C(O)CH_2CH_3$, $C(O)CH_2CH_2CH_3$, $C(O)CH(CH_3)_2$, $C(O)C(CH_3)_3$, $C(O)CD_2H$, $C(O)CDH_2$, $C(O)CD_3$, $C(O)CF_3$, $C(O)CHF_2$, $C(O)CH_2F$, $C(O)CH_2CH_2F$, $C(O)CF_2CF_3$, $C(O)CH_2CH_2D$, $C(O)CH_2CD_2H$, and $C(O)CD_2CD_3$.

In some embodiments, $R^{11}$, $R^{13}$, $R^{15}$, $R^{16}$, and $R^{17}$ are independently selected from H and $C_1$-$C_4$alkyl wherein available hydrogen atoms are optionally replaced with a halogen atom and/or available atoms are optionally replaced with an alternate isotope thereof. In some embodiments, $R^{11}$, $R^{13}$, $R^{15}$, $R^{16}$, and $R^{17}$ are independently selected from H and $C_1$-$C_4$alkyl wherein available hydrogen atoms are optionally replaced with an iodine atom, a fluorine atom, and/or a chlorine atom and/or available hydrogen atoms are optionally replaced with deuterium. In some embodiments, $R^{11}$, $R^{13}$, $R^{15}$, $R^{16}$, and $R^{17}$ are independently selected from H and $C_1$-$C_4$alkyl wherein available hydrogen atoms are optionally replaced with a fluorine atom and/or a chlorine atom and/or available hydrogen atoms are optionally replaced with deuterium.

In some embodiments, $R^{11}$, $R^{13}$, $R^{15}$, $R^{16}$, and $R^{17}$ are independently selected from H, D, $C_1$-$C_4$alkyl, $C_1$-$C_4$fluoroalkyl, $C_1$-$C_4$deuteroalkyl, and $C_1$-$C_4$deuterofluoroalkyl. In some embodiments, $R^{11}$, $R^{13}$, $R^{15}$, $R^{16}$, and $R^{17}$ are independently selected from H, D, F, Br, Cl, $CH_3$, $CD_2H$, $CDH_2$, $CD_3$, $CF_3$, $CHF_2$, $CH_2F$, $CH_2CH_3$, $CH_2CH_2F$, $CF_2CF_3$, $CH_2CH_2D$, $CH_2CD_2H$, and $CD_2CD_3$. In some embodiments, $R^{11}$, $R^{13}$, $R^{15}$, $R^{16}$, and $R^{17}$ are independently selected from H, $CH_3$, $CF_3$, $CHF_2$, $CD_2H$, $CDH_2$, and $CD_3$. In some embodiments, $R^{11}$, $R^{13}$, $R^{15}$, $R^{16}$, and $R^{17}$ are independently selected from H, D, $CH_3$, $CF_3$, $CHF_2$, $CH_2F$, $CD_2H$, $CDH_2$, and $CD_3$. In some embodiments, $R^{11}$, $R^{13}$, $R^{15}$, $R^{16}$, and $R^{17}$ are independently selected from H, D, $CH_3$, $CF_3$, and $CD_3$.

In some embodiments, particularly when X is selected from S, S(O), and $SO_2$, as well for X being O or absent, $R^6$ is selected from $CH_3$, $CD_3$, $CF_3$, $CH_2CH_3$, $CH_2CH_2CH_3$, $CH(CH_3)_2$, $CH_2C(CH_3)_3$, $CH_2CH_2C(CH_3)_3$, $CH_2F$, $CHF_2$, $CH_2CHF_2$, $CH_2CF_3$, $CH_2CH_2CF_3$,

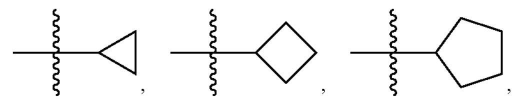
, , ,

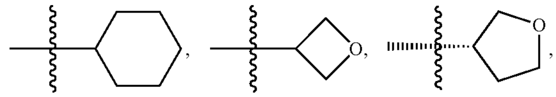
, , ,

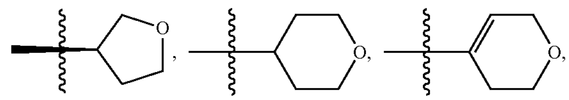
, , ,

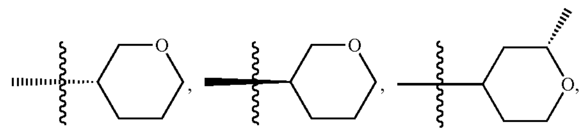
, , ,

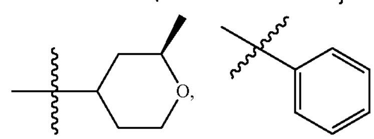
, ,

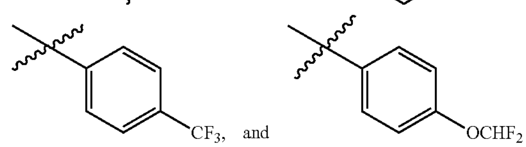
and

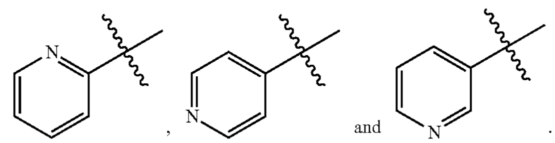
, and .

In some embodiments, $R^{10}$ is selected from (particularly for when X is S, S(O), or $SO_2$, as well as other embodiments in which X is O or is absent) or $R^6$ and $R^{10}$ are independently selected from (particularly for when X is absent or oxygen, as well as for other embodiments of X):

H, $CH_3$, $CD_3$, $CF_3$, $CH_2CH_3$, $CH_2CH_2CH_3$, $CH(CH_3)_2$, $CH_2C(CH_3)_3$, $CH_2CH_2C(CH_3)_3$, $CH_2F$, $CHF_2$, $CH_2CHF_2$, $CH_2CF_3$, $CH_2CH_2CF_3$, $C_1$-$C_4$alkyleneOCH$_3$, $C_1$-$C_4$alkyleneOCHF$_2$, $C_1$-$C_4$alkyleneOCH$_2$F,

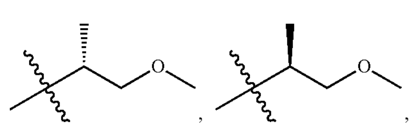
, ,

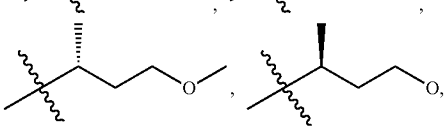
, ,

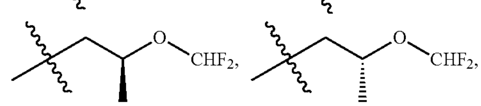
, ,

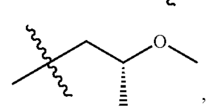
, $C_1$-$C_4$alkyleneC(O)$CHF_2$, $C_1$-$C_4$alkyleneC(O)$CF_3$,
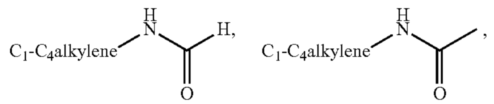
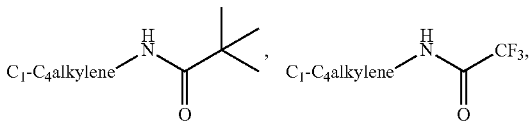
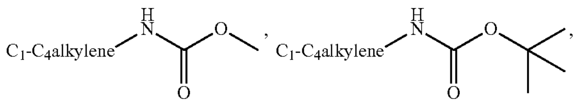
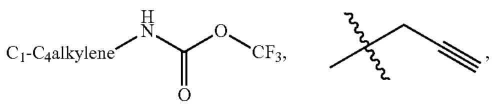
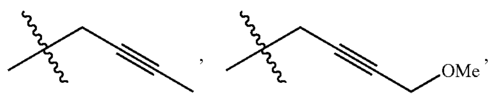
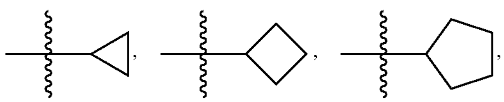
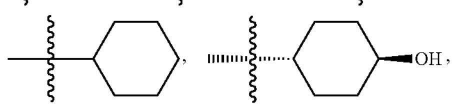
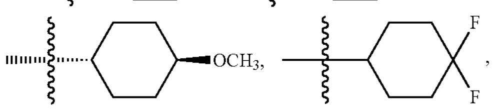
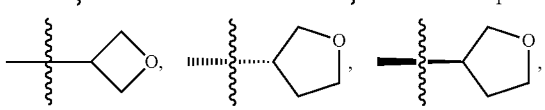
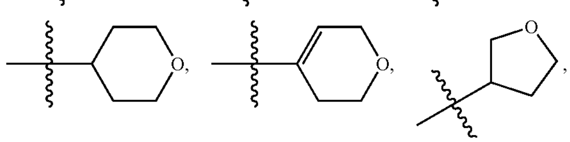
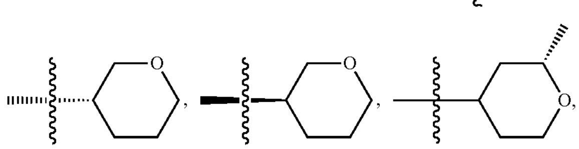
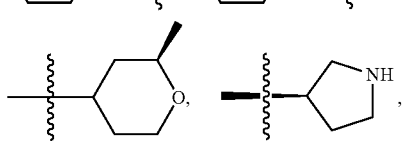
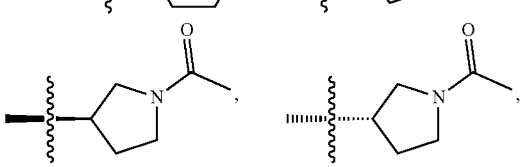
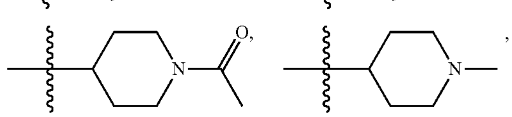
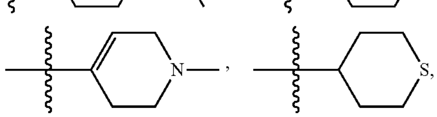
-continued
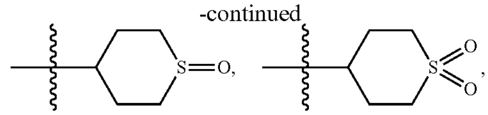
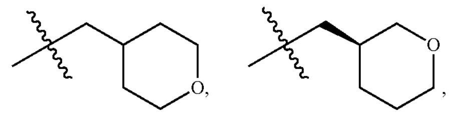
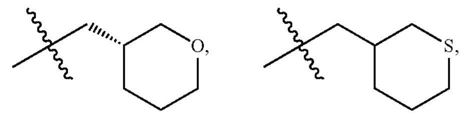
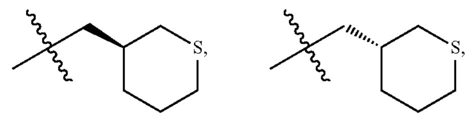
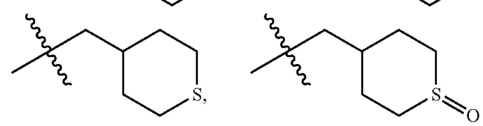
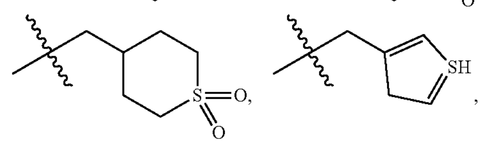
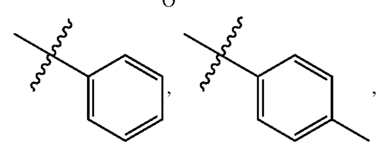
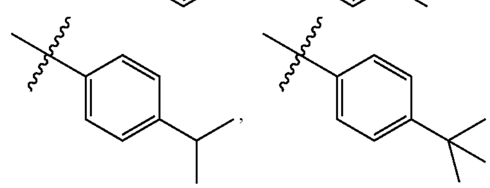
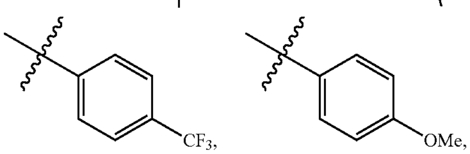
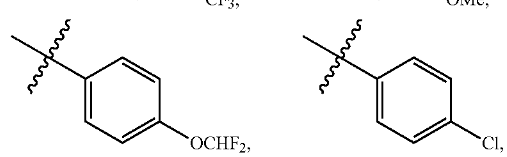
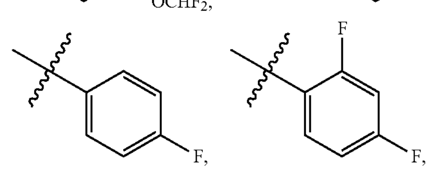
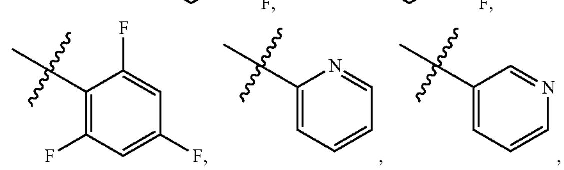
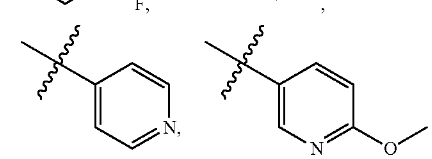

-continued
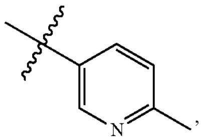,
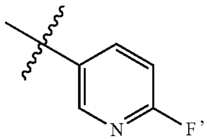,
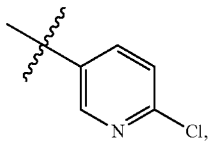,
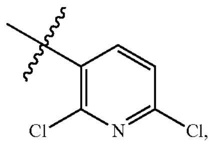,
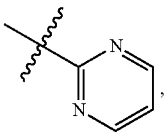,
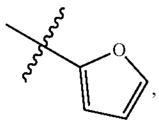,
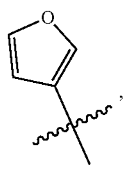,
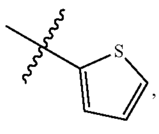,
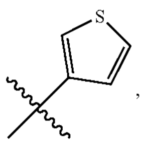,
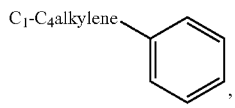,
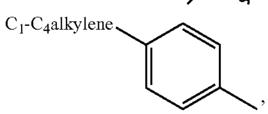,
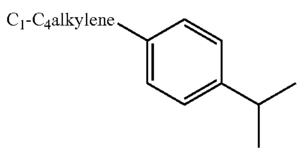,
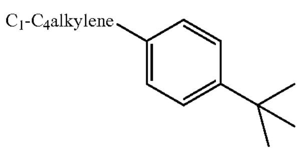,
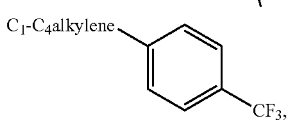,
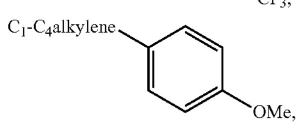,
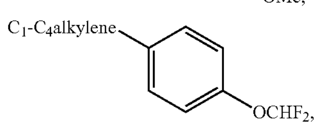,
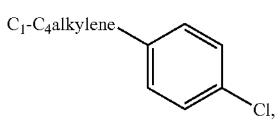,
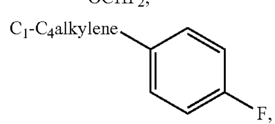,
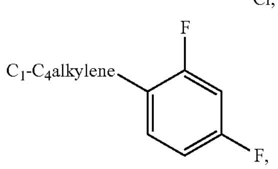,
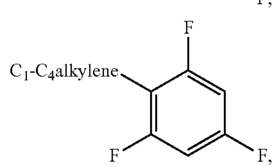,
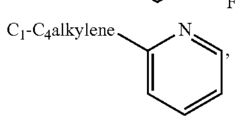,
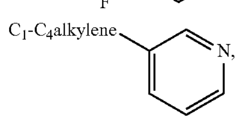,
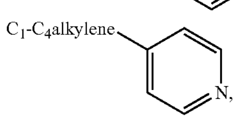,
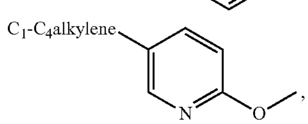,
-continued
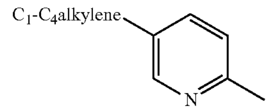,
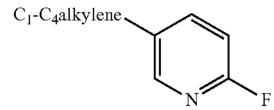,
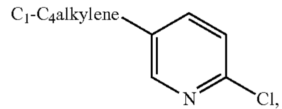,
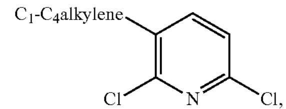,
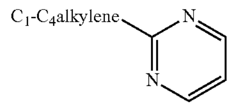,
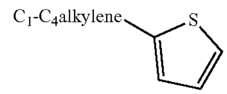,
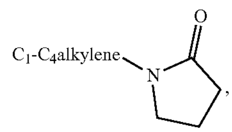,
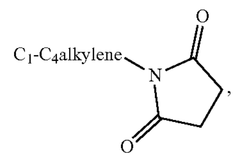,
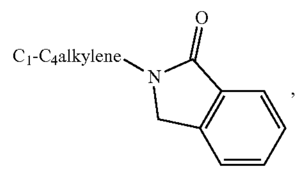,
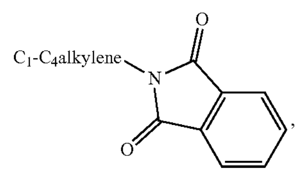,
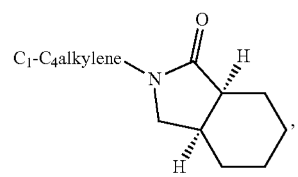,
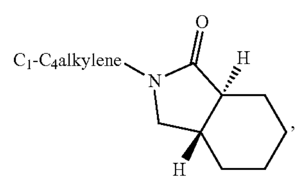,
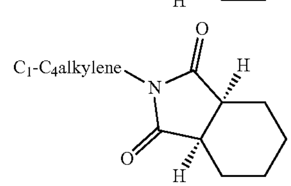,
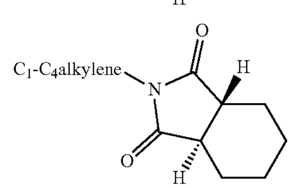,
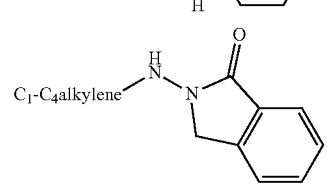, -continued

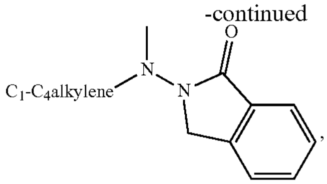,
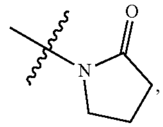,
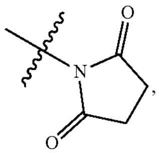,
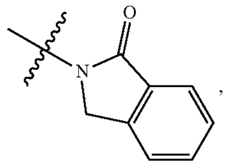,
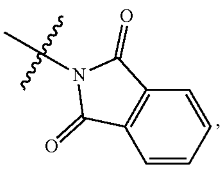,
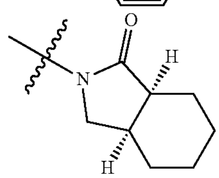,
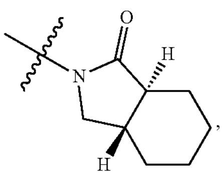,
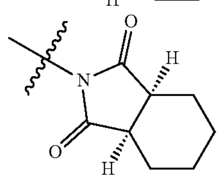,
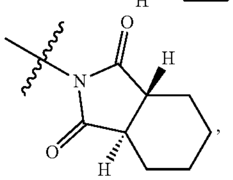,
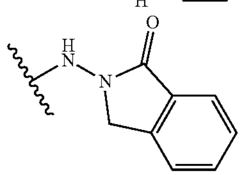, and
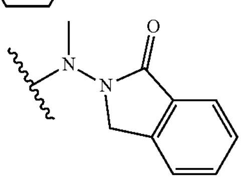.

In the above embodiments and in other embodiments using the term herein, $C_1$-$C_4$alkylene includes, for example, —$CH_2$, —$CH_2CH_2$—, —$CH_2CH_2CH_2$, —$CH_2CH_2CH_2CH_2$—, —$CH(CH_3)CH_2$—, —$CH_2CH(CH_3)$—, —$C(CH_3)_2$—, —$CH(CH_3)CH_2CH_2$—, —$CH_2CH(CH_3)CH_2$—, —$CH_2CH_2CH(CH_3)$—, —$C(CH_3)_2CH_2$—, —$CH_2C(CH_3)_2$—, and —$CH(CH_3)CH(CH_3)$—. Available hydrogen(s) on the $C_1$-$C_4$alkylene is/are optionally substituted with deuterium and/or one or more halogen atoms, for example but not limited to, —$CF_2$—, —$CBr_2$—, —$CCl_2$—, —CHD-, —$CD_2$-, —CDF—, —$CF_2CF_2$—, —$CH_2CD_2$-, —$CD_2CH_2$—, —$CH_2$CHD-, —CHD$CH_2$—, —$CH_2$CHY—, —CHY$CH_2$—, —$CH_2CY_2$—, —$CY_2CH_2$—, —CHYCHY—, —CHDCHY—, —CHY-CHD-, —$CD_2$CHY—, CHY$CD_2$, —CHD$CY_2$—, —$CY_2$CHD-, —$CY_2CD_2$-, —$CD_2CY_2$—, —$CD_2$CHD-, —CHD$CD_2$-, —$CD_2CD_2$-, —$CD_2CD_2CD_2$-, —$CH_2CD_2CD_2$-, —$CD_2CH_2CH_2$—, —$CH_2CH_2CD_2$-, —$CD_2CD_2CH_2$—, —$CH_2CD_2CH_2$—, —$CH_2CH_2$CHD-, —CHDCHD$CH_2$—, —$CH_2$CHDCHD-, —$CD_2CD(CH_3)$—, —$CD_2$CHD$CH_2$—, —$CH_2CD(CH_3)$—, —$CH_2$CHD$CH_2$—, —$CD_2CH(CH_3)$—, —CHD$CH_2CH_2$—, —CHDCH$(CH_3)$—, etc. (wherein each Y is independently selected from F, Cl, Br, and I).

In some embodiments, particularly when X is absent or oxygen, as well as for other embodiments in which X is S, S(O), or $SO_2$, $R^{10}$ in addition to the list above, is further independently H.

In some embodiments, the compound of Formula (I) is a compound of Formula (I-A):

Formula (I-A)

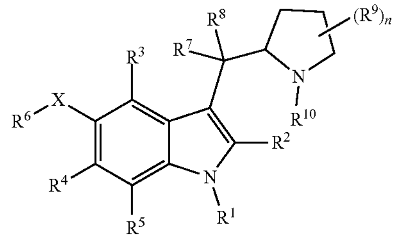

or a pharmaceutically acceptable salt, solvate, and/or prodrug thereof, wherein:

X, n, $R^1$, $R^2$, $R^3$, $R^4$, $R^5$, $R^6$, $R^7$, $R^8$, $R^9$, and $R^{10}$ are as defined in Formula (I) including embodiments thereof, wherein X is selected from S, S(O), and $SO_2$;

available hydrogen atoms are optionally replaced with a halogen atom and/or available atoms are optionally replaced with an alternate isotope thereof, provided when $R^9$ is selected from halo and $C_1$-$C_6$alkyl, $R^{10}$ is selected from H and $C_1$-$C_6$alkyl, n is 0, 1, 2, 3, or 4, and $R^6$ is selected from H, substituted or unsubstituted $C_1$-$C_6$alkyl, $C_2$-$C_6$alkenyl, $C_2$-$C_6$alkynyl, $C_3$-$C_7$cycloalkyl, $C_3$-$C_7$heterocycloalkyl, $C_6$-$C_{10}$aryl, and $C_5$-$C_{10}$heteroaryl, then the compound does not comprise deuterium.

In some embodiments, the compound of Formula (I) is a compound of Formula (I-B):

Formula (I-B)

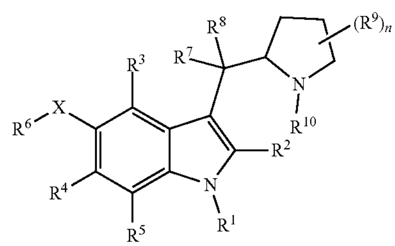

or a pharmaceutically acceptable salt, solvate, and/or prodrug thereof, wherein

X, n, $R^1$, $R^2$, $R^3$, $R^4$, $R^5$, $R^6$, $R^7$, $R^8$, $R^9$, and $R^{10}$ are as defined in Formula (I) including embodiments thereof, wherein X is selected from S, S(O), and $SO_2$; and available hydrogen atoms are optionally replaced with a halogen atom.

In some embodiments, the compound of Formula (I) is a compound of Formula (I-C):

Formula (I-C)

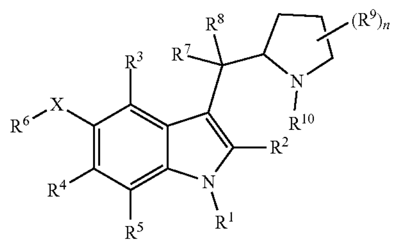

or a pharmaceutically acceptable salt, solvate, and/or prodrug thereof, wherein:

each $R^9$ is independently selected from OH, $OC_1$-$C_6$alkyl, $C_1$-$C_6$alkyleneOH, and $C_1$-$C_6$alkyleneO$C_1$-$C_6$alkyl;

X, $R^1$, $R^2$, $R^3$, $R^4$, $R^5$ $R^6$, $R^7$, $R^8$, and $R^{10}$, and n are as defined in Formula (I) including embodiments thereof, wherein X is selected from S, S(O), and $SO_2$; and available hydrogen atoms are optionally replaced with a halogen atom and/or available atoms are optionally replaced with an alternate isotope thereof.

In some embodiments, the compound of Formula (I) is a compound of Formula (I-D):

Formula (I-D)

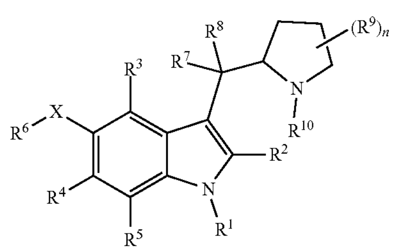

or a pharmaceutically acceptable salt, solvate, and/or prodrug thereof, wherein:

$R^{10}$ is selected from $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, $C_1$-$C_6$alkylene$C_5$-$C_{10}$heteroaryl, the latter eight groups being optionally substituted with one to four substituents independently selected from halo, $C_1$-$C_6$alkyl, $OR^{15}$, and $C(O)R^{15}$;

X, Z', $R^1$, $R^2$, $R^3$, $R^4$, $R^5$ $R^6$, $R^7$, $R^8$, $R^9$, $R^{14}$, $R^{15}$, and n are as defined in Formula (I) including embodiments thereof, wherein X is selected from S, S(O), and $SO_2$; and available hydrogen atoms are optionally replaced with a halogen atom and/or available atoms are optionally replaced with an alternate isotope thereof.

In some embodiments, the compound of Formula (I) is a compound of Formula (I-E):

Formula (I-E)

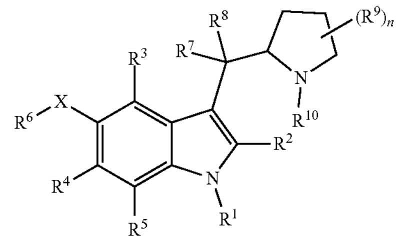

or a pharmaceutically acceptable salt, solvate, and/or prodrug thereof, wherein:

$R^6$ is selected from $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_7$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{13}$, and $C(O)R^{13}$;

X, Z, $R^1$, $R^2$, $R^3$, $R^4$, $R^5$, $R^7$, $R^8$, $R^9$, $R_{10}$. $R^{12}$, and $R^{13}$, and n are as defined in Formula (I) including embodiments thereof, wherein X is selected from S, S(O), and $SO_2$; and available hydrogen atoms are optionally replaced with a halogen atom and/or available atoms are optionally replaced with an alternate isotope thereof.

In some embodiments, X is S and $R^2$, $R^3$, $R^4$, and $R^5$ are all H and the compound of Formula (I) is a compound of Formula (I-F). Accordingly, in some embodiments, the present disclosure includes a compound of Formula (I-F):

Formula (I-F)

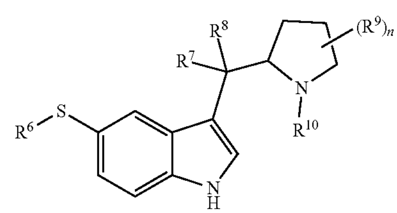

or a pharmaceutically acceptable salt, solvate, and/or prodrug thereof, wherein:

$R^6$, $R^7$, $R^8$, $R^9$, $R^{10}$, and n are as defined in Formula (I) including embodiments thereof;

wherein available hydrogen atoms are optionally replaced with a halogen atom and/or available atoms are optionally replaced with an alternate isotope thereof.

In some embodiments, in the compound of Formula (I-F), $R^{10}$ is selected from $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, I, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, $C_1$-$C_6$alkylene$C_5$-$C_{10}$heteroaryl, the latter eight groups being optionally substituted with one to four substituents independently selected from halo, $C_1$-$C_6$alkyl, $OR^{15}$, and C(O)$R^{15}$, wherein Z', $R^{14}$, and $R^{15}$ are as defined in Formula (I) including embodiments thereof.
In some embodiments, the compound of Formula (I) is selected from one or more of the compounds listed in Table 1 below:
TABLE 1
| Compound | Structure |
|---|---|
| (R) I-1 | 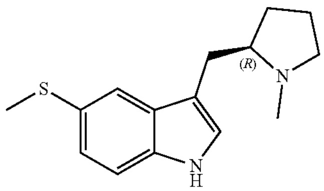 |
| (S) I-1 | 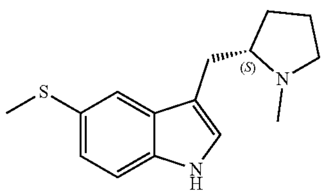 |
| (R) I-2 | 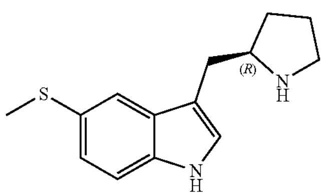 |
| (S) I-2 | 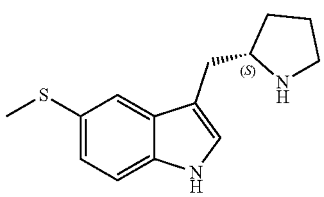 |
| (R) I-3 | 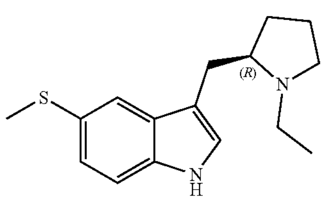 |
| (R) I-4 | 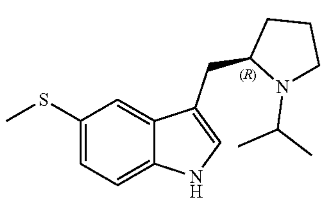 |
| (R) I-5 | 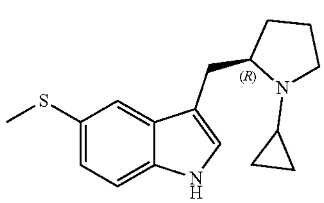 |
TABLE 1-continued
| Compound | Structure |
|---|---|
| (R) I-6 | 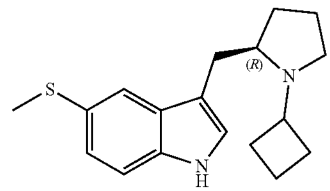 |
| (R) I-7 | 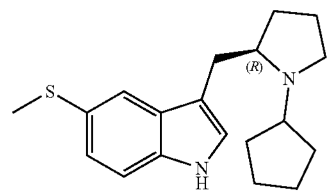 |
| (R, R) I-8 | 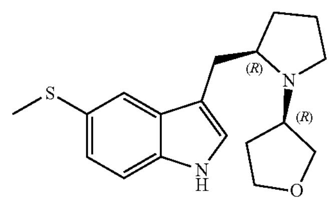 |
| (R, S) I-8 | 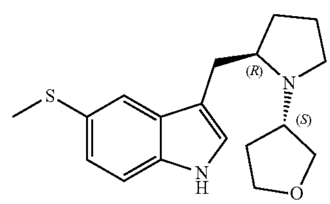 |
| (R, S) I-9 | 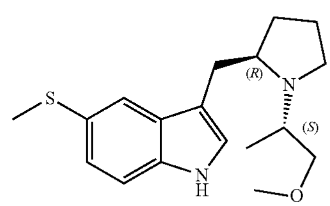 |
| (R, R) I-9 | 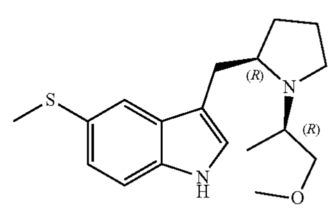 |
| (R) I-10 | 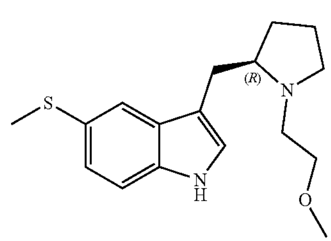 |

TABLE 1-continued
| Compound | Structure |
|---|---|
| (R) I-11 | 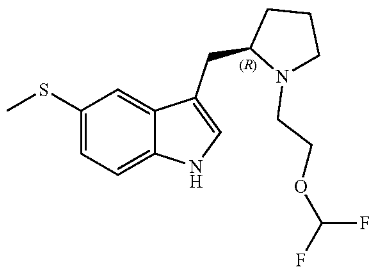 |
| (R) I-12 | 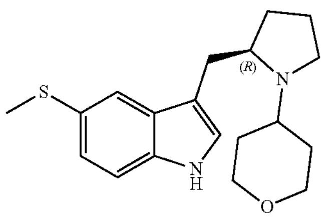 |
| (R, S) I-13 | 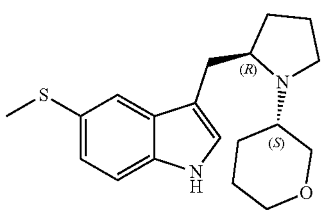 |
| (R, R) I-13 | 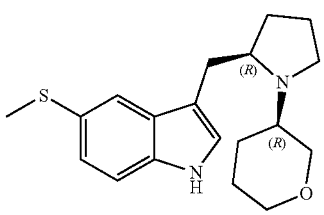 |
| (R) I-14 | 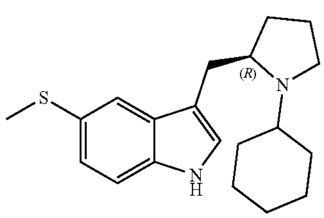 |
| trans (R) I-15 | 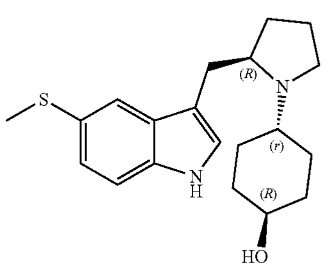 |
TABLE 1-continued
| Compound | Structure |
|---|---|
| trans (R) I-16 | 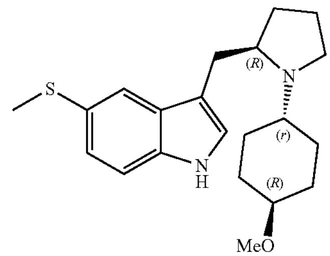 |
| (R, R) I-17 | 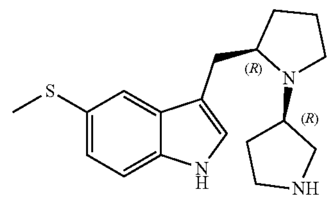 |
| (R) I-18 | 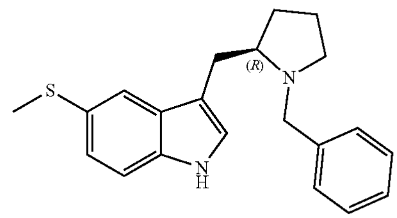 |
| (R) I-19 | 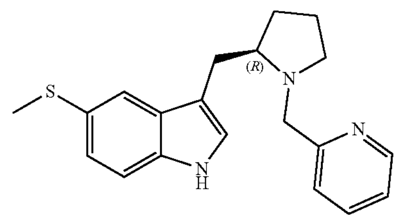 |
| (R) I-20 | 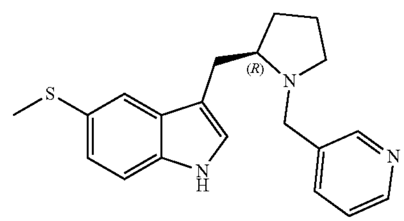 |
| (R) I-21 | 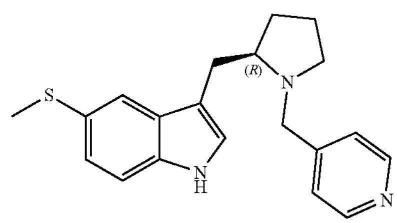 |
| (R) I-22 | 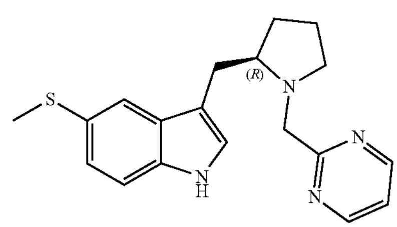 |

TABLE 1-continued
| Compound | Structure |
| --- | --- |
| (R) I-23 | 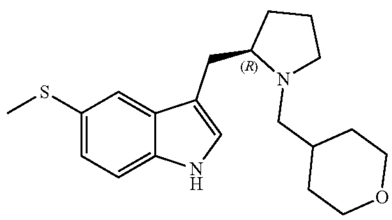 |
| (R, S) I-24 | 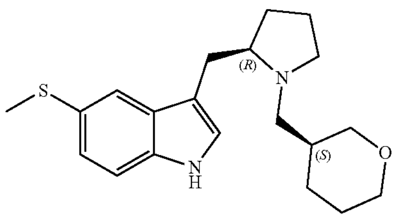 |
| (R, R) I-24 | 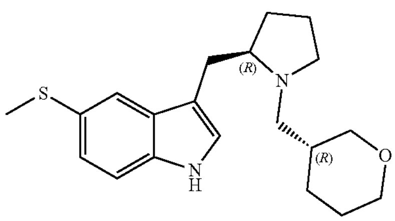 |
| (R, S) I-25 | 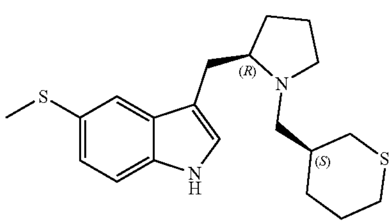 |
| (R, R) I-25 | 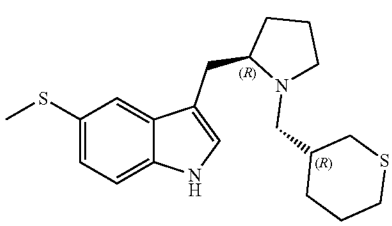 |
| (R) I-26 | 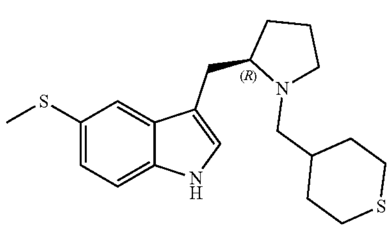 |
| (R) I-27 | 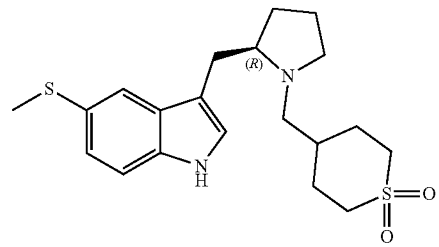 |
| (R) I-28 | 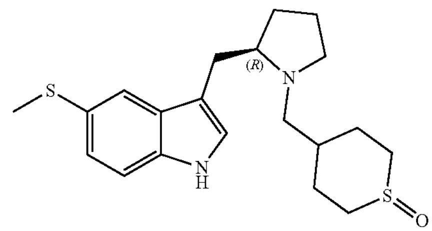 |
| (R) I-29 | 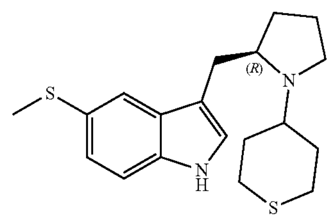 |
| (R) I-30 | 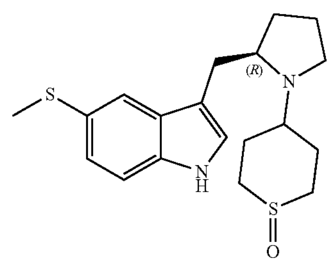 |
| (R) I-31 | 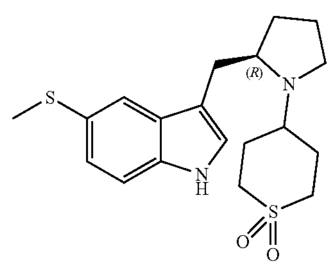 |
| (R) I-32 | 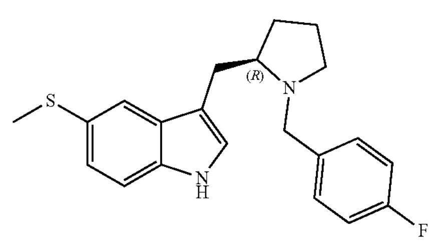 |

TABLE 1-continued
| Compound | Structure |
|---|---|
| (R) I-33 | 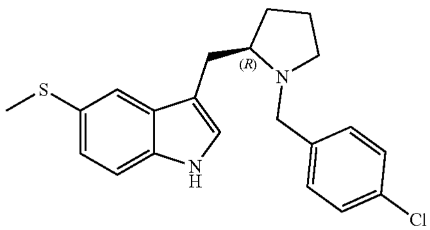 |
| (R) I-34 | 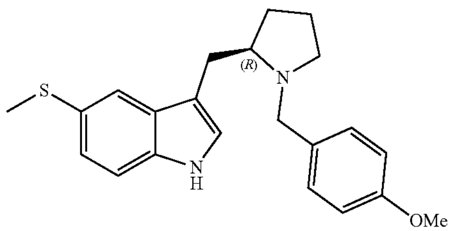 |
| (R) I-35 | 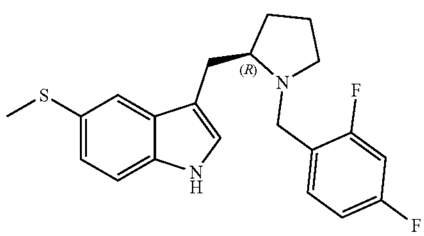 |
| (R) I-36 | 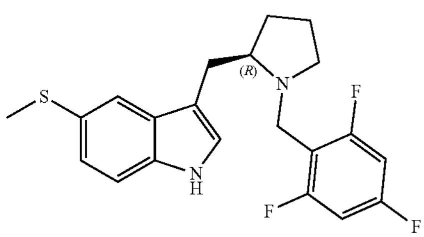 |
| (R) I-37 | 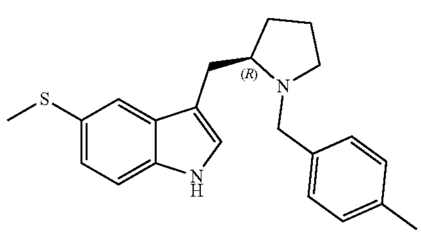 |
| (R) I-38 | 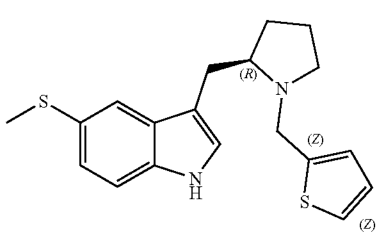 |
TABLE 1-continued
| Compound | Structure |
|---|---|
| (R) I-39 | 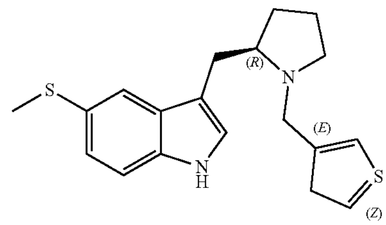 |
| (R) I-40 | 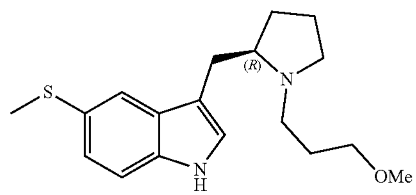 |
| (R, S) I-41 | 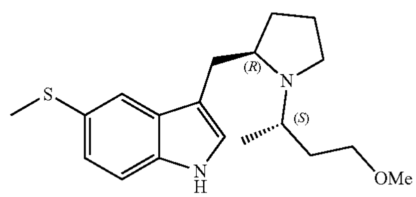 |
| (R, R) I-41 | 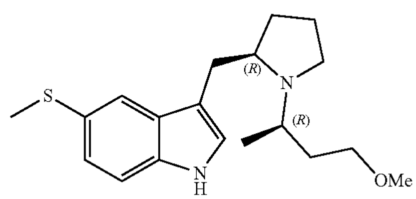 |
| (R, S) I-42 | 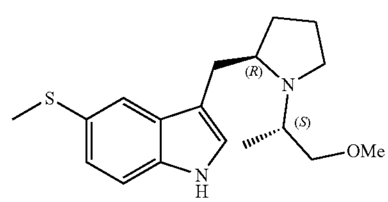 |
| (R, R) I-42 | 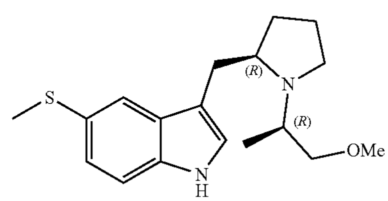 |
| (R) I-43 | 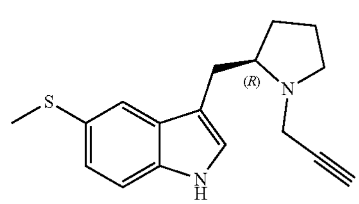 |

TABLE 1-continued
| Compound | Structure |
|---|---|
| (R) I-44 | 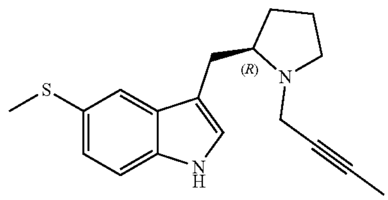 |
| (R) I-45 | 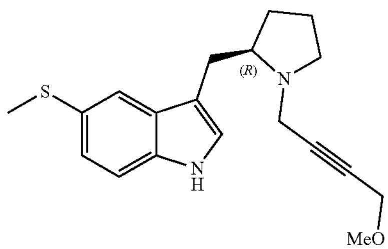 |
| (R) I-46 | 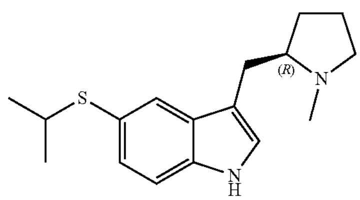 |
| (R) I-47 | 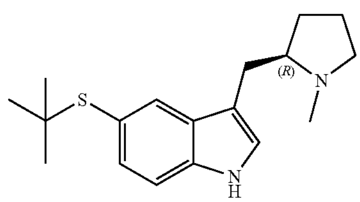 |
| (R) I-48 | 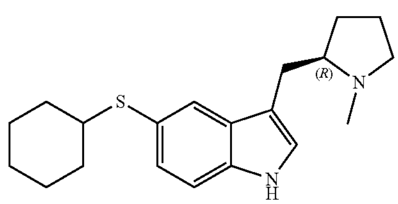 |
| (R) I-49 | 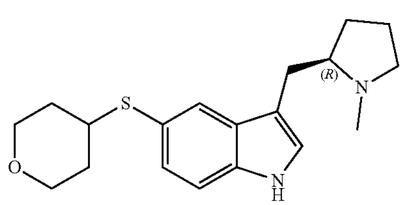 |
| (R) I-50 | 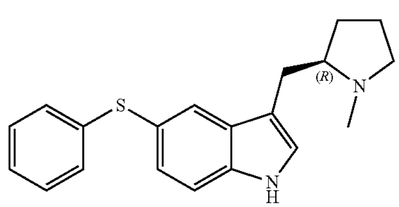 |
TABLE 1-continued
| Compound | Structure |
|---|---|
| (R) I-51 | 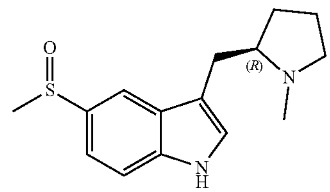 |
| (R) I-52 | 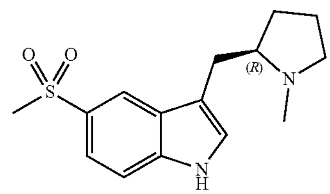 |
| (R) I-53 | 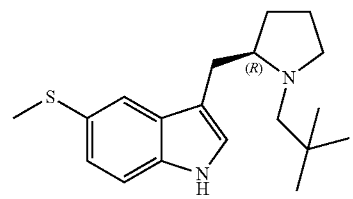 |
| (R) I-54 | 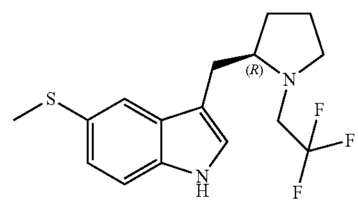 |
| (R) I-55 | 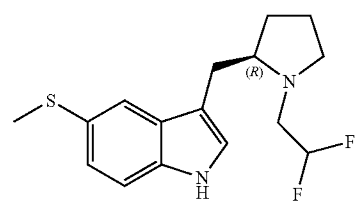 |
| (R) I-56 | 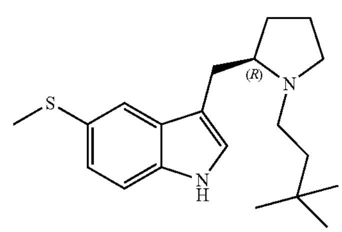 |
| (R) I-57 | 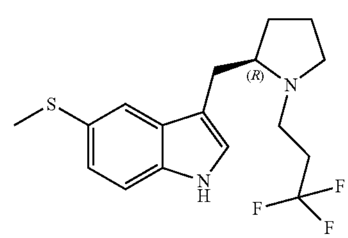 |

TABLE 1-continued
| Compound | Structure |
|---|---|
| (R) I-58 | 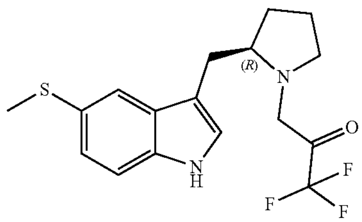 |
| (R) I-59 | 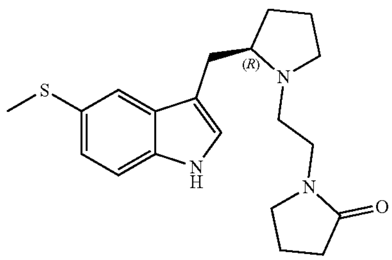 |
| (R) I-60 | 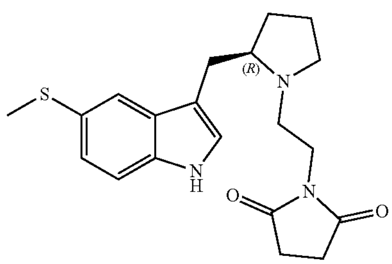 |
| (R) I-61 | 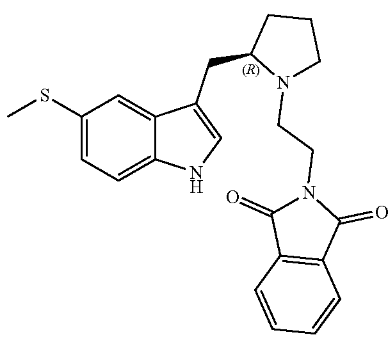 |
| (R) I-62 | 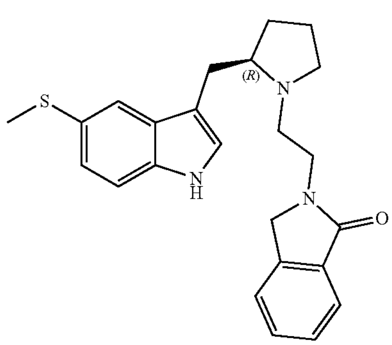 |
TABLE 1-continued
| Compound | Structure |
|---|---|
| (R) I-63 | 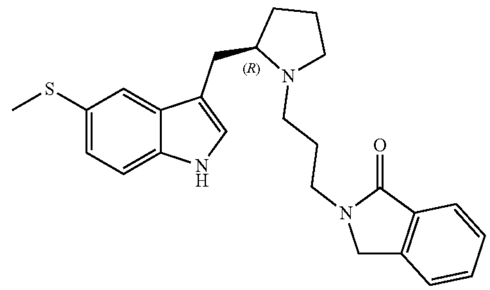 |
| (R) I-64 | 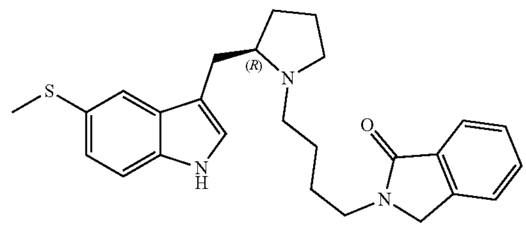 |
| (R) I-65 | 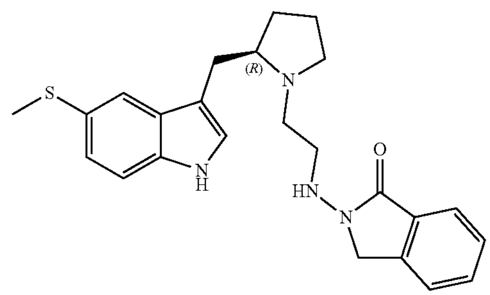 |
| (R) I-66 | 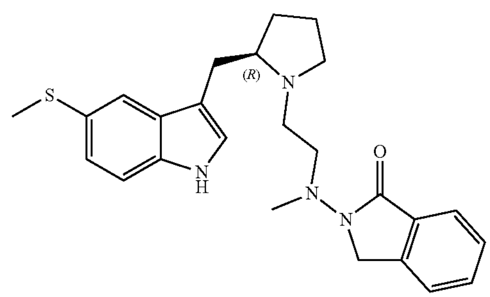 |
| (R) I-67 | 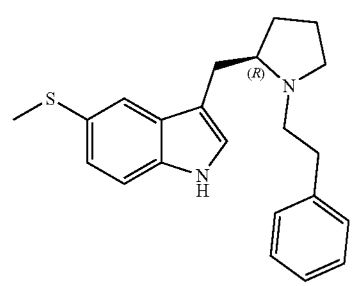 |

TABLE 1-continued
| Compound | Structure |
|---|---|
| (R) I-68 | 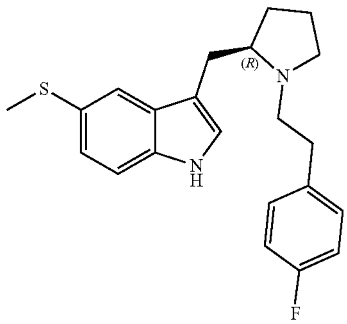 |
| (R) I-69 | 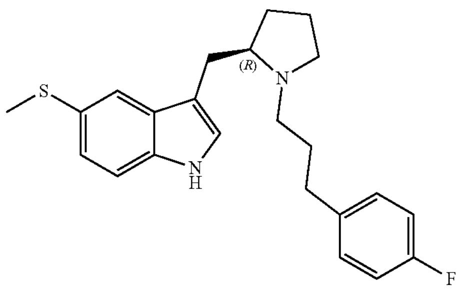 |
| (R) I-70 | 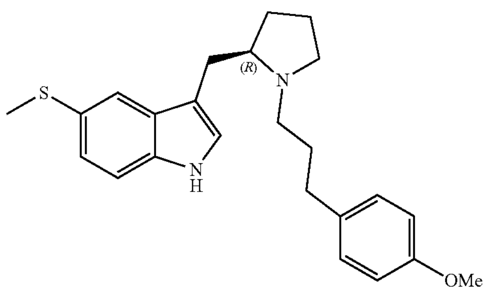 |
| (R) I-71 | 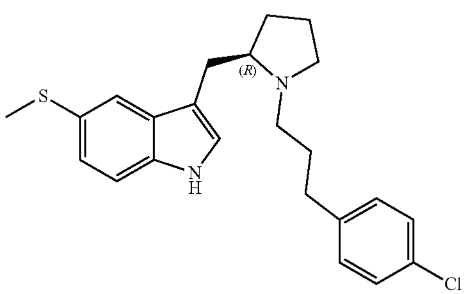 |
| (R) I-72 | 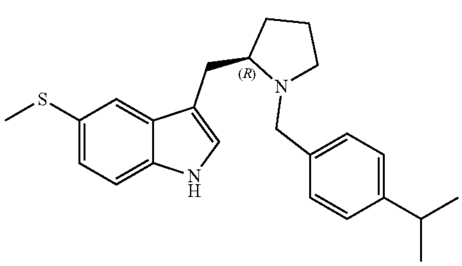 |
TABLE 1-continued
| Compound | Structure |
|---|---|
| (R) I-73 | 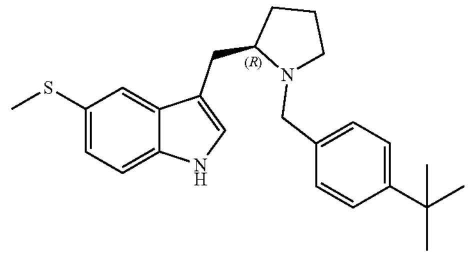 |
| (R) I-74 | 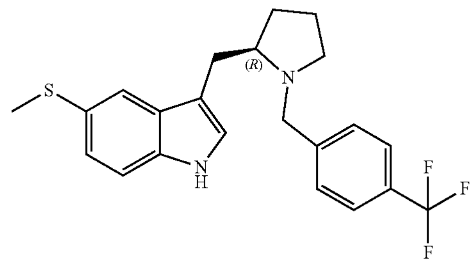 |
| (R) I-75 | 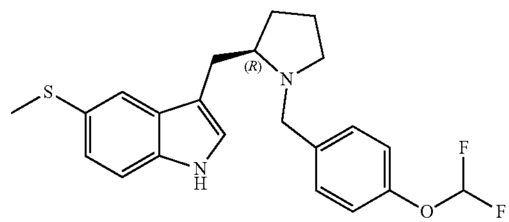 |
| (R) I-76 | 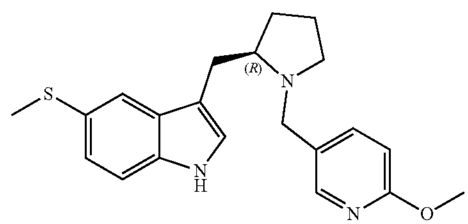 |
| (R) I-77 | 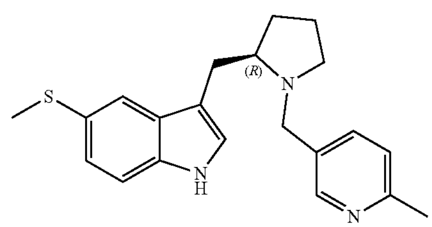 |
| (R) I-78 | 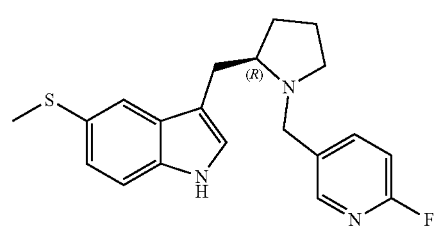 |

TABLE 1-continued
| Compound | Structure |
|---|---|
| (R) I-79 | 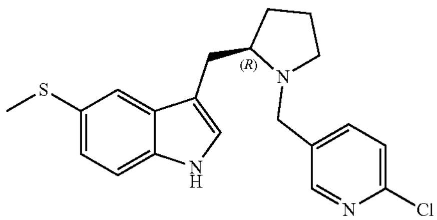 |
| (R) I-80 | 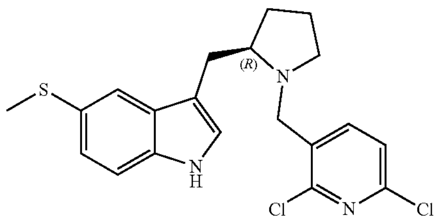 |
| (R) I-81 | 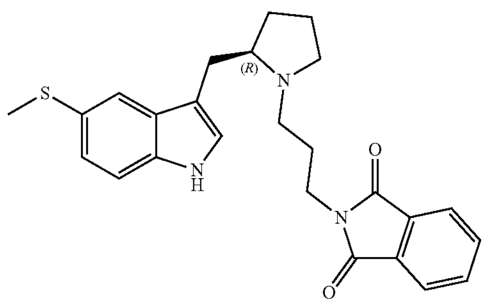 |
| cis-(R) I-82 | 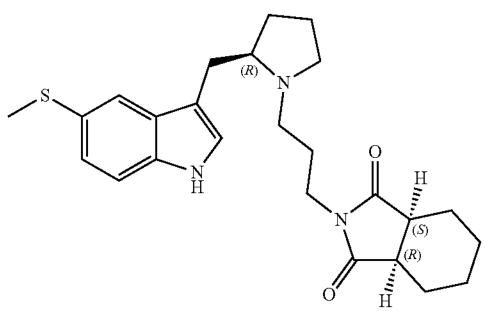 |
| trans-(R) I-82 | 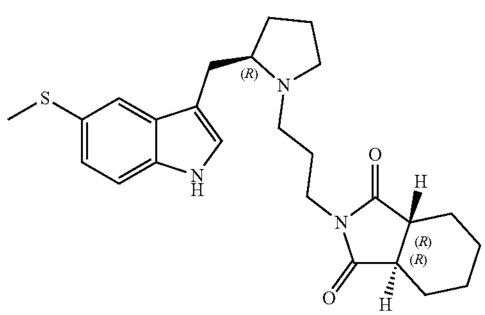 |
| (R) I-83 | 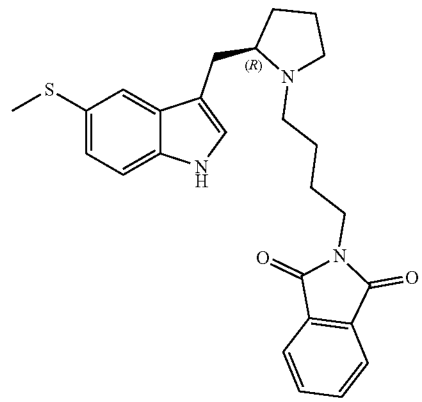 |
| (R) I-84 | 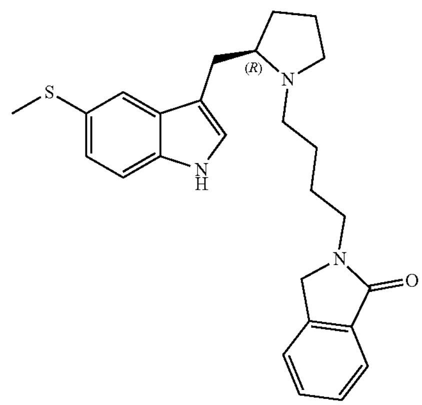 |
| cis-(R) I-85 | 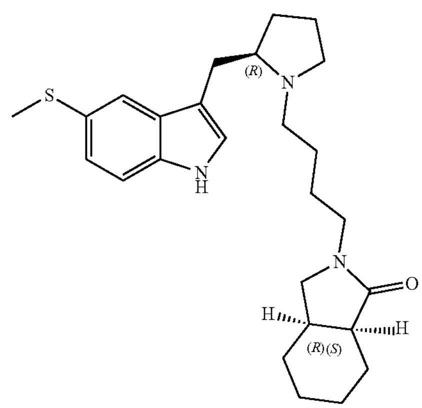 |

TABLE 1-continued
| Compound | Structure |
| --- | --- |
| cis-(R) I-86 | 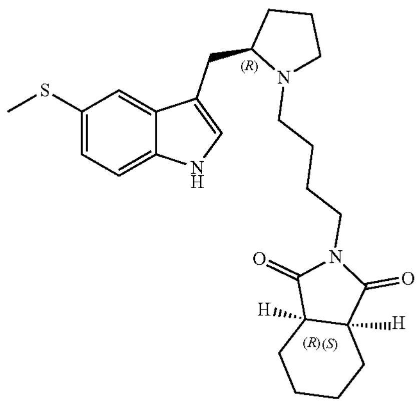 |
| trans-(R) I-86 | 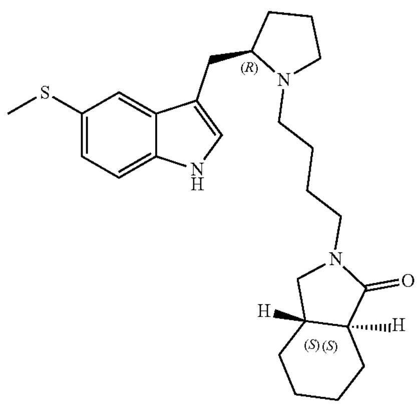 |
| (R) I-87 | 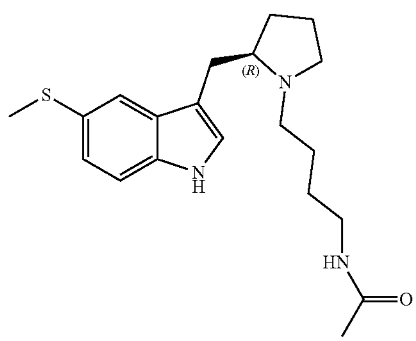 |
| (R) I-88 | 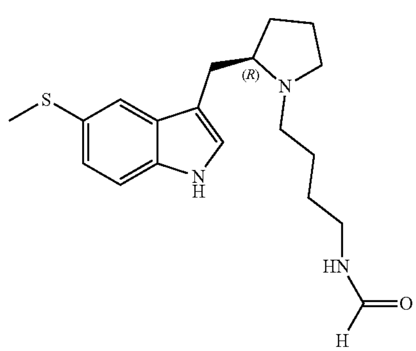 |
| (R) I-89 | 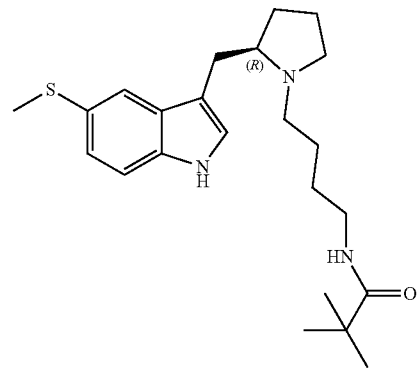 |
| (R) I-90 | 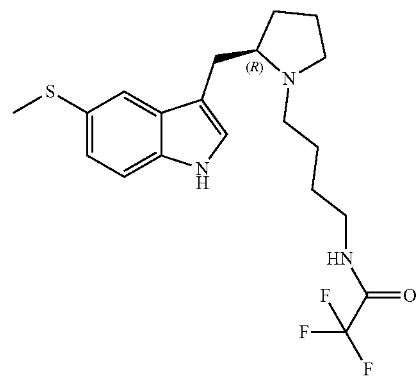 |
| (R) I-91 | 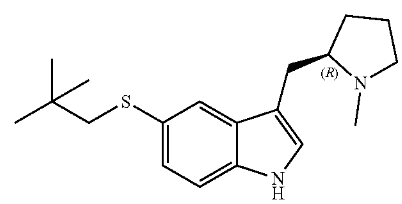 |
| (R) I-92 | 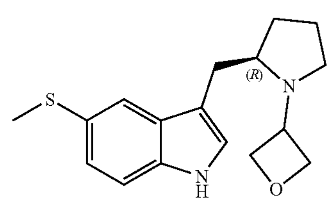 |
| (R, S) I-93 | 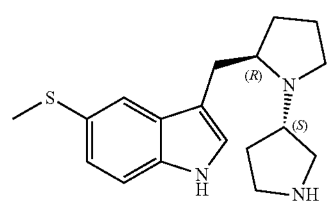 |

TABLE 1-continued
| Compound | Structure |
| --- | --- |
| (R, S) I-94 | 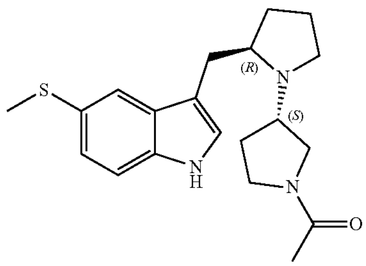 |
| (R) I-95 | 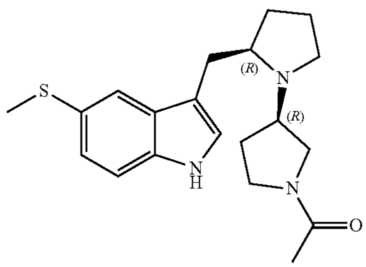 |
| (R) I-96 | 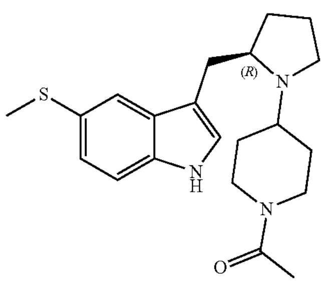 |
| | and |
| (R) I-97 | 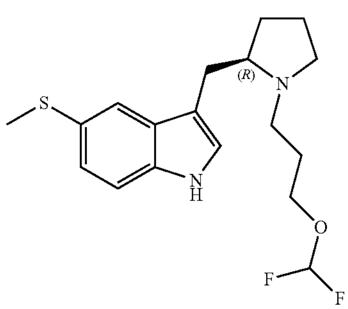 |
or a pharmaceutically acceptable salt, solvate, and/or prodrug thereof.
In some embodiments, the compound of Formula (I) is selected from one or more of the compounds listed in Table 2 below:
TABLE 2
| Compound | Structure |
| --- | --- |
| II-1 | 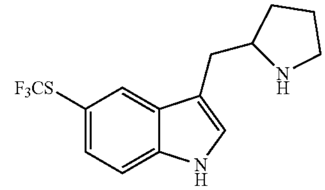 |
| (R) II-2 | 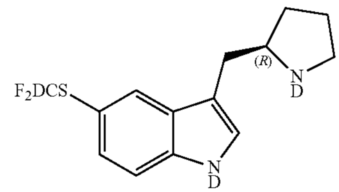 |
| II-3 | 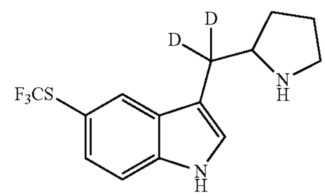 |
| II-4 | 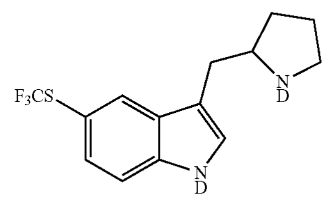 |
| II-5 | 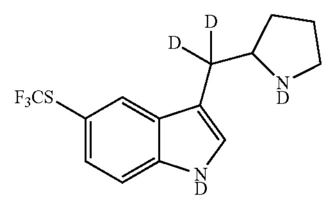 |
| (R) II-6 | 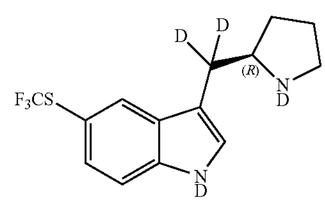 |
| (R) II-7 | 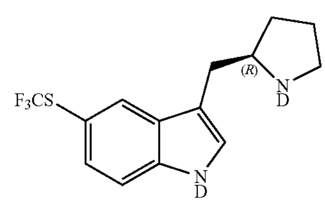 |
| (R) II-8 | 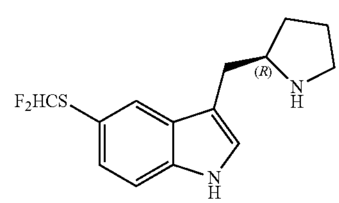 |

TABLE 2-continued
| Compound | Structure |
|---|---|
| (R) II-9 | 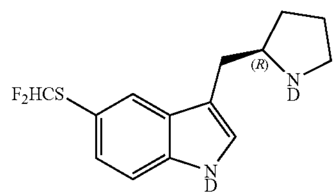 |
| (R) II-10 | 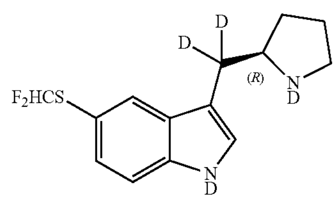 |
| (R) II-11 | 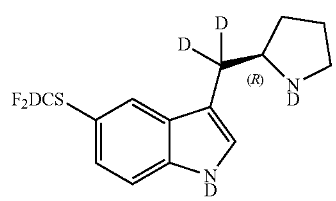 |
| (R) II-12 | 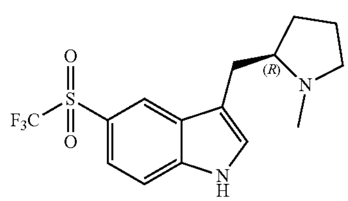 |
| (R) II-13 | 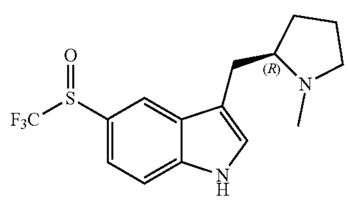 |
| (R) II-14 | 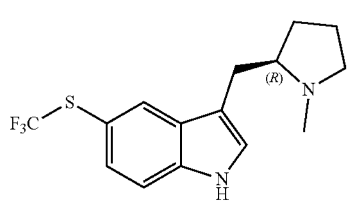 |
| (R) II-15 | 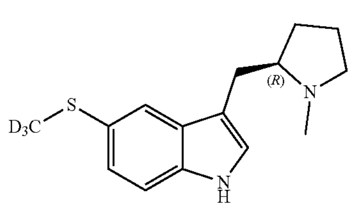 |
TABLE 2-continued
| Compound | Structure |
|---|---|
| (R) II-16 | 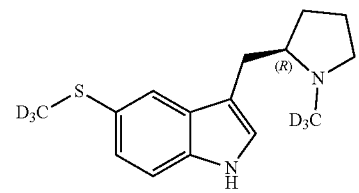 |
| (R) II-17 | 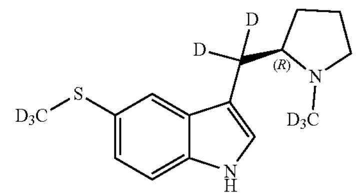 |
| (R) II-18 | 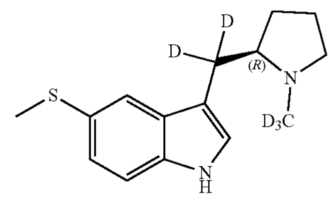 |
| (R) II-19 | 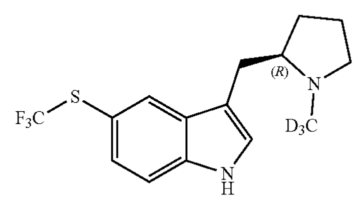 |
| (R) II-20 | 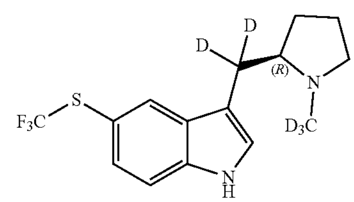 |
| (R) II-21 | 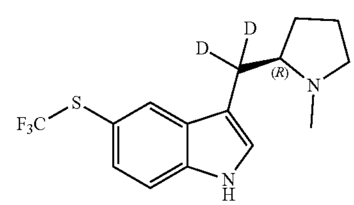 |
| (R) II-22 | 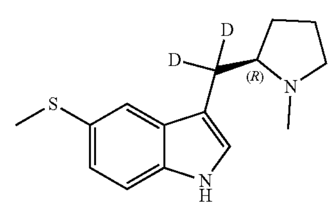 |

TABLE 2-continued
| Compound | Structure |
| --- | --- |
| (R) II-23 | 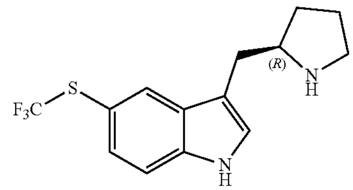 |
| (R) II-24 | 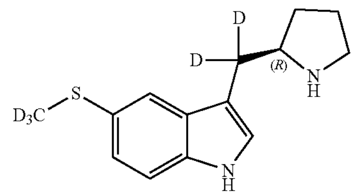 |
| (R) II-25 | 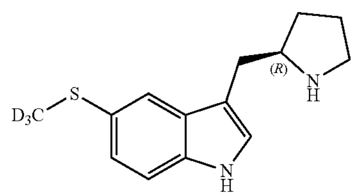 |
| (R) II-26 | 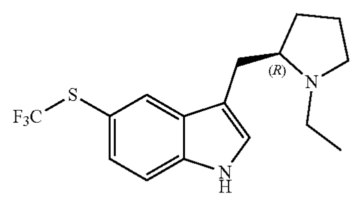 |
| (R) II-27 | 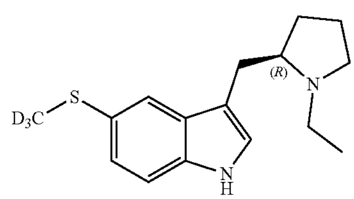 |
| (R) II-28 | 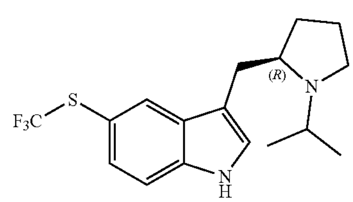 |
| (R) II-29 | 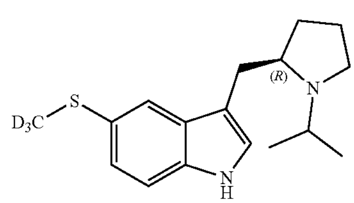 |
| (R) II-30 | 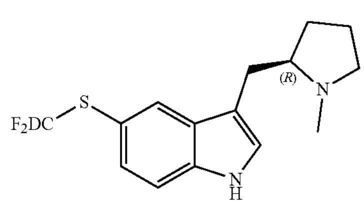 |
TABLE 2-continued
| Compound | Structure |
| --- | --- |
| (R) II-31 | 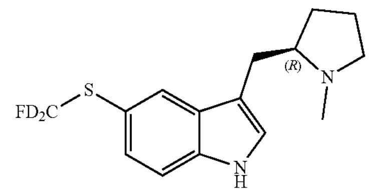 |
| (R) II-32 | 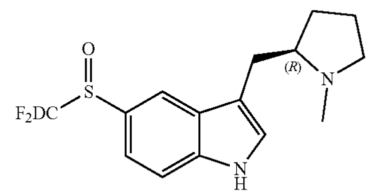 |
| (R) II-33 | 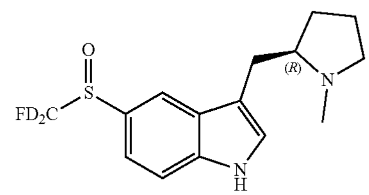 |
| (R) II-34 | 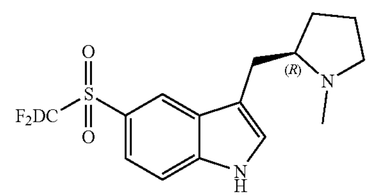 |
| (R) II-35 | 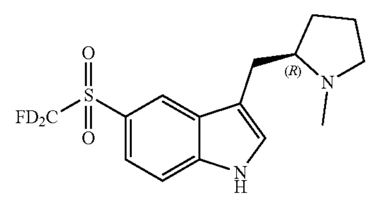 |
| (R) II-36 | 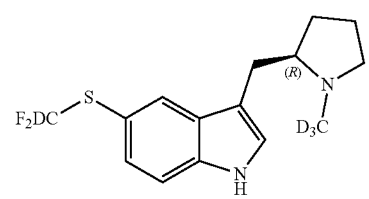 |
| (R) II-37 | 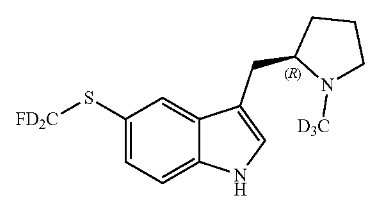 |
| (R) II-38 | 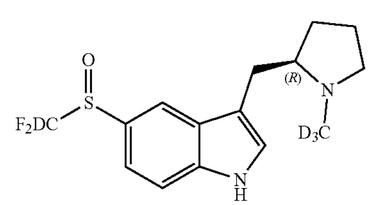 |

TABLE 2-continued
| Compound | Structure |
| --- | --- |
| (R) II-39 | 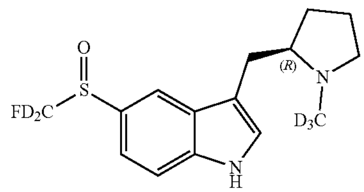 |
| (R) II-40 | 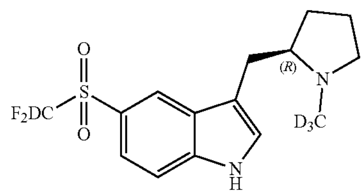 |
| (R) II-41 | 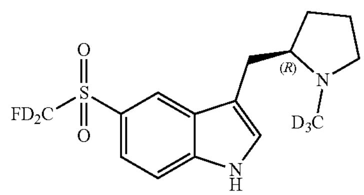 |
| (R) II-42 | 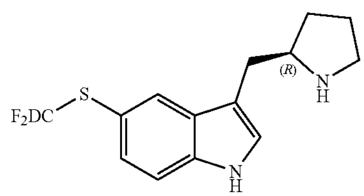 |
| (R) II-43 | 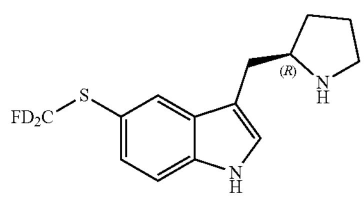 |
| (R) II-44 | 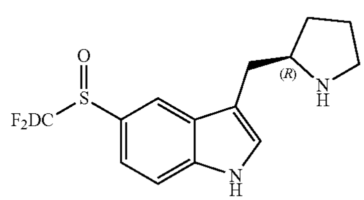 |
| (R) II-45 | 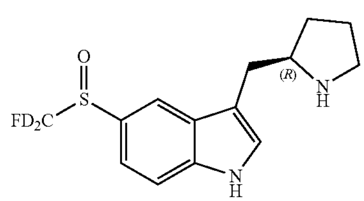 |
| (R) II-46 | 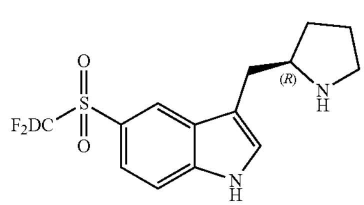 |
TABLE 2-continued
| Compound | Structure |
| --- | --- |
| (R) II-47 | 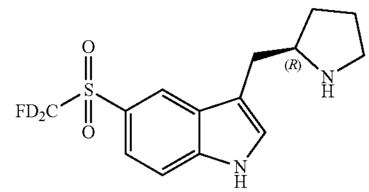 |
| (R) II-48 | 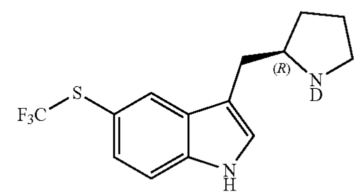 |
| (R) II-49 | 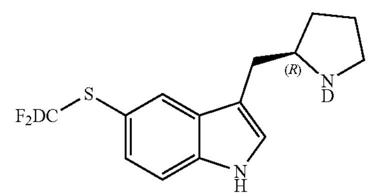 |
| (R) II-50 | 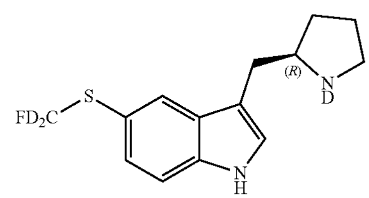 |
| (R) II-51 | 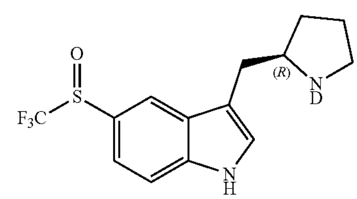 |
| (R) II-52 | 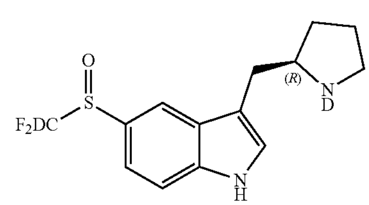 |
| (R) II-53 | 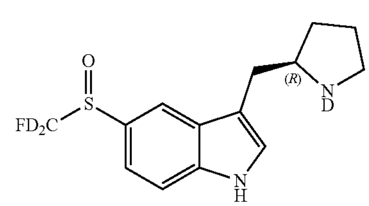 |

TABLE 2-continued

| Compound | Structure |
|---|---|
| (R) II-54 | 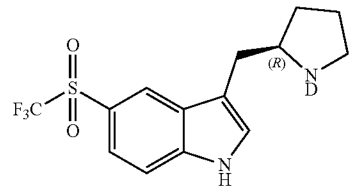 |
| (R) II-55 | 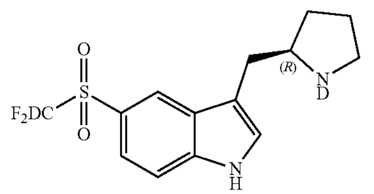 |
| | and |
| (R) II-56 | 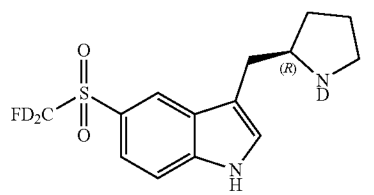 |

or a pharmaceutically acceptable salt, solvate, and/or prodrug thereof.

In some embodiments, the compound of Formula (I) is a compound of Formula (I-G):

Formula (I-G)

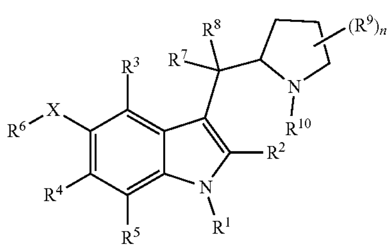

or a pharmaceutically acceptable salt, solvate, and/or prodrug thereof, wherein:

X, n, $R^1$, $R^2$, $R^3$, $R^4$, $R^5$, $R^6$, $R^7$, $R^8$, $R^9$, and $R^{10}$ are as defined in Formula (I) including embodiments thereof, wherein X is absent or oxygen;

available hydrogen atoms are optionally replaced with a halogen atom and/or available atoms are optionally replaced with an alternate isotope thereof;

provided when X is O, $R^9$ is selected from halo and $C_1$-$C_6$alkyl, $R^{10}$ is selected from H and $C_1$-$C_6$alkyl, n is 0, 1, 2, 3, or 4 and $R^6$ is selected from H, substituted or unsubstituted $C_1$-$C_6$alkyl, $C_2$-$C_6$alkenyl, $C_2$-$C_6$alkynyl, $C_3$-$C_7$cycloalkyl, $C_3$-$C_7$heterocycloalkyl, $C_6$-$C_{10}$aryl, and $C_5$-$C_{10}$heteroaryl, then the compound does not comprise deuterium;

provided when X is O, $R^1$, $R^2$, $R^3$, $R^4$, $R^5$, $R^7$, and $R^8$ are H or D, n is 0, and $R^6$ is H, $CH_3$, or $CD_3$, then $R^{10}$ is not H, $CH_3$, or $CD_3$;

provided when X is O, $R^1$, $R^2$, $R^3$, $R^4$, $R^5$, $R^7$, and $R^8$ are H or D and n is 0, and $R^6$ is $CH_3$ or $CHF_2$, then $R^{10}$ is not H, $CH_3$, or $CD_3$; and provided when X is absent and $R^6$ is H, then either n is not 0 or $R^{10}$ is not H or $C_1$-$C_6$alkyl.

In some embodiments, the compound of Formula (I) is a compound of Formula (I-H):

Formula (I-H)

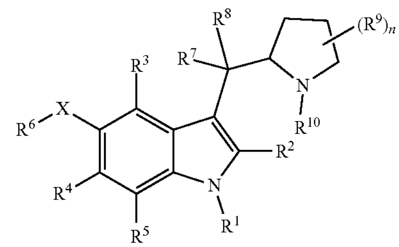

or a pharmaceutically acceptable salt, solvate, and/or prodrug thereof, wherein:

X, n, $R^1$, $R^2$, $R^3$, $R^4$, $R^5$, $R^6$, $R^7$, $R^8$, $R^9$, and $R^{10}$ are as defined in Formula (I) including embodiments thereof, wherein X is absent or oxygen; and available hydrogen atoms are optionally replaced with a halogen, provided when X is O, $R^9$ is halo, $C_1$-$C_6$alkyl or $C_1$-$C_6$haloalkyl, n is 0, 1, 2, 3, or 4, and $R^{10}$ is H, $C_1$-$C_6$alkyl, or $C_1$-$C_6$haloalkyl, then $R^6$ is not H, $C_1$-$C_6$alkyl, or $C_1$-$C_6$haloalkyl;

provided when X is O, $R^1$, $R^2$, $R^3$, $R^4$, $R^5$, $R^7$, and $R^8$ are H or D, n is 0 and $R^6$ is H, $CH_3$, or $CD_3$, then $R^{10}$ is not H, $CH_3$, or $CD_3$;

provided when X is O, $R^1$, $R^2$, $R^3$, $R^4$, $R^5$, $R^7$, and $R^8$ are H or D and n is 0, and $R^6$ is $CH_3$ or $CHF_2$, then $R^{10}$ is not H, $CH_3$, or $CD_3$; and provided when X is absent and $R^6$ is H, then either n is not 0 or $R^{10}$ is not H or $C_1$-$C_6$alkyl.

In some embodiments, the compound of Formula (I) is a compound of Formula (I-I):

Formula (I-I)

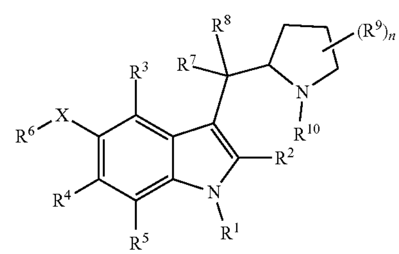

or a pharmaceutically acceptable salt, solvate, and/or prodrug thereof, wherein:

n is an integer selected from 1, 2, 3, and 4;

each $R^9$ is independently selected from OH, $OC_1$-$C_6$alkyl, $C_1$-$C_6$alkyleneOH, and $C_1$-$C_6$alkyleneO$C_1$-$C_6$alkyl;

X, $R^1$, $R^2$, $R^3$, $R^4$, $R^5$, $R^6$, $R^7$, $R^8$, and $R^{10}$ are as defined in Formula (I) including embodiments thereof, wherein X is absent or oxygen; and available hydrogen atoms are optionally replaced with a halogen atom and/or available atoms are optionally replaced with an alternate isotope thereof.

In some embodiments, the compound of Formula (I) is a compound of Formula (I-J):

Formula (I-J)

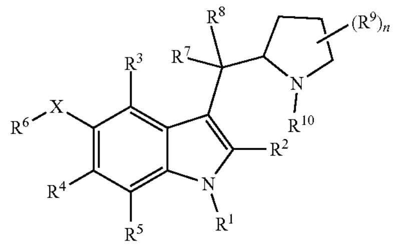

or a pharmaceutically acceptable salt, solvate, and/or prodrug thereof, wherein:

$R^{10}$ is selected from $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{15}$, and $C(O)R^{15}$;

X, Z', $R^1$, $R^2$, $R^3$, $R^4$, $R^5$, $R^6$, $R^7$, $R^8$, $R^9$, $R^{14}$, $R^{15}$, and n are as defined in Formula (I) including embodiments thereof, wherein X is absent or oxygen; and available hydrogen atoms are optionally replaced with a halogen atom and/or available atoms are optionally replaced with an alternate isotope thereof.

In some embodiments, the compound of Formula (I) is a compound of Formula (I-K):

Formula (I-K)

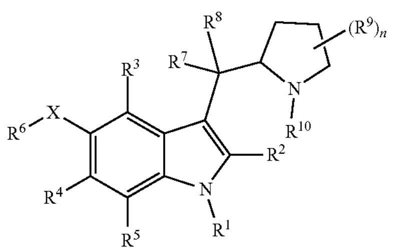

or a pharmaceutically acceptable salt, solvate, and/or prodrug thereof, wherein:

$R^6$ is selected from $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_7$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{13}$, and $C(O)R^{13}$;

X, Z, $R^1$, $R^2$, $R^3$, $R^4$, $R^5$, $R^7$, $R^8$, $R^9$, $R^{10}$, $R^{12}$, $R^{13}$, and n are as defined in Formula (I) including embodiments thereof, wherein X is absent or oxygen; and available hydrogen atoms are optionally replaced with a halogen atom and/or available atoms are optionally replaced with an alternate isotope thereof.

In some embodiments, $R^2$, $R^3$, $R^4$, and $R^5$ are all H and the compound of Formula (I) is a compound of Formula (I-L). Accordingly, in some embodiments, the present disclosure includes a compound of Formula (I-L):

Formula (I-L)

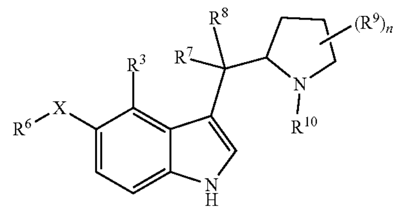

or a pharmaceutically acceptable salt, solvate, and/or prodrug thereof, wherein:

X, n, $R^6$, $R^7$, $R^8$, $R^9$, and $R^{10}$ are as defined in Formula (I) including embodiments thereof, wherein X is absent or oxygen;

available hydrogen atoms are optionally replaced with a halogen atom and/or available atoms are optionally replaced with an alternate isotope thereof, provided when X is O, $R^7$ and $R^8$ are H or D, n is 0 and $R^6$ is H, $CH_3$, or $CD_3$, then $R^{10}$ is not H, $CH_3$, or $CD_3$;

provided when X is O, $R^7$ and $R^8$ are H or D, n is 0, and $R^6$ is $CH_3$ or $CHF_2$, then $R^{10}$ is not H, $CH_3$, or $CD_3$; and provided when X is absent and $R^6$ is H, then either n is not 0 or $R^{10}$ is not H or $C_1$-$C_6$alkyl.

In some embodiments, X is absent and the compound of Formula (I) is a compound of Formula (I-M). Accordingly, in some embodiments, the present disclosure includes a compound of Formula (I-M):

Formula (I-M)

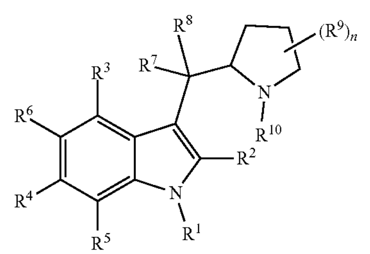

or a pharmaceutically acceptable salt, solvate, and/or prodrug thereof, wherein:

X is absent;

n, $R^1$, $R^2$, $R^3$, $R^4$, $R^5$, $R^6$, $R^7$, $R^8$, $R^9$, and $R^{10}$ are as defined in Formula (I) including embodiments thereof; and available hydrogen atoms are optionally replaced with a halogen atom and/or available atoms are optionally replaced with an alternate isotope thereof, provided when $R^6$ is H, then either n is not 0 or $R^{10}$ is not H or $C_1$-$C_6$alkyl.

In some embodiments, the compound of Formula (I) is selected from one or more of the compounds listed in Table 3 below:

TABLE 3
| Compound | Structure |
|---|---|
| (R) I-98 | 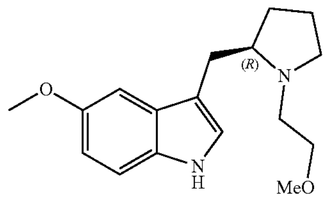 |
| (R) I-99 | 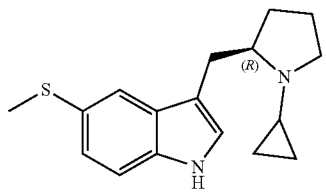 |
| (R) I-100 | 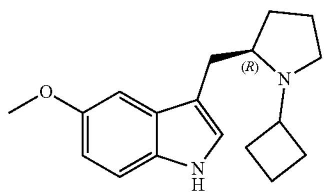 |
| (R) I-101 | 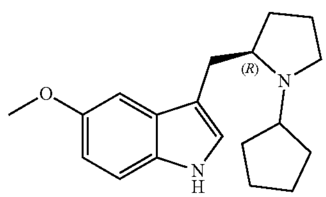 |
| (R,R) I-102 | 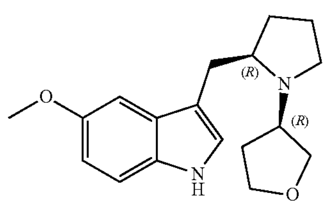 |
| (R,S) I-102 | 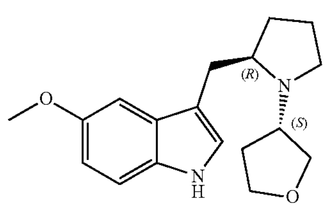 |
| (R,S) I-103 | 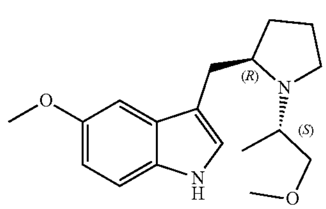 |

TABLE 3-continued
| Compound | Structure |
|---|---|
| (R,R) I-103 | 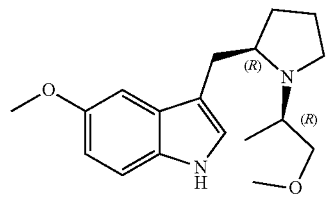 |
| (S) I-104 | 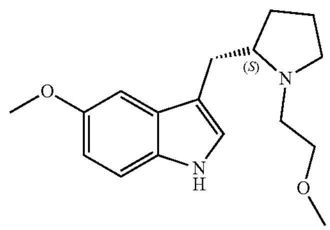 |
| (R) I-105 | 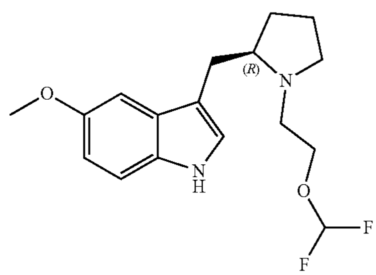 |
| (R) I-106 | 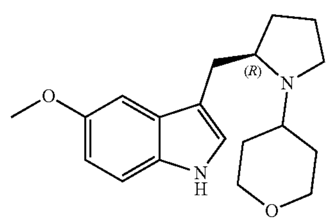 |
| (R,S) I-107 | 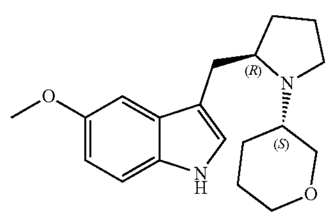 |
| (R,R) I-107 | 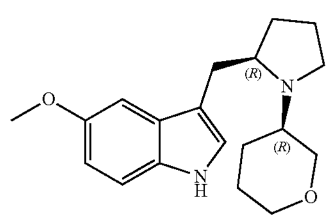 |
| (R) I-108 | 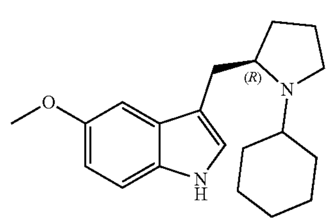 |

TABLE 3-continued
| Compound | Structure |
| --- | --- |
| Trans-(R) I-109 | 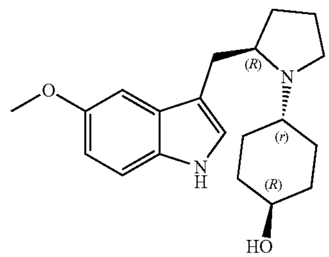 |
| Trans (R) I-110 | 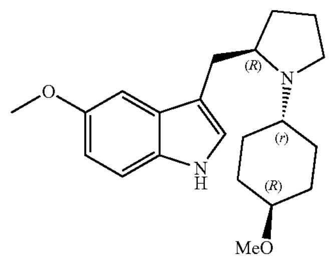 |
| (R,R) I-111 | 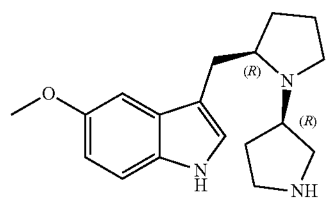 |
| (R) I-112 | 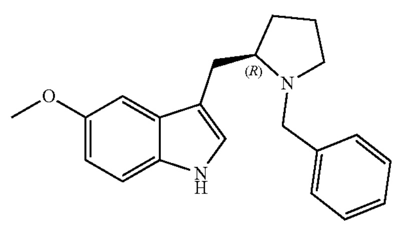 |
| (R) I-113 | 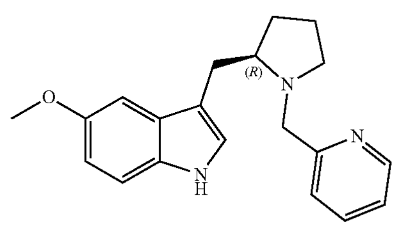 |
| (R) I-114 | 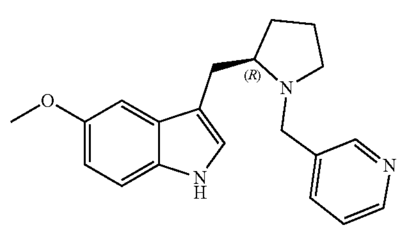 |

TABLE 3-continued
| Compound | Structure |
|---|---|
| (R) I-115 | 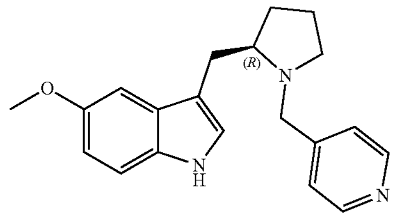 |
| (R) I-116 | 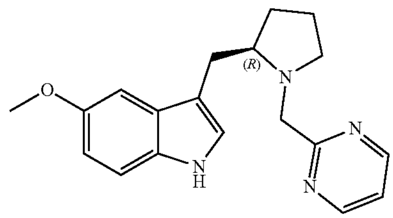 |
| (R) I-117 | 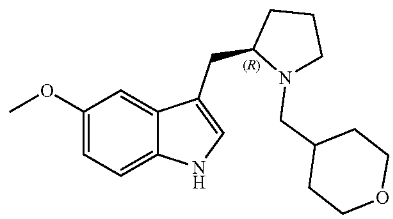 |
| (R,S) I-118 | 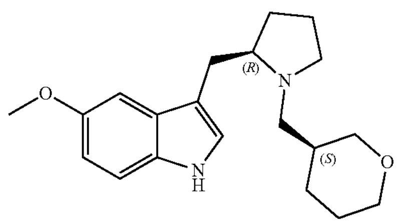 |
| (R,R) I-118 | 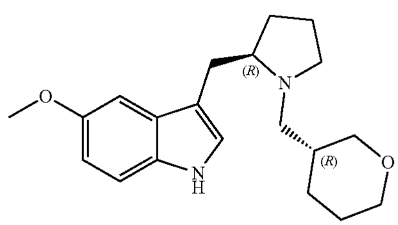 |
| (R,R) I-119 | 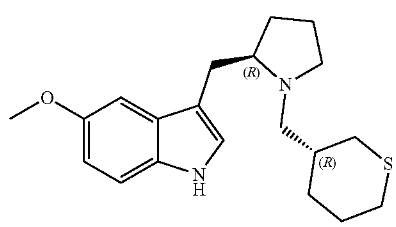 |
| (R,S) I-119 | 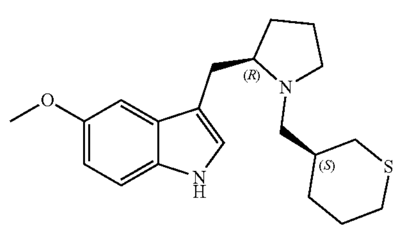 |

TABLE 3-continued
| Compound | Structure |
| --- | --- |
| (R) I-120 | 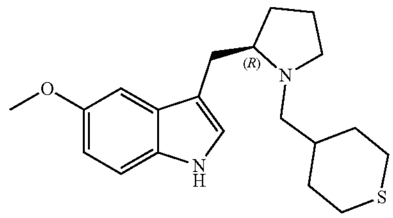 |
| (R) I-121 | 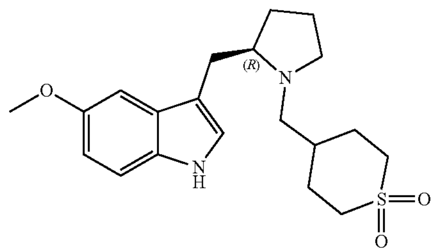 |
| (R) I-122 | 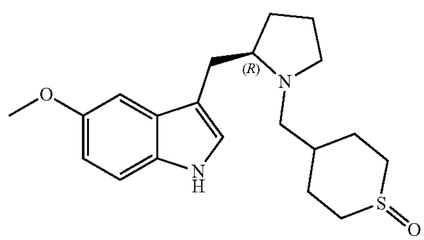 |
| (R) I-123 | 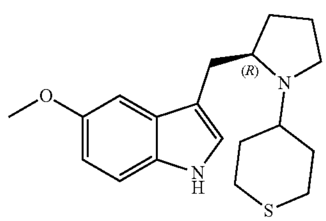 |
| (R) I-124 | 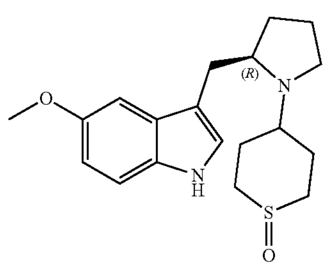 |
| (R) I-125 | 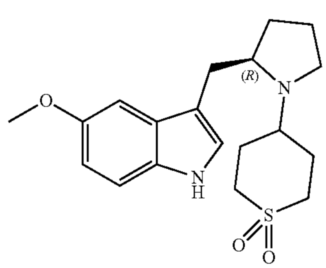 |

TABLE 3-continued
| Compound | Structure |
| --- | --- |
| (R) I-126 | 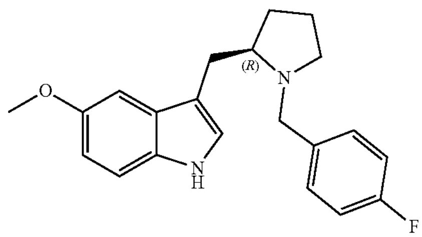 |
| (R) I-127 | 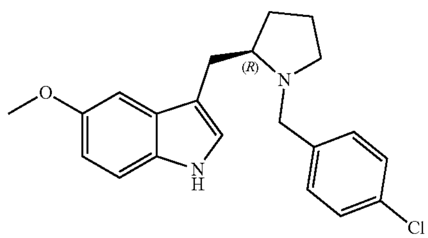 |
| (R) I-128 | 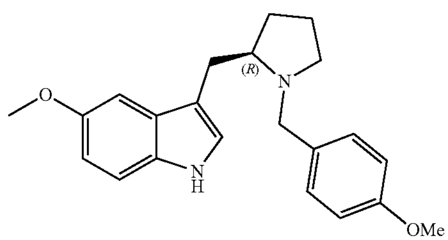 |
| (R) I-129 | 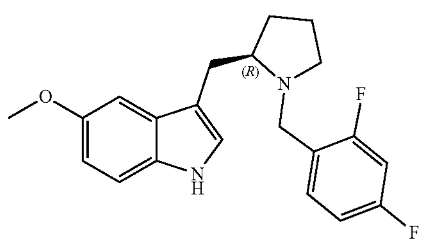 |
| (R) I-130 | 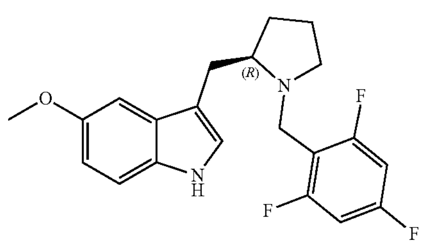 |
| (R) I-131 | 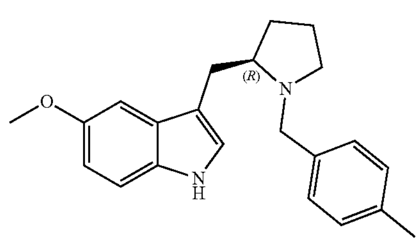 |

TABLE 3-continued
| Compound | Structure |
| --- | --- |
| (R) I-132 | 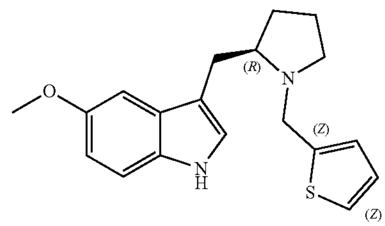 |
| (R) I-133 | 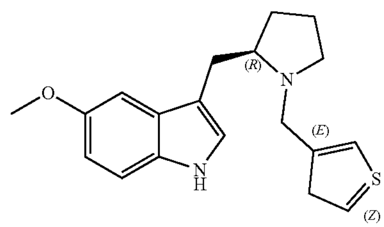 |
| (R) I-134 | 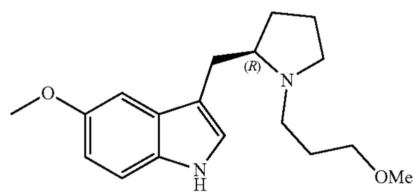 |
| (R,S) I-135 | 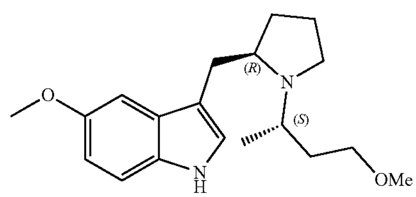 |
| (R,R) I-135 | 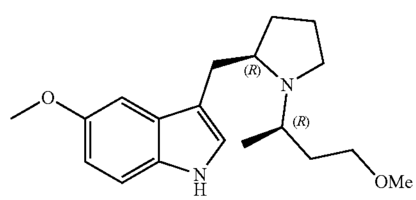 |
| (R,S) I-136 | 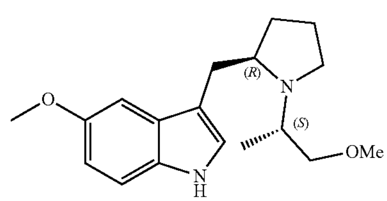 |
| (R,R) I-136 | 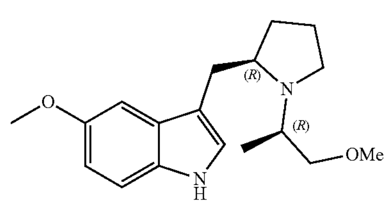 |

TABLE 3-continued
| Compound | Structure |
|---|---|
| (R) I-137 | 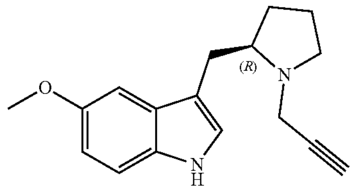 |
| (R) I-138 | 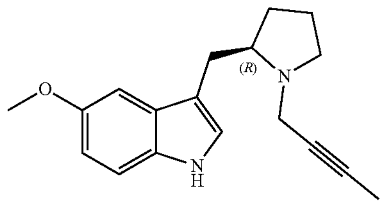 |
| (R) I-139 | 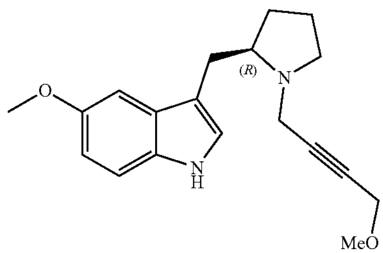 |
| (R) I-140 | 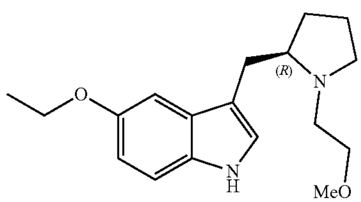 |
| (R) I-141 | 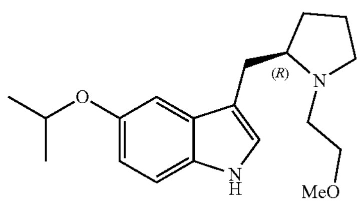 |
| (R) I-142 | 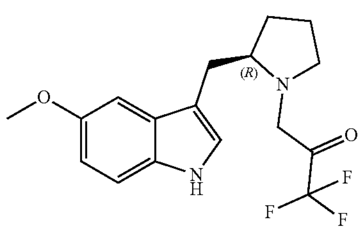 |
| (R) I-143 | 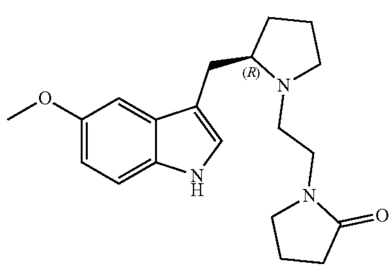 |

TABLE 3-continued
| Compound | Structure |
|---|---|
| (R) I-144 | 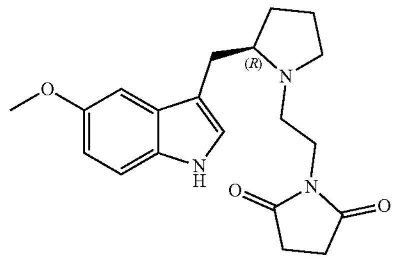 |
| (R) I-145 | 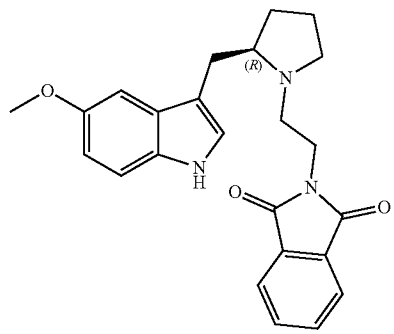 |
| (R) I-146 | 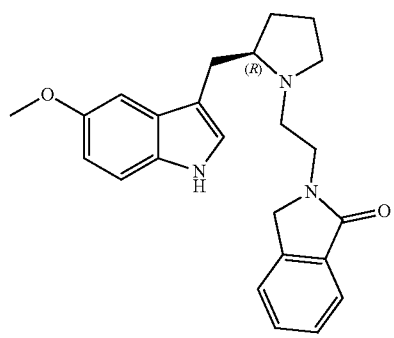 |
| (R) I-147 | 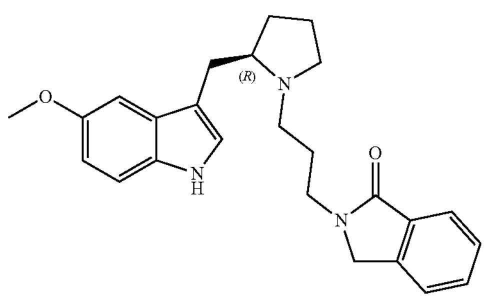 |
| (R) I-148 | 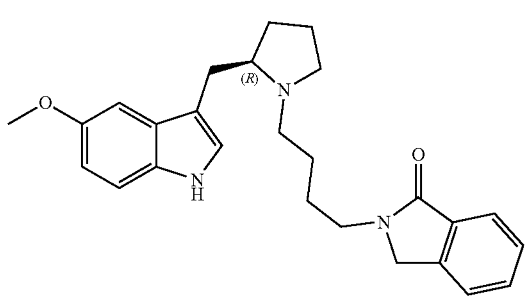 |

TABLE 3-continued
| Compound | Structure |
|---|---|
| (R) I-149 | 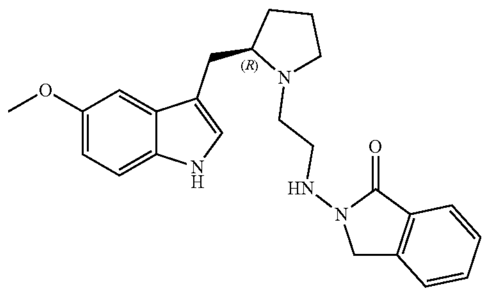 |
| (R) I-150 | 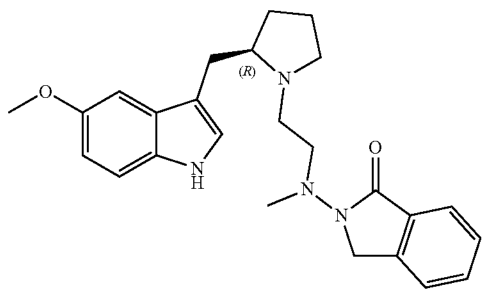 |
| (R) I-151 | 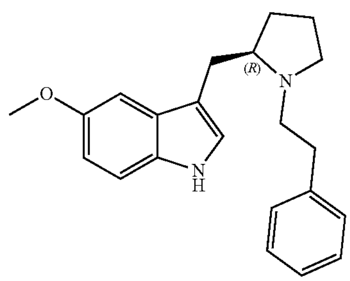 |
| (R) I-152 | 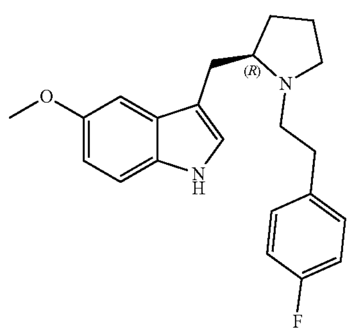 |
| (R) I-153 | 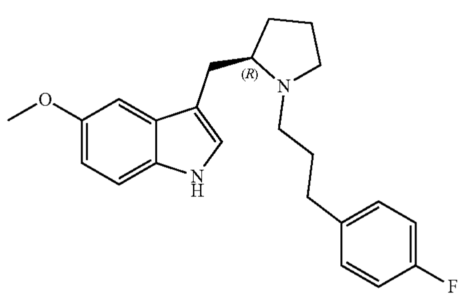 |

TABLE 3-continued
| Compound | Structure |
|---|---|
| (R) I-154 | 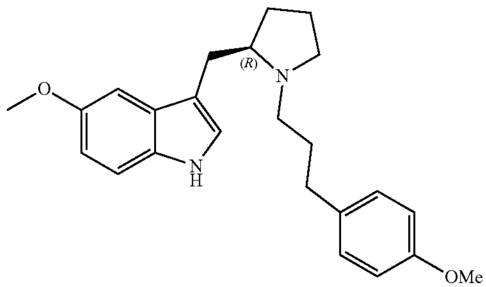 |
| (R) I-155 | 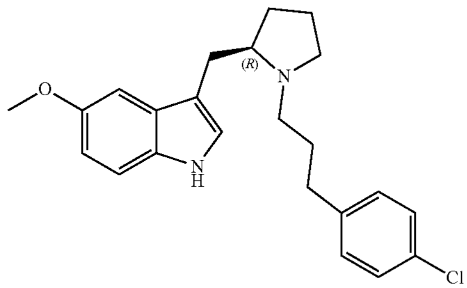 |
| (R) I-156 | 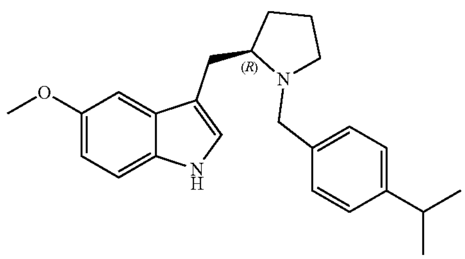 |
| (R) I-157 | 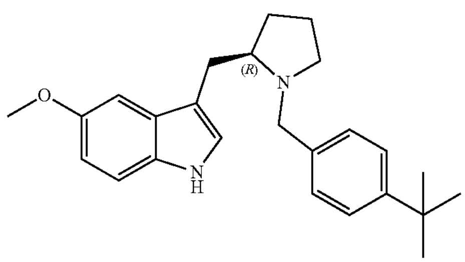 |
| (R) I-158 | 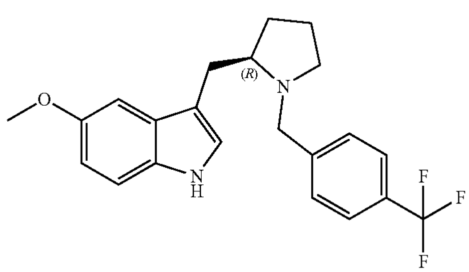 |
| (R) I-159 | 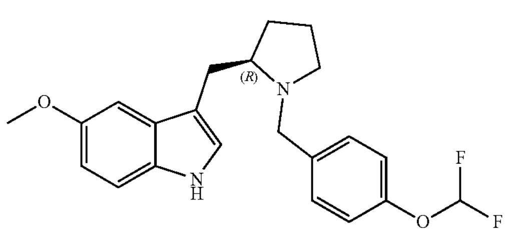 |

TABLE 3-continued
| Compound | Structure |
| --- | --- |
| (R) I-160 | 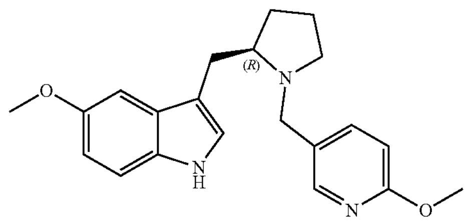 |
| (R) I-161 | 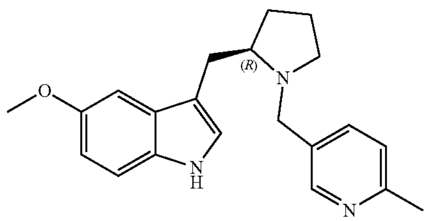 |
| (R) I-162 | 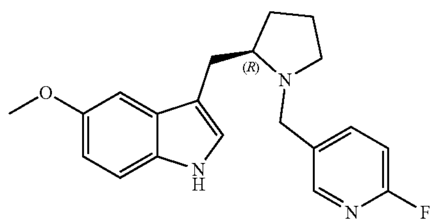 |
| (R) I-163 | 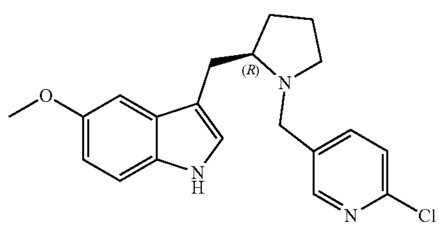 |
| (R) I-164 | 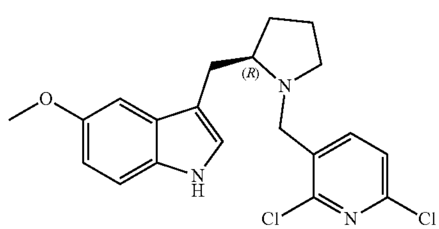 |
| (R) I-165 | 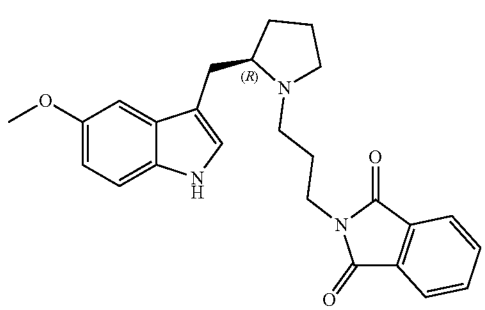 |

TABLE 3-continued
| Compound | Structure |
| --- | --- |
| Cis (R) I-166 | 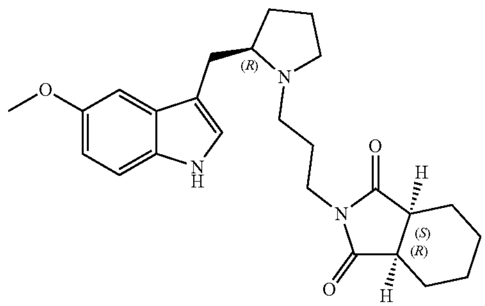 |
| Trans (R) I-167 | 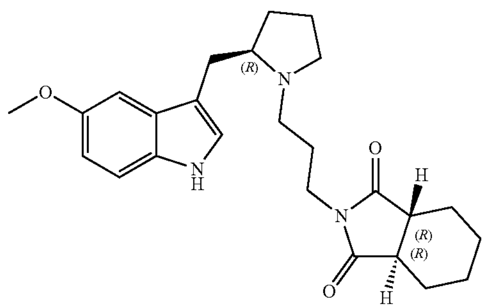 |
| (R) I-168 | 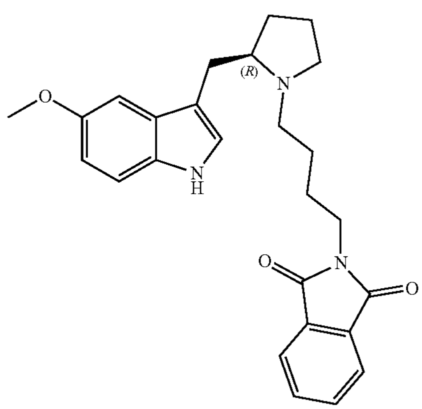 |
| (R) I-169 | 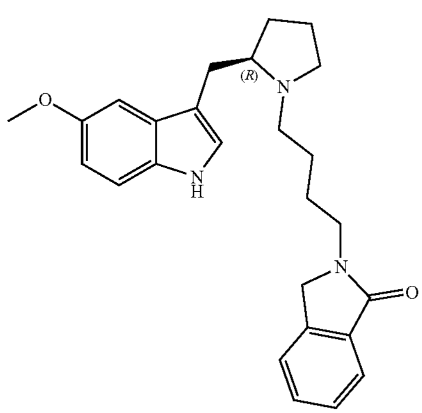 |

TABLE 3-continued
| Compound | Structure |
| --- | --- |
| Cis (R) I-170 | 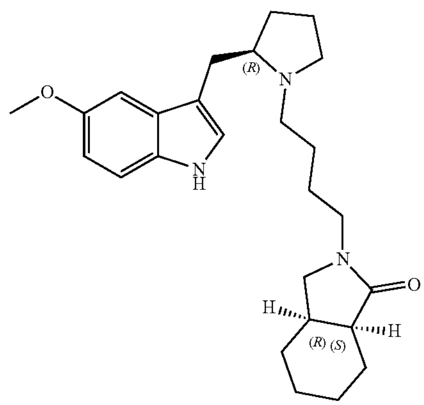 |
| Cis (R) I-171 | 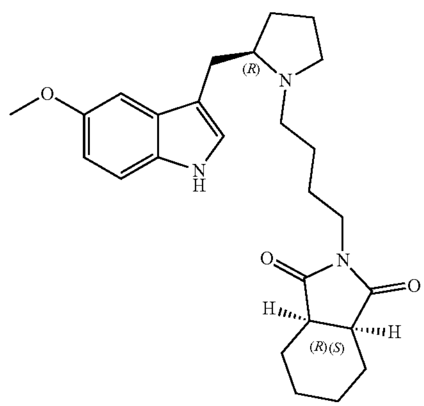 |
| Trans (R) I-172 | 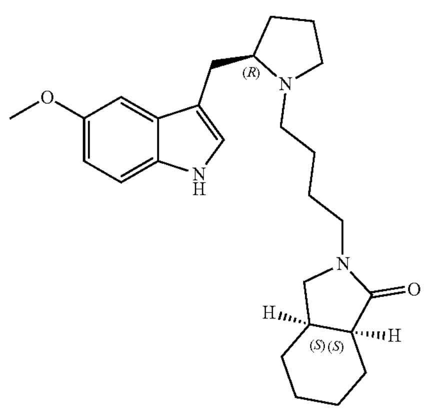 |
| (R) I-173 | 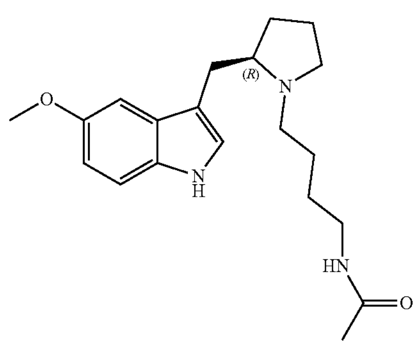 |

TABLE 3-continued
| Compound | Structure |
| --- | --- |
| (R) I-174 | 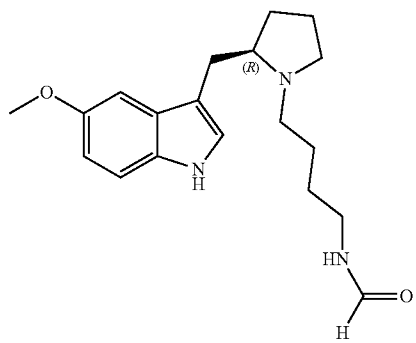 |
| (R) I-175 | 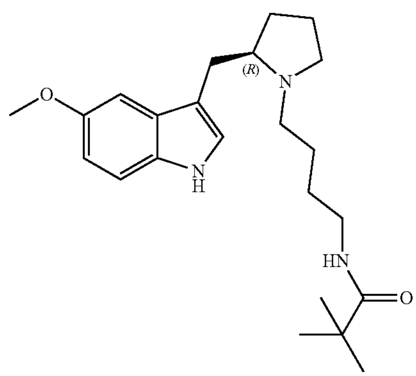 |
| (R) I-176 | 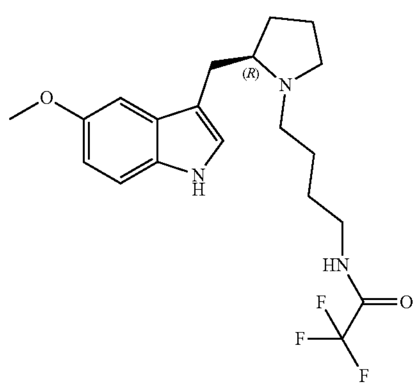 |
| (R) I-177 | 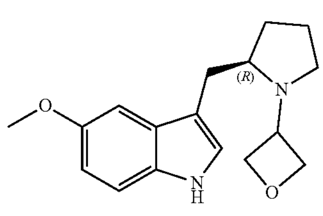 |
| (R,S) I-178 | 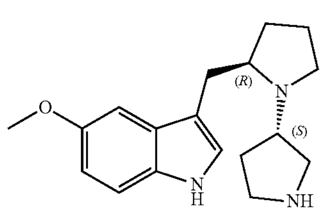 |

TABLE 3-continued
| Compound | Structure |
|---|---|
| (R,S) I-179 | 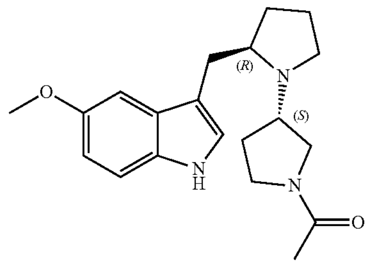 |
| (R,R) I-180 | 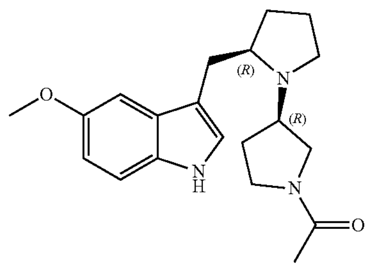 |
| (R) I-181 | 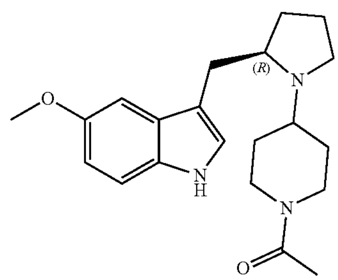 |
| (R) I-182 | 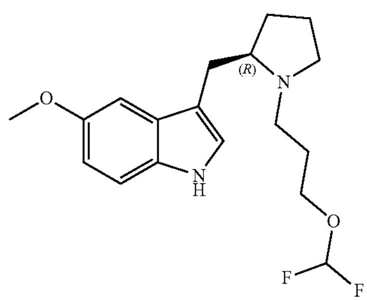 |
| (R) I-183 | 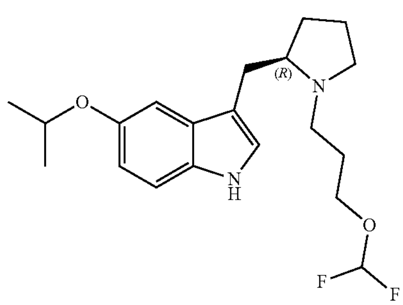 |

TABLE 3-continued
| Compound | Structure |
| --- | --- |
| (R) I-184 | 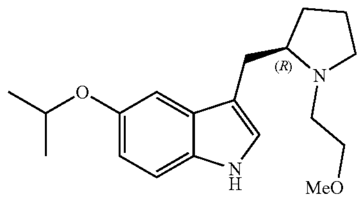 |
| (R) I-185 | 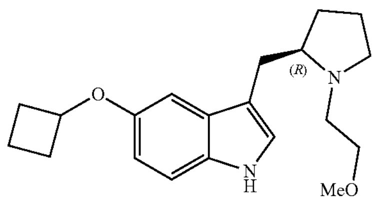 |
| (R) I-186 | 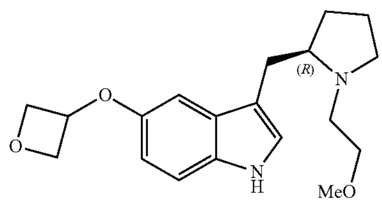 |
| (R) I-187 | 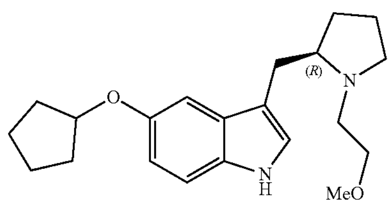 |
| (R) I-188 | 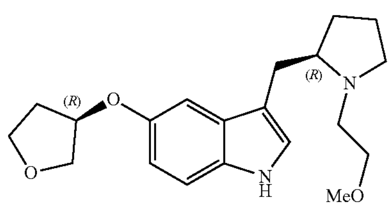 |
| (R) I-189 | 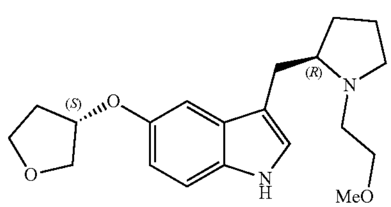 |
| (R) I-190 | 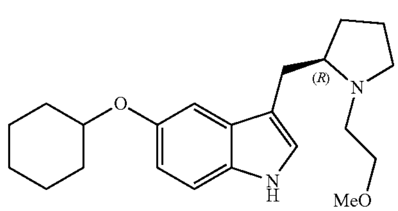 |

TABLE 3-continued
| Compound | Structure |
| --- | --- |
| (R) I-191 | 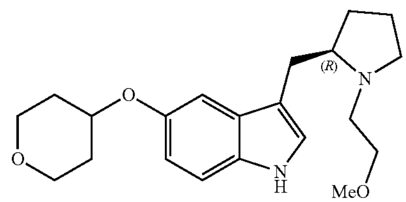 |
| (R) I-192 | 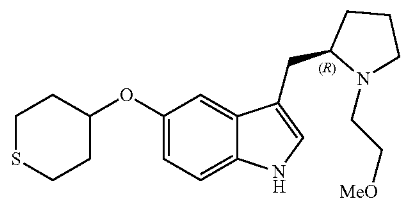 |
| (R) I-193 | 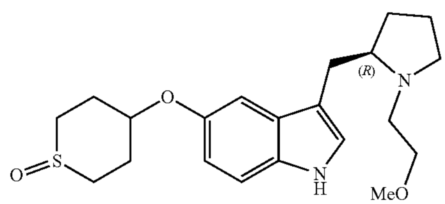 |
| (R) I-194 | 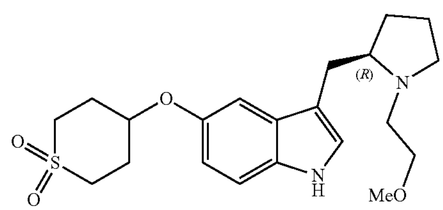 |
| (R) I-195 | 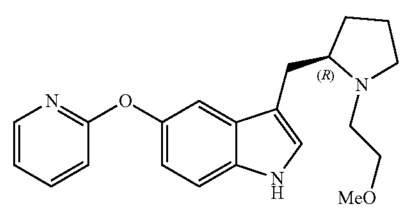 |
| (R) I-196 | 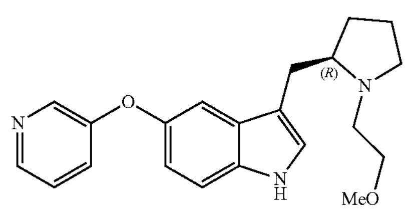 |
| (R) I-197 | 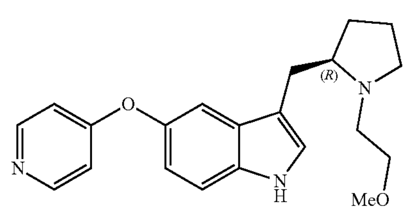 |

TABLE 3-continued
| Compound | Structure |
|---|---|
| (R) I-198 | 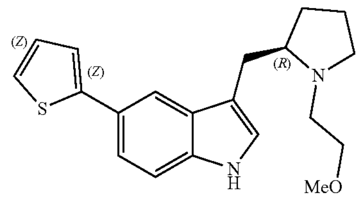 |
| (R) I-198-A | 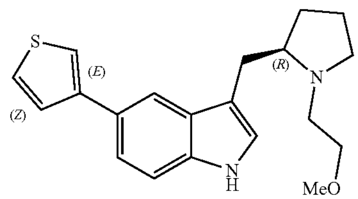 |
| (R) I-199 | 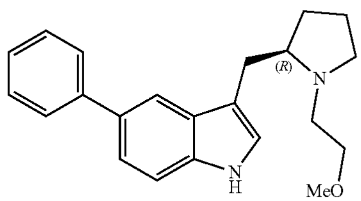 |
| (R) I-200 | 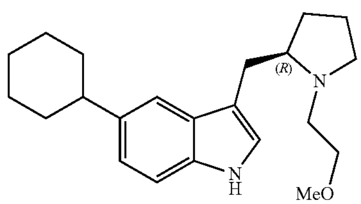 |
| (R) I-201 | 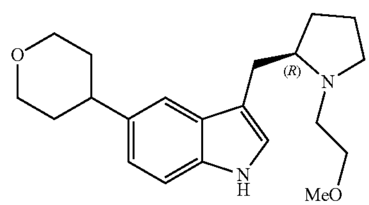 |
| (R) I-202 | 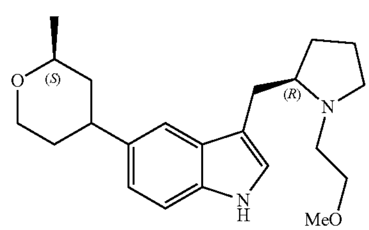 |
| (R) I-203 | 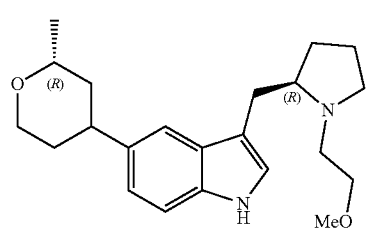 |

TABLE 3-continued
| Compound | Structure |
| --- | --- |
| (R) I-204 | 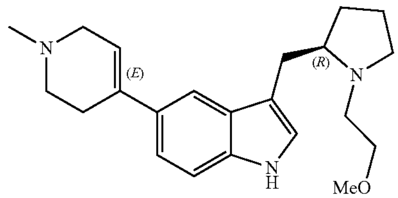 |
| (R) I-205 | 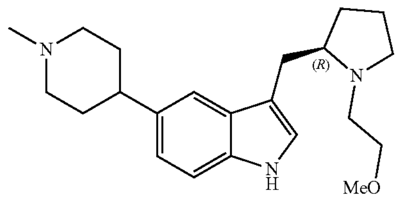 |
| (R) I-206 | 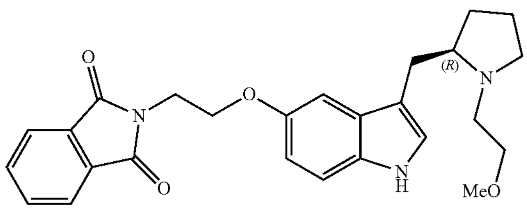 |
| (R) I-207 | 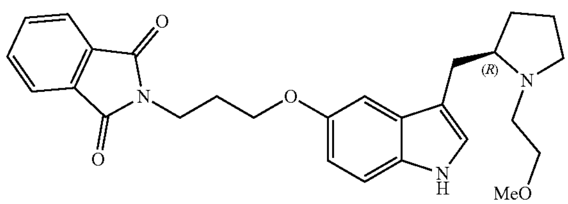 |
| (R) I-208 | 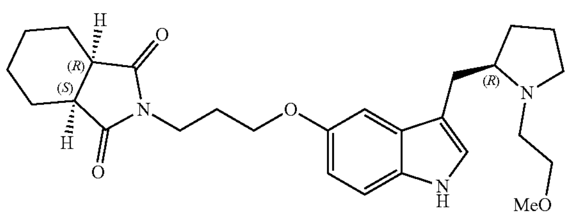 |
| (R) I-209 | 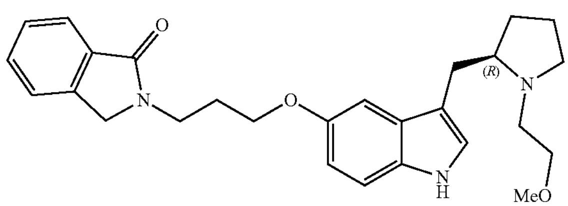 |
| (R) I-210 | 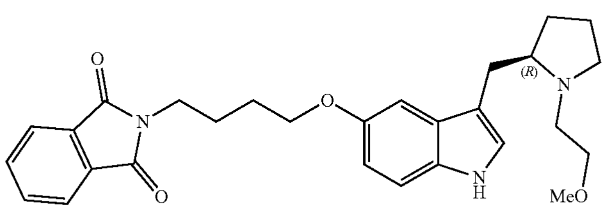 |

TABLE 3-continued
| Compound | Structure |
| --- | --- |
| (R) I-211 | 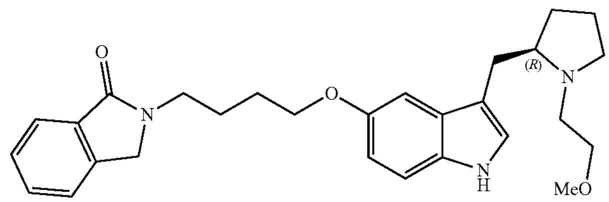 |
| (R) I-212 | 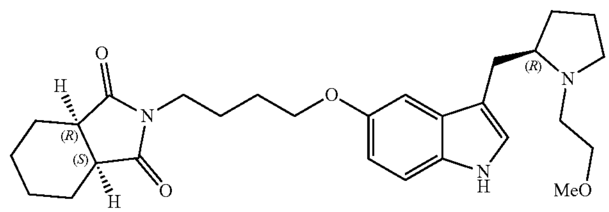 |
| (R) I-213 | 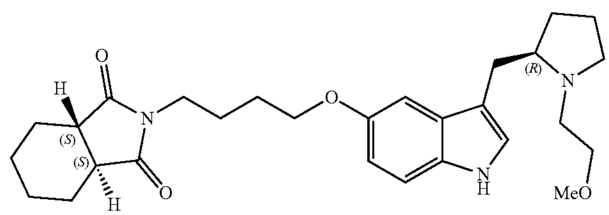 |
| (R) I-214 | 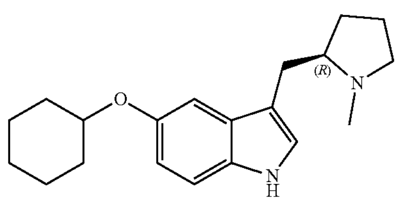 |
| (R) I-215 | 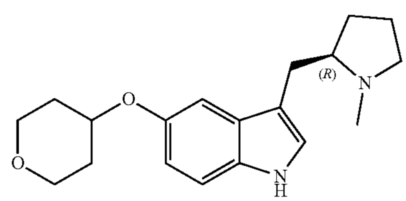 |
| (R) I-216 | 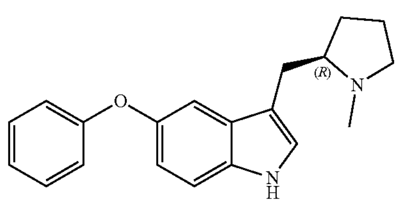 |
| (R) I-217 | 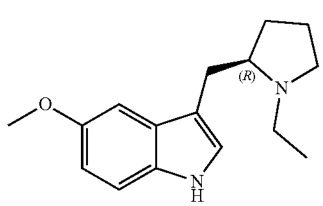 |

TABLE 3-continued
| Compound | Structure |
|---|---|
| (R) I-218 | 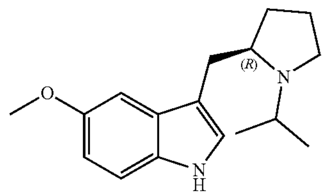 |
| (R) I-219 | 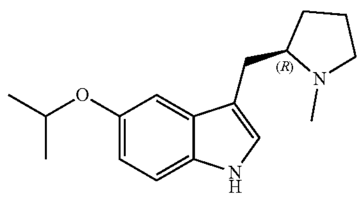 |
| (R) I-220 | 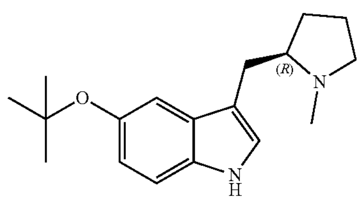 |
| (R) I-221 | 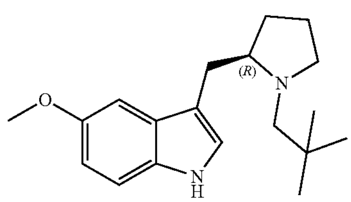 |
| (R) I-222 | 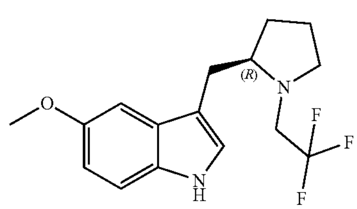 |
| (R) I-223 | 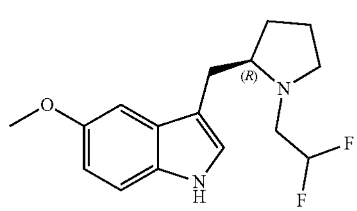 |
| (R) I-224 | 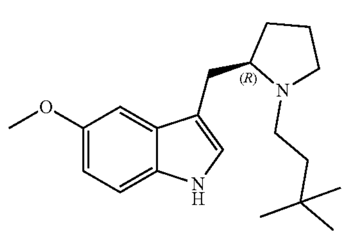 |

TABLE 3-continued
| Compound | Structure |
|---|---|
| (R) I-225 | 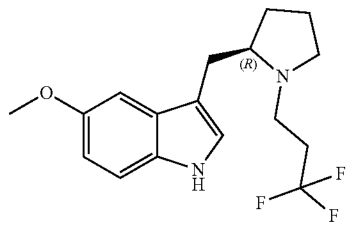 |
| (R) I-226 | 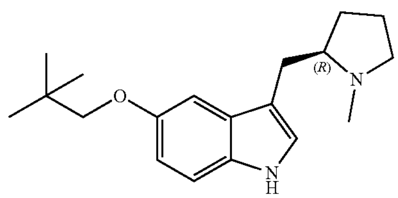 |
| (R) I-227 | 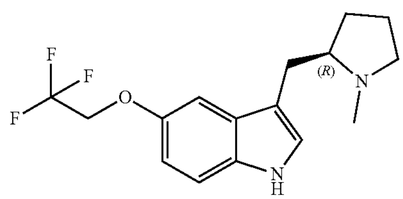 |
| (R) I-228 | 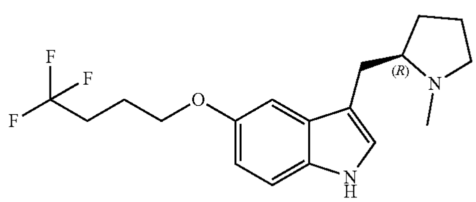 |
| (R) I-229 | 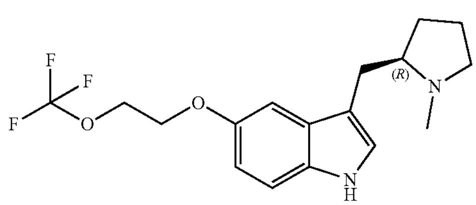 |
| (R) I-230 | 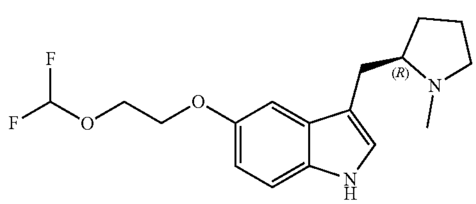 |
| (R) I-231 | 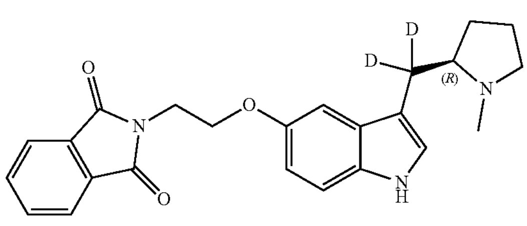 |

TABLE 3-continued
| Compound | Structure |
|---|---|
| (R) I-232 | 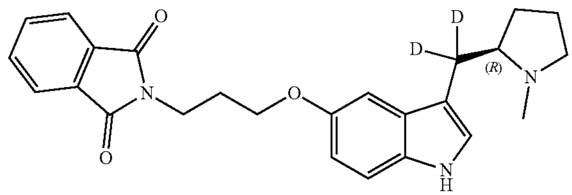 |
| (R) I-233 | 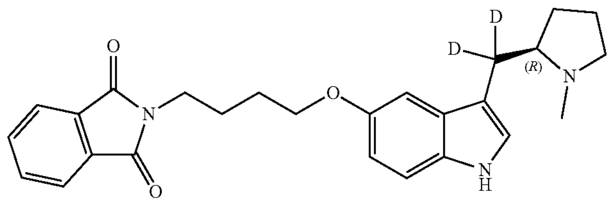 |
| (R) I-234 | 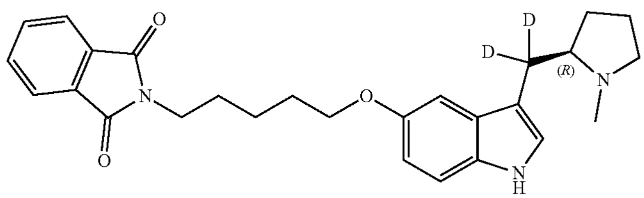 |
| Cis (R) I-235 | 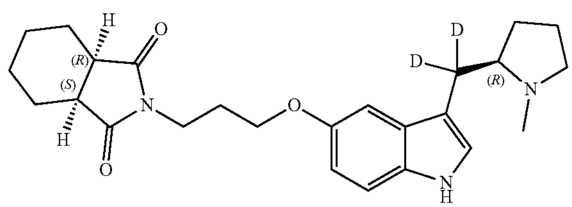 |
| Cis (R) I-236 | 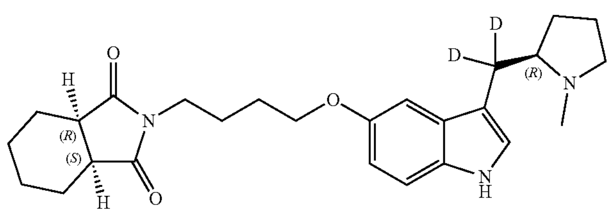 |
| (R) I-237 | 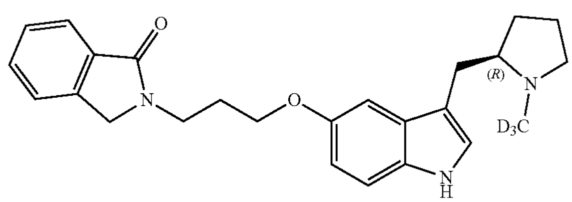 |
| (R) I-238 | 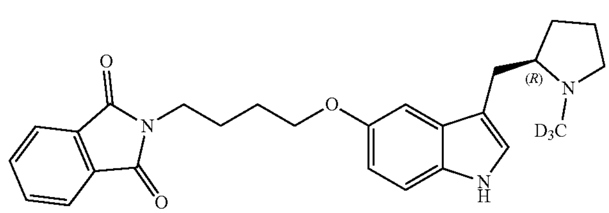 |

TABLE 3-continued
| Compound | Structure |
|---|---|
| (R) I-239 | 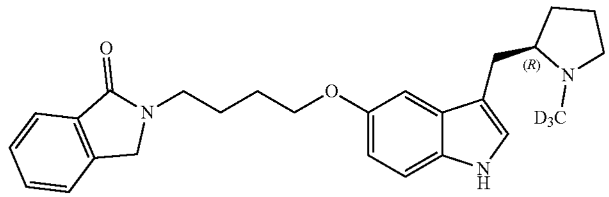 |
| Cis (R) I-240 | 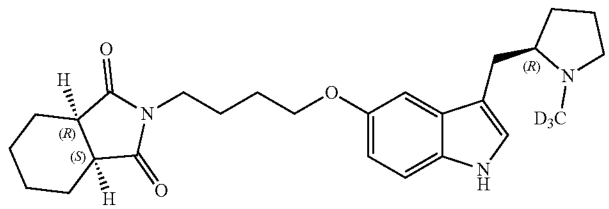 |
| Trans (R) I-241 | 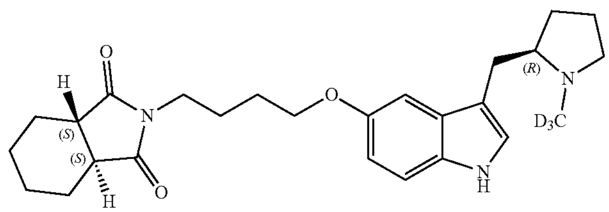 |
| (R) I-242 | 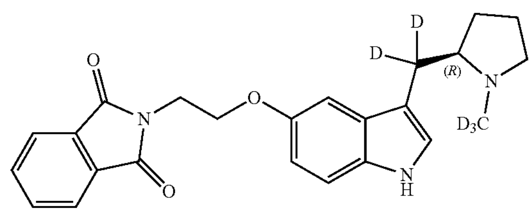 |
| (R) I-243 | 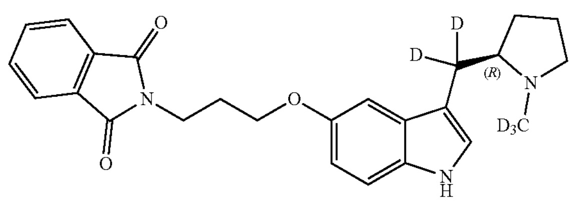 |
| (R) I-244 | 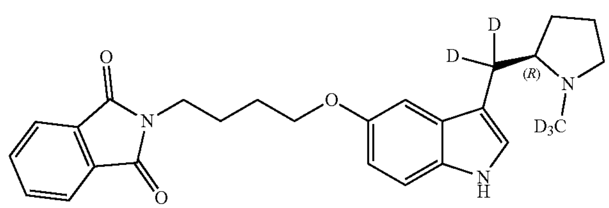 |
| (R) I-245 | 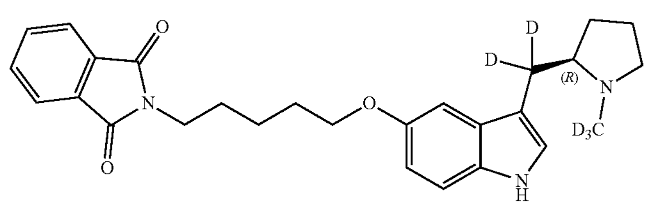 |

TABLE 3-continued
| Compound | Structure |
|---|---|
| Cis (R) I-246 | 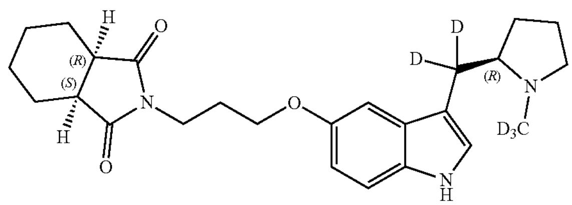 |
| Cis (R) I-247 | 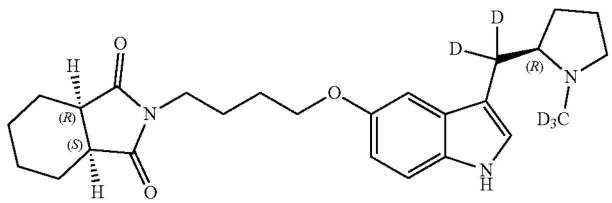 |
| Cis (R) I-248 | 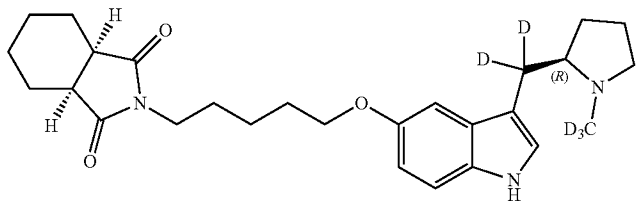 |
| Rac (R) I-248 | 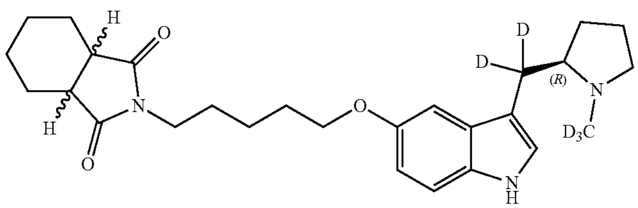 and |
| (R) I-249 | 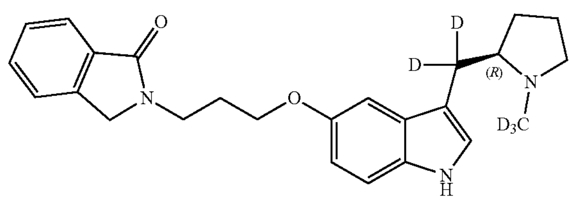 |
or a pharmaceutically acceptable salt, solvate, and/or prodrug thereof.
In some embodiments, the compound of Formula (I) is selected from one or more of the compounds listed in Tables 4 and 5 below:
TABLE 4
| Compound | Structure | IUPAC Name |
|---|---|---|
| (R) I-250 | 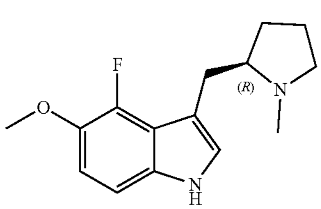 | (R)-4-fluoro-5-methoxy-3-((1-methylpyrrolidin-2-yl)methyl)-1H-indole |

TABLE 4-continued

| Compound | Structure | IUPAC Name |
| --- | --- | --- |
| (R) I-251 | 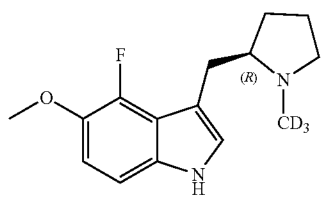 | (R)-4-fluoro-5-methoxy-3-((1-(methyl-d3)pyrrolidin-2-yl)methyl)-1H-indole |
| (R) I-252 | 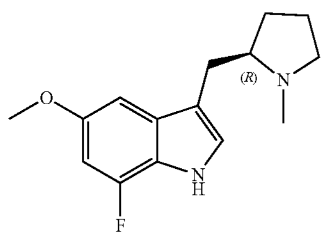 | (R)-7-fluoro-5-methoxy-3-((1-methylpyrrolidin-2-yl)methyl)-1H-indole |
| (R) I-253 | 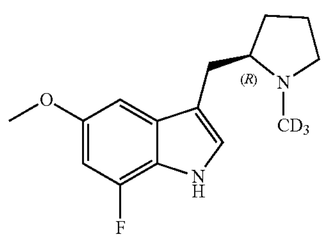 | (R)-7-fluoro-5-methoxy-3-((1-(methyl-d3)pyrrolidin-2-yl)methyl)-1H-indole |
| (R) I-254 | 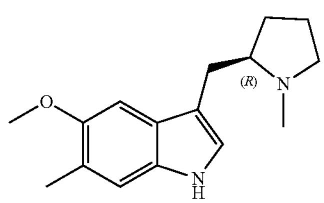 | (R)-5-methoxy-6-methyl-3-((1-methylpyrrolidin-2-yl)methyl)-1H-indole |
| (R) I-255 | 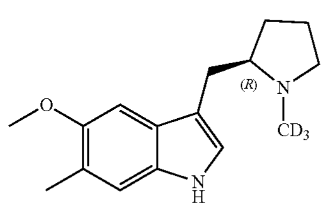 | (R)-5-methoxy-6-methyl-3-((1-(methyl-d3)pyrrolidin-2-yl)methyl)-1H-indole |
| (R) I-256 | 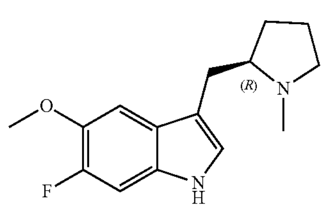 | (R)-6-fluoro-5-methoxy-3-((1-methylpyrrolidin-2-yl)methyl)-1H-indole |
| (R) I-257 | 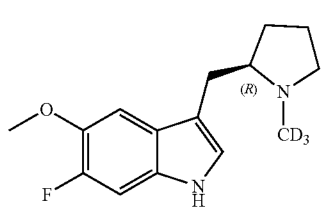 | (R)-6-fluoro-5-methoxy-3-((1-(methyl-d3)pyrrolidin-2-yl)methyl)-1H-indole and |

TABLE 4-continued
| Compound | Structure | IUPAC Name |
|---|---|---|
| (R) I-258 | 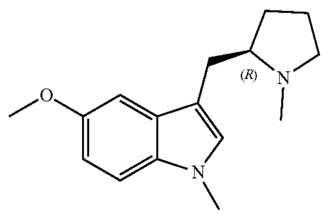 | (R)-5-methoxy-1-methyl-3-((1-methylpyrrolidin-2-yl)methyl)-1H-indole |
or a pharmaceutically acceptable salt, solvate, and/or prodrug thereof.
TABLE 5
| Compound | Structure |
|---|---|
| (R) I-259 | 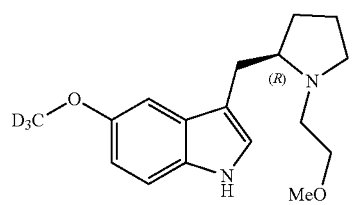 |
| (R) I-260 | 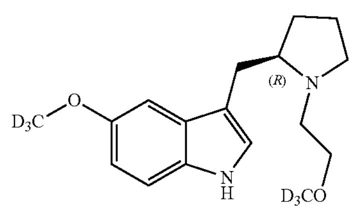 |
| (R) I-261 | 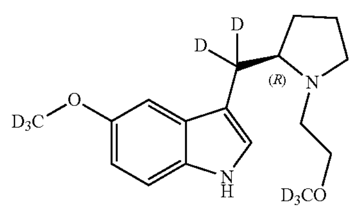 |
| (R) I-262 | 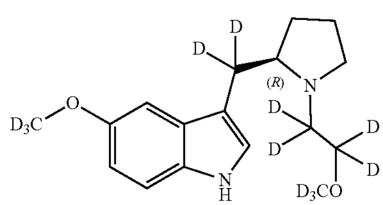 |
| (R) I-263 | 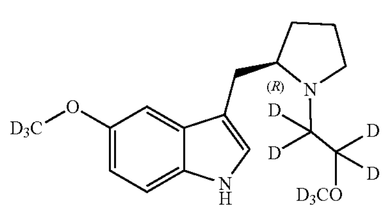 |

TABLE 5-continued
| Compound | Structure |
|---|---|
| (R) I-264 | 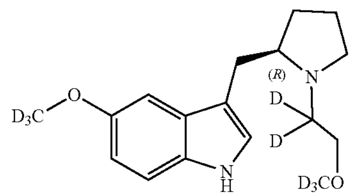 |
| (R) I-265 | 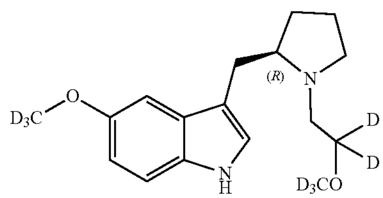 |
| (R) I-266 | 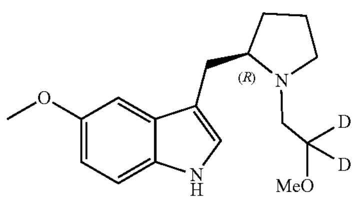 |
| (R) I-267 | 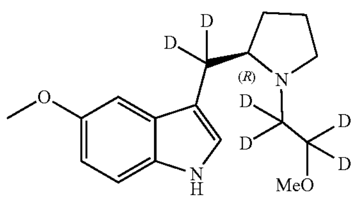 |
| (R) I-268 | 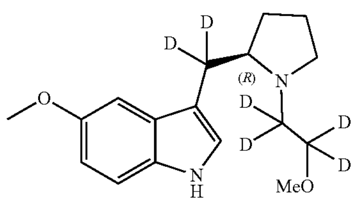 |
| (R) I-269 | 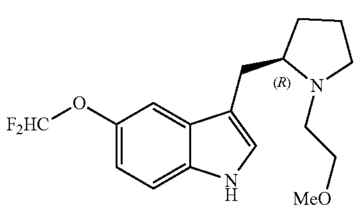 |
| (R) I-270 | 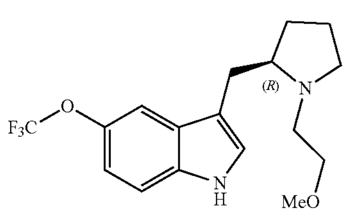 |

TABLE 5-continued
| Compound | Structure |
| --- | --- |
| (R) 1-271 | 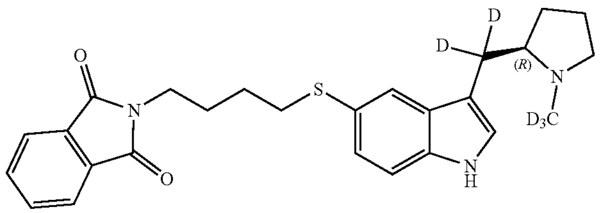 |
| (R) I-272 | 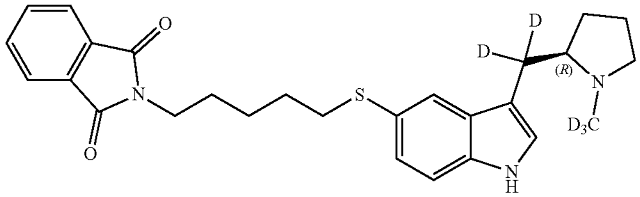 |
| (R) I-273 | 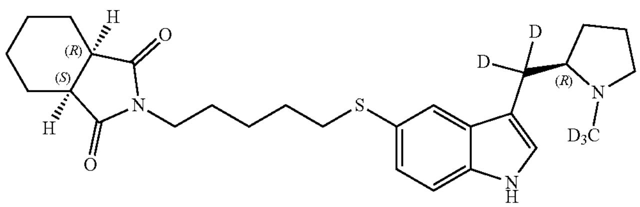 |
| (R) I-274 | 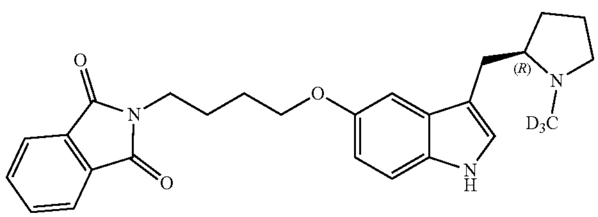 |
| (R) I-275 | 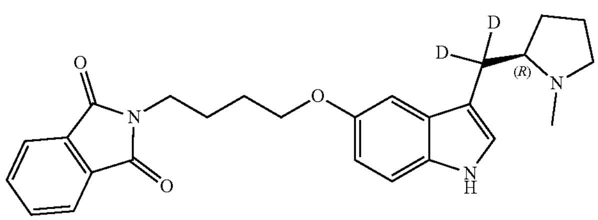 |
| (R) I-276 | 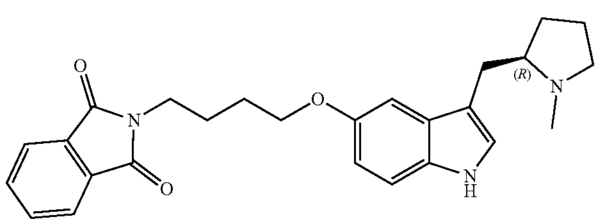 |
| (R) I-277 | 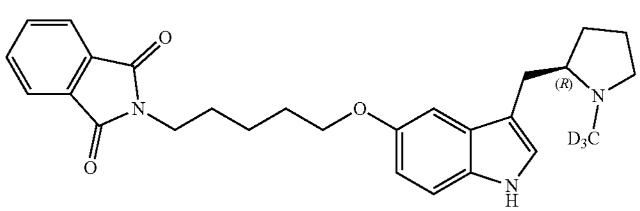 |

TABLE 5-continued
| Compound | Structure |
|---|---|
| (R) I-278 | 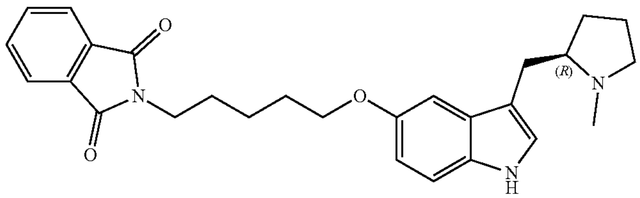 |
| (R) I-279 | 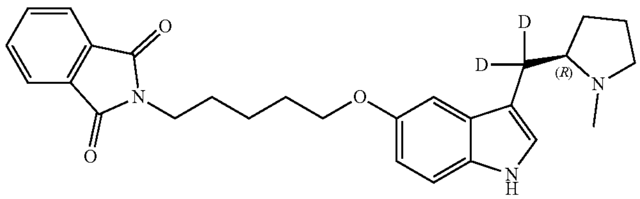 |
| (R) I-280 | 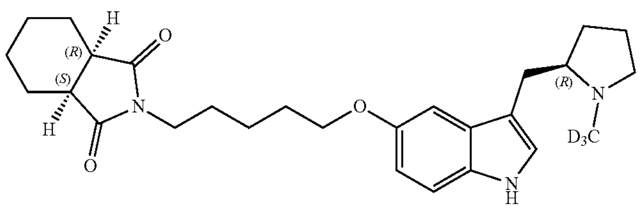 |
| (R) I-281 | 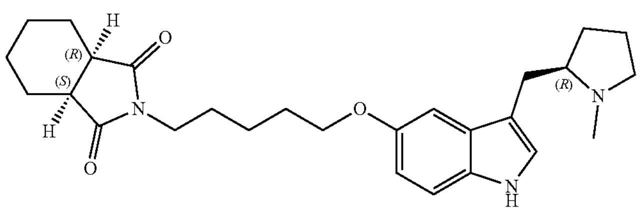 |
| (R) I-282 | 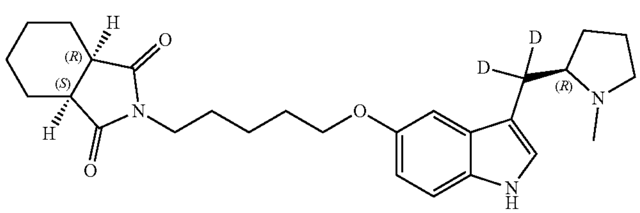 |
| (R) I-283 | 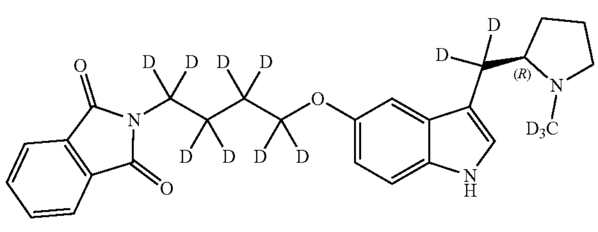 |
| (R) I-284 | 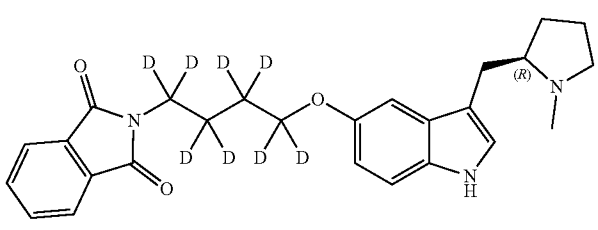 |

TABLE 5-continued
| Compound | Structure |
|---|---|
| (R) I-285 | 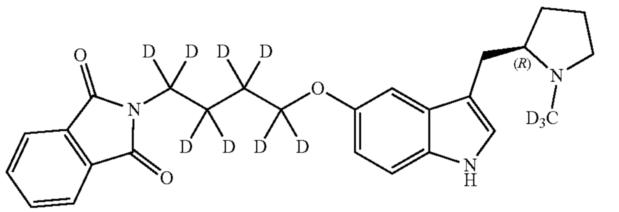 |
| (R) I-286 | 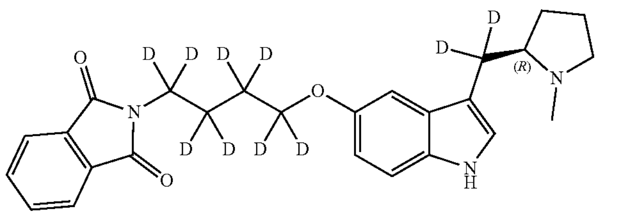 |
| (R) I-287 | 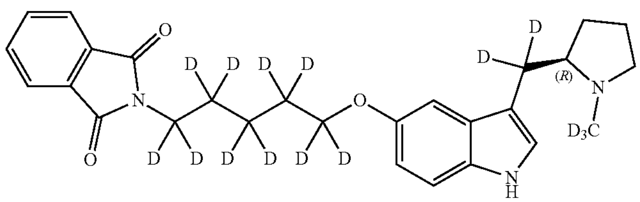 |
| (R) I-288 | 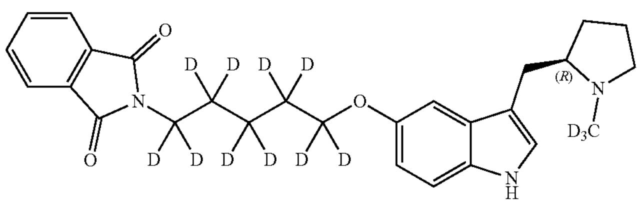 |
| (R) I-289 | 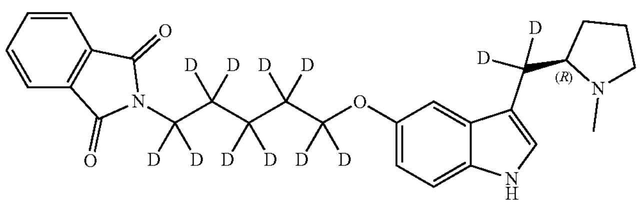 |
| (R) I-290 | 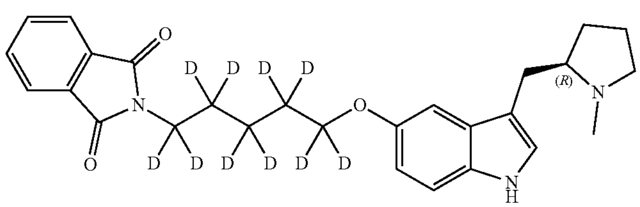 |
| (R) I-291 | 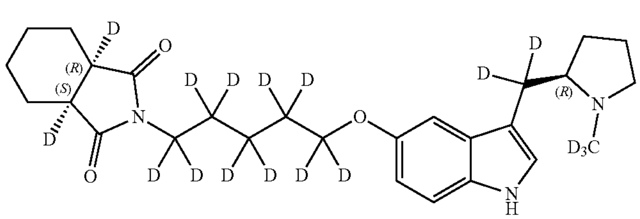 |

TABLE 5-continued
| Compound | Structure |
| --- | --- |
| (R) I-292 | 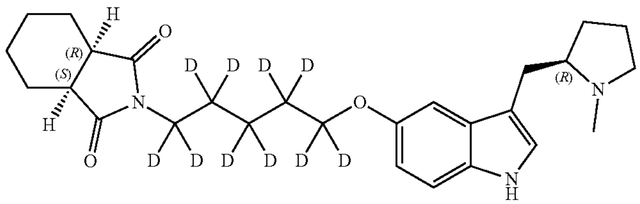 |
| (R) I-293 | 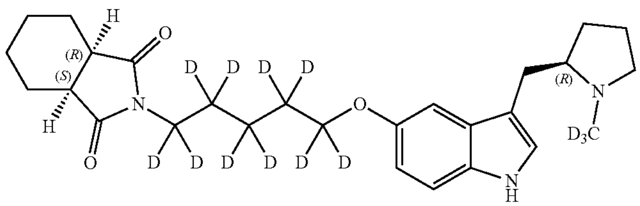 |
| (R) I-294 | 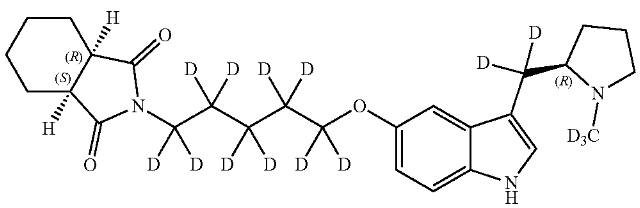 |
| (R) I-295 | 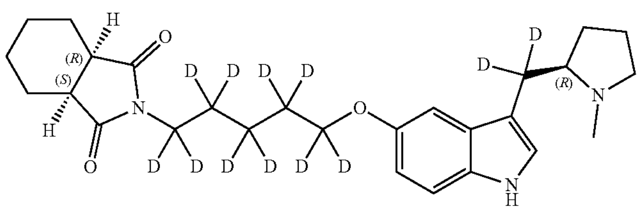 |
| (R) I-296 | 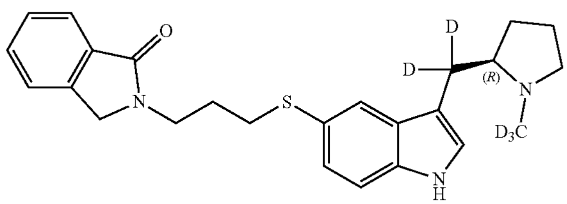 |
| (R) I-297 | 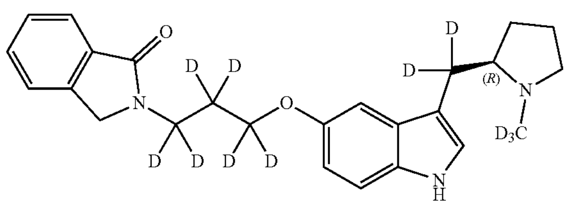 |
| (R) I-298 | 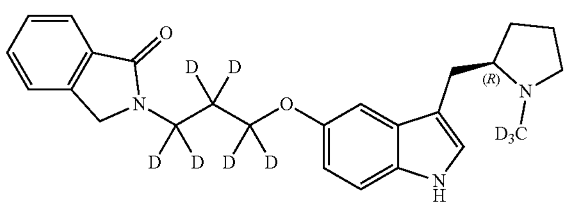 |

TABLE 5-continued
| Compound | Structure |
|---|---|
| (R) I-299 | 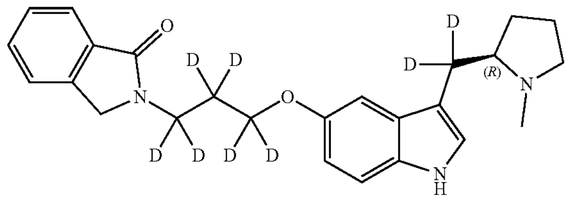 |
| (R) I-300 | 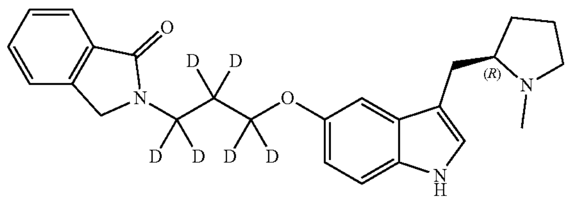 |
| (R) I-301 | 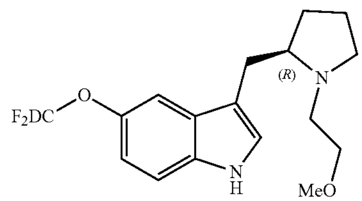 |
| (R) I-302 | 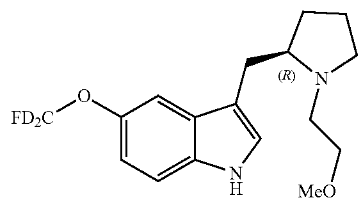 |
| (R) I-303 | 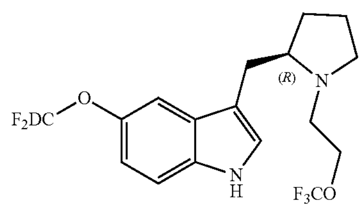 |
| (R) I-304 | 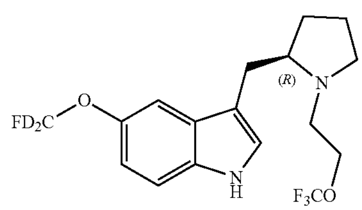 |
| (R) I-305 | 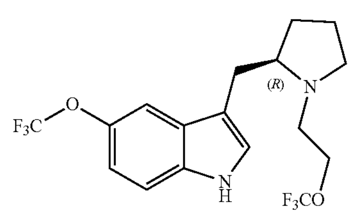 |

TABLE 5-continued
| Compound | Structure |
|---|---|
| (R) I-306 | 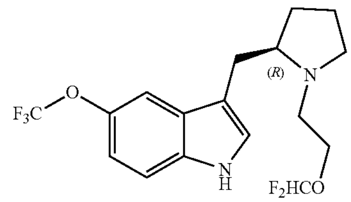 |
| (R) I-307 | 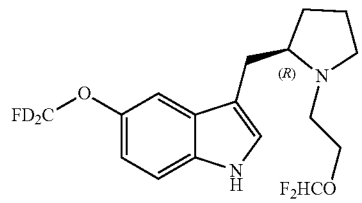 |
| (R) I-308 | 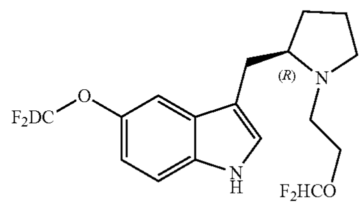 |
| (R) I-309 | 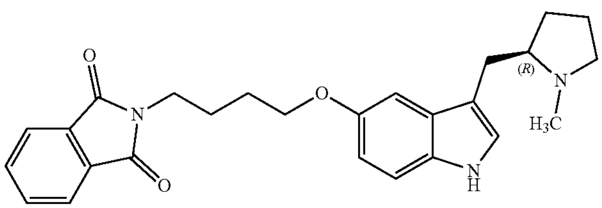 |
| (R) I-310 | 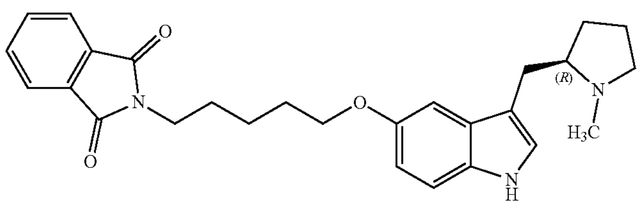 |
| (R) I-311 | 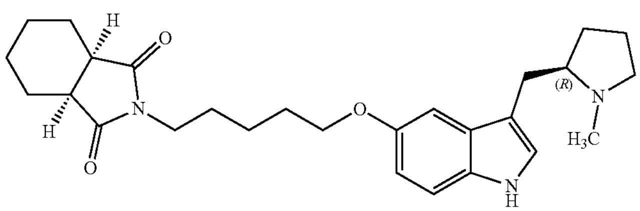 |
| (R) I-312 | 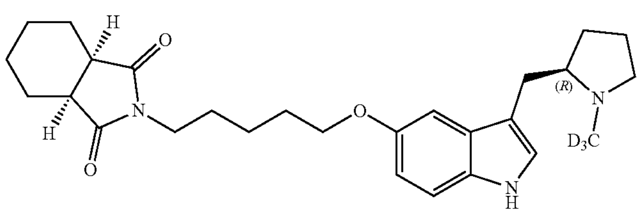 |

TABLE 5-continued

| Compound | Structure |
|---|---|
| (R) I-313 | 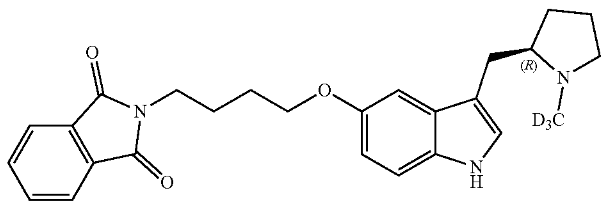 |
| | and |
| (R) I-314 | 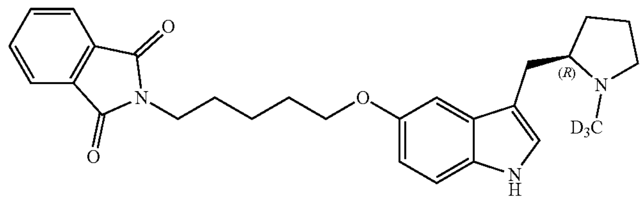 |

or a pharmaceutically acceptable salt, solvate, and/or prodrug thereof.

In some embodiments, the pharmaceutically acceptable salt is an acid addition salt or a base addition salt. The selection of a suitable salt may be made by a person skilled in the art. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Additionally, acids that are generally considered suitable for the formation of pharmaceutically useful salts from basic pharmaceutical compounds are discussed, for example, by P. Stahl et al, Camille G. (eds.) and Handbook of Pharmaceutical Salts. Properties, Selection and Use. (2002) Zurich: Wiley VCH; S. Berge et al, Journal of Pharmaceutical Sciences 1977 66(1) 1-19; P. Gould, International J. of Pharmaceutics (1986) 33 201-217; Anderson et al, The Practice of Medicinal Chemistry (1996), Academic Press, New York; and in The Orange Book (Food and Drug Administration, Washington, D.C. on their website).

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di-, and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid, and other sulfonic acids such as methanesulfonic acid, ethanesulfonic acid, and 2-hydroxyethanesulfonic acid. In some embodiments, exemplary acid addition salts also include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates), and the like. In some embodiments, the mono- or di-acid salts are formed and such salts exist in either a hydrated, solvated, or substantially anhydrous form. In general, acid addition salts are more soluble in water and various hydrophilic organic solvents and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the disclosure for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium, or barium hydroxide as well as ammonia. Illustrative organic bases which form suitable salts include aliphatic, alicyclic, or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. The selection of the appropriate salt may be useful, for example, so that an ester functionality, if any, elsewhere in a compound is not hydrolyzed. The selection criteria for the appropriate salt will be known to one skilled in the art. In some embodiments, exemplary basic salts also include ammonium salts, alkali metal salts such as sodium, lithium, and potassium salts, alkaline earth metal salts such as calcium and magnesium salts, salts with organic bases (for example, organic amines) such as dicyclohexylamine, butyl amine, choline, and salts with amino acids such as arginine, lysine, and the like. Basic nitrogen containing groups may be quarternized with agents such as lower alkyl halides (e.g., methyl, ethyl, and butyl chlorides, bromides, and iodides), dialkyl sulfates (e.g., dimethyl, diethyl, and dibutyl sulfates), long chain halides (e.g., decyl, lauryl, and stearyl chlorides, bromides, and iodides), aralkyl halides (e.g., benzyl and phenethyl bromides), and others. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

All such acid salts and base salts are intended to be pharmaceutically acceptable salts within the scope of the disclosure and all acid and base salts are considered equivalent to the free forms of the corresponding compounds for purposes of the disclosure. In addition, when a compound of the disclosure contains both a basic moiety, such as, but not limited to an aliphatic primary, secondary, tertiary, or cyclic amine, an aromatic or heteroaryl amine, pyridine, or imidazole and an acidic moiety, such as, but not limited to tetrazole or carboxylic acid, zwitterions ("inner salts") may be formed and are included within the terms "salt(s)," as used herein. It is understood that certain compounds of the disclosure may exist in zwitterionic form, having both anionic and cationic centers within the same compound and a net neutral charge. Such zwitterions are included within the disclosure.

Solvates of compounds of the disclosure include, for example, those made with solvents that are pharmaceutically acceptable. Examples of such solvents include water (resulting solvate is called a hydrate) and ethanol and the like. Suitable solvents are physiologically tolerable at the dosage administered.

Prodrugs of the compounds of the present disclosure include, for example, conventional esters formed with available hydroxy, thiol, amino, or carboxyl groups. Some common esters which have been utilized as prodrugs are phenyl esters, aliphatic ($C_1$-$C_{24}$) esters, acyloxymethyl esters, carbamates, and amino acid esters.

It is understood and appreciated that in some embodiments, compounds of the present disclosure may have at least one chiral center and therefore can exist as enantiomers and/or diastereomers. It is to be understood that all such isomers and mixtures thereof in any proportion are encompassed within the scope of the present disclosure. It is to be further understood that while the stereochemistry of the compounds may be as shown in any given compound listed herein, such compounds may also contain certain amounts (for example, less than 20%, suitably less than 10%, more suitably less than 5%) of compounds of the present disclosure having an alternate stereochemistry. It is intended that any optical isomers, as separated, pure, or partially purified optical isomers or racemic mixtures thereof are included within the scope of the present disclosure.

In some embodiments, the compounds of the present disclosure can also include tautomeric forms, such as keto-enol tautomers and the like. Tautomeric forms can be in equilibrium or sterically locked into one form by appropriate substitution. It is intended that any tautomeric forms which the compounds form, as well as mixtures thereof, are included within the scope of the present disclosure.

The compounds of the present disclosure may further exist in varying amorphous and polymorphic forms and it is contemplated that any amorphous forms, polymorphs, or mixtures thereof, which form are included within the scope of the present disclosure.

In the compounds of general Formula (I) and pharmaceutically acceptable salts, solvates, and/or prodrug thereof, the atoms may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds of the disclosure and pharmaceutically acceptable salts, solvates, and/or prodrug thereof. For example, different isotopic forms of hydrogen (H) include protium (1H), deuterium (2H), and tritium (3H). Protium is the predominant hydrogen isotope found in nature.

The compounds of the present disclosure may further be radiolabeled and accordingly all radiolabeled versions of the compounds of the disclosure are included within the scope of the present disclosure. Therefore, the compounds of the disclosure also include those in which one or more radioactive atoms are incorporated within their structure.

III. Compositions

The compounds of the present disclosure are suitably formulated in a conventional manner into compositions using one or more carriers. Accordingly, the present disclosure also includes a composition comprising one or more compounds of the disclosure and a carrier. The compounds of the disclosure are suitably formulated into pharmaceutical compositions for administration to subjects in a biologically compatible form suitable for administration in vivo. Accordingly, the present disclosure further includes a pharmaceutical composition comprising one or more compounds of the disclosure and a pharmaceutically acceptable carrier. In embodiments of the disclosure the pharmaceutical compositions are used in the treatment of any of the diseases, disorders, or conditions described herein.

The compounds of the disclosure are administered to a subject in a variety of forms depending on the selected route of administration, as will be understood by those skilled in the art. For example, a compound of the disclosure is administered by oral, inhalation, parenteral, buccal, sublingual, insufflation, epidurally, nasal, rectal, vaginal, patch, pump, minipump, topical, or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000—20th edition) and in The United States Pharmacopeia: The National Formulary (USP 24 NF 19) published in 1999.

Parenteral administration includes systemic delivery routes other than the gastrointestinal (GI) tract and includes, for example intravenous, intra-arterial, intraperitoneal, subcutaneous, intramuscular, transepithelial, nasal, intrapulmonary (for example, by use of an aerosol), intrathecal, rectal, and topical (including the use of a patch or other transdermal delivery device) modes of administration. Parenteral administration may be by continuous infusion over a selected period of time.

In some embodiments, a compound of the disclosure is orally administered, for example, with an inert diluent or with an assimilable edible carrier, or it is enclosed in hard- or soft-shell gelatin capsules, or it is compressed into tablets, or it is incorporated directly with the food of the diet. In some embodiments, the compound is incorporated with excipient(s) and used in the form of ingestible tablets, buccal tablets, troches, capsules, caplets, pellets, granules, lozenges, chewing gum, powders, syrups, elixirs, wafers, aqueous solutions, suspensions, and the like. In the case of tablets, carriers that are used include lactose, corn starch, sodium citrate, and salts of phosphoric acid. Pharmaceutically acceptable excipients include binding agents (e.g., pregelatinized maize starch, polyvinylpyrrolidone, or hydroxypropyl methylcellulose); fillers (e.g., lactose, microcrystalline cellulose, or calcium phosphate); lubricants (e.g., magnesium stearate, talc, or silica); disintegrants (e.g., potato starch or sodium starch glycolate); wetting agents (e.g., sodium lauryl sulphate); and/or solvents (e.g., medium chain triglycerides, ethanol, or water). In embodiments, the tablets are coated by methods well known in the art. In the case of tablets, capsules, caplets, pellets, or granules for oral administration, pH sensitive enteric coatings, such as Eudragits™, designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for example, as liposomes or those wherein the active compound is protected with differentially degradable coatings, such as by microencapsulation, multiple coatings, etc. Liposome delivery systems include, for example, small unilamellar vesicles, large unilamellar vesicles, and multilamellar vesicles. In some embodiments, liposomes are formed from a variety of phospholipids, such as cholesterol, stearylamine, or phosphatidylcholines. For oral administration in a capsule form, useful carriers, solvents, or diluents include lactose, medium chain triglycerides, ethanol, and dried corn starch.

In some embodiments, liquid preparations for oral administration take the form of, for example, solutions, syrups, or suspensions, or they are suitably presented as a dry product for constitution with water or other suitable vehicle before use. When aqueous suspensions and/or emulsions are administered orally, the compound of the disclosure is suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose, or hydrogenated edible fats); emulsifying agents (e.g., lecithin or acacia); non-aqueous vehicles (e.g., medium chain triglycerides, almond oil, oily esters, or ethyl alcohol); and/or preservatives (e.g., methyl or propyl p-hydroxybenzoates or sorbic acid). Useful diluents include lactose and high molecular weight polyethylene glycols.

It is also possible to freeze-dry the compounds of the disclosure and use the lyophilizates obtained, for example, for the preparation of products for injection.

In some embodiments, a compound of the disclosure is administered parenterally. For example, solutions of a compound of the disclosure are prepared in water suitably mixed with a surfactant such as hydroxypropylcellulose. In some embodiments, dispersions are prepared in glycerol, liquid polyethylene glycols, DMSO, and mixtures thereof with or without alcohol and in oils. Under ordinary conditions of storage and use, these preparations contain a preservative to prevent the growth of microorganisms. A person skilled in the art would know how to prepare suitable formulations. For parenteral administration, sterile solutions of the compounds of the disclosure are usually prepared and the pH's of the solutions are suitably adjusted and buffered. For intravenous use, the total concentration of solutes should be controlled to render the preparation isotonic. For ocular administration, ointments, or droppable liquids are delivered, for example, by ocular delivery systems known to the art such as applicators or eye droppers. In some embodiments, such compositions include mucomimetics such as hyaluronic acid, chondroitin sulfate, hydroxypropyl methylcellulose, or polyvinyl alcohol, preservatives such as sorbic acid, EDTA, or benzyl chromium chloride, and the usual quantities of diluents or carriers. For pulmonary administration, diluents or carriers will be selected to be appropriate to allow the formation of an aerosol.

In some embodiments, a compound of the disclosure is formulated for parenteral administration by injection, including using conventional catheterization techniques or infusion. Formulations for injection are, for example, presented in unit dosage form, e.g., in ampoules or in multi-dose containers, with an added preservative. In some embodiments, the compositions take such forms as sterile suspensions, solutions, or emulsions in oily or aqueous vehicles and contain formulating agents such as suspending, stabilizing, and/or dispersing agents. In all cases, the form must be sterile and must be fluid to the extent that easy syringability exists. Alternatively, the compounds of the disclosure are suitably in a sterile powder form for reconstitution with a suitable vehicle, e.g., sterile pyrogen-free water, before use.

In some embodiments, compositions for nasal administration are conveniently formulated as aerosols, drops, gels, and powders. For intranasal administration or administration by inhalation, the compounds of the disclosure are conveniently delivered in the form of a solution, dry powder formulation, or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide, or another suitable gas. In the case of a pressurized aerosol, the dosage unit is suitably determined by providing a valve to deliver a metered amount. In some embodiments, the pressurized container or nebulizer contains a solution or suspension of the active compound. Capsules and cartridges (made, for example, from gelatin) for use in an inhaler or insufflator are, for example, formulated containing a powder mix of a compound of the disclosure and a suitable powder base such as lactose or starch. The aerosol dosage forms can also take the form of a pump-atomizer.

Compositions suitable for buccal or sublingual administration include tablets, lozenges, and pastilles, wherein a compound of the disclosure is formulated with a carrier such as sugar, acacia, tragacanth, or gelatin, and glycerine. Compositions for rectal administration are conveniently in the form of suppositories containing a conventional suppository base such as cocoa butter.

Suppository forms of the compounds of the disclosure are useful for vaginal, urethral, and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: Remington's Pharmaceutical Sciences, 16th Ed., Mack Publishing, Easton, PA, 1980, pp. 1530-1533 for further discussion of suppository dosage forms.

In some embodiments a compound of the disclosure is coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, in some embodiments, a compound of the disclosure is coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

A compound of the disclosure including pharmaceutically acceptable salts, solvates, and/or prodrugs thereof is suitably used on their own but will generally be administered in the form of a pharmaceutical composition in which the one or more compounds of the disclosure (the active ingredient) is in association with a pharmaceutically acceptable carrier. Depending on the mode of administration, the pharmaceutical composition will comprise from about 0.05 wt % to about 99 wt %, or about 0.10 wt % to about 70 wt %, of the active ingredient and from about 1 wt % to about 99.95 wt %, or about 30 wt % to about 99.90 wt % of a pharmaceutically acceptable carrier, all percentages by weight being based on the total composition.

In some embodiments, the compounds of the disclosure including pharmaceutically acceptable salts, solvates, and/or prodrugs thereof are used are administered in a composition comprising an additional therapeutic agent. Therefore, the present disclosure also includes a pharmaceutical composition comprising one or more compounds of the disclosure, or pharmaceutically acceptable salts, solvates, and/or prodrugs thereof and an additional therapeutic agent, and optionally one or more pharmaceutically acceptable excipients. In some embodiments, the additional therapeutic agent is another known agent useful for treatment of a disease, disorder, or condition by activation of a serotonin receptor, for example those listed in the Methods and Uses section below. In some embodiments, the additional therapeutic agent is a psychoactive drug.

In the above, the term "a compound" also includes embodiments wherein one or more compounds are referenced.

IV. Methods and Uses of the Disclosure

The compounds of the disclosure are serotonergic binding agents that act as agonists or partial agonists at a serotonin receptor.

Accordingly, the present disclosure includes a method for activating a serotonin receptor in a cell, either in a biological sample or in a patient, comprising administering an effective amount of one or more compounds of the disclosure to the cell. The disclosure also includes or of one or more compounds of the disclosure for activating a serotonin receptor in a cell as well as use of one or more compounds of the disclosure for the preparation of a medicament for activating a serotonin receptor in a cell. The disclosure further includes one or more compounds of the disclosure for use in activating a serotonin receptor in a cell. In some embodiments, the method for activating a serotonin receptor is in or on a cell.

As the compounds of the disclosure are capable of activating a serotonin receptor, the compounds of the disclosure are useful for treating diseases, disorders, or conditions by activating a serotonin receptor. Therefore, the compounds of the present disclosure are useful as medicaments. Accordingly, the disclosure also includes a compound of the disclosure for use as a medicament.

The present disclosure also includes a method of treating a disease, disorder, or condition by activation of a serotonin receptor comprising administering a therapeutically effective amount of one or more compounds of the disclosure to a subject in need thereof.

The present disclosure also includes use of one or more compounds of the disclosure for treatment of a disease, disorder, or condition by activation of a serotonin receptor as well as use of one or more compounds of the disclosure for the preparation of a medicament for treatment of a disease, disorder, or condition by activation of a serotonin receptor. The disclosure further includes one or more compounds of the disclosure for use in treating a disease, disorder, or condition by activation of a serotonin receptor.

In some embodiments, the serotonin receptor is 5-$HT_{2A}$. Accordingly, the present disclosure includes a method for activating 5-$HT_{2A}$ in a cell, either in a biological sample or in a patient, comprising administering an effective amount of one or more compounds of the disclosure to the cell. The disclosure also includes use of one or more compounds of the disclosure for activating 5-$HT_{2A}$ in a cell as well as use of one or more compounds of the disclosure for the preparation of a medicament for activating 5-$HT_{2A}$ in a cell. The disclosure further includes one or more compounds of the disclosure for use in activating 5-$HT_{2A}$ in a cell. In some embodiments, the method for activating 5-$HT_{2A}$ is in or on a cell.

The present disclosure also includes a method of treating a disease, disorder, or condition by activation of 5-$HT_{2A}$ comprising administering a therapeutically effective amount of one or more compounds of the disclosure to a subject in need thereof. The present disclosure also includes use of one or more compounds of the disclosure for treatment of a disease, disorder, or condition by activation of 5-$HT_{2A}$ as well as use of one or more compounds of the disclosure for the preparation of a medicament for treatment of a disease, disorder, or condition by activation of 5-$HT_{2A}$. The disclosure further includes one or more compounds of the disclosure for use in treating a disease, disorder, or condition by activation of 5-$HT_{2A}$.

In some embodiments, the compounds of the disclosure are useful for preventing, treating, and/or reducing the severity of a mental illness disorder and/or condition in a subject. Therefore, in some embodiments, the disease, disorder, or condition that is treated by activation of a serotonin receptor is a mental illness. Accordingly, the present disclosure also includes a method of treating a mental illness comprising administering a therapeutically effective amount of one or more compounds of the disclosure to a subject in need thereof. The present disclosure also includes use of one or more compounds of the disclosure for treatment a mental illness, as well as use of one or more compounds of the disclosure for the preparation of a medicament for treatment of a mental illness. The disclosure further includes one or more compounds of the disclosure for use in treating a mental illness.

In some embodiments, the mental illness is selected from anxiety disorders such as generalized anxiety disorder, panic disorder, social anxiety disorder and specific phobias; depression such as, hopelessness, loss of pleasure, fatigue, and suicidal thoughts; mood disorders, such as depression, bipolar disorder, cancer-related depression, major depressive disorder (MDD), treatment-resistant depression (TRD), postpartum depression (PPD), anxiety, and cyclothymic disorder; psychotic disorders, such as hallucinations, delusions, and schizophrenia; impulse control, and addiction disorders, such as pyromania (starting fires), kleptomania (stealing), and compulsive gambling; alcohol addiction (e.g., reduction in alcohol consumption); drug addiction, such as opioid addiction; personality disorders, such as antisocial personality disorder, obsessive-compulsive personality disorder, and paranoid personality disorder; obsessive-compulsive disorder (OCD), such as thoughts or fears that cause a subject to perform certain rituals or routines; post-traumatic stress disorder (PTSD); stress response syndromes (formerly called adjustment disorders); dissociative disorders, formerly called multiple personality disorder, or "split personality," and depersonalization disorder; factitious disorders; sexual and gender disorders, such as sexual dysfunction, gender identity disorder and the paraphilia's; somatic symptom disorders, formerly known as a psychosomatic disorder or somatoform disorder; body dysmorphic disorder; influencing goal-directed behavior; emotional state disorders (e.g., diminishment of negative emotions and promoting positive emotions); enhancements in creativity; and combinations thereof.

In some embodiments, the disease, disorder, or condition that is treated by activation of a serotonin receptor comprises cognitive impairment (e.g., amplifies cognitive capabilities, enhance and/or improve cognitive flexibility); ischemia including stroke; neurodegeneration; refractory substance use disorders; sleep disorders; pain, such as social pain, acute pain, cancer pain, chronic pain, breakthrough pain, bone pain, soft tissue pain, nerve pain, referred pain, phantom pain, neuropathic pain, cluster headaches, and migraine; obesity and eating disorders; epilepsies and seizure disorders; neuronal cell death; excitotoxic cell death; inflammation (e.g., autoimmune neuroinflammation); or a combination thereof.

In some embodiments, the mental illness is selected from hallucinations and delusions and a combination thereof.

In some embodiments, the hallucinations are selected from visual hallucinations, visual disorders (e.g., Prosopometamorphopsia (PMO), influencing facial recognition, and improving the processing of emotional faces in treatment-resistant depression (TRD)), auditory hallucinations, olfactory hallucinations, gustatory hallucinations, tactile hallucinations, proprioceptive hallucinations, equilibrioceptive hallucinations, nociceptive hallucinations, thermoceptive hallucinations, and chronoceptive hallucinations, and a combination thereof.

In some embodiments, the disease, disorder, or condition that is treated by activation of a serotonin receptor is psychosis or psychotic symptoms. Accordingly, the present disclosure also includes a method of treating psychosis or psychotic symptoms comprising administering a therapeutically effective amount of one or more compounds of the disclosure to a subject in need thereof.

The present disclosure also includes use of one or more compounds of the disclosure for treatment of psychosis or psychotic symptoms, as well as use of one or more compounds of the disclosure for the preparation of a medicament for treatment of psychosis or psychotic symptoms. The disclosure further includes one or more compounds of the disclosure for use in treating psychosis or psychotic symptoms.

In some embodiments, administering to said subject in need thereof a therapeutically effective amount of the compounds of the disclosure does not result in a worsening of psychosis or psychotic symptoms such as, but not limited to, hallucinations and delusions. In some embodiments, administering to said subject in need thereof a therapeutically effective amount of the compounds of the disclosure results in an improvement of psychosis or psychotic symptoms such as, but not limited to, hallucinations and delusions. In some embodiments, administering to said subject in need thereof a therapeutically effective amount of the compounds of the disclosure results in an improvement of psychosis or psychotic symptoms.

In some embodiments, the disease, disorder, or condition that is treated by activation of a serotonin receptor is a central nervous system (CNS) disease, disorder, or condition and/or a neurological disease, disorder, or condition. Accordingly, the present disclosure also includes a method of treating a CNS disease, disorder, or condition and/or a neurological disease, disorder, or condition that is treated by activation of a serotonin receptor comprising administering a therapeutically effective amount of one or more compounds of the disclosure to a subject in need thereof, that is a subject having the central nervous system (CNS) disease, disorder, or condition and/or a neurological disease, disorder, or condition. The present disclosure also includes use of one or more compounds of the disclosure for treatment a CNS disease, disorder, or condition and/or a neurological disease, disorder, or condition that is treated by activation of a serotonin receptor, as well as use of one or more compounds of the disclosure for the preparation of a medicament for treatment of a CNS disease, disorder, or condition and/or a neurological disease, disorder, or condition that is treated by activation of a serotonin receptor. The disclosure further includes one or more compounds of the disclosure for use in treating a CNS disease, disorder, or condition and/or a neurological disease, disorder, or condition that is treated by activation of a serotonin receptor.

In some embodiments the CNS disease, disorder, or condition, and/or neurological disease, disorder, or condition is selected from neurological diseases including neurodevelopmental diseases and neurodegenerative diseases such as Alzheimer's disease (e.g., restoring mGluR2 expression); presenile dementia; senile dementia; vascular dementia; Lewy body dementia; cognitive impairment; Parkinson's disease and Parkinsonian related disorders such as Parkinson's dementia, corticobasal degeneration, and supranuclear palsy; epilepsy; CNS trauma; CNS infections; CNS inflammation; stroke; multiple sclerosis; Huntington's disease; mitochondrial disorders; Fragile X syndrome; Angelman syndrome; hereditary ataxias; neuro-otological and eye movement disorders; neurodegenerative diseases of the retina amyotrophic lateral sclerosis; tardive dyskinesias; hyperkinetic disorders; attention deficit hyperactivity disorder, and attention deficit disorders; restless leg syndrome; Tourette's syndrome; schizophrenia; autism spectrum disorders; tuberous sclerosis; Rett syndrome; cerebral palsy; disorders of the reward system including eating disorders such as anorexia nervosa ("AN"), and bulimia nervosa ("BN"); and binge eating disorder ("BED"); pica; rumination disorder; avoidant/restrictive food intake disorder; trichotillomania; dermotillomania; nail biting; migraine; fibromyalgia; and peripheral neuropathy of any etiology; reduction in convergent thinking; increase in spontaneous divergent thinking and goal-oriented divergent thinking; and combinations thereof.

The present disclosure also includes a method of treating nonpsychiatric conditions, such as: fibromyalgia, irritable bowel syndrome (IBS), Fragile X, short-lasting unilateral neuralgiform headache attacks with cranial autonomic symptoms (SUHNA), chronic cluster, persistent post-concussive syndrome (PPCS), Alzheimer's disease, Lyme disease, neuropathic pain, migraines, Parkinson's disease, cluster headache, stroke, traumatic brain injury (TBI), pain, obesity, and smoking cessation.

In some embodiments, the subject is a mammal. In another embodiment, the subject is human. In some embodiments, the subject is a non-human animal. In some embodiments, the subject is canine. In some embodiments, the subject is feline. Accordingly, the compounds, methods, and uses of the present disclosure are directed to both human and veterinary diseases, disorders, and conditions.

In some embodiments, the "subject in need thereof" is a subject having the disease, disorder, or condition to be treated.

In some embodiments, the compounds of the disclosure are useful for treating behavioral problems in subjects that are felines or canines.

Therefore, in some embodiments, the disease, disorder, or condition that is treated by activation of a serotonin receptor is behavioral problems in subjects that are felines or canines. Accordingly, the present disclosure also includes a method of treating a behavioral problem comprising administering a therapeutically effective amount of one or more compounds of the disclosure to a non-human subject in need thereof. The present disclosure also includes use of one or more compounds of the disclosure for treatment of a behavioral problem in a non-human subject, as well as use of one or more compounds of the disclosure for the preparation of a medicament for treatment of a behavioral problem in a non-human subject. The disclosure further includes one or more compounds of the disclosure for use in treating a behavioral problem in a non-human subject.

In some embodiments, the behavioral problems are selected from, but are not limited to, anxiety, fear, stress, sleep disturbances, cognitive dysfunction, aggression, excessive noise making, scratching, biting, and a combination thereof.

In some embodiments, the non-human subject is canine. In some embodiments, the non-human subject is feline.

The present disclosure also includes a method of treating a disease, disorder, or condition by activation of a serotonin receptor comprising administering a therapeutically effective amount of one or more compounds of the disclosure in combination with another known agent useful for treatment of a disease, disorder, or condition by activation of a serotonin receptor to a subject in need thereof. The present disclosure also includes use of one or more compounds of the disclosure in combination with another known agent useful for treatment of a disease, disorder, or condition by activation of a serotonin receptor for treatment of a disease, disorder, or condition by activation of a serotonin receptor, as well as use of one or more compounds of the disclosure in combination with another known agent useful for treatment of a disease, disorder, or condition by activation of a serotonin receptor for the preparation of a medicament for treatment of a disease, disorder, or condition by activation of a serotonin receptor. The disclosure further includes one or more compounds of the disclosure in combination with another known agent useful for treatment of a disease, disorder, or condition by activation of a serotonin receptor for use in treating a disease, disorder, or condition by activation of a serotonin receptor.

In some embodiments, the disease, disorder, or condition that is treated by activation of a serotonin receptor is a mental illness. In some embodiments, the mental illness is selected from hallucinations and delusions and a combination thereof. In some embodiments, the disease, disorder, or condition that is treated by activation of a serotonin receptor is a central nervous system (CNS) disorder. In some embodiments, the disease, disorder, or condition that is treated by activation of a serotonin receptor is psychosis or psychotic symptoms. In some embodiments, the disease, disorder, or condition that is treated by activation of a serotonin receptor is behavioral problems in a non-human subject.

In some embodiments, the disease, disorder, or condition that is treated by activation of a serotonin receptor is a mental illness and the one or more compounds of the disclosure are administered in combination with one or more additional treatments for a mental illness. In some embodiments, the additional treatments for a mental illness is selected from antipsychotics, including typical antipsychotics and atypical antipsychotics; antidepressants including selective serotonin reuptake inhibitors (SSRIs) and selective norepinephrine reuptake inhibitors (SNRIs), tricyclic antidepressants, and monoamine oxidase inhibitors (MAOIs) (e.g., bupropion); anti-anxiety medication including benzodiazepines such as alprazolam; mood stabilizers such as lithium; and anticonvulsants such as carbamazepine, divalproex (valproic acid), lamotrigine, gabapentin, and topiramate.

In some embodiments, the disease, disorder, or condition that is treated by activation of a serotonin receptor is selected from attention deficit hyperactivity disorder and attention deficit disorder and a combination thereof. In some embodiments, the disease, disorder, or condition that is treated by activation of a serotonin receptor is attention deficit hyperactivity disorder and/or attention deficit disorder and a combination thereof and the one or more compounds of the disclosure are administered in combination with one or more additional treatments for attention deficit hyperactivity disorder and/or attention deficit disorder and a combination thereof. In some embodiments, the additional treatments for attention deficit hyperactivity disorder and/or attention deficit disorder are selected from methylphenidate, atomoxetine, amphetamine, and a combination thereof.

In some embodiments, the disease, disorder, or condition that is treated by activation of a serotonin receptor is dementia or Alzheimer's disease and the one or more compounds of the disclosure are administered in combination with one or more additional treatments for dementia or Alzheimer's disease. In some embodiments, the additional treatments for dementia and Alzheimer's disease are selected from acetylcholinesterase inhibitors, NMDA antagonists, and muscarinic agonists and antagonists, and nicotinic agonists.

In some embodiments, the acetylcholinesterase inhibitors are selected from donepezil, galantamine, rivastigmine, phenserine, and combinations thereof.

In some embodiments, the NMDA antagonists are selected from MK-801, ketamine, phencyclidine, memantine, and combinations thereof.

In some embodiments, the nicotinic agonist is nicotine, nicotinic acid, nicotinic alpha7 agonist, alpha2 beta4 agonist, or combinations thereof.

In some embodiments, the muscarinic agonist is a muscarinic M1 agonist, a muscarinic M4 agonist, or combinations thereof.

In some embodiments, the muscarinic antagonist is a muscarinic M2 antagonist.

In some embodiments, the disease, disorder, or condition that is treated by activation of a serotonin receptor is psychosis or psychotic symptoms and the one or more compounds of the disclosure are administered in combination with one or more additional treatments for psychosis or psychotic symptoms. In some embodiments, the additional treatments for psychosis or psychotic symptoms are selected from typical antipsychotics and atypical antipsychotics.

In some embodiments, the typical antipsychotics are selected from acepromazine, acetophenazine, benperidol, bromperidol, butaperazine, carfenazine, chlorproethazine, chlorpromazine, chlorprothixene, clopenthixol, cyamemazine, dixyrazine, droperidol, fluanisone, flupentixol, fluphenazine, fluspirilene, haloperidol, levomepromazine, lenperone, loxapine, mesoridazine, metitepine, molindone, moperone, oxypertine, oxyprotepine, penfluridol, perazine, periciazine, perphenazine, pimozide, pipamperone, piperacetazine, pipotiazine, prochlorperazine, promazine, prothipendyl, spiperone, sulforidazine, thiopropazate, thioproperazine, thioridazine, thiothixene, timiperone, trifluoperazine, trifluperidol, triflupromazine, zuclopenthixol, and combinations thereof.

In some embodiments, the atypical antipsychotics are selected from amoxapine, amisulpride, aripiprazole, asenapine, blonanserin, brexpiprazole, cariprazine, carpipramine, clocapramine, clorotepine, clotiapine, clozapine, iloperidone, levosulpiride, lurasidone, melperone, mosapramine, nemonapride, olanzapine, paliperidone, perospirone, quetiapine, remoxipride, reserpine, risperidone, sertindole, sulpiride, sultopride, tiapride, veralipride, ziprasidone, zotepine, and combinations thereof.

In some embodiments, the disease, disorder, or condition that is treated by activation of a serotonin receptor is a mental illness and the one or more compounds of the disclosure are administered in combination with one or more additional treatments for a mental illness. In some embodiments, the additional treatment for a mental illness is selected from typical antipsychotics and atypical antipsychotics.

In some embodiments, effective amounts vary according to factors such as the disease state, age, sex, and/or weight of the subject or species. In some embodiments, the amount of a given compound or compounds that will correspond to an effective amount will vary depending upon factors, such as the given drug(s) or compound(s), the pharmaceutical formulation, the route of administration, the type of condition, disease, or disorder, the identity of the subject being treated, and the like, but can nevertheless be routinely determined by one skilled in the art.

In some embodiments, the compounds of the disclosure are administered one, two, three, or four times a year. In some embodiments, the compounds of the disclosure are administered at least once a week. However, in another embodiment, the compounds are administered to the subject from about one time per one week, two weeks, three weeks, or one month. In another embodiment, the compounds are administered about one time per week to about once daily. In another embodiment, the compounds are administered 1, 2, 3, 4, 5, or 6 times daily. The length of the treatment period depends on a variety of factors, such as the severity of the disease, disorder, or condition, the age of the subject, the concentration and/or the activity of the compounds of the disclosure and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration is required. For example, the compounds are administered to the subject in an amount and for duration sufficient to treat the subject.

In some embodiments, the compounds of the disclosure are administered at doses that are hallucinogenic or psychotomimetic and taken in conjunction with psychotherapy or therapy and may occur once, twice, three, or four times a year. However, in some embodiments, the compounds are administered to the subject once daily, once every two days, once every 3 days, once a week, once every two weeks, once a month, once every two months, or once every three months at doses that are not hallucinogenic or psychotomimetic.

A compound of the disclosure is either used alone or in combination with other known agent(s) useful for treating diseases, disorders, or conditions by activation of a serotonin receptor, such as the compounds of the disclosure. When used in combination with other known agents useful in treating diseases, disorders, or conditions by activation of a serotonin receptor, it is an embodiment that a compound of the disclosure is administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present disclosure that a combination of agents is administered to a subject in a non-contemporaneous fashion. In some embodiments, a compound of the present disclosure is administered with another therapeutic agent simultaneously or sequentially in separate unit dosage forms or together in a single unit dosage form. Accordingly, the present disclosure provides a single unit dosage form comprising one or more compounds of the disclosure, an additional therapeutic agent and/or a pharmaceutically acceptable carrier.

The dosage of a compound of the disclosure varies depending on many factors such as the pharmacodynamic properties of the compound, the mode of administration, the age, health, and weight of the recipient, the nature and extent of the symptoms, the frequency of the treatment, and the type of concurrent treatment, if any, and the clearance rate of the compound in the subject to be treated. One of skill in the art can determine the appropriate dosage based on the above factors. In some embodiments, one or more compounds of the disclosure are administered initially in a suitable dosage that is adjusted as required, depending on the clinical response. Dosages will generally be selected to maintain a serum level of the one or more compounds of the disclosure from about 0.01 μg/cc to about 1000 μg/cc, or about 0.1 μg/cc to about 100 μg/cc. As a representative example, oral dosages of one or more compounds of the disclosure will range between about 10 μg per day to about 1000 mg per day for an adult, suitably about 10 μg per day to about 500 mg per day, more suitably about 10 μg per day to about 200 mg per day. For parenteral administration, a representative amount is from about 0.0001 mg/kg to about 10 mg/kg, about 0.0001 mg/kg to about 1 mg/kg, about 0.01 mg/kg to about 0.1 mg/kg, or about 0.0001 mg/kg to about 0.01 mg/kg will be administered. For oral administration, a representative amount is from about 0.001 μg/kg to about 10 mg/kg, about 0.1 μg/kg to about 10 mg/kg, about 0.01 μg/kg to about 1 mg/kg, or about 0.1 μg/kg to about 1 mg/kg. For administration in suppository form, a representative amount is from about 0.1 mg/kg to about 10 mg/kg or about 0.1 mg/kg to about 1 mg/kg. In some embodiments of the disclosure, compositions are formulated for oral administration and the one or more compounds are suitably in the form of tablets containing 0.1, 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950, or 1000 mg of active ingredient (one or more compounds of the disclosure) per tablet. In some embodiments of the disclosure the one or more compounds of the disclosure are administered in a single daily, weekly, or monthly dose or the total daily dose is divided into two, three, or four daily doses.

In some embodiments, the compounds of the disclosure are used or administered in an effective amount which comprises administration of doses or dosage regimens that are devoid of clinically meaningful psychedelic/psychotomimetic actions. In some embodiments, the compounds of the disclosure are used or administered in an effective amount which comprises administration of doses or dosage regimens that provide clinical effects similar to those exhibited by a human plasma psilocin $C_{max}$ of 4 ng/ml or less and/or human 5-$HT_{2A}$ human CNS receptor occupancy of 40% or less or those exhibited by a human plasma psilocin $C_{max}$ of 1 ng/ml or less and/or human 5-$HT_{2A}$ human CNS receptor occupancy of 30% or less. In some embodiments, the compounds of the disclosure are used or administered in an effective amount which comprises administration of doses or dosage regimens that provide clinical effects similar to those exhibited by a human plasma psilocin $T_{max}$ in excess of 60 minutes, in excess of 120 minutes or in excess of 180 minutes.

To be clear, in the above, the term "a compound" also includes embodiments wherein one or more compounds are referenced. Likewise, the term "compounds of the disclosure" also includes embodiments wherein only one compound is referenced.

V. Preparation of Compounds

Compounds of the present disclosure can be prepared by various synthetic processes. The choice of particular structural features and/or substituents may influence the selection of one process over another. The selection of a particular process to prepare a given compound of the disclosure is within the purview of the person of skill in the art. Some starting materials for preparing compounds of the present disclosure are available from commercial chemical sources or may be extracted from cells, plants, animals, or fungi. Other starting materials, for example as described below, are readily prepared from available precursors using straightforward transformations that are well known in the art. In the Schemes below showing some embodiments of methods of preparation of compounds of the disclosure, all variables are as defined in Formula (I), unless otherwise stated.

In some embodiments, the compounds of Formula (I) are prepared as shown in Scheme I.

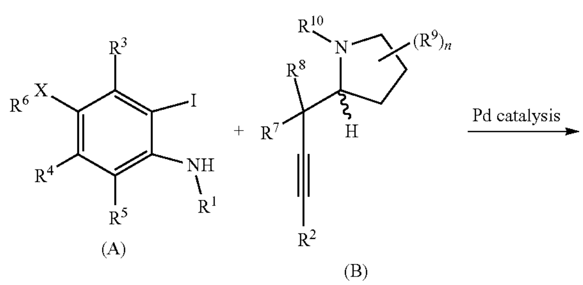

(A) (B)

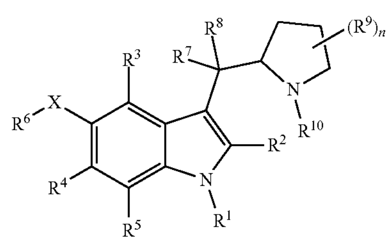

Formula (I)

Therefore, ortho-iodoanilin compounds of Formula (A) are coupled with suitable unsaturated precursors such as disubstituted alkyne compound of Formula (B) in the presence of a catalyst, such as a Pd catalyst, to provide a compound of Formula (I) through known methods, for example, using the Pd catalysis procedure found in Chem. Eur. J. 2019, 25, 897-903.

In some embodiments, the compounds of Formula (I) are synthesized according to Scheme II.

Scheme II

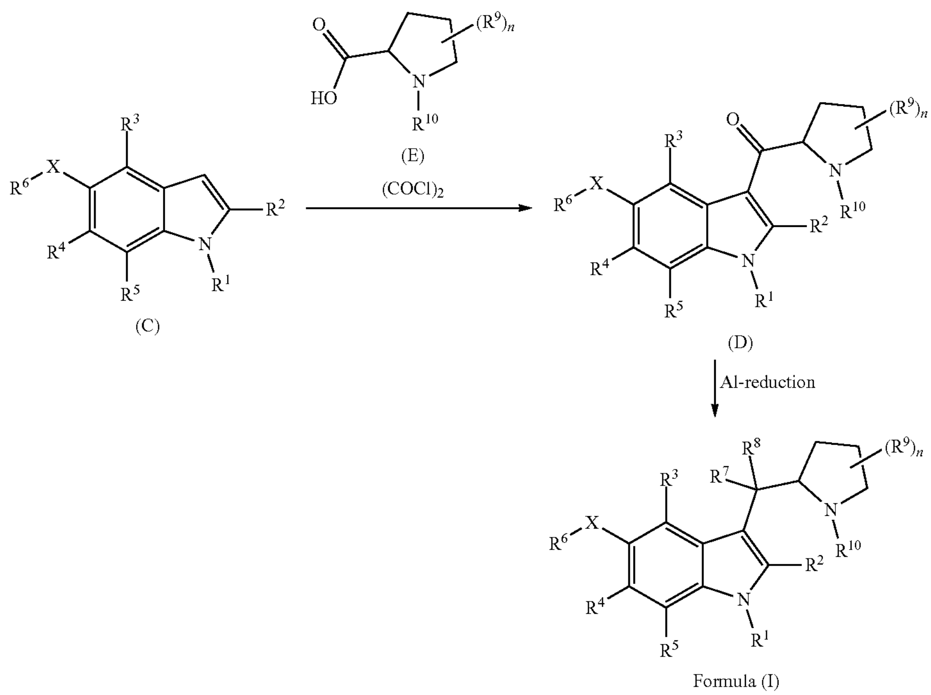

Therefore, a substituted indole compound of Formula (C) is coupled with a suitable pyrrolidine carboxylic acid compound of Formula (E) in the present of suitable coupling reagents such as oxalyl chloride to provide compounds of Formula (D). The compounds of Formula (D) are reduced with suitable reducing agents such as Al-based reducing agents to provide the compounds of general Formula (I).

In some embodiments, the compounds of Formula (I) are synthesized according to Scheme III Scheme III

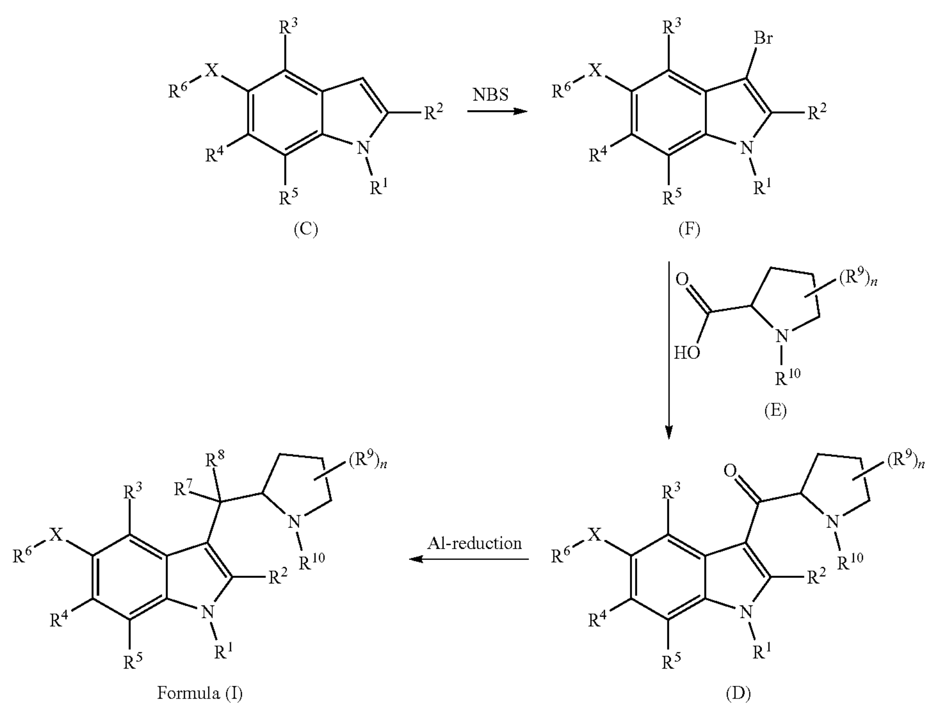

In some embodiments, as shown in Scheme III, the compounds of Formula (I) are prepared using known methods, for example using the synthetic procedures found in Gerasimov et al., J. Med. Chem. 1999, 42, 4257-4263 and/or Macor et al., J. Med. Chem. 1992, 35, 4503-4505. Therefore, a substituted indole compound of Formula (C) is brominated with a suitable brominated reagent such as N-bromosuccinimide (NBS) to provide brominated indole compounds of Formula (F). The compounds of Formula (F) are coupled with a suitable pyrrolidine carboxylic acid compound of Formula (E) in the present of suitable coupling reagents such as oxalyl chloride to provide compounds of Formula (D). The compounds of Formula (D) are reduced with suitable reducing agents such as Al-based reducing agents to provide the compounds of general Formula (I).

In some embodiments, compounds of Formula (C) wherein X is S are prepared as shown in Scheme IV.

Scheme IV

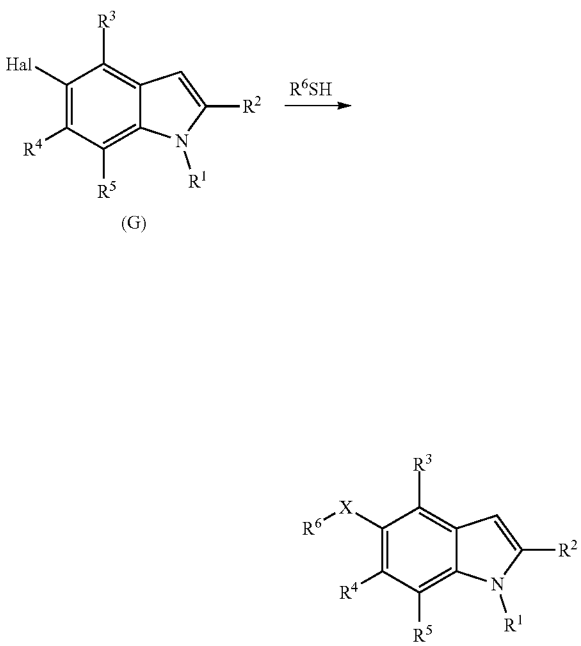

(G)

(C)

Therefore, in some embodiments, as shown in Scheme IV, compounds of Formula (C) wherein X is S are synthesized by coupling the indole of compound (G) wherein Hal is halide, such as I or Br with a thiol compound of Formula $R^6SH$ under suitable coupling conditions such as in the presence of a suitable catalyst such as a palladium catalyst (e.g., bis(dibenzylideneacetone)palladium(0) ($Pd(dba)_2$)), ligand (e.g., 4,5-Bis(diphenylphosphino)-9,9-dimethylxanthen (Xantphos)), and base such as ethyldiisopropylamine in a suitable inert solvent such as dioxane.

In some embodiments, compounds of Formula (C) wherein X is S are synthesized using methods known in the art as shown in Scheme IV, for example, the methods described in Shmatova, O. I., Eur. J. Org. Chem. 2015, 6479-6488.

In some embodiments, compounds of Formula (C) wherein X is S are prepared as shown in Scheme V.

Scheme V

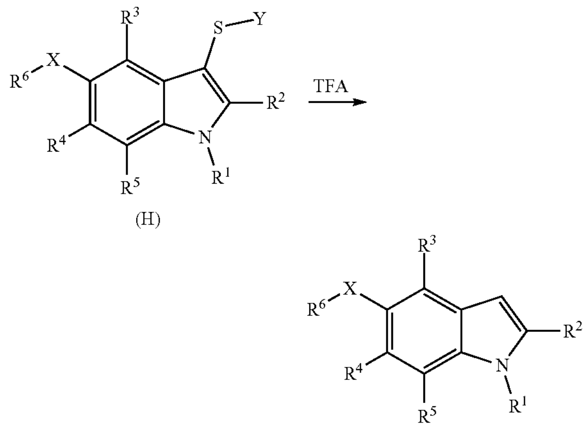

(H)

(C)

Therefore, in some embodiments, as shown in Scheme V, compounds of Formula (C) wherein X is S are synthesized by the desulfenylation of a compound of Formula (H) wherein Y is a suitable alkyl or aryl group in the presence of trifluoroacetic acid and a thiol as trapping agent, such as methyl thiosalicylate.

In some embodiments, compounds of Formula (C) wherein X is S are prepared as shown in Scheme V using methods known in the art, for example, the methods described in Hamel, P., J. Org. Chem. 1994, 59, 6372-6377.

In some embodiments, compounds of Formula (C) wherein X is S are prepared as shown in Scheme VI.

Scheme VI

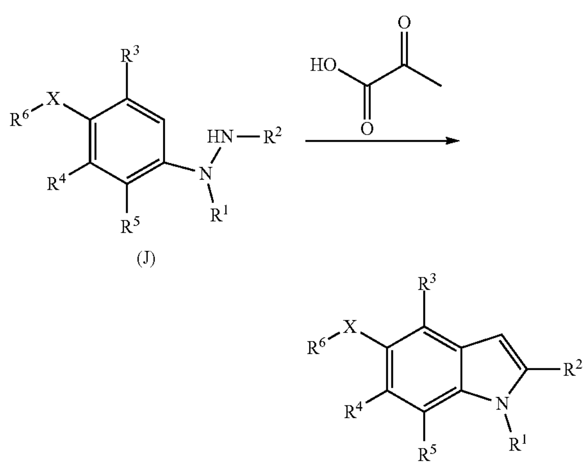

(J)

(C)

Therefore, in some embodiments, as shown in Scheme VI, compounds of Formula (C) wherein X is S are synthesized using the Fischer indole synthesis method. For example, in some embodiments, hydrazine compounds of compound J are reacted with pyruvic acid under suitable conditions such as in the presence of zinc chloride and phosphorus pentachloride to provide the compounds of Formula (C).

In some embodiments, compounds of Formula (C) wherein X is S are prepared as shown in Scheme VI using methods known in the art, for example, the methods described in Bratulescu, G., Letters 49 (2008) 984-986.

In some embodiments, compounds of Formula (I) wherein X is S(O) (compounds of Formula I(b)) and X is $SO_2$ (compounds of Formula I(c)) are prepared from compounds of Formula (I) wherein X is S (compounds of Formula I(a)) according to Scheme VII.

Scheme VII

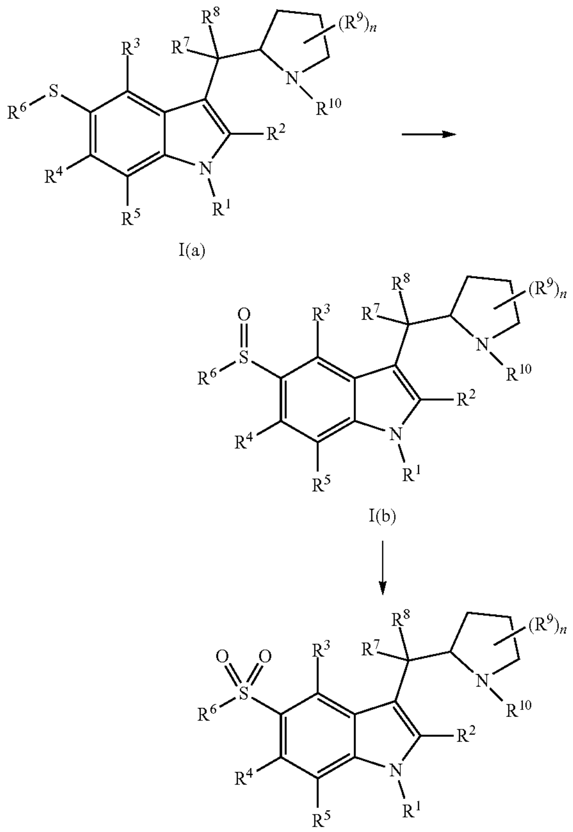

I(a)

I(b)

I(c)

In some embodiments, as shown in Scheme VII, compounds of Formula (I) wherein X is S (compounds of Formula I(a)) are oxidized to compounds of Formula (I) wherein X is S(O) compounds of Formula I(b)) under suitable oxidizing conditions such about one equivalent of meta-chloroperoxybenzoic acid (m-CPBA). Compounds of Formula (I) wherein X is S(O) (compounds of Formula I(b)) are then oxidized under suitable oxidizing conditions such as meta-chloroperoxybenzoic acid (m-CP BA) to compounds of Formula (I) wherein X is $SO_2$ (compounds of Formula I(c)).

In some embodiments, compounds of Formula (I) wherein X is S(O) (compounds of Formula I(b)) and X is $SO_2$ (compounds of Formula I(c)) are prepared from compounds of Formula (I) wherein X is S (compounds of Formula I(a)) as shown in Scheme VII using methods known in the art, for example, the methods described in United States patent application 2004/0043965.

In some embodiments, compounds of Formula (C) wherein X is S and $R^6$ is $CD_3$ (compounds of Formula C') are prepared as shown in Scheme VIII.

Scheme VIII

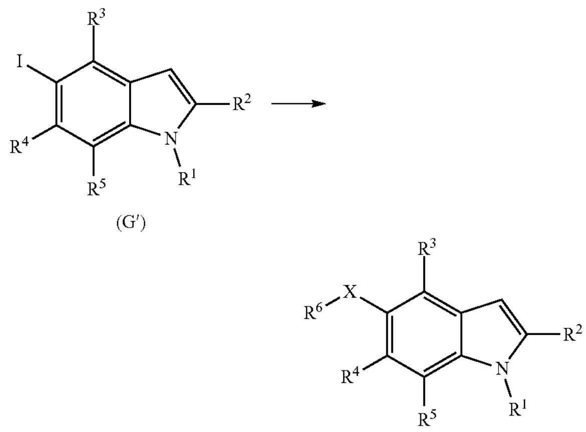

(G')

(C')

Therefore, in some embodiments, as shown in Scheme VII, compounds of Formula (C) wherein X is S and $R^6$ is $CD_3$ (compounds of Formula (C')) are synthesized by coupling the indole of compound (G) wherein Hal is I (compound of Formula G') in the presence of a suitable catalyst such as a nickel based catalyst (e.g., nickel acetate) with a suitable electrophilic $SCD_3$ reagent such as S-(methyl-D3) 4-methylbenzenesulfonothioate

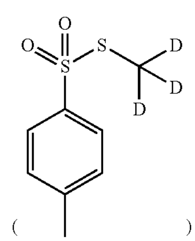

in the presence of a suitable reductant such as zinc powder and a base such as 2,2-bipyridyl to provide compounds of Formula (C) wherein X is S and $R^6$ is $CD_3$ (compounds of Formula C').

In some embodiments, compounds of Formula (C) wherein X is S and $R^6$ is $CD_3$ (compounds of Formula C') as shown ins Scheme VII are synthesized using methods known in the art, for example, the methods described in Zhang, Y., Org. Lett. 2022, 24, 6794-6799.

Compounds of Formula (I), wherein one or more of $R^1$-$R^5$ are deuterium are available, for example, using a hydrogen-deuterium exchange reaction on a suitable starting substrate, wherein this exchange reaction is catalyzed by Pd/C in $D_2O$ as described in Esaki, H. et al., Tetrahedron, 2006, 62:10954-10961, and modifications thereof known to a person skilled in the art.

Especially for embodiments in which X is absent or oxygen, as well as for other embodiments of X, compounds of Formula (I) wherein X—$R^6$ is $OCD_3$ are available, for example, using methods as described in Xu, Y-Z and Chen, C. J. Label Compd. Radiopharm. (2006) 49:897-902, and modifications thereof and modifications thereof known to a person skilled in the art.

A person skilled in the art would appreciate that further manipulation of the substituent groups using known chemistry can be performed on the intermediates and final compounds in the Schemes above to provide alternative compounds of the disclosure.

For example, especially for embodiments in which X is S, S(O), or $SO_2$, as well as for other embodiments of X, a person skilled in the art would appreciate that $R^1$ is H in a compound of Formula (I), then the compound of Formula (I) wherein $R^1$ is H can be further reacted to prepare further compounds of Formula (I). For example, the compound of Formula (I) wherein $R^1$ is H can be alkylated with an alkyl halide in the presence of suitable based such as NaH, NaOtBu, or LiHMDS.

For example, especially for embodiments in which X is absent or oxygen, as well as for other embodiments of X, a person skilled in the art would appreciate that $R^1$ is H in compounds C and D above (see, e.g., Schemes II and III) resulting in a compound of Formula (I) wherein $R^1$ is H, then the compound of Formula (I) wherein $R^1$ is H can be further reacted to prepare further compounds of Formula (I). For example, the compound of Formula (I) wherein $R^1$ is H can be alkylated with an alkyl halide in the presence of suitable based such as NaH, NaOtBu, or LiHMDS.

Salts of compounds of the disclosure may be formed by methods known to those of ordinary skill in the art, for example, by reacting a compound of the disclosure with an amount of acid or base, such as an equivalent amount, in a medium such as one in which the salt precipitates or in aqueous medium followed by lyophilization.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art. Examples of suitable solvents are ethanol, water, and the like. When water is the solvent, the molecule is referred to as a "hydrate." The formation of solvates of the compounds of the disclosure will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Isotopically-enriched compounds of the disclosure and pharmaceutically acceptable salts, solvates, and/or prodrug thereof, can be prepared without undue experimentation by conventional techniques well known to those skilled in the art or by processes analogous to those described in the Schemes and Examples herein using suitable isotopically-enriched reagents and/or intermediates.

Throughout the processes described herein it is to be understood that, where appropriate, suitable protecting groups will be added to and subsequently removed from, the various reactants and intermediates in a manner that will be readily understood by one skilled in the art. Conventional procedures for using such protecting groups as well as examples of suitable protecting groups are described, for example, in "Protective Groups in Organic Synthesis," T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities and ways to circumvent them by carrying out appropriate transformations and synthetic steps in a suitable order, will be readily understood to one skilled in the art. Examples of transformations are given herein and itis to be understood that the described transformations are not limited only to the generic groups or substituents for which the transformations are exemplified. References and descriptions of other suitable transformations are given in "Comprehensive Organic Transformations—A Guide to Functional Group Preparations," R. C. Larock, VHC Publishers, Inc. (1989). References and descriptions of other suitable reactions are described in textbooks of organic chemistry, for example, "Advanced Organic Chemistry," March, 4th ed. McGraw Hill (1992) or, "Organic Synthesis," Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations-A Guide to Functional Group Preparations," R. C. Larock, VHC Publishers, Inc. (1989). References and descriptions of other suitable reactions are described in textbooks of organic chemistry, for example, "*Advanced Organic Chemistry*," March, 4th ed. McGraw Hill (1992) or, "*Organic Synthesis*," Smith, McGraw Hill, (1994).

Techniques for purification of intermediates and final products include, for example, straight and reversed phase chromatography on column or rotating plate, recrystallisation, distillation, and liquid-liquid or solid-liquid extraction, which will be readily understood by one skilled in the art.

The products of processes disclosed in the disclosure may be isolated according to known methods, for example, the compounds may be isolated by evaporation of the solvent, by filtration, centrifugation, chromatography, or other suitable method.

Prodrugs of the compounds of the present disclosure may be, for example, conventional esters formed with available hydroxy, thiol, amino, or carboxyl groups. For example, available hydroxy or amino groups may be acylated using an activated acid in the presence of a base, and optionally, in inert solvent (e.g., an acid chloride in pyridine).

One skilled in the art will recognize that where a reaction step of the present disclosure is carried out in a variety of solvents or solvent systems, said reaction step may also be carried out in a mixture of the suitable solvents or solvent systems.

EXAMPLES

The following non-limiting examples are illustrative of the present disclosure.

General Methods

All starting materials used herein were commercially available or earlier described in the literature. The $^1$H and $^{13}$C NMR spectra were measured using a Bruker 300, Bruker DPX400, or Varian +400 spectrometer operating at 300, 400, and 400 MHz for $^1$H NMR respectively. TMS or the residual solvent signal was used as an internal reference; deuterated chloroform was used as the solvent unless otherwise indicated. All reported chemical shifts are in ppm on the delta-scale, and the fine splitting of the signals as appearing in the recordings is generally indicated, for example as s: singlet, br s: broad singlet, d: doublet, t: triplet, q: quartet, m: multiplet. Unless otherwise indicated, in the tables below, $^1$H NMR data was obtained at 400 MHZ, using $CDCl_3$ as the solvent.

Purification of products was carried out using Chem Elut Extraction Columns (Varian, cat #1219-8002), Mega BE-SI (Bond Elut Silica) SPE Columns (Varian, cat #12256018; 12256026; 12256034) or by flash chromatography in silica-filled glass columns.

IUPAC names were generated with CHEMDRAW Professional 22.2.0 64-bit.

The following compounds were prepared using one or more of the synthetic methods outlined in Schemes I and II.

Part I

A. Synthesis of Exemplary Compounds of the Disclosure

Example 1: (R)-3-((1-Methylpyrrolidin-2-yl)methyl)-5-(methylthio)-1H-indole ((R) I-1)

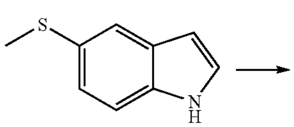

1

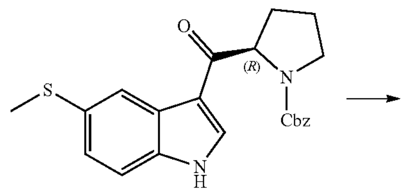

2

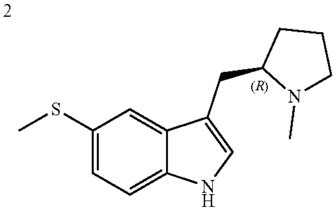

(R) I-1

Synthesis of (R)-2-(2-(5-(methylthio)-1H-indole-3-carbonyl)pyrrolidin-1-yl)-1-phenylethan-1-one (2)

A solution of 1-(2-oxo-2-phenylethyl)-D-proline (3.0 g, 12.03 mmol) in dry THF (50 mL) was treated with thionyl chloride (1.75 mL, 24.07 mmol) at 0° C. The reaction was brought to room temperature, then refluxed for 2 h. The reaction was brought to room temperature, solvent was evaporated and crude was dried under vacuum to obtain the corresponding acid chloride.

A solution of 5-(methylthio)-1H-indole (1.96 g, 12.03 mmol) in dry $CH_2Cl_2$ (50 mL) at 5-10° C. was treated with above crude acid chloride in dry $CH_2Cl_2$ (30 mL) and ethyl magnesium bromide (8.0 mL, 24.07 mmol, 3 M in THF (tetrahydrofuran)) simultaneously over a period of 15 min. and stirred at same temperature for further 15 min. The reaction was quenched with con. HCl (5 mL) followed by water (50 mL) and product was extracted into $CH_2Cl_2$ (2×50 mL). $CH_2Cl_2$ layer was washed with sat. $NaHCO_3$ solution (50 mL), brine (25 mL), and dried ($Na_2SO_4$). Solvent was evaporated and crude was purified by flash column chromatography ($CH_2Cl_2$ to EtOAc: $CH_2Cl_2$, 1:4) on silica gel to obtain the title compound 2 (6.67 g, 75.3%) as a light brown foam. $^1$H NMR (DMSO-$d_6$): δ 12.07, 12.05 (2s, 1H), 8.47, 8.44 (2d, 1H, J=6.0 Hz), 8.16, 8.12 (2s, 1H), 7.47-7.33 (m, 3H), 7.23-7.01 (m, 3H), 5.25-4.90 (m, 3H), 3.55-3.50 (m, 2H), 3.34 (s, 3H), 2.45-2.29 (m, 1H), 1.91-1.84 (m, 3H); ESI-MS (m/z, %): 453 (100), 417 (M+Na).

Synthesis of (R)-3-((1-methylpyrrolidin-2-yl)methyl)-5-(methylthio)-1H-indole ((R) I-1)

A solution of (R)-2-(2-(5-(methylthio)-1H-indole-3-carbonyl)pyrrolidin-1-yl)-1-phenylethan-1-one (2.5 g, 6.33 mmol) in dry THF (50 mL) was treated with $LiAlH_4$ (1.2 g, 31.68 mmol) at 0° C. over a period of 10 min. The reaction was brought to room temperature and then refluxed for overnight (16 h). The reaction was cooled to 0° C., quenched with water (1.2 mL), 4 N NaOH solution (1.2 mL) and water (1.2 mL). The reaction was brought to room temperature and stirred for additional 30 min. The reaction was filtered through a pad of sodium sulfate and washed with THF (3×25 mL). Combined THF layer was evaporated and crude was purified by column chromatography (2 M $NH_3$ in MeOH: $CH_2Cl_2$, 5:95) on silica gel to obtain the title compound (R) I-1 (1.53 g, 88.4%) as a pale-yellow solid. $^1$H NMR (DMSO-$d_6$): δ 10.84 (s, 1H), 7.47 (s, 1H), 7.30 (d, 1H, J=6.0 Hz), 7.15 (s, 1H), 7.07 (dd, 1H, J=3.0, 6.0 Hz), 3.04-2.95 (m, 2H), 2.50-2.31 (m, 8H), 2.14-2.07 (m, 1H), 1.74-1.40 (m, 4H); ESI-MS (m/z, %): 261 ($MH^+$, 100).

B. Biological Testing

Example 2: Human 5-$HT_{2A}$: Functional Fluorometric Imaging Plate Reader (FLIPR) Assay

Objective

The potential excitatory effects of compounds targeting human 5-hydroxytryptamine receptor 2A (5-$HT_{2A}$) under agonist mode was assessed.

1 Materials and Instrumentation 1.1 Cell Line (Table 6)

| Cell line Name | Target | Host cell |
|---|---|---|
| HTR2A&Gα15-HEK293 | 5-$HT_{2A}$ | FIp-In-293 |

1.2 Materials (Table 7)

| Regents | Vendor | Cat# |
|---|---|---|
| DMEM | Gibco | 10569-010 |
| Dialyzed FBS | BIOSUN | BS-0005-500 |
| Penicillin-Streptomycin | Invitrogen | 15140 |
| Hygromycin B | Invivogen | Ant-hg-5 |
| Tetracycline hydrochloride | Abcam | ab141223 |
| TrypLE ™Express | Gibco | 12604-013 |
| DPBS | Gibco | 14190250 |
| DMSO | Millipore | 1029312500 |
| Probenecid | Sigma | P8761 |
| FLIPR Calcium 6 Assay Kit | Molecular Device | R8191 |
| HEPES | Invitrogen | 15630 |
| Hank's Buffered Saline Solution | Invitrogen | 14025 |
| Serotonin HCl | Selleck | S4244 |

1.3 Instrumentation and Consumables (Table 8)

| Item | Supplier | Cat# |
|---|---|---|
| Fluorometric Imaging Plate Reader (FLIPR) | Molecular Device | Tetra |
| Countess Automated Cell Counter | Invitrogen | Countess |
| Cell Counting Chamber Slides | Invitrogen | C10312 |
| STERI-CYCLE CO2 Incubator | Thermo | 371 |
| 1300 Series Class II Biological Safety Cabinet | Thermo | 1389 |
| Table-type Large Capacity Low Speed Centrifuge | Cence | L550 |
| Centrifuge | Eppendorf | 5702 |
| Echo | Labcyte | 550 |
| Echo | Labcyte | 655 |
| Electro-thermal incubator | Shanghai Yiheng | DHP-9031 |
| plate shaker | IKA | MS3 digital |
| Water Purification System | ULUPURE | UPH-III-20T |
| Versatile and Universal pH and Conductivity Meters | Mettler Toledo | S220 |
| 384-Well plate | Corning | 3764 |
| 384-Well LDV Clear microplate | LABCYTE | LP-0200 |
| 384-Well Polypropylene microplate | LABCYTE | PP-0200 |
| 384-well compound plate | Corning | 3657 |
| T25 cell culture flask | Corning | 430639 |
| 50 mL Polypropylene Centrifuge Tube | JET | CFT011500 |
| 15 mL Polypropylene Centrifuge Tube | JET | CFT011150 |

2 Experimental Methods 2.1 Cell Culture $HTR_{2A}$&Gα15-HEK293 cells were cultured in DMEM medium containing 10% dialyzed FBS and 1× penicillin-streptomycin, 100 μg/mL Hygromycin B and 300 μg/mL G418. The cells were passaged about three times a week, maintained between ~30% to ~90% confluence.

2.2 Cell Plating

1. The cell culture medium (DMEM medium containing 10% dialyzed FBS and 1× penicillin-streptomycin, 100 μg/mL Hygromycin B and 300 μg/mL G418), TrypLE™ Express and DPBS to room temperature was warmed in advance.

2. For induction, 1 μg/ml tetracycline (final concentration) was added to cell culture medium and incubated for 48 hours prior to seeding cells into plate at 37° C., 5% (v/v) CO2. The cell culture medium was removed from flask. Cells were washed with DP BS.

3. 2 mL TrypLE™ Express was added to the flask, mixed well by gentle shaking and cells were incubated at 37° C. for a few minutes.

4. The cells were checked for morphological change under microscope, the digestion was stopped by adding 4 mL cell culture medium to the flask when most of cells turned to round.

5. The cell suspension was transferred into a 15 mL centrifuge tube, and then centrifuged at 1,200 rpm for 5 minutes.

6. The supernatant was removed. The cell pellet was resuspended with 2 ml cell culture medium.

7. The cell density was counted using cell counter. Only cells with >85% viability were used for the assay.

8. Cells were diluted to $6.67\times10^5$/mL with cell culture medium.

9. 30 μL/well cell suspensions added into a 384-well cell plate (The cell density was 20,000 cells/well).

10. The cell plate was incubated overnight at 37° C., 5% (v/v) $CO_2$.

2.3 Cell Handling

On the day of experiments, culture medium was removed from the cell plate.

10 μL of assay buffer (20 mM HEPES, in 1×HBSS, pH 7.4) was added to each well of the cell plate.

2× dye solution was prepared following the manual of the FLIPR® Calcium 6 Assay Kit:

i. The dye was diluted with assay buffer.

ii. Probenecid was added to the final concentration of 5 mM.

iii. Vortexed vigorously for 1-2 minutes.

4. 10 μL of 2× dye solution was added to each well of the cell plate

5. The cell plate was placed on plate shaker, followed by shaking at 600 rpm for 2 minutes.

6. The plate was incubated at 37° C. for 2 hours followed by an additional 15-minute incubation at 25° C.

2.4 Prepare 3× Compound.

1. Serotonin HCl was prepared to the concentration of 10 mM with DMSO.

2. The test compounds were prepared to the concentration of 10 mM with DMSO.

3. The compounds were added to a 384-well compound source plate.

4. 3-folds serial dilutions were performed with DMSO.

5. 90 nL/well of serial diluted compounds was transferred from source plate to a 384-well compound plate by using an Echo.

6. 30 μL/well of assay buffer (20 mM HEPES in 1×HBSS, pH 7.4) was added to the compound plate.

7. The plate was mixed on-plate shaker for 2 minutes.

2.5 FLIPR Assay

1. After the cells were incubated with dye solution, the cell plate, compound plate containing 3× compounds and FLIPR tips were placed into FLIPR.

2. 10 μL of 3× compounds transferred from the compound plate to the cell plate by FLIPR.

3. The plate was read for 160 sec with 1 sec interval and the data of agonist mode was obtained.

3 Data Analysis

1. The normalized fluorescence reading (RFU) was calculated as shown below, wherein $F_{max}$ and $F_{min}$ stand for maximum and minimum of calcium signal during defined time window:

$$RFU = F_{max} - F_{min}$$

2. $EC_{50}$ by fitting RFU against log of compound concentrations with Hill equation was calculated using XLfit.

Results and Discussion

The results of potential competition binding properties of the exemplary compounds of the disclosure targeting the human 5-hydroxytryptamine receptor 2A (5-$HT_{2A}$) are summarized in Table 9. The results of exemplary compounds of the disclosure are presented as $EC_{50}$ is provided in Table 9.

Table 9: Effect of Exemplary Compounds of Formula (I) Using FLIPR Functional Assay on Human 5-$HT_{2A}$ Receptor

| Example | h5-$HT_{2A}$, $EC_{50}$ [nM] | RFU@10 μM [(1)] |
|---|---|---|
| 5-MeO-DMT | 63 | 5,667 |
| DMT | 163 | 3,493 |
| (R) I-1 | 47 | 5,663 |

[(1)] Curve fitting with activation (%) @ 10 mM with RFU

Exemplary compounds of Formula (I) were evaluated using FLIPR functional assay on human 5-$HT_{2A}$ receptor. $EC_{50}$ (nM) concentrations are illustrated in Table 9. This assay confirms that compounds of the disclosure are effective agonists of the target human 5-$HT_{2A}$ receptors.

Example 2A: Human-5-$HT_{2A}$-β-Arrestin Assay

Protocol

Compound potency ($EC_{50}$) and efficacy (Max response) against the human 5-$HT_{2A}$ receptor in stably transfected U2OS cells were determined in a G protein-coupled receptors (GPCR) cell based β-arrestin reporter assay.

Cells were seeded in a total volume of 20 μL into white walled, 384-well microplates and incubated at 37° C. overnight before analysis. For agonist determination, cells were incubated with samples to induce response. Intermediate dilution of sample stocks was performed to generate 5× samples in assay buffer. 5 μL of 5× samples were added to cells and incubated at 37° C. for 120 minutes. The final assay vehicle concentration was 1%. The results are expressed as percent efficacy relative to the maximum response of the control ligand (serotonin) in Table 10.

TABLE 10

Effect of exemplary compounds of Formula (I) using a β-arrestin reporter assay on human 5-$HT_{2A}$ receptor

| Compound ID | $EC_{50}$ (μM) | $E_{max}$ (% of serotonin) |
|---|---|---|
| DMT | 0.1136 | 38.86 |
| 5MeO-DMT | 0.02945 | 72.41 |
| (R) I-1 | 0.025396 | 79.27 |

Example 2B: Human-5$HT_{1A}$-CAMP Assay

Protocol

Compound potency ($EC_{50}$) and efficacy (Max response) against the human 5-$HT_{1A}$ receptor in stably transfected CHO-K1 cells were determined in a GPCR cell-based CAMP assay.

Cells were seeded in a total volume of 20 μL into white walled, 384-well microplates and incubated at 37° C. overnight before analysis. Prior to testing, cell plating media was exchanged with 10 μL of Assay buffer (HBSS+10 mM HEPES). Briefly, intermediate dilution of sample stocks were performed to generate 4× sample in assay buffer. 5 μL of 4× samples+5 μL of 4× forskolin were added to cells and incubated at 37° C. for 30 minutes (mins). The final assay vehicle concentration was 1%. The results are expressed as percent efficacy relative to the maximum response of the control ligand (serotonin) in Table 11.

TABLE 11

Effect of exemplary compounds of Formula (I) using cAMP functional assay on human 5-$HT_{1A}$ receptor

| Compound ID | $EC_{50}$ (μM) | $E_{max}$ (% of serotonin) |
|---|---|---|
| DMT | 0.97437 | 87.1 |
| 5MeO-DMT | 0.012699 | 99.98 |
| (R) I-1 | 0.011138 | 99.41 |

Example 2C: Human-5$HT_{2B}$ FLIPR Assay

Protocol

Compound potency ($EC_{50}$) and efficacy (Max response) against the human 5-$HT_{2B}$ receptor in stably transfected HEK293 cells were determined in a calcium mobilization-based assay.

Cells were seeded in a total volume of 20 μL into white walled, 384-well microplates and incubated at 37° C. overnight. Prior to testing, cell plating media was exchanged with 20 μL of Dye Loading buffer (HBSS+20 mM HEPES containing 1× Dye, 1× Additive A, and 2.5 mM Probenecid). Plates were incubated at 37° C. for 45 mins followed by 15 mins at room temperature.

10 μL of assay buffer (HBSS+20 mM HEPES) were added to cells. Intermediate dilution of sample stocks was performed to generate 4× samples in assay buffer. Assay plates and compound plates were loaded into the FLIPR instrument. 10 μL of sample was added using the FLIPR onboard robotics after 5 seconds of starting calcium measurement. A final assay vehicle concentration was 1%. The results are expressed as percent efficacy relative to the maximum response of the control ligand (serotonin) in Table 12.

TABLE 12

Effect of exemplary compounds of Formula (I) using FLIPR functional assay on human 5-$HT_{2B}$ receptor

| Compound ID | $EC_{50}$ (μM) | $E_{max}$ (% of serotonin) |
|---|---|---|
| DMT | >10 | 13.4 |
| 5MeO-DMT | 0.015452 | 28.88 |
| (R) I-1 | 0.0027402 | 62.94 |

Example 2D: Human-5$HT_{2C}$ FLIPR Assay

Protocol

Compound potency ($EC_{50}$) and efficacy (Max response) against the human 5-$HT_{2C}$ receptor in stably transfected U2OS cells was determined in a calcium mobilization-based assay.

Cells were seeded in a total volume of 20 μL into white walled, 384-well microplates and incubated at 37° C. overnight. Prior to testing, cell plating media was exchanged with 20 μL of Dye Loading buffer (HBSS+20 mM HEPES containing 1× Dye, 1× Additive A, and 2.5 mM Probenecid). Plates were incubated at 37° C. for 45 mins followed by 15 mins at room temperature.

10 μL of assay buffer (HBSS+20 mM HEPES) was added to cells. Intermediate dilution of sample stocks were performed to generate 4× samples in assay buffer. Assay plates and compound plates were loaded into the FLIPR instrument. 10 μL of sample was added using the FLIPR onboard robotics after 5 seconds of starting calcium measurement. The final assay vehicle concentration was 1%. The results are expressed as percent efficacy relative to the maximum response of the control ligand (serotonin) in Table 13.

TABLE 13

Effect of exemplary compounds of Formula (I) using FLIPR functional assay on human 5-$HT_{2C}$ receptor

| Compound ID | $EC_{50}$ (μM) | $E_{max}$ (% of serotonin) |
|---|---|---|
| DMT | 0.01112 | 94.56 |
| 5MeO-DMT | 0.0027312 | 95.42 |
| (R) I-1 | 0.00060025 | 95.27 |

Example 2E: Human-5$HT_{2B}$ Positive Allosteric Modulator (PAM) Assay

Protocol

Compound potency ($EC_{50}$) and efficacy (Max response) against the human 5-$HT_{2B}$ receptor in stably transfected HEK293 cells were determined in a GPCR cell-based assay.

For Positive Allosteric Modulator determination, cells were pre-incubated with sample followed by EC20 addition. Intermediate dilution of sample stocks were performed to generate 5× samples in assay buffer. 5 μL of 5× samples were added to cells and incubated at 37° C. for 10 mins. 5 μL of agonist at 6×EC20 concentration was added and cells were incubated at 37° C. for 120 mins. Final assay vehicle concentration was 1%. The results are expressed as percent efficacy relative to the maximum response of the control ligand (serotonin) in Table 14.

TABLE 14

Effect of exemplary compounds of Formula (–I) using PAM functional assay on human 5-$HT_{2B}$ receptor

| Compound ID | $EC_{50}$ (μM) | $E_{max}$ (% of serotonin) |
|---|---|---|
| DMT | >10 | 0 |
| 5MeO-DMT | >10 | 0 |
| (R) I-1 | >10 | 0 |

Example 3: Human 5-$HT_{2A}$: Radioligand Binding Assay

Objective

The objective of this study was to evaluate the binding properties of exemplary compounds of Formula (I) on 5-hydroxytryptamine receptor 2A (5-$HT_{2A}$).

1 Materials and Instrumentation 1.1 Regents (Table 15)

| Items | Vendor | Cat# |
|---|---|---|
| Ketanserin Hydrochloride, [Ethylene-3H]– | PerkinElmer | NET791250UC |
| Ketanserin | MedChemExpress | HY-10562 |
| Bovine Serum Albumin (BSA) | Sigma | A1933 |
| Calcium chloride ($CaCl_2$) | Sigma | C5670 |
| Tris(hydroxymethyl)aminomethane (Tris) | Alfa Aesar | A18494 |
| Polyethylenimine, branched (PEI) | Sigma | 408727 |

1.2 Instrumentation and Consumables (Table 16)

| Item | Supplier | Cat# |
|---|---|---|
| Microbeta$^2$ Microplate Counter | PerkinElmer | 2450-0060 |
| UniFilter-96 GF/B | PerkinElmer | 6005177 |
| TopSeal | Biotss | SF-800 |
| MicroBeta Filtermate-96 | PerkinElmer | D961962 |
| Seven Compact pH meter | Mettler Toledo | S220 |
| Ultrapure Water Meter | Sichuan Ulupure | UPH-III-20T |
| Benchtop Centrifuge | Hunan Xiangyi | L550 |
| Microplate Shaker | Allsheng | MX100-4A |
| 384-Well Polypropylene Microplate | Labcyte | PP-0200 |
| 96 Round Well Plate | Corning | 3799 |
| 96 Round Deep Well Plate | Axygen | P-DW-11-C |
| Echo | LABCYTE | 550 |

2 Experimental Methods

1. The assay buffer was prepared following Table 17 below.

| Reagent | Concentration |
|---|---|
| Tris | 50 mM |
| $CaCl_2$ | 4 mM |
| BSA | 0.1% (w/v) |

Adjust pH to 7.4 followed by 0.2 μM sterile filtration 2. 8 doses of reference and test compounds starting from 10 mM stock solution as required were prepared by 5-fold serial dilutions with 100% (v/v) DMSO.
3. UniFilter-96 GF/B plate was pretreated:
i. 50 μl/well of 0.5% (v/v) PEI was added to UniFilter-96 GF/C plates. The plates were sealed and incubated at 4° C. for 3 hours (hrs).
ii. After incubation, the plates were washed 3 times with ice-cold wash buffer (50 mM Tris, pH7.4).
4. The assay plate was prepared:
i. Cell membrane was diluted with assay buffer and 330 μl/well was added to 96 round deep well plates to reach a concentration of 20 μg/well.

ii. 8 concentrations of reference or test compounds were prepared and 110 μl/well was added to 96 round deep well plates.

iii. [3H]-ketanserin was diluted with assay buffer to 5 nM (5× final concentration) and 110 μl/well was added to 96 round deep well plates.

5. The plate was centrifuged at 1000 rpm for 30 seconds (secs) and then agitated at 600 rpm at room temperature for 5 min.

6. The plates were sealed and the plate incubated at 27° C. for 90 min.

7. The incubation was stopped by vacuum filtration onto GF/B filter plates followed by 4 times washing with ice-cold wash buffer (50 mM Tris, pH7.4).

8. The plates were dried at 37° C. for 45 min.

8. The filter plates were sealed and 40 μl/well of scintillation cocktail was added.

10. The plate was read by using a Microbeta$^2$ microplate counter.

3 Data Analysis

1. For reference and test compounds, the results were expressed as % Inhibition, using the normalization equation: $N=100-100\times(U-C2)/(C_1-C_2)$, where U is the unknown value, C1 is the average of high controls, and C2 is the average of low controls.

2. The $IC_{50}$ was determined by fitting percentage of inhibition as a function of compound concentrations with Hill equation using XLfit.

Results and Discussion

The results of potential competition binding properties of the exemplary compound of the disclosure targeting the human 5-hydroxytryptamine receptor 2A (5-$HT_{2A}$) are summarized in Table 18. The results of exemplary compounds of the disclosure are presented as $IC_{50}$ provided in Table 18.

TABLE 18

Effect of exemplary compounds of Formula (I) using Radioligand binding assay on human 5-$HT_{2A}$ receptor

| Compound ID | h5-$HT_{2A}$, $IC_{50}$ [nM] |
|---|---|
| 5-MeO-DMT | 603 |
| DMT | 954 |
| (R) I-1 | 154 |

II. Results and Discussion

Exemplary compounds of Formula (I) were evaluated using radioligand binding assay on human 5-$HT_{2A}$ receptor. $IC_{50}$ (nM) concentrations are illustrated in Table 18. This assay confirms that compounds of the disclosure are effective ligands of the target human 5-$HT_{2A}$ receptors.

Example 4: Human 5-$HT_{1A}$: Functional FLIPR Assay

1 Objective

The potential excitatory effects of compounds targeting on 5-hydroxytryptamine receptor 1A (5-$HT_{1A}$) under agonist mode was assessed.

2 Materials and Instrumentation 2.1 Cell Line (Table 19)

| Cell line Name | Target | Host cell |
|---|---|---|
| HTR1A&Gα15-CHO | 5-$HT_{1A}$ | Flp-in CHO |

2.2 Materials (Table 20)

| Regents | Vendor | Cat# |
|---|---|---|
| DMEM/F12 | Gibco | 11330057 |
| Dialyzed FBS | BIOSUN | BS-0005-500 |
| Penicillin-Streptomycin | Invitrogen | 15140 |
| Hygromycin B | Invivogen | Ant-hg-5 |
| TrypLE ™ Express | Gibco | 12604-013 |
| DPBS | Gibco | 14190250 |
| DMSO | Millipore | 1029312500 |
| Probenecid | Sigma | P8761 |
| FLIPR Calcium 6 Assay Kit | Molecular Device | R8191 |
| HEPES | Invitrogen | 15630 |
| Hank's Buffered Saline Solution | Invitrogen | 14025 |
| Serotonin HCl | Selleck | S4244 |

2.3 Instrumentation and Consumables (Table 21)

| Item | Supplier | Cat# |
|---|---|---|
| Fluorometric Imaging Plate Reader (FLIPR) | Molecular Device | Tetra |
| Countess Automated Cell Counter | Invitrogen | Countess |
| Cell Counting Chamber Slides | Invitrogen | C10312 |
| STERI-CYCLE CO2 Incubator | Thermo | 371 |
| 1300 Series Class II Biological Safety Cabinet | Thermo | 1389 |
| Table-type Large Capacity Low Speed Centrifuge | Cence | L550 |
| Centrifuge | Eppendorf | 5702 |
| Echo | Labcyte | 550 |
| Echo | Labcyte | 655 |
| Electro-thermal incubator | Shanghai Yiheng | DHP-9031 |
| plate shaker | IKA | MS3 digital |
| Water Purification System | ULUPURE | UPH-III-20T |
| Versatile and Universal pH and Conductivity Meters | Mettler Toledo | S220 |
| 384-Well plate | Corning | 3764 |
| 384-Well LDV Clear microplate | LABCYTE | LP-0200 |
| 384-Well Polypropylene microplate | LABCYTE | PP-0200 |
| 384-well compound plate | Corning | 3657 |
| T25 cell culture flask | Corning | 430639 |
| 50 mL Polypropylene Centrifuge Tube | JET | CFT011500 |
| 15 mL Polypropylene Centrifuge Tube | JET | CFT011150 |

3 Experimental Methods 3.1 Cell Culture

HTR1A&Gα15-CHO cells were cultured in DMEM/F12 medium containing 10% dialyzed FBS, 1× penicillin-streptomycin and 600 μg/mL Hygromycin B. The cells were passaged about three times a week, maintained between ~30% to ~90% confluence.

3.2 Cell Plating

1. The cell culture medium (DME M/F12 medium containing 10% dialyzed FBS, 1× penicillin-streptomycin and 600 μg/mL Hygromycin B), TrypLE™ Express and DPBS was warmed to room temperature in advance.

2. The cell culture medium was removed from flask. Washed cells with DP BS.

3. 1 mL TrypLE™ Express was added to the flask, mixed well by gentle shaking and cells were incubated at 37° C. for a few minutes.

4. The cells were checked for morphological change under microscope, the digestion was stopped by adding 2 mL cell culture medium to the flask when most of cells turned to round.

5. The cell suspension was transferred into a 15 mL centrifuge tube, and then centrifuged at 1,200 rpm for 5 minutes.

6. The supernatant was removed. The cell pellet were resuspended with 2 mL cell culture medium.

7. The cell density were counted using cell counter. Only cells with >85% viability were used for the assay.

8. Cells were diluted to $4\times10^5$/mL with cell culture medium.

9. 30 µL/well cell suspensions were added into a 384-well cell plate (The cell density was 12,000 cells/well).

10. The cell plate was incubated overnight at 37° C., 5% (v/v) $CO_2$.

3.3 Cell Handling

1. On the day of experiments, culture medium was removed from the cell plate.

2. 10 µL of assay buffer (20 mM HEPES, in 1×HBSS, pH 7.4) was added to each well of the cell plate.

3. 2× dye solution was prepared following the manufacture's instruction of the FLIPR® Calcium 6 assay kit:

i. The dye was diluted with assay buffer.

ii. probenecid was added to the final concentration of 5 mM.

iii. Vortexed vigorously for 1-2 minutes, adjust pH to 7.4.

4. 10 µL of 2× dye solution was added to each well of the cell plate.

5. The cell plate was placed on plate shaker, followed by shaking at 600 rpm for 2 minutes.

6. The plate was incubated at 37° C. for 2 hours followed by an additional 15-minute incubation at 25° C.

3.4 Prepare 3× Compounds.

1. Serotonin was prepared to the concentration of 10 mM with DMSO, 3-folds serial dilutions were performed with DMSO.

2. Prepare the test compound to the concentration of 10 mM with DMSO, preform 3-folds serial dilutions with DMSO.

3. The compounds were added to a 384-well compound source plate.

4. 90 nL/well of serial diluted compounds were transferred from source plate to a 384-well compound plate by using an Echo.

5. 30 µL/well of assay buffer was added to the compound plate.

6. The plate was mixed on-plate shaker for 2 minutes.

3.5 FLIPR Assay

1. After the cells incubate with dye solution, the cell plate, compound plate containing 3× compounds and FLIPR tips were placed into FLIPR.

2. 10 µL of 3× compounds were transferred from the compound plate to the cell plate by FLIPR.

3. The plate was read for 160 sec with 1 sec interval to obtain the data of agonist mode.

4 Data Analysis

1. The normalized fluorescence reading (RFU) was calculated as shown below, wherein $F_{max}$ and $F_{min}$ stand for maximum and minimum of calcium signal during defined time window:

$$RFU = F_{max} - F_{min}$$

2. $EC_{50}$ was calculated by fitting RFU against log of compound concentrations with Hill equation using XLfit.

Results and Discussion

The results of potential competition binding properties of the exemplary compounds of the disclosure targeting the human 5-hydroxytryptamine receptor 1A (5-$HT_{1A}$) are summarized in Table 22. The results of exemplary compounds of the disclosure are presented as $EC_{50}$ provided in Table 22.

Table 22: Effect of Exemplary Compounds of Formula (I) Using FLIPR Functional Assay on Human 5-$HT_{1A}$ Receptor

| Compound ID | h5-$HT_{1A}$, $EC_{50}$ [nM] | RFU@10 µM (1) |
|---|---|---|
| 5-MeO-DMT | 1,066 | 3,891 |
| DMT | ND (2) | 204 |
| (R) I-1 | 581 | 3,355 |

(1) Curve fitting with activation (%) @ 10 mM with RFU (2) Not detected

Exemplary compounds of Formula (I) were evaluated using functional FLIPR assay on human 5-$HT_{1A}$ receptor. $EC_{50}$ (nM) concentrations are illustrated in Table 22. This assay confirms that compounds of the disclosure are functionally active at the target human 5-$HT_{1A}$ receptors.

Example 5: Human 5-$HT_{1A}$: Radioligand Binding Assay

1 Objective

The objective of this study was to evaluate the binding properties of test compounds on 5-hydroxytryptamine receptor 1A (5-$HT_{1A}$).

2 Materials and Instrumentation

TABLE 23

| 2.1 Regents | | |
|---|---|---|
| Items | Vendor | Cat# |
| [3H]-8-Hydroxy-DPAT | PE | NET929250UC |
| Serotonin HCl | Selleck | S4244 |
| Bovine Serum Albumin (BSA) | Sigma | A1933 |
| Calcium chloride ($CaCl_2$) | Sigma | C5670 |
| $MgCl_2$ | Sigma | M1028 |
| Tris(hydroxymethyl)aminomethane (Tris) | Alfa Aesar | A18494 |
| Polyethylenimine, branched (PEI) | Sigma | 408727 |

TABLE 24

| 2.2 Instrumentation and Consumables | | |
|---|---|---|
| Item | Supplier | Cat# |
| Microbeta$^2$ Microplate Counter | PerkinElmer | 2450-0060 |
| UniFilter-96 GF/B | PerkinElmer | 6005177 |
| TopSeal | Biotss | SF-800 |
| MicroBeta Filtermate-96 | PerkinElmer | D961962 |
| Seven Compact pH meter | Mettler Toledo | S220 |

TABLE 24-continued

| 2.2 Instrumentation and Consumables | | |
|---|---|---|
| Item | Supplier | Cat# |
| Ultrapure Water Meter | Sichuan Ulupure | UPH-III-20T |
| Benchtop Centrifuge | Hunan Xiangyi | L550 |
| Microplate Shaker | Allsheng | MX100-4A |
| 384-Well Polypropylene Microplate | Labcyte | PP-0200 |
| 96 Round Well Plate | Corning | 3799 |
| 96 Round Deep Well Plate | Axygen | P-DW-11-C |
| Echo | LABCYTE | 550 |

3 Experimental Methods

1. The assay buffer was prepared following Table 25 below.

TABLE 25

| Reagent | Concentration |
|---|---|
| Tris | 25 mM |
| $MgCl_2$ | 10 mM |
| $CaCl_2$ | 1 mM |
| BSA | 0.5% (w/v) |

Adjust pH to 7.4 followed by 0.2 μM sterile filtration 2. 8 doses of reference and test compounds were prepared starting from 10 mM stock solution as required by 5-fold serial dilutions with 100% (v/v) DMSO.

3. UniFilter-96 GF/B plate was pretreated:

i. 50 μl/well of 0.5% (v/v) PEI was added to UniFilter-96 GF/B plates. The plates were sealed and incubated at 4° C. for 3 hrs.

ii. After incubation, the plates were washed 3 times with ice-cold wash buffer (50 mM Tris, pH7.4).

4. Assay plate was prepared:

i. Cell membrane was diluted with assay buffer and 100 μl/well was added to 96 round well plates to reach a concentration of 20 μg/well.

ii. 8 concentrations of reference or test compounds were prepared and 50 μl/well was added to 96 round deep well plates.

iii. [3H]-8-Hydroxy-DPAT was diluted with assay buffer to 2 nM (4× final concentration) and 50 μl/well was added to 96 round well plates.

5. The plate was centrifuged at 1000 rpm for 30 secs and then agitated at 600 rpm at room temperature for 5 min.

6. The plates were sealed and the plate was incubated at 27° C. for 90 min.

7. The incubation was stopped by vacuum filtration onto GF/B filter plates followed by 4 times washing with ice-cold wash buffer (50 mM Tris, pH7.4).

8. The plates were dried at 37° C. for 45 min.

9. The filter plates were sealed and 40 μl/well of scintillation cocktail was added.

10. The plate was read by using a Microbeta$^2$ microplate counter.

4 Data Analysis

1. For reference and test compounds, the results were expressed as % Inhibition, using the normalization equation: $N=100-100\times(U-C2)/(C_1-C_2)$, where U is the unknown value, C1 is the average of high controls, and C2 is the average of low controls.

2. The $IC_{50}$ was determined by fitting percentage of inhibition as a binding of compound concentrations with Hill equation using XLfit.

Results and Discussion

The results of potential competition binding properties of the exemplary compounds presented as $IC_{50}$ of the disclosure targeting the human 5-hydroxytryptamine receptor (5-$HT_{1A}$) are summarized in Table 26.

TABLE 26

| Effect of exemplary compounds of Formula (I) using Radioligand binding assay on human 5-$HT_{1A}$ receptor | |
|---|---|
| Compound ID | h5-$HT_{1A}$, $IC_{50}$ [nM] |
| 5-MeO-DMT | 6 |
| DMT | 689 |
| (R) I-1 | 3 |

Results and Discussion

Exemplary compounds of Formula (I), thereof were evaluated using radioligand binding assay on human 5-$HT_{1A}$ receptor. $IC_{50}$ (nM) concentrations are illustrated in Table 26. This assay confirms that compounds of Formula (I) of the disclosure are effective ligands of the target human 5-$HT_{1A}$ receptors.

Example 5A: Human 5-$HT_{2B}$: Radioligand Binding Assay

The objective of this study was to evaluate the binding properties of test compounds on 5-$HT_{2B}$.

TABLE 27

| Materials and Instruments | | |
|---|---|---|
| Materials | Vendor | Cat# |
| [3H]-LSD | PerkinElmer | NET638250UC |
| Yohimbine | MedChemExpress | HY-N0127 |
| Bovine Serum Albumin (BSA) | Sigma | A1933 |
| Calcium chloride ($CaCl_2$) | Sigma | C5670 |
| Tris(hydroxymethyl)amino-methane (Tris) | Alfa Aesar | A18494 |
| Polyethylenimine, branched (PEI) | Sigma | 408727 |

TABLE 28

| Instrumentation and Consumables | | |
|---|---|---|
| Item | Supplier | Cat# |
| Microbeta2 Microplate Counter | PerkinElmer | 2450-0060 |
| UniFilter-96 GF/B | PerkinElmer | 6005177 |
| TopSeal | Biotss | SF-800 |
| MicroBeta Filtermate-96 | PerkinElmer | D961962 |
| Seven Compact pH meter | Mettler Toledo | S220 |
| Ultrapure Water Meter | Sichuan Ulupure | UPH-III-20T |
| Benchtop Centrifuge | Hunan Xiangyi | L550 |
| Microplate Shaker | Allsheng | MX100-4A |
| 384-Well Polypropylene Microplate | Labcyte | PP-0200 |
| 96 Round Well Plate | Corning | 3799 |
| 96 Round Deep Well Plate | Axygen | P-DW-11-C |
| Echo | LABCYTE | 550 |

Experimental Methods

1) The assay buffer was prepared following Table 29 below.

TABLE 29

| Reagent | Concentration |
|---|---|
| Tris | 50 mM |
| $CaCl_2$ | 4 mM |
| BSA | 0.1% (w/v) |

Adjust to 7.4 followed by 0.2 μM sterile filtration

2) Eight doses of reference and test compounds starting from 10 mM stock solution as requested by 5-fold serial dilutions with 100% (v/v) DMSO.

3) UniFilter-96 GF/B plate was pretreated:

a. 50 μL/well of 0.5% (v/v) PEI to UniFilter-96 GF/B plates. The plates were sealed and incubated at 4° C. for 3 hrs.

b. After incubation, the plates were washed 3 times with ice-cold wash buffer (50 mM Tris, pH 7.4).

4) Assay plate preparation:

a. Cell membrane was diluted with assay buffer and 330 μL/well added to 96 round deep well plates to reach a concentration of 1 unit/well.

b. Eight concentrations of reference or test compounds were prepared and 110 μL/well added to 96 round deep well plates.

c. [3H]-LSD was diluted with assay buffer to 5 nM (5× final concentration) and 110 μL/well was added to 96 round deep well plates.

5) The plate was centrifuged at 1000 rpm for 30 secs and then agitated at 600 rpm at room temperature for 5 mins.

6) The plates were sealed and incubated at 37° C. for 90 mins.

7) The incubation was stopped by vacuum filtration onto GF/B filter plates followed by washing four times with ice-cold wash buffer (50 mM Tris, pH7.4).

8) The plates were dried at 37° C. for 45 min.

9) The filter plates were sealed and 40 μL/well of scintillation cocktail was added.

10) The plate was read using a Microbeta2 microplate counter.

Data Analysis

For reference and test compounds, the results are expressed as % Inhibition, using the normalization equation: $N=100-100\times(U-C2)/(C_1-C_2)$, where U is the unknown value, C1 is the average of high controls, and C2 is the average of low controls. The $IC_{50}$ is determined by fitting percentage of inhibition as a function of compound concentrations with Hill equation.

TABLE 30

Effect of exemplary compounds of Formula (I) using Radioligand binding assay on human-5-$HT_{2B}$ receptor

| Compound ID | 5-$HT_{2B}$, $IC_{50}$ [nM] | 5-$HT_{2B}$, Ki [nM] |
|---|---|---|
| 5-MeO-DMT | 248.92 | 128.79 |
| DMT | 423.14 | 218.92 |
| (R) I-1 | 18.99 | 9.82 |

Example 6: Psychedelic-Like Effect of Exemplary Compounds of Formula (I)

The effect of different doses of exemplary compounds of Formula (I) were evaluated on head-twitch response (HTR) as a behavior-based model of psychedelic activity.

Head Twitch Response (HTR) Assay Protocol:

Adult C57BL/6J mice (body weight range 20-30 g) were each placed into an open-top test cage made of transparent plastic for 20-30 min of habituation prior to testing. Habituation and testing were both conducted under low light conditions (~100 lux). Mice received a subcutaneous (SC) injection of either vehicle, positive control substance (e.g., 2,5-dimethoxy-4-iodoamphetamine (DOI)), or test compound at appropriate doses and volumes (10 ml/kg). Immediately post-treatment each mouse was placed back in its respective test cage. The cages were placed at approximately 50 cm from each other on a white, adjustable height table/flat surface so that the experimenter could easily monitor fine behaviors of both mice within the testing environment. An opaque divider was placed between the cages to prevent animals from observing each other. Immediately after placing the mice back into the test cages, the experimenter sat directly in front of the two containers, and recorded in real time the number of head twitch responses (HTR, defined as rapid side-to-side rotational shaking of the head) performed by each mouse for 20 min, subdivided in 5 min intervals with the use of a silent timer. To ensure scoring accuracy and consistency, one experienced experimenter performed HTR recording for all mice included in a study. While mice were subjected to HTR testing, another mouse pair underwent habituation in a separate set of test cages, so that at the end of the HTR scoring period new animals were ready to undergo substance administration and testing. Between individual HTR tests, cages were cleaned with water, disinfected with a 70% ethanol aqueous solution, and dried using paper towels.

Results and Discussion

FIG. 1 is a graph showing the effect of various doses of exemplary compound of Formula (I), (R) I-1, on head-twitch response (HTR) in male C57BL6 mice. The mice were treated with exemplary compounds (R) I-1 by SC route, and the total number of head twitches were recorded over a 20 min period. Data is expressed as mean±SEM. The induction of head twitches elicited by 5-$HT_{2A}$ receptor agonists is believed to represent a behavioral proxy of their psychedelic effects.

Example 7: Pharmacokinetic Studies in Rat

Protocol

Study Details:

Animals: Male Sprague-Dawley rats (~225-350 g) from Charles River Labs were acclimatized for a minimum of 5 days prior to start of study procedures. Body weights were recorded on the day of dosing.

Food restriction: None.

Clinical observations: Animals were observed at the time of dosing and each sample collection. Any abnormalities were documented including presence/absence of wet dog shakes/back muscle contractions (WDS/BMC).

Dosing: Formulations were administered intravenously (i.v.) via the tail vein using a 25 G needle connected to a 1 cc syringe.

Formulation:

The exemplary compounds of Formula (I) were freshly prepared at the appropriate concentrations in 5% Tween-80 in saline.

Sample Collection:

Blood collection time (h): 0, 25, 1 and 4

Volume/time-point: ~0.25 mL (saphenous vein)

Bioanalytical Method Development and Sample Analysis:

Analytes: Compounds of Formula (I)

Matrix: Rat plasma.

Instrumentation: AB Sciex QTRAP 4000 or 6500 MS/MS system equipped with an LC system with a binary pump, a solvent degasser, a thermostated column compartment, and a multiplate autosampler.

Bioanalytical Method(s) Development Included:

1. The ion transition for the test compounds and potential internal standards was selected (i.e., identification of the parent and product ions).

2. The mass spectrometric operating parameters were optimized.

3. The chromatographic condition for the analytes was established.

4. An appropriate internal standard (IS) was selected.

5. S sample clean-up method using protein precipitation was developed.

Method(s) Qualification:

1. The quantification dynamic range using non-zero calibration standards (STDs) in singlet was determined. The STDs consisted of a blank matrix sample (without IS), a zero sample (with IS), and at least 6 non-zero STDs covering the expected range and including the lower level of quantitation (LLOQ).

2. Triplicate injections of a system suitability sample (neat solution containing the analyte and IS) bracketing the batch were done.

Method(s) Acceptance Criteria:

1. At least 75% of non-zero STDs was included in the calibration curve with all back-calculated concentrations within ±20% deviation from nominal concentrations (±25% for the lower level of quantification, LLOQ).

2. The correlation coefficient (r) of the calibration curve was greater than or equal to 0.99 using quadratic regression analysis ($1/x^2$ weighting).

3. The area ratio variation between the pre- and post-run injections of the system suitability samples was within ±25%.

Sample Analysis Batch:

1. Triplicate injections of a system suitability sample bracketing the batch were done.

2. The STDs were placed in ascending order.

3. The study samples and the dosing solutions were diluted as 3 independent dilutions into blank matrix (plasma).

4. For more than 40 study samples in a batch, two sets of STDs bracketing the samples were utilized.

Samples which were 25% greater than the highest calibration standard, were diluted and re-assayed along with a corresponding dilution quality control standard. Dilution standards were acceptable if they were within 25% accuracy of the target concentration.

PK Analysis

Analysis software: Phoenix® WinNonlin® 8.3 (Pharsight, Certara, Mountainview, CA).

Analysis methods: non-compartmental analysis, linear up/log down trapezoidal rule.

PK parameters: $t_{1/2}$ and $AUC_{0\text{-}tlast}$ was estimated.

Results

Table 31 shows the plasma concentration of exemplary compound (R) I-1 following a dose of 1.19 i.v. administration.

TABLE 31

Plasma concentrations of (R) I-1 following 1.10 mg/kg i.v. administration (Group 2).

| Example ID | Dose (mg/kg) | Experimental time (h)/Rat# | Plasma concentration (ng/mL) R01 | R02 | R03 | Mean ± SD |
|---|---|---|---|---|---|---|
| (R) I-1 | 1.19 | 0.25 | 120 | 112 | 94.7 | 109 ± 12.9 |
| | | 1 | 42.3 | 30.3 | 65.8 | 46.1 ± 18.1 |
| | | 4 | 7.04 | 1.56 | 3.27 | 3.96 ± 2.80 |

*Values in italics are below the lower limit of quantitation (BLQ, 0.5 ng/mL) but were included in calculations.

*BLQ denotes below the lower limit of quantitation (0.5 ng/mL).

Table 32 is a summary of the plasma apparent $t_{1/2}$ and $AUC_{0\text{-}tlast}$ for exemplary compound I-1 following 1.10 mg/kg i.v. administration (Group 2).

TABLE 32

Summary of plasma apparent $t_{1/2}$ and $AUC_{0\text{-}tlast}$ for I-1 following 1.19 mg/kg i.v. administration (Group 2).

| Example ID | Dose (mg/kg) | Parameter | Parameter estimate for each animal R01 | R02 | R03 | Mean ± SD |
|---|---|---|---|---|---|---|
| (R) I-1 | 1.19 | Apparent $t_{1/2}$ (h)[a] | 0.975 | 0.632 | 0.748 | 0.785 ± 0.174 |
| | | $AUC_{0\text{-}tlast}$ (h*ng/mL) | 151 | 111 | 147 | 136 ± 22.0 |

[a]Apparent $t_{1/2}$ was estimated from 2 points only

Example 8: Human, Rat and Mouse Liver Microsomes Stability

Objective

The objective of this study was to estimate in vitro metabolic stability of exemplary compounds of Formula (I) or a pharmaceutically acceptable salt, solvate, and/or prodrug thereof in pooled human, male rat, and male mouse liver microsomes. The concentrations of compounds in reaction systems were evaluated by LC-MS/MS for estimating the stability in pooled human, male rat, and male mouse liver microsomes. The in vitro intrinsic clearances of test compounds were determined as well.

Protocol

A master solution in the "Incubation Plate" containing phosphate buffer, ultra-pure $H_2O$, $MgCl_2$ solution and liver microsomes was made according to Table 33. The mixture was pre-warmed at 37° C. water bath for 5 minutes.

TABLE 33

| Preparation of master solution | | | |
|---|---|---|---|
| Reagent | Stock Concentration | Volume | Final Concentration |
| Phosphate buffer | 200 mM | 200 μL | 100 mM |
| Ultra-pure $H_2O$ | — | 106 μL | — |
| $MgCl_2$ solution | 50 mM | 40 μL | 5 mM |
| Microsomes | 20 mg/mL | 10 μL | 0.5 mg/mL |

40 μL of 10 mM nicotinamide adenine dinucleotide phosphate (NADPH) solution was added to each well. The final concentration of NADPH was 1 mM. The negative control samples were prepared by replacing NADPH with 40 μL of ultra-pure $H_2O$. Samples were prepared in duplicate. Negative controls were prepared in singlet.

The reaction was started with the addition of 4 μL of 200 μM exemplary test compounds of the disclosure or control compounds to each master solution to get the final concentration of 2 μM. This study was performed in duplicate.

Aliquots of 50 μL were taken from the reaction solution at 0, 15, 30, 45, and 60 minutes. The reaction solutions were stopped by the addition of 4 volumes of cold methanol with IS (100 nM alprazolam, 200 nM imipramine, 200 nM labetalol, and 2 μM ketoprofen). Samples were centrifuged at 3,220 g for 40 minutes. Aliquot of 90 μL of the supernatant was mixed with 90 μL of ultra-pure $H_2O$ and then was used for LC-MS/MS analysis.

LC/MS analysis was performed for all samples from this study using a Shimadzu liquid chromatograph separation system equipped with degasser DGU-20A5R; solvent delivery unit LC-30AD; system controller SIL-30AC; column oven CTO-30A; CTC Analytics HTC PAL System. Mass spectrometric analysis was performed using a Triple Quad™ 5500 instrument.

All calculations were carried out using Microsoft Excel. Peak area ratios of test compound to internal standard (listed in the below table) were determined from extracted ion chromatograms.

All calculations were carried out using Microsoft Excel. Peak areas were determined from extracted ion chromatograms. The slope value, k, was determined by linear regression of the natural logarithm of the remaining percentage of the parent drug vs. incubation time curve.

The in vitro half-life (in vitro $t_{1/2}$) was determined from the slope value:

$$\text{in vitro } t_{1/2} = -(0.693/k)$$

Conversion of the in vitro $t_{1/2}$ (min) into the in vitro intrinsic clearance (in vitro $CL_{int}$, in μL/min/mg proteins) was done using the following equation (mean of duplicate determinations):

$$\text{in vitro } CL_{int} = \left(\frac{0.693}{(t_{1/2})}\right) * \left(\frac{\text{volume of incubation } (\mu L)}{\text{amount of proteins (mg)}}\right)$$

For the exemplary compounds of the disclosure or control compound that showed an initial fast disappearance followed by a slow disappearance, only the time points that were within the initial rate were included in the calculation.

Results and Discussion

Human, rat, and mouse liver microsomes contain a wide variety of drug metabolizing enzymes and are commonly used to support in vitro ADME (absorption, distribution, metabolism, and excretion) studies. These microsomes are used to examine the potential first-pass metabolism by-products of orally administered drugs. Representative compounds of the disclosure were evaluated for their stability in human, rat, and mouse liver microsomes.

Most of the exemplary compounds of the disclosure in three species, human, rat, and mouse liver microsomes were recovered within a 60-minute time period indicating that the compounds were not rapidly cleared (see Tables 34 and 35 for Exemplary compounds of Formula (I)).

TABLE 34

Metabolic Stability of Test Compounds in Liver Microsomes of Different Species (a)

| Compound ID | Species | $T_{1/2}$ (min) | C $L_{int}$ (μL/min/mg protein) | Scaled-up $CL_{int}$ (mL/min/Kg) | Predicted hepatic CL (mL/min/kg) |
|---|---|---|---|---|---|
| Diclofenac | Human | 10.73 | 129.12 | 161.94 | 18.35 |
| | Rat | 15.22 | 91.05 | 163.16 | 41.25 |
| | Mouse | 43.31 | 32.00 | 140.00 | 54.78 |
| 5-MeO-DMT | Human | 12.14 | 114.19 | 143.22 | 18.09 |
| | Rat | 5.68 | 244.17 | 437.56 | 49.02 |
| | Mouse | 44.52 | 31.13 | 136.21 | 54.19 |
| Diclofenac | Human | 10.73 | 129.12 | 161.94 | 18.35 |
| | Rat | 15.22 | 91.05 | 163.16 | 41.25 |
| | Mouse | 43.31 | 32.00 | 140.00 | 54.78 |
| (R) I-1 | Human | 24.03 | 57.68 | 72.34 | 16.09 |
| | Rat | 10.45 | 132.67 | 237.74 | 44.80 |
| | Mouse | <4.51 | >307.01 | >1343.17 | >84.35 |

Notes:
1. For the compounds that showed an initial fast disappearance followed by a slow disappearance, only the time points that were within the initial rate were included in the calculation.
2. If % remaining at 30 minutes was lower than 1%, then $CL_{int}$ and $t_{1/2}$ will be reported as ">307.01" and "<4.51," respectively.

TABLE 35

Metabolic Stability of Test Compounds in Liver Microsomes of Different Species (b)

| Compound ID | Species | Assay Format | Remaining Percentage (%) 0 min | 30 min | 60 min |
|---|---|---|---|---|---|
| Diclofenac | Human | With Cofactors | 100.00 | 5.01 | 1.77 |
| | | Without Cofactors | 100.00 | 112.67 | 96.67 |
| | Rat | With Cofactors | 100.00 | 11.86 | 6.35 |
| | | Without Cofactors | 100.00 | 102.19 | 100.63 |
| | Mouse | With Cofactors | 100.00 | 45.55 | 33.71 |
| | | Without Cofactors | 100.00 | 89.49 | 96.59 |
| 5-MeO-DMT | Human | With Cofactors | 100.00 | 19.24 | 3.25 |
| | | Without Cofactors | 100.00 | 18.58 | 3.00 |
| | Rat | With Cofactors | 100.00 | 2.57 | 0.36 |
| | | Without Cofactors | 100.00 | 49.55 | 23.82 |
| | Mouse | With Cofactors | 100.00 | 61.84 | 39.30 |
| | | Without Cofactors | 100.00 | 104.76 | 95.24 |
| (R) I-1 | Human | With Cofactors | 100.00 | 50.51 | 17.72 |
| | | Without Cofactors | 100.00 | 101.47 | 97.56 |
| | Rat | With Cofactors | 100.00 | 13.67 | 0.44 |
| | | Without Cofactors | 100.00 | 93.44 | 95.17 |
| | Mouse | With Cofactors | 100.00 | 0.15 | 0.23 |
| | | Without Cofactors | 100.00 | 98.55 | 103.02 |

Discussion

Exemplary compounds of the disclosure, represented by (R) I-1, were evaluated for their stability in human, rat, and mouse liver microsomes. Table 34 and Table 35 show the results of the stability studies. These results show that the compounds of the disclosure show a spectrum of stability across different species, including human, rat, and mouse.

Example 9: Protein Binding Measurements in Different Species, (Human, Rat, Mouse, and Dog) Plasma Using Equilibrium Dialysis Method Protocol 1. The Frozen Plasma (Stored at −80° C.) was Thawed Immediately in a 37° C. Water Bath.

TABLE 36 Materials

| Plasma information | | | |
|---|---|---|---|
| Species | Strain/Gender | Batch No. | Source |
| Human | Pooled; Male & Female | HUMANPLK2PNNV20230717 | Healthy Asian volunteers from local vendor (collected in domestic hospital with Ethical approval) |
| Dog | Beagle; Pooled; Male & Female | PH-Dog-20230612 | Local Supplier |
| Rat | SD; Pooled; Male & Female | RAT542174 | BioIVT |
| Mouse | CD-1; Pooled; Male & Female | MSE441125 | BioIVT |

2. Preparation of Working Solution

The working solution of test compounds and control compound was prepared in DMSO at the concentration of 200 μM, and then the working solution was spiked into plasma. The final concentration of compound was 1 μM. The final concentration of DMSO was 0.5%. Ketoconazole was used as positive control in the assay.

3. Preparation of Dialysis Membranes

The dialysis membranes were soaked in ultrapure water for 60 minutes to separate strips, then in 20% ethanol for 20 minutes, finally in dialysis buffer for 20 minutes.

4. Procedure for Equilibrium Dialysis

The dialysis set up was assembled according to the manufacturer's instruction. Each Cell was with 150 μL of plasma sample and dialyzed against equal volume of dialysis buffer (PBS). The assay was performed in duplicate. The dialysis plate was sealed and incubated in an incubator at 37° C. with 5% CO2 at 100 rpm for 6 hours. At the end of incubation, 50 μL of samples from both buffer and plasma chambers were transferred to wells of a 96-well plate.

5. Procedure for Sample Analysis

50 μL of plasma was added to each buffer samples and an equal volume of PBS was supplemented to the collected plasma sample. 400 μL of precipitation buffer acetonitrile containing internal standards (IS, 200 nM labetalol, 100 nM tolbutamide and 100 nM ketoprofen) was added to precipitate protein and release compounds. Samples were vortexed for 2 minutes and centrifuged for 30 minutes at 3,220 g. Aliquot of 50 μL of the supernatant was diluted by 150 μL acetonitrile containing internal standards: ultra-pure H2O=1:1, and the mixture was used for LC-MS/MS analysis.

6. Data Analysis

All calculations were carried out using Microsoft Excel. The concentrations of test compounds in the buffer and plasma chambers were determined from peak area ratios. The percentages of bound compound were calculated as follows:

$$\%\ \text{Free} = (\text{Peak Area Ratio buffer chamber}/\text{Peak Area Ratio plasma chamber}) * 100\%$$

$$\%\ \text{Bound} = 100\% - \%\ \text{Free}$$

-continued $$\%\ \text{Recovery} = (\text{Peak Area Ratio buffer chamber} + \text{Peak Area Ratio plasma chamber})/\text{Peak Area Ratio total sample} * 100\%$$

| Bioanalytical Method (Table 37) | | | | | | | |
|---|---|---|---|---|---|---|---|
| A | Time (min) | 0 | 0.2 | 0.6 | 1.1 | 1.2 | 1.4 |
| | % B | 5 | 5 | 100 | 100 | 5 | 5 |
| B | Time (min) | 0 | 2.4 | 2.5 | 2.6 | 3 | |
| | % B | 5 | 100 | 100 | 5 | 5 | |

TABLE 38

| Injection Volume | |
|---|---|
| A | 3 μL |
| B | 20 μL |

Flow rate: 0.65 mL/min

Column temperature: 40° C.

MS parameters:

Ion source: Turbo spray

Ionization model: ESI

Scan type: MRM

Collision gas: 6 L/min

Curtain gas: 30 L/min

Nebulize gas: 50 L/min

Auxiliary gas: 50 L/min

Temperature: 500 Degree Celsius

Ion spray voltage: +5500 v (positive MRM)

Results and Discussion

Table 39 shows the results of protein binding measurements in different species using exemplary compounds of the disclosure.

TABLE 39

| Compound ID | Species | % Bound | % Recovery | % Remaining @ 6 hours |
|---|---|---|---|---|
| Ketoconazole | Human | 99.12 | 111.51 | 114.03 |
| | Dog | 99.01 | 87.17 | 92.22 |
| | Rat | 99.55 | 105.06 | 101.20 |
| | Mouse | 99.32 | 108.90 | 103.60 |
| (R) I-1 | Human | 84.03 | 101.61 | 103.38 |
| | Dog | 82.60 | 92.92 | 95.50 |
| | Rat | 46.57 | 103.10 | 105.76 |
| | Mouse | 47.88 | 113.26 | 112.85 |

Part II

The following compounds were prepared using one or more of the synthetic methods outlined in Schemes I and II.

A. Synthesis of Exemplary Compounds of the Disclosure

Example 10: (R)-5-Methoxy-3-((1-(2-methoxyethyl) pyrrolidin-2-yl)methyl)-1H-indole ((R) I-98,)

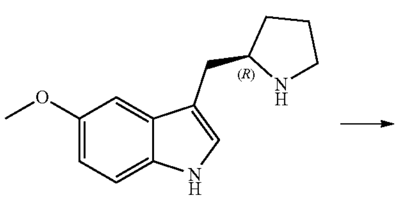

1

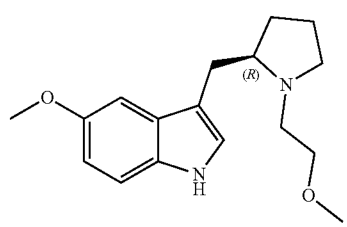

(R) I-98

Synthesis of (R)-5-methoxy-3-(pyrrolidin-2-ylmethyl)-1H-indole (1): Prepared according to literature procedure (WO2022183288A1). $^1$H NMR (DMSO-$d_6$): δ 10.68 (s, 1H), 7.23 (d, 1H, J=6.0 Hz), 7.14 (s, 1H), 7.02 (d, 1H, J=3.0 Hz), 6.72 (dd, 1H, J=3.0, 6.0 Hz), 3.38 (s, 3H), 3.36-3.31 (m, 1H), 3.01-2.95 (m, 1H), 2.87-2.72 (m, 3H), 1.82-1.62 (m, 3H), 1.44-1.37 (m, 1H); ESI-MS (m/z, %): 231 ($MH^+$, 100).

Synthesis of (R)-5-methoxy-3-((1-(2-methoxyethyl)pyrrolidin-2-yl)methyl)-1H-indole (2): A solution of (R)-5-methoxy-3-(pyrrolidin-2-ylmethyl)-1H-indole (1.1 g, 4.77 mmol) in dry DMF (20 mL) was treated with 2-methoxyethyl 4-methylbenzenesulfonate (1.32 g, 5.73 mmol) and triethyl amine (1.65 mL, 11.94 mmol) at room temperature and stirred for overnight (16 h). The reaction was quenched with water (50 mL) and product was extracted into ethyl acetate (2×50 mL). Combined ethyl acetate layer was washed with water (25 mL), brine (25 mL) and dried ($Na_2SO_4$). Solvent was evaporated and crude was purified by column chromatography (2 M $NH_3$ in MeOH:$CH_2Cl_2$, 5:95) on silica gel to obtain the title compound (R) I-98 (1.0 g, 73%) as a light brown glue. $^1$H NMR (DMSO-$d_6$): δ 10.60 (s, 1H), 7.21 (d, 1H, J=6.0 Hz), 7.09 (s, 1H), 6.98 (s, 1H), 6.70 (dd, 1H, J=3.0, 6.0 Hz), 3.76 (s, 3H), 3.47 (t, 2H, J=6.0 Hz), 3.13 (s, 3H), 3.09-3.06 (m, 2H), 2.97-2.93 (m, 1H), 2.65-2.60 (m, 1H), 2.48-2.37 (m, 2H), 2.22-2.15 (m, 1H), 1.71-1.57 (m, 3H), 1.48-1.42 (m, 1H); ESI-MS (m/z, %): 289 ($MH^+$, 100).

Example 11: (R)-2-(4-((3-((1-(Methyl-$d_3$)pyrrolidin-2-yl)methyl-$d_2$)-1H-indol-5-yl)oxy)butyl)isoindoline-1,3-dione ((R) I-244)

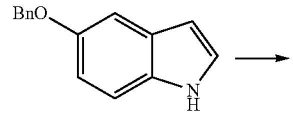

3

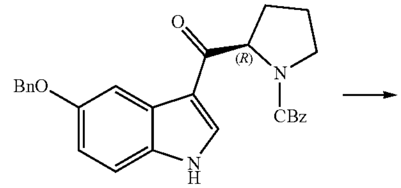

4

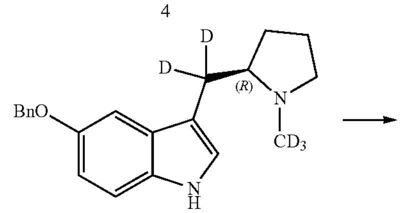

5

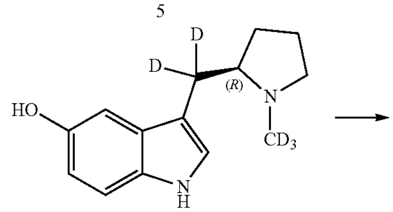

6

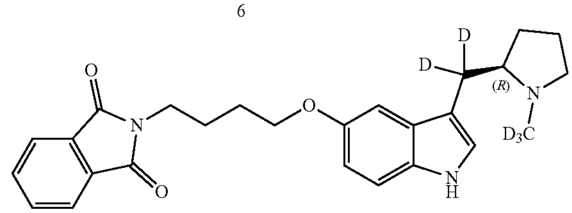

(R) I-244

Synthesis of (R)-2-(2-(5-(benzyloxy)-1H-indole-3-carbonyl)pyrrolidin-1-yl)-1-phenylethan-1-one (4)

A solution of 1-(2-oxo-2-phenylethyl)-D-proline (4.0 g, 16.04 mmol) in dry THF (50 mL) was treated with thionyl chloride (2.34 mL, 32.09 mmol) at 0° C. The reaction was brought to room temperature, then refluxed for 2 h. The reaction was brought to room temperature, solvent was evaporated, and crude was dried under vacuum to obtain the corresponding acid chloride.

A solution of 5-(benzyloxy)-1H-indole (3.58 g, 16.04 mmol) in dry $CH_2Cl_2$ (50 mL) at 5-10° C. was treated with above crude acid chloride in dry $CH_2Cl_2$ (30 mL) and ethyl magnesium bromide (10.7 mL, 32.09 mmol, 3 M in THF) simultaneously over a period of 15 min. and stirred at same temperature for further 15 min. The reaction was quenched with con. HCl (10 mL), followed by water (100 mL), and product was extracted into $CH_2Cl_2$ (2×100 mL). Combined $CH_2Cl_2$ layer was washed with water (50 mL), brine (50 mL) and dried ($Na_2SO_4$). Solvent was evaporated and crude was purified by column chromatography (EtOAc: $CH_2Cl_2$, 1:4) on silica gel to obtain the title compound 4 (5.6 g, 76.7%) as a light brown solid. $^1$H NMR (DMSO-$d_6$): δ 11.94, 11.92 (2s, 1H), 8.40, 8.38 (2d, 1H, J=3.0 Hz), 7.85, 7.81 (2d, 1H, J=3.0 Hz), 7.51-7.34 (m, 9H), 7.15-6.94 (m, 3H), 5.24-4.92 (m, 5H), 3.55-3.50 (m, 2H), 2.44-2.29 (m, 1H), 2.29-1.83 (m, 3H); ESI-MS (m/z, %): 514 (100), 477 (M+Na), 455 ($MH^+$).

Synthesis of (R)-5-(benzyloxy)-3-((1-(methyl-$d_3$) pyrrolidin-2-yl)methyl-$d_2$)-1H-indole (5)

A solution of (R)-2-(2-(5-(benzyloxy)-1H-indole-3-carbonyl)pyrrolidin-1-yl)-1-phenylethan-1-one (5.5 g, 12.10 mmol) in dry THF (100 mL) was treated with $LiAlD_4$ (2.54 g, 60.50 mmol) at 0° C. over a period of 15 min. The reaction was brought to room temperature and then refluxed for overnight (16 h). The reaction was cooled to 0° C., quenched with water (2.54 mL), 4 N NaOH solution (2.54 mL) and water (2.54 mL). The reaction was brought to room temperature and stirred for additional 30 min. The reaction was filtered through a pad of sodium sulfate and washed with THF (3×50 mL). Combined THF layer was evaporated and crude was purified by column chromatography (2 M $NH_3$ in MeOH:$CH_2Cl_2$, 5:95) on silica gel to obtain the title compound 5 (3.6 g, 91.4%) as a pale-yellow glue. $^1$H NMR (DMSO-$d_6$): δ 10.62 (s, 1H), 7.49-7.30 (m, 5H), 7.23 (d, 1H, J=6.0 Hz), 7.09-7.05 (m, 1H), 6.80 (dd, 1H, J=3.0, 6.0 Hz), 5.11 (s, 2H), 2.99-2.95 (m, 1H), 2.32-2.28 (m, 1H), 2.11-2.07 (m, 1H), 1.66-1.41 (m, 4H); ESI-MS (m/z, %): 326 ($MH^+$, 100).

Synthesis of (R)-3-((1-(methyl-$d_3$)pyrrolidin-2-yl) methyl-$d_2$)-1H-indol-5-ol (6)

A solution of (R)-5-(benzyloxy)-3-((1-(methyl-$d_3$)pyrrolidin-2-yl)methyl-$d_2$)-1H-indole (3.55 g, 10.90 mmol) in methanol (60 mL) was treated with palladium on carbon (0.35 g, 10% dry basis) and stirred under hydrogen atm (balloon pressure) for additional 16 h (overnight). The reaction was filtered through a pad of celite and washed with methanol (3×15 mL). Combined methanol layer was evaporated, and crude was purified through flash column chromatography (2 M $NH_3$ in MeOH:$CH_2Cl_2$, 5:95) on silica gel to obtain the title compound 6 (2.35 g, 91.4%) as an off-white foam. $^1$H NMR (DMSO-$d_6$): δ 10.44 (s, 1H), 8.55 (s, 1H), 7.11 (d, 1H, J=6.0 Hz), 7.02 (d, 1H, J=3.0 Hz), 6.81 (d, 1H, J=3.0 Hz), 6.58 (dd, 1H, J=3.0, 6.0 Hz), 3.00-2.96 (m, 1H), 2.34-2.30 (m, 1H), 2.15-2.10 (m, 1H), 1.69-1.42 (m, 4H); ESI-MS (m/z, %): 236 ($MH^+$, 100).

Synthesis of (R)-2-(4-((3-((1-(methyl-$d_3$)pyrrolidin-2-yl)methyl-$d_2$)-1H-indol-5-yl)oxy)butyl)isoindoline-1,3-dione ((R) I-244)

A solution of (R)-3-((1-(methyl-$d_3$)pyrrolidin-2-yl) methyl-$d_2$)-1H-indol-5-ol (1.0 g, 4.24 mmol) in dry DMF (30 mL) was treated with $Cs_2CO_3$ (2.07 g, 6.37 mmol) followed by 2-(4-bromobutyl)isoindoline-1,3-dione (1.32 g, 5.73 mmol) at room temperature and stirred for additional 48 h. The reaction was quenched with water (100 mL) and product was extracted into ethyl acetate (2×50 mL). Combined ethyl acetate layer was washed with water (50 mL), brine (50 mL) and dried ($Na_2SO_4$). Solvent was evaporated and crude was purified by column chromatography (2 M $NH_3$ in MeOH:$CH_2Cl_2$, 5:95) on silica gel to obtain the title compound (R) I-244 (0.81 g, 44%) as a pale-yellow glue. $^1$H NMR (DMSO-$d_6$): δ 10.59 (s, 1H), 7.89-7.83 (m, 4H), 7.18 (d, 1H, J=6.0 Hz), 7.07 (s, 1H), 6.95 (s, 1H), 6.69 (d, 1H, J=6.0 Hz), 3.98 (t, 2H, J=3.0, 6.0 Hz), 3.66 (t, 2H, J=3.0, 6.0 Hz), 2.97 (t, 1H, J=6.0 Hz), 2.35-2.30 (m, 1H), 2.15-2.10 (m, 1H), 1.79-1.42 (m, 8H), ESI-MS (m/z, %): 437 ($MH^+$, 100).

Example 12: (R)-2-(5-((3-((1-(Methyl-$d_3$)pyrrolidin-2-yl)methyl-$d_2$)-1H-indol-5-yl)oxy)pentyl)isoindoline-1,3-dione ((R) I-245)

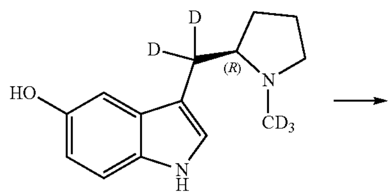

6

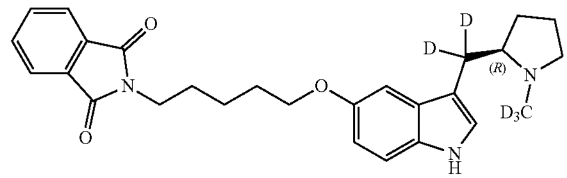

(R) I-245

Synthesis of (R)-2-(5-((3-((1-(methyl-$d_3$)pyrrolidin-2-yl)methyl-$d_2$)-1H-indol-5-yl)oxy)pentyl)isoindoline-1,3-dione ((R) I-245)

A solution of (R)-3-((1-(methyl-$d_3$)pyrrolidin-2-yl) methyl-$d_2$)-1H-indol-5-ol (1.0 g, 4.24 mmol) in dry DMF (30 mL) was treated with $Cs_2CO_3$ (2.07 g, 6.37 mmol) followed by 2-(5-bromopentyl)isoindoline-1,3-dione (2.51 g, 8.49 mmol) at room temperature and stirred for additional 48 h. The reaction was worked-up and purified as described for compound (R) I-244 to obtain title compound (R) I-245 (0.8 g, 42%) as a pale-yellow glue. $^1$H NMR (DMSO-$d_6$): δ 10.58 (s, 1H), 7.89-7.83 (m, 4H), 7.18 (d, 1H, J=6.0 Hz), 7.07 (s, 1H), 6.95 (s, 1H), 6.67 (dd, 1H, J=1.5, 6.0 Hz), 3.94 (t, 2H, J=3.0, 6.0 Hz), 3.62 (t, 2H, J=3.0, 6.0 Hz), 2.96 (t, 1H, J=3.0, 6.0 Hz), 2.32 (t, 1H, J=6.0 Hz), 2.10-2.06 (m, 1H), 1.78-1.43 (m, 10H); ESI-MS (m/z, %): 451 ($MH^+$, 100).

Example 13:2-(5-((3-(((R)-1-(Methyl-$d_3$)pyrrolidin-2-yl)methyl-$d_2$)-1H-indol-5-yl)oxy)pentyl)hexahydro-1H-isoindole-1,3(2H)-dione ((R) I-248) (Mixture of Cis-Diastereomers)

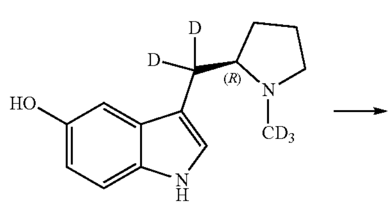

6

-continued

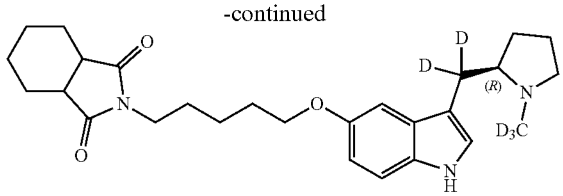

(R) I-248

Synthesis of 2-(5-((3-(((R)-1-(methyl-$d_3$)pyrrolidin-2-yl)methyl-$d_2$)-1H-indol-5-yl)oxy)pentyl)hexahydro-1H-isoindole-1,3(2H)-dione (9) (Mixture of Cis-Diastereomers)

A solution of (R)-3-((1-(methyl-$d_3$)pyrrolidin-2-yl)methyl-$d_2$)-1H-indol-5-ol (0.78 g, 3.31 mmol) in dry DMF (20 mL) was treated with $Cs_2CO_3$ (1.62 g, 4.97 mmol) followed by cis-2-(4-bromobutyl)hexahydro-1H-isoindole-1,3(2H)-dione (2.0 g, 6.62 mmol) at room temperature and stirred for additional 48 h. The reaction was worked-up and purified as described for compound (R) I-248 to obtain title compound (R) I-248 (0.88 g, 58%) as a light brown glue. $^1$H NMR (DMSO-$d_6$): δ 10.59 (s, 1H), 7.20 (d, 1H, J=6.0 Hz), 7.08 (d, 1H, J=1.5 Hz), 6.95 (d, 1H, J=1.5 Hz), 6.69 (dd, 1H, J=3.0, 6.0 Hz), 3.93 (t, 2H, J=6.0 Hz), 3.40 (t, 2H, J=6.0 Hz), 3.00-2.89 (m, 3H), 2.35 (t, 1H, J=3.0, 6.0 Hz), 2.15-2.09 (m, 1H), 1.74-1.25 (m, 18H); ESI-MS (m/z, %): 457 ($MH^+$, 100).

Example 13A: Synthesis of (R)-4-Fluoro-5-methoxy-3-((1-methylpyrrolidin-2-yl)methyl)-1H-indole (R) I-250

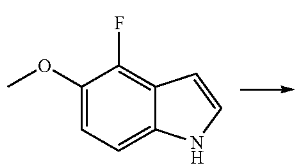

1A

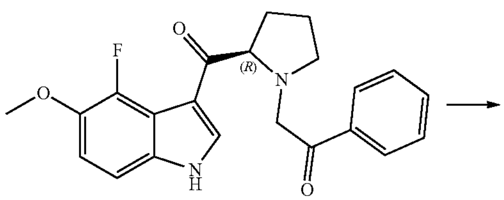

2A

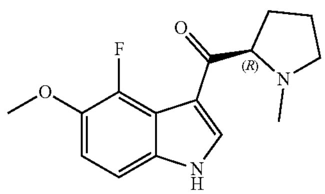

(R) I-250

Synthesis of (R)-2-(2-(4-fluoro-5-methoxy-1H-indole-3-carbonyl)pyrrolidin-1-yl)-1-phenylethan-1-one 2A: A solution of 1-(2-oxo-2-phenylethyl)-D-proline (2.2 g, 8.83 mmol) in dry THF (40 mL) was treated with thionyl chloride (1.28 mL, 17.65 mmol) at 0° C. The reaction was brought to room temperature, then refluxed for 2 hrs. The reaction was brought to room temperature, the solvent was evaporated, and the crude acid chloride was dried under vacuum to obtain the corresponding acid chloride.

A solution of 4-fluoro-5-methoxy-1H-indole (1.45 g, 8.83 mmol) in dry $CH_2Cl_2$ (50 mL) at 5-10° C. was treated with above crude acid chloride in dry $CH_2Cl_2$ (20 mL) and ethyl magnesium bromide (6.2 mL, 18.53 mmol, 3 M in diethyl ether) simultaneously over a period of 5 mins. and stirred at the same temperature for a further 15 mins. The reaction was quenched with concentrated HCl (10 mL) followed by water (50 mL) and product was extracted into $CH_2Cl_2$ (2×100 mL). $CH_2Cl_2$ layer was washed with saturated $NaHCO_3$ solution (50 mL), brine (25 mL) and dried ($Na_2SO_4$). Solvent was evaporated and the crude product was purified by crystallization from a mixture of $CH_2Cl_2$, Hexanes 1:5 to obtain the title compound 2A (2.25 g, 64.3%) as a beige solid. $^1$H NMR (DMSO-$d_6$): δ 12.15, 12.13 (2s, 1H), 8.44 (d, 1H, J=12.0 Hz), 7.39-7.05 (m, 7H), 5.30-5.22 (m, 1H), 5.11-4.91 (m, 2H), 3.86 (s, 3H), 3.54-3.48 (m, 2H), 2.42-2.30 (m, 1H), 1.90-1.75 (m, 3H); ESI-MS (m/z, %): 397 ($MH^+$), 419 (M+Na).

Synthesis of (R)-4-fluoro-5-methoxy-3-((1-methylpyrrolidin-2-yl)methyl)-1H-indole (R) I-250

A solution of (R)-2-(2-(4-fluoro-5-methoxy-1H-indole-3-carbonyl)pyrrolidin-1-yl)-1-phenylethan-1-one (2.0 g, 5.04 mmol) in dry THF (30 mL) was treated with lithium aluminum hydride (26 mL, 25.22 mmol, 1M solution in THF) at 0° C. over a period of 10 mins. The reaction was brought to room temperature, then refluxed for additional 16 hrs. The reaction was brought to room temperature, then cooled to 0° C. and quenched with the sequential addition of water (1.0 mL), 4N NaOH solution (1.0 mL) and water (1.0 mL). The reaction was brought to room temperature and stirred for additional 30 mins. The reaction was filtered, and washed with THF (2×50 mL). Combined THF layer was evaporated and the crude product was purified by column chromatography (2 M $NH_3$ in MeOH:$CH_2Cl_2$, 5:95) on silica gel to obtain the title compound (R) I-250 (1.0 g, 75.7%) as a pale-yellow glue. $^1$H NMR (DMSO-$d_6$): δ 10.87 (s, 1H), 7.12 (s, 1H), 7.06 (d, 1H, J=6.0 Hz), 6.93 (t, 1H, J=6.0 Hz), 3.81 (s, 3H), 3.15-3.10 (m, 1H), 2.99-2.95 (m, 1H), 2.48-2.45 (m, 1H), 2.36-2.30 (m, 4H), 2.14-2.00 (m, 1H), 1.66-1.46 (m, 4H); ESI-MS (m/z, %): 263 ($MH^+$, 100).

Example 13B: Synthesis of (R)-4-Fluoro-5-methoxy-3-((1-(methyl-$d_3$)pyrrolidin-2-yl)methyl)-1H-indole (R) I-251

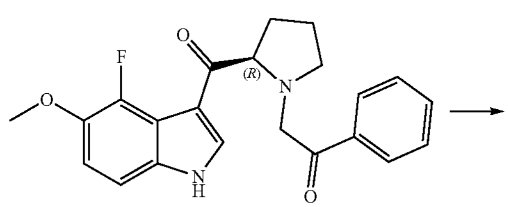

2A

-continued

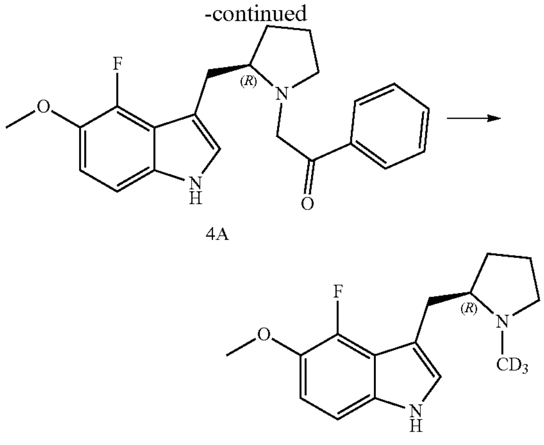

4A (R) I-251

Synthesis of (R)-2-(2-((4-fluoro-5-methoxy-1H-indol-3-yl)methyl)pyrrolidin-1-yl)-1-phenylethan-1-one 4A A solution of (R)-2-(2-(4-fluoro-5-methoxy-1H-indole-3-carbonyl)pyrrolidin-1-yl)-1-phenylethan-1-one (2.5 g, 6.31 mmol) in dry THF (30 mL) was treated with a solution of lithium borohydride (12.61 mL, 25.23 mmol, 2 M solution in THF) at room temperature over a period of 5 mins. and the reaction was refluxed for additional 4 hrs. The reaction was cooled to 0° C., quenched with the careful addition of methanol (25 mL) over a period of 15 mins. The reaction was brought to room temperature and was stirred for an additional 1 hr. The reaction was treated with saturated $NaHCO_3$ solution (30 mL) and product was extracted into ethyl acetate (3×50 mL). The combined ethyl acetate layer was washed with brine (20 mL) and dried ($Na_2SO_4$). The solvent was evaporated and the crude product was purified by flash column chromatography (MeOH; $CH_2Cl_2$, 2:98) on silica gel to obtain the title compound 4A (1.2 g, 49.8%) as a pale yellow semi-solid. The compound was used in the subsequent step without any characterization.

Synthesis of (R)-4-fluoro-5-methoxy-3-((1-(methyl-$d_3$)pyrrolidin-2-yl)methyl)-1H-indole (R) I-251

A suspension of (R)-2-(2-((4-fluoro-5-methoxy-1H-indol-3-yl)methyl)pyrrolidin-1-yl)-1-phenylethan-1-one (1.2 g, 3.14 mmol) in dry THF (25 mL) was treated with lithium aluminum deuteride (0.32 g, 7.57 mmol) at 0° C. The reaction was brought to room temperature, then refluxed for additional 16 hrs. The reaction was brought to room temperature, and then cooled to 0° C. and quenched with the sequential addition of water (1.0 mL), 4N NaOH solution (1.0 mL) and water (1.0 mL). The reaction was brought to room temperature and stirred for additional 30 mins. The reaction was filtered and washed with THF (2×50 mL). The combined THF layer was evaporated and the crude product was purified by column chromatography (2 M $NH_3$ in MeOH:$CH_2Cl_2$, 5:95) on silica gel to obtain the title compound (R) I-251 (0.73 g, 87.7%) as an off-white solid. $^1H$ NMR (DMSO-$d_6$): δ 10.86 (s, 1H), 7.12 (s, 1H), 7.06 (d, 1H, J=6.0 Hz), 6.93 (t, 1H, J=6.0 Hz), 3.81 (s, 3H), 3.14-3.10 (m, 1H), 2.99-2.95 (m, 1H), 2.51-2.45 (m, 1H), 2.38-2.32 (m, 1H), 2.14-2.06 (m, 1H), 1.64-1.45 (m, 4H); ESI-MS (m/z, %): 266 ($MH^+$, 100).

Example 13C: Synthesis of (R)-5-Methoxy-6-methyl-3-((1-methylpyrrolidin-2-yl)methyl)-1H-indole (R) I-254

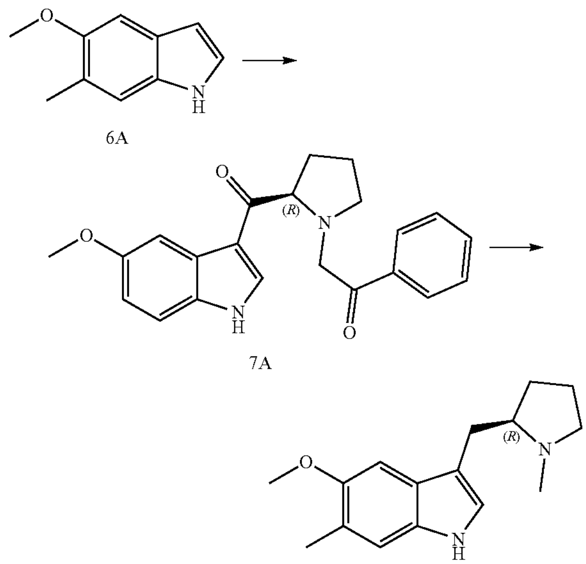

6A

7A (R) I-254

Synthesis of (R)-2-(2-(5-methoxy-6-methyl-1H-indole-3-carbonyl)pyrrolidin-1-yl)-1-phenylethan-1-one 7A A solution of 1-(2-oxo-2-phenylethyl)-D-proline (3.0 g, 12.03 mmol) in dry THF (30 mL) was treated with thionyl chloride (1.75 mL, 24.07 mmol) at 0° C. The reaction was brought to room temperature, then refluxed for 2 hrs. The reaction was brought back to room temperature, the solvent was evaporated, and the crude product was dried under vacuum to obtain the corresponding acid chloride.

A solution of 5-methoxy-6-methyl-1H-indole (1.94 g, 12.03 mmol) in dry $CH_2Cl_2$ (50 mL) at 5-10° C. was treated with above crude acid chloride in dry $CH_2Cl_2$ (20 mL) and ethyl magnesium bromide (8.4 mL, 25.27 mmol, 3 M in diethyl ether) simultaneously over a period of 5 mins. and stirred at the same temperature for further a 15 mins. The reaction was quenched with concentrated HCl (10 mL) followed by water (50 mL) and then the product was extracted into $CH_2Cl_2$ (2×100 mL). $CH_2Cl_2$ layer was washed with saturated $NaHCO_3$ solution (50 mL), brine (25 mL) and dried ($Na_2SO_4$). Solvent was evaporated and the crude product was purified by crystallization from a mixture of $CH_2Cl_2$, Hexanes 1:5 to obtain the title compound 7A (3.3 g, 70.2%) as a light brown solid. $^1H$ NMR (DMSO-$d_6$): δ 11.81 (s, 1H), 8.31 (dd, 1H, J=3.0 Hz), 7.68 (d, 1H, J=12.0 Hz), 7.40-7.32 (m, 2H), 7.15 (d, 1H, J=3.0 Hz), 7.11-7.03 (m, 3H), 5.24-4.91 (m, 3H), 3.83 (s, 3H), 3.56-3.49 (m, 2H), 2.43-2.25 (m, 4H), 1.90-1.80 (m, 3H); ESI-MS (m/z, %): 393 ($MH^+$), 415 (M+Na).

Synthesis of (R)-5-methoxy-6-methyl-3-((1-methylpyrrolidin-2-yl)methyl)-1H-indole (R) I-254: A solution of (R)-2-(2-(5-methoxy-6-methyl-1H-indole-3-carbonyl)pyrrolidin-1-yl)-1-phenylethan-1-one (1.2 g, 3.05 mmol) in dry THF (20 mL) was treated with lithium aluminum hydride (15.3 mL, 15.29 mmol, 1M solution in THF) at 0° C. over a period of 10 mins. The reaction was brought to room temperature, then refluxed for additional 16 hrs. The reaction was brought back to room temperature, then cooled to 0° C. and quenched with the sequential addition of water (1.0 mL), 4N NaOH solution (1.0 mL) and water (1.0 mL). The reaction was brought to room temperature and stirred for an additional 30 mins. The reaction was filtered and washed with THF (2×50 mL). The combined THF layer was evaporated, and the crude product was purified by column chromatography (2 M $NH_3$ in MeOH:$CH_2Cl_2$, 5:95) on silica gel to obtain the title compound (R) I-254 (0.75 g, 94.5%) as an off-white solid. $^1$H NMR (DMSO-$d_6$): δ 10.45 (s, 1H), 7.08 (s, 1H), 6.98 (s, 1H), 6.93 (s, 1H), 3.79 (s, 3H), 3.01-2.95 (m, 2H), 2.49-2.43 (m, 1H), 2.38-2.32 (m, 4H), 2.22 (s, 3H), 2.10-2.06 (m, 1H), 1.76-1.41 (m, 4H); ESI-MS (m/z, %): 259 ($MH^+$, 100).

Example 13D: Synthesis of (R)-5-Methoxy-6-methyl-3-((1-(methyl-$d_3$)pyrrolidin-2-yl)methyl)-1H-indole (R) I-255

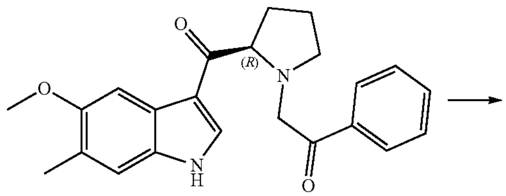

7A

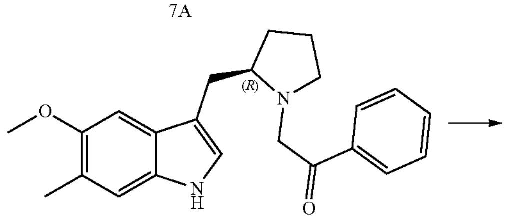

9A

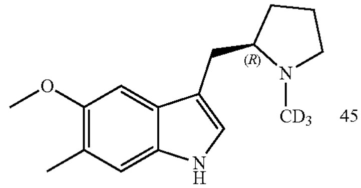

(R) I-255

Synthesis of (R)-2-(2-((5-methoxy-6-methyl-1H-indol-3-yl)methyl)pyrrolidin-1-yl)-1-phenylethan-1-one 9A A solution of (R)-2-(2-(5-methoxy-6-methyl-1H-indole-3-carbonyl)pyrrolidin-1-yl)-1-phenylethan-1-one (2.0 g, 5.10 mmol) in dry THF (30 mL) was treated with a solution of lithium borohydride (10.2 mL, 20.38 mmol, 2 M solution in THF) at room temperature over a period of 5 mins. and the reaction was refluxed for additional 4 hrs. The reaction was cooled to 0° C., quenched with the careful addition of methanol (25 mL) over a period of 15 mins. The reaction was brought to room temperature and stirred for an additional 1 hr. The reaction was treated with saturated $NaHCO_3$ solution (30 mL) and the product was extracted into ethyl acetate (3×50 mL). The combined ethyl acetate layer was washed with brine (20 mL) and dried ($Na_2SO_4$). The solvent was evaporated and the crude product was purified by flash column chromatography (MeOH; $CH_2Cl_2$, 2:98) on silica gel to obtain the title compound 9A (1.32 g, 68.7%) as a pale-yellow foam. The compound was used in the subsequent step without any characterization.

Synthesis of (R)-5-methoxy-6-methyl-3-((1-(methyl-$d_3$)pyrrolidin-2-yl)methyl)-1H-indole (R) I-255

A solution of (R)-2-(2-((5-methoxy-6-methyl-1H-indol-3-yl)methyl)pyrrolidin-1-yl)-1-phenylethan-1-one (1.3 g, 3.43 mmol) in dry THF (20 mL) was treated with lithium aluminum deuteride (0.36 g, 8.58 mmol) at 0° C. over a period of 10 mins. The reaction was brought to room temperature, then refluxed for additional 16 hrs. The reaction was brought to room temperature, then cooled to 0° C. and quenched with the sequential addition of water (1.0 mL), 4N NaOH solution (1.0 mL) and water (1.0 mL). The reaction was brought to room temperature and stirred for additional 30 mins. The reaction was filtered and washed with THF (2×50 mL). The combined THF layer was evaporated, and the crude product was purified by column chromatography (2 M $NH_3$ in MeOH:$CH_2Cl_2$, 5:95) on silica gel to obtain the title compound (R) I-255 (0.75 g, 84.6%) as an off-white solid. $^1$H NMR (DMSO-$d_6$): δ10.46 (s, 1H), 7.08 (s, 1H), 6.98 (s, 1H), 6.93 (s, 1H), 3.79 (s, 3H), 3.01-2.95 (m, 2H), 2.49-2.43 (m, 4H), 2.37-2.32 (m, 1H), 2.22 (s, 3H), 2.11-2.07 (m, 1H), 1.76-1.41 (m, 4H); ESI-MS (m/z, %): 262 ($MH^+$, 100).

Example 13E: Synthesis of (R)-6-Fluoro-5-methoxy-3-((1-methylpyrrolidin-2-yl)methyl)-1H-indole (R) I-256

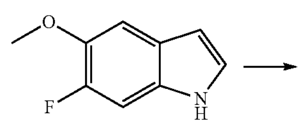

11A

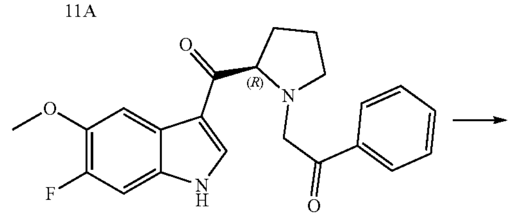

12A

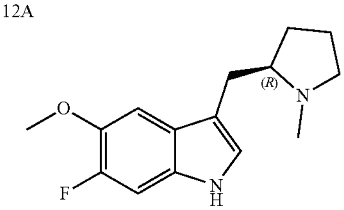

(R) I-256

Synthesis of (R)-2-(2-(6-fluoro-5-methoxy-1H-indole-3-carbonyl)pyrrolidin-1-yl)-1-phenylethan-1-one 12A A solution of 1-(2-oxo-2-phenylethyl)-D-proline (4.6 g, 18.45 mmol) in dry THF (50 mL) was treated with thionyl chloride (2.7 mL, 36.90 mmol) at 0° C. The reaction was brought to room temperature, then refluxed for 2 hrs. The reaction was brought to room temperature, solvent was evaporated, and the crude product was dried under vacuum to obtain the corresponding acid chloride.

A solution of 6-fluoro-5-methoxy-1H-indole (3.0 g, 18.45 mmol) in dry $CH_2Cl_2$ (50 mL) at 5-10° C. was treated with above crude acid chloride in dry $CH_2Cl_2$ (20 mL) and ethyl magnesium bromide (12.9 mL, 38.74 mmol, 3 M in diethyl ether) simultaneously over a period of 5 mins. and stirred at same temperature for a further 15 mins. The reaction was quenched with concentrated HCl (10 mL) followed by water (50 mL) and product was extracted into $CH_2Cl_2$ (2×100 mL). The $CH_2Cl_2$ layer was washed with saturated $NaHCO_3$ solution (50 mL), brine (25 mL) and dried ($Na_2SO_4$). Solvent was evaporated and the crude product was purified by crystallization from a mixture of $CH_2Cl_2$, Hexanes 1:5 to obtain the title compound 12A (5.7 g, 78.8%) as a beige solid. $^1H$ NMR (DMSO-$d_6$): δ 11.96, 11.95 (2s, 1H), 8.40 (dd, 1H, J=3.0, 6.0 Hz), 7.85, 7.84 (2d, 1H, J=6.0 Hz), 7.39-7.34 (m, 3H), 7.15-7.02 (m, 3H), 5.24-4.91 (m, 3H), 3.87 (s, 3H), 3.56-3.49 (m, 2H), 2.40-2.28 (m, 1H), 1.92-1.84 (m, 3H); ESI-MS (m/z, %): 397 ($MH^+$), 419 (M+Na).

Synthesis of (R)-6-fluoro-5-methoxy-3-((1-methylpyrrolidin-2-yl)methyl)-1H-indole (R) I-256

A solution of (R)-2-(2-(6-fluoro-5-methoxy-1H-indole-3-carbonyl)pyrrolidin-1-yl)-1-phenylethan-1-one (2.0 g, 5.04 mmol) in dry THF (30 mL) was treated with lithium aluminum hydride (25.2 mL, 25.22 mmol, 1M solution in THF) at 0° C. over a period of 10 mins. The reaction was brought to room temperature, then refluxed for additional 16 hrs. The reaction was brought to room temperature, then cooled to 0° C. and quenched with the sequential addition of water (1.0 mL), 4N NaOH solution (1.0 mL) and water (1.0 mL). The reaction was brought back to room temperature and stirred for an additional 30 mins. The reaction was filtered and washed with THF (2×50 mL). The combined THF layer was evaporated and the crude product was purified by column chromatography (2 M $NH_3$ in MeOH: $CH_2Cl_2$, 5:95) on silica gel to obtain the title compound (R) I-256 (0.93 g, 70.4%) as an off-white foam. $^1H$ NMR (DMSO-$d_6$): δ 10.69 (s, 1H), 7.16-7.08 (m, 3H), 3.84 (s, 3H), 3.02-2.95 (m, 2H), 2.47-2.42 (m, 1H), 2.38-2.30 (m, 4H), 2.14-2.08 (m, 1H), 1.75-1.41 (m, 4H); ESI-MS (m/z, %): 263 ($MH^+$, 100).

Example 13F: Synthesis of (R)-6-Fluoro-5-methoxy-3-((1-(methyl-$d_3$)pyrrolidin-2-yl)methyl)-1H-indole (R) I-257

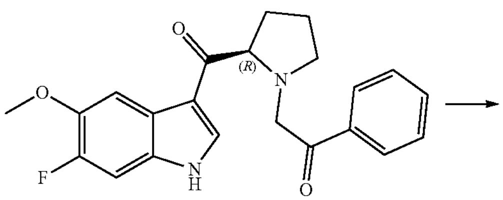

12A

-continued

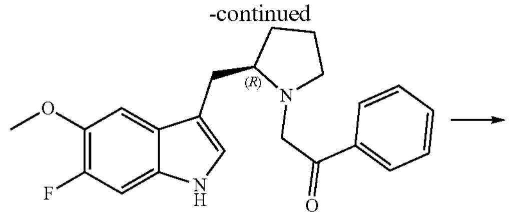

14A

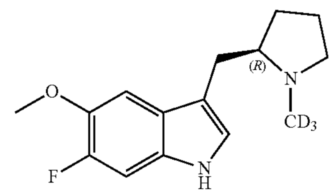

(R) I-257

Synthesis of (R)-2-(2-((6-fluoro-5-methoxy-1H-indol-3-yl)methyl)pyrrolidin-1-yl)-1-phenylethan-1-one 14A A solution of (R)-2-(2-(6-fluoro-5-methoxy-1H-indole-3-carbonyl)pyrrolidin-1-yl)-1-phenylethan-1-one (2.5 g, 6.31 mmol) in dry THF (30 mL) was treated with a solution of lithium borohydride (12.6 mL, 25.22 mmol, 2 M solution in THF) at room temperature over a period of 5 mins. and the reaction was refluxed for additional 4 hrs. The reaction was cooled to 0° C. and quenched with the careful addition of methanol (25 mL) over a period of 15 mins. The reaction was brought to room temperature and stirred for additional 1 hr. The reaction was treated with saturated $NaHCO_3$ solution (30 mL) and product was extracted into ethyl acetate (3×50 mL). Combined ethyl acetate layer was washed with brine (20 mL) and dried ($Na_2SO_4$). The solvent was evaporated and the crude product was purified by flash column chromatography (MeOH; $CH_2Cl_2$, 2:98) on silica gel to obtain the title compound 14A (1.65 g, 68.5%) as a pale-yellow glue. The compound was used in the subsequent step with out any characterization.

Synthesis of (R)-6-fluoro-5-methoxy-3-((1-(methyl-$d_3$)pyrrolidin-2-yl)methyl)-1H-indole (R) I-257

A solution of (R)-2-(2-((6-fluoro-5-methoxy-1H-indol-3-yl)methyl)pyrrolidin-1-yl)-1-phenylethan-1-one (1.65 g, 4.31 mmol) in dry THF (25 mL) was treated with lithium aluminum deuteride (0.45 g, 10.78 mmol) at 0° C. over a period of 10 mins. The reaction was brought to room temperature, then refluxed for additional 16 hrs. The reaction was brought to room temperature, then cooled to 0° C. and quenched with the sequential addition of water (1.0 mL), 4N NaOH solution (1.0 mL) and water (1.0 mL). The reaction was brought back to room temperature and stirred for additional 30 mins. The reaction was filtered and washed with THF (2×50 mL). The combined THF layer was evaporated and the crude product was purified by column chromatography (2 M $NH_3$ in MeOH:$CH_2Cl_2$, 5:95) on silica gel to obtain the title compound (R) I-257 (0.97 g, 85.1%) as an off-white solid. $^1H$ NMR (DMSO-$d_6$): δ10.69 (s, 1H), 7.16-7.08 (m, 3H), 3.84 (s, 3H), 3.01-2.95 (m, 2H), 2.49-2.45 (m, 1H), 2.38-2.29 (m, 1H), 2.14-2.07 (m, 1H), 1.77-1.40 (m, 4H); ESI-MS (m/z, %): 266 ($MH^+$, 100).

B. Biological Testing

Example 14: Human 5-$HT_{2A}$: Functional FLIPR Assay

Objective

The potential excitatory effects of compounds targeting human 5-hydroxytryptamine receptor 2A (5-$HT_{2A}$) under agonist mode was assessed.

1. Materials and Instrumentation

TABLE 40

1.1 Cell line

| Cell line Name | Target | Host cell |
|---|---|---|
| HTR2A&Gα15-HEK293 | 5-$HT_{2A}$ | Flp-In-293 |

TABLE 41

1.2 Materials

| Regents | Vendor | Cat# |
|---|---|---|
| DMEM | Gibco | 10569-010 |
| Dialyzed FBS | BIOSUN | BS-0005-500 |
| Penicillin-Streptomycin | Invitrogen | 15140 |
| Hygromycin B | Invivogen | Ant-hg-5 |
| Tetracycline hydrochloride | Abcam | ab141223 |
| TrypLE ™Express | Gibco | 12604-013 |
| DPBS | Gibco | 14190250 |
| DMSO | Millipore | 1029312500 |
| Probenecid | Sigma | P8761 |
| FLIPR Calcium 6 Assay Kit | Molecular Device | R8191 |
| HEPES | Invitrogen | 15630 |
| Hank's Buffered Saline Solution | Invitrogen | 14025 |
| Serotonin HCl | Selleck | S4244 |

TABLE 42

1.3 Instrumentation and consumables

| Item | Supplier | Cat# |
|---|---|---|
| Fluorometric Imaging Plate Reader (FLIPR) | Molecular Device | Tetra |
| Countess Automated Cell Counter | Invitrogen | Countess |
| Cell Counting Chamber Slides | Invitrogen | C10312 |
| STERI-CYCLE CO2 Incubator | Thermo | 371 |
| 1300 Series Class II Biological Safety Cabinet | Thermo | 1389 |
| Table-type Large Capacity Low Speed Centrifuge | Cence | L550 |
| Centrifuge | Eppendorf | 5702 |
| Echo | Labcyte | 550 |
| Echo | Labcyte | 655 |
| Electro-thermal incubator | Shanghai Yiheng | DHP-9031 |
| plate shaker | IKA | MS3 digital |
| Water Purification System | ULUPURE | UPH-III-20T |
| Versatile and Universal pH and Conductivity Meters | Mettler Toledo | S220 |
| 384-Well plate | Corning | 3764 |
| 384-Well LDV Clear microplate | LABCYTE | LP-0200 |
| 384-Well Polypropylene microplate | LABCYTE | PP-0200 |
| 384-well compound plate | Corning | 3657 |
| T25 cell culture flask | Corning | 430639 |

TABLE 42-continued 1.3 Instrumentation and consumables

| Item | Supplier | Cat# |
|---|---|---|
| 50 mL Polypropylene Centrifuge Tube | JET | CFT011500 |
| 15 mL Polypropylene Centrifuge Tube | JET | CFT011150 |

2. Experimental Methods 2.1 Cell Culture

HTR2A&Gα15-HEK293 cells were cultured in DMEM medium containing 10% dialyzed FBS and 1× penicillin-streptomycin, 100 μg/mL Hygromycin B and 300 μg/mL G418. The cells were passaged about three times a week, maintained between ~30% to ~90% confluence.

2.2 Cell Plating

1. The cell culture medium (DMEM medium containing 10% dialyzed FBS and 1× penicillin-streptomycin, 100 μg/mL Hygromycin B and 300 μg/mL G418), TrypLE™ Express and DPBS to room temperature was warmed in advance.

2. For induction, 1 μg/ml tetracycline (final concentration) was added to cell culture medium and incubated for 48 hours prior to seeding cells into plate at 37° C., 5% (v/v) CO2. The cell culture medium was removed from flask. Cells were washed with DP BS.

3. 2 mL TrypLE™ Express was added to the flask, mixed well by gentle shaking and cells were incubated at 37° C. for a few minutes.

4. The cells were checked for morphological change under microscope, the digestion was stopped by adding 4 mL cell culture medium to the flask when most of cells turned to round.

5. The cell suspension was transferred into a 15 mL centrifuge tube, and then centrifuged at 1,200 rpm for 5 minutes.

6.

The supernatant was removed. The cell pellet was resuspended with 2 ml cell culture medium.

7. The cell density was counted using cell counter. Only cells with >85% viability were used for the assay.

8. Cells were diluted to $6.67\times10^5$/mL with cell culture medium.

9. 30 μL/well cell suspensions added into a 384-well cell plate (The cell density was 20,000 cells/well).

10. The cell plate was incubated overnight at 37° C., 5% (v/v) $CO_2$.

2.3 Cell Handling

1. On the day of experiments, culture medium was removed from the cell plate.

2. 10 μL of assay buffer (20 mM HEPES, in 1×HBSS, pH 7.4) was added to each well of the cell plate.

3. 2× dye solution was prepared following the manual of the FLIPR® Calcium 6 Assay Kit:

i. The dye was diluted with assay buffer.

ii. Probenecid was added to the final concentration of 5 mM.

iii. Vortexed vigorously for 1-2 minutes.

4. 10 μL of 2× dye solution was added to each well of the cell plate

5. The cell plate was placed on plate shaker, followed by shaking at 600 rpm for 2 minutes.

6. The plate was incubated at 37° C. for 2 hours followed by an additional 15-minute incubation at 25° C.

2.4 Prepare 3× Compound.

1. Serotonin HCl was prepared to the concentration of 10 mM with DMSO.

2. The test compounds were prepared to the concentration of 10 mM with DMSO.

3. The compounds were added to a 384-well compound source plate.

4. 3-folds serial dilutions were performed with DMSO.

5. 90 nL/well of serial diluted compounds was transferred from source plate to a 384-well compound plate by using an Echo.

6. 30 μL/well of assay buffer (20 mM HEPES in 1×HBSS, pH 7.4) was added to the compound plate.

7. The plate was mixed on-plate shaker for 2 minutes.

2.5 FLIPR Assay:

1. After the cells were incubated with dye solution, the cell plate, compound plate containing 3× compounds and FLIPR tips were placed into FLIPR.

2. 10 μL of 3× compounds transferred from the compound plate to the cell plate by FLIPR.

3. The plate was read for 160 sec with 1 sec interval and the data of agonist mode was obtained.

3. Data Analysis

1. The normalized fluorescence reading (RFU) was calculated as shown below, wherein $F_{max}$ and $F_{min}$ stand for maximum and minimum of calcium signal during defined time window:

$$RFU=F_{max}-F_{min}$$

2. $EC_{50}$ by fitting RFU against log of compound concentrations with Hill equation was calculated using XLfit.

Results and Discussion

The results of potential competition binding properties of the exemplary compounds of the disclosure targeting the human 5-hydroxytryptamine receptor 2A (5-$HT_{2A}$) are summarized in Table 43. The results of exemplary compounds of the disclosure are presented as $EC_{50}$ is provided in Table 43.

TABLE 43

Effect of exemplary compounds of Formula (I) using FLIPR functional assay on human 5-$HT_{2A}$ receptor

| Example | h5-$HT_{2A}$, $EC_{50}$ [nM] | RFU@10 μM [(1)] |
|---|---|---|
| 5-MeO-DMT | 63 | 5,667 |
| DMT | 163 | 3,493 |
| (R) I-98 | 13 | 8,298 |
| (R) I-244 | 50 | 7,945 |
| (R) I-245 | 120 | 8,322 |
| Rac (R) I-248 | 54 | 8,240 |

[(1)] Curve fitting with activation (%) @ 10 mM with RFU

II. Results and Discussion

Exemplary compounds of Formula (I) were evaluated using FLIPR functional assay on human 5-$HT_{2A}$ receptor. $EC_{50}$ (nM) concentrations are illustrated in Table 43. This assay confirms that compounds of the disclosure are effective agonists of the target human 5-$HT_{2A}$ receptors.

Example 15: Human 5-$HT_{2A}$: Radioligand Binding Assay

Objective

The objective of this study was to evaluate the binding properties of exemplary compounds of Formula (I) on 5-hydroxytryptamine receptor 2A (5-$HT_{2A}$).

1. Materials and Instrumentation

TABLE 44

1.1 Regents

| Items | Vendor | Cat# |
|---|---|---|
| Ketanserin Hydrochloride, [Ethylene-3H]— | PerkinElmer | NET791250UC |
| Ketanserin | MedChemExpress | HY-10562 |
| Bovine Serum Albumin (BSA) | Sigma | A1933 |
| Calcium chloride ($CaCl_2$) | Sigma | C5670 |
| Tris(hydroxymethyl)aminomethane (Tris) | Alfa Aesar | A18494 |
| Polyethylenimine, branched (PEI) | Sigma | 408727 |

TABLE 45

1.2 Instrumentation and Consumables

| Item | Supplier | Cat# |
|---|---|---|
| Microbeta$^2$ Microplate Counter | PerkinElmer | 2450-0060 |
| UniFilter-96 GF/B | PerkinElmer | 6005177 |
| TopSeal | Biotss | SF-800 |
| MicroBeta Filtermate-96 | PerkinElmer | D961962 |
| Seven Compact pH meter | Mettler Toledo | S220 |
| Ultrapure Water Meter | Sichuan Ulupure | UPH-III-20T |
| Benchtop Centrifuge | Hunan Xiangyi | L550 |
| Microplate Shaker | Allsheng | MX100-4A |
| 384-Well Polypropylene Microplate | Labcyte | PP-0200 |
| 96 Round Well Plate | Corning | 3799 |
| 96 Round Deep Well Plate | Axygen | P-DW-11-C |
| Echo | LABCYTE | 550 |

2. Experimental Methods

1. The assay buffer was prepared following Table 46 below.

TABLE 46

| Reagent | Concentration |
|---|---|
| Tris | 50 mM |
| $CaCl_2$ | 4 mM |
| BSA | 0.1% (w/v) |

Adjust pH to 7.4 followed by 0.2 μM sterile filtration 2. 8 doses of reference and test compounds starting from 10 mM stock solution as required was prepared by 5-fold serial dilutions with 100% (v/v) DMSO.

3. UniFilter-96 GF/B plate was pretreated:

i. 50 μl/well of 0.5% (v/v) PEI was added to UniFilter-96 GF/C plates. The plates were sealed and incubated at 4° C. for 3 hrs.

ii. After incubation, the plates were washed 3 times with ice-cold wash buffer (50 mM Tris, pH 7.4).

4. The assay plate was prepared:

i. Cell membrane was diluted with assay buffer and 330 μl/well was added to 96 round deep well plates to reach a concentration of 20 μg/well.

ii. 8 concentrations of reference or test compounds were prepared and 110 μl/well was added to 96 round deep well plates.

iii. [3H]-ketanserin was diluted with assay buffer to 5 nM (5× final concentration) and 110 μl/well was added to 96 round deep well plates.

5. The plate was centrifuged at 1000 rpm for 30 secs and then agitated at 600 rpm at room temperature for 5 mins.

6. The plates were sealed and the plate incubated at 27° C. for 90 min.

7. The incubation was stopped by vacuum filtration onto GF/B filter plates followed by 4 times washing with ice-cold wash buffer (50 mM Tris, pH7.4).

8. The plates were dried at 37° C. for 45 min.

9. The filter plates were sealed and 40 μl/well of scintillation cocktail was added.

10. The plate was read by using a Microbeta$^2$ microplate counter.

3. Data Analysis

1. For reference and test compounds, the results were expressed as % Inhibition, using the normalization equation: $N=100-100\times(U-C2)/(C_1-C_2)$, where U is the unknown value, C1 is the average of high controls, and C2 is the average of low controls.

2. The $IC_{50}$ was determined by fitting percentage of inhibition as a function of compound concentrations with Hill equation using XLfit.

Results and Discussion

The results of potential competition binding properties of the exemplary compound of the disclosure targeting the human 5-hydroxytryptamine receptor 2A ($5\text{-HT}_{2A}$) are summarized in Table 47. The results of exemplary compounds of the disclosure are presented as $IC_{50}$ provided in Table 47.

TABLE 47

Effect of exemplary compounds of Formula (I) using Radioligand binding assay on human 5- receptor

| Compound ID | h5-$HT_{2A}$, $IC_{50}$ [nM] |
|---|---|
| 5-MeO-DMT | 603 |
| DMT | 954 |
| (R) I-98 | 350 |
| (R) I-244 | 129 |
| (R) I-245 | 225 |
| rac (R) I-248 | 310 |

II. Results and Discussion

Exemplary compounds of Formula (I) were evaluated using radioligand binding assay on human $5\text{-HT}_{2A}$ receptor. $IC_{50}$ (nM) concentrations are illustrated in Table 47. This assay confirms that exemplary compounds of the disclosure are effective ligands of the target human $5\text{-HT}_{2A}$ receptors.

Example 15A: Human-$5HT_{2A}$-β-Arrestin Assay

Protocol

Compound potency ($EC_{50}$) and efficacy (Max response) against the human $5\text{-HT}_{2A}$ receptor in stably transfected U2OS cells was determined in a GPCR cell based β-arrestin reporter assay.

Cells were seeded in a total volume of 20 μL into white walled, 384-well microplates and incubated at 37° C. overnight before analysis. For agonist determination, cells were incubated with sample to induce response. Intermediate dilution of sample stocks was performed to generate 5× samples in assay buffer. 5 μL of 5× samples were added to cells and incubated at 37° C. for 120 mins. The final assay vehicle concentration was 1%. The results are expressed as percent efficacy relative to the maximum response of the control ligand (serotonin) in Table 48.

TABLE 48

Effect of exemplary compounds of Formula (I) using a β-arrestin reporter assay on human $5\text{-HT}_{2A}$ receptor

| Compound ID | $EC_{50}$ (μM) | $E_{max}$ (% of serotonin) |
|---|---|---|
| DMT | 0.1136 | 38.86 |
| 5MeO-DMT | 0.02945 | 72.41 |
| (R) I-98 | 0.025792 | 81.67 |
| (R) I-244 | 0.0067093 | 79.58 |
| (R) I-245 | 0.028375 | 82.18 |
| Cis (R) I-248 | 0.11174 | 84.4 |

Example 16: Human $5\text{-HT}_{1A}$: Functional FLIPR Assay

1. Objective

The potential excitatory effects of compounds targeting on 5-hydroxytryptamine receptor 1A ($5\text{-HT}_{1A}$) under agonist mode was assessed.

2. Materials and Instrumentation

TABLE 49

2.1 Cell line

| Cell line Name | Target | Host cell |
|---|---|---|
| HTR1A&Gα15-CHO | $5\text{-HT}_{1A}$ | Flp-in CHO |

TABLE 50

2.2 Materials

| Regents | Vendor | Cat# |
|---|---|---|
| DMEM/F12 | Gibco | 11330057 |
| Dialyzed FBS | BIOSUN | BS-0005-500 |
| Penicillin-Streptomycin | Invitrogen | 15140 |
| Hygromycin B | Invivogen | Ant-hg-5 |
| TrypLE ™Express | Gibco | 12604-013 |
| DPBS | Gibco | 14190250 |
| DMSO | Millipore | 1029312500 |

TABLE 50-continued

| 2.2 Materials | | |
|---|---|---|
| Regents | Vendor | Cat# |
| Probenecid | Sigma | P8761 |
| FLIPR Calcium 6 Assay Kit | Molecular Device | R8191 |
| HEPES | Invitrogen | 15630 |
| Hank's Buffered Saline Solution | Invitrogen | 14025 |
| Serotonin HCl | Selleck | S4244 |

TABLE 51

| 2.3 Instrumentation and consumables | | |
|---|---|---|
| Item | Supplier | Cat# |
| Fluorometric Imaging Plate Reader (FLIPR) | Molecular Device | Tetra |
| Countess Automated Cell Counter | Invitrogen | Countess |
| Cell Counting Chamber Slides | Invitrogen | C10312 |
| STERI-CYCLE CO2 Incubator | Thermo | 371 |
| 1300 Series Class II Biological Safety Cabinet | Thermo | 1389 |
| Table-type Large Capacity Low Speed Centrifuge | Cence | L550 |
| Centrifuge | Eppendorf | 5702 |
| Echo | Labcyte | 550 |
| Echo | Labcyte | 655 |
| Electro-thermal incubator | Shanghai Yiheng | DHP-9031 |
| plate shaker | IKA | MS 3 digital |
| Water Purification System | ULUPURE | UPH-III-20T |
| Versatile and Universal pH and Conductivity Meters | Mettler Toledo | S220 |
| 384-Well plate | Corning | 3764 |
| 384-Well LDV Clear microplate | LABCYTE | LP-0200 |
| 384-Well Polypropylene microplate | LABCYTE | PP-0200 |
| 384-well compound plate | Corning | 3657 |
| T25 cell culture flask | Corning | 430639 |
| 50 mL Polypropylene Centrifuge Tube | JET | CFT011500 |
| 15 mL Polypropylene Centrifuge Tube | JET | CFT011150 |

3. Experimental Methods 3.1 Cell Culture

HTR1A&Gα15-CHO cells were cultured in DMEM/F12 medium containing 10% dialyzed FBS, 1× penicillin-streptomycin and 600 μg/mL Hygromycin B. The cells were passaged about three times a week, maintained between ~30% to ~90% confluence.

3.2 Cell Plating

1. The cell culture medium (DME M/F12 medium containing 10% dialyzed FBS, 1× penicillin-streptomycin and 600 μg/mL Hygromycin B), TrypLE™ Express and DPBS was warmed to R.T. in advance.

2. The cell culture medium was removed from flask. Washed cells with DPBS.

3. 1 mL TrypLE™ Express was added to the flask, mixed well by gentle shaking and cells were incubated at 37° C. for a few minutes.

4. The cells were checked for morphological change under microscope, the digestion was stopped by adding 2 mL cell culture medium to the flask when most of cells turned to round.

5. The cell suspension was transferred into a 15 mL centrifuge tube, and then centrifuged at 1,200 rpm for 5 minutes.

6. The supernatant was removed. The cell pellets were resuspended with 2 mL cell culture medium.

7. The cell density was counted using cell counter. Only cells with >85% viability were used for the assay.

8. Cells were diluted to $4\times10^5$/mL with cell culture medium.

9. 30 μL/well cell suspensions were added into a 384-well cell plate (The cell density was 12,000 cells/well).

10. The cell plate was incubated overnight at 37° C., 5% (v/v) $CO_2$.

3.3 Cell Handling

1. On the day of experiments, culture medium was removed from the cell plate.

2. 10 μL of assay buffer (20 mM HEPES, in 1×HBSS, pH 7.4) was added to each well of the cell plate.

3. 2× dye solution was prepared following the manufacture's instruction of the FLIPR® Calcium 6 assay kit:

i. The dye was diluted with assay buffer.

ii. probenecid was added to the final concentration of 5 mM.

iii. Vortexed vigorously for 1-2 minutes, adjust pH to 7.4.

4. 10 μL of 2× dye solution was added to each well of the cell plate.

5. The cell plate was placed on plate shaker, followed by shaking at 600 rpm for 2 minutes.

6. The plate was incubated at 37° C. for 2 hours followed by an additional 15-minute incubation at 25° C.

3.4 Prepare 3× Compounds.

1. Serotonin was prepared to the concentration of 10 mM with DMSO, 3-folds serial dilutions were performed with DMSO.

2. Prepare the test compound to the concentration of 10 mM with DMSO, preform 3-folds serial dilutions with DMSO.

3. The compounds were added to a 384-well compound source plate.

4. 90 nL/well of serial diluted compounds were transferred from source plate to a 384-well compound plate by using an Echo.

5. 30 μL/well of assay buffer was added to the compound plate.

6. The plate was mixed on-plate shaker for 2 minutes.

3.5 FLIPR Assay

1. After the cells were incubated with dye solution, the cell plate, compound plate containing 3× compounds and FLIPR tips were placed into FLIPR.

2. 10 μL of 3× compounds were transferred from the compound plate to the cell plate by FLIPR.

3. The plate was read for 160 sec with 1 sec interval to obtain the data of agonist mode.

4. Data Analysis

1. The normalized fluorescence reading (RFU) was calculated as shown below, wherein $F_{max}$ and $F_{min}$ stand for maximum and minimum of calcium signal during defined time window:

$$RFU = F_{max} - F_{min}$$

2. $EC_{50}$ was calculated by fitting RFU against log of compound concentrations with Hill equation using XLfit.

Results and Discussion

The results of potential competition binding properties of the exemplary compounds of the disclosure targeting the human 5-hydroxytryptamine receptor 1A (5-$HT_{1A}$) are summarized in Table 52. The results of exemplary compounds of the disclosure are presented as $EC_{50}$ provided in Table 52.

TABLE 52

Effect of exemplary compounds of Formula (I) using FLIPR functional assay on human 5-$HT_{1A}$ receptor

| Compound ID | h5-$HT_{1A}$, $EC_{50}$ [nM] | RFU@10 μM [(1)] |
|---|---|---|
| 5-MeO-DMT | 1,066 | 3,891 |
| DMT | ND[(2)] | 204 |
| (R) I-98 | 3,171 | 1,666 |
| (R) I-244 | ND | 616 |
| (R) I-245 | ND | 899 |
| rac (R) I-248 | ND | 601 |

[(1)] Curve fitting with activation (%) @ 10 mM with RFU (2) Not detected

Exemplary compounds of Formula (I) were evaluated using functional FLIPR assay on human 5-$HT_{1A}$ receptor. $EC_{50}$ (nM) concentrations are illustrated in Table 52. This assay confirms that compounds of the disclosure are functionally active at the target human 5-$HT_{1A}$ receptors.

Example 17: Human 5-$HT_{1A}$: Radioligand Binding Assay

1. Objective

The objective of this study was to evaluate the binding properties of test compounds on 5-hydroxytryptamine receptor 1A (5-$HT_{1A}$).

2. Materials and Instrumentation

TABLE 53

2.1 Regents

| Items | Vendor | Cat# |
|---|---|---|
| [3H]-8-Hydroxy-DPAT | PE | NET929250UC |
| Serotonin HCl | Selleck | S4244 |
| Bovine Serum Albumin (BSA) | Sigma | A1933 |
| Calcium chloride (CaCl2) | Sigma | C5670 |
| $MgCl_2$ | Sigma | M1028 |
| Tris(hydroxymethyl)aminomethane (Tris) | Alfa Aesar | A18494 |
| Polyethylenimine, branched (PEI) | Sigma | 408727 |

TABLE 54

2.2 Instrumentation and Consumables

| Item | Supplier | Cat# |
|---|---|---|
| Microbeta[2] Microplate Counter | PerkinElmer | 2450-0060 |
| UniFilter-96 GF/B | PerkinElmer | 6005177 |
| TopSeal | Biotss | SF-800 |
| MicroBeta Filtermate-96 | PerkinElmer | D961962 |
| Seven Compact pH meter | Mettler Toledo | S220 |
| Ultrapure Water Meter | Sichuan Ulupure | UPH-III-20T |
| Benchtop Centrifuge | Hunan Xiangyi | L550 |
| Microplate Shaker | Allsheng | MX100-4A |
| 384-Well Polypropylene Microplate | Labcyte | PP-0200 |
| 96 Round Well Plate | Corning | 3799 |
| 96 Round Deep Well Plate | Axygen | P-DW-11-C |
| Echo | LABCYTE | 550 |

3 Experimental Methods

1. The assay buffer was prepared following Table 55 below.

TABLE 55

| Reagent | Concentration |
|---|---|
| Tris | 25 mM |
| $MgCl_2$ | 10 mM |
| $CaCl_2$ | 1 mM |
| BSA | 0.5% (w/v) |

Adjust pH to 7.4 followed by 0.2 μM sterile filtration 2. 8 doses of reference and test compounds were prepared starting from 10 mM stock solution as required by 5-fold serial dilutions with 100% (v/v) DMSO.

3. UniFilter-96 GF/B plate was pretreated:

i. 50 μL/well of 0.5% (v/v) PEI was added to UniFilter-96 GF/B plates. The plates were sealed and incubated at 4° C. for 3 hrs.

ii. After incubation, the plates were washed 3 times with ice-cold wash buffer (50 mM Tris, pH7.4).

4. Assay plate was prepared:

i. Cell membrane was diluted with assay buffer and 100 μl/well was added to 96 round well plates to reach a concentration of 20 μg/well.

ii. 8 concentrations of reference or test compounds were prepared and 50 μl/well was added to 96 round deep well plates.

iii. [3H]-8-Hydroxy-DPAT was diluted with assay buffer to 2 nM (4× final concentration) and 50 μL/well was added to 96 round well plates.

5. The plate was centrifuged at 1000 rpm for 30 secs and then agitated at 600 rpm at room temperature for 5 min.

6. The plates were sealed and the plate was incubated at 27° C. for 90 min.

7. The incubation was stopped by vacuum filtration onto GF/B filter plates followed by 4 times washing with ice-cold wash buffer (50 mM Tris, pH7.4).

8. The plates were dried at 37° C. for 45 min.

9. The filter plates were sealed and 40 μl/well of scintillation cocktail was added.

10. The plate was read by using a Microbeta[2] microplate counter.

4 Data Analysis

1. For reference and test compounds, the results were expressed as % Inhibition, using the normalization equation: $N=100-100\times(U-C2)/(C_1-C_2)$, where U is the unknown value, C1 is the average of high controls, and C2 is the average of low controls.

2. The $IC_{50}$ was determined by fitting percentage of inhibition as a binding of compound concentrations with Hill equation using XLfit.

Results and Discussion

The results of potential competition binding properties of the exemplary compounds presented as $IC_{50}$ of the disclosure targeting the human 5-hydroxytryptamine receptor (5-$HT_{1A}$) are summarized in Table 56.

TABLE 56

| Effect of exemplary compounds of Formula (I) using Radioligand binding assay on human 5-$HT_{1A}$ receptor | |
|---|---|
| Compound ID | h5-$HT_{1A}$, $IC_{50}$ [nM] |
| 5-MeO-DMT | 6 |
| DMT | 689 |
| (R) I-98 | 5 |
| (R) I-244 | 15 |
| (R ) I-245 | 5 |
| rac (R) I-248 | 8.3 |

Results and Discussion

Exemplary compounds of Formula (I), thereof were evaluated using radioligand binding assay on human 5-$HT_{1A}$ receptor. $IC_{50}$ (nM) concentrations are illustrated in Table 56. This assay confirms that compounds of Formula (I) of the disclosure are effective ligands of the target human 5-$HT_{1A}$ receptors.

Example 17A: Human 5-$HT_{2B}$: Radioligand Binding Assay

The objective of this study is to evaluate the binding properties of test compounds on 5-$HT_{2B}$.

| Materials and Instruments (Table 57) | | |
|---|---|---|
| Materials | Vendor | Cat# |
| [3H]-LSD | PerkinElmer | NET638250UC |
| Yohimbine | MedChemExpress | HY-N0127 |
| Bovine Serum Albumin (BSA) | Sigma | A1933 |
| Calcium chloride ($CaCl_2$) | Sigma | C5670 |
| Tris(hydroxymethyl)aminomethane (Tris) | Alfa Aesar | A18494 |
| Polyethylenimine, branched (PEI) | Sigma | 408727 |

| Instrumentation and Consumables (Table 58) | | |
|---|---|---|
| Item | Supplier | Cat# |
| Microbeta2 Microplate Counter | PerkinElmer | 2450-0060 |
| UniFilter-96 G F/B | PerkinElmer | 6005177 |
| TopSeal | Biotss | SF-800 |
| MicroBeta Filtermate-96 | PerkinElmer | D961962 |
| Seven Compact pH meter | Mettler Toledo | S 220 |
| Ultrapure Water Meter | Sichuan Ulupure | UPH-III-20T |
| Benchtop Centrifuge | Hunan Xiangyi | L550 |
| Microplate Shaker | Allsheng | MX100-4A |
| 384-Well Polypropylene Microplate | Labcyte | PP-0200 |
| 96 Round Well Plate | Corning | 3799 |
| 96 Round Deep Well Plate | Axygen | P-DW-11-C |
| Echo | LABCYTE | 550 |

Experimental Methods

1) The assay buffer was prepared following Table 59 below.

TABLE 59

| Reagent | Concentration |
|---|---|
| Tris | 50 mM |
| $CaCl_2$ | 4 mM |
| BSA | 0.1% (w/v) |

Adjust pH to 7.4 followed by 0.2 μM sterile filtration

2) Eight doses of reference and test compounds starting from 10 mM stock solution as requested by 5-fold serial dilutions with 100% (v/v) DMSO.

3) UniFilter-96 GF/B plate was pretreated:

a. 50 μL/well of 0.5% (v/v) PEI to UniFilter-96 GF/B plates. The plates were sealed and incubate at 4° C. for 3 hrs.

b. After incubation, the plates were washed three times with ice-cold wash buffer (50 mM Tris, pH7.4).

4) Assay plate preparation:

a. Cell membrane was diluted with assay buffer and 330 μL/well added to 96 round deep well plates to reach a concentration of 1 unit/well.

b. Eight concentrations of reference or test compounds were prepared and 110 μL/well added to 96 round deep well plates.

c. [3H]-LSD was diluted with assay buffer to 5 nM (5× final concentration) and 110 μL/well was added to 96 round deep well plates.

5) The plate was centrifuged at 1000 rpm for 30 secs and then agitated at 600 rpm at room temperature for 5 min.

6) The plates were sealed and incubated at 37° C. for 90 mins.

7) The incubation was stopped by vacuum filtration onto GF/B filter plates followed by washing four times with ice-cold wash buffer (50 mM Tris, pH7.4).

8) The plates were dried at 37° C. for 45 mins.

9) The filter plates were sealed and 40 μL/well of scintillation cocktail was added.

10) The plate was read using a $Microbeta^2$ microplate counter.

Data Analysis

For reference and test compounds, the results are expressed as % Inhibition, using the normalization equation: $N=100-100\times(U-C2)/(C_1-C_2)$, where U is the unknown value, C1 is the average of the high controls, and C2 is the average of the low controls. The $IC_{50}$ is determined by fitting percentage of inhibition as a function of compound concentrations with Hill equation.

TABLE 60

| Compound ID | 5-$HT_{2B}$, $IC_{50}$ [nM] | 5-$HT_{2B}$, Ki [nM] |
|---|---|---|
| 5-MeO-DMT | 248.92 | 128.79 |
| DMT | 423.14 | 218.92 |
| (R) I-98 | 45.56 | 23.57 |
| (R) I-244 | 21.44 | 11.09 |
| rac (R) 1-248 | 46.30 | 23.95 |

Example 17B: Human-5$HT_{1A}$-CAMP Assay

Protocol

Compound potency ($EC_{50}$) and efficacy (Max response) against the human 5-$HT_{1A}$ receptor in stably transfected CHO-K1 cells were determined in a GPCR cell-based CAMP assay.

Cells were seeded in a total volume of 20 μL into white walled, 384-well microplates and incubated at 37° C. overnight before analysis. Prior to testing, cell plating media was exchanged with 10 μL of Assay buffer (HBSS+10 mM HEPES). Briefly, intermediate dilution of sample stocks was performed to generate 4× samples in assay buffer. 5 μL of 4× samples+5 μL of 4× forskolin was added to cells and incubated at 37° C. for 30 mins. The final assay vehicle concentration was 1%. The results are expressed as percent efficacy relative to the maximum response of the control ligand (serotonin) in Table 61.

TABLE 61

Effect of exemplary compounds of Formula (I) using CAMP functional assay on human 5-HT1A receptor

| Compound ID | $EC_{50}$ (μM) | $E_{max}$ (% of serotonin) |
|---|---|---|
| DMT | 0.97437 | 87.1 |
| 5MeO-DMT | 0.012699 | 99.98 |
| (R) I-98 | 0.040309 | 96.42 |
| (R) 1-244 | 0.0063038 | 99.01 |
| (R) 1-245 | 0.01948 | 99.14 |
| Cis (R) 1-248 | 0.052683 | 96.76 |

Example 17C: Human-5HT$_{2B}$ FLIPR Assay

Protocol

Compound potency ($EC_{50}$) and efficacy (Max response) against the human 5-HT$_{2B}$ receptor in stably transfected HE K293 cells was determined in a calcium mobilization-based assay.

Cells were seeded in a total volume of 20 μL into white walled, 384-well microplates and incubated at 37° C. overnight. Prior to testing, cell plating media was exchanged with 20 μL of Dye Loading buffer (HBSS+20 mM HEPES containing 1× Dye, 1× Additive A, and 2.5 mM Probenecid). Plates were incubated at 37° C. for 45 mins followed by 15 mins at room temperature.

10 μL of assay buffer (HBSS+20 mM HEPES) was added to cells. Intermediate dilution of sample stocks was performed to generate 4× samples in assay buffer. Assay plates and compound plates were loaded into the FLIPR instrument. 10 μL of samples were added using the FLIPR onboard robotics after 5 secs of starting calcium measurement. The final assay vehicle concentration was 1%. The results are expressed as percent efficacy relative to the maximum response of the control ligand (serotonin) in Table 62.

TABLE 62

Effect of exemplary compounds of Formula (I) using FLIPR functional assay on human-5-HT2B receptor

| Compound ID | $EC_{50}$ (μM) | $E_{max}$ (% of serotonin) |
|---|---|---|
| DMT | >10 | 13.4 |
| 5MeO-DMT | 0.015452 | 28.88 |
| (R) I-98 | 0.0028832 | 52.7 |
| (R) I-244 | 0.0024999 | 92.75 |
| (R) I-245 | 0.011171 | 53.91 |
| Cis (R) I-248 | 0.02494 | 69.85 |

Example 17D: Human-5HT$_{2C}$ FLIPR Assay

Protocol

Compound potency ($EC_{50}$) and efficacy (Max response) against the human 5-HT$_{2B}$ receptor in stably transfected U2OS cells was determined in a calcium mobilization-based assay.

Cells were seeded in a total volume of 20 μL into white walled, 384-well microplates and incubated at 37° C. overnight. Prior to testing, cell plating media was exchanged with 20 μL of Dye Loading buffer (HBSS+20 mM HEPES containing 1× Dye, 1× Additive A, and 2.5 mM Probenecid). Plates were incubated at 37° C. for 45 mins followed by 15 mins at room temperature.

10 μL of assay buffer (HBSS+20 mM HEPES) was added to the cells. Intermediate dilution of sample stocks was performed to generate 4× samples in assay buffer. Assay plates and compound plates were loaded into the FLIPR instrument 10 μL of samples were added using the FLIPR onboard robotics after 5 seconds of starting calcium measurement. The final assay vehicle concentration was 1%. The results are expressed as percent efficacy relative to the maximum response of the control ligand (serotonin) in Table 63.

TABLE 63

Effect of exemplary compounds of Formula (I) using FLIP R functional assay on human 5-HT2c receptor

| Compound ID | $EC_{50}$ (μM) | $E_{max}$ (% of serotonin) |
|---|---|---|
| DMT | 0.01112 | 94.56 |
| 5MeO-DMT | 0.0027312 | 95.42 |
| (R) I-98 | 0.0065076 | 95.23 |
| (R) I-244 | 0.0025278 | 87.27 |
| (R) I-245 | 0.042251 | 83.29 |
| Cis (R) I-248 | 0.15081 | 89.99 |

Example 17E: Human-5HT$_{2B}$ Positive Allosteric Modulator (PAM) Assay

Protocol

Compound potency ($EC_{50}$) and efficacy (Max response) against the human 5-HT$_{2B}$ receptor in stably transfected HEK293 cells was determined in a GPCR cell-based assay.

For Positive Allosteric Modulator determination, cells were pre-incubated with sample followed by EC20 addition. Intermediate dilution of sample stocks was performed to generate 5× samples in assay buffer. 5 μL of 5× samples were added to cells and incubated at 37° C. for 10 mins. 5 μL of agonist at 6×EC20 concentration was added and the cells were incubated at 37° C. for 120 mins. The final assay vehicle concentration was 1%. The results are expressed as percent efficacy relative to the maximum response of the control ligand (serotonin) in Table 64.

TABLE 64

Effect of exemplary compounds of Formula (I) using PAM functional assay on human 5-HT 2B receptor

| Compound ID | $EC_{50}$ (μM) | $E_{max}$ (% of serotonin) |
|---|---|---|
| DMT | >10 | 0 |
| 5MeO-DMT | >10 | 0 |
| (R) I-98 | >10 | 0 |
| (R) I-244 | 0.097371 | 26.89 |
| (R) I-245 | >3.3333 | 0 |
| Cis (R) I-248 | >10 | 7.97 |

Example 18: Psychedelic-Like Effect of Exemplary Compounds of Formula (I)

The effect of different doses of exemplary compounds of Formula (I) were evaluated on head-twitch response (HTR) as a behavior-based model of psychedelic activity.

Mouse Head Twitch Response (HTR) Test:

Protocols

Adult C57BL/6J mice (body weight range 20-30 g) were each placed into an open-top test cage made of transparent plastic for 20-30 min of habituation prior to testing. Habituation and testing were both conducted under low light conditions (~100 lux). Mice received a subcutaneous (SC) injection of either vehicle, positive control substance (e.g., 2,5-dimethoxy-4-iodoamphetamine (DOI)), or test compound at appropriate doses and volumes (10 mL/kg). Immediately post-treatment each mouse was placed back in its respective test cage. The cages were placed at approximately 50 cm from each other on a white, adjustable height table/flat surface so that the experimenter could easily monitor fine behaviors of both mice within the testing environment. An opaque divider was placed between the cages to prevent animals from observing each other. Immediately after placing the mice back into the test cages, the experimenter sat directly in front of the two containers, and recorded in real time the number of head twitch responses (HTR, defined as rapid side-to-side rotational shaking of the head) performed by each mouse for 20 min, subdivided in 5 min intervals with the use of a silent timer. To ensure scoring accuracy and consistency, one experienced experimenter performed HTR recording for all mice included in a study. While mice were subjected to HTR testing, another mouse pair underwent habituation in a separate set of test cages, so that at the end of the HTR scoring period new animals were ready to undergo substance administration and testing. Between individual HTR tests, cages were cleaned with water, disinfected with a 70% ethanol aqueous solution, and dried using paper towels.

Results and Discussion

FIG. 2, FIG. 3, FIG. 4, and FIG. 5 are graphs showing the effect of various doses of exemplary compounds of Formula (I), specifically, (R) I-98, (R) I-244, (R) I-245, and Cis (R) I-248, on head-twitch response (HTR) in male C57BL6 mice. The mice were treated with exemplary compound (R) I-98, (R) I-244, (R) I-245, or Cis (R) I-248 by SC route, and the total number of head twitches were recorded over a 20 min period. Data is expressed as mean±SEM. The induction of head twitches elicited by 5-$HT_{2A}$ receptor agonists is believed to represent a behavioral proxy of their psychedelic effects. Also, locomotor activity and other 5-HT receptor signs were measured (FIGS. 2-5).

Example 19: Pharmacokinetic Studies in Rat

Protocol

Study Details:

Animals: Male Sprague-Dawley rats (~225-350 g) from Charles River Labs were acclimatized for a minimum of 5 days prior to start of study procedures. Body weights were recorded on the day of dosing.

Food restriction: None.

Clinical observations: Animals were observed at the time of dosing and each sample collection. Any abnormalities were documented including presence/absence of wet dog shakes/back muscle contractions (WDS/BMC).

Dosing: Formulations were administered intravenously (i.v.) via the tail vein using a 25 G needle connected to a 1 cc syringe.

Formulation:

The Compounds of Formula (I) were freshly prepared at the appropriate concentrations in 5% Tween-80 in saline.

Sample Collection:

Blood collection time (h): 0, 25, 1 and 4

Volume/time-point: ~0.25 mL (saphenous vein)

Bioanalytical Method Development and Sample Analysis:

Analytes: Compounds of Formula (I)

Matrix: Rat plasma.

Instrumentation: AB Sciex QTRAP 4000 or 6500 MS/MS system equipped with an LC system with a binary pump, a solvent degasser, a thermostated column compartment and a multiplate autosampler.

Bioanalytical method(s) development include:

1. The selection of the ion transition for the test compounds and potential internal standards (i.e., identification of the parent and product ions).
2. The optimization of mass spectrometric operating parameters.
3. The establishment of the chromatographic condition for the analytes.
4. The selection of an appropriate internal standard (IS).
5. The development of sample clean-up method using protein precipitation.

Method(s) Qualification:

1. The determination of the quantification dynamic range using non-zero calibration standards (STDs) in singlet. The STDs will consist of a blank matrix sample (without IS), a zero sample (with IS), and at least 6 non-zero STDs covering the expected range and including the lower level of quantitation (LLOQ).

2. Triplicate injections of a system suitability sample (neat solution containing the analyte and IS) bracketing the batch.

Method(s) Acceptance Criteria:

1. At least 75% of non-zero STDs must be included in the calibration curve with all back-calculated concentrations within ±20% deviation from nominal concentrations (±25% for the lower level of quantification, LLOQ).

2. The correlation coefficient (r) of the calibration curve must be greater than or equal to 0.99 using quadratic regression analysis ($1/x^2$ weighting).

3. The area ratio variation between the pre- and post-run injections of the system suitability samples is within ±25%.

Sample Analysis Batch:

1. Triplicate injections of a system suitability sample bracketing the batch.

2. The STDs in ascending order.

3. The study samples and the dosing solutions diluted as 3 independent dilutions into blank matrix (plasma).

4. For more than 40 study samples in a batch, two sets of STDs bracketing the samples will be utilized.

Samples which are 25% greater than the highest calibration standard, will be diluted and re-assayed along with a corresponding dilution quality control standard. Dilution standards will be acceptable if they are within 25% accuracy of the target concentration.

PK Analysis

Analysis software: Phoenix® WinNonlin® 8.3 (Pharsight, Certara, Mountainview, CA).

Analysis methods: non-compartmental analysis, linear up/log down trapezoidal rule.

PK parameters: $t_{1/2}$ and $AUC_{0\text{-}tlast}$ will be estimated.

Results

Table 65 shows the plasma concentration of exemplary compounds of Formula (I) following i.v. administration.

TABLE 65

Plasma concentrations of exemplary compounds of Formula (I) following 1.10 mg/kg i.v. administration (Group 2).

| Example ID | Dose (mg/kg) | Experimental time (h)/Rat# | Plasma concentration (ng/mL) | | | |
|---|---|---|---|---|---|---|
| (R) I-98 | 1.32 | | R07 | R08 | R09 | Mean ± SD |
| | | 0.25 | 411 | 479 | 449 | 446 ± 34.1 |
| | | 1 | 128 | 110 | 100 | 113 ± 14.2 |
| | | 4 | 2.48 | 2.25 | 2.23 | 2.32 ± 0.139 |
| rac (R) I-248 | 2.09 | | R04 | R05 | R06 | Mean ± SD |
| | | 0.25 | 235 | 437 | 459 | 377 ± 123 |
| | | 1 | 134 | 135 | 162 | 144 ± 15.9 |
| | | 4 | 27.8 | 11.5 | 17.0 | 18.8 ± 8.29 |
| (R) I-245 | 2.06 | | R01 | R02 | R03 | Mean ± SD |
| | | 0.25 | 307 | 154 | 71.8 | 178 ± 119 |
| | | 1 | 170 | 121 | 98.3 | 130 ± 36.6 |
| | | 4 | 39.9 | 43.6 | 48.3 | 43.9 ± 4.21 |
| (R) I-244 | 2 | | R10 | R11 | R12 | Mean ± SD |
| | | 0.25 | 252 | 360 | 263 | 292 ± 59.4 |
| | | 1 | 132 | 150 | 107 | 130 ± 21.6 |
| | | 4 | 20.7 | 23.8 | 21.4 | 22.0 ± 1.63 |

*Values in italics are below the lower limit of quantitation (BLQ, 0.5 ng/mL) but were included in calculations.
*BLQ denotes below the lower limit of quantitation (0.5 ng/mL).

Table 66 is a summary of the plasma apparent $t_{1/2}$ and $AUC_{0\text{-}tlast}$ for exemplary compounds of Formula (I) 1 following 1.10 mg/kg i.v. administration (Group 2).

TABLE 66

Summary of plasma apparent $t_{1/2}$ and $AUC_{0\text{-}tlast}$ for I-1 following 1.10 mg/kg i.v. administration (Group 2).

| Example ID | Dose (mg/kg) | Parameter | Parameter estimate for each animal | | | |
|---|---|---|---|---|---|---|
| (R) I-98 | 1.32 | | R07 | R08 | R09 | Mean ± SD |
| | | Apparent $t_{1/2}$ (h)[a] | 0.514 | 0.498 | 0.505 | 0.506 ± 0.00788 |
| | | $AUC_{0\text{-}tlast}$ (h*ng/mL) | 403 | 426 | 397 | 409 ± 15.1 |
| rac (R) I-248 | 2.09 | | R04 | R05 | R06 | Mean ± SD |
| | | Apparent $t_{1/2}$ (h)[a] | 1.25 | 0.747 | 0.823 | 0.939 ± 0.269 |
| | | $AUC_{0\text{-}tlast}$ (h*ng/mL) | 402 | 477 | 544 | 474 ± 71.0 |
| (R) I-245 | 2.6 | | R01 | R02 | R03 | Mean ± SD |
| | | Apparent $t_{1/2}$ (h)[a] | 1.32 | 2.05 | 2.93 | 2.10 ± 0.806 |
| | | $AUC_{0\text{-}tlast}$ (h*ng/mL) | 528 | 370 | 293 | 397 ± 120 |
| (R) I-244 | 2 | | R10 | R11 | R12 | Mean ± SD |
| | | Apparent $t_{1/2}$ (h)[a] | 1.06 | 1.00 | 1.10 | 1.05 ± 0.0494 |
| | | $AUC_{0\text{-}tlast}$ (h*ng/mL) | 390 | 490 | 366 | 415 ± 65.7 |

[a]Apparent $t_{1/2}$ was estimated from 2 points only

Discussion

Exemplary compounds of the disclosure were evaluated for pharmacokinetics profile rat via i.v. administration. Table 65 and Table 66 summarize the results of three representative compounds of formula 1 for plasma concentrations and plasma apparent $t_{1/2}$ and $AUC_{0\text{-}tlast}$, respectively. of. These results show that the compounds of the disclosure show a spectrum of plasma $t_{1/2}$ and exposure profiles.

Example 20: Human, Rat and Mouse Liver Microsomes Stability

Objective

The objective of this study was to estimate in vitro metabolic stability of exemplary compounds of Formula (I) or a pharmaceutically acceptable salt, solvate and/or prodrug thereof in pooled human, male rat and male mouse liver microsomes. The concentrations of compounds in reaction systems were evaluated by LC-MS/MS for estimating the stability in pooled human, male rat and male mouse liver microsomes. The in vitro intrinsic clearances of test compounds were determined as well.

Protocol

A master solution in the "Incubation Plate" containing phosphate buffer, ultra-pure $H_2O$, $MgCl_2$ solution and liver microsomes was made according to Table 67. The mixture was pre-warmed at 37° C. water bath for 5 minutes.

TABLE 67

Preparation of master solution

| Reagent | Stock Concentration | Volume | Final Concentration |
|---|---|---|---|
| Phosphate buffer | 200 mM | 200 µL | 100 mM |
| Ultra-pure $H_2O$ | — | 106 µL | — |
| $MgCl_2$ solution | 50 mM | 40 µL | 5 mM |
| Microsomes | 20 mg/mL | 10 µL | 0.5 mg/mL |

40 µL of 10 mM NADPH solution was added to each well. The final concentration of NADPH was 1 mM. The negative control samples were prepared by replacing NADPH with 40 μL of ultra-pure $H_2O$. Samples were prepared in duplicate. Negative controls were prepared in singlet The reaction was started with the addition of 4 μL of 200 μM exemplary test compounds of the disclosure or control compounds to each master solution to get the final concentration of 2 μM. This study was performed in duplicate.

Aliquots of 50 μL were taken from the reaction solution at 0, 15, 30, 45 and 60 minutes. The reaction solutions were stopped by the addition of 4 volumes of cold methanol with IS (100 nM alprazolam, 200 nM imipramine, 200 nM labetalol and 2 μM ketoprofen). Samples were centrifuged at 3,220 g for 40 minutes. Aliquot of 90 μL of the supernatant was mixed with 90 μL of ultra-pure $H_2O$ and then was used for LC-MS/MS analysis.

LC/MS analysis was performed for all samples from this study using a Shimadzu liquid chromatograph separation system equipped with degasser DGU-20A5R; solvent delivery unit LC-30AD; system controller SIL-30AC; column oven CTO-30A; CTC Analytics HTC PAL System. Mass spectrometric analysis was performed using a Triple Quad™ 5500 instrument.

All calculations were carried out using Microsoft Excel. Peak area ratios of test compound to internal standard (listed in the below table) were determined from extracted ion chromatograms.

All calculations were carried out using Microsoft Excel. Peak areas were determined from extracted ion chromatograms. The slope value, k, was determined by linear regression of the natural logarithm of the remaining percentage of the parent drug vs. incubation time curve.

The in vitro half-life (in vitro $t_{1/2}$) was determined from the slope value:

$$\text{in vitro } t_{1/2} = -(0.693/k)$$

Conversion of the in vitro $t_{1/2}$ (min) into the in vitro intrinsic clearance (in vitro C Lint, in μL/min/mg proteins) was done using the following equation (mean of duplicate determinations):

$$\text{in vitro } CL_{int} = \left(\frac{0.693}{(t_{1/2})}\right) * \left(\frac{\text{volume of incubation } (\mu L)}{\text{amount of proteins (mg)}}\right)$$

For the exemplary compounds of the disclosure or control compound that showed an initial fast disappearance followed by a slow disappearance, only the time points that were within the initial rate were included in the calculation.

Results and Discussion

Human, rat and mouse liver microsomes contain a wide variety of drug metabolizing enzymes and are commonly used to support in vitro ADME (absorption, distribution, metabolism and excretion) studies. These microsomes are used to examine the potential first-pass metabolism by-products of orally administered drugs. Representative compounds of the disclosure were evaluated for their stability in human, rat and mouse liver microsomes.

Most of the exemplary compounds of the disclosure in three species, human, rat and mouse liver microsomes were recovered within a 60-minute time period indicating that the compounds were not rapidly cleared (see Table 68 for exemplary compounds of Formula (I)).

TABLE 68

Metabolic Stability of Compounds of Formula 1 in Liver Microsomes of Different Species (Human, Rat and Mouse)

| Compound ID | Species | $T_{1/2}$ (min) | $CL_{int}$ (μL/min/mg protein) | Scaled-up $CL_{int}$ (mL/min/Kg) | Predicted hepatic CL (mL/min/kg) |
|---|---|---|---|---|---|
| Diclofenac | Human | 10.59 | 130.91 | 164.18 | 18.38 |
| | Rat | 15.27 | 90.79 | 162.69 | 41.22 |
| | Mouse | 40.69 | 34.06 | 149.03 | 56.11 |
| (R) I-98 | Human | 64.33 | 21.55 | 27.02 | 11.72 |
| | Rat | 10.04 | 138.11 | 247.50 | 45.13 |
| | Mouse | 14.39 | 96.32 | 421.38 | 74.16 |
| rac (R) I-248 | Human | <4.51 | >307.01 | >385.04 | >19.64 |
| | Rat | <4.51 | >307.01 | >550.16 | >50.17 |
| | Mouse | <4.51 | >307.01 | >1343.17 | >84.35 |
| (R) I-244 | Human | 5.98 | 231.63 | 290.50 | 19.32 |
| | Rat | 6.89 | 201.05 | 360.28 | 47.87 |
| | Mouse | <4.51 | >307.01 | >1343.17 | >84.35 |
| (R) I-245 | Human | 12.00 | 115.46 | 144.81 | 18.11 |
| | Rat | <4.51 | >307.01 | >550.16 | >50.17 |
| | Mouse | 5.12 | 270.81 | 1184.81 | 83.65 |

Notes:

1. For the compounds that showed an initial fast disappearance followed by a slow disappearance, only the time points that were within the initial rate were included in the calculation.

2. If % remaining at 30 minutes was lower than 1%, then $CL_{int}$ and $t_{1/2}$ will be reported as ">307.01" and "<4.51," respectively.

TABLE 69

Metabolic Stability of Test Compounds in Liver Microsomes of Different Species (b)

| Compound ID | Species | Assay Format | Remaining Percentage (%) 0 min | 30 min | 60 min |
|---|---|---|---|---|---|
| Diclofenac | Human | With Cofactors | 100.00 | 5.01 | 1.77 |
| | | Without Cofactors | 100.00 | 112.67 | 96.67 |
| | Rat | With Cofactors | 100.00 | 11.86 | 6.35 |
| | | Without Cofactors | 100.00 | 102.19 | 100.63 |
| | Mouse | With Cofactors | 100.00 | 45.55 | 33.71 |
| | | Without Cofactors | 100.00 | 89.49 | 96.59 |
| 5-MeO-DMT | Human | With Cofactors | 100.00 | 19.24 | 3.25 |
| | | Without Cofactors | 100.00 | 18.58 | 3.00 |
| | Rat | With Cofactors | 100.00 | 2.57 | 0.36 |
| | | Without Cofactors | 100.00 | 49.55 | 23.82 |
| | Mouse | With Cofactors | 100.00 | 61.84 | 39.30 |
| | | Without Cofactors | 100.00 | 104.76 | 95.24 |
| (R) I-98 | Human | With Cofactors | With Cofactors | 100.00 | 67.04 |

TABLE 69-continued

| Metabolic Stability of Test Compounds in Liver Microsomes of Different Species (b) | | | | | |
|---|---|---|---|---|---|
| Compound | | | Remaining Percentage (%) | | |
| ID | Species | Assay Format | 0 min | 30 min | 60 min |
| | | Without Cofactors | Without Cofactors | 100.00 | 98.21 |
| | Rat | With Cofactors | With Cofactors | 100.00 | 14.43 |
| | | Without Cofactors | Without Cofactors | 100.00 | 103.23 |
| | Mouse | With Cofactors | With Cofactors | 100.00 | 14.54 |
| | | Without Cofactors | Without Cofactors | 100.00 | 100.99 |
| rac (R) | Human | With Cofactors | 100.00 | 0.04 | 0.00 |
| I-248 | | Without Cofactors | 100.00 | 100.47 | 98.60 |
| | Rat | With Cofactors | 100.00 | 0.95 | 0.19 |
| | | Without Cofactors | 100.00 | 94.04 | 94.04 |
| | Mouse | With Cofactors | 100.00 | 0.15 | 0.19 |
| | | Without Cofactors | 100.00 | 99.54 | 95.85 |
| (R) I-245 | Human | With Cofactors | 100.00 | 14.62 | 3.13 |
| | | Without Cofactors | 100.00 | 101.09 | 98.91 |
| | Rat | With Cofactors | 100.00 | 0.62 | 0.00 |
| | | Without Cofactors | 100.00 | 95.83 | 94.10 |
| | Mouse | With Cofactors | 100.00 | 1.72 | 0.25 |
| | | Without Cofactors | 100.00 | 100.00 | 93.17 |
| (R) I-244 | Human | With Cofactors | 100.00 | 3.10 | 0.00 |
| | | Without Cofactors | 100.00 | 94.44 | 88.07 |
| | Rat | With Cofactors | 100.00 | 4.90 | 0.57 |
| | | Without Cofactors | 100.00 | 94.87 | 87.40 |
| | Mouse | With Cofactors | 100.00 | 0.00 | 0.00 |
| | | Without Cofactors | 100.00 | 98.38 | 86.59 |

Discussion

Exemplary compounds of the disclosure were evaluated for their stability in human, rat and mouse liver microsomes. Table 68 and Table 69 illustrate the results of the stability studies. These results show that the compounds of the disclosure show a spectrum of stability across different species, including human, rat and mouse.

Example 21: Protein Binding Measurements in Different Species, (Human, Rat, Mouse and Dog) Plasma Using Equilibrium Dialysis Method

Protocol

1. The Frozen Plasma (Stored at −80° C.) was Thawed Immediately in a 37° C. Water Bath.

2. Preparation of Working Solution

The working solution of test compounds and control compound was prepared in DMSO at the concentration of 200 μM, and then the working solution was spiked into plasma. The final concentration of compound was 1 M. The final concentration of DMSO was 0.5%. Ketoconazole was used as positive control in the assay.

3. Preparation of Dialysis Membranes

The dialysis membranes were soaked in ultrapure water for 60 minutes to separate strips, then in 20% ethanol for 20 minutes, finally in dialysis buffer for 20 minutes.

4. Procedure for Equilibrium Dialysis

The dialysis set up was assembled according to the manufacturer's instruction. Each Cell was with 150 μL of plasma sample and dialyzed against equal volume of dialysis buffer (PBS). The assay was performed in duplicate. The dialysis plate was sealed and incubated in an incubator at 37° C. with 5% $CO_2$ at 100 rpm for 6 hours. At the end of incubation, 50 μL of samples from both buffer and plasma chambers were transferred to wells of a 96-well plate.

5. Procedure for Sample Analysis

50 μL of plasma was added to each buffer samples and an equal volume of PBS was supplemented to the collected plasma sample. 400 μL of precipitation buffer acetonitrile containing internal standards (IS, 200 nM labetalol, 100 nM tolbutamide and 100 nM ketoprofen) was added to precipitate protein and release compounds. Samples were vortexed for 2 minutes and centrifuged for 30 minutes at 3,220 g. Aliquot of 50 μL of the supernatant was diluted by 150 μL acetonitrile containing internal standards: ultra-pure $H_2O$=1:1, and the mixture was used for LC-MS/MS analysis.

6. Data Analysis

All calculations were carried out using Microsoft Excel. The concentrations of test compounds in the buffer and plasma chambers were determined from peak area ratios. The percentages of bound compound were calculated as follows:

$$\%\ \text{Free} = \left(\text{Peak Area Ratio}_{buffer\ chamber}/\text{Peak Area Ratio}_{plasma\ chamber}\right) * 100\%$$

$$\%\ \text{Bound} = 100\% - \%\ \text{Free}$$

$$\%\ \text{Recovery} = (\text{Peak Area Ratio}_{buffer\ chamber} + \text{Peak Area Ratio}_{plasma\ chamber})/\text{Peak Area Ratio}_{total\ sample} * 100\%$$

Materials

| Plasma information (Table 70) | | | |
|---|---|---|---|
| Species | Strain/Gender | Batch No. | Source |
| Human | Pooled; Male & Female | HUMANPLK2PNNV20230717 | Healthy Asian volunteers from local vendor (collected in domestic hospital with Ethical approval) |
| Dog | Beagle; Pooled; Male & Female | PH-Dog-20230612 | Local Supplier |
| Rat | SD; Pooled; Male & Female | RAT542174 | BioIVT |
| Mouse | CD-1; Pooled; Male & Female | MSE441125 | BioIVT |

| Bioanalytical Method (Table 71) | | | | | | | |
|---|---|---|---|---|---|---|---|
| A | Time (min) | 0 | 0.2 | 0.6 | 1.1 | 1.2 | 1.4 |
| | % B | 5 | 5 | 100 | 100 | 5 | 5 |
| B | Time (min) | 0 | 2.4 | 2.5 | 2.6 | 3 | |
| | % B | 5 | 100 | 100 | 5 | 5 | |

| Injection Volume (Table 72) | |
|---|---|
| A | 3 μL |
| B | 20 μL |

Column temperature: 40° C.
MS parameters:
Ion source: Turbo spray
Ionization model: ESI
Scan type: MRM
Collision gas: 6 L/min
Curtain gas: 30 L/min
Nebulize gas: 50 L/min
Auxiliary gas: 50 L/min
Temperature: 500° C.
Ion spray voltage: +5500 v (positive MRM)

Results and Discussion

TABLE 73

| Protein Binding Results for Test Compounds and Control Compound in Human, Dog, Rat and Mouse Plasma | | | | |
|---|---|---|---|---|
| Compound ID | Species | % Bound | % Recovery | % Remaining @ 6 hours |
| Ketoconazole | Human | 99.24 | 100.62 | 99.64 |
| | Dog | 98.95 | 86.06 | 87.36 |
| | Rat | 99.39 | 100.71 | 109.42 |
| | Mouse | 99.32 | 94.67 | 108.54 |
| (R) I-98 | Human | 83.24 | 101.48 | 104.64 |
| | Dog | 84.26 | 103.74 | 110.92 |
| | Rat | 43.14 | 87.98 | 96.55 |
| | Mouse | 36.83 | 96.43 | 103.70 |
| (R) I-244 | Human | 98.58 | 90.12 | 105.89 |
| | Dog | 97.19 | 94.57 | 94.07 |
| | Rat | 81.05 | 86.53 | 85.45 |
| | Mouse | 89.89 | 84.79 | 94.96 |
| rac (R) I-245 | Human | 99.86 | 106.81 | 112.41 |
| | Dog | 99.16 | 96.29 | 96.81 |
| | Rat | 86.06 | 97.30 | 100.74 |
| | Mouse | 87.49 | 95.03 | 111.37 |

Discussion

Exemplary compounds of the disclosure were evaluated for their protein Binding profile compared control compound, Ketoconazole, in Human, Dog, Rat and Mouse Plasma. These results show that the compounds of the disclosure illustrate high to moderate % bond with good recovery across different species.

Additional embodiments described herein include intermediate compounds, including but not limited to those in Table 74 below:

TABLE 74

| Compound | Structure | IUPAC Name |
|---|---|---|
| Intermediate 1; | 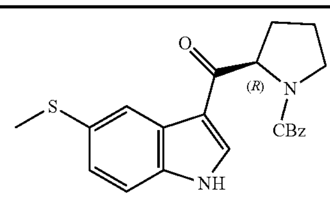 | (R)-2-(2-(5-(methylthio)-1H-indole-3-carbonyl)pyrrolidin-1-yl)-1-phenylethan-1-one |

TABLE 74-continued

| Compound | Structure | IUPAC Name |
| --- | --- | --- |
| Intermediate 2; | 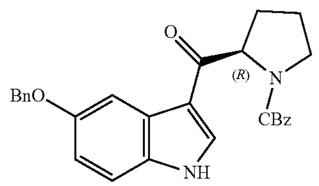 | (R)-2-(2-(5-(benzyloxy)-1H-indole-3-carbonyl)pyrrolidin-1-yl)-1-phenylethan-1-one |
| Intermediate 3; | 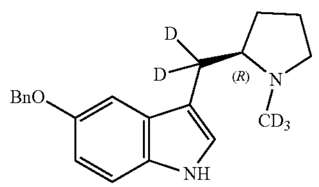 | R)-5-(benzyloxy)-3-((1-(methyl-$d_3$)pyrrolidin-2-yl)methyl-d2)-1H-indole |
| Intermediate 4; | 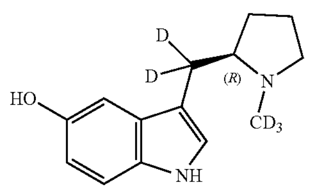 | (R)-3-((1-(methyl-$d_3$)pyrrolidin-2-yl)methyl-d2)-1H-indol-5-ol |
| Intermediate 2A | 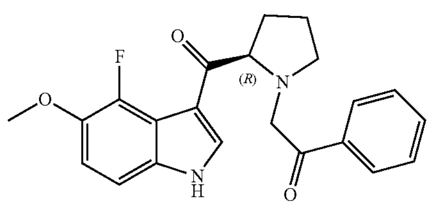 | (R)-2-(2-(4-fluoro-5-methoxy-1H-indole-3-carbonyl)pyrrolidin-1-yl)-1-phenylethan-1-one |
| Intermediate 4A | 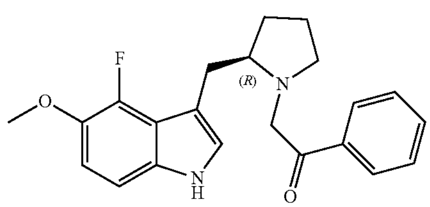 | (R)-2-(2-((4-fluoro-5-methoxy-1H-indol-3-yl)methyl)pyrrolidin-1-yl)-1-phenylethan-1-one |
| Intermediate 7A | 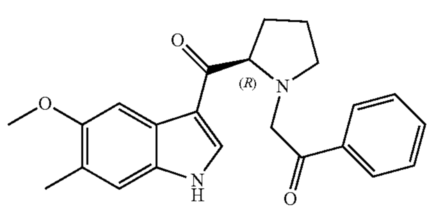 | (R)-2-(2-(5-methoxy-6-methyl-1H-indole-3-carbonyl)pyrrolidin-1-yl)-1-phenylethan-1-one |
| Intermediate 9A | 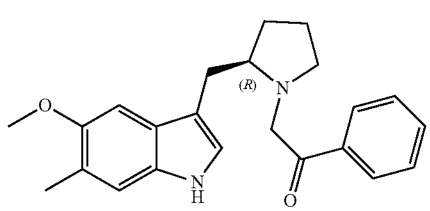 | (R)-2-(2-((5-methoxy-6-methyl-1H-indol-3-yl)methyl)pyrrolidin-1-yl)-1-phenylethan-1-one |

TABLE 74-continued

| Compound | Structure | IUPAC Name |
|---|---|---|
| Intermediate 12A | 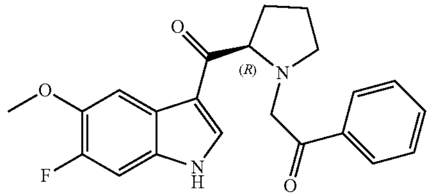 | (R)-2-(2-(6-fluoro-5-methoxy-1H-indole-3-carbonyl)pyrrolidin-1-yl)-1-phenylethan-1-one |
| Intermediate 14A | 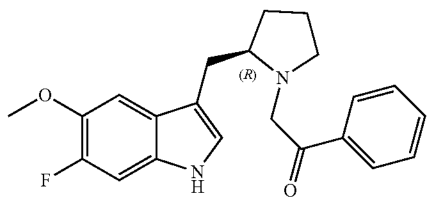 | (R)-2-(2-((6-fluoro-5-methoxy-1H-indol-3-yl)methyl)pyrrolidin-1-yl)-1-phenylethan-1-one |

EXEMPLARY EMBODIMENTS

E1: A compound of Formula (I)

Formula (I)

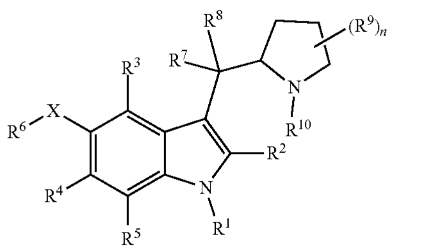

or a pharmaceutically acceptable salt, solvate, and/or prodrug thereof, wherein:

X is absent or selected from O, S, S(O), and $SO_2$;

$R^1$ is selected from H, $C_1$-$C_6$alkyl, $C_1$-$C_6$alkyleneP(O)$(OR^{11})_2$, $C_1$-$C_6$alkyleneOP(O)$(OR^{11})_2$, C(O)$R^{11}$, $CO_2R^{11}$, C(O)N$(R^{11})_2$, S(O)$R^{11}$, and $SO_2R^{11}$;

$R^2$ is selected from H, halo, and $C_1$-$C_6$alkyl;

$R^3$, $R^4$, and $R^5$ are independently selected from H, CN, halo, $C_1$-$C_6$alkyl, $C_2$-$C_6$alkenyl, and $C_2$-$C_6$alkynyl;

$R^6$ is selected from H, $C_1$-$C_{10}$alkyl, $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_7$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{13}$, and C(O)$R^{13}$;

$R^7$ and $R^8$ are independently selected from H, halo, and $C_1$-$C_6$alkyl;

each $R^9$ is independently selected from halo, $C_1$-$C_6$alkyl, OH, $OC_1$-$C_6$alkyl, $C_1$-$C_6$alkyleneOH, and $C_1$-$C_6$alkyleneO$C_1$-$C_6$alkyl;

$R^{10}$ is selected from H, $C_1$-$C_6$alkyl, $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{15}$, and C(O)$R^{15}$;

Z is selected from O, C(O), $NR^{16}$C(O), $NR^{16}$C(O)O, C(O)$NR^{16}$, OC(O)$NR^{16}$, and $NR^{16}$.

Z' is selected from O, C(O), $NR^{17}$C(O), $NR^{17}$C(O)O, C(O)$NR^{17}$, OC(O)$NR^{17}$, and $NR^{17}$.

n is an integer selected from 0, 1, 2, 3, and 4;

$R^{11}$, $R^{13}$, $R^{15}$, $R^{16}$, and $R^{17}$ are independently selected from H and $C_1$-$C_6$alkyl;

$R^{12}$ and $R^{14}$ are independently selected from H, $C_1$-$C_6$alkyl, $C_3$-$C_7$cycloalkyl, $C_3$-$C_{10}$heterocycloalkyl, $C_6$-$C_{10}$aryl, and $C_5$-$C_{10}$heteroaryl, the latter four groups being optionally substituted with one to four substituents independently selected from halo, $C_1$-$C_4$alkyl, $OC_1$-$C_4$alkyl, and C(O)$C_1$-$C_4$alkyl, and available hydrogen atoms are optionally replaced with a halogen atom and/or available atoms are optionally replaced with an alternate isotope thereof, provided when X is O, $R^1$, $R^2$, $R^3$, $R^4$, $R^5$, $R^7$, and $R^8$ are H or D, n is 0, and $R^6$ is H, $CH_3$, or $CD_3$, then $R^{10}$ is not H, $CH_3$, or $CD_3$;

when X is O, $R^1$, $R^2$, $R^3$, $R^4$, $R^5$, $R^7$, and $R^8$ are H or D and n is 0, and $R^6$ is $CH_3$, or $CHF_2$, then $R^{10}$ is not H, $CH_3$, or $CD_3$; and when X is absent and $R^6$ is H, then either n is not 0 or $R^{10}$ is not H or $C_1$-$C_6$alkyl.

E2: The compound of E1, provided (1) when X is absent, then $R^6$ is not H, D, or halogen, and (2) when X is O, S, S(O), or $SO_2$, then each $R^9$ is not independently selected from H, D, halogen, $C_1$-$C_6$alkyl, $C_1$-$C_6$deuteroalkyl, $C_1$-$C_6$haloalkyl, and $C_1$-$C_6$deuterohaloalkyl and/or $R_{10}$ is not selected from H, D, halogen, $C_1$-$C_6$alkyl, $C_1$-$C_6$deuteroalkyl, $C_1$-$C_6$haloalkyl, and $C_1$-$C_6$deuterohaloalkyl.

E3: The compound of E1, provided when X is absent, then $R^6$ is not H, D, or halogen.

E4: The compound of E1, provided when X is O, S, S(O), or $SO_2$, each $R^9$ is not independently selected from H, D, halogen, $C_1$-$C_6$alkyl, $C_1$-$C_6$deuteroalkyl, $C_1$-$C_6$haloalkyl, and $C_1$-$C_6$deuterohaloalkyl.

E5: The compound of E1, provided when X is O, S, S(O), or $SO_2$, then $R_{10}$ is not selected from H, D, halogen, $C_1$-$C_6$alkyl, $C_1$-$C_6$deuteroalkyl, $C_1$-$C_6$haloalkyl, and $C_1$-$C_6$deuterohaloalkyl.

E6: The compound of E1, provided (1) when X is absent, then $R^6$ is not H, D, or halogen, and (2) when X is O, S, S(O), or $SO_2$, then each $R^9$ is not independently selected from H, D, halogen, $C_1$-$C_6$alkyl, $C_1$-$C_6$deuteroalkyl, $C_1$-$C_6$haloalkyl, and $C_1$-$C_6$deuterohaloalkyl.

E7: The compound of E1, when X is absent, then $R^6$ is not H, D, or halogen, and (2) when X is O, S, S(O), or $SO_2$, then $R^{10}$ is not selected from H, D, halogen, $C_1$-$C_6$alkyl, $C_1$-$C_6$deuteroalkyl, $C_1$-$C_6$haloalkyl, and $C_1$-$C_6$deuterohaloalkyl.

E8: The compound of any one of E1 to E7, wherein available hydrogen atoms are optionally independently replaced with an iodine atom, a fluorine atom, and/or a chlorine atom and/or available hydrogen atoms are optionally replaced with deuterium.

E9: The compound of any one of E1 to E8, wherein X is S(O) or $SO_2$.

E10: The compound of any one of E1 or E8, wherein X is S.

E11: The compound of any one of E1 to E8, wherein X is absent.

E12: The compound of any one of E1 to E8, wherein X is O.

E13: The compound of any one of E1 to E12, wherein $R^1$ is selected from $S(O)R^{11}$ and $SO_2R^{11}$.

E14: The compound of any one of E1 to E12, wherein $R^1$ is selected from H, $C_1$-$C_4$alkyl, $C_1$-$C_4$alkyleneP(O)$(OR^{11})_2$, $C_1$-$C_4$alkyleneOP(O)$(OR^{11})_2$, C(O)$R^{11}$, $CO_2R^{11}$, and C(O)N$(R^{11})_2$, wherein available hydrogen atoms are optionally independently replaced with a fluorine atom and/or a chlorine atom and/or available hydrogen atoms are optionally replaced with deuterium.

E15: The compound of E14, wherein $R^1$ is selected from H, $C_1$-$C_3$alkyl, $CH_2P(O)(OR^{11})_2$, $CH_2CH_2P(O)(OR^{11})_2$, $CH_2CH(CH_3)P(O)(OR^{11})_2$, $CH(CH_3)CH_2P(O)(OR^{11})_2$, $CH(CH_3)P(O)(OR^{11})_2$, $CH(CH_2CH_3)P(O)(OR^{11})_2$, $(CH_2)OP(O)(OR^{11})_2$, C(O)$R^{11}$, and $CO_2R^{11}$, wherein available hydrogen atoms are optionally independently replaced with a fluorine atom and/or a chlorine atom and/or available hydrogen atoms are optionally replaced with deuterium.

E16: The compound of any one of E1 to E15, wherein $R^2$ is selected from H, halo, and $C_1$-$C_4$alkyl, wherein available hydrogen atoms are optionally independently replaced with a fluorine atom and/or a chlorine atom and/or available hydrogen atoms are optionally replaced with deuterium.

E17: The compound of E16, wherein $R^2$ is selected from H, D, F, Cl, Br, $C_1$-$C_4$alkyl, $C_1$-$C_4$fluoroalkyl, $C_1$-$C_4$deuteroalkyl, and $C_1$-$C_4$deuterofluoroalkyl.

E18: The compound of E17, wherein $R^2$ is selected from H, D, $CH_3$, $CF_3$, and $CD_3$.

E19: The compound of any one of E1 to E18, wherein $R^3$ is selected from H, D, halo, CN, $C_1$-$C_4$alkyl, $C_2$-$C_4$alkenyl, and $C_2$-$C_4$alkynyl, wherein available hydrogen atoms are optionally independently replaced with a fluorine atom and/or a chlorine atom and/or available hydrogen atoms are optionally replaced with deuterium.

E20: The compound of E19, wherein $R^3$ is selected from H, D, CN, halo, $C_1$-$C_4$alkyl, $C_1$-$C_4$fluoroalkyl, $C_1$-$C_4$deuteroalkyl, $C_1$-$C_4$deuterofluoroalkyl, $C_2$-$C_4$alkenyl, $C_2$-$C_4$fluoroalkenyl, $C_2$-$C_4$deuteroalkenyl, $C_2$-$C_4$deuterofluoroalkenyl, $C_2$-$C_4$alkynyl, $C_2$-$C_4$deuteroalkynyl, $C_2$-$C_4$fluoroalkynyl, and $C_2$-$C_4$deuterofluoroalkynyl.

E21: The compound of E20, wherein $R^3$ is selected from H, D, CN, F, Br, Cl, $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3$, $CF_2CF_3$, $CH_2CH_2D$, $CH_2CD_2H$, $CH_2CD_3$, and $CD_2CD_3$.

E22: The compound of E21, wherein $R^3$ is selected from H, F, and Cl.

E23: The compound of any one of E1 to E22, wherein $R^4$ and $R^5$ are independently selected from H, halo, CN, $C_1$-$C_4$alkyl, $C_2$-$C_4$alkenyl, and $C_2$-$C_4$alkynyl, wherein available hydrogen atoms are optionally independently replaced with a fluorine atom and/or a chlorine atom and/or available hydrogen atoms are optionally replaced with deuterium.

E24: The compound of E23, wherein $R^4$ and $R^5$ are independently selected from H, D, CN, halo, $C_1$-$C_4$alkyl, $C_1$-$C_4$fluoroalkyl, $C_1$-$C_4$deuteroalkyl, $C_1$-$C_4$deuterofluoroalkyl, $C_2$-$C_4$alkenyl, $C_2$-$C_4$fluoroalkenyl, $C_2$-$C_4$deuteroalkenyl, $C_2$-$C_4$deuterofluoroalkenyl, $C_2$-$C_4$alkynyl, $C_2$-$C_4$deuteroalkynyl, $C_2$-$C_4$fluoroalkynyl, and $C_2$-$C_4$deuterofluoroalkynyl.

E25: The compound of E24, wherein $R^4$ and $R^5$ are independently selected from H, D, CN, F, Cl, Br, $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3$, $CF_2CF_3$, $CH_2CH_2D$, $CH_2CD_2H$, $CH_2CD_3$, and $CD_2CD_3$.

E26: The compound of E25, wherein $R^4$ and $R^5$ are independently selected from H and D.

E27: The compound of any one of E1 to E26, wherein $R^6$ is selected from H, $C_1$-$C_6$alkyl, $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted with one to four substituents independently selected from halo, $C_1$-$C_6$alkyl, $OR^{13}$, and C(O)$R^{13}$, and wherein available hydrogen atoms are optionally replaced with a halogen atom and/or available atoms are optionally replaced with an alternate isotope thereof.

E28: The compound of E27, wherein $R^6$ is $C_1$-$C_6$alkyl, wherein available hydrogen atoms are optionally independently replaced with a fluorine atom and/or a chlorine atom and/or available hydrogen atoms are optionally replaced with deuterium.

E29: The compound of E28, wherein $R^6$ is selected from $C_1$-$C_6$alkyl, $C_1$-$C_6$fluoroalkyl, $C_1$-$C_6$deuteroalkyl and $C_1$-$C_6$deuterofluoroalkyl.

E30: The compound of E29, wherein $R^6$ is selected from $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3$, $CF_2CF_3$, $CH_2CH_2D$, $CH_2CD_2H$, $CH_2CD_3CD_2CD_3$, $CH_2CH_2CH_3$, $CH_2CH_2CHF_2$, $CH_2CH_2CFH_2$, $CH_2CH_2CF_3$, $CH_2CH_2CHD_2$, $CH_2CH_2CDH_2$, $CH_2CH_2CD_3CH(CH_3)_2$, $CH(CF_3)_2$, $CH(CHF_2)_2$, $CH(CFH_2)_2$, $CH(CD_3)_2$, $CH(CHD_2)_2$, $CH(CDH_2)_2$, $C(CH_3)_3$, $C(CF_3)_3$, $C(CHF_2)_3$, $C(CFH_2)_3$, $C(CD_3)_3$, $C(CHD_2)_3$, $C(CDH_2)_3$, $CH_2CH_2CH_2CH_3$, $CH_2CH_2CH_2CF_3$, $CH_2CH_2CH_2CD_3$, $CH_2CH(CH_3)_2$, $CH_2CH(CD_3)_2$, $CH_2CH(CF_3)_2$, $CH(CH_3)CH_2CH_3$, $CH(CH_3)CH_2CF_3$, $CH(CH_3)CH_2CD_3$, $CH_2CH(CH_3)CH_3$, $CH_2CH(CH_3)$ $CF_3$, $CH_2CH(CH_3)$ $CD_3$, $CH_2C(CH_3)_3$, $CH_2C(CF_3)_3$, $CH_2C(CD_3)_3$, $CH_2CH_2C(CH_3)_3$, $CH_2CH_2C(CF_3)_3$, and $CH_2CH_2C(CD_3)_3$.

E31: The compound of E30, wherein $R^6$ is selected from H, D, $CH_3$, $CD_2H$, $CDH_2$, $CD_3$, $CF_2H$, $CFH_2$, $CF_3$, $CH_2CF_2H$, $CH_2CH_3$, $CH_2CH_2CH_3$, $CH_2CH_2CF_3$, $CH_2CH_2CH_2CF_3$, $CH(CH_3)_2$, $C(CH_3)_3$, $CH_2CH(CH_3)_2$, $CH(CH_3)CH_2CH_3$, and $CH_2C(CH_3)_3$.

E32: The compound of E27, wherein $R^6$ is selected from $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted with one to four substituents independently selected from halo, $C_1$-$C_6$alkyl, $OR^{13}$, and $C(O)R^{13}$, and wherein available hydrogen atoms are optionally independently replaced with a fluorine atom and/or a chlorine atom and/or available hydrogen atoms are optionally replaced with deuterium.

E33: The compound of E32, wherein $R^6$ is selected from $C_4$-$C_6$alkenyl and $C_2$-$C_6$alkynyl, wherein available hydrogen atoms are optionally independently replaced with a fluorine atom and/or a chlorine atom and/or available hydrogen atoms are optionally replaced with deuterium.

E34: The compound of E33, wherein $R^6$ is selected from $CH{=}CH_2$, $CH_2CH{=}CH_2$, $CF_2CH{=}CH_2$, $CD_2CH{=}CH_2$, $CH{=}CH_2CH_3$, $CH{=}CH_2CF_3$, $CH{=}CH_2CHF_2$, $CH{=}CH_2CH_2F$, $CH{=}CH_2CD_3$, $CH{=}CH_2CHD_2$, $CH{=}CH_2CH_2D$, $C{\equiv}CH$, $C{\equiv}CCH_3$, $C{\equiv}CCF_3$, $C{\equiv}CCHF_2$, $C{\equiv}CCFH_2$, $C{\equiv}CCD_3$, $C{\equiv}CCHD_2$, $C{\equiv}CCDH_2$, $CH_2C{\equiv}CH$, $CF_2C{\equiv}CH$, $CD_2C{\equiv}CH$, $CH_2C{\equiv}CCH_3$, $CF_2C{\equiv}CCH_3$, $CD_2C{\equiv}CCH_3$, $CH_2C{\equiv}CCD_3$, $CF_2C{\equiv}CCD_3$, $CD_2C{\equiv}CCD_3$, $CH_2C{\equiv}CCF_3$, $CF_2C{\equiv}CCF_3$, $CD_2C{\equiv}CCF_3$, $CH_2C{\equiv}CCHD_2$, $CF_2C{\equiv}CHD_2$, $CD_2C{\equiv}CHD_2$, $CH_2C{\equiv}CHF_2$, $CF_2C{\equiv}CHF_2$, and $CD_2C{\equiv}CHF_2$.

E35: The compound of E32, wherein $R^6$ is selected from $C_1$-$C_6$alkylene$ZR^{12}$, $C_2$-$C_6$alkenylene$ZR^{12}$, and $C_2$-$C_6$alkynylene$ZR^{12}$, wherein available hydrogen atoms are optionally independently replaced with a fluorine atom and/or a chlorine atom and/or available hydrogen atoms are optionally replaced with deuterium.

E36: The compound of E35, wherein $R^6$ is selected from $C_1$-$C_6$alkylene$ZR^{12}$, $C_1$-$C_6$fluoroalkylene$ZR^{12}$, $C_1$-$C_6$deuteroalkylene$ZR^{12}$, $C_1$-$C_6$deuterofluoroalkylene$ZR^{12}$, $C_2$-$C_6$alkenylene$ZR^{12}$, $C_2$-$C_6$fluoroalkenylene$ZR^{12}$, $C_2$-$C_6$deuteroalkenylene$ZR^{12}$, $C_2$-$C_6$deuterofluoroalkenylene$ZR^{12}$, $C_2$-$C_6$alkynylene$ZR^{12}$, $C_2$-$C_6$fluoroalkynylene$ZR^{12}$, $C_2$-$C_6$deuteroalkynylene$ZR^{12}$, and $C_2$-$C_6$deuteroalkynylene$ZR^{12}$.

E37: The compound of E36, wherein $R^6$ is selected from $CH_2ZR^{12}$, $CH_2CH_2ZR^{12}$, $CH_2CH_2CH_2ZR^{12}$, $CH_2CH_2CH_2CH_2ZR^{12}$, $CH(CH_3)CH_2ZR^{12}$, $CH(CH_3)CH_2CH_2ZR^{12}$, $CH_2CH(CH_3)\ ZR^{12}$, $CF_2ZR^{12}$, $CFHZR^{12}$, $CH_2CHFZR^{12}$, $CH_2CF_2ZR^{12}$, $CF_2CF_2ZR^{12}$, $CH_2CH_2CF_2ZR^{12}$, $CH_2CH_2CFHZR^{12}$, $CH_2CH_2CF_2ZR^{12}$, $CH(CH_3)\ CF_2ZR^{12}$, $CH(CH_3)CHFZR^{12}$, $CH_2CH_2CH_2CF_2ZR^{12}$, $CH_2CH_2CH_2CHFZR^{12}$, $CH(CH_3)CH_2CF_2ZR^{12}$, $CH(CH_3)CH_2CHFZR^{12}$, $CD_2ZR^{12}$, $CDHZR^{12}$, $CH_2CHDZR^{12}$, $CH_2CD_2ZR^{12}$, $CD_2CD_2ZR^{12}$, $CH_2CH_2CD_2ZR^{12}$, $CH_2CH_2CDHZR^{12}$, $CH_2CH_2CD_2ZR^{12}$, $CH(CH_3)\ CD_2ZR^{12}$, $CH(CH_3)CHDZR^{12}$, $CH_2CH_2CH_2CD_2ZR^{12}$, $CH_2CH_2CH_2CHDZR^{12}$, $CH(CH_3)CH_2CD_2ZR^{12}$, $CH(CH_3)CH_2CHDZR^{12}$, $CH{=}CHZR^{12}$, $CH_2CH{=}CHZR^{12}$, $C{\equiv}CZR^{12}$, $C{\equiv}CCH_2ZR^{12}$, $CH_2C{\equiv}CZR^{12}$, and $CH_2C{\equiv}CH_2ZR^{12}$.

E38: The compound of E37, wherein $R^6$ is selected from $CH_2ZR^{12}$, $CH_2CH_2ZR^{12}$, $CH_2CH_2CH_2ZR^{12}$, $CH_2CH_2CH_2CH_2ZR^{12}$, $CH(CH_3)CH_2ZR^{12}$, $CH(CH_3)CH_2CH_2ZR^{12}$, $CH_2CH(CH_3)\ ZR^{12}$, $CH{=}CHZR^{12}$, $CH_2CH{=}CHZR^{12}$, $CH{=}CH_2CHZR^{12}$, $C{\equiv}CCH_2ZR^{12}$, $CH_2C{\equiv}CZR^{12}$, and $CH_2C{\equiv}CH_2ZR^{12}$.

E39: The compound of E32, wherein $R^6$ is selected from $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, each of which is optionally substituted with one to four substituents independently selected from halo, $C_1$-$C_6$alkyl, $OR^{13}$, and $C(O)R^{13}$, and wherein available hydrogen atoms are optionally independently replaced with a fluorine atom and/or a chlorine atom and/or available hydrogen atoms are optionally replaced with deuterium.

E40: The compound of E39, wherein $R^6$ is selected from $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, $C_1$-$C_4$alkylene$C_5$-$C_{10}$heteroaryl, $C_1$-$C_4$fluoroalkylene$C_3$-$C_7$cycloalkyl, $C_1$-$C_4$fluoroalkylene$C_3$-$C_{10}$heterocycloalkyl, $C_1$-$C_4$fluoroalkylene$C_6$-$C_{10}$aryl, $C_1$-$C_4$fluoroalkylene$C_5$-$C_{10}$heteroaryl, $C_1$-$C_4$deuteroalkylene$C_3$-$C_7$cycloalkyl, $C_1$-$C_4$deuteroalkylene$C_3$-$C_{10}$heterocycloalkyl, $C_1$-$C_4$deuteroalkylene$C_6$-$C_{10}$aryl, $C_1$-$C_4$deuteroalkylene$C_5$-$C_{10}$heteroaryl, $C_1$-$C_4$deuterofluoroalkylene$C_3$-$C_7$cycloalkyl, $C_1$-$C_4$deuterofluoroalkylene$C_3$-$C_{10}$heterocycloalkyl, $C_1$-$C_4$deuterofluoroalkylene$C_6$-$C_{10}$aryl, and $C_1$-$C_4$deuterofluoroalkylene$C_5$-$C_{10}$heteroaryl, in which each of the cyclic groups is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{13}$, and $C(O)R^{13}$, and wherein available hydrogen atoms are optionally independently replaced with a fluorine atom and/or a chlorine atom and/or available hydrogen atoms are optionally replaced with deuterium.

E41: The compound of E40, wherein the substituents on $R^6$ are independently selected from one to four of F, Cl, Br, $CH_3$, $CH_2CH_3$, $CH_2CH_2CH_3$, $CH(CH_3)_2$, $C(CH_3)_3$, $CD_2H$, $CDH_2$, $CD_3$, $CF_3$, $CHF_2$, $CH_2F$, $CH_2CH_2F$, $CF_2CF_3$, $CH_2CH_2D$, $CH_2CD_2H$, $CD_2CD_3$, $OR^{14}$, and $C(O)R^{14}$.

E42: The compound of any one of E35 to E38, wherein Z is selected from $NR^{16}C(O)$, $NR^{16}C(O)O$, $C(O)NR^{16}$, $OC(O)NR^{16}$, and $NR^{16}$.

E43: The compound of any one of E35 to E38, wherein Z is selected from O, C(O), $NR^{16}C(O)$, and $NR^{16}C(O)O$.

E44: The compound of any one of E1 to E43, wherein $R^7$ and $R^8$ are independently selected from H, halo, and $C_1$-$C_4$alkyl, wherein available hydrogen atoms are optionally independently replaced with a fluorine atom and/or a chlorine atom and/or available hydrogen atoms are optionally replaced with deuterium.

E45: The compound of E44, wherein $R^7$ and $R^8$ are independently selected from H, D, F, Cl, Br, $C_1$-$C_4$alkyl, $C_1$-$C_4$fluoroalkyl, $C_1$-$C_4$deuteroalkyl, and $C_1$-$C_4$deuterofluoroalkyl.

E46: The compound of E45, wherein $R^7$ and $R^8$ are independently selected from H, F, Br, Cl, D, $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3CF_2CF_3$, $CH_2CH_2D$, $CH_2CD_2H$, and $CD_2CD_3$.

E47: The compound of E46, wherein $R^7$ and $R^8$ are independently selected from H, F, and D.

E48: The compound of E47, wherein $R^7$ and $R^8$ are independently selected from H and D.

E49: The compound of any one of E1 to E48, wherein each $R^9$ is independently selected from D, halo, $C_1$-$C_4$alkyl, OH, $OC_1$-$C_4$alkyl, $C_1$-$C_4$alkyleneOH, and $C_1$-$C_4$alkylene$OC_1$-$C_6$alkyl, wherein available hydrogen atoms are optionally independently replaced with a fluorine atom and/or a chlorine atom and/or available hydrogen atoms are optionally replaced with deuterium.

E50: The compound of E49, wherein at least one $R^9$ is selected from halo and $C_1$-$C_4$alkyl, wherein available hydrogen atoms are optionally independently replaced with a fluorine atom and/or a chlorine atom and/or available hydrogen atoms are optionally replaced with deuterium.

E51: The compound of E50, wherein at least one $R^9$ is selected from F, Cl, Br, OH, $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3$, $CF_2CF_3$, $CH_2CH_2D$, $CH_2CD_2H$, $CH_2CD_3CD_2CD_3$, $CH_2CH_2CH_3$, $CH_2CH_2CHF_2$, $CH_2CH_2CFH_2$, $CH_2CH_2CF_3$, $CH_2CH_2CHD_2$, $CH_2CH_2CDH_2$, $CH_2CH_2CD_3CH(CH_3)_2$, $CH(CF_3)_2$, $CH(CHF_2)_2$, $CH(CFH_2)_2$, $CH(CD_3)_2$, $CH(CHD_2)_2$, $CH(CDH_2)_2$, $C(CH_3)_3$, $C(CF_3)_3$, $C(CHF_2)_3$, $C(CFH_2)_3$, $C(CD_3)_3$, $C(CHD_2)_3$, $C(CDH_2)_3$, $CH_2CH_2CH_2CH_3$, $CH_2CH_2CH_2CF_3$, $CH_2CH_2CH_2CD_3$, $CH_2CH(CH_3)_2$, $CH_2CH(CD_3)_2$, $CH_2CH(CF_3)_2$, $CH(CH_3)CH_2CH_3$, $CH(CH_3)CH_2CF_3$, $CH(CH_3)CH_2CD_3$, $CH_2C(CH_3)_3$, $CH_2C(CF_3)_3$, $CH_2C(CD_3)_3$, $CH_2CH_2C(CH_3)_3$, $CH_2CH_2C(CF_3)_3$, and $CH_2CH_2C(CD_3)_3$.

E52: The compound of E49, wherein at least one $R^9$ is selected from OH, $OC_1$-$C_4$alkyl, $C_1$-$C_4$alkyleneOH, and $C_1$-$C_4$alkyleneOC$_1$-$C_6$alkyl, wherein available hydrogen atoms are optionally independently replaced with a fluorine atom and/or a chlorine atom and/or available hydrogen atoms are optionally replaced with deuterium.

E53: The compound of E52, wherein at least one $R^9$ is selected from OH, $OC_1$-$C_4$alkyl, $OC_1$-$C_4$deuteroalkyl, $OC_1$-$C_4$fluoroalkyl, $OC_1$-$C_4$deuterofluoroalkyl, $C_1$-$C_4$alkyleneOH, $C_1$-$C_4$fluoroalkyleneOH, $C_1$-$C_4$deuteroalkyleneOH, $C_1$-$C_4$deuterofluoroalkyleneOH, $C_1$-$C_4$alkyleneOC$_1$-$C_4$alkyl, $C_1$-$C_4$alkyleneOC$_1$-$C_4$fluoroalkyl, $C_1$-$C_4$alkyleneOC$_1$-$C_4$deuteroalkyl, $C_1$-$C_4$alkyleneOC$_1$-$C_4$deuterofluoroalkyl, $C_1$-$C_4$fluoroalkyleneOC$_1$-$C_4$alkyl, $C_1$-$C_4$deuteroalkyleneOC$_1$-$C_4$alkyl, $C_1$-$C_4$deuterofluoroalkyleneOC$_1$-$C_4$alkyl, $C_1$-$C_4$fluoroalkyleneOC$_1$-$C_4$fluoroalkyl, $C_1$-$C_4$fluoroalkyleneOC$_1$-$C_4$deuteroalkyl, $C_1$-$C_4$deuteroalkyleneOC$_1$-$C_4$fluoroalkyl, $C_1$-$C_4$deuteroalkyleneOC$_1$-$C_4$deuteroalkyl, $C_1$-$C_4$deuterofluoroalkyleneOC$_1$-$C_4$fluoroalkyl, $C_1$-$C_4$fluoroalkyleneOC$_1$-$C_4$deuterofluoroalkyl, and $C_1$-$C_4$deuterofluoroalkyleneOC$_1$-$C_4$deuterofluoroalkyl.

E54: The compound of E53, wherein at least one $R^9$ is selected from OH, $OCH_3$, $OCD_2H$, $OCDH_2$, $OCD_3$, $OCF_2H$, $OCFH_2$, $OCF_3$, $OCH_2CH_3$, $OCH_2CH_2F$, $OCH_2CF_2H$, $OCH_2CF_3$, $OCF_2CF_3$, $OCH_2CH_2D$, $OCH_2CD_2H$, $OCH_2CD_3OCD_2CD_3$, $OCH_2CH_2CH_3$, $OCH_2CH_2CHF_2$, $OCH_2CH_2CFH_2$, $OCH_2CH_2CF_3$, $OCH_2CH_2CHD_2$, $OCH_2CH_2CDH_2$, $OCH_2CH_2CD_3$, $OCH(CH_3)_2$, $OCH(CF_3)_2$, $OCH(CHF_2)_2$, $OCH(CFH_2)_2$, $OCH(CD_3)_2$, $OCH(CHD_2)_2$, $OCH(CDH_2)_2$, $OC(CH_3)_3$, $OC(CF_3)_3$, $OC(CHF_2)_3$, $OC(CFH_2)_3$, $OC(CD_3)_3$, $OC(CHD_2)_3$, $OC(CDH_2)_3$, $OCH_2CH_2CH_2CH_3$, $OCH_2CH_2CH_2CF_3$, $OCH_2CH_2CH_2CD_3$, $OCH_2CH(CH_3)_2$, $OCH_2CH(CD_3)_2$, $OCH_2CH(CF_3)_2$, $OCH(CH_3)CH_2CH_3$, $OCH(CH_3)CH_2CF_3$, $OCH(CH_3)CH_2CD_3$, $OCH_2C(CH_3)_3$, $OCH_2C(CF_3)_3$, $OCH_2C(CD_3)_3$, $OCH_2CH_2C(CH_3)_3$, $OCH_2CH_2C(CF_3)_3$, $OCH_2CH_2C(CD_3)_3$, $CH_2OH$, $CF_2OH$, $CD_2OH$, $CH_2CH_2OH$, $CF_2CF_2OH$, $CH_2CF_2OH$, $CH_2CD_2OH$, $CD_2CD_2OH$, $CH_2OCH_3$, $CH_2OCD_2H$, $CH_2OCDH_2$, $CH_2OCD_3$, $CH_2OCF_3$, $CH_2OCHF_2$, $CH_2OCH_2F$, $CH_2CH_2OCH_3$, $CH_2CH_2OCD_2H$, $CH_2CH_2OCDH_2$, $CH_2CH_2OCD_3$, $CH_2CH_2OCF_3$, $CH_2CH_2OCHF_2$, and $CH_2CH_2OCH_2F$.

E55: The compound of E54, wherein at least one $R^9$ is selected from OH, $OCH_3$, $OCF_2H$, $OCFH_2$, $OCF_3$, and $OCD_3$.

E56: The compound of any one of E1 to E55, wherein n is an integer selected from 0 and 1.

E57: The compound of any one of E1 to E56, wherein $R^{10}$ is selected from H, $C_1$-$C_6$alkyl, $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkyleneC$_3$-$C_7$cycloalkyl, $C_1$-$C_4$alkyleneC$_3$-$C_{10}$heterocycloalkyl, $C_1$-$C_4$alkyleneC$_6$-$C_{10}$aryl, and $C_1$-$C_4$alkyleneC$_5$-$C_{10}$heteroaryl, the latter eight groups being optionally substituted with one to four substituents independently selected from halo, $C_1$-$C_6$alkyl, $OR^{15}$ and $C(O)R^{15}$, and wherein available hydrogen atoms are optionally independently replaced with a fluorine atom and/or a chlorine atom and/or available hydrogen atoms are optionally replaced with deuterium.

E58: The compound of E57, wherein $R^{10}$ is selected from H, D, $C_1$-$C_6$alkyl, $C_1$-$C_6$deuteroalkyl, $C_1$-$C_6$fluoroalkyl, and $C_1$-$C_6$deuterofluoroalkyl.

E59: The compound of E58, wherein $R^{10}$ is selected from H, D, $CH_3$, $CD_2H$, $CDH_2$, $CD_3$, $CF_2H$, $CFH_2$, $CF_3$, $CH_2CH_3$, $CH_2CH_2F$, $CH_2CF_2H$, $CH_2CF_3$, $CF_2CF_3$, $CH_2CH_2D$, $CH_2CD_2H$, $CH_2CD_3CD_2CD_3$, $CH_2CH_2CH_3$, $CH_2CH_2CHF_2$, $CH_2CH_2CFH_2$, $CH_2CH_2CF_3$, $CH_2CH_2CHD_2$, $CH_2CH_2CDH_2$, $CH_2CH_2CD_3CH(CH_3)_2$, $CH(CF_3)_2$, $CH(CHF_2)_2$, $CH(CFH_2)_2$, $CH(CD_3)_2$, $CH(CHD_2)_2$, $CH(CDH_2)_2$, $C(CH_3)_3$, $C(CF_3)_3$, $C(CHF_2)_3$, $C(CFH_2)_3$, $C(CD_3)_3$, $C(CHD_2)_3$, $C(CDH_2)_3$, $CH_2CH_2CH_2CH_3$, $CH_2CH_2CH_2CF_3$, $CH_2CH_2CH_2CD_3$, $CH_2CH(CH_3)_2$, $CH_2CH(CD_3)_2$, $CH_2CH(CF_3)_2$, $CH(CH_3)CH_2CH_3$, $CH(CH_3)CH_2CF_3$, $CH(CH_3)CH_2CD_3$, $CH_2CH(CH_3)CH_3$, $CH_2CH(CH_3)$ $CF_3$, $CH_2CH(CH_3)$ $CD_3$, $CH_2C(CH_3)_3$, $CH_2C(CF_3)_3$, $CH_2C(CD_3)_3$, $CH_2CH_2C(CH_3)_3$, $CH_2CH_2C(CF_3)_3$, and $CH_2CH_2C(CD_3)_3$ E60: The compound of E57, wherein $R^{10}$ is selected from $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkyleneC$_3$-$C_7$cycloalkyl, $C_1$-$C_4$alkyleneC$_3$-$C_{10}$heterocycloalkyl, $C_1$-$C_4$alkyleneC$_6$-$C_{10}$aryl, and $C_1$-$C_4$alkyleneC$_5$-$C_{10}$heteroaryl, the latter eight groups being optionally substituted one to four substituents independently selected from halo, $C_1$-$C_6$alkyl, $OR^{15}$, and $C(O)R^{15}$, and wherein available hydrogen atoms are optionally independently replaced with a fluorine atom and/or a chlorine atom and/or available hydrogen atoms are optionally replaced with deuterium.

E61: The compound of E57, wherein $R^{10}$ is selected from $C_2$-$C_6$alkenyl, $C_2$-$C_6$fluoroalkenyl, $C_2$-$C_6$deuteroalkenyl, $C_2$-$C_6$deuterofluoroalkenyl, $C_2$-$C_6$alkynyl, $C_2$-$C_6$fluoroalkynyl, $C_2$-$C_6$deuteroalkynyl, and $C_2$-$C_6$deuterofluoroalkynyl.

E62: The compound of E61, wherein $R^{10}$ is selected from $CH{=}CH_2$, $CH_2CH{=}CH_2$, $CF_2CH{=}CH_2$, $CD_2CH{=}CH_2$, $CH{=}CH_2CH_3$, $CH{=}CH_2CF_3$, $CH{=}CH_2CHF_2$, $CH{=}CH_2CH_2F$, $CH{=}CH_2CD_3$, $CH{=}CH_2CHD_2$, $CH{=}CH_2CH_2D$, $C{\equiv}CH$, $C{\equiv}CCH_3$, $C{\equiv}CCF_3$, $C{\equiv}CCHF_2$, $C{\equiv}CCFH_2$, $C{\equiv}CCD_3$, $C{\equiv}CCHD_2$, $C{\equiv}CCDH_2$, $CH_2C{\equiv}CH$, $CF_2C{\equiv}CH$, $CD_2C{\equiv}CH$, $CH_2C{\equiv}CCH_3$, $CF_2C{\equiv}CCH_3$, $CD_2C{\equiv}CCH_3$, $CH_2C{\equiv}CCD_3$, $CF_2C{\equiv}CCD_3$, $CD_2C{\equiv}CCD_3$, $CH_2C{\equiv}CCF_3$, $CF_2C{\equiv}CCF_3$, $CD_2C{\equiv}CCF_3$, $CH_2C{\equiv}CCHD_2$, $CF_2C{\equiv}CHD_2$, $CD_2C{\equiv}CHD_2$, $CH_2C{\equiv}CHF_2$, $CF_2C{\equiv}CHF_2$, and $CD_2C{\equiv}CHF_2$.

E63: The compound of E57, wherein $R^{10}$ is selected from $C_1$-$C_6$alkyleneZ'$R^{14}$, $C_2$-$C_6$alkenyleneZ'$R^{14}$, and $C_2$-$C_6$alkynyleneZ'$R^{14}$, wherein available hydrogen atoms are optionally independently replaced with a fluorine atom and/or a chlorine atom and/or available hydrogen atoms are optionally replaced with deuterium.

E64: The compound of E63, wherein $R^{10}$ is selected from $C_1$-$C_4$alkyleneZ'$R^{14}$, $C_1$-$C_4$fluoroalkyleneZ'$R^{14}$, $C_1$-$C_4$deuteroalkyleneZ'$R^{14}$, $C_1$-$C_4$deuterofluoroalkyleneZ'$R^{14}$, $C_2$-$C_4$alkenyleneZ'$R^{14}$, $C_2$-$C_4$fluoroalkenyleneZ'$R^{14}$, $C_2$-$C_4$deuteroalkenyleneZ'$R^{14}$, $C_2$-$C_4$deuterofluoroalkenyleneZ'$R^{14}$, $C_2$-$C_4$alkynyleneZ'$R^{14}$, $C_2$-$C_4$fluoroalkynyleneZ'$R^{14}$, $C_2$-$C_4$deuteroalkynyleneZ'$R^{14}$, and $C_2$-$C_4$deuterofluoroalkynyleneZ'$R^{14}$.

E65: The compound of E64, wherein $R^{10}$ is selected from $CH_2Z'R^{14}$, $CH_2CH_2Z'R^{14}$, $CH_2CH_2CH_2Z'R^{14}$, $CH_2CH_2CH_2CH_2Z'R^{14}$, $CH(CH_3)CH_2Z'R^{14}$, $CH(CH_3)CH_2CH_2Z'R^{14}$, $CH_2CH(CH_3)Z'R^{14}$, $CF_2Z'R^{14}$, $CFHZ'R^{14}$, $CH_2CHFZ'R^{14}$, $CH_2CF_2Z'R^{14}$, $CF_2CF_2Z'R^{14}$, $CH_2CH_2CF_2Z'R^{14}$, $CH_2CH_2CFHZ'R^{14}$, $CH_2CH_2CF_2Z'R^{14}$, $CH(CH_3)CF_2Z'R^{14}$, $CH(CH_3)CHFZ'R^{14}$, $CH_2CH_2CH_2CF_2Z'R^{14}$, $CH_2CH_2CH_2CHFZ'R^{14}$, $CH(CH_3)CH_2CF_2Z'R^{14}$, $CH(CH_3)CH_2CHFZ'R^{14}$, $CD_2Z'R^{14}$, $CDHZ'R^{14}$, $CH_2CHDZ'R^{14}$, $CH_2CD_2Z'R^{14}$, $CD_2CD_2Z'R^{14}$, $CH_2CH_2CD_2Z'R^{14}$, $CH_2CH_2CDHZ'R^{14}$, $CH_2CH_2CD_2Z'R^{14}$, $CH(CH_3)CD_2Z'R^{14}$, $CH(CH_3)CHDZ'R^{14}$, $CH_2CH_2CH_2CD_2Z'R^{14}$, $CH_2CH_2CH_2CHDZ'R^{14}$, $CH(CH_3)CH_2CD_2Z'R^{14}$, $CH(CH_3)CH_2CHDZ'R^{14}$, $CH{=}CHZ'R^{14}$, $CH_2CH{=}CHZ'R^{14}$, $C{\equiv}CZ'R^{14}$, $C{\equiv}CCH_2Z'R^{14}$, $CH_2C{\equiv}CZ'R^{14}$, and $CH_2C{\equiv}CH_2Z'R^{14}$.

E66: The compound of E57, wherein $R^{10}$ is selected from $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, $C_1$-$C_4$alkylene$C_5$-$C_{10}$heteroaryl, $C_1$-$C_4$fluoroalkylene$C_3$-$C_7$cycloalkyl, $C_1$-$C_4$fluoroalkylene$C_3$-$C_{10}$heterocycloalkyl, $C_1$-$C_4$fluoroalkylene$C_6$-$C_{10}$aryl, $C_1$-$C_4$fluoroalkylene$C_5$-$C_{10}$heteroaryl, $C_1$-$C_4$deuteroalkylene$C_3$-$C_7$cycloalkyl, $C_1$-$C_4$deuteroalkylene$C_3$-$C_{10}$heterocycloalkyl, $C_1$-$C_4$deuteroalkylene$C_6$-$C_{10}$aryl, $C_1$-$C_4$deuteroalkylene$C_5$-$C_{10}$heteroaryl, $C_1$-$C_4$deuterofluoroalkylene$C_3$-$C_7$cycloalkyl, $C_1$-$C_4$deuterofluoroalkylene$C_3$-$C_{10}$heterocycloalkyl, $C_1$-$C_4$deuterofluoroalkylene$C_6$-$C_{10}$aryl, and $C_1$-$C_4$deuterofluoroalkylene$C_5$-$C_{10}$heteroaryl, in which each of the cyclic groups is optionally substituted with one to four substituents independently selected from F, Cl, Br, $C_1$-$C_4$alkyl, $C_1$-$C_4$fluoroalkyl, $C_1$-$C_4$deuteroalkyl, $C_1$-$C_4$deuterofluoroalkyl, $OR^{15}$, and $C(O)R^{15}$, and wherein available hydrogen atoms are optionally independently replaced with a fluorine atom and/or a chlorine atom and/or available hydrogen atoms are optionally replaced with deuterium.

E67: The compound of E66, wherein the substituents on $R^{10}$ are independently selected from one to three of F, Cl, $CH_3$, $CH_2CH_3$, $CH_2CH_2CH_3$, $CH(CH_3)_2$, $CH(CH_3)_2$, $CD_2H$, $CDH_2$, $CD_3$, $CF_3$, $CHF_2$, $CH_2F$, $OR^{15}$, and $C(O)R^{15}$.

E68: The compound of one of E57, E60, and E63 to E65, wherein Z' is selected from $NR^{17}C(O)$, $NR^{17}C(O)O$, $C(O)NR^{17}$, $OC(O)NR^{17}$, and NR 17.

E69: The compound of one of E57, E60, and E63 to E65 wherein Z' is selected from O, C(O), $NR^{17}C(O)$, and $NR^{17}C(O)O$.

E70: The compound of one of E1 to E69, wherein $R^{12}$ and $R^{14}$ are independently selected from H, $C_1$-$C_4$alkyl, $C_3$-$C_7$cycloalkyl, $C_3$-$C_7$heterocycloalkyl, $C_6$-$C_{10}$aryl, and $C_5$-$C_{10}$heteroaryl, the latter four groups being optionally substituted with one to four substituents independently selected from F, Cl, Br, $C_1$-$C_4$alkyl, $OC_1$-$C_4$alkyl, and $C(O)C_1$-$C_4$alkyl, and wherein available hydrogen atoms are optionally independently replaced with a fluorine atom and/or a chlorine atom and/or available hydrogen atoms are optionally replaced with deuterium.

E71: The compound of one of E1 to E70, wherein $R^{11}$, $R^{13}$, $R^{15}$, $R^{16}$, and $R^{17}$ are independently selected from H, D, $C_1$-$C_4$alkyl, $C_1$-$C_4$fluoroalkyl, $C_1$-$C_4$deuteroalkyl, and $C_1$-$C_4$deuterofluoroalkyl.

E72: The compound of any one of E1 to E26 and E44 to E71, wherein X is selected from S, S(O), and $SO_2$, and wherein $R^6$ is selected from $CH_3$, $CD_3$, $CF_3$, $CH_2CH_3$, $CH_2CH_2CH_3$, $CH(CH_3)_2$, $CH_2C(CH_3)_3$, $CH_2CH_2C(CH_3)_3$, $CH_2F$, $CHF_2$, $CH_2CHF_2$, $CH_2CF_3$, $CH_2CH_2CF_3$,

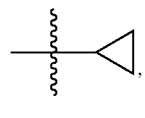, 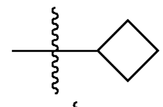, 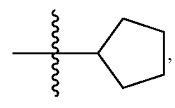,

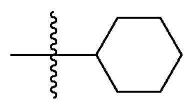, 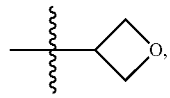, 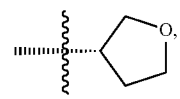,

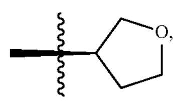, 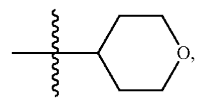, 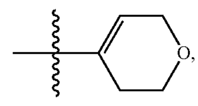,

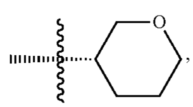, 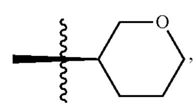, 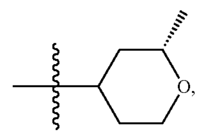,

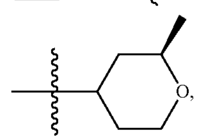, 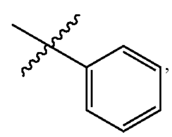,

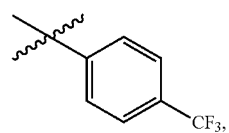, and 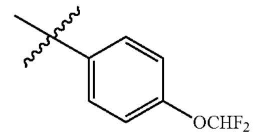

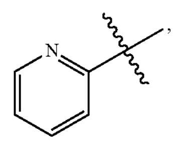, 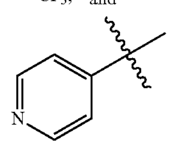 and 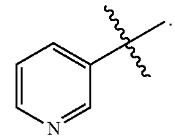.

E73: The compound of any one of E1 to E56 and E70 to E72, X is selected from S, S(O), and $SO_2$, and wherein $R^{10}$ is selected from $CH_3$, $CD_3$, $CH_2CH_3$, $CH_2CH_2CH_3$, $CH(CH_3)_2$, $CH_2C(CH_3)_3$, $CH_2CH_2C(CH_3)_3$, $CH_2F$, $CHF_2$, $CH_2CHF_2$, $CH_2CF_3$, $CH_2CH_2CF_3$, $C_1$-$C_4$alkyleneOCH$_3$, $C_1$-$C_4$alkyleneOCHF$_2$, $C_1$-$C_4$alkyleneOCH$_2$F,

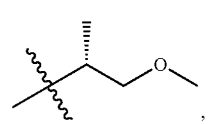, 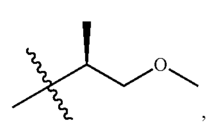,

-continued
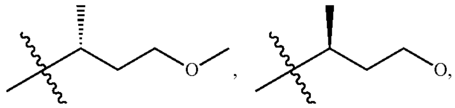
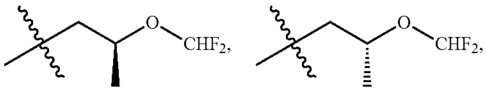
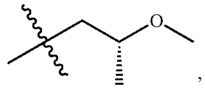
$C_1$-$C_4$alkleneC(O)$CHF_2$, $C_1$-$C_4$alkleneC(O)$CF_3$,
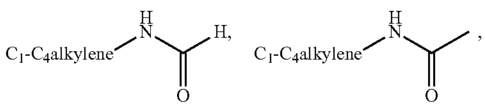
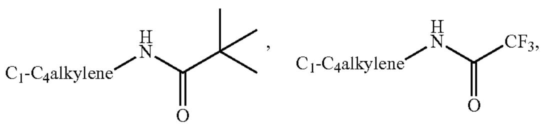
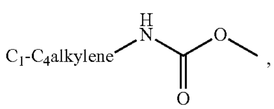
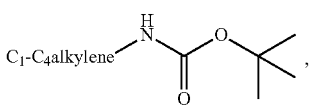
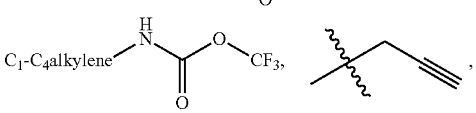
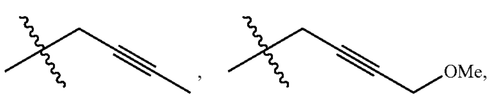
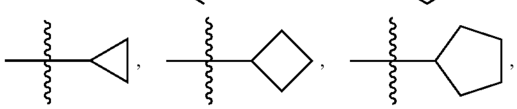
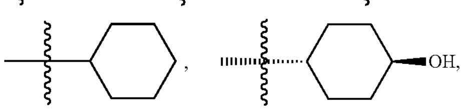
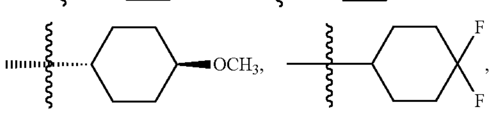
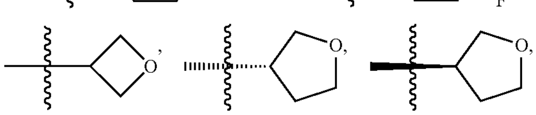
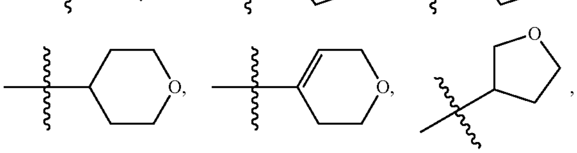
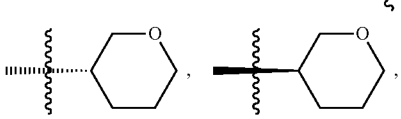
-continued
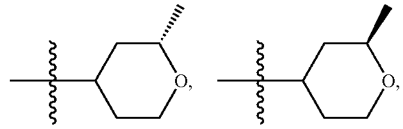
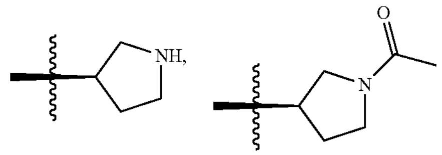
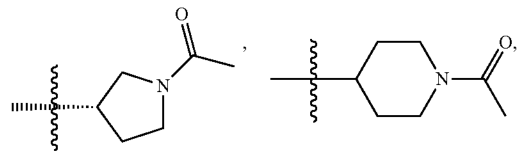
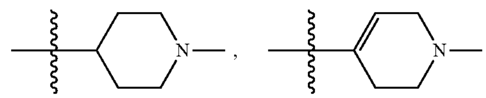
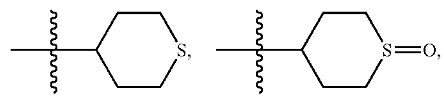
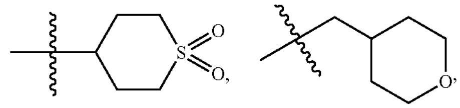
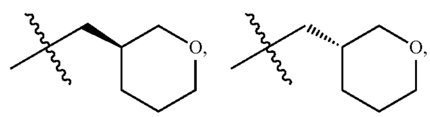
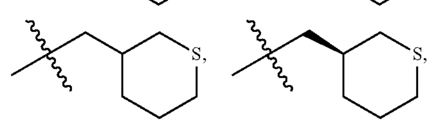
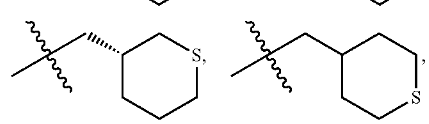
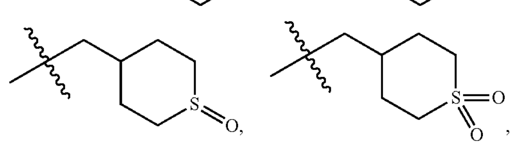
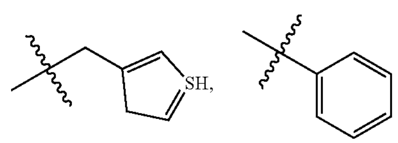
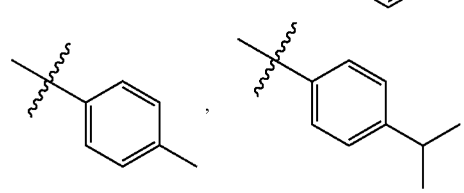
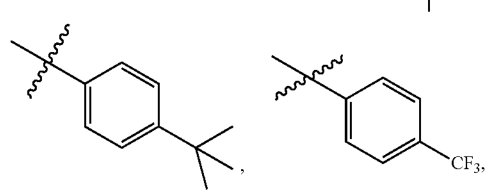

-continued
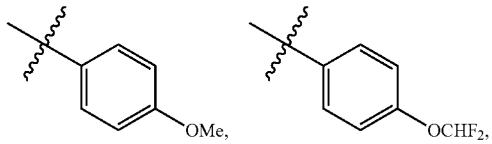
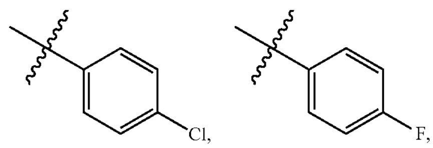
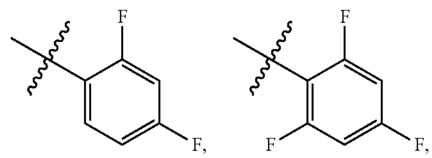
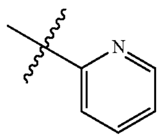
,
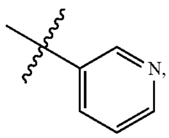
,
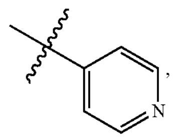
,
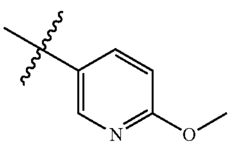
,
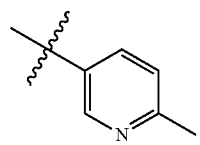
,
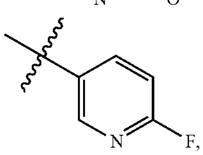
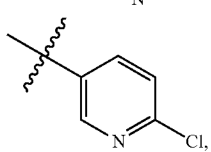
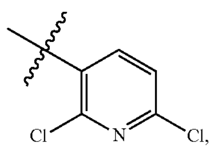
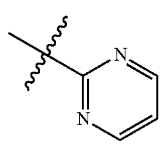
,
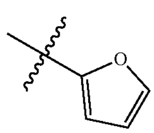
,
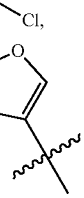
,
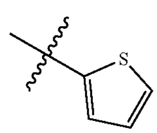
,
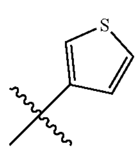
,
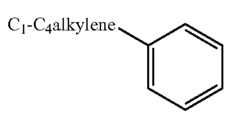
,
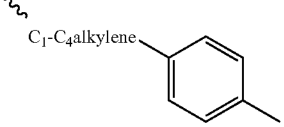
,
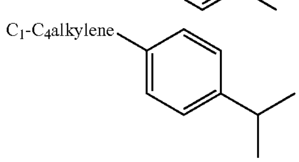
,
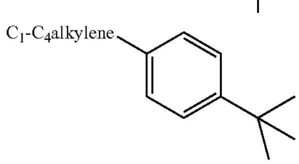
,
-continued
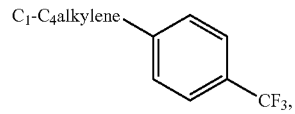
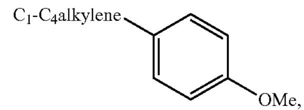
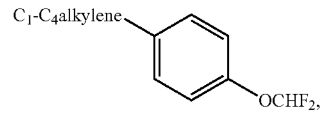
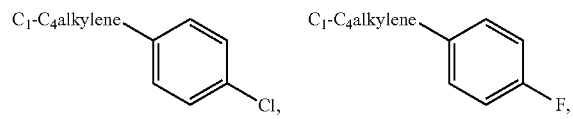
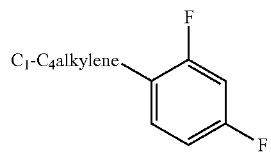
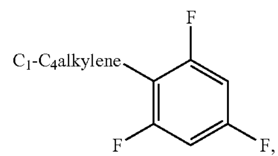
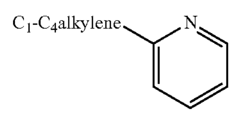
,
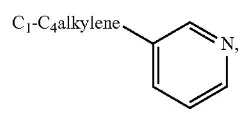
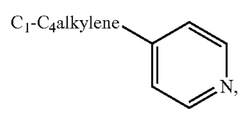
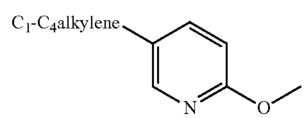
,
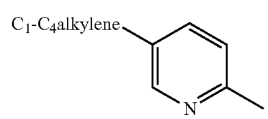
,
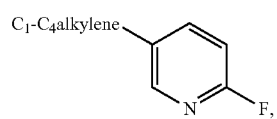
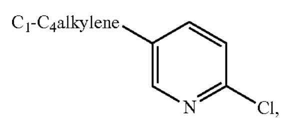
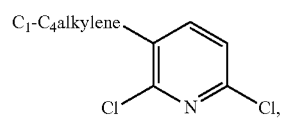
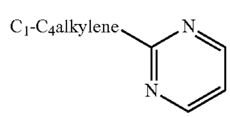
,
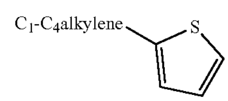
,
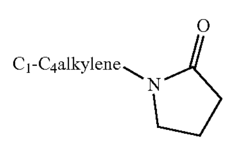
,
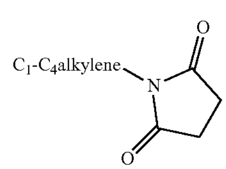
,
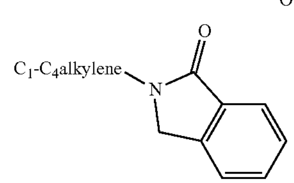
,
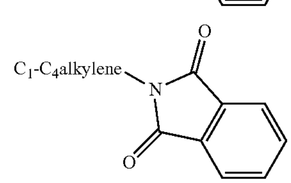
, -continued

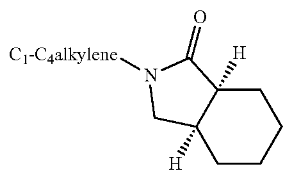,

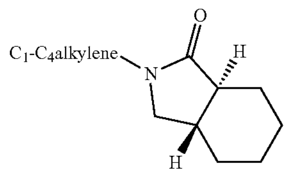,

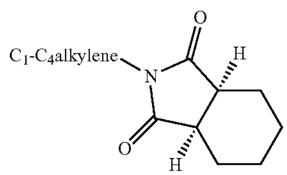,

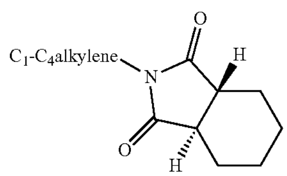,

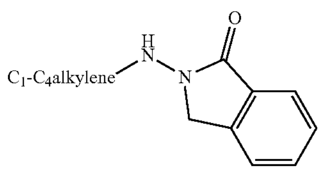,

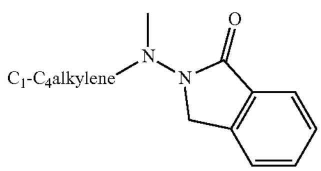,

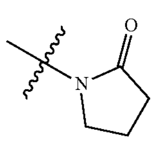, 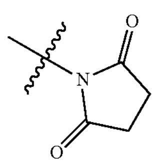, 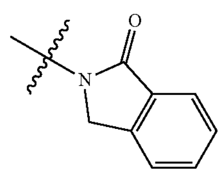,

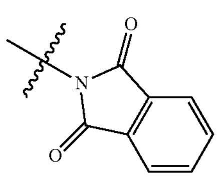, 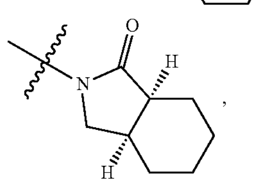,

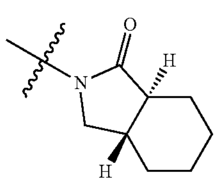, 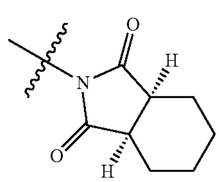,

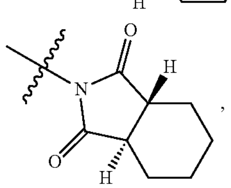, 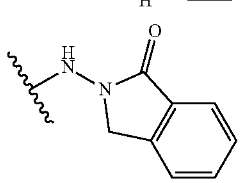, and

-continued

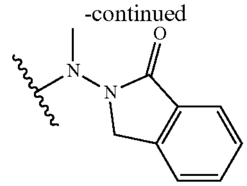.

E74: The compound of any one of E1 to E26, E44 to E56, E70, and E71, wherein X is absent or oxygen, and wherein $R^6$ and $R^{10}$ are independently selected from $CH_3$, $CD_3$, $CH_2CH_3$, $CH_2CH_2CH_3$, $CH(CH_3)_2$, $CH_2C(CH_3)_3$, $CH_2CH_2C(CH_3)_3$, $CH_2F$, $CHF_2$, $CH_2CHF_2$, $CH_2CF_3$, $CH_2CH_2CF_3$, $C_1$-$C_4$alkyleneOC$H_3$, $C_1$-$C_4$alkyleneOCH$F_2$, $C_1$-$C_4$alkyleneOC$H_2$F,

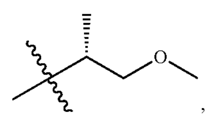, 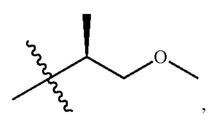,

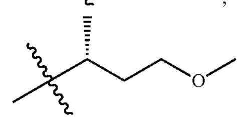, 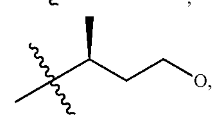,

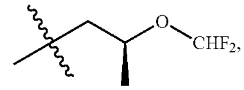 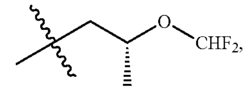

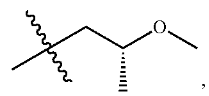, $C_1$-$C_4$alkleneC(O)CH$F_2$, $C_1$-$C_4$alkleneC(O)C$F_3$,

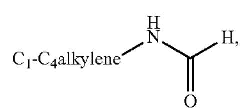 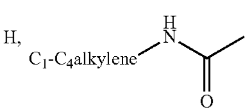,

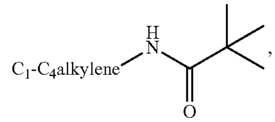, 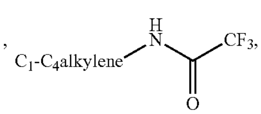

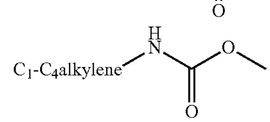, 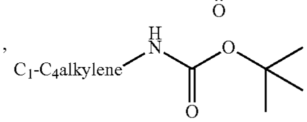,

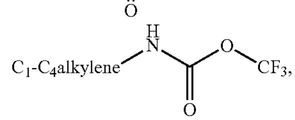 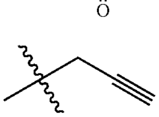,

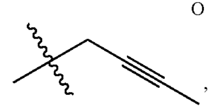, 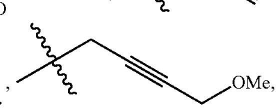

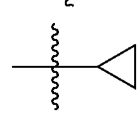, 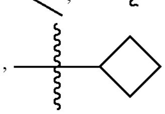, 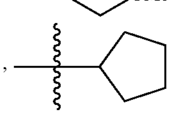,

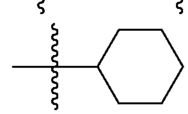, 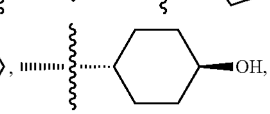

-continued
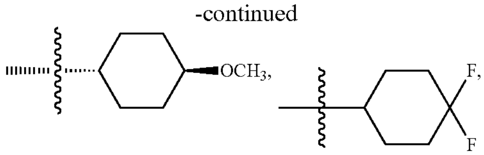
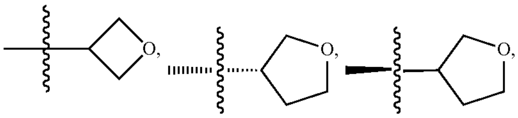
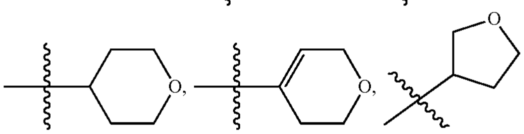
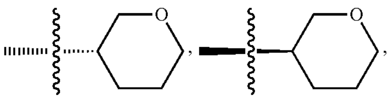
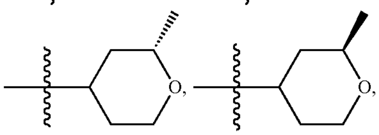
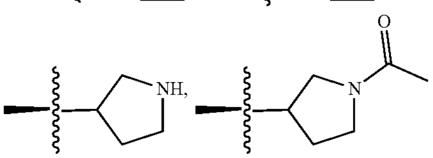
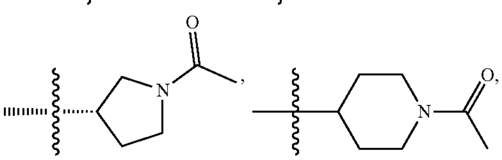
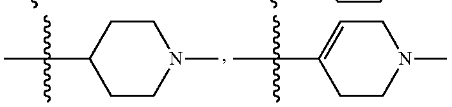
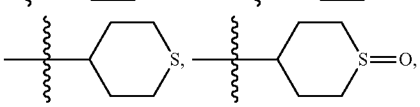
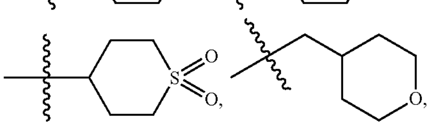
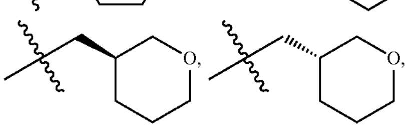
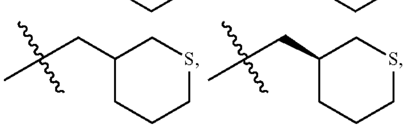
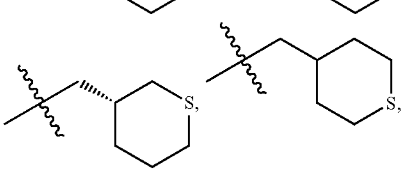
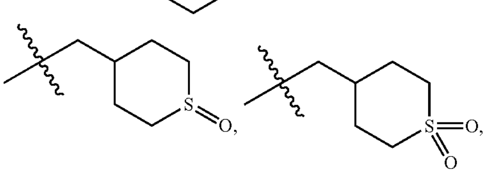
-continued
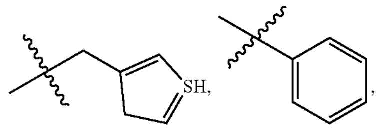
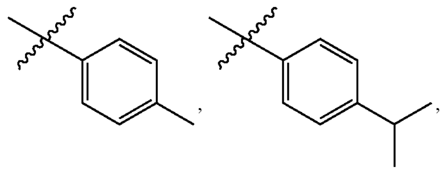
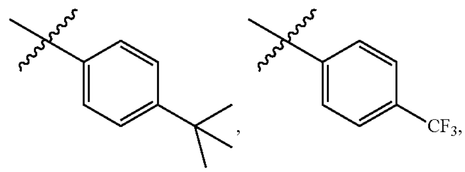
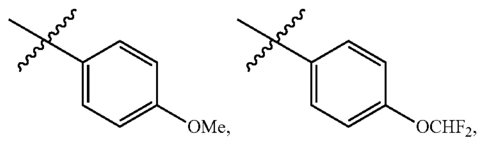
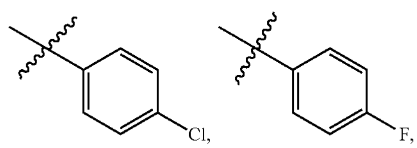
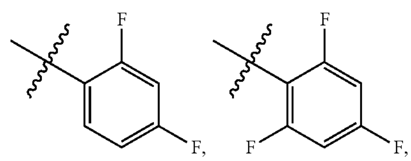
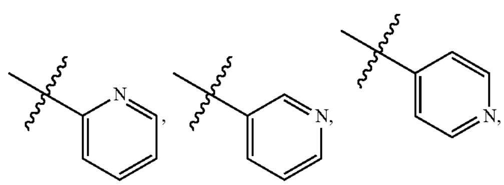
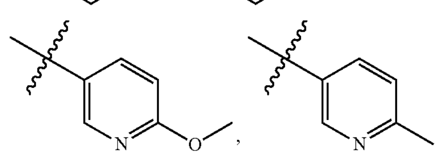
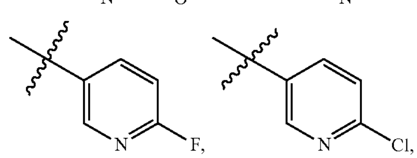
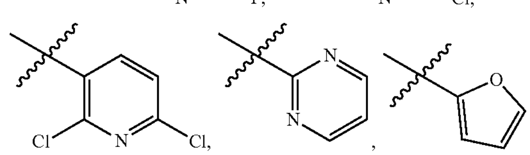
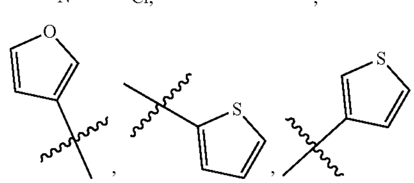

-continued
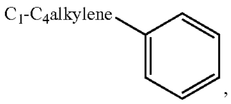,
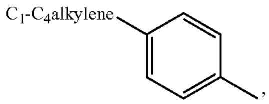,
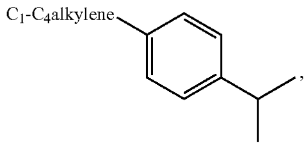,
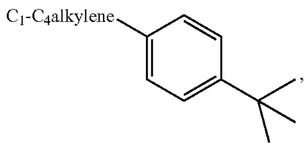,
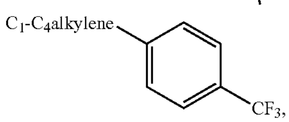,
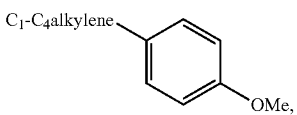,
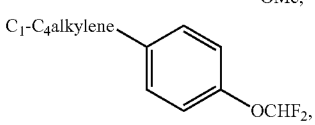,
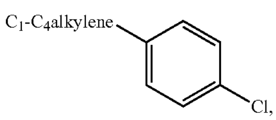,
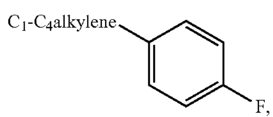,
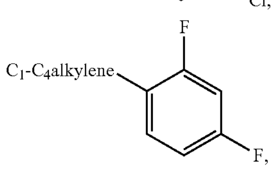,
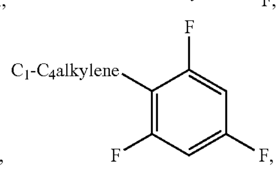,
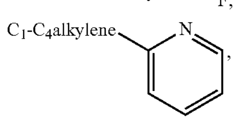,
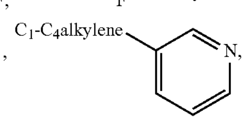,
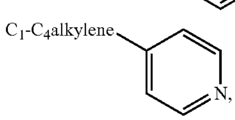,
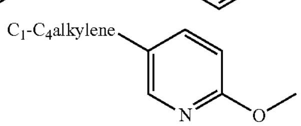,
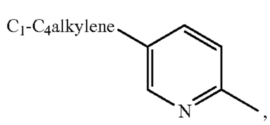,
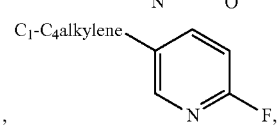,
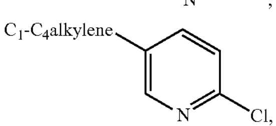,
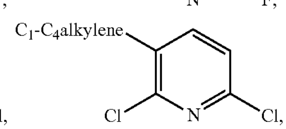,
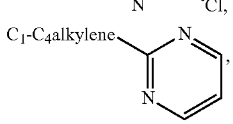,
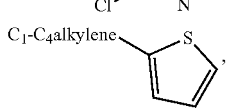,
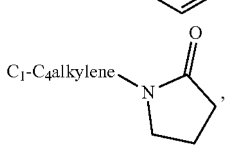,
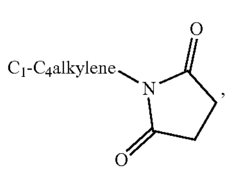,
-continued
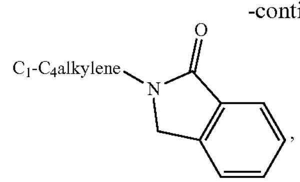,
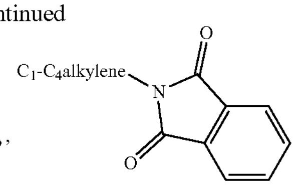,
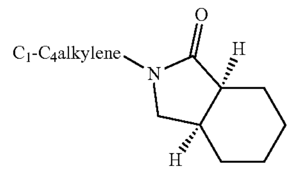,
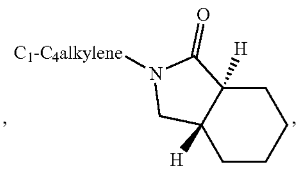,
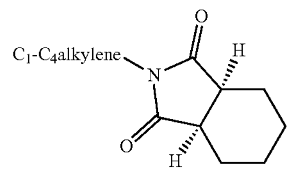,
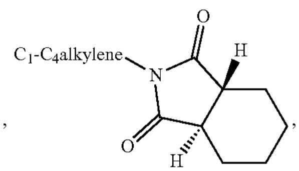,
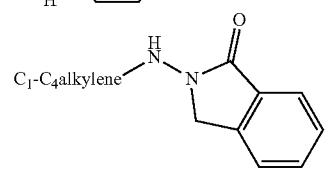,
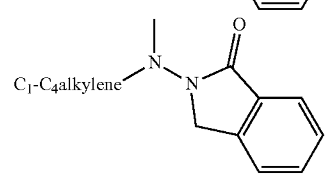,
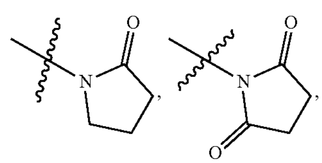,
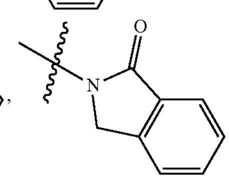,
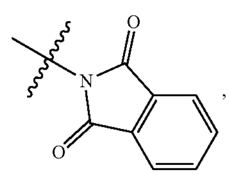,
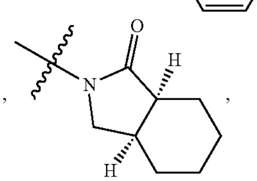,
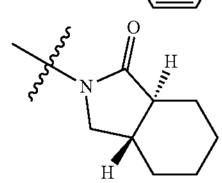,
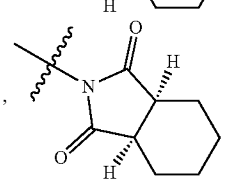,
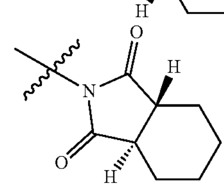,
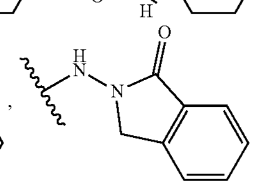, and
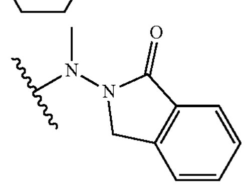.
E75: The compound of any one of E1 to E8, wherein the compound of Formula (I) is selected from the table below:

| Compound | Structure |
|---|---|
| (R) I-1 | 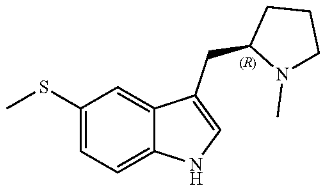 |
| (S) I-1 | 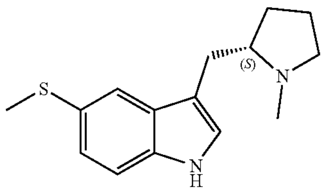 |
| (R) I-2 | 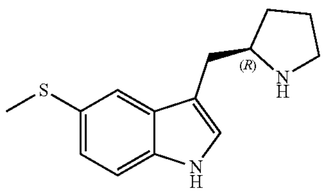 |
| (S) I-2 | 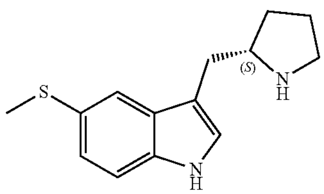 |
| (R) I-3 | 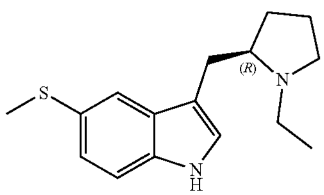 |
| (R) I-4 | 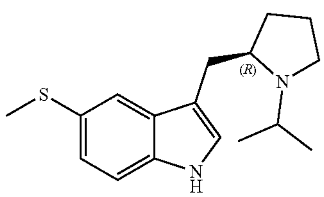 |
| (R) I-5 | 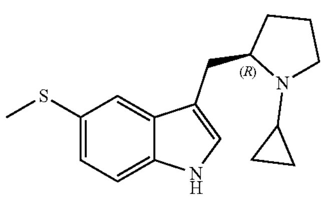 |
| (R) I-6 | 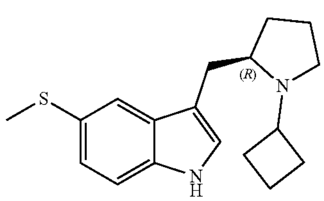 |
-continued
| Compound | Structure |
|---|---|
| (R) I-7 | 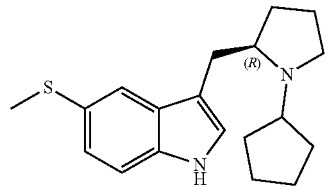 |
| (R, R) I-8 | 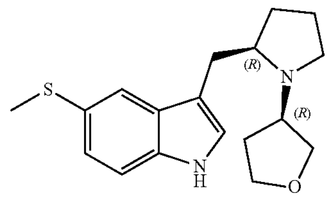 |
| (R, S) I-8 | 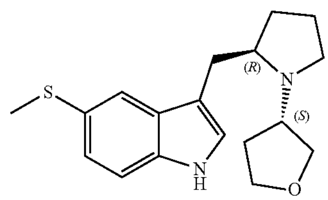 |
| (R, S) I-9 | 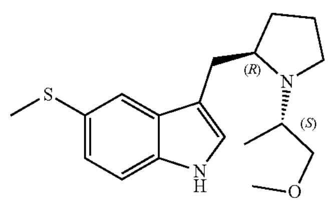 |
| (R, R) I-9 | 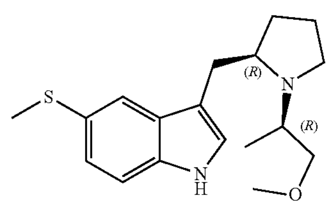 |
| (R) I-10 | 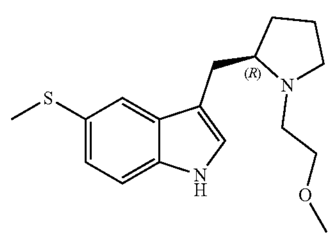 |
| (R) I-11 | 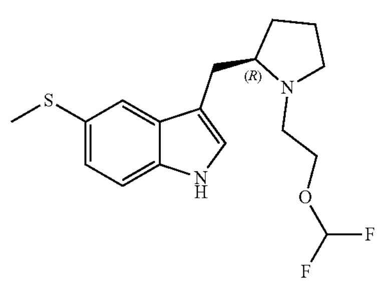 |

-continued
| Compound | Structure |
| --- | --- |
| (R) I-12 | 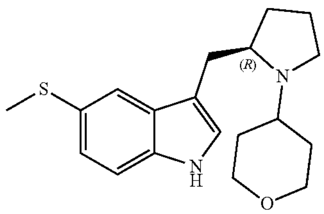 |
| (R, S) I-13 | 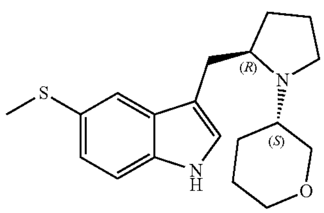 |
| (R, R) I-13 | 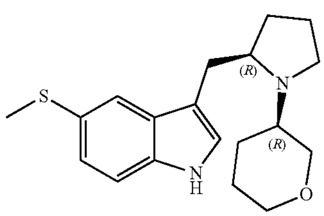 |
| (R) I-14 | 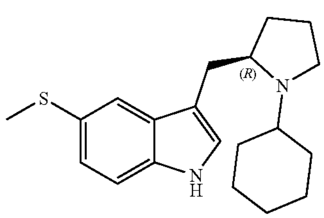 |
| trans (R) I-15 | 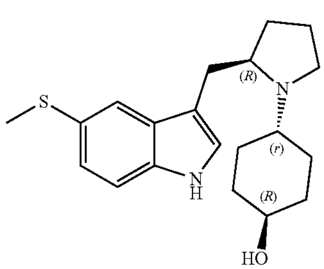 |
| trans (R) I-16 | 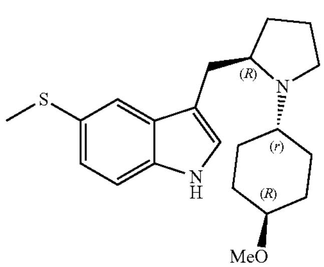 |
-continued
| Compound | Structure |
| --- | --- |
| (R, R) I-17 | 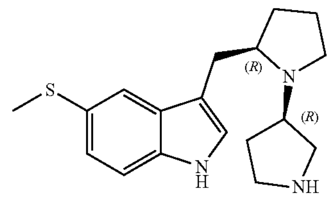 |
| (R) I-18 | 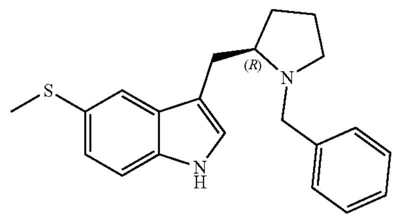 |
| (R) I-19 | 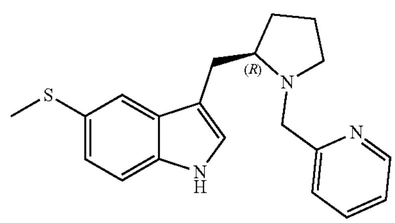 |
| (R) I-20 | 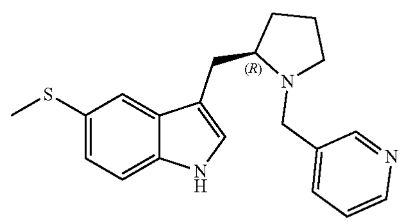 |
| (R) I-21 | 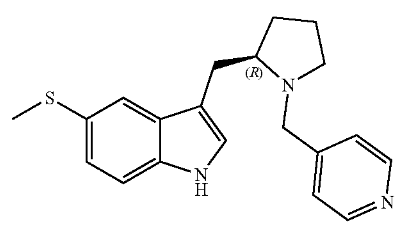 |
| (R) I-22 | 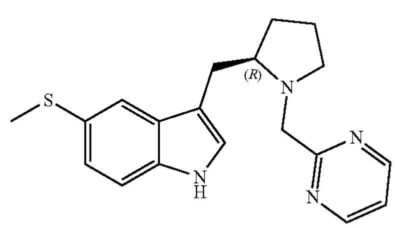 |
| (R) I-23 | 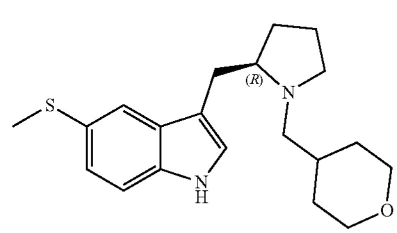 |

-continued
| Compound | Structure |
| --- | --- |
| (R, S) I-24 | 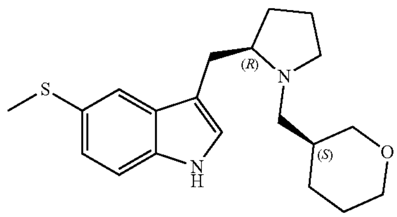 |
| (R, R) I-24 | 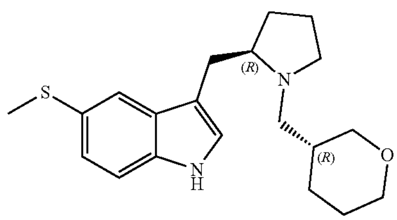 |
| (R, S) I-25 | 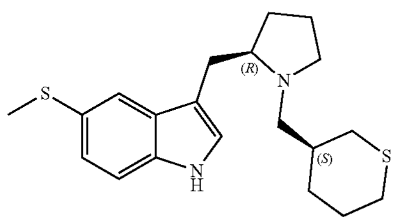 |
| (R, R) I-25 | 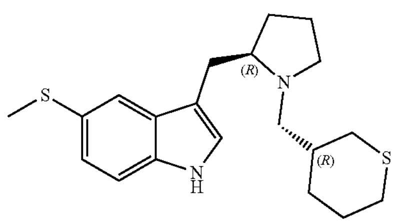 |
| (R) I-26 | 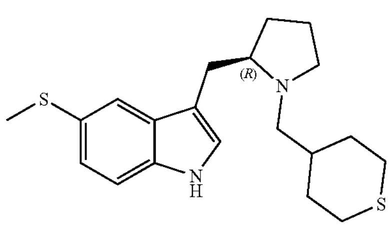 |
| (R) I-27 | 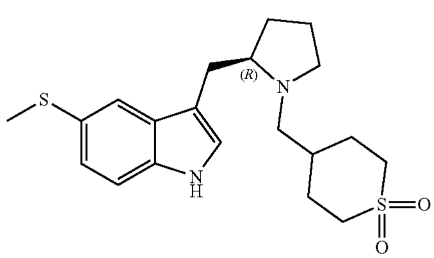 |
-continued
| Compound | Structure |
| --- | --- |
| (R) I-28 | 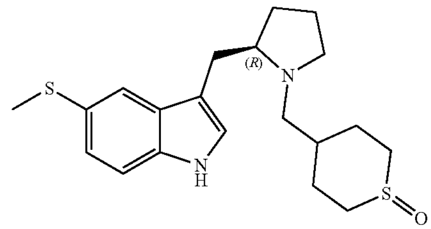 |
| (R) I-29 | 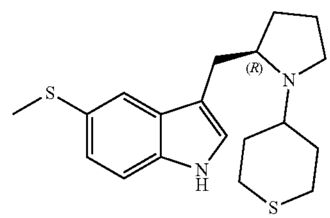 |
| (R) I-30 | 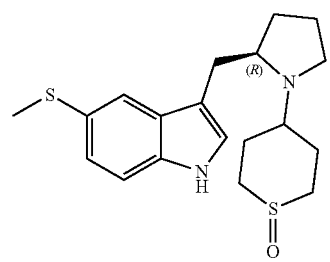 |
| (R) I-31 | 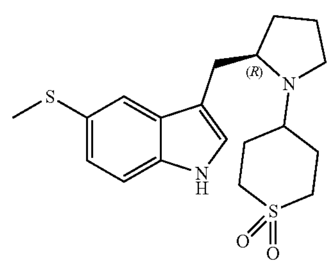 |
| (R) I-32 | 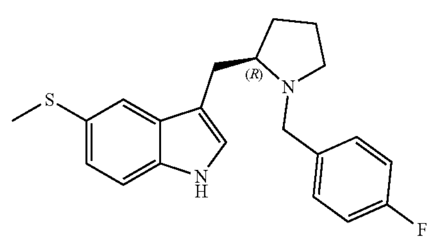 |
| (R) I-33 | 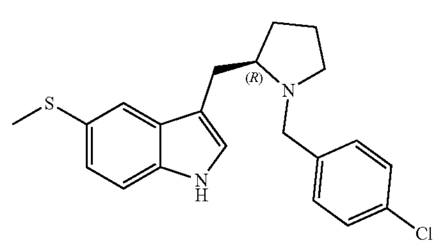 |

-continued
| Compound | Structure |
|---|---|
| (R) I-34 | 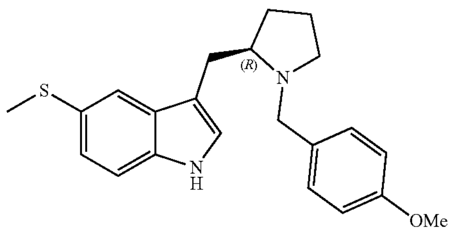 |
| (R) I-35 | 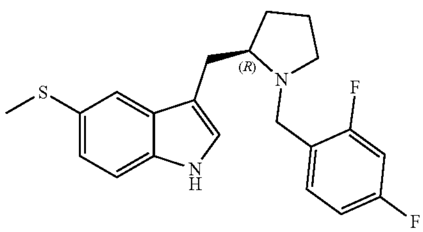 |
| (R) I-36 | 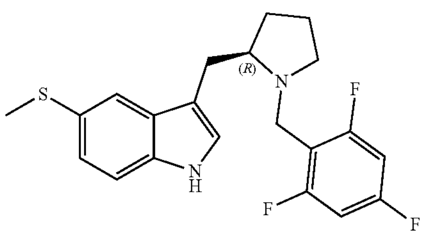 |
| (R) I-37 | 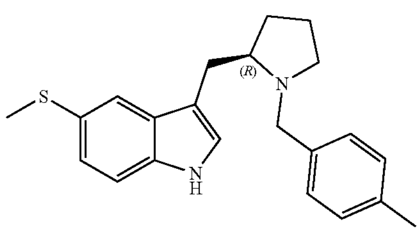 |
| (R) I-38 | 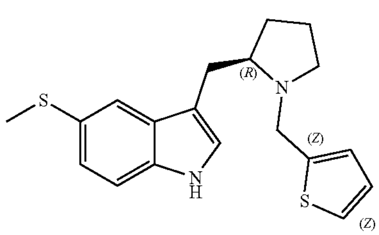 |
| (R) I-39 | 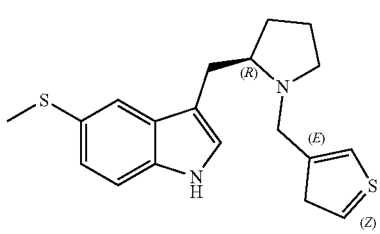 |
-continued
| Compound | Structure |
|---|---|
| (R) I-40 | 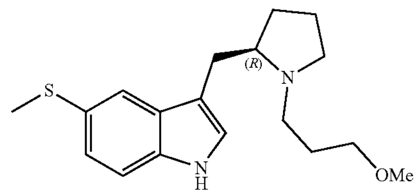 |
| (R, S) I-41 | 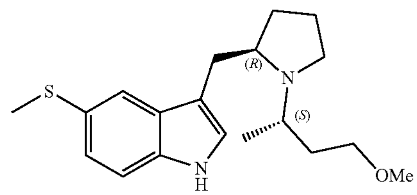 |
| (R, R) I-41 | 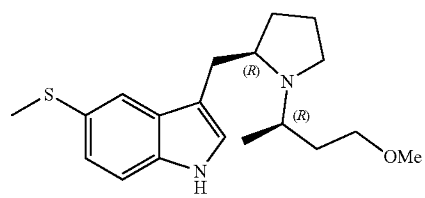 |
| (R, S) I-42 | 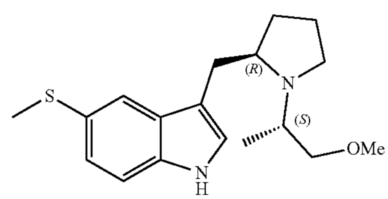 |
| (R, R) I-42 | 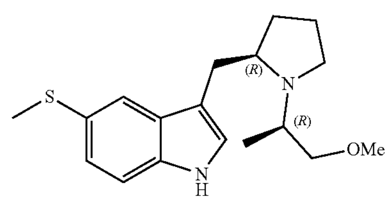 |
| (R) I-43 | 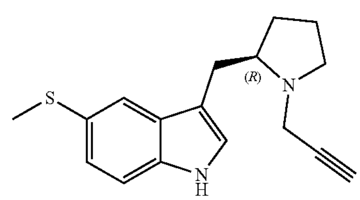 |
| (R) I-44 | 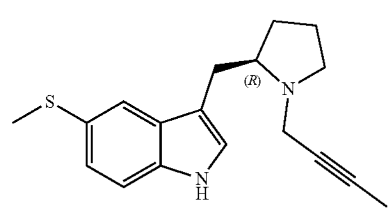 |

| Compound | Structure |
|---|---|
| (R) I-45 | 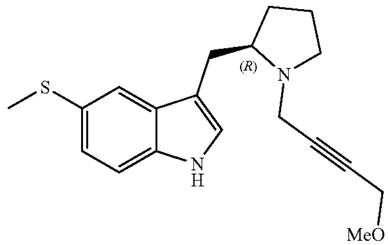 |
| (R) I-46 | 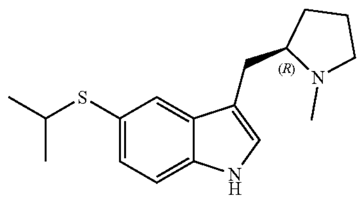 |
| (R) I-47 | 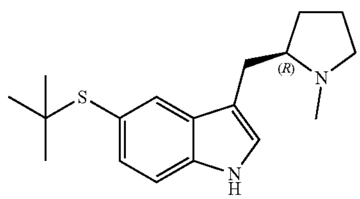 |
| (R) I-48 | 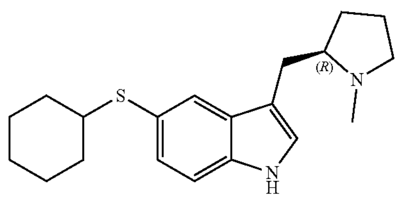 |
| (R) I-49 | 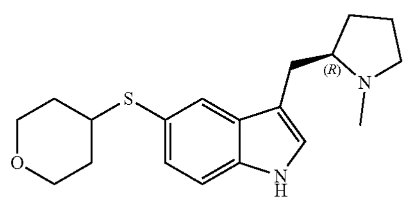 |
| (R) I-50 | 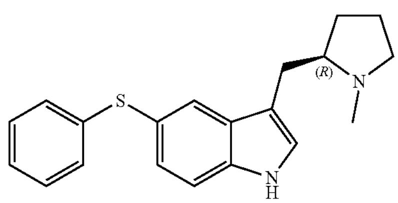 |
| (R) I-51 | 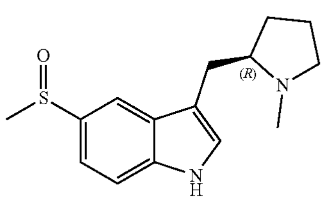 |
| Compound | Structure |
|---|---|
| (R) I-52 | 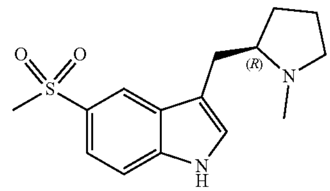 |
| (R) I-53 | 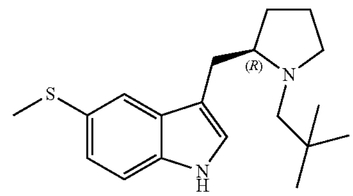 |
| (R) I-54 | 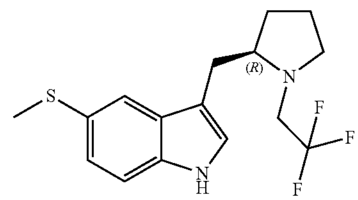 |
| (R) I-55 | 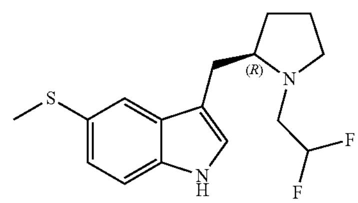 |
| (R) I-56 | 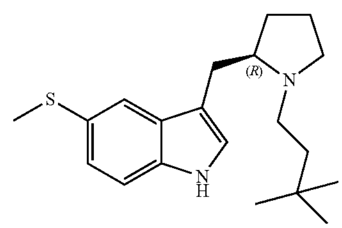 |
| (R) I-57 | 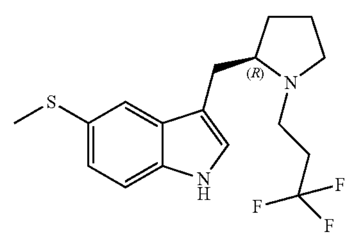 |
| (R) I-58 | 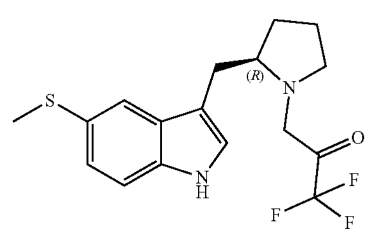 |

-continued
| Compound | Structure |
|---|---|
| (R) I-59 | 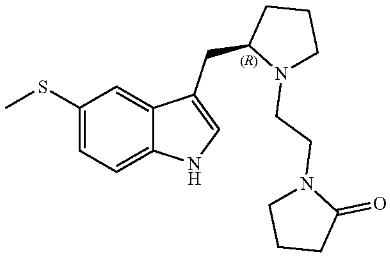 |
| (R) I-60 | 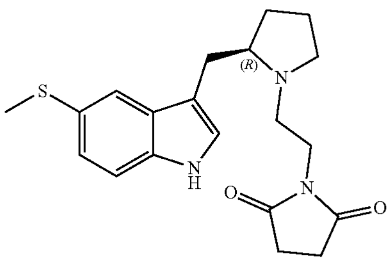 |
| (R) I-61 | 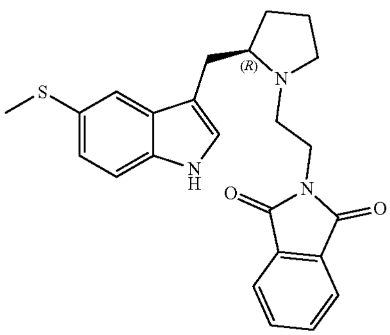 |
| (R) I-62 | 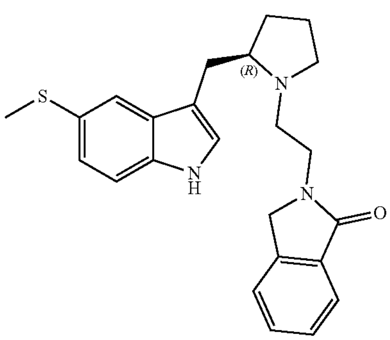 |
| (R) I-63 | 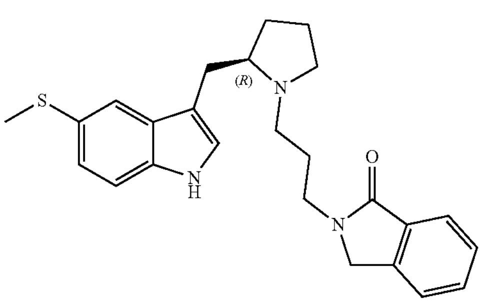 |
-continued
| Compound | Structure |
|---|---|
| (R) I-64 | 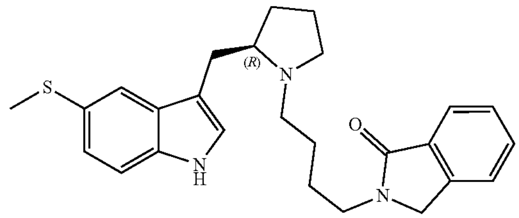 |
| (R) I-65 | 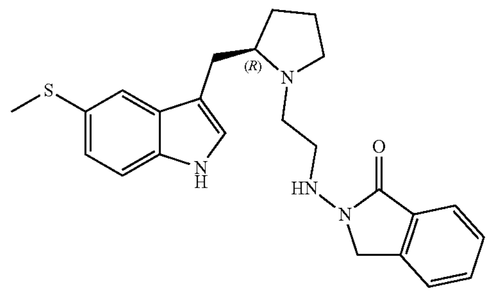 |
| (R) I-66 | 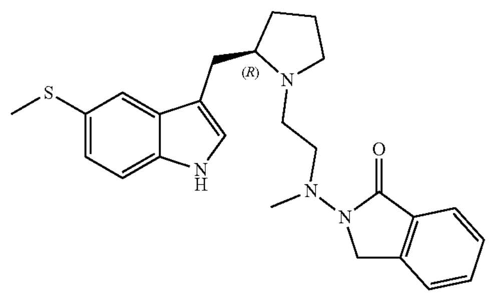 |
| (R) I-67 | 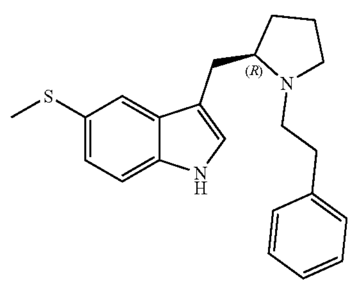 |
| (R) I-68 | 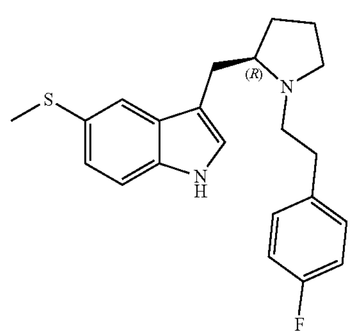 |

-continued
| Compound | Structure |
| --- | --- |
| (R) I-69 | 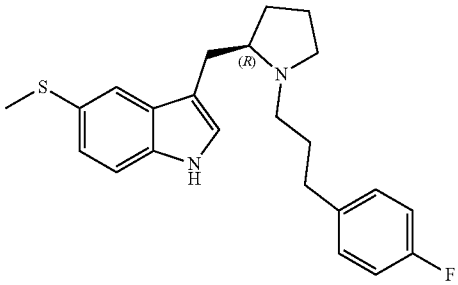 |
| (R) I-70 | 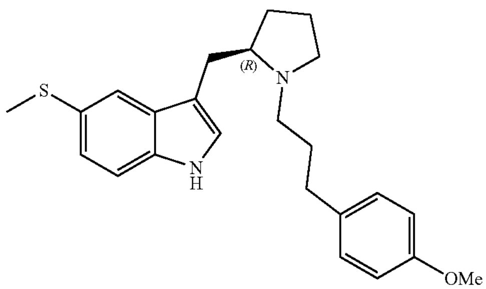 |
| (R) I-71 | 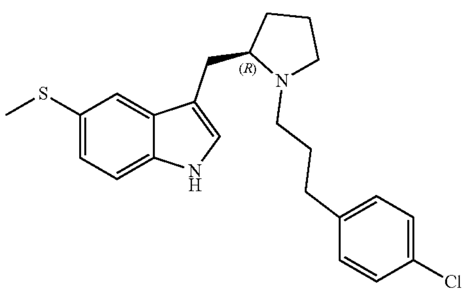 |
| (R) I-72 | 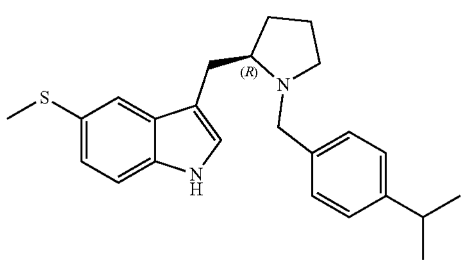 |
| (R) I-73 | 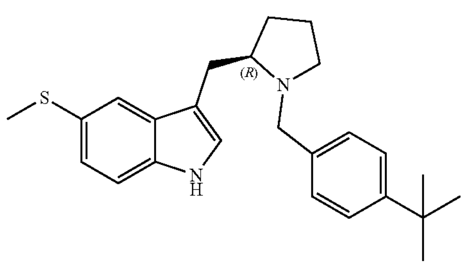 |
-continued
| Compound | Structure |
| --- | --- |
| (R) I-74 | 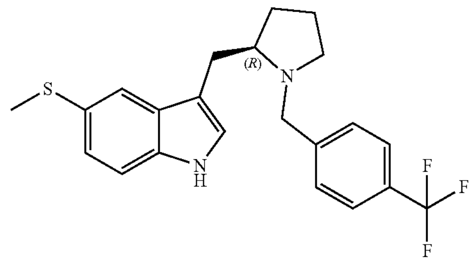 |
| (R) I-75 | 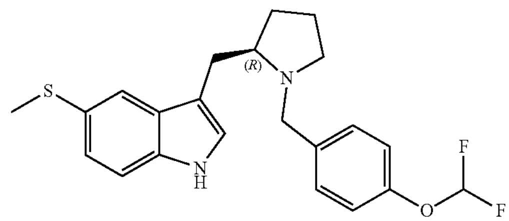 |
| (R) I-76 | 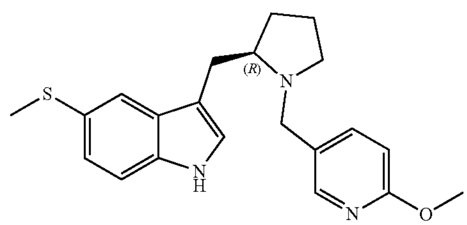 |
| (R) I-77 | 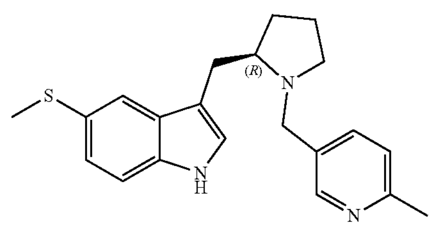 |
| (R) I-78 | 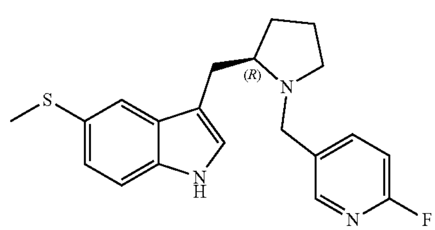 |
| (R) I-79 | 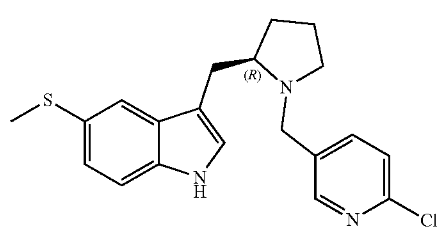 |

-continued
| Compound | Structure |
|---|---|
| (R) I-80 | 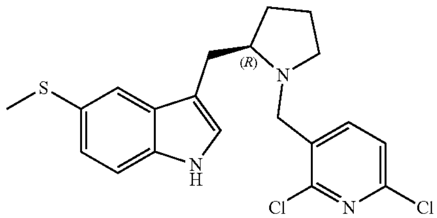 |
| (R) I-81 | 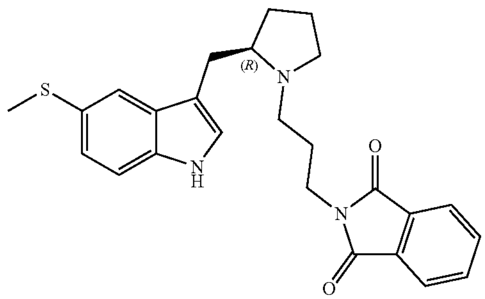 |
| cis-(R) I-82 | 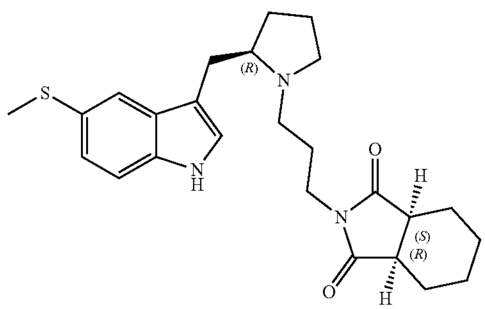 |
| trans-(R) I-82 | 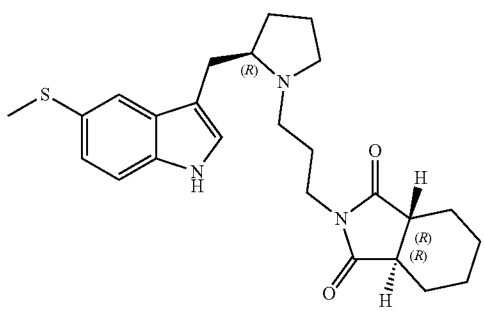 |
| (R) I-83 | 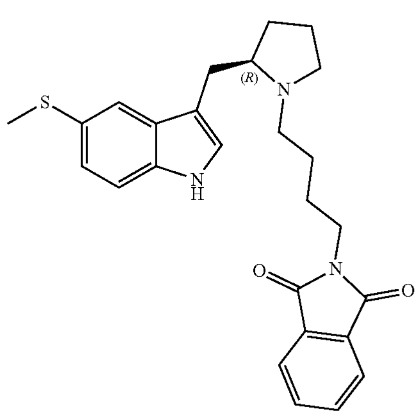 |
-continued
| Compound | Structure |
|---|---|
| (R) I-84 | 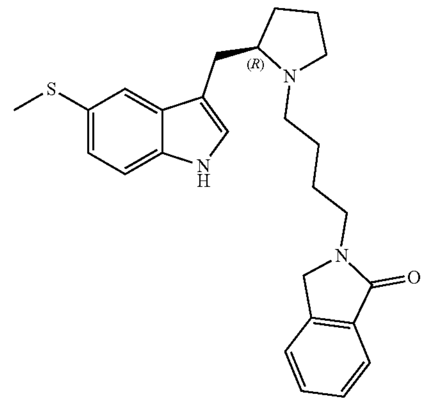 |
| cis-(R) I-85 | 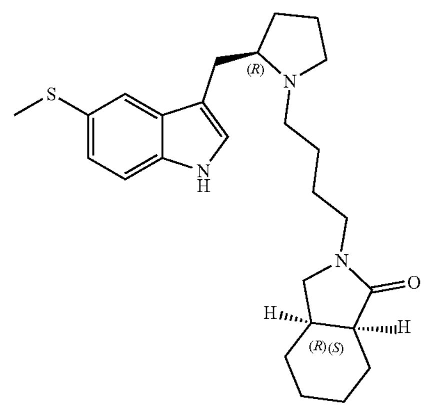 |
| cis-(R) I-86 | 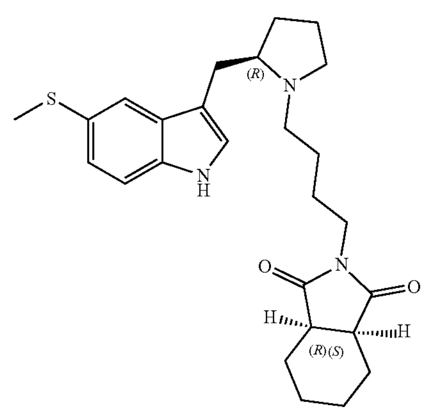 |

-continued
| Compound | Structure |
|---|---|
| trans-(R) I-86 | 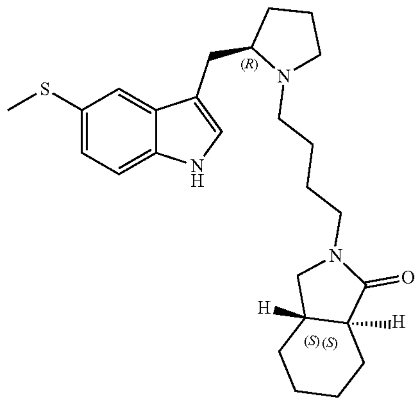 |
| (R) I-87 | 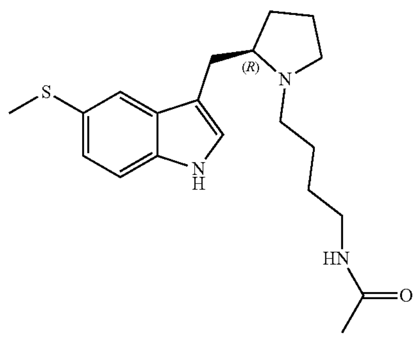 |
| (R) I-88 | 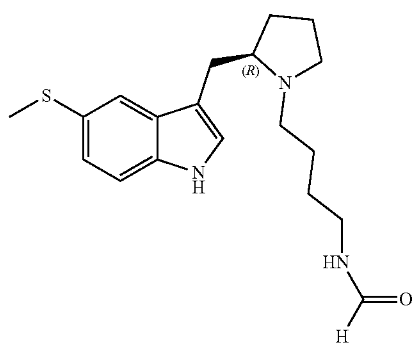 |
| (R) I-89 | 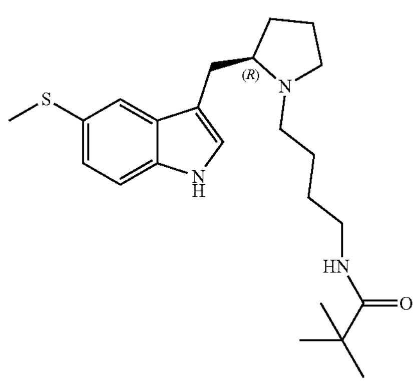 |
-continued
| Compound | Structure |
|---|---|
| (R) I-90 | 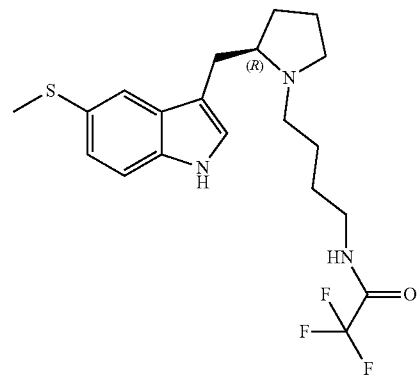 |
| (R) I-91 | 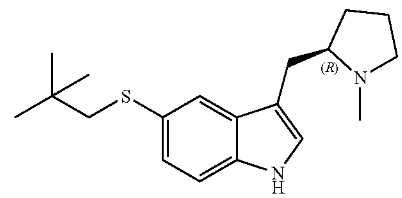 |
| (R) I-92 | 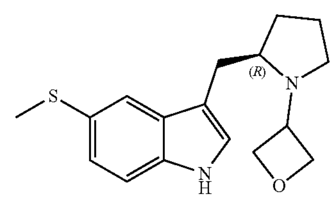 |
| (R, S) I-93 | 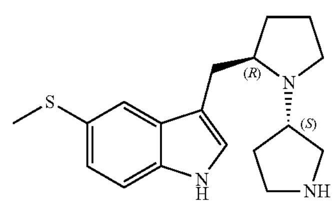 |
| (R, S) I-94 | 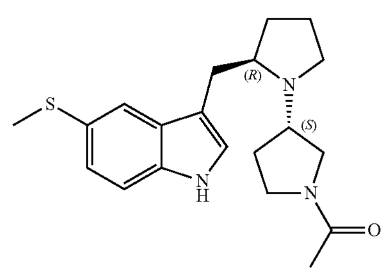 |
| (R) I-95 | 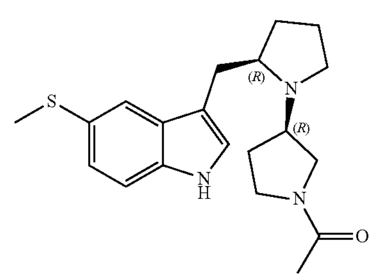 |

-continued
| Compound | Structure |
|---|---|
| (R) I-96 | 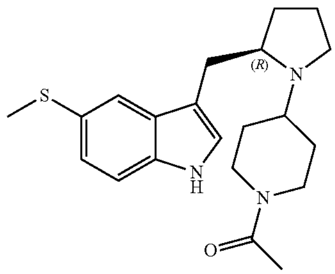 and |
| (R) I-97 | 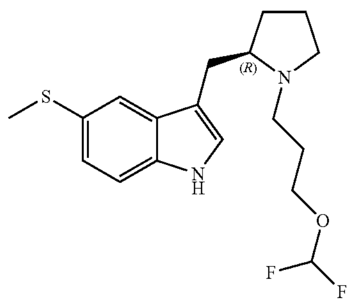 |
or a pharmaceutically acceptable salt, solvate, and/or prodrug thereof.
E76: The compound of any one of E1 to E8, wherein the compound of Formula (I) is selected from the table below:
| Compound | Structure |
|---|---|
| II-1 | 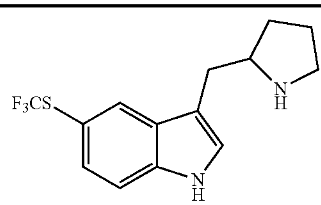 |
| (R) II-2 | 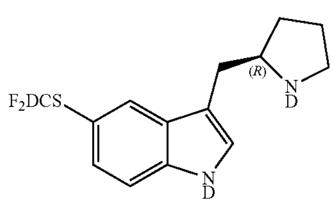 |
| II-3 | 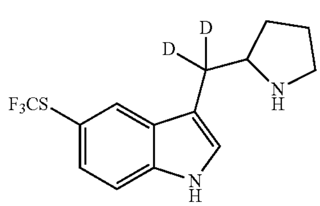 |
| II-4 | 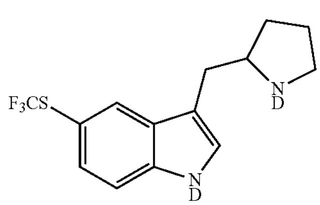 |
-continued
| Compound | Structure |
|---|---|
| II-5 | 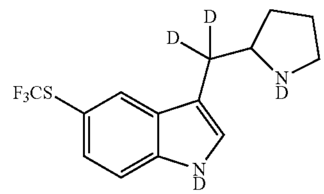 |
| (R) II-6 | 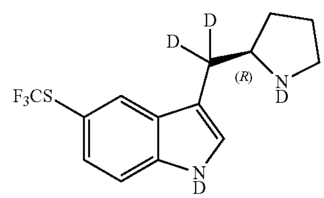 |
| (R) II-7 | 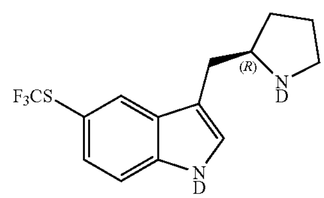 |
| (R) II-8 | 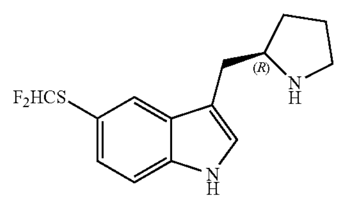 |
| (R) II-9 | 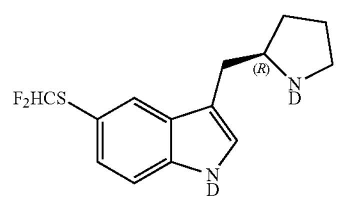 |
| (R) II-10 | 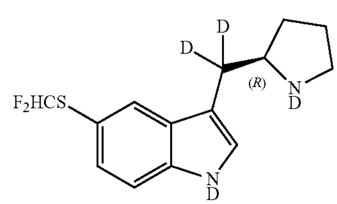 |
| (R) II-11 | 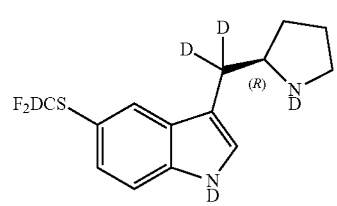 |

-continued
| Compound | Structure |
|---|---|
| (R) II-12 | 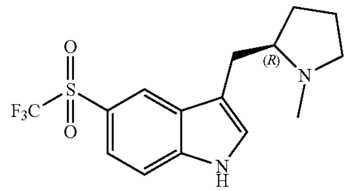 |
| (R) II-13 | 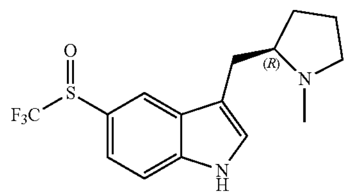 |
| (R) II-14 | 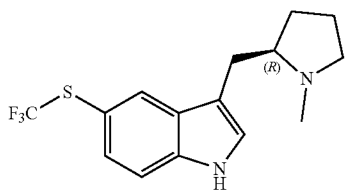 |
| (R) II-15 | 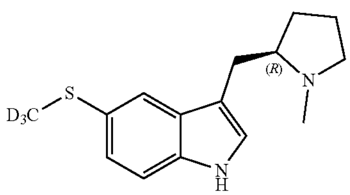 |
| (R) II-16 | 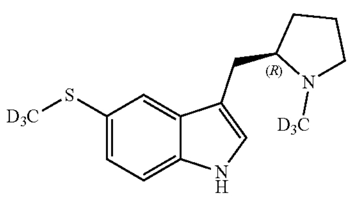 |
| (R) II-17 | 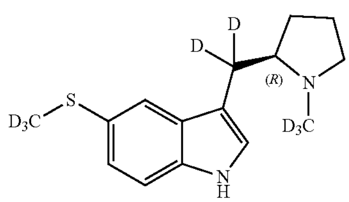 |
| (R) II-18 | 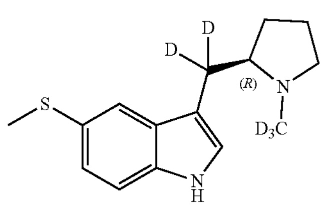 |
-continued
| Compound | Structure |
|---|---|
| (R) II-19 | 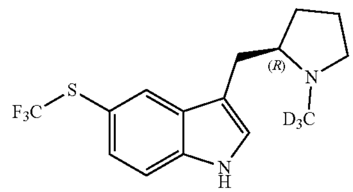 |
| (R) II-20 | 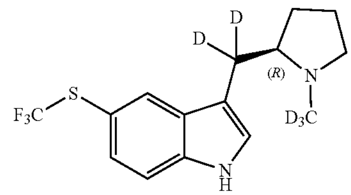 |
| (R) II-21 | 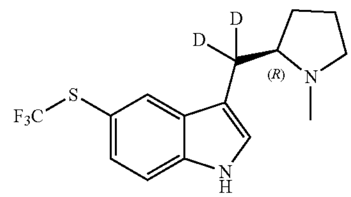 |
| (R) II-22 | 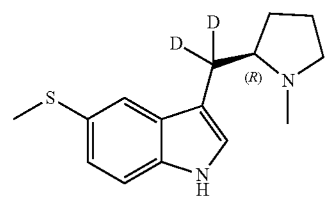 |
| (R) II-23 | 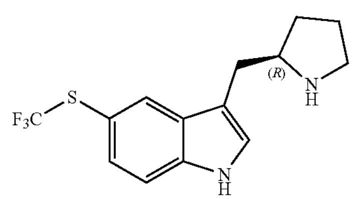 |
| (R) II-24 | 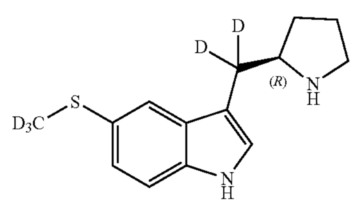 |
| (R) II-25 | 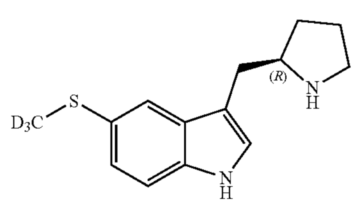 |

-continued
| Compound | Structure |
|---|---|
| (R) II-26 | 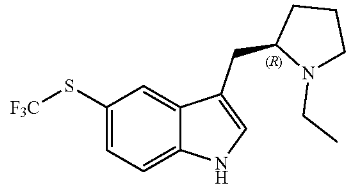 |
| (R) II-27 | 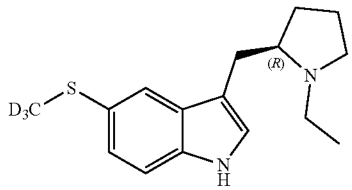 |
| (R) II-28 | 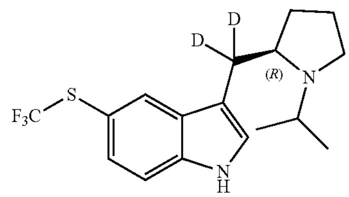 |
| (R) II-29 | 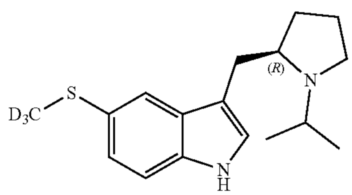 |
| (R) II-30 | 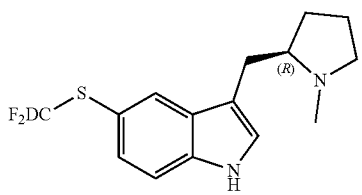 |
| (R) II-31 | 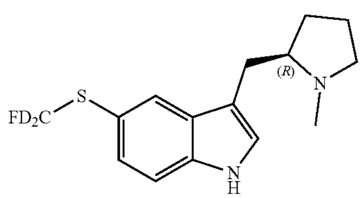 |
| (R) II-32 | 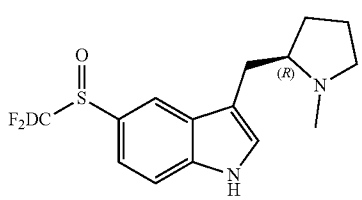 |
| (R) II-33 | 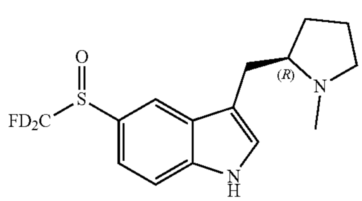 |
-continued
| Compound | Structure |
|---|---|
| (R) II-34 | 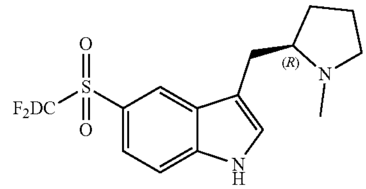 |
| (R) II-35 | 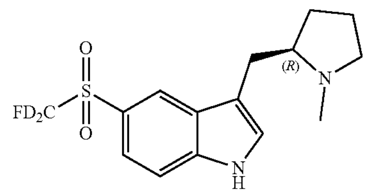 |
| (R) II-36 | 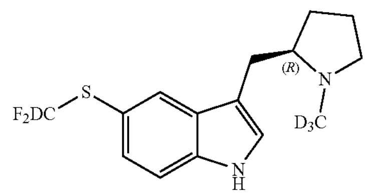 |
| (R) II-37 | 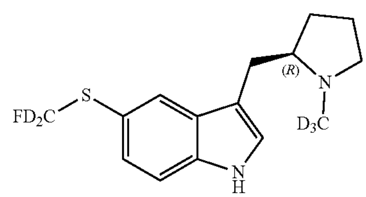 |
| (R) II-38 | 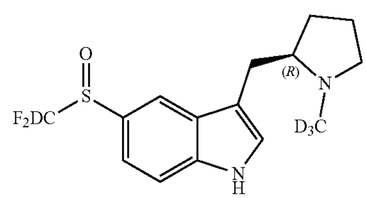 |
| (R) II-39 | 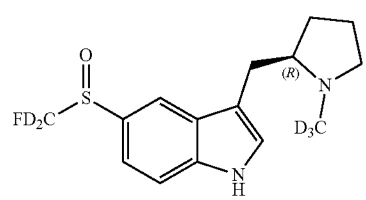 |
| (R) II-40 | 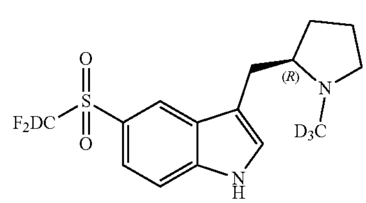 |

-continued
| Compound | Structure |
| --- | --- |
| (R) II-41 | 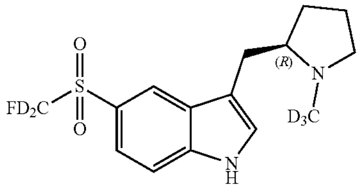 |
| (R) II-42 | 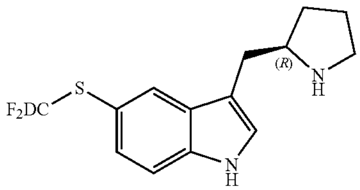 |
| (R) II-43 | 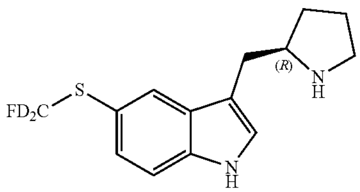 |
| (R) II-44 | 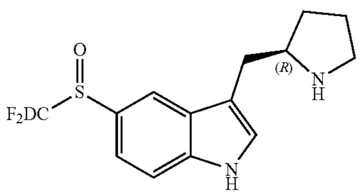 |
| (R) II-45 | 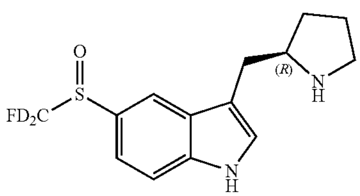 |
| (R) II-46 | 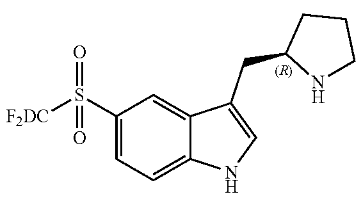 |
| (R) II-47 | 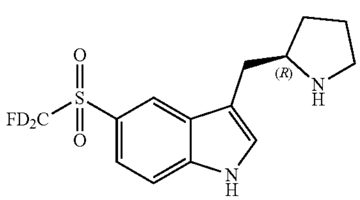 |
| (R) II-48 | 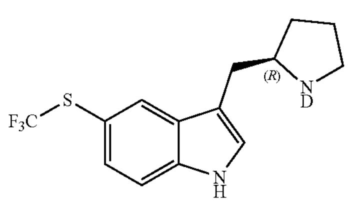 |
-continued
| Compound | Structure |
| --- | --- |
| (R) II-49 | 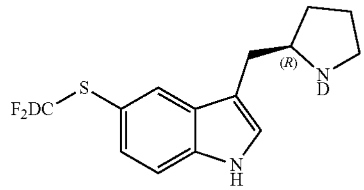 |
| (R) II-50 | 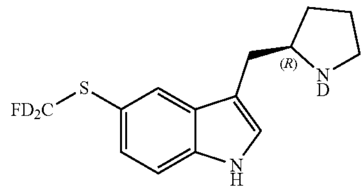 |
| (R) II-51 | 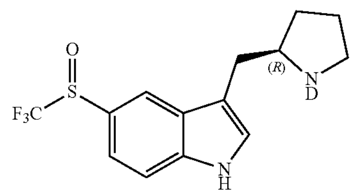 |
| (R) II-52 | 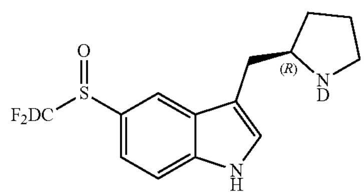 |
| (R) II-53 | 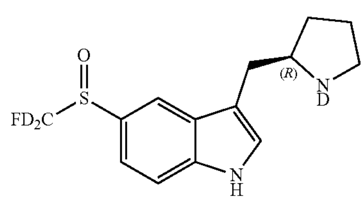 |
| (R) II-54 | 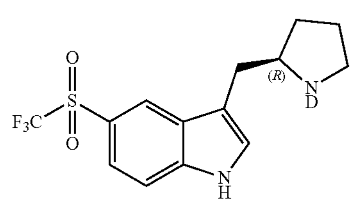 |

-continued
| Compound | Structure |
|---|---|
| (R) II-55 | 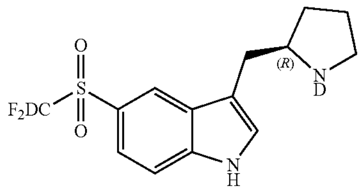 and |
| (R) II-56 | 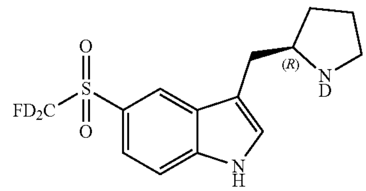 |
or a pharmaceutically acceptable salt, solvate, and/or prodrug thereof.
E77: The compound of any one of E1 to E8, wherein the compound of Formula (I) is selected from the table below:
| Compound | Structure |
|---|---|
| (R) I-98 | 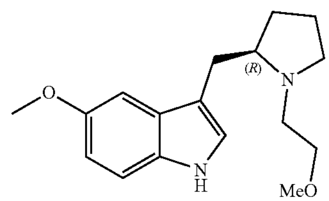 |
| (R) I-99 | 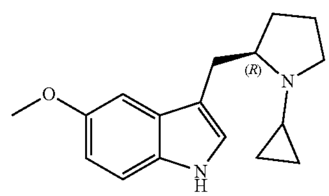 |
| (R) I-100 | 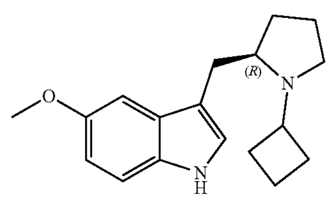 |
| (R) I-101 | 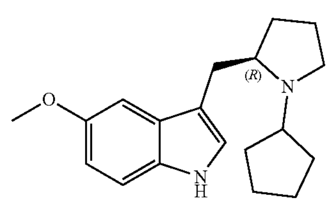 |
| (R, R) I-102 | 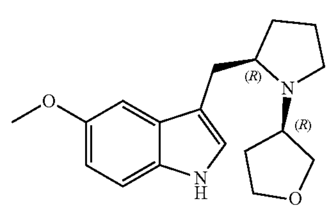 |

-continued
| Compound | Structure |
| --- | --- |
| (R, S) I-102 | 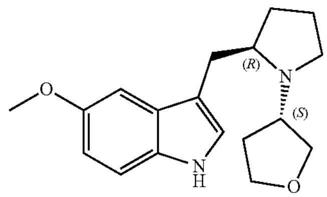 |
| (R, S) I-103 | 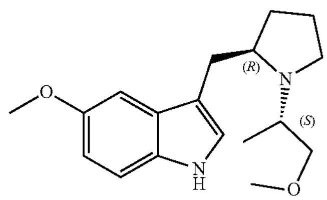 |
| (R, R) I-103 | 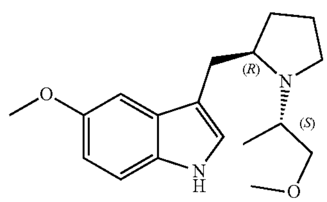 |
| (S) I-104 | 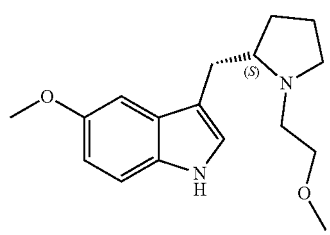 |
| (R) I-105 | 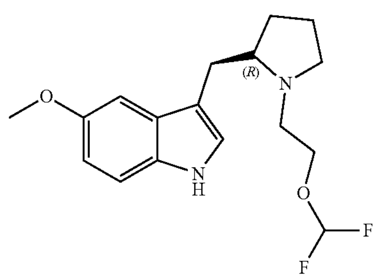 |
| (R) I-106 | 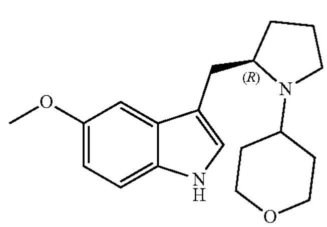 |
| (R, S) I-107 | 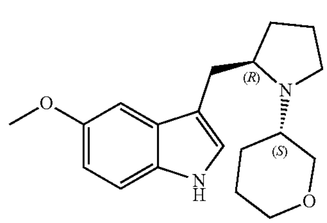 |

-continued
| Compound | Structure |
|---|---|
| (R, R) I-107 | 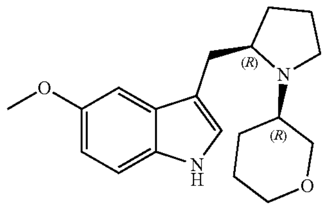 |
| (R) I-108 | 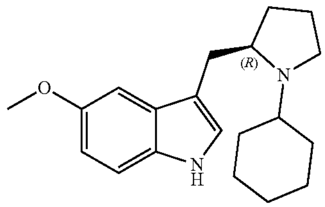 |
| Trans-(R) I-109 | 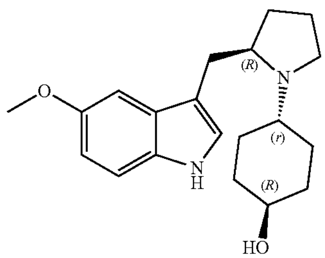 |
| Trans (R) I-110 | 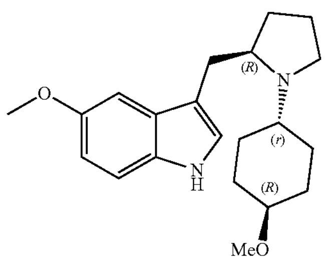 |
| (R, R) I-111 | 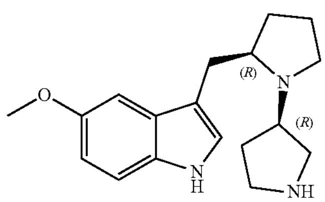 |
| (R) I-112 | 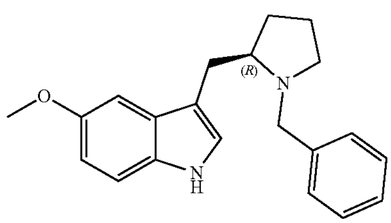 |
| (R) I-113 | 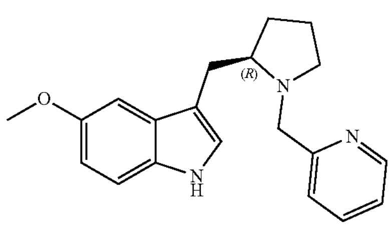 |

-continued
| Compound | Structure |
| --- | --- |
| (R) I-114 | 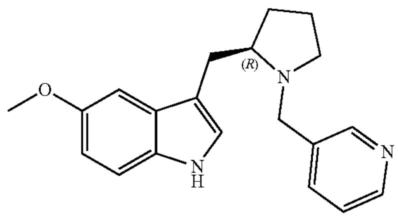 |
| (R) I-115 | 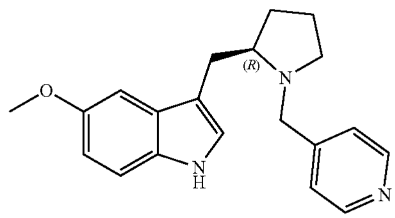 |
| (R) I-116 | 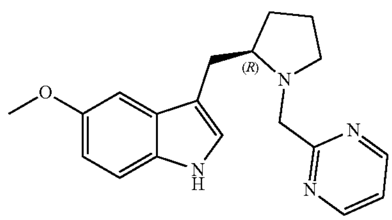 |
| (R) I-117 | 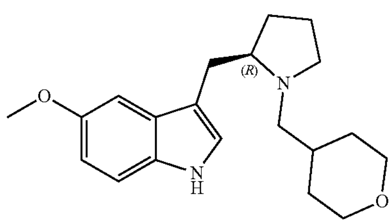 |
| (R, S) I-118 | 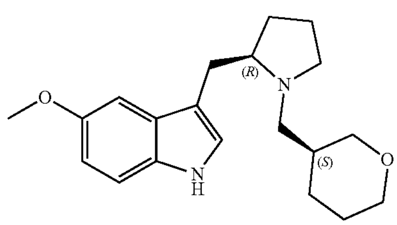 |
| (R, R) I-118 | 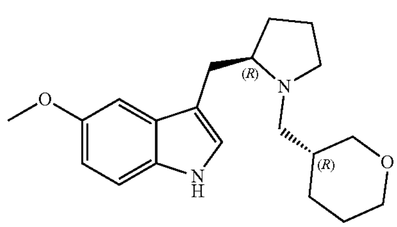 |
| (R, R) I-119 | 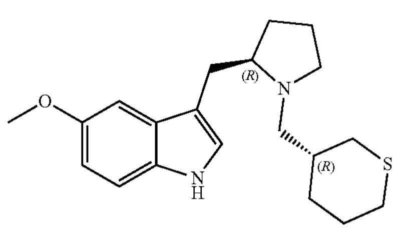 |

-continued
| Compound | Structure |
| --- | --- |
| (R,S) I-119 | 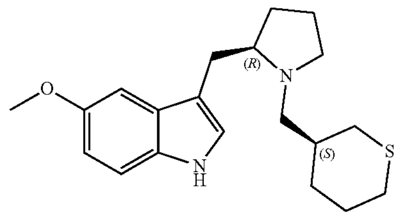 |
| (R) I-120 | 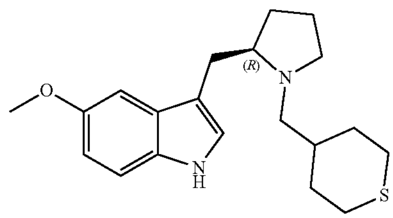 |
| (R) I-121 | 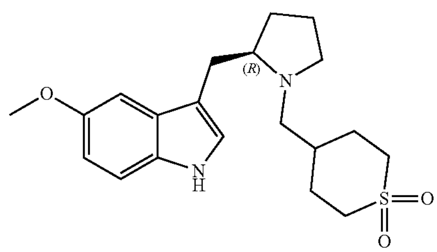 |
| (R) I-122 | 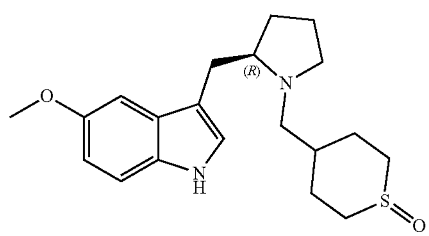 |
| (R) I-123 | 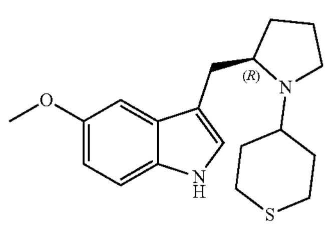 |
| (R) I-124 | 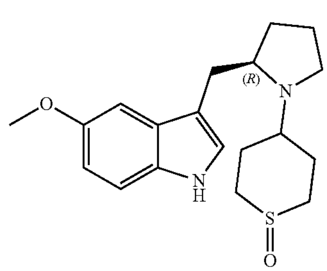 |

-continued
| Compound | Structure |
|---|---|
| (R) I-125 | 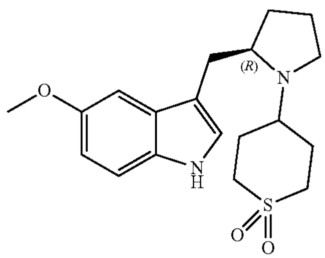 |
| (R) I-126 | 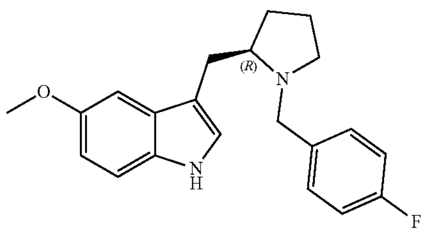 |
| (R) I-127 | 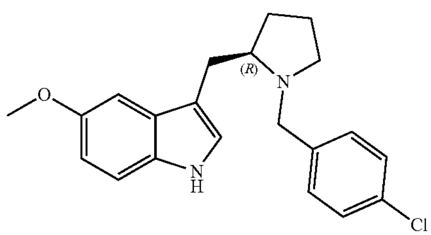 |
| (R) I-128 | 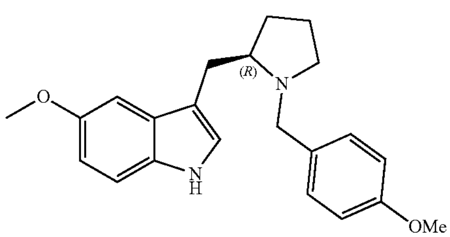 |
| (R) I-129 | 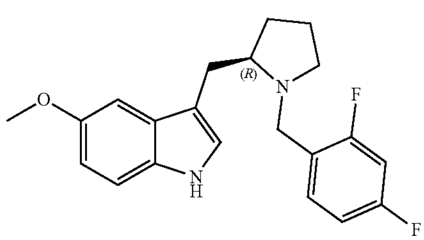 |
| (R) I-130 | 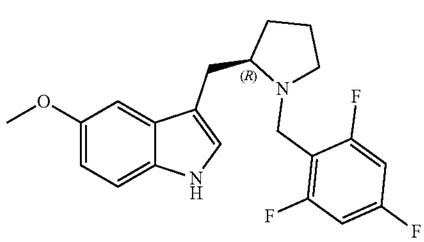 |

-continued
| Compound | Structure |
|---|---|
| (R) I-131 | 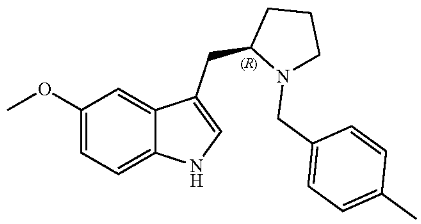 |
| (R) I-132 | 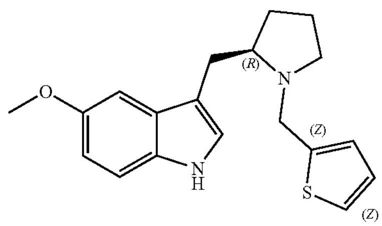 |
| (R) I-133 | 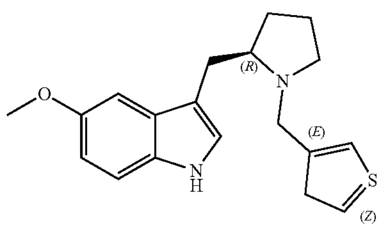 |
| (R) I-134 | 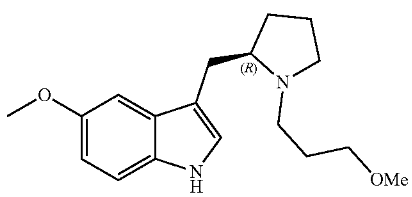 |
| (R, S) I-135 | 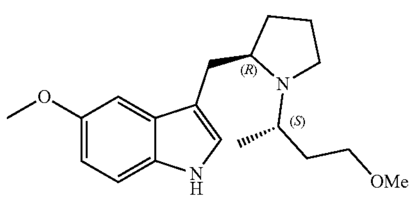 |
| (R, R) I-135 | 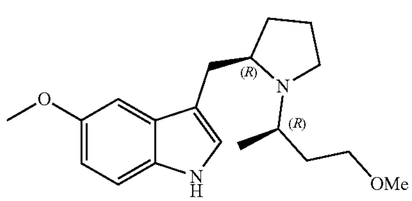 |
| (R, S) I-136 | 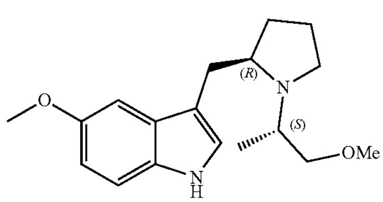 |

-continued
| Compound | Structure |
| --- | --- |
| (R, R) I-136 | 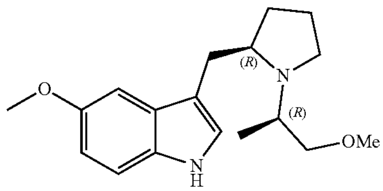 |
| (R) I-137 | 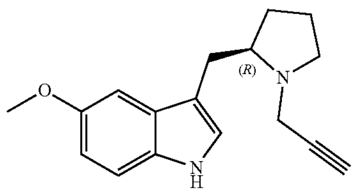 |
| (R) I-138 | 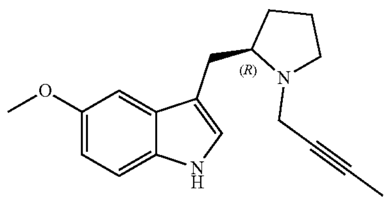 |
| (R) I-139 | 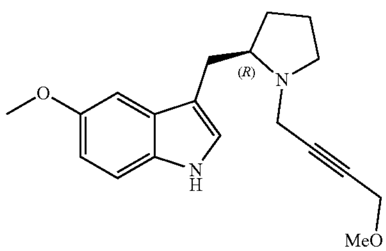 |
| (R) I-140 | 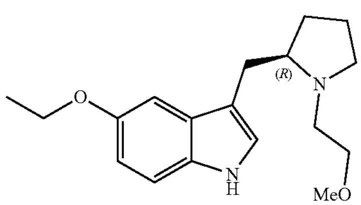 |
| (R) I-141 | 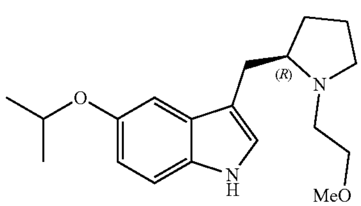 |
| (R) I-142 | 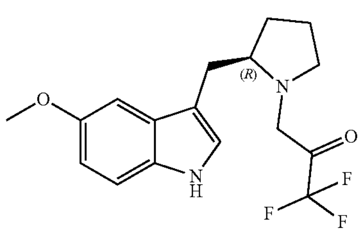 |

-continued
| Compound | Structure |
| --- | --- |
| (R) I-143 | 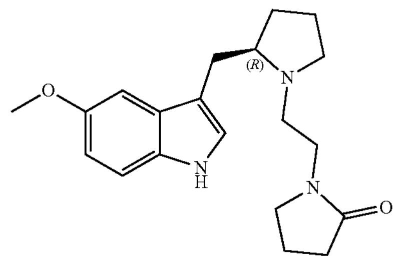 |
| (R) I-144 | 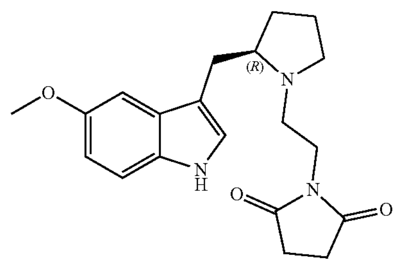 |
| (R) I-145 | 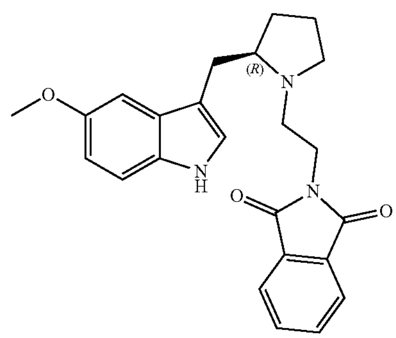 |
| (R) I-146 | 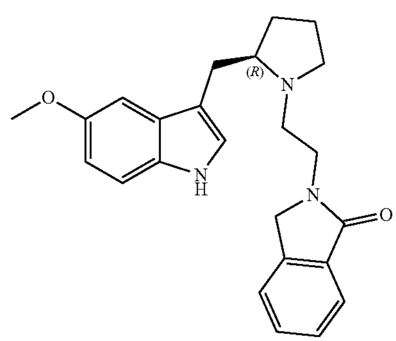 |
| (R) I-147 | 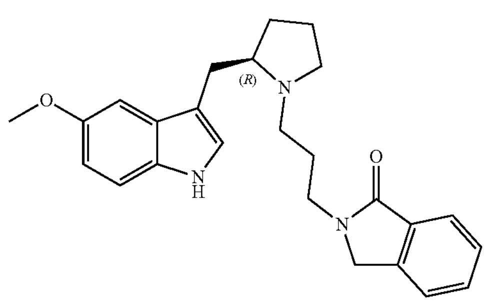 |

-continued
| Compound | Structure |
|---|---|
| (R) I-148 | 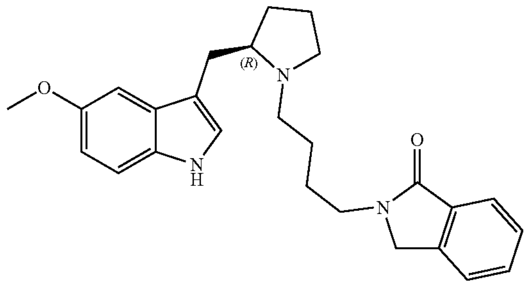 |
| (R) I-149 | 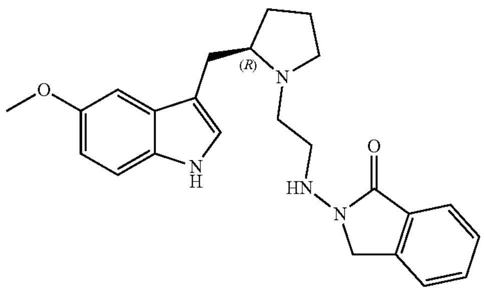 |
| (R) I-150 | 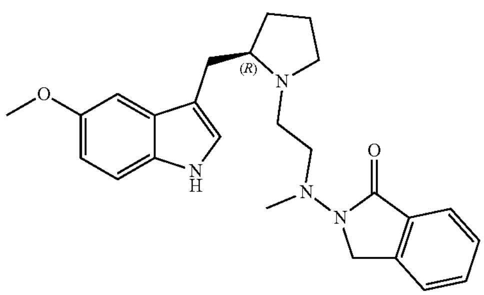 |
| (R) I-151 | 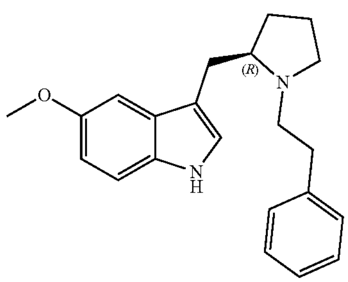 |
| (R) I-152 | 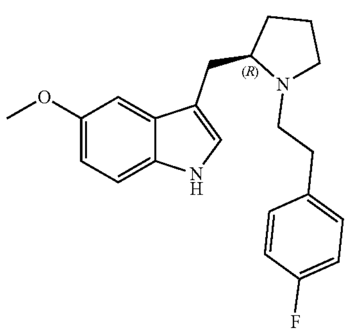 |

-continued
| Compound | Structure |
| --- | --- |
| (R) I-153 | 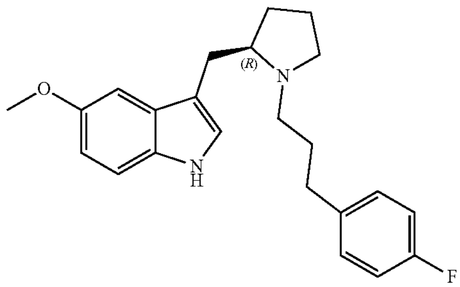 |
| (R) I-154 | 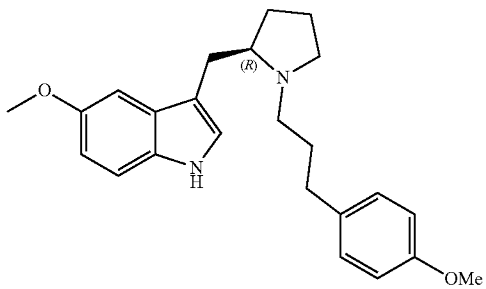 |
| (R) I-155 | 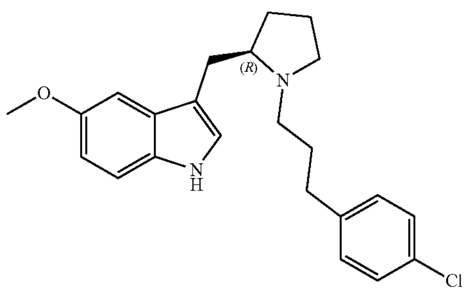 |
| (R) I-156 | 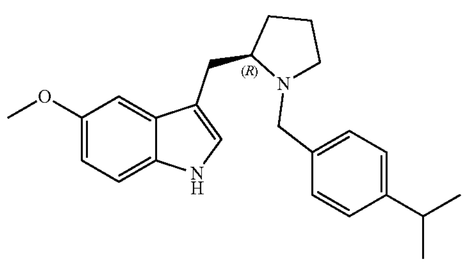 |
| (R) I-157 | 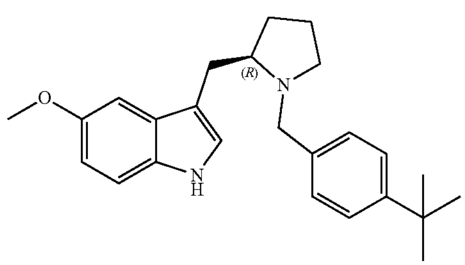 |

-continued
| Compound | Structure |
|---|---|
| (R) I-158 | 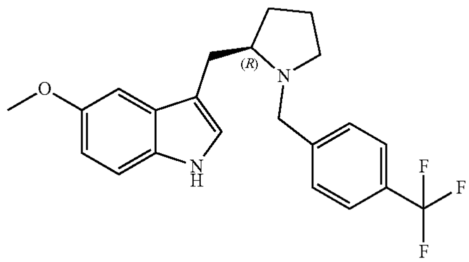 |
| (R) I-159 | 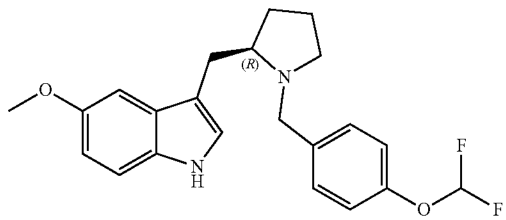 |
| (R) I-160 | 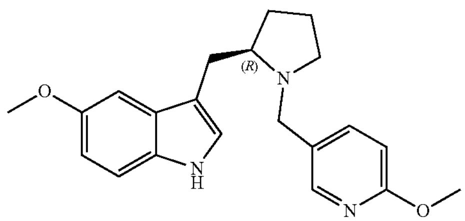 |
| (R) I-161 | 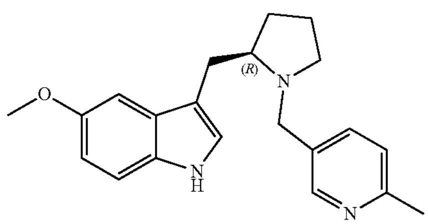 |
| (R) I-162 | 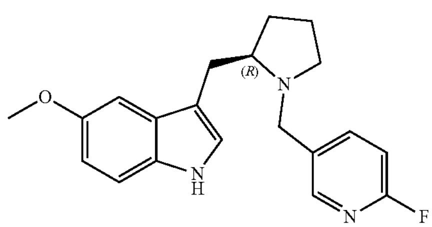 |
| (R) I-163 | 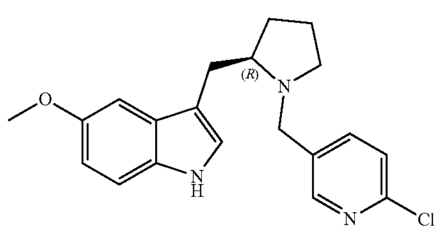 |

-continued
| Compound | Structure |
| --- | --- |
| (R) I-164 | 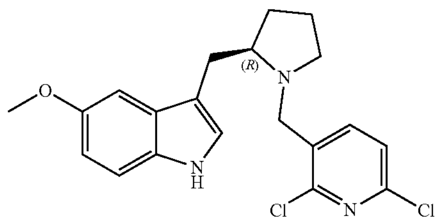 |
| (R) I-165 | 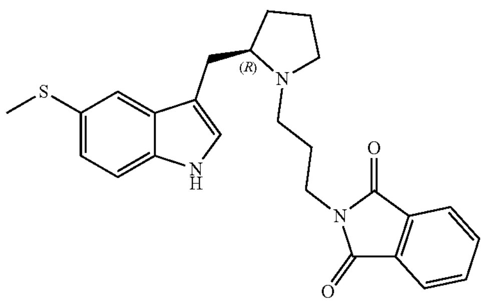 |
| Cis (R) I-166 | 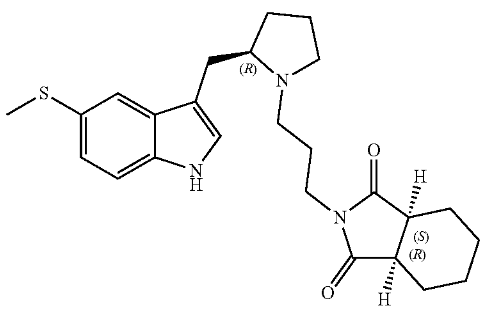 |
| Trans (R) I-167 | 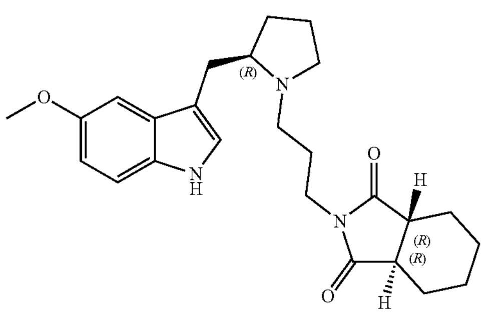 |
| (R) I-168 | 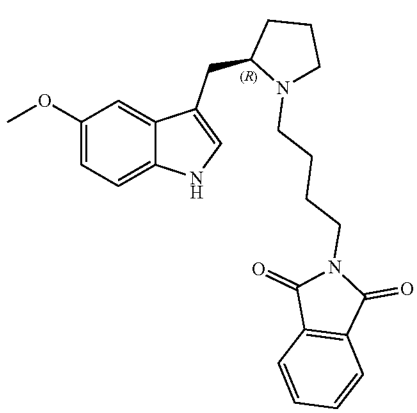 |

-continued
| Compound | Structure |
|---|---|
| (R) I-169 | 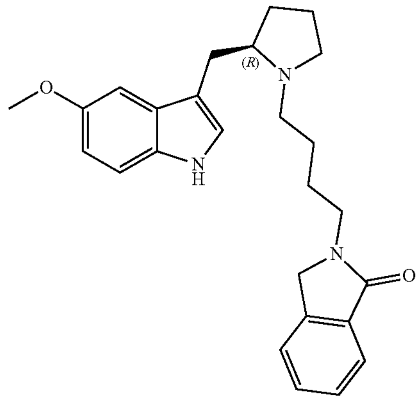 |
| Cis (R) I-170 | 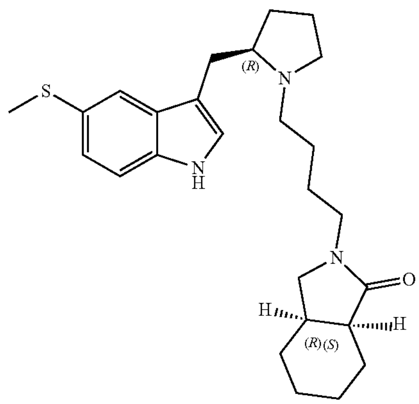 |
| Cis (R) I-171 | 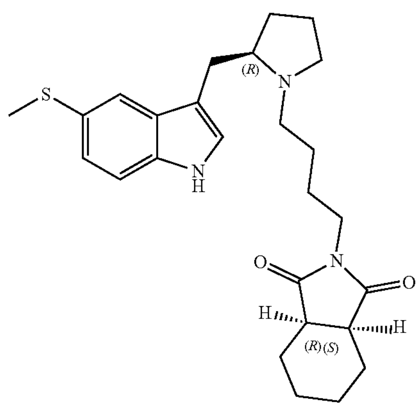 |
| Trans (R) I-172 | 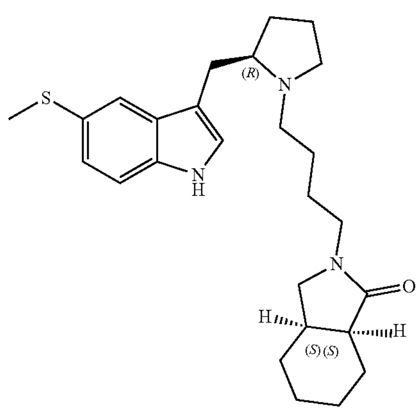 |

-continued
| Compound | Structure |
|---|---|
| (R) I-173 | 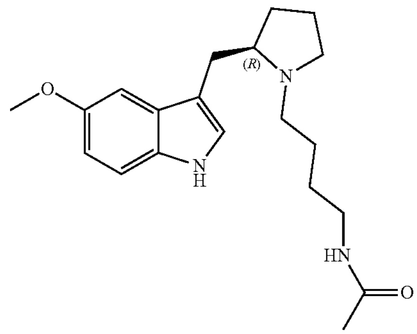 |
| (R) I-174 | 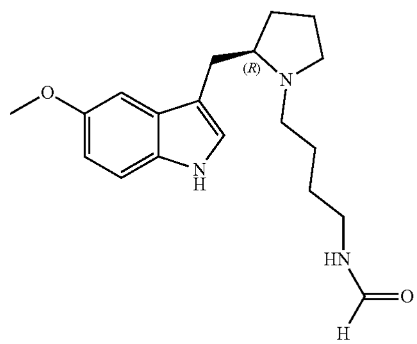 |
| (R) I-175 | 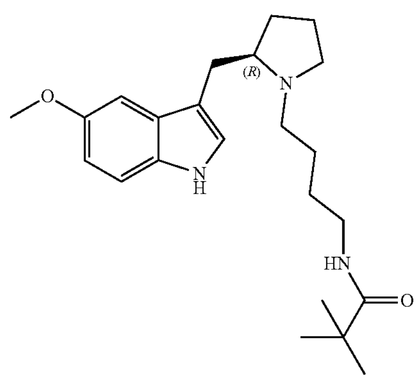 |
| (R) I-176 | 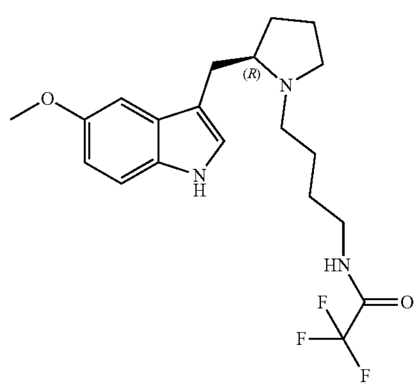 |

-continued
| Compound | Structure |
| --- | --- |
| (R) I-177 | 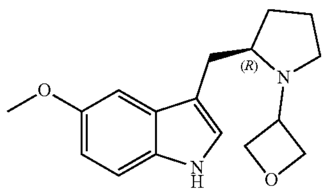 |
| (R, S) I-178 | 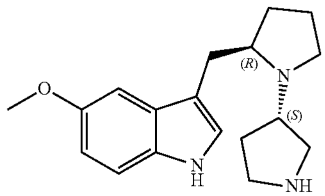 |
| (R, S) I-179 | 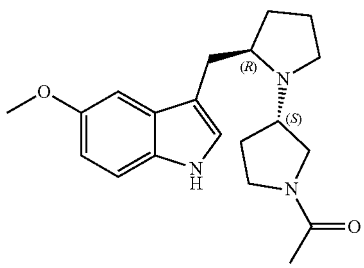 |
| (R, R) I-180 | 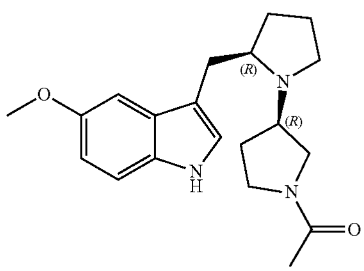 |
| (R) I-181 | 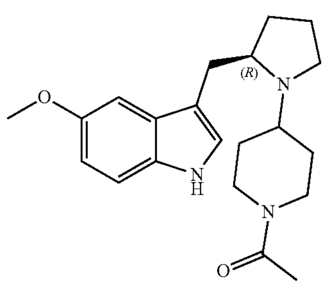 |
| (R) I-182 | 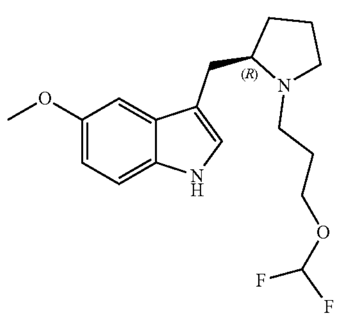 |

-continued
| Compound | Structure |
|---|---|
| (R) I-183 | 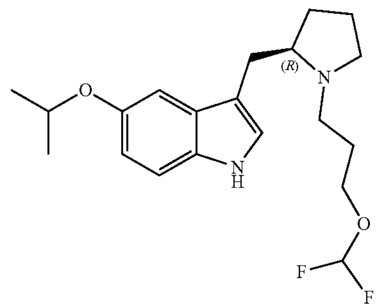 |
| (R) I-184 | 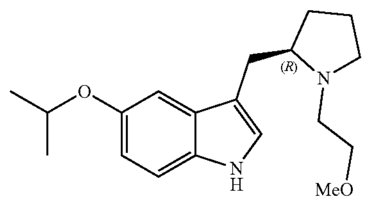 |
| (R) I-185 | 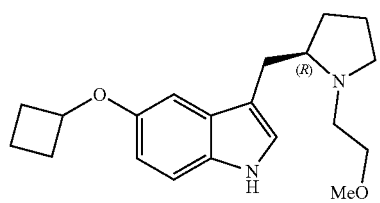 |
| (R) I-186 | 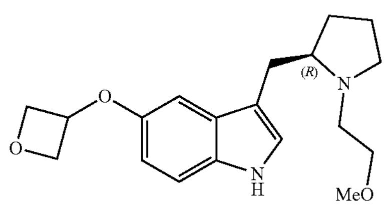 |
| (R) I-187 | 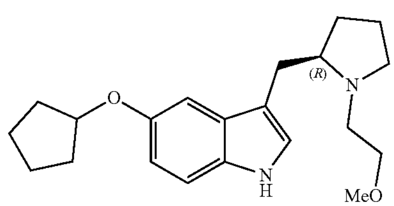 |
| (R) I-188 | 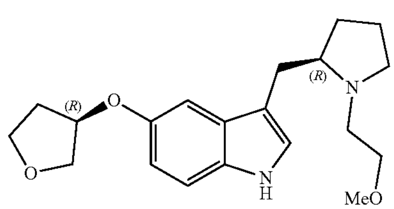 |
| (R) I-189 | 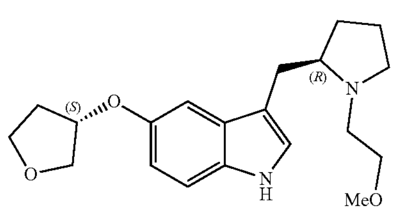 |

-continued
| Compound | Structure |
|---|---|
| (R) I-190 | 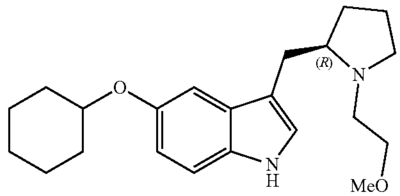 |
| (R) I-191 | 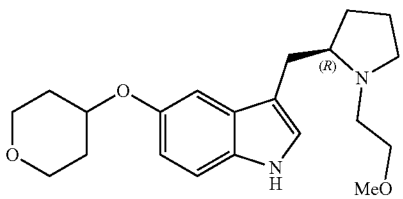 |
| (R) I-192 | 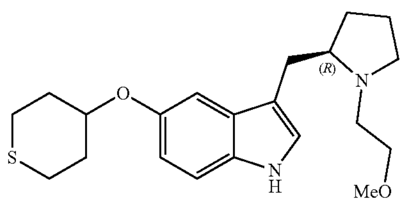 |
| (R) I-193 | 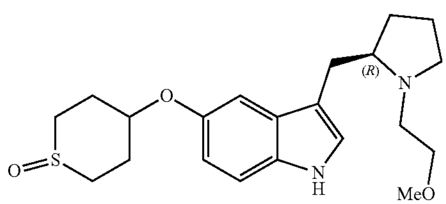 |
| (R) I-194 | 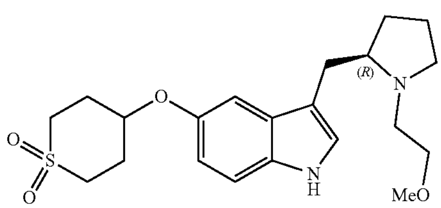 |
| (R) I-195 | 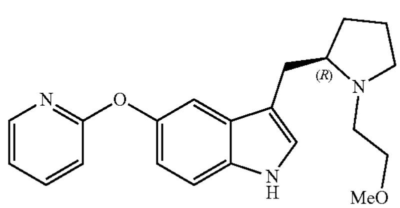 |
| (R) I-196 | 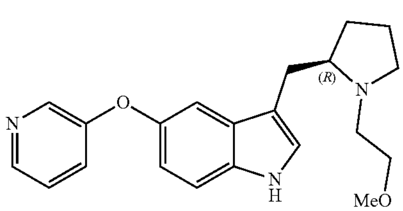 |

-continued
| Compound | Structure |
|---|---|
| (R) I-197 | 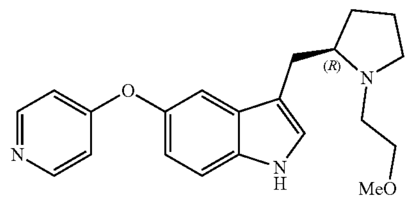 |
| (R) I-198 | 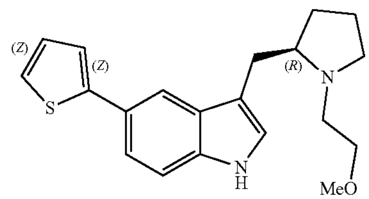 |
| (R) I-198-A | 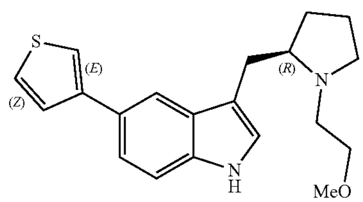 |
| (R) I-199 | 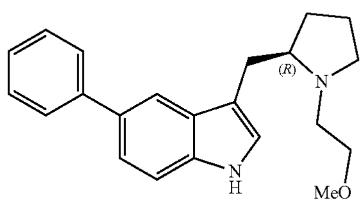 |
| (R) I-200 | 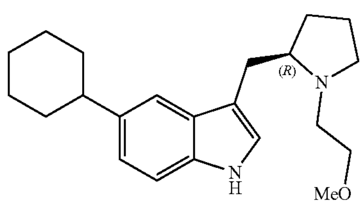 |
| (R) I-201 | 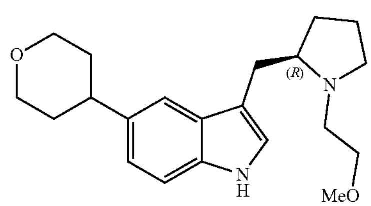 |
| (R) I-202 | 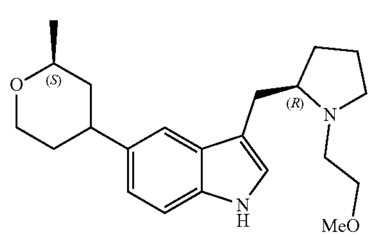 |

-continued
| Compound | Structure |
|---|---|
| (R) I-203 | 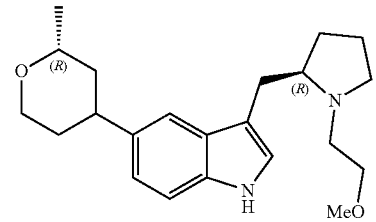 |
| (R) I-204 | 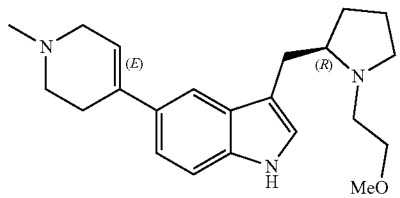 |
| (R) I-205 | 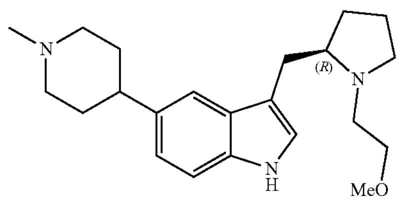 |
| (R) I-206 | 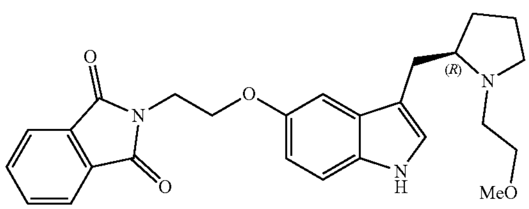 |
| (R) I-207 | 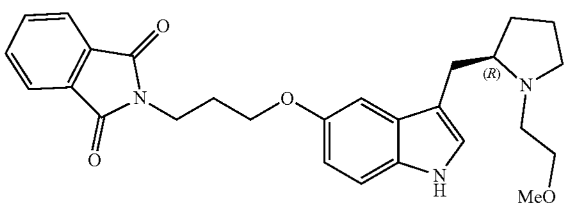 |
| (R) I-208 | 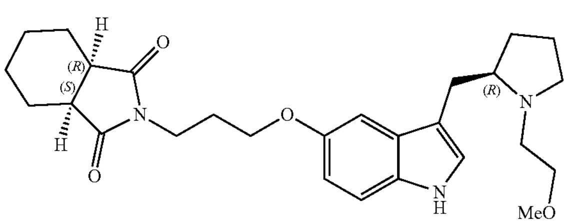 |
| (R) I-209 | 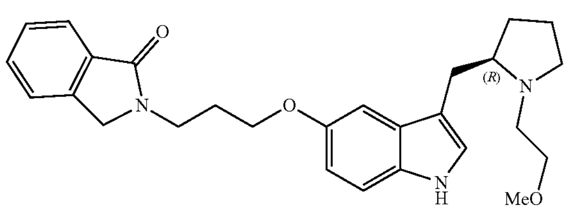 |

-continued
| Compound | Structure |
|---|---|
| (R) I-210 | 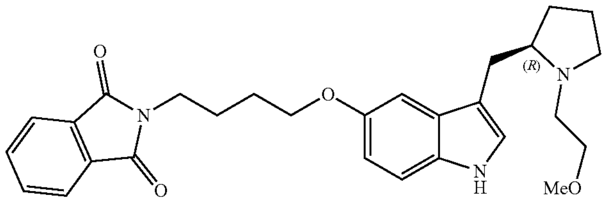 |
| (R) I-211 | 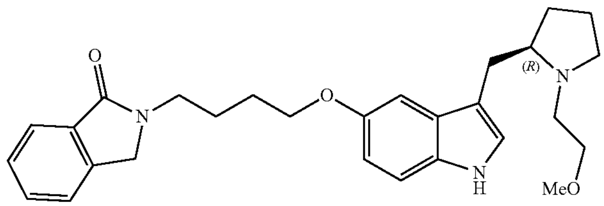 |
| (R) I-212 | 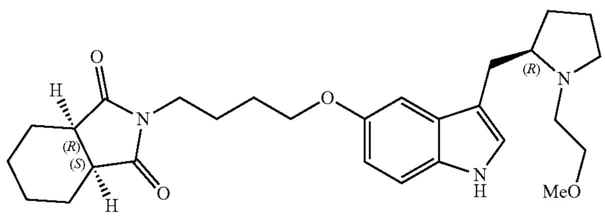 |
| (R) I-213 | 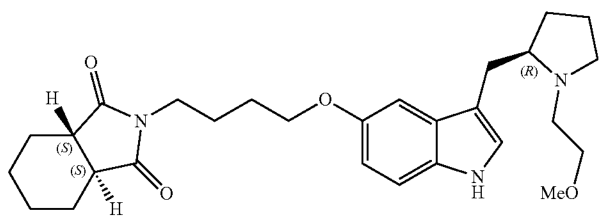 |
| (R) I-214 | 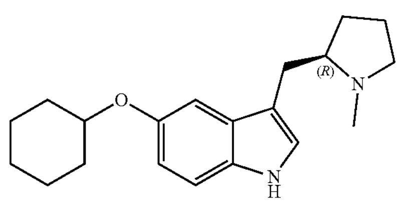 |
| (R) I-215 | 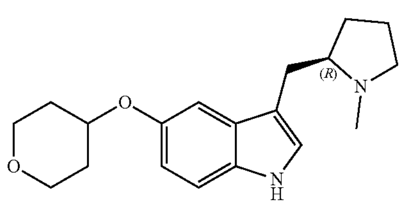 |
| (R) I-216 | 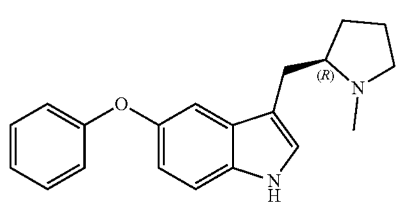 |

-continued
| Compound | Structure |
| --- | --- |
| (R) I-217 | 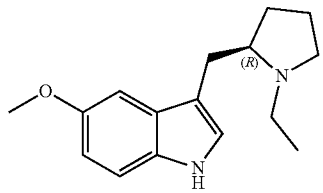 |
| (R) I-218 | 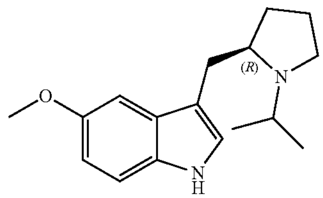 |
| (R) I-219 | 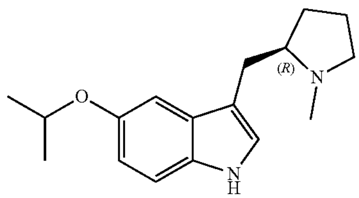 |
| (R) I-220 | 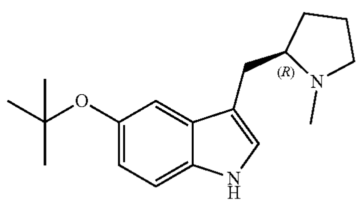 |
| (R) I-221 | 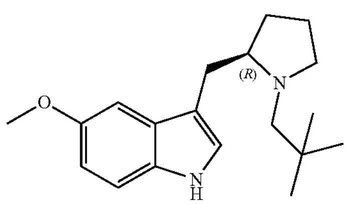 |
| (R) I-222 | 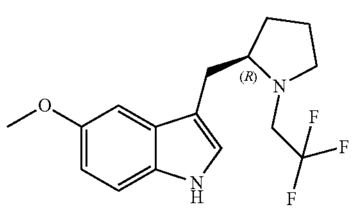 |
| (R) I-223 | 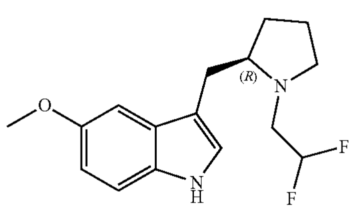 |

-continued
| Compound | Structure |
|---|---|
| (R) I-224 | 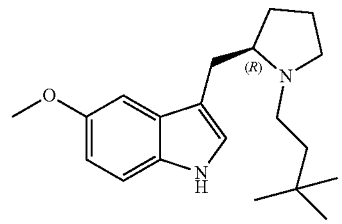 |
| (R) I-225 | 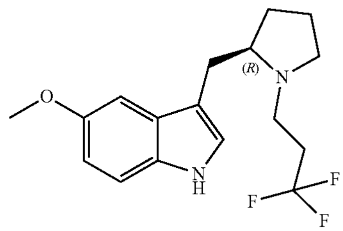 |
| (R) I-226 | 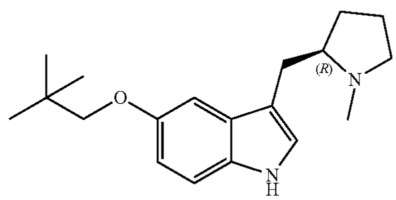 |
| (R) I-227 | 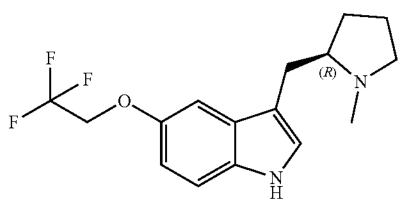 |
| (R) I-228 | 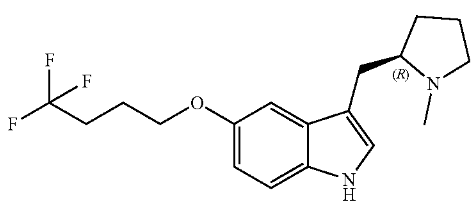 |
| (R) I-229 | 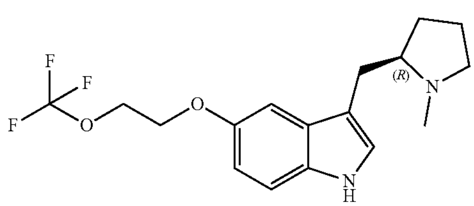 |
| (R) I-330 | 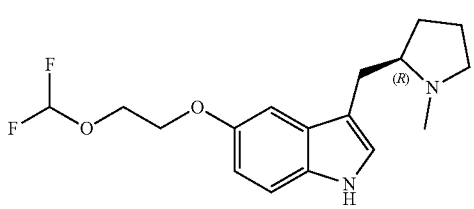 |

-continued
| Compound | Structure |
|---|---|
| (R) I-231 | 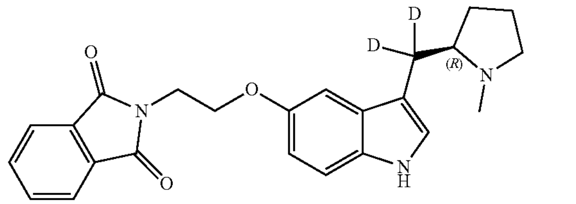 |
| (R) I-232 | 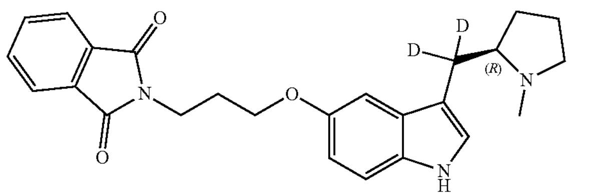 |
| (R) I-233 | 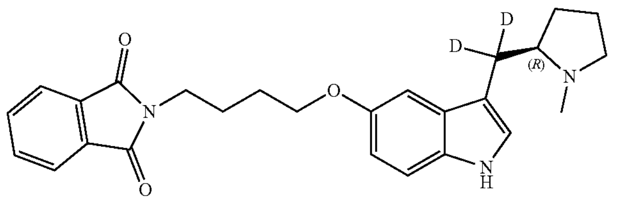 |
| (R) I-234 | 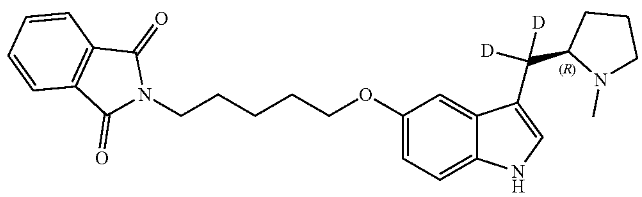 |
| Cis (R) I-235 | 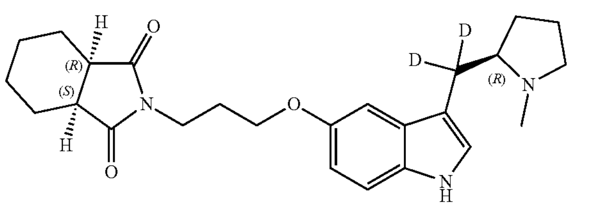 |
| Cis (R) I-236 | 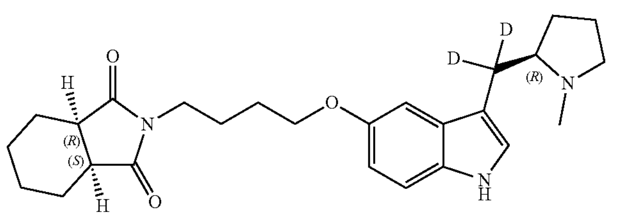 |
| (R) I-237 | 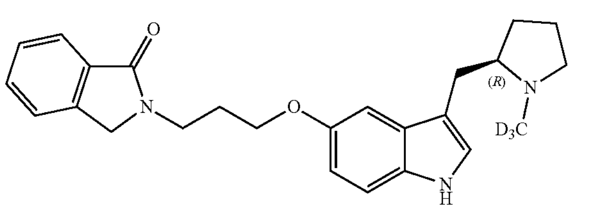 |

-continued
| Compound | Structure |
| --- | --- |
| (R) I-238 | 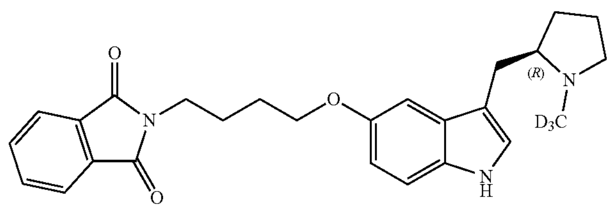 |
| (R) I-239 | 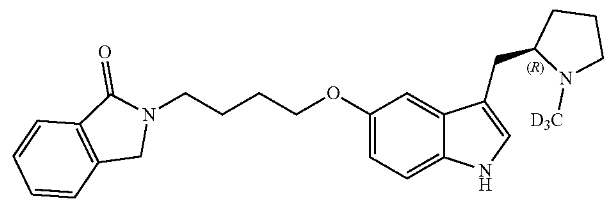 |
| Cis (R) I-240 | 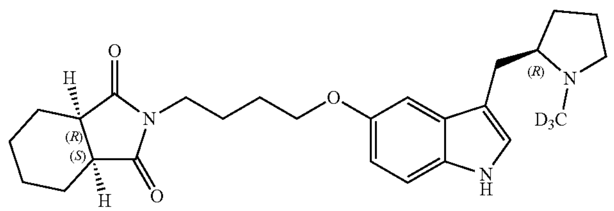 |
| Trans (R) I-241 | 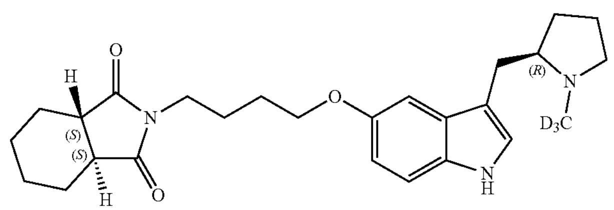 |
| (R) I-242 | 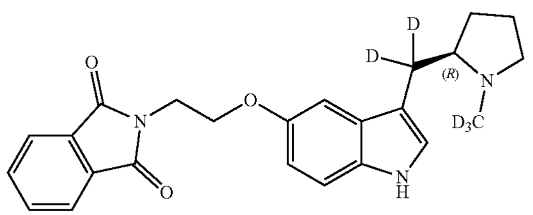 |
| (R) I-243 | 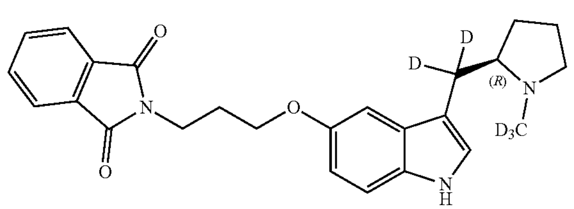 |
| (R) I-244 | 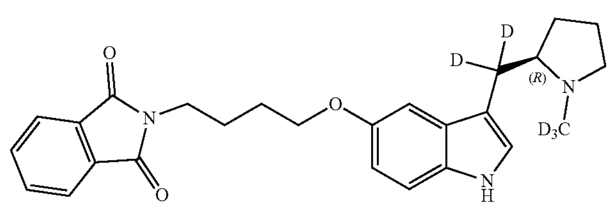 |

-continued
| Compound | Structure |
| --- | --- |
| (R) I-245 | 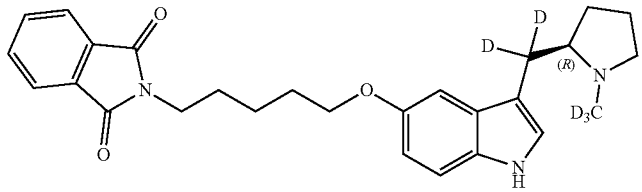 |
| Cis (R) I-246 | 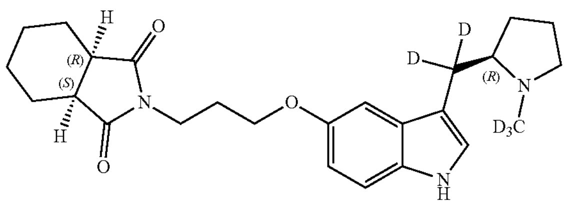 |
| Cis (R) I-247 | 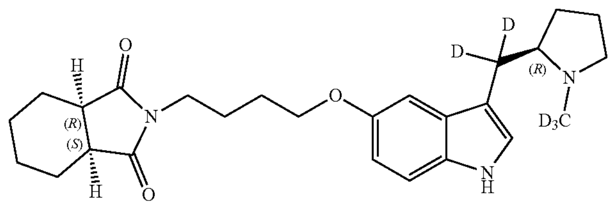 |
| Cis (R) I-248 | 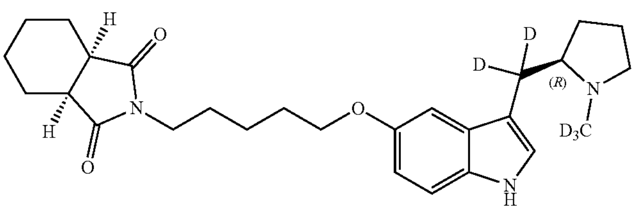 |
| Rac (R) I-248 | 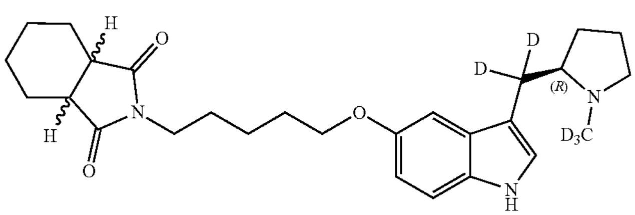 |
| | and |
| (R) I-249 | 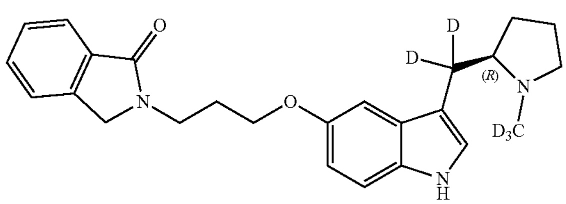 |
or a pharmaceutically acceptable salt, solvate, and/or prodrug thereof.
E78: The compound of any one of E1 to E8, wherein the compound of Formula (I) is selected from the table below:

| Compound | Structure |
|---|---|
| (R) I-250 | 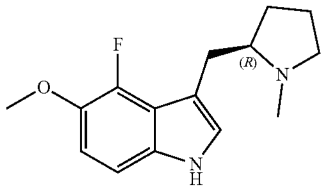 |
| (R) I-251 | 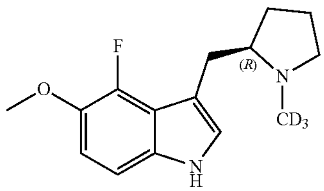 |
| (R) I-252 | 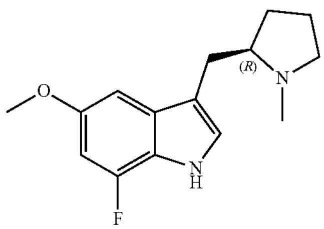 |
| (R) I-253 | 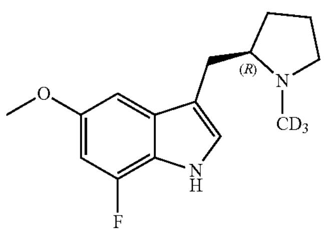 |
| (R) I-254 | 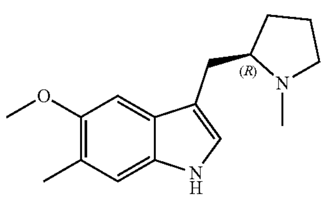 |
| (R) I-255 | 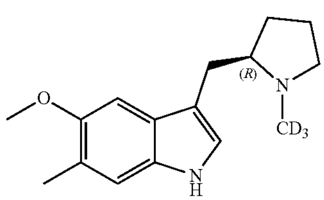 |
| (R) I-256 | 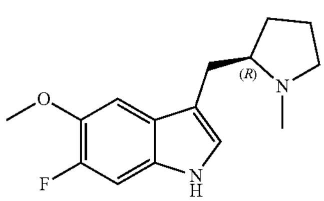 |

-continued
| Compound | Structure |
| --- | --- |
| (R) I-257 | 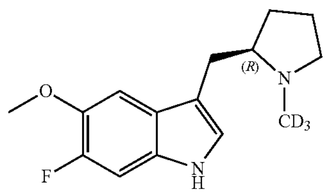 |
| (R) I-258 | 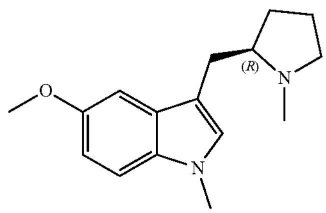 |
| (R) I-259 | 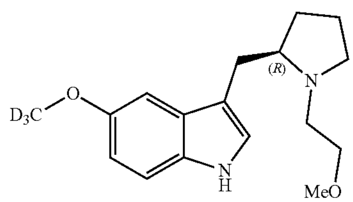 |
| (R) I-260 | 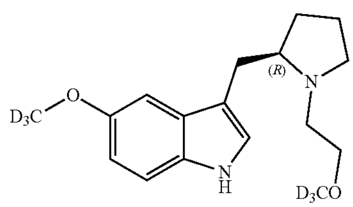 |
| (R) I-261 | 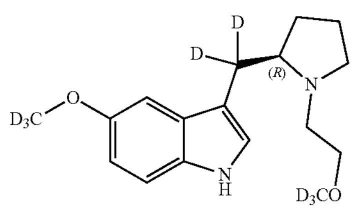 |
| (R) I-262 | 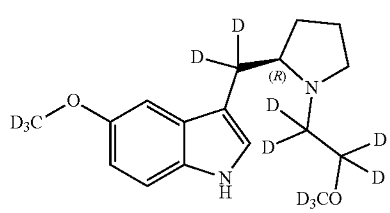 |
| (R) I-263 | 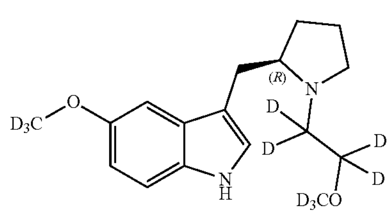 |

-continued
| Compound | Structure |
|---|---|
| (R) I-264 | 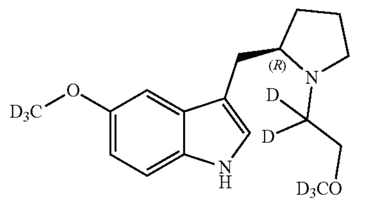 |
| (R) I-265 | 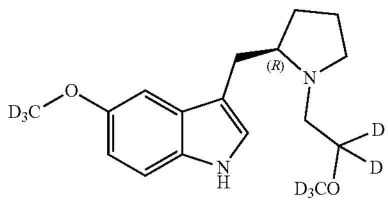 |
| (R) I-266 | 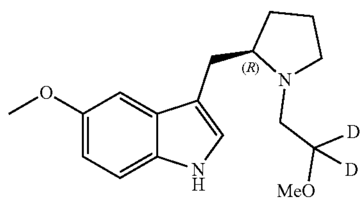 |
| (R) I-267 | 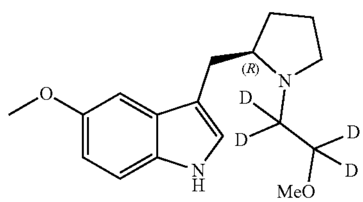 |
| (R) I-268 | 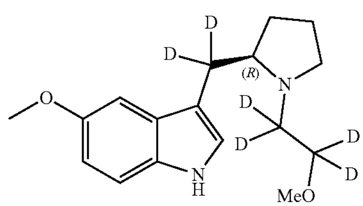 |
| (R) I-269 | 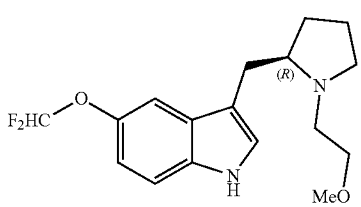 |
| (R) I-270 | 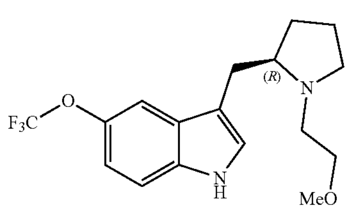 |

-continued
| Compound | Structure |
|---|---|
| (R) I-271 | 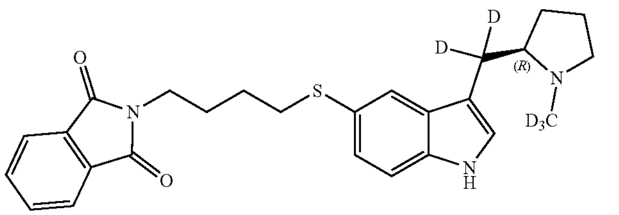 |
| (R) I-272 | 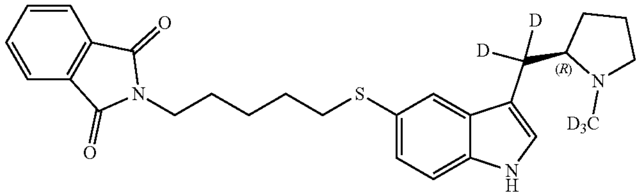 |
| (R) I-273 | 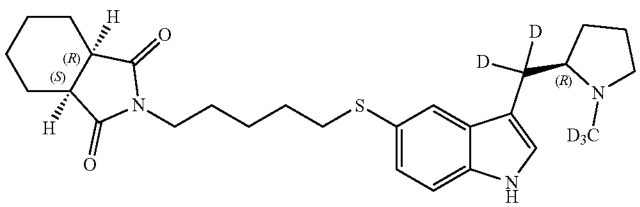 |
| (R) I-274 | 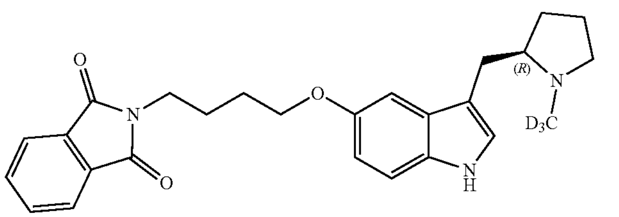 |
| (R) I-275 | 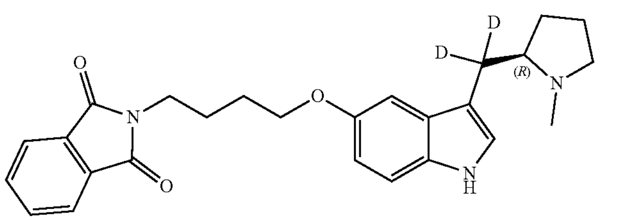 |
| (R) I-276 | 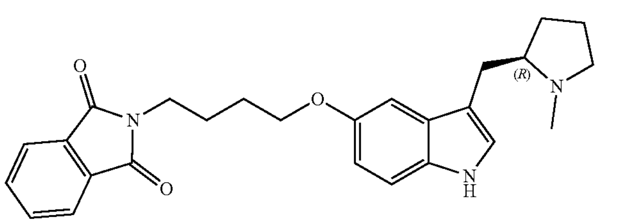 |
| (R) I-277 | 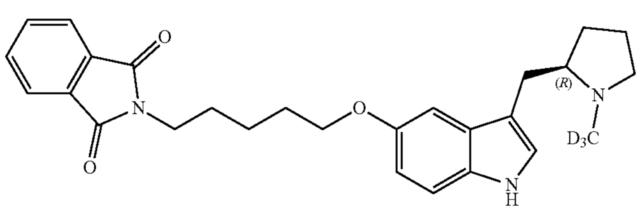 |

-continued
| Compound | Structure |
|---|---|
| (R) I-278 | 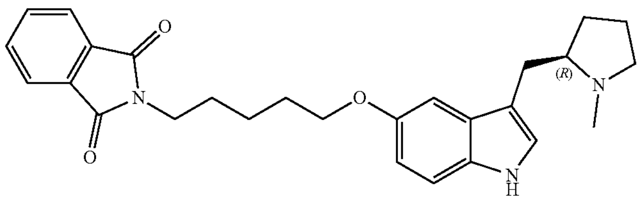 |
| (R) I-279 | 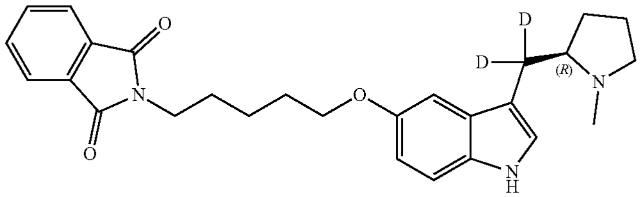 |
| (R) I-280 | 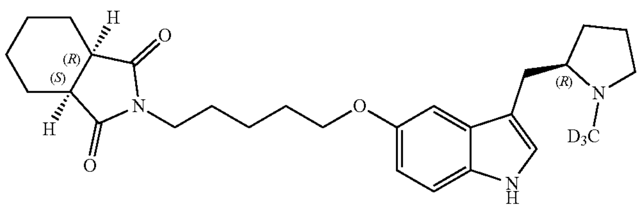 |
| (R) I-281 | 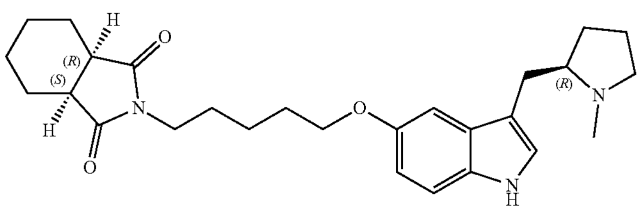 |
| (R) I-282 | 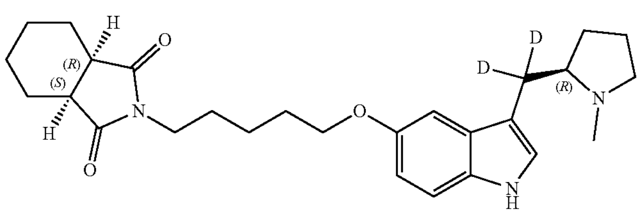 |
| (R) I-283 | 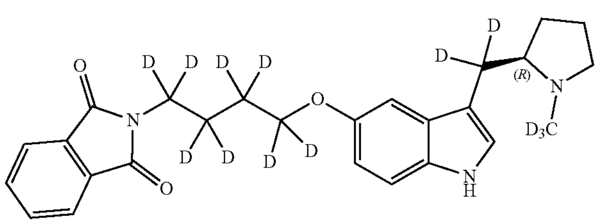 |
| (R) I-284 | 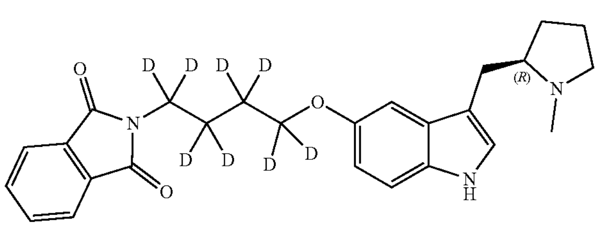 |

-continued
| Compound | Structure |
| --- | --- |
| (R) I-285 | 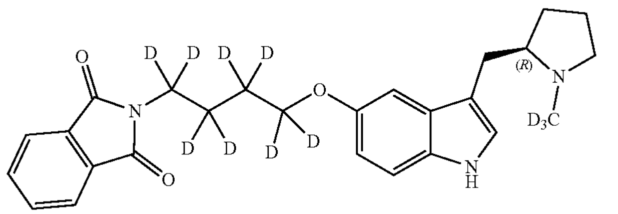 |
| (R) I-286 | 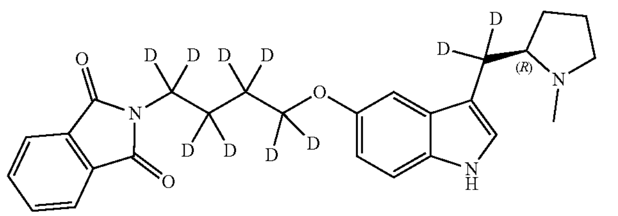 |
| (R) I-287 | 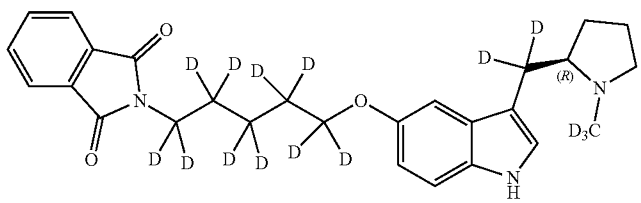 |
| (R) I-288 | 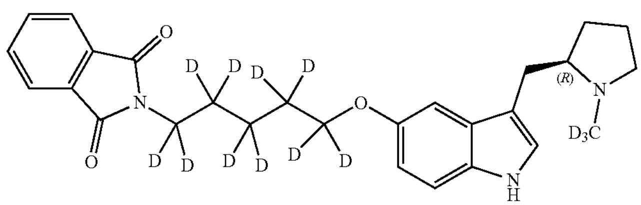 |
| (R) I-289 | 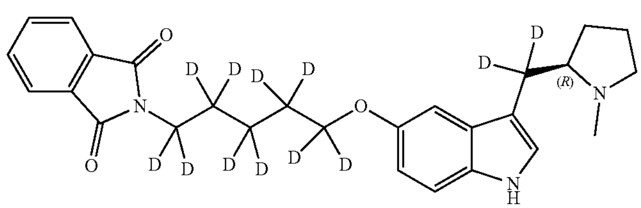 |
| (R) I-290 | 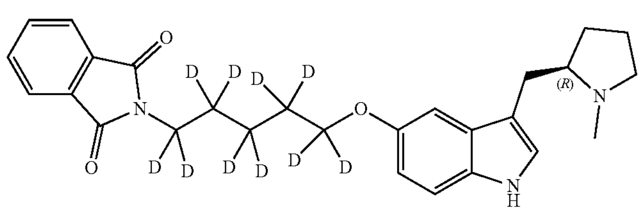 |
| (R) I-291 | 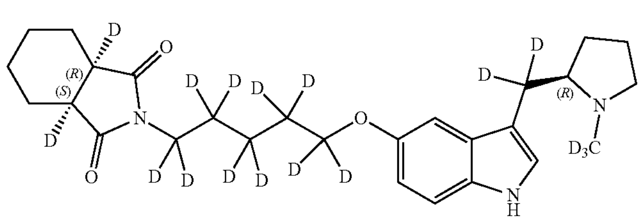 |

-continued
| Compound | Structure |
| --- | --- |
| (R) I-292 | 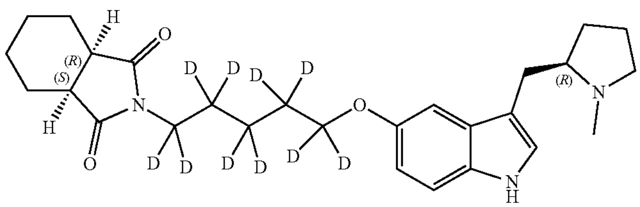 |
| (R) I-293 | 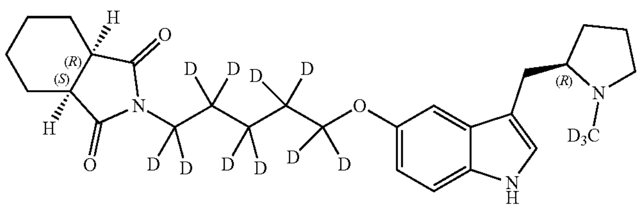 |
| (R) I-294 | 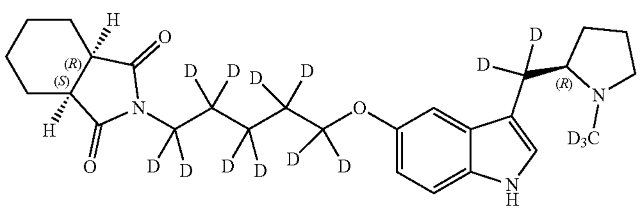 |
| (R) I-295 | 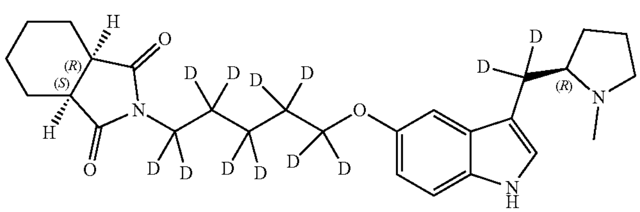 |
| (R) I-296 | 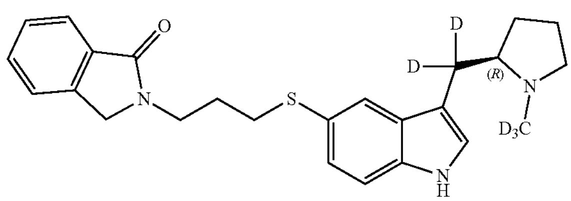 |
| (R) I-297 | 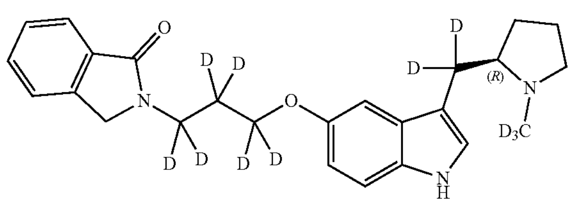 |
| (R) I-298 | 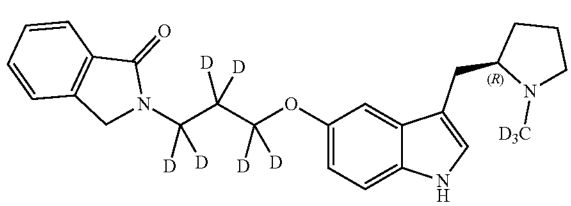 |

-continued
| Compound | Structure |
|---|---|
| (R) I-299 | 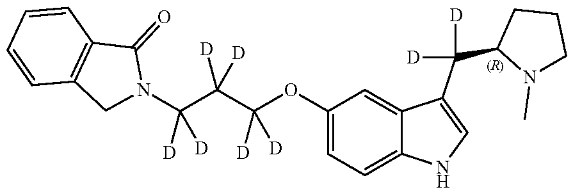 |
| (R) I-300 | 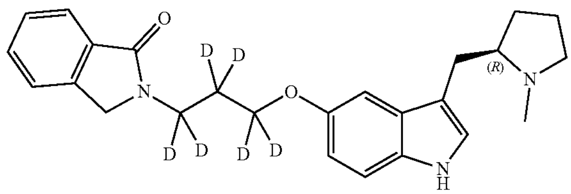 |
| (R) I-301 | 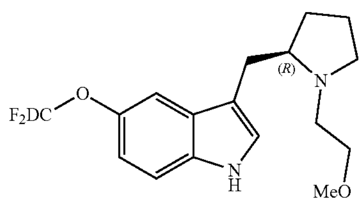 |
| (R) I-302 | 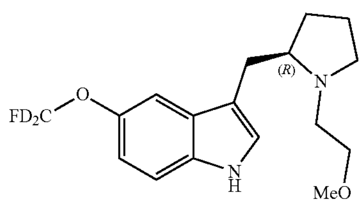 |
| (R) I-303 | 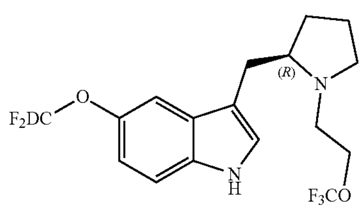 |
| (R) I-304 | 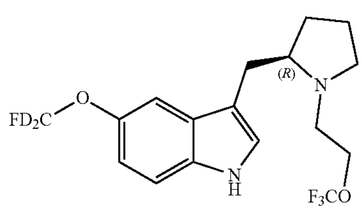 |
| (R) I-305 | 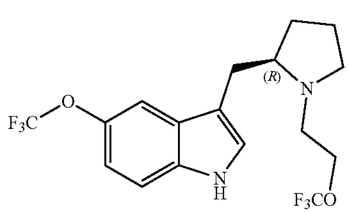 |

-continued
| Compound | Structure |
| --- | --- |
| (R) I-306 | 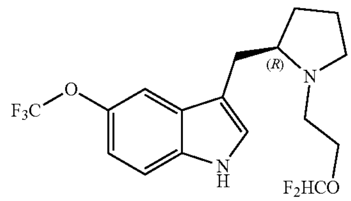 |
| (R) I-307 | 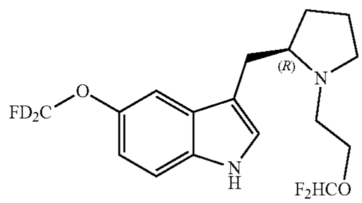 |
| (R) I-308 | 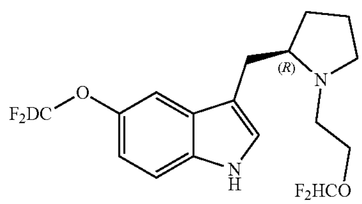 |
| (R) I-309 | 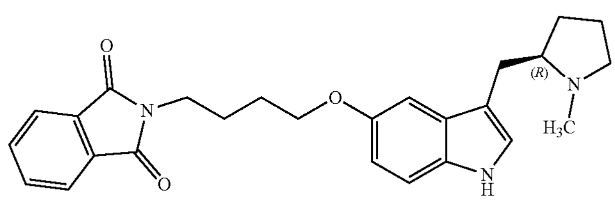 |
| (R) I-310 | 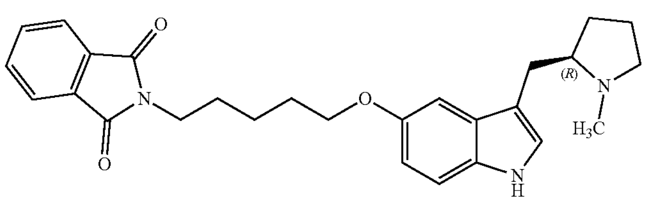 |
| (R) I-311 | 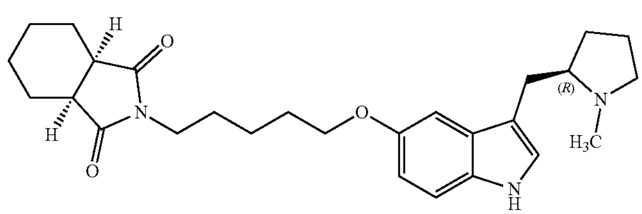 |
| (R) I-312 | 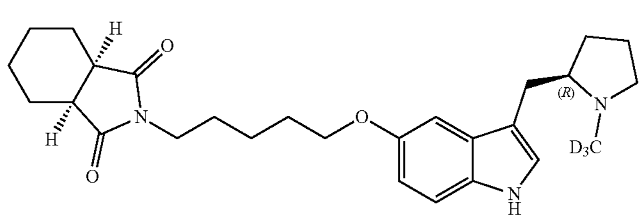 |

-continued

| Compound | Structure |
|---|---|
| (R) I-313 | 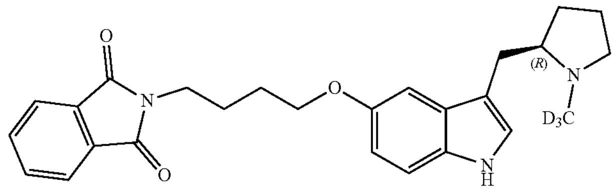 and |
| (R) I-314 | 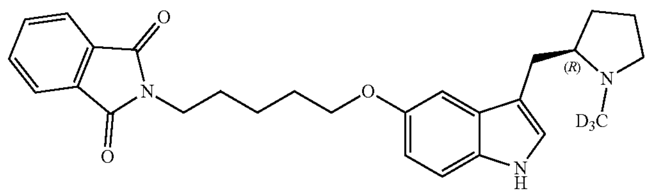 |

or a pharmaceutically acceptable salt, solvate, and/or prodrug thereof.

E79: A composition comprising one or more compounds of any one of E1 to E78 and a carrier.

E80: A pharmaceutical composition comprising one or more compounds of any one of E1 to E78 and a pharmaceutically acceptable carrier.

E81: A method for activating a serotonin receptor in a cell, either in a biological sample or in a patient, comprising administering an effective amount of one or more compounds of any one of E1 to E78 to the cell.

E82: A method of treating a disease, disorder, or condition by activation of a serotonin receptor comprising administering a therapeutically effective amount of one or more compounds of any one of E1 to E78 to a subject in need thereof.

E83: A method for activating a 5-$HT_{1A}$ and 5-$HT_{2A}$ in a cell, either in a biological sample or in a patient, comprising administering an effective amount of one or more compounds of any one of E1 to E78 to the cell.

E84: A method of treating a mental illness comprising administering a therapeutically effective amount of one or more compounds of any one of E1 to E78 to a subject in need thereof.

E85: The method of E84, wherein the mental illness is selected from hallucinations, delusions, and a combination thereof.

E86: The method of E84, wherein the mental illness is selected anxiety disorders; depression; mood disorders; psychotic disorders; impulse control and addiction disorders and behaviors; drug addiction; obsessive-compulsive disorder (OCD); post-traumatic stress disorder (PTSD); stress response syndromes; dissociative disorders; depersonalization disorder; factitious disorders; sexual and gender disorders; and somatic symptom disorders; and combinations thereof.

E87: A method of treating psychosis or psychotic symptoms comprising administering a therapeutically effective amount of one or more compounds of any one of E1 to E78 to a subject in need thereof.

E88: A method of treating a central nervous system (CNS) disease, disorder, or condition and/or a neurological disease, disorder, or condition comprising administering a therapeutically effective amount of one or more compounds of any one of E1 to E78 to a subject in need thereof.

E89: The method of E88, wherein the CNS disease, disorder, or condition and/or neurological disease, disorder, or condition is selected from neurological diseases including neurodevelopmental diseases and neurodegenerative diseases such as Alzheimer's disease; presenile dementia; senile dementia; vascular dementia; Lewy body dementia; cognitive impairment, Parkinson's disease and Parkinsonian related disorders such as Parkinson dementia, corticobasal degeneration, and supranuclear palsy; epilepsy; CNS trauma; CNS infections; CNS inflammation; stroke; multiple sclerosis; Huntington's disease; mitochondrial disorders; Fragile X syndrome; Angelman syndrome; hereditary ataxias; neuro-otological and eye movement disorders; neurodegenerative diseases of the retina amyotrophic lateral sclerosis; tardive dyskinesias; hyperkinetic disorders; attention deficit hyperactivity disorder and attention deficit disorders; restless leg syndrome; Tourette's syndrome; schizophrenia; autism spectrum disorders; tuberous sclerosis; Rett syndrome; cerebral palsy; disorders of the reward system including eating disorders such as anorexia nervosa ("AN") and bulimia nervosa ("BN"); and binge eating disorder ("BED"); pica; rumination disorder; avoidant/restrictive food intake disorder; trichotillomania, dermotillomania, nail biting; migraine; fibromyalgia; and peripheral neuropathy of any etiology; reduction in convergent thinking; increase in spontaneous divergent thinking and goal-oriented divergent thinking; and combinations thereof.

E90: A method of treating a behavioral problem comprising administering a therapeutically effective amount of one or more compounds of any one of E1 to E78 to a non-human subject in need thereof.

E91: The method of E90, wherein the non-human subject is a canine or feline suffering from neurological diseases, behavioral problems, trainability problems, and/or a combination thereof.

E92: The method of E91, wherein and the neurological diseases, behavioral problems, and trainability problems are selected from anxiety, fear and stress, sleep disturbances, cognitive dysfunction, aggression, and a combination thereof.

E93: A method of treating a disease, disorder, or condition by activation of a serotonin receptor comprising administering a therapeutically effective amount of one or more compounds of any one of E1 to E78 in combination with another known agent useful for treatment of a disease, disorder, or condition by activation of a serotonin receptor to a subject in need thereof.

E94: A pharmaceutical composition comprising a compound of any one of E1 to E78 and an additional therapeutic agent.

E95: The composition of E94, wherein the additional therapeutic agent is a psychoactive drug.

While the present disclosure has been described with reference to examples, it is to be understood that the scope of the claims should not be limited by the embodiments set forth in the examples but should be given the broadest interpretation consistent with the description as a whole.

All patents, patent applications, and publications cited herein are hereby incorporated by reference in their entirety. The disclosures of these publications in their entireties are hereby incorporated by reference into this application in order to more fully describe the state of the art as known to those skilled therein as of the date of the application described and claimed herein.

The invention claimed is:

1. A compound of Formula (I)

Formula (I)

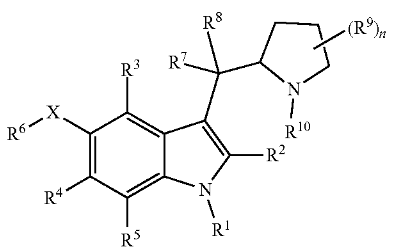

or a pharmaceutically acceptable salt, solvate, and/or prodrug thereof, wherein:

X is selected from S, S(O), and $SO_2$;

$R^1$ is selected from H, $C_1$-$C_6$alkyl, $C_1$-$C_6$alkyleneP(O)$(OR^{11})_2$, $C_1$-$C_6$alkyleneOP(O)$(OR^{11})_2$, C(O)$R^{11}$, $CO_2R^{11}$, C(O)N$(R^{11})_2$, S(O)$R^{11}$, and $SO_2R^{11}$;

$R^2$ is selected from H, halo, and $C_1$-$C_6$alkyl;

$R^3$ is selected from H, CN, halo, $C_1$-$C_6$alkyl, $C_2$-$C_6$alkenyl, and $C_2$-$C_6$alkynyl;

$R^4$ is selected from H, CN, halo, $C_1$-$C_6$alkyl, $C_2$-$C_6$alkenyl, and $C_2$-$C_6$alkynyl;

$R^5$ is selected from H, CN, halo, $C_1$-$C_6$alkyl, $C_2$-$C_6$alkenyl, and $C_2$-$C_6$alkynyl;

$R^6$ is selected from H, $C_1$-$C_{10}$alkyl, $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{13}$, and C(O)$R^{13}$;

$R^7$ is selected from H, halo, and $C_1$-$C_6$alkyl;

$R^8$ is selected from H, halo, and $C_1$-$C_6$alkyl;

each $R^9$ is independently selected from halo, $C_1$-$C_6$alkyl, OH, O$C_1$-$C_6$alkyl, $C_1$-$C_6$alkyleneOH, and $C_1$-$C_6$alkyleneO$C_1$-$C_6$alkyl;

$R^{10}$ is selected from H, $C_1$-$C_6$alkyl, $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_6$alkylene$C_3$-$C_7$cycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter eight groups being optionally substituted with one to four substituents independently selected from halo, $C_1$-$C_6$alkyl, $OR^{15}$, and C(O)$R^{15}$;

Z is selected from O, C(O), $NR^{16}$C(O), $NR^{16}$C(O)O, C(O)$NR^{16}$, OC(O)$NR^{16}$, and $NR^{16}$;

Z' is selected from O, C(O), $NR^{17}$C(O), $NR^{17}$C(O)O, C(O)$NR^{17}$, OC(O)$NR^{17}$, and $NR^{17}$;

n is an integer selected from 0, 1, 2, 3, and 4;

$R^{11}$ is independently selected from H and $C_1$-$C_6$alkyl;

$R^{12}$ is selected from H, $C_1$-$C_6$alkyl, $C_3$-$C_7$cycloalkyl, $C_3$-$C_{10}$heterocycloalkyl, $C_6$-$C_{10}$aryl, and $C_5$-$C_{10}$heteroaryl, the latter four groups being optionally substituted with one to four substituents independently selected from halo, $C_1$-$C_4$alkyl, O$C_1$-$C_4$alkyl, and C(O) $C_1$-$C_4$alkyl;

$R^{13}$ is selected from H and $C_1$-$C_6$alkyl;

$R^{14}$ is selected from H, $C_1$-$C_6$alkyl, $C_3$-$C_7$cycloalkyl, $C_3$-$C_{10}$heterocycloalkyl, $C_6$-$C_{10}$aryl, and $C_5$-$C_{10}$heteroaryl, the latter four groups being optionally substituted with one to four substituents independently selected from halo, $C_1$-$C_4$alkyl, O$C_1$-$C_4$alkyl, and C(O) $C_1$-$C_4$alkyl;

$R^{15}$ is selected from H and $C_1$-$C_6$alkyl;

$R^{16}$ is selected from H and $C_1$-$C_6$alkyl;

$R^{17}$ is selected from H and $C_1$-$C_6$alkyl, and available hydrogen atoms are optionally replaced with a halogen atom and/or available hydrogen atoms are optionally replaced with deuterium.

2. The compound of claim 1, wherein available hydrogen atoms are optionally independently replaced with an iodine atom, a fluorine atom, and/or a chlorine atom and/or available hydrogen atoms are optionally replaced with deuterium.

3. The compound of claim 1, wherein X is S (O) or S.

4. The compound of claim 3, wherein $R^6$ is selected from H, $C_1$-$C_6$alkyl, $C_2$-$C_6$alkenyl, $C_2$-$C_6$alkynyl, $C_1$-$C_6$alkyleneZ$R^{12}$, $C_2$-$C_6$alkenyleneZ$R^{12}$, $C_2$-$C_6$alkynyleneZ$R^{12}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted with one to four substituents independently selected from halo, $C_1$-$C_6$alkyl, $OR^{13}$, and C(O)$R^{13}$, and wherein available hydrogen atoms are optionally replaced with a halogen atom and/or available hydrogen atoms are optionally replaced with deuterium.

5. The compound of claim 3, wherein $R^6$ is a member selected from $C_3$-$C_{10}$heterocycloalkyl, $C_3$-$C_{10}$heterocycloalkenyl, $C_3$-$C_{10}$heterocycloalkynyl, $C_5$-$C_{10}$heteroaryl, $C_1$-$C_6$alkylene$C_3$-$C_{10}$heterocycloalkyl, $C_1$-$C_6$alkylene$C_3$-$C_{10}$heterocycloalkenyl, $C_1$-$C_6$alkylene$C_3$ $C_{10}$heterocycloalkynyl, and $C_1$-$C_6$alkylene$C_5$-$C_{10}$heteroaryl including one or more heteromoieties selected from O, S, S (O), $SO_2$, and N, wherein $R^6$ optionally comprises one or two C═O groups, wherein $R^6$ is optionally substituted with one to four substituents independently selected from halo, $C_1$-$C_6$alkyl, $OR^{13}$, and C(O)$R^{13}$, wherein $R^6$ is optionally a substituted or unsubstituted polycyclic group or a substituted or unsubstituted benzofused group, and wherein available hydrogen atoms are optionally and independently replaced with a halogen atom and/or available hydrogen atoms are optionally replaced with deuterium.

6. The compound of claim 3, wherein:

$R^7$ is selected from H, D, F, Cl, Br, $C_1$-$C_4$alkyl, $C_1$-$C_4$fluoroalkyl, $C_1$-$C_4$deuteroalkyl, and $C_1$-$C_4$deuterofluoroalkyl; and $R^8$ is selected from H, D, F, Cl, Br, $C_1$-$C_4$alkyl, $C_1$-$C_4$fluoroalkyl, $C_1$-$C_4$deuteroalkyl, and $C_1$-$C_4$deuterofluoroalkyl.

7. The compound of claim 3, wherein:

$R^7$ is selected from H, F, and D; and $R^8$ is selected from H, F, and D.

8. The compound of claim 3, wherein at least one $R^9$ is selected from halo, $C_1$-$C_4$alkyl, $C_1$-$C_4$deuteroalkyl, $C_1$-$C_4$haloalkyl, and $C_1$-$C_4$deuterohaloalkyl.

9. The compound of claim 3, wherein at least one $R^9$ is selected from OH, $OC_1$-$C_4$alkyl, $OC_1$-$C_4$deuteroalkyl, $OC_1$-$C_4$fluoroalkyl, $OC_1$-$C_4$deuterofluoroalkyl, $C_1$-$C_4$alkyleneOH, $C_1$-$C_4$fluoroalkyleneOH, $C_1$-$C_4$deuteroalkyleneOH, $C_1$-$C_4$deuterofluoroalkyleneOH, $C_1$-$C_4$alkyleneO$C_1$-$C_4$alkyl, $C_1$-$C_4$alkyleneO$C_1$-$C_4$fluoroalkyl, $C_1$-$C_4$alkyleneO$C_1$-$C_4$deuteroalkyl, $C_1$-$C_4$alkyleneO$C_1$-$C_4$deuterofluoroalkyl, $C_1$-$C_4$fluoroalkyleneO$C_1$-$C_4$alkyl, $C_1$-$C_4$deuteroalkyleneO$C_1$-$C_4$alkyl, $C_1$-$C_4$deuterofluoroalkyleneO$C_1$-$C_4$alkyl, $C_1$-$C_4$fluoroalkyleneO$C_1$-$C_4$fluoroalkyl, $C_1$-$C_4$fluoroalkyleneO$C_1$-$C_4$deuteroalkyl, $C_1$-$C_4$deuteroalkyleneO$C_1$-$C_4$fluoroalkyl, $C_1$-$C_4$deuteroalkyleneO$C_1$-$C_4$deuteroalkyl, $C_1$-$C_4$deuterofluoroalkyleneO$C_1$-$C_4$fluoroalkyl, $C_1$-$C_4$fluoroalkyleneO$C_1$-$C_4$deuterofluoroalkyl, and $C_1$-$C_4$deuterofluoroalkyleneO$C_1$-$C_4$deuterofluoroalkyl.

10. The compound of claim 3, wherein $R^{10}$ is selected from H, $C_1$-$C_6$alkyl, $C_2$-$C_6$alkenyl, $C_2$-$C_6$alkynyl, $C_1$-$C_6$alkyleneZ'$R^{14}$, $C_2$-$C_6$alkenyleneZ'$R^{14}$, $C_2$-$C_6$alkynyleneZ'$R^{14}$, $C_3$-$C_7$cycloalkyl, $C_3$-$C_{10}$heterocycloalkyl, $C_6$-$C_{10}$aryl, $C_5$-$C_{10}$heteroaryl, $C_1$-$C_4$alkylene$C_3$-$C_7$cycloalkyl, $C_1$-$C_4$alkylene$C_3$-$C_{10}$heterocycloalkyl, $C_1$-$C_4$alkylene$C_6$-$C_{10}$aryl, and $C_1$-$C_4$alkylene$C_5$-$C_{10}$heteroaryl, the latter eight groups being optionally substituted with one to four substituents independently selected from halo, $C_1$-$C_6$alkyl, $OR^{15}$, and $C(O)R^{15}$, and wherein available hydrogen atoms are optionally independently replaced with a fluorine atom and/or a chlorine atom and/or available hydrogen atoms are optionally replaced with deuterium.

11. The compound of claim 3, wherein $R^{10}$ is a member selected from $C_3$-$C_{10}$heterocycloalkyl, $C_3$-$C_{10}$heterocycloalkenyl, $C_3$-$C_{10}$heterocycloalkynyl, $C_5$-$C_{10}$heteroaryl, $C_1$-$C_6$alkylene$C_3$-$C_{10}$heterocycloalkyl, $C_1$-$C_6$alkylene$C_3$-$C_{10}$heterocycloalkenyl, $C_1$-$C_6$alkylene$C_3$-$C_{10}$heterocycloalkynyl, $C_1$-$C_6$alkylene$C_5$-$C_{10}$heteroaryl, and $C_1$-$C_6$alkyleneZ'$R^{14}$, $C_2$-$C_6$alkenyleneZ'$R^{14}$, and $C_2$-$C_6$alkynyleneZ'$R^{14}$ in which $R^{14}$ is $C_3$-$C_{10}$heterocycloalkyl or $C_5$-$C_{10}$heteroaryl, wherein $R^{10}$ includes one or more heteromoieties selected from O, S, S(O), $SO_2$, and N, wherein $R^{10}$ optionally includes one or two C═O groups, wherein $R^{10}$ is optionally substituted with one to four substituents independently selected from halo, $C_1$-$C_6$alkyl, $OR^{15}$, and $C(O)R^{15}$, wherein $R^{10}$ is optionally a substituted or unsubstituted polycyclic group or a substituted or unsubstituted benzofused group, and wherein available hydrogen atoms are optionally and independently replaced with a halogen atom and/or available hydrogen atoms are optionally replaced with deuterium.

12. The compound of claim 3, wherein $R^6$ is selected from $CH_3$, $CD_3$, $CF_3$, $CH_2CH_3$, $CH_2CH_2CH_3$, $CH(CH_3)_2$, $CH_2C(CH_3)_3$, $CH_2CH_2C(CH_3)_3$, $CH_2F$, $CHF_2$, $CH_2CHF_2$, $CH_2CF_3$, $CH_2CH_2CF_3$,

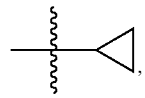, 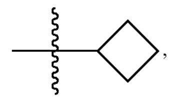, 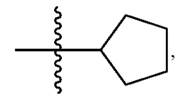,

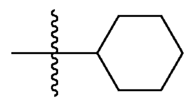, 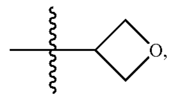, 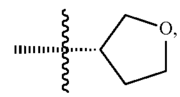,

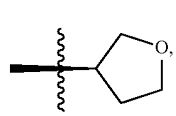, 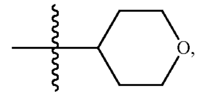, 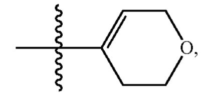,

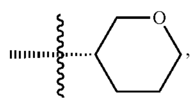, 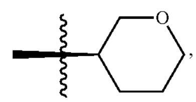, 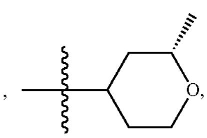,

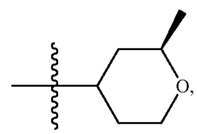, 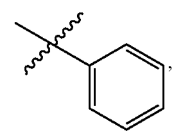,

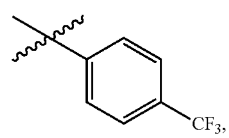, and 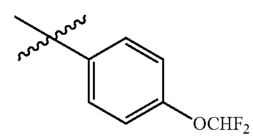

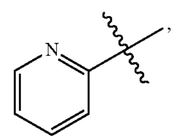, 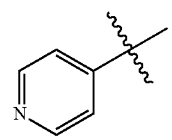 and 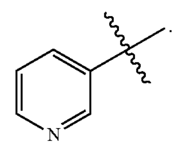.

13. The compound of claim 3, wherein:

$R^6$ is selected from $CH_3$, $CD_3$, $CH_2CH_3$, $CH_2CH_2CH_3$, $CH(CH_3)_2$, $CH_2C(CH_3)_3$, $CH_2CH_2C(CH_3)_3$, $CH_2F$, $CHF_2$, $CH_2CHF_2$, $CH_2CF_3$, $CH_2CH_2CF_3$, $C_1$-$C_4$alkyleneO$CH_3$, $C_1$-$C_4$alkyleneO$CHF_2$, $C_1$-$C_4$alkyleneO$CH_2F$,

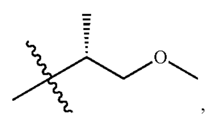, 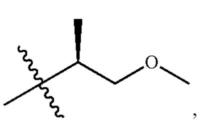,

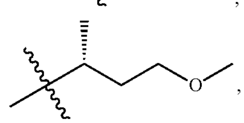, 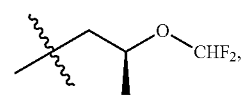,

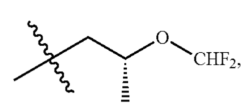, 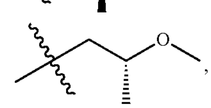, $C_1$-$C_4$alkleneC(O)$CHF_2$, $C_1$-$C_4$alkleneC(O) $CF_3$,
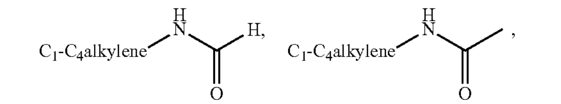
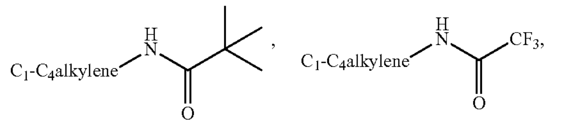
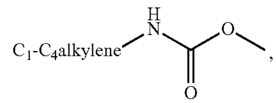
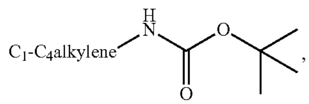
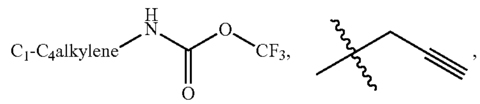
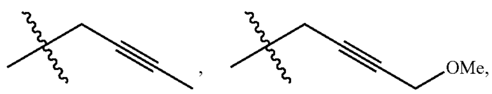
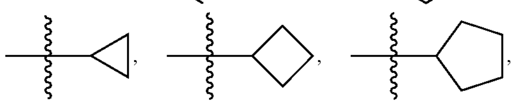
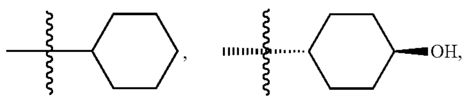
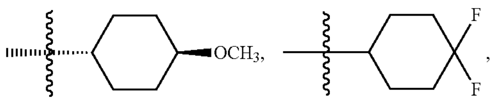
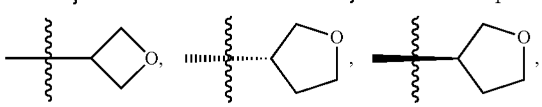
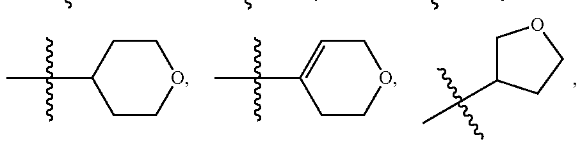
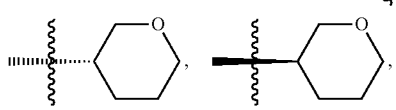
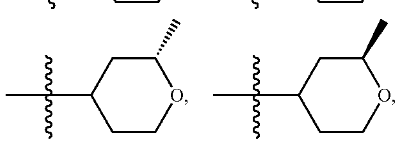
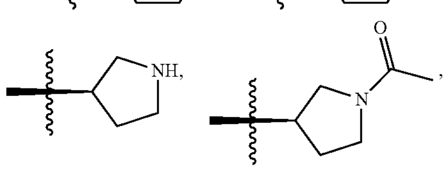
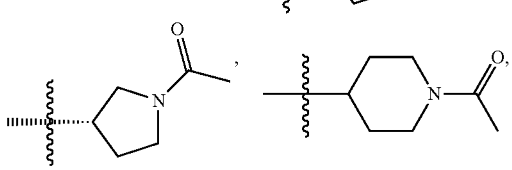
-continued
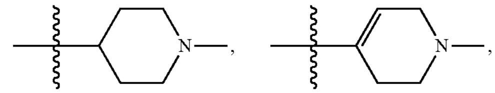
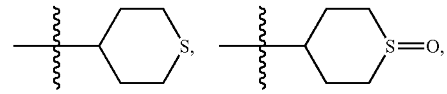
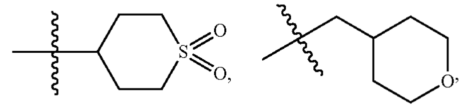
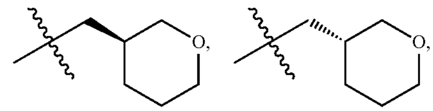
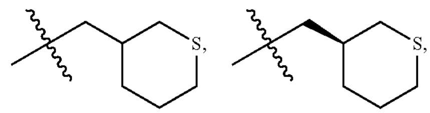
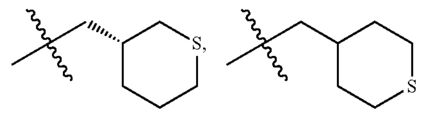
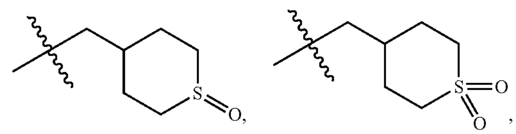
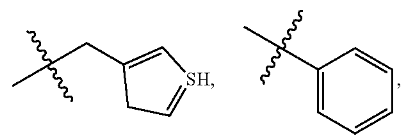
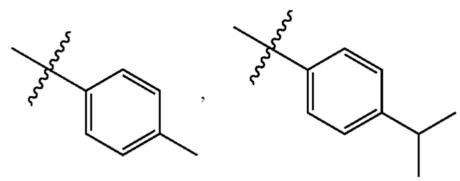
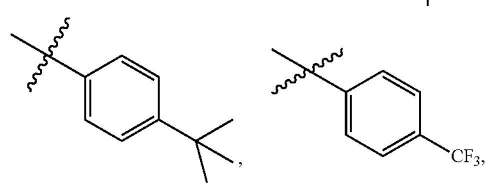
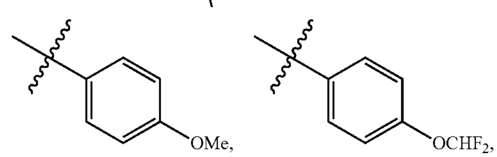
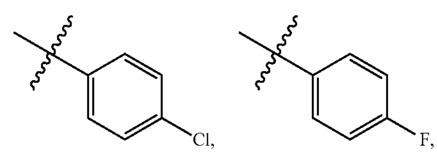
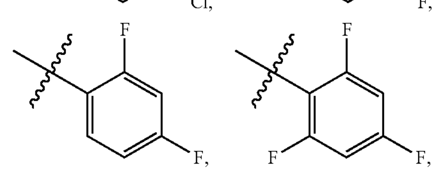

-continued
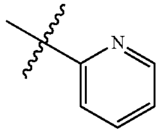,
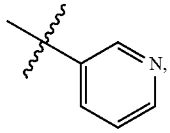
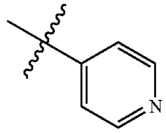,
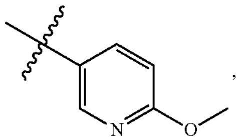,
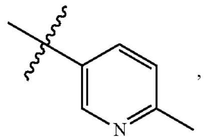,
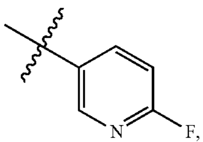
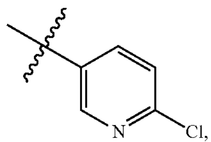
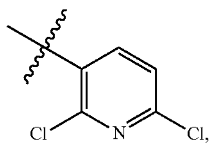
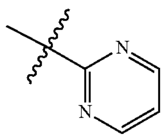,
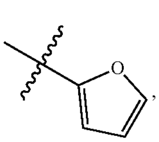,
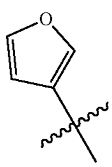,
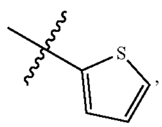,
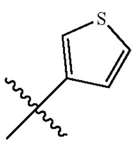,
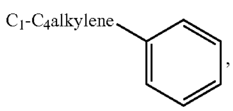,
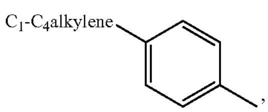,
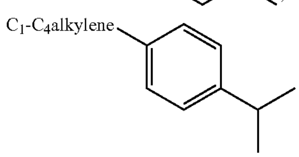,
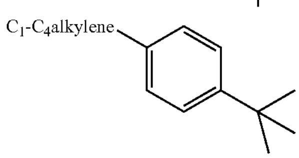,
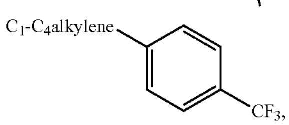
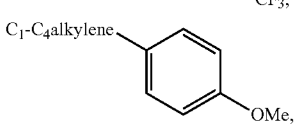
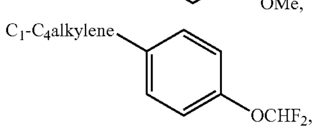
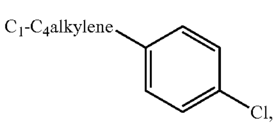
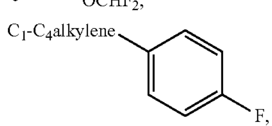
-continued
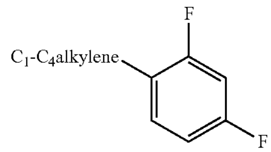
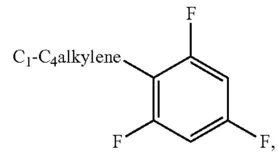
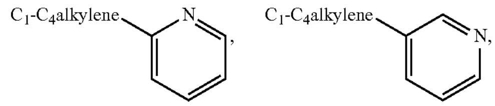
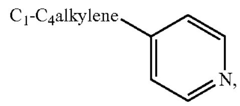
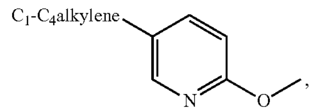
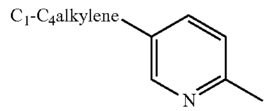
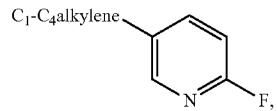
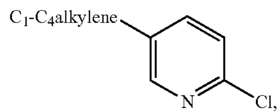
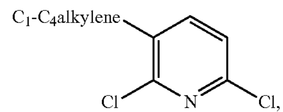
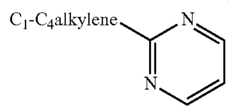
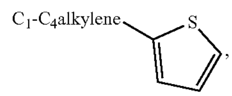
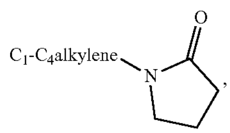
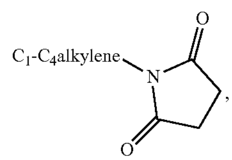
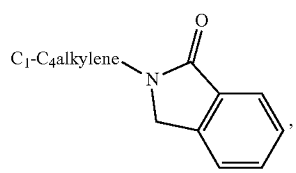
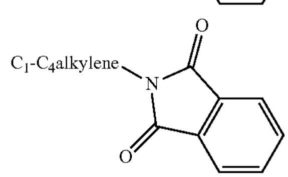
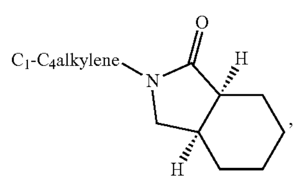
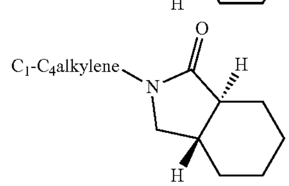
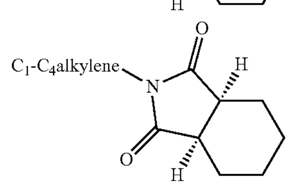

-continued
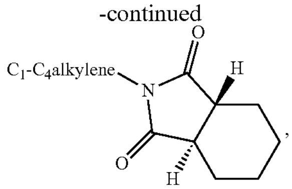,
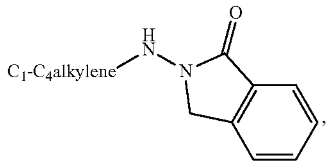,
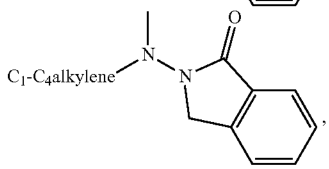,
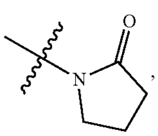, 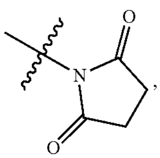, 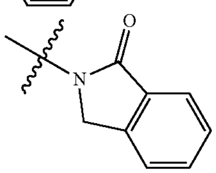,
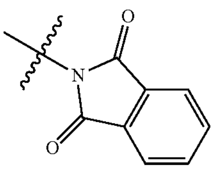, 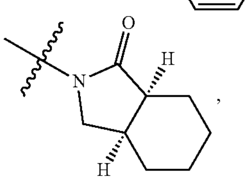,
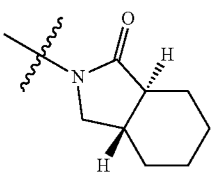, 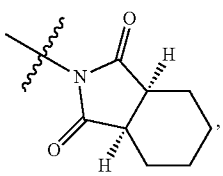,
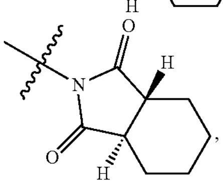, 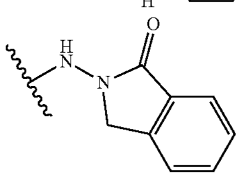, and
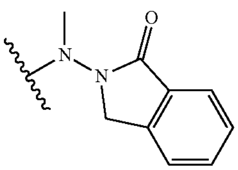;
and
$R^{10}$ is selected from
$CH_3$, $CD_3$, $CH_2CH_3$, $CH_2CH_2CH_3$, $CH(CH_3)_2$, $CH_2C(CH_3)_3$, $CH_2CH_2C(CH_3)_3$, $CH_2F$, $CHF_2$, $CH_2CHF_2$, $CH_2CF_3$, $CH_2CH_2CF_3$, $C_1$-$C_4$alkyleneOCH$_3$, $C_1$-$C_4$alkyleneOCHF$_2$, $C_1$-$C_4$alkyleneOCH$_2$F,
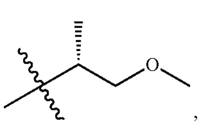, 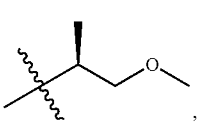,
-continued
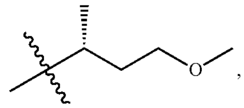, 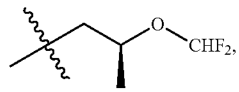,
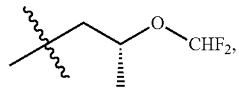, 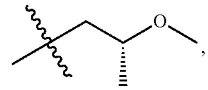,
$C_1$-$C_4$alkleneC(O)CHF$_2$, $C_1$-$C_4$alkleneC(O) CF$_3$,
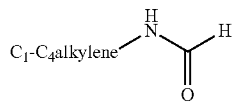, 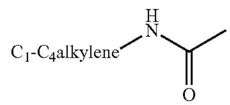,
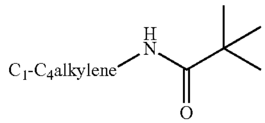, 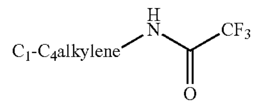,
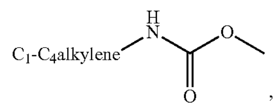,
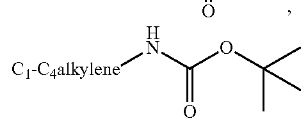,
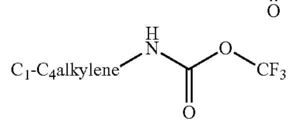, 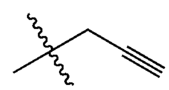,
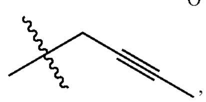, 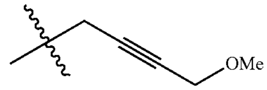,
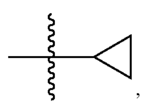, 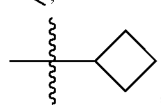, 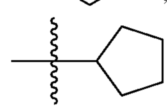,
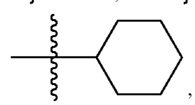, 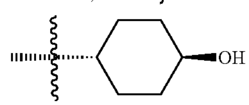,
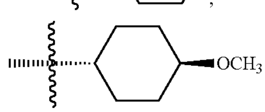, 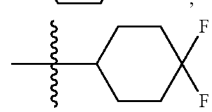
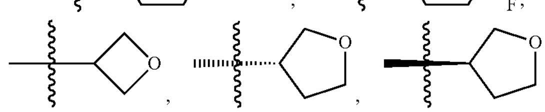
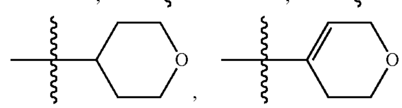
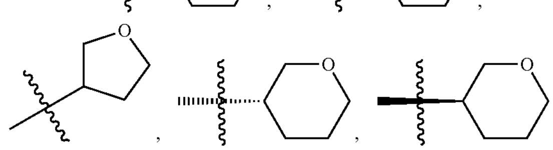
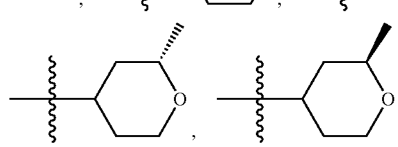

-continued
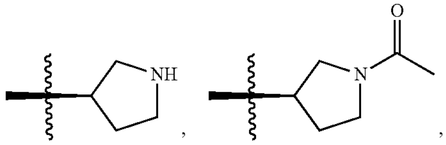,
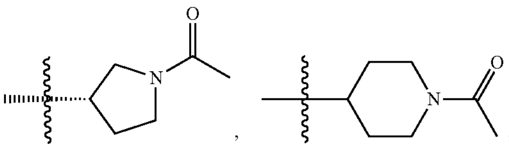,
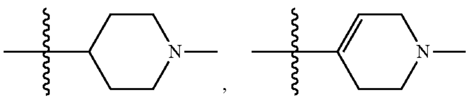,
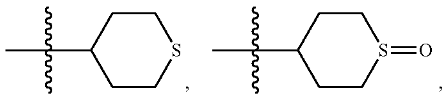,
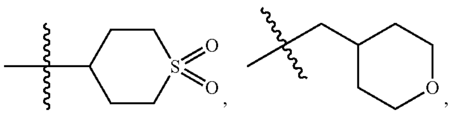,
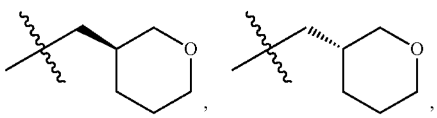,
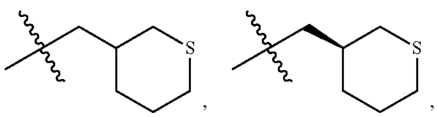,
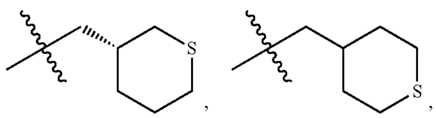,
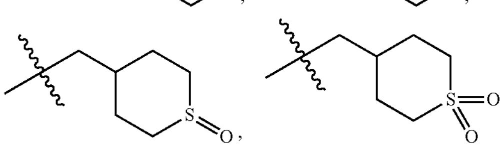,
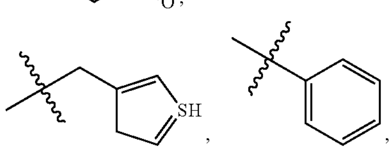,
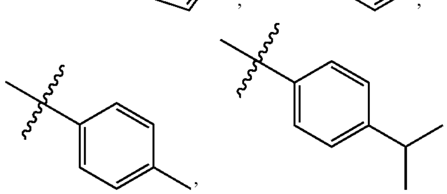,
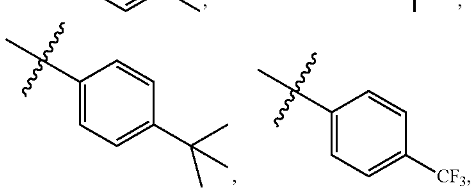,
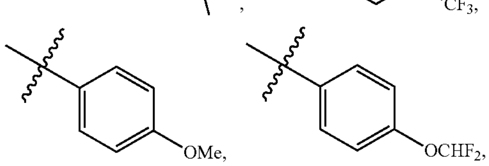,
-continued
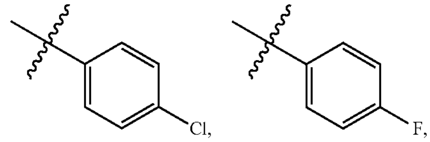,
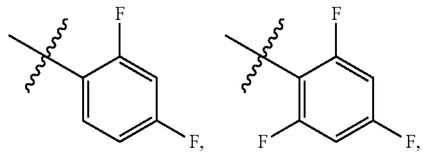,
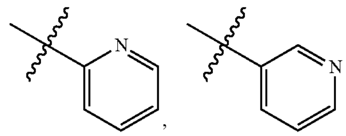,
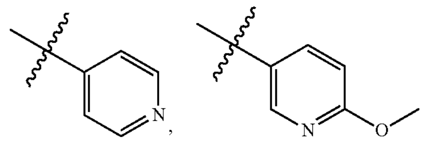,
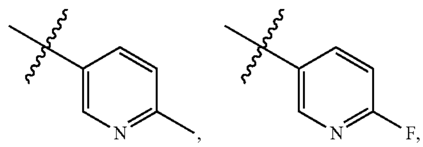,
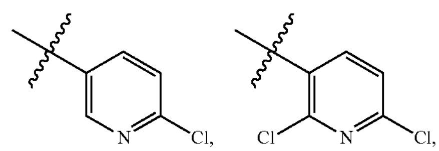,
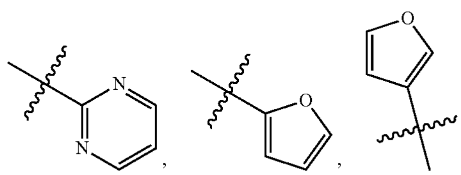,
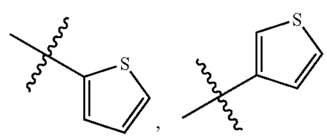,
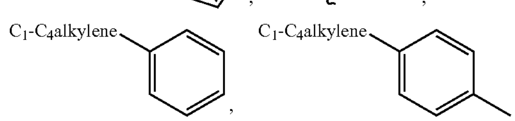,
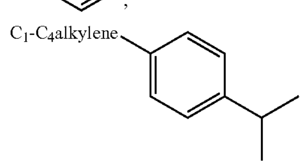,
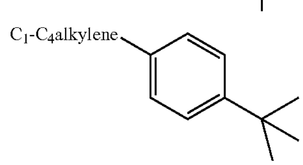,
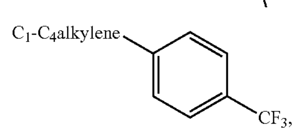, -continued
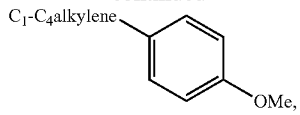
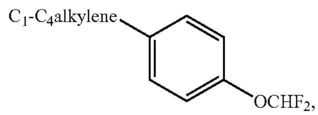
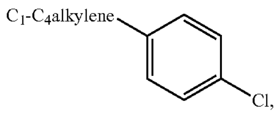
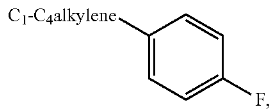
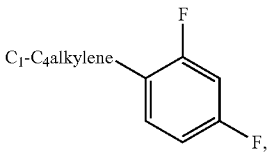
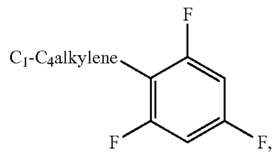
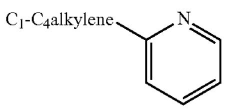
,
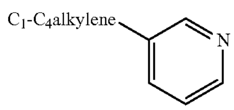
,
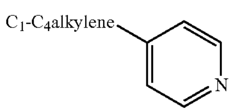
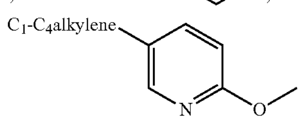
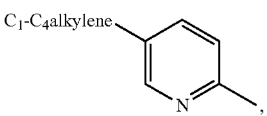
,
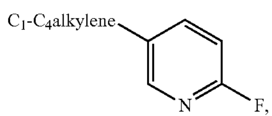
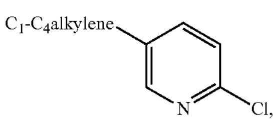
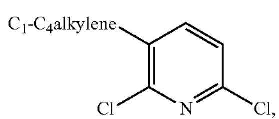
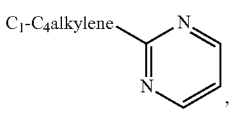
,
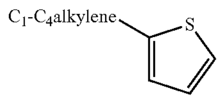
,
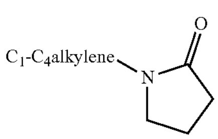
,
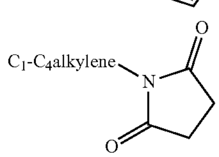
,
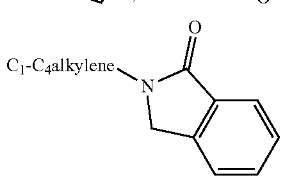
,
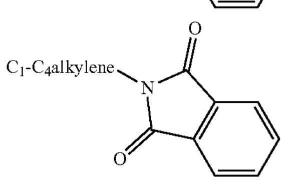
,
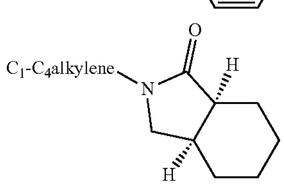
,
-continued
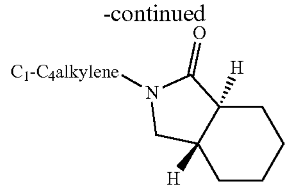
,
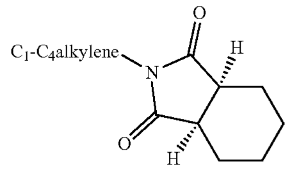
,
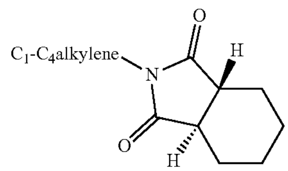
,
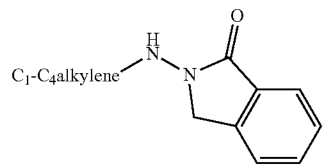
,
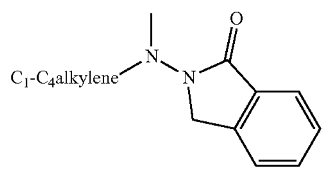
,
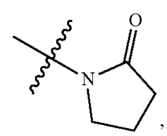
,
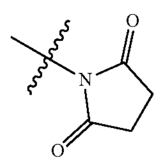
,
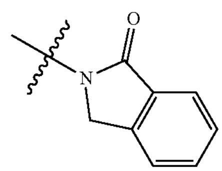
,
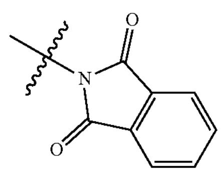
,
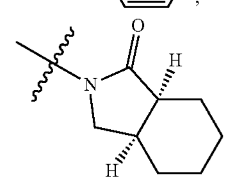
,
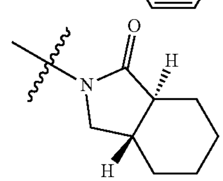
,
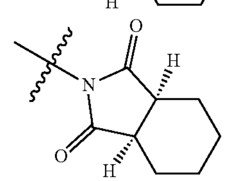
,
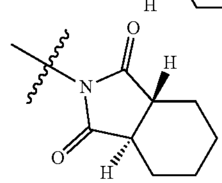
,
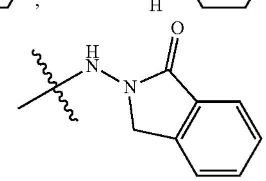
, and
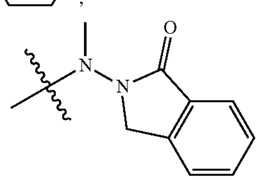
.
14. The compound of claim 1, wherein X is S.

15. The compound of claim 14, wherein:

$R^1$ is H;

$R^2$ is H;

$R^3$ is H;

$R^4$ is H;

$R^5$ is H;

$R^6$ is selected from $C_1$-$C_6$alkyl, $C_3$-$C_7$cycloalkyl, $C_3$-$C_{10}$heterocycloalkyl, and $C_6$-$C_{10}$aryl;

$R^7$ is H;

$R^8$ is H;

$R^{10}$ is selected from H, $C_1$-$C_6$alkyl, $C_2$-$C_6$alkynyl, $C_1$-$C_6$alkyleneZ'$R^{14}$, $C_2$-$C_6$alkynyleneZ'$R^{14}$, $C_3$-$C_7$cycloalkyl, $C_3$-$C_{10}$heterocycloalkyl, $C_1$-$C_6$alkylene$C_3$-$C_{10}$heterocycloalkyl, $C_1$-$C_6$alkylene$C_6$-$C_{10}$aryl, and $C_1$-$C_6$alkylene$C_5$-$C_{10}$heteroaryl, the latter five groups being optionally substituted with one to four substituents independently selected from halo, $C_1$-$C_6$alkyl, $OR^{15}$, and $C(O)R^{15}$; and n is 0.

16. The compound of claim 15, wherein:

Z' is selected from O, C(O), $NR^{17}C(O)$, and $NR^{17}$; and $R^{14}$ is selected from H, $C_1$-$C_6$alkyl, and $C_3$-$C_{10}$heterocycloalkyl.

17. The compound of claim 15, wherein:

$R^6$ is selected from $CH_3$, $CH(CH_3)_2$, $C(CH_3)_3$, $CH_2C(CH_3)_3$,

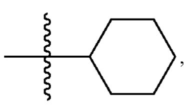, 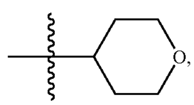 and

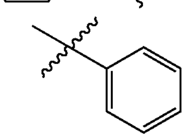;

and $R^{10}$ is selected from H, $CH_3$, $CH_2CH_3$, $CH(CH_3)_2$, $CH_2C(CH_3)_3$, $CH_2CH_2C(CH_3)_3$, $CH_2CHF_2$, $CH_2CF_3$, $CH_2CH_2CF_3$, $C_1$-$C_4$alkyleneOCH$_3$, $C_1$-$C_4$alkyleneOCHF$_2$,

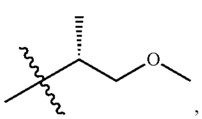, 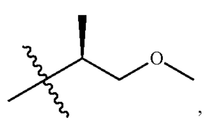,

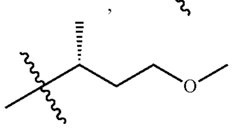, $C_1$-$C_4$alkyleneC(O) $CF_3$,

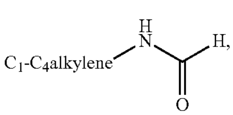 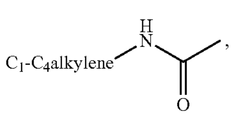,

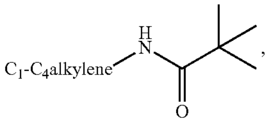, 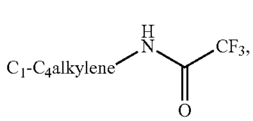

-continued

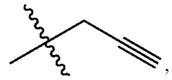, 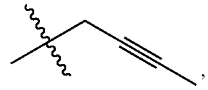,

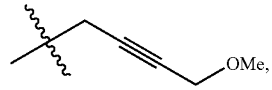 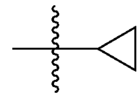,

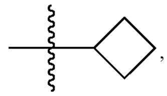, 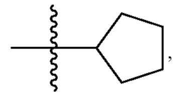, 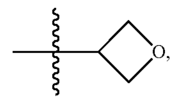

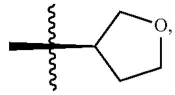 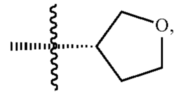 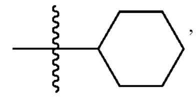,

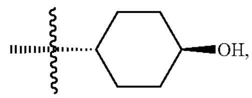 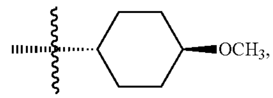

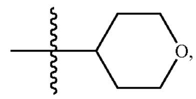 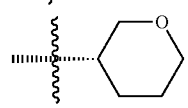,

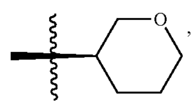, 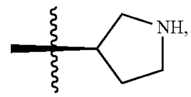

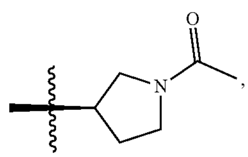, 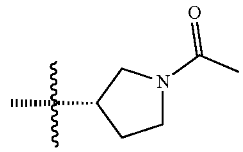,

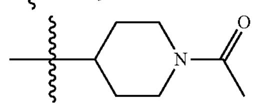, 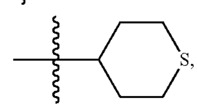

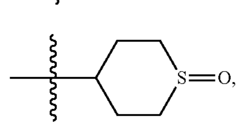 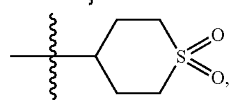

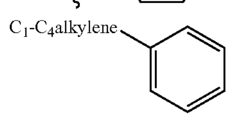, 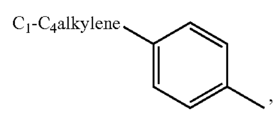,

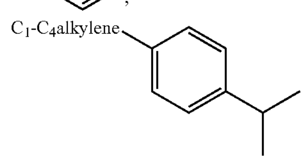,

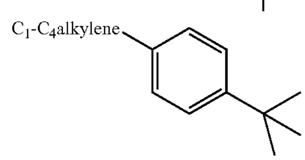,

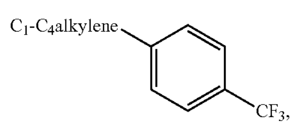 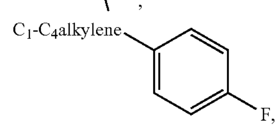

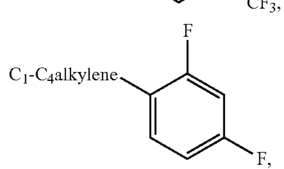 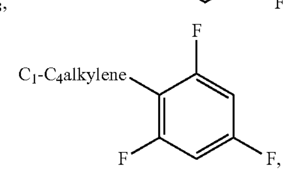

-continued

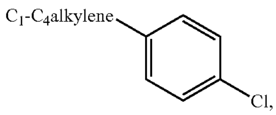, 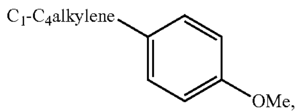, 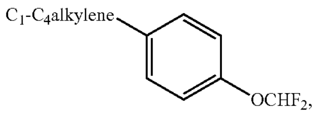, 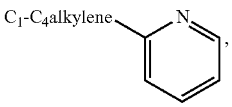, 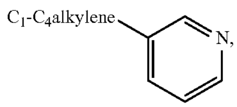, 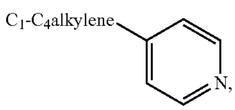, 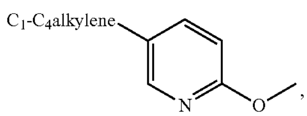, 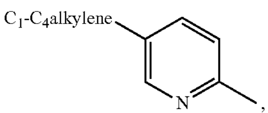, 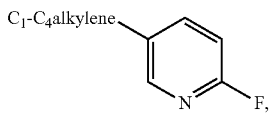, 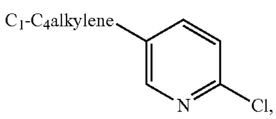, 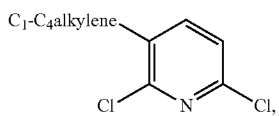, 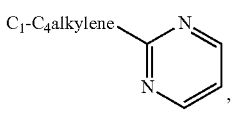, 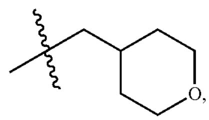, 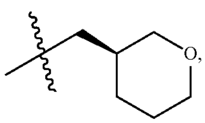, 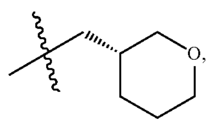, 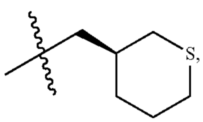, 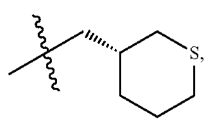, 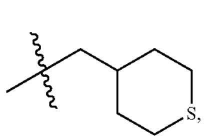, 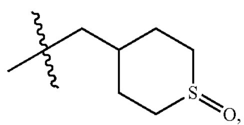, 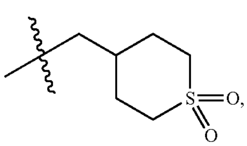, 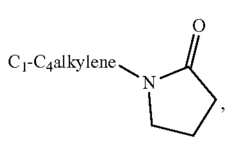, 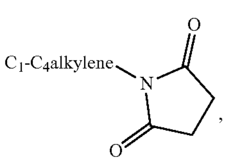, 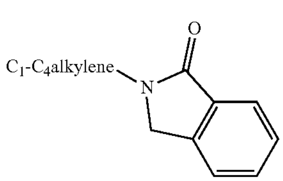, 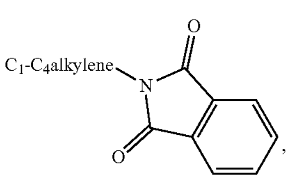, -continued

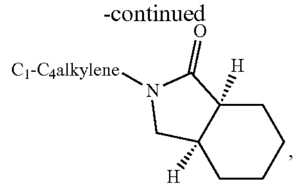, 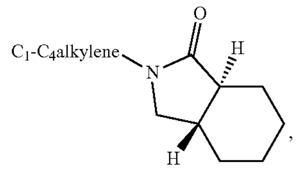, 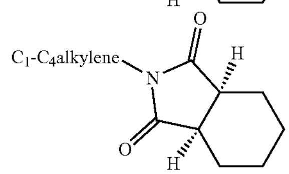, 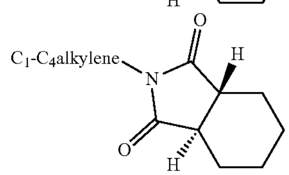, 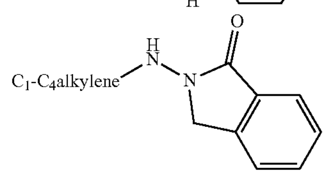, 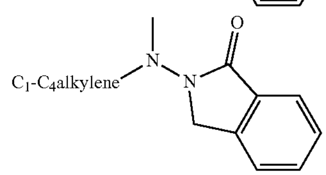, 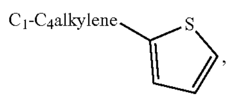, and 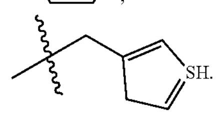

18. The compound of claim 14, wherein:
$R^1$ is selected from H and D;
$R^2$ is H;
$R^3$ is H;
$R^4$ is H;
$R^5$ is H;
$R^6$ is selected from methyl, deuteromethyl, fluoromethyl, deuterofluoromethyl, and $C_1$-$C_6$alkylene$C_3$-$C_{10}$heterocycloalkyl;
$R^7$ is selected from H and D;
$R^8$ is selected from H and D;
$R^{10}$ is selected from H, D, $C_1$-$C_6$alkyl, and deuteromethyl; and
n is 0.

19. The compound of claim 1, wherein X is S (O).

20. The compound of claim 19, wherein:
$R^1$ is H;
$R^2$ is H;
$R^3$ is H;
$R^4$ is H;
$R^5$ is H;
$R^6$ is selected from methyl, fluoromethyl, and deuterofluoromethyl;

$R^7$ is H;

$R^8$ is H;

$R^{10}$ is selected from H, D, methyl, and deuteromethyl; and n is 0.

21. The compound of claim 1, wherein X is $SO_2$.

22. The compound of claim 21, wherein:

$R^1$ is H;

$R^2$ is H;

$R^3$ is H;

$R^4$ is H;

$R^5$ is H;

$R^6$ is selected from methyl, fluoromethyl, and deutero-fluoromethyl;

$R^7$ is H;

$R^8$ is H;

$R^{10}$ is selected from H, D, methyl, and deuteromethyl; and n is 0.

23. The compound of claim 1, wherein the compound of Formula (I) is selected from the table below:

| Compound | Structure |
|---|---|
| (R) I-1 | 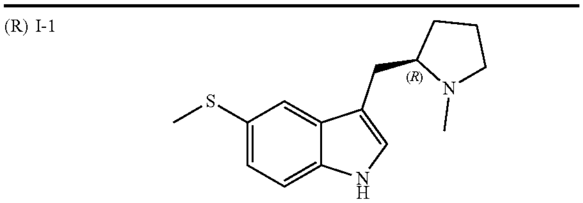 |
| (S) I-1 | 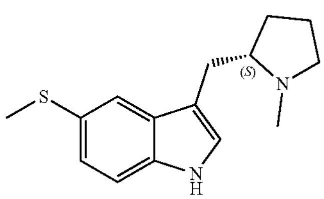 |
| (R) I-2 | 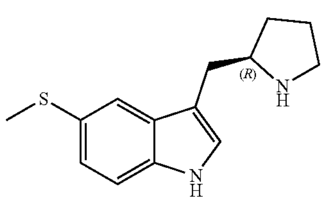 |
| (S) I-2 | 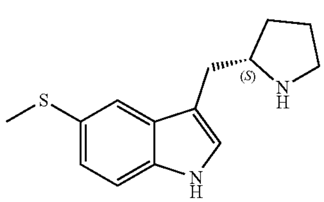 |
| (R) I-3 | 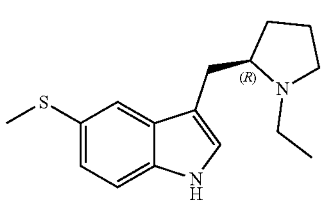 |

-continued

| Compound | Structure |
|---|---|
| (R) I-4 | 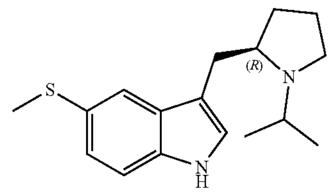 |
| (R) I-5 | 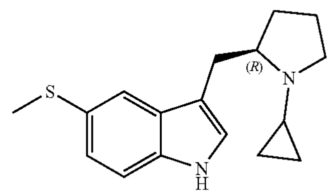 |
| (R) I-6 | 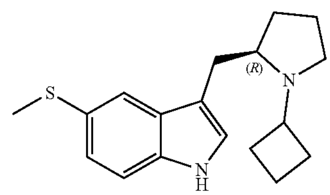 |
| (R) I-7 | 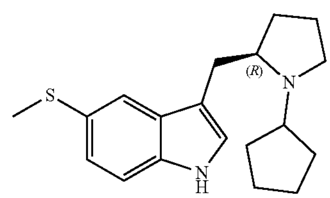 |
| (R, R) I-8 | 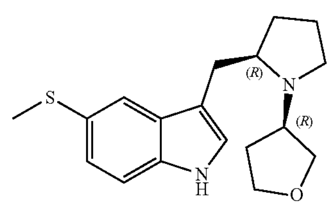 |
| (R, S) I-8 | 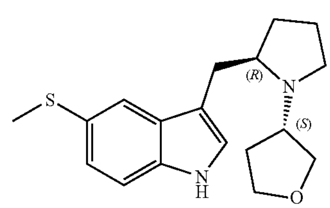 |
| (R, S) I-9 | 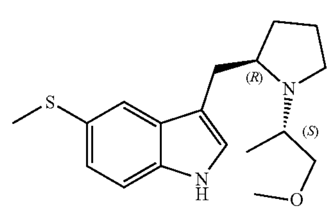 |

-continued
| Compound | Structure |
|---|---|
| (R, R) I-9 | 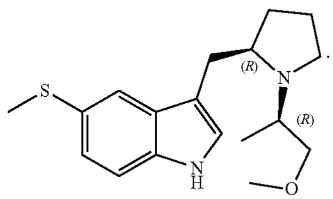 |
| (R) I-10 | 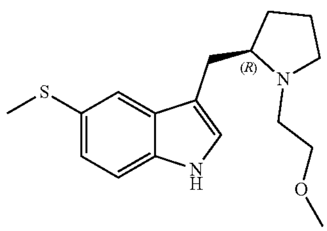 |
| (R) I-11 | 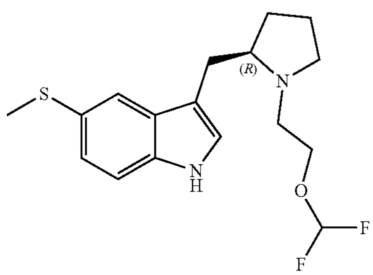 |
| (R) I-12 | 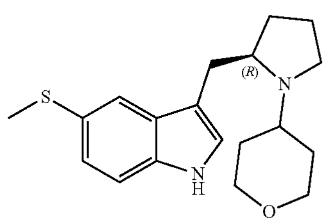 |
| (R, S) I-13 | 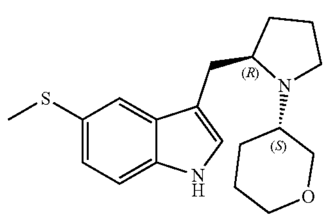 |
| (R, R) I-13 | 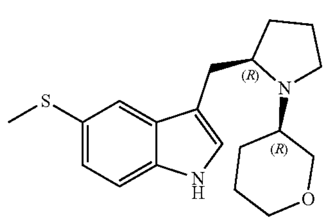 |
| (R) I-14 | 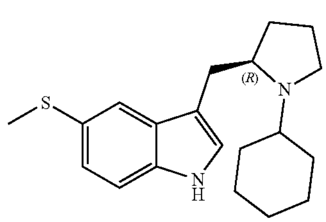 |
-continued
| Compound | Structure |
|---|---|
| trans (R) I-15 | 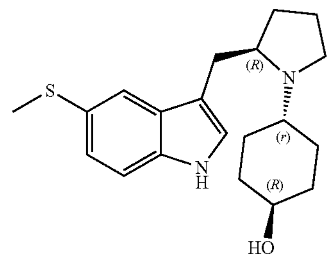 |
| trans (R) I-16 | 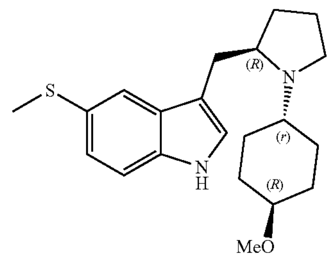 |
| (R, R) I-17 | 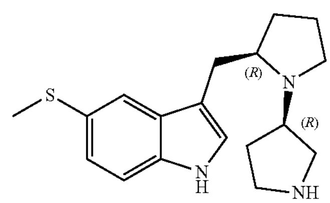 |
| (R) I-18 | 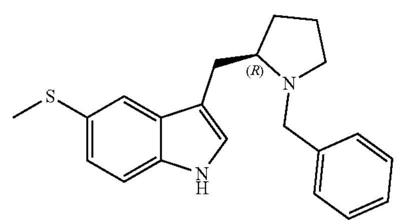 |
| (R) I-19 | 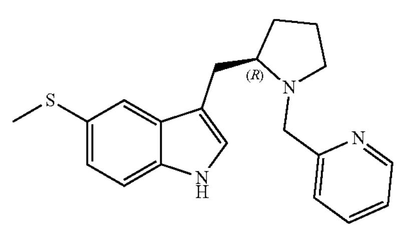 |
| (R) I-20 | 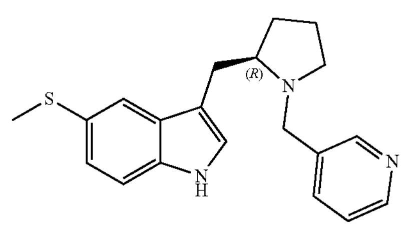 |

-continued
| Compound | Structure |
|---|---|
| (R) I-21 | 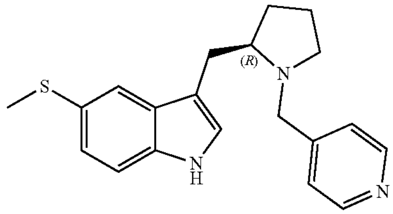 |
| (R) I-22 | 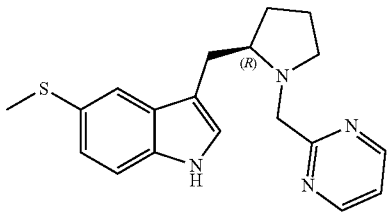 |
| (R) I-23 | 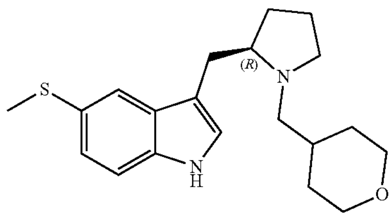 |
| (R, S) I-24 | 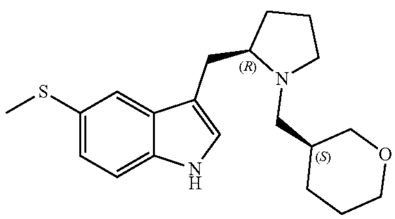 |
| (R, R) I-24 | 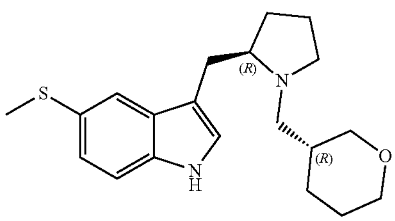 |
| (R, S) I-25 | 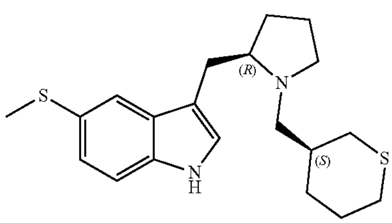 |
| (R, R) I-25 | 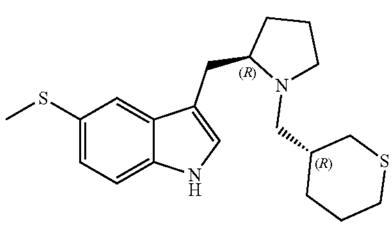 |
-continued
| Compound | Structure |
|---|---|
| (R) I-26 | 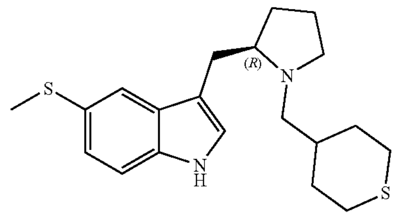 |
| (R) I-27 | 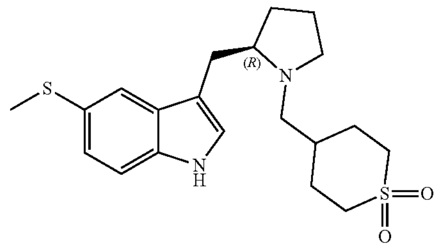 |
| (R) I-28 | 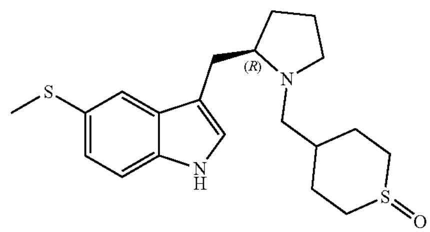 |
| (R) I-29 | 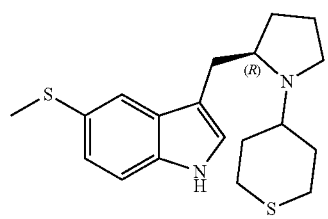 |
| (R) I-30 | 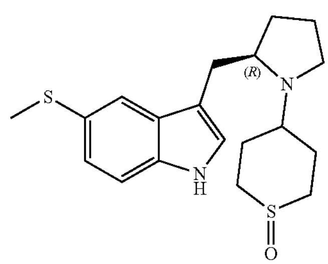 |
| (R) I-31 | 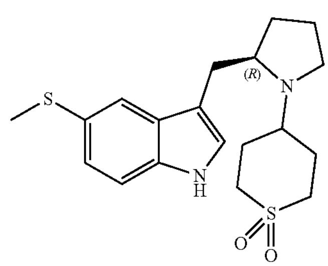 |

-continued
| Compound | Structure |
| --- | --- |
| (R) I-32 | 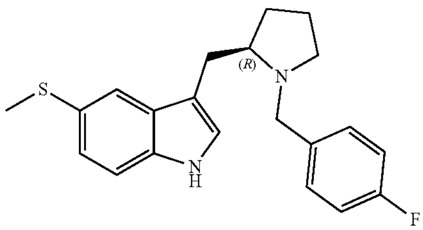 |
| (R) I-33 | 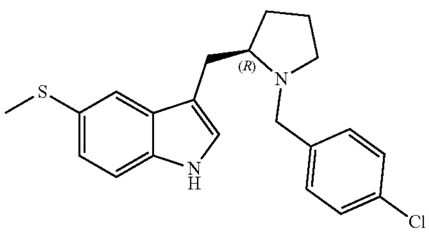 |
| (R) I-34 | 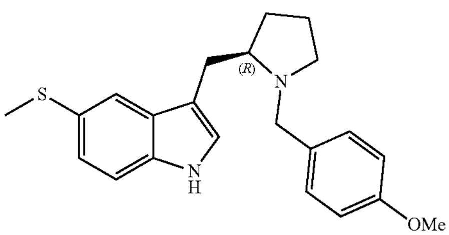 |
| (R) I-35 | 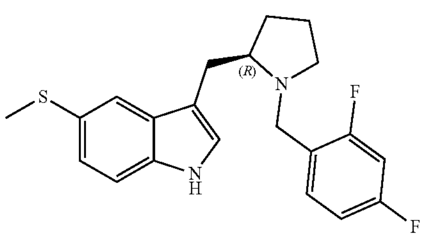 |
| (R) I-36 | 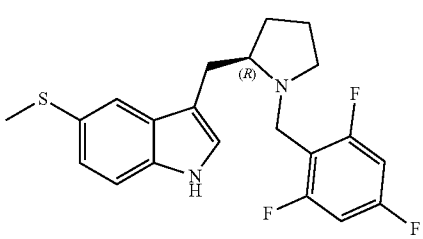 |
| (R) I-37 | 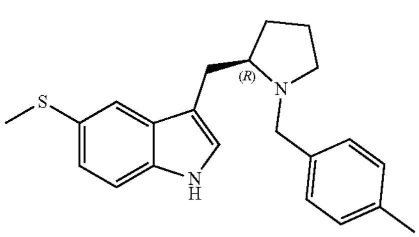 |
-continued
| Compound | Structure |
| --- | --- |
| (R) I-38 | 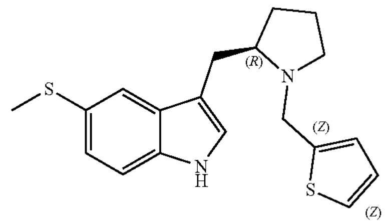 |
| (R) I-39 | 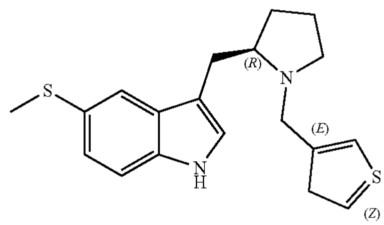 |
| (R) I-40 | 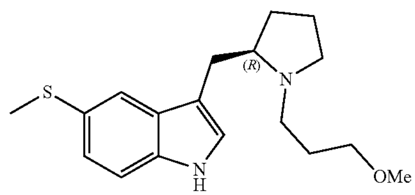 |
| (R, S) I-41 | 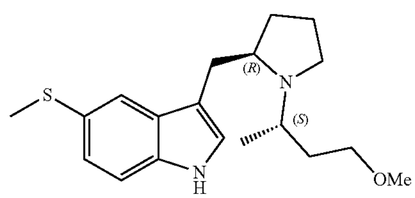 |
| (R, R) I-41 | 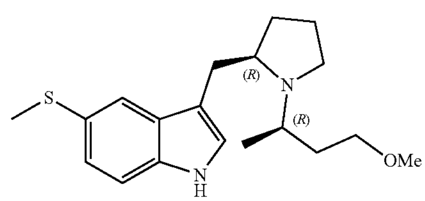 |
| (R, S) I-42 | 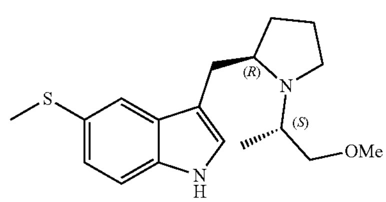 |
| (R, R) I-42 | 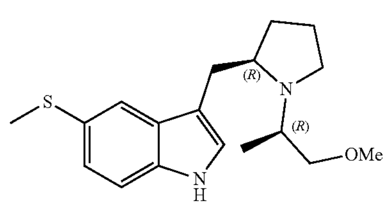 |

-continued
| Compound | Structure |
|---|---|
| (R) I-43 | 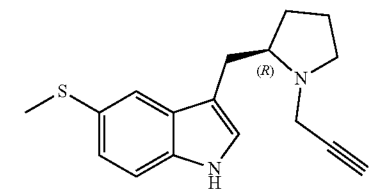 |
| (R) I-44 | 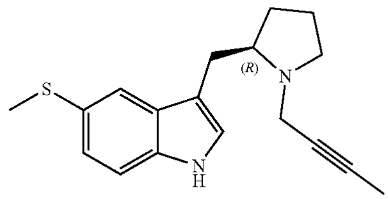 |
| (R) I-45 | 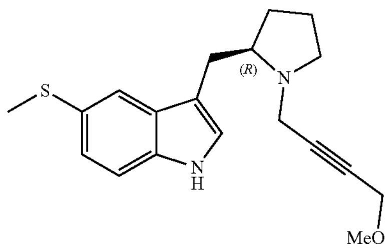 |
| (R) I-46 | 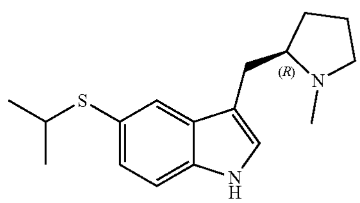 |
| (R) I-47 | 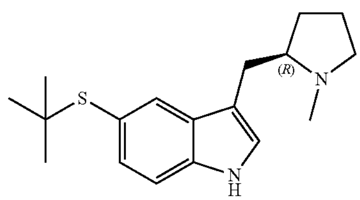 |
| (R) I-48 | 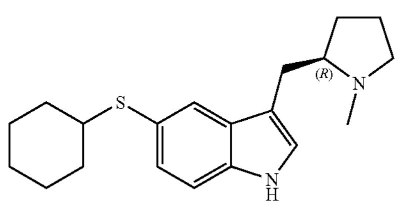 |
| (R) I-49 | 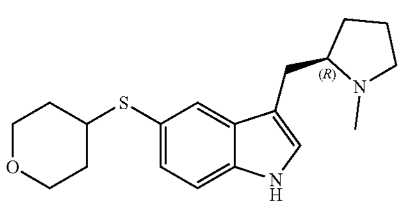 |
-continued
| Compound | Structure |
|---|---|
| (R) I-50 | 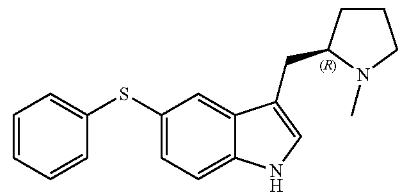 |
| (R) I-51 | 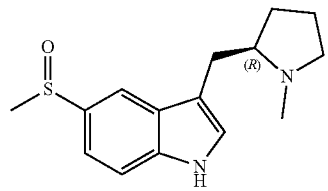 |
| (R) I-52 | 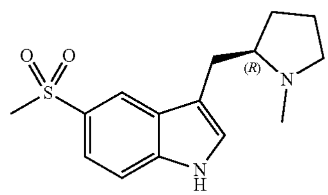 |
| (R) I-53 | 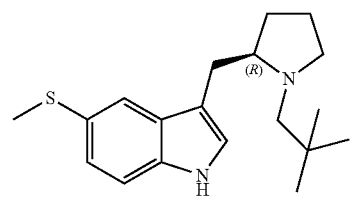 |
| (R) I-54 | 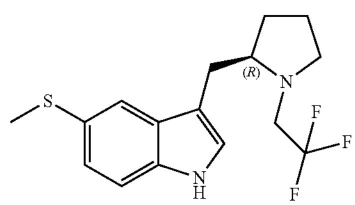 |
| (R) I-55 | 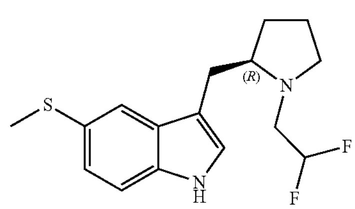 |
| (R) I-56 | 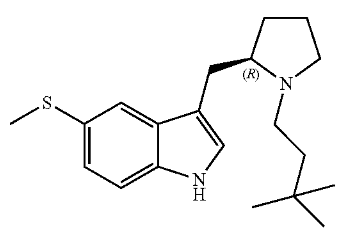 |

-continued
| Compound | Structure |
|---|---|
| (R) I-57 | 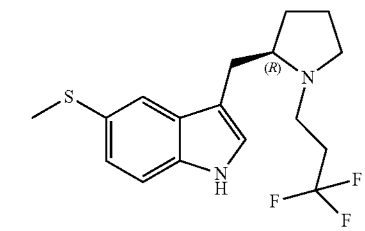 |
| (R) I-58 | 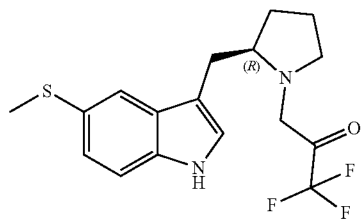 |
| (R) I-59 | 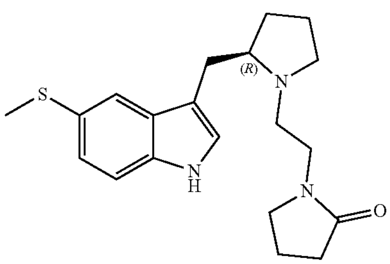 |
| (R) I-60 | 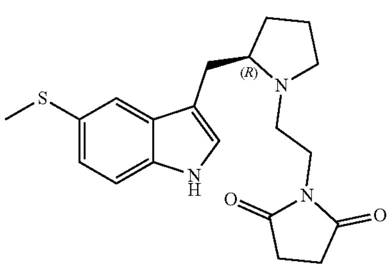 |
| (R) I-61 | 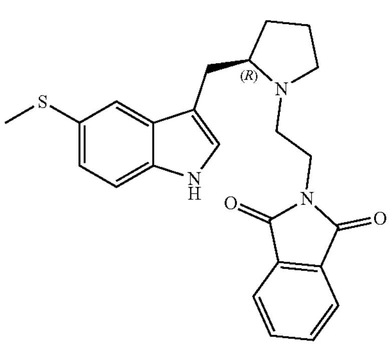 |
-continued
| Compound | Structure |
|---|---|
| (R) I-62 | 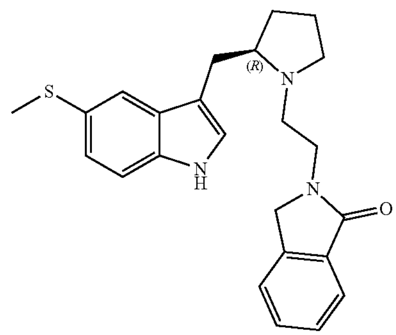 |
| (R) I-63 | 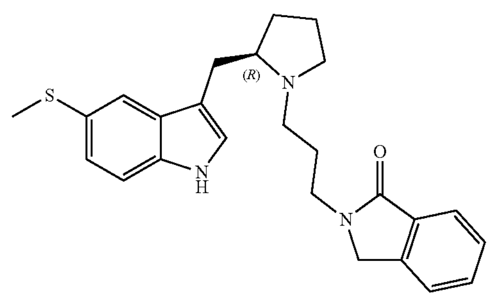 |
| (R) I-64 | 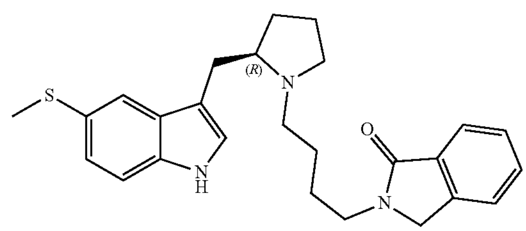 |
| (R) I-65 | 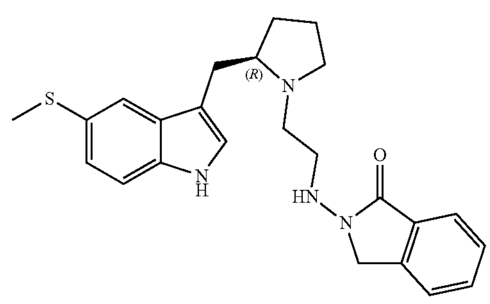 |
| (R) I-66 | 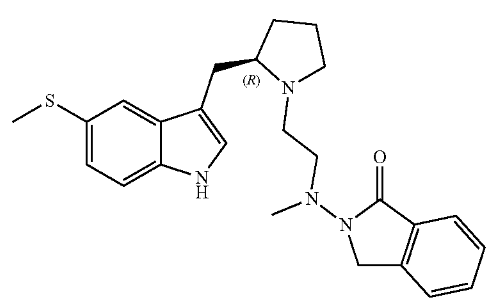 |

-continued
| Compound | Structure |
| --- | --- |
| (R) I-67 | 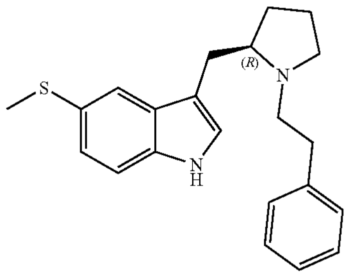 |
| (R) I-68 | 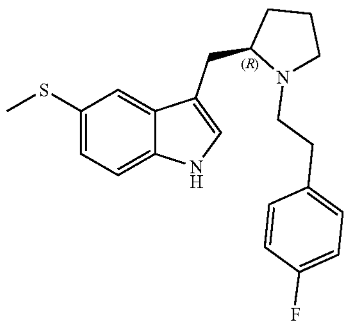 |
| (R) I-69 | 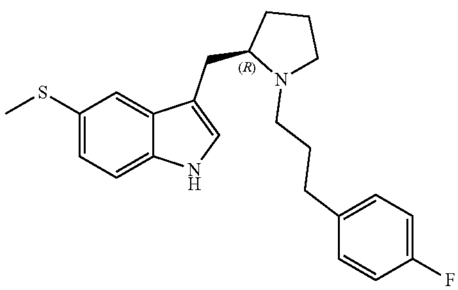 |
| (R) I-70 | 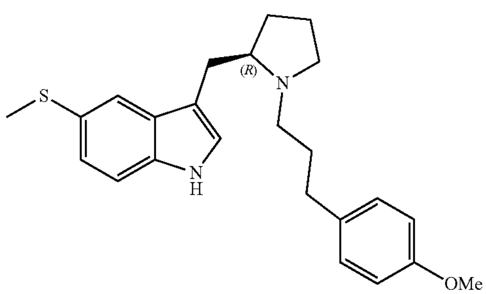 |
| (R) I-71 | 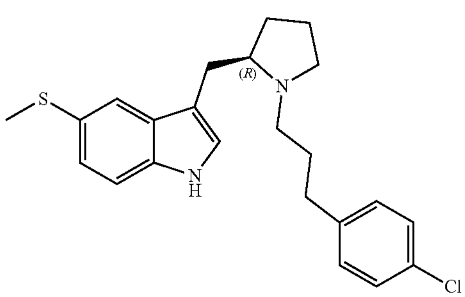 |
-continued
| Compound | Structure |
| --- | --- |
| (R) I-72 | 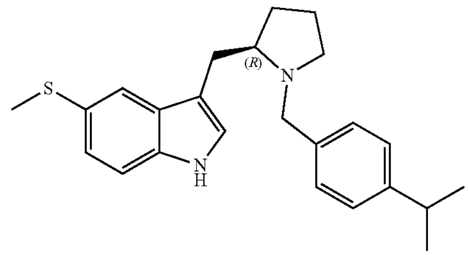 |
| (R) I-73 | 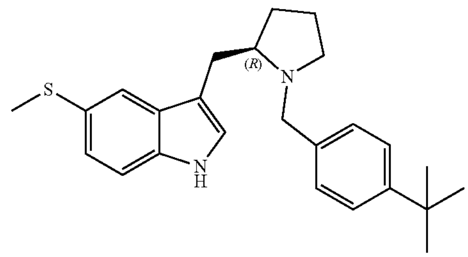 |
| (R) I-74 | 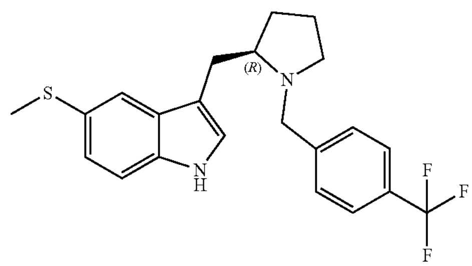 |
| (R) I-75 | 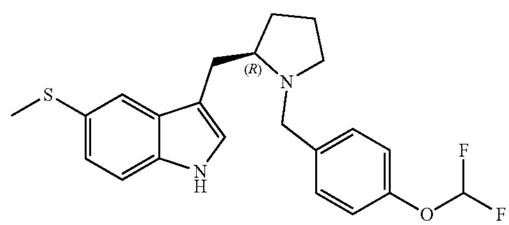 |
| (R) I-76 | 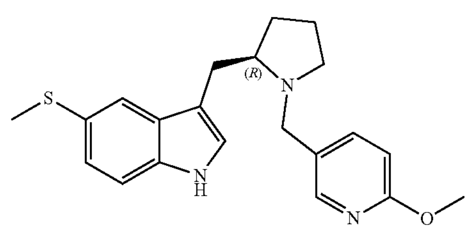 |
| (R) I-77 | 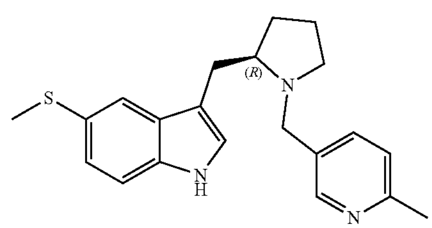 |

-continued
| Compound | Structure |
|---|---|
| (R) I-78 | 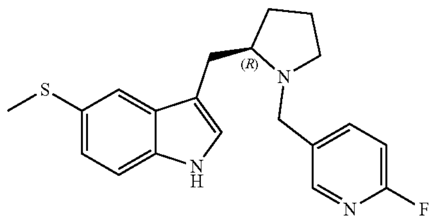 |
| (R) I-79 | 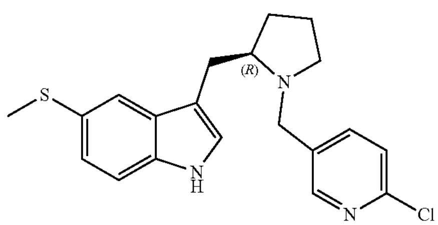 |
| (R) I-80 | 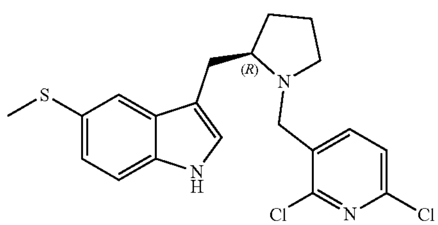 |
| (R) I-81 | 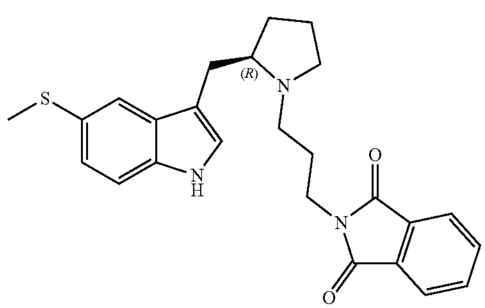 |
| cis - (R) I-82 | 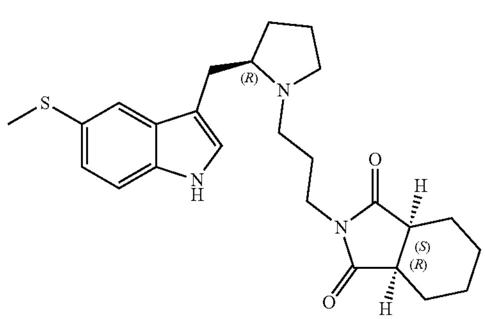 |
-continued
| Compound | Structure |
|---|---|
| trans - (R) I-82 | 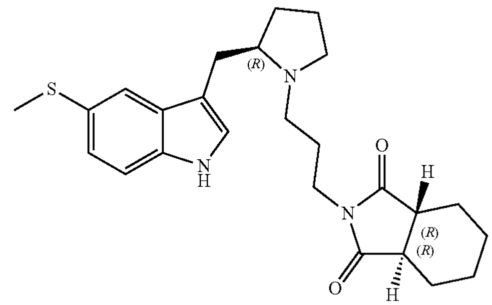 |
| (R) I-83 | 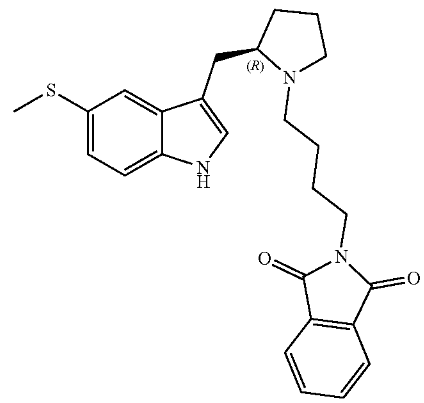 |
| (R) I-84 | 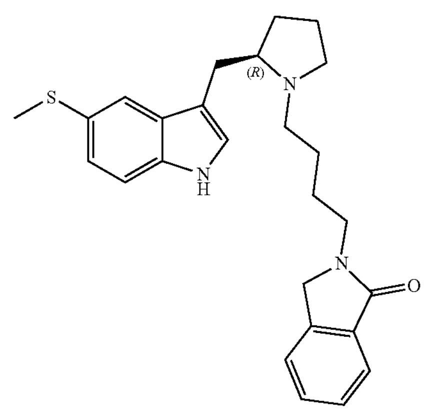 |
| cis - (R) I-85 | 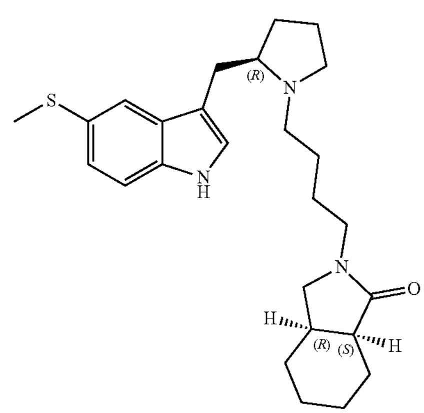 |

-continued
| Compound | Structure |
|---|---|
| cis - (R) I-86 | 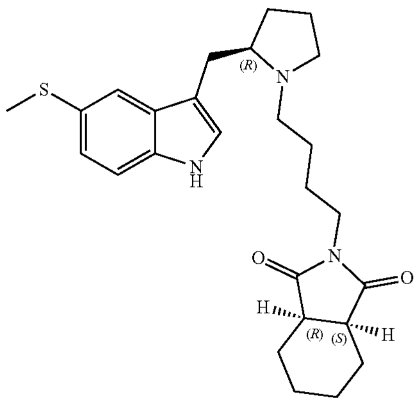 |
| trans - (R) I-86 | 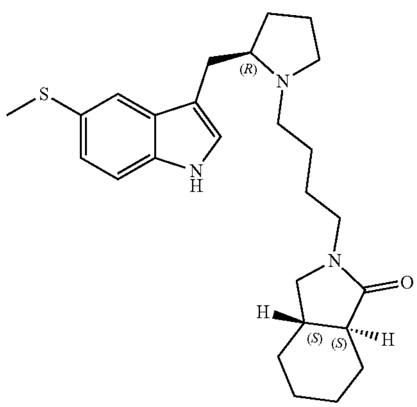 |
| (R) I-87 | 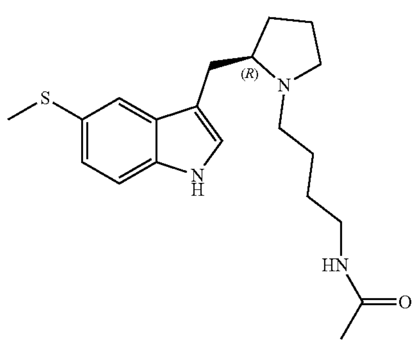 |
| (R) I-88 | 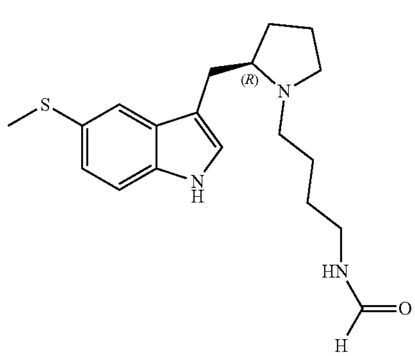 |
-continued
| Compound | Structure |
|---|---|
| (R) I-89 | 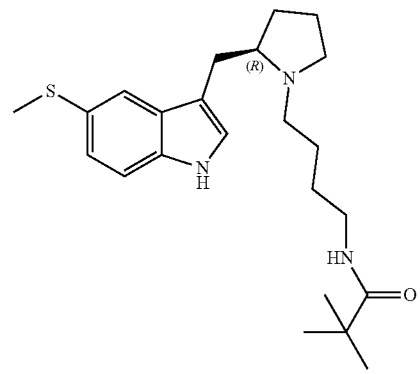 |
| (R) I-90 | 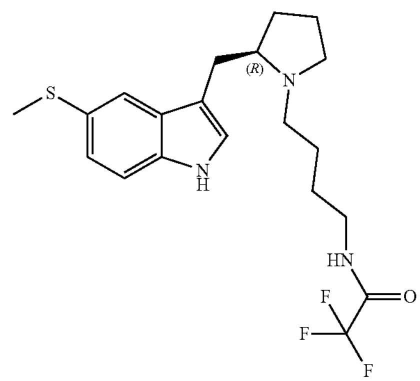 |
| (R) I-91 | 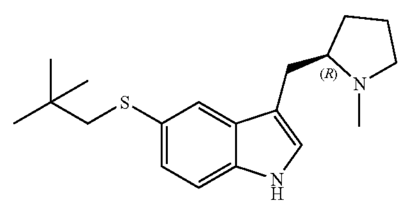 |
| (R) I-92 | 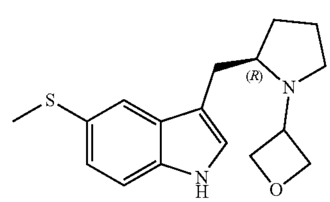 |
| (R, S) I-93 | 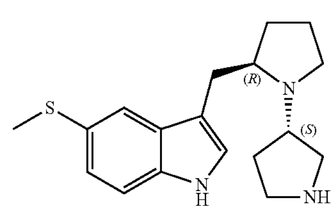 |

-continued
| Compound | Structure |
|---|---|
| (R, S) I-94 | 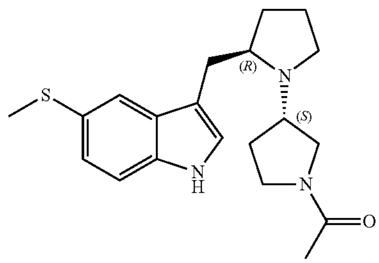 |
| (R) I-95 | 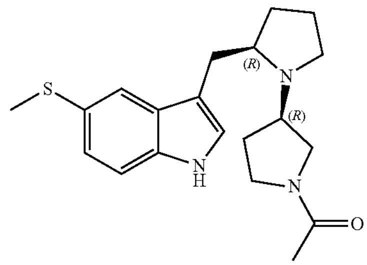 |
| (R) I-96 | 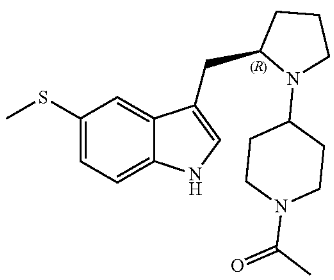 |
| | and |
| (R) I-97 | 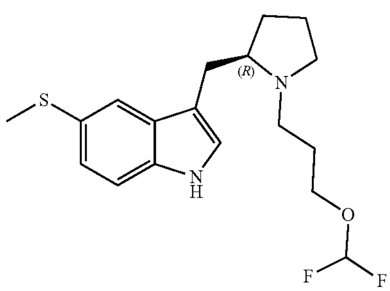 |
or a pharmaceutically acceptable salt, solvate, and/or prodrug thereof.
24. The compound of claim 1, wherein the compound of Formula (I) is selected from the table below:
| Compound | Structure |
|---|---|
| II-1 | 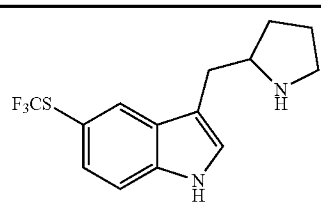 |
| (R) II-2 | 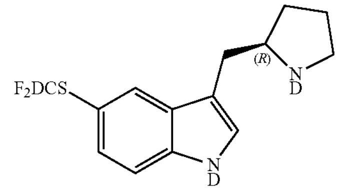 |
| II-3 | 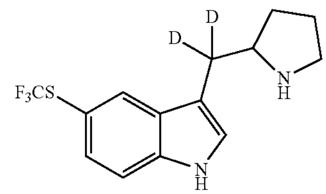 |
| II-4 | 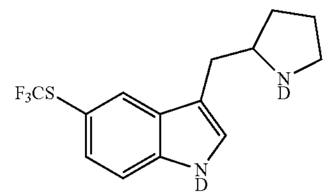 |
| II-5 | 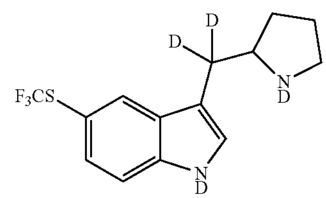 |
| (R) II-6 | 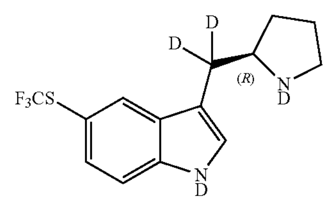 |
| (R) II-7 | 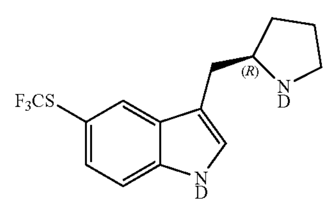 |
| (R) II-8 | 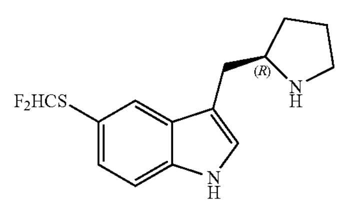 |
| (R) II-9 | 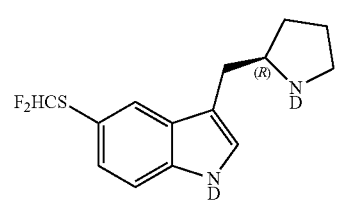 |

-continued
| Compound | Structure |
|---|---|
| (R) II-10 | 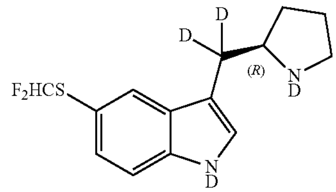 |
| (R) II-11 | 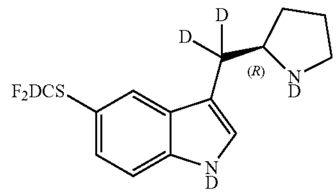 |
| (R) II-13 | 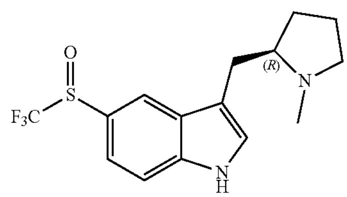 |
| (R) II-14 | 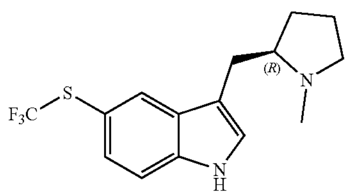 |
| (R) II-15 | 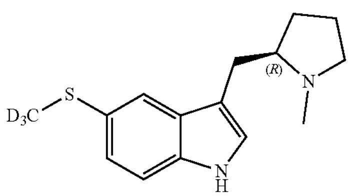 |
| (R) II-16 | 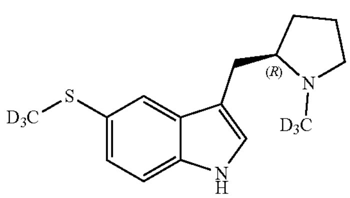 |
| (R) II-17 | 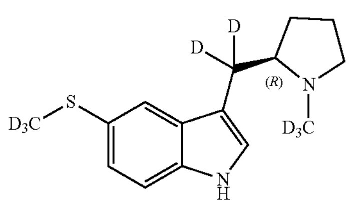 |
-continued
| Compound | Structure |
|---|---|
| (R) II-18 | 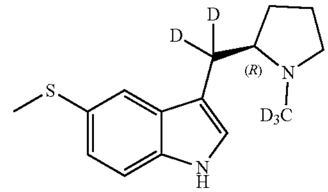 |
| (R) II-19 | 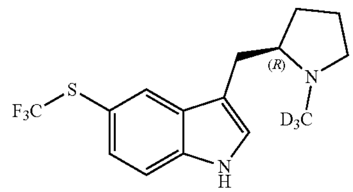 |
| (R) II-20 | 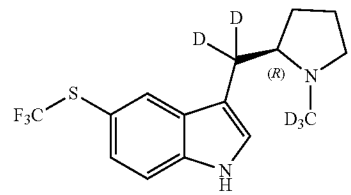 |
| (R) II-21 | 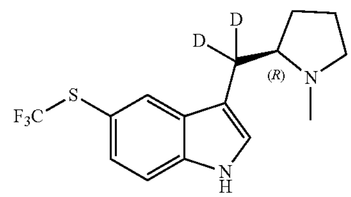 |
| (R) II-22 | 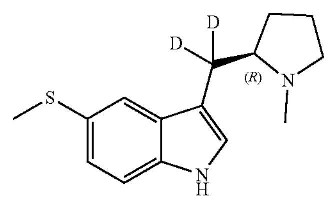 |
| (R) II-23 | 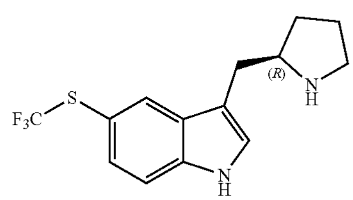 |
| (R) II-24 | 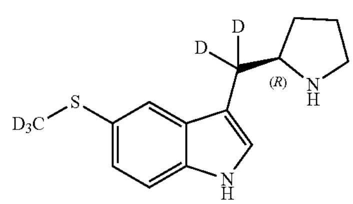 |

-continued
| Compound | Structure |
|---|---|
| (R) II-25 | 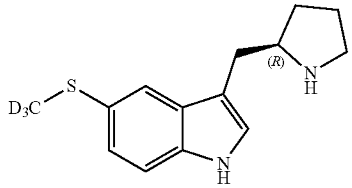 |
| (R) II-26 | 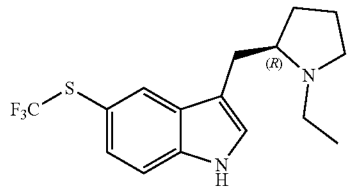 |
| (R) II-27 | 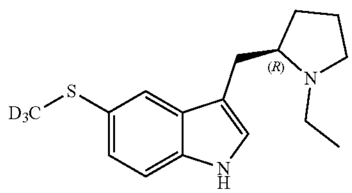 |
| (R) II-28 | 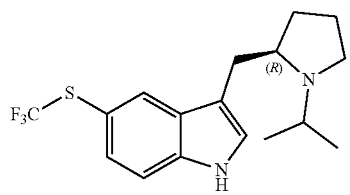 |
| (R) II-29 | 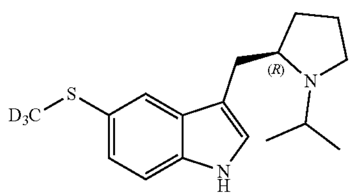 |
| (R) II-30 | 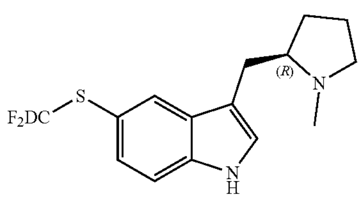 |
| (R) II-31 | 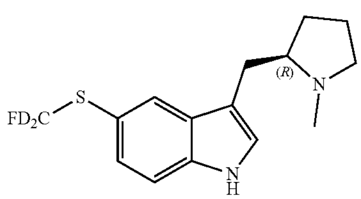 |
| (R) II-32 | 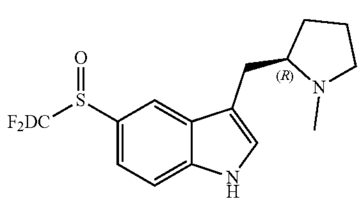 |
-continued
| Compound | Structure |
|---|---|
| (R) II-33 | 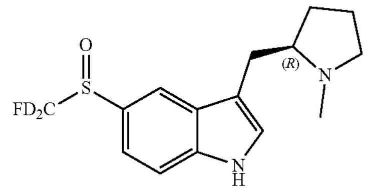 |
| (R) II-36 | 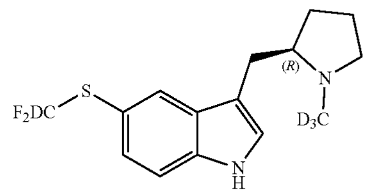 |
| (R) II-37 | 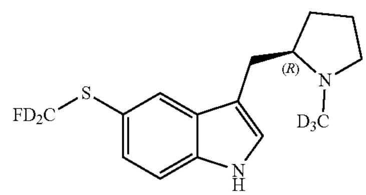 |
| (R) II-38 | 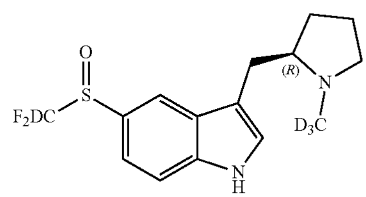 |
| (R) II-39 | 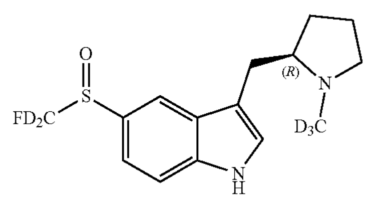 |
| (R) II-42 | 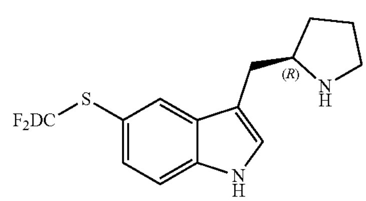 |
| (R) II-43 | 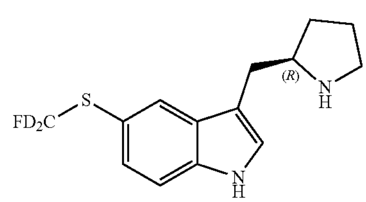 |

-continued
| Compound | Structure |
|---|---|
| (R) II-44 | 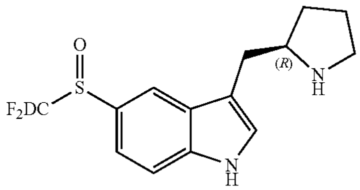 |
| (R) II-45 | 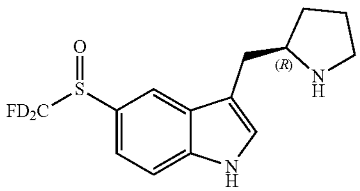 |
| (R) II-48 | 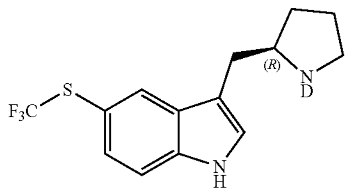 |
| (R) II-49 | 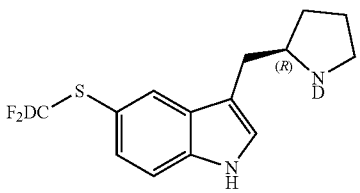 |
| (R) II-50 | 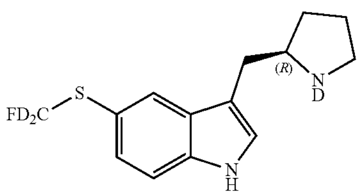 |
| (R) II-51 | 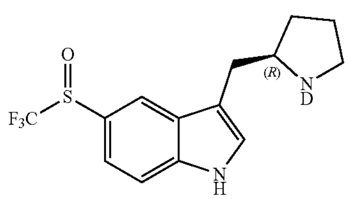 |
| (R) II-52 | 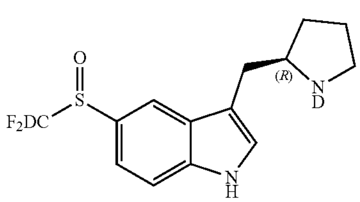 |
| (R) II-53 | 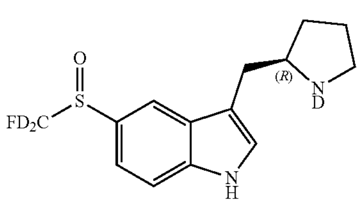 |
-continued
| Compound | Structure |
|---|---|
| (R) I-271 | 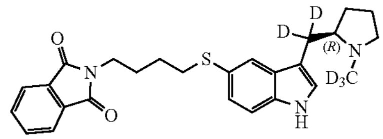 |
| (R) I-272 | 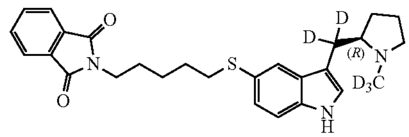 |
| (R) I-273 | 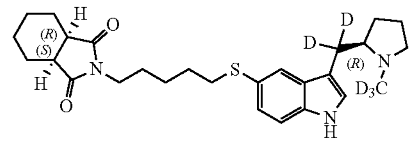 |
| (R) I-296 | 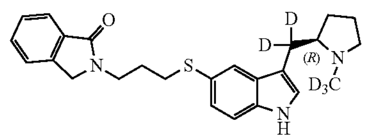 |
or a pharmaceutically acceptable salt, solvate, and/or prodrug thereof.
25. The compound of claim 1, wherein the compound of Formula (I) is selected from the table below:
| Compound | Structure |
|---|---|
| (R) II-12 | 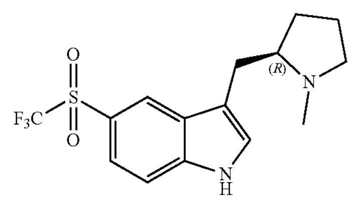 |
| (R) II-34 | 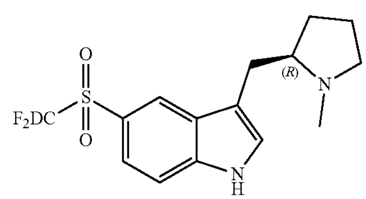 |
| (R) II-35 | 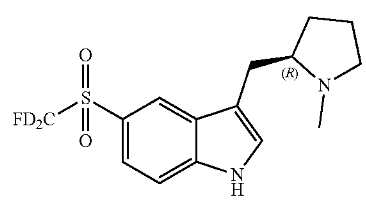 |

-continued
| Compound | Structure |
| --- | --- |
| (R) II-40 | 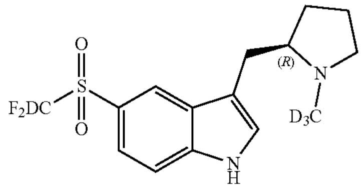 |
| (R) II-41 | 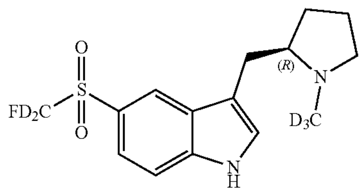 |
| (R) II-46 | 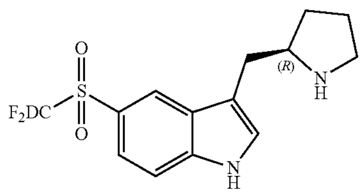 |
| (R) II-47 | 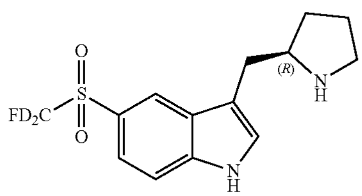 |
-continued
| Compound | Structure |
| --- | --- |
| (R) II-54 | 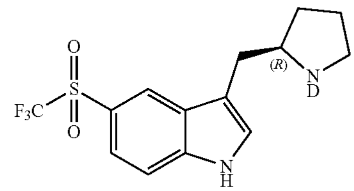 |
| (R) II-55 | 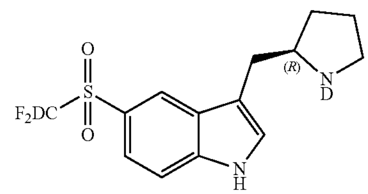 |
| | and |
| (R) II-56 | 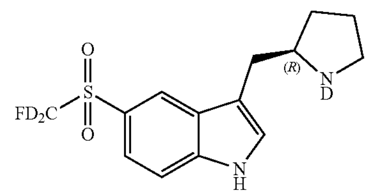 |
or a pharmaceutically acceptable salt, solvate, and/or prodrug thereof.
26. A composition comprising one or more compounds of claim 1 and a carrier.
* * * * *